(12) United States Patent
Jenkins et al.

(10) Patent No.: US 9,040,032 B2
(45) Date of Patent: *May 26, 2015

(54) COMPOSITIONS COMPRISING ENZYME-CLEAVABLE OPIOID PRODRUGS AND INHIBITORS THEREOF

(71) Applicant: Signature Therapeutics, Inc., San Carlos, CA (US)

(72) Inventors: Thomas E. Jenkins, Half Moon Bay, CA (US); Craig O. Husfeld, San Mateo, CA (US); Julie D. Seroogy, San Carlos, CA (US); Jonathan W. Wray, San Francisco, CA (US)

(73) Assignee: Signature Therapeutics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,725

(22) Filed: Nov. 27, 2012

(65) Prior Publication Data

US 2013/0210701 A1 Aug. 15, 2013

Related U.S. Application Data

(63) Continuation of application No. 12/764,877, filed on Apr. 21, 2010, now abandoned.

(51) Int. Cl.
*A61K 31/74* (2006.01)
*A61K 47/48* (2006.01)
(Continued)

(52) U.S. Cl.
CPC ............ *A61K 47/48246* (2013.01); *A61K 9/51* (2013.01); *A61K 31/485* (2013.01); *A61K 47/4813* (2013.01); *C07D 489/02* (2013.01); *C07D 489/08* (2013.01); *C12Q 1/37* (2013.01); *G01N 33/5088* (2013.01); *G01N 33/9486* (2013.01); *G01N 2333/976* (2013.01); *G01N 2500/00* (2013.01)

(58) Field of Classification Search
CPC ..................................................... A61K 9/51
See application file for complete search history.

(56) References Cited

U.S. PATENT DOCUMENTS

| 4,454,338 A | 6/1984 | Fujii et al. |
| 4,532,255 A | 7/1985 | Fujii et al. |

(Continued)

FOREIGN PATENT DOCUMENTS

| EP | 1782834 | 5/2007 |
| WO | 0243767 | 6/2002 |

(Continued)

OTHER PUBLICATIONS

Bak, Pharmaceutical Research, 1999, 16, 24-29.*

(Continued)

*Primary Examiner* — Paul Dickinson
(74) *Attorney, Agent, or Firm* — Carol L. Francis; Khin K. Chin; Bozicevic, Field & Francis LLP

(57) ABSTRACT

Pharmaceutical compositions and their methods of use are provided, where the pharmaceutical compositions comprise an opioid prodrug that provides enzymatically-controlled release of an opioid, and an enzyme inhibitor that interacts with the enzyme(s) that mediates the enzymatically-controlled release of the opioid from the opioid prodrug so as to attenuate enzymatic cleavage of the opioid prodrug.

51 Claims, 39 Drawing Sheets

(51) Int. Cl.
 A61K 9/51 (2006.01)
 A61K 31/485 (2006.01)
 C07D 489/02 (2006.01)
 C07D 489/08 (2006.01)
 C12Q 1/37 (2006.01)
 G01N 33/50 (2006.01)
 G01N 33/94 (2006.01)

(56) References Cited

U.S. PATENT DOCUMENTS

| | | |
|---|---|---|
| 5,109,118 A | 4/1992 | Mizushima et al. |
| 5,352,704 A | 10/1994 | Okuyama et al. |
| 6,388,122 B1 | 5/2002 | Kido et al. |
| 6,586,196 B1 | 7/2003 | Bronstein et al. |
| 7,060,290 B1 | 6/2006 | Morimoto et al. |
| 7,189,414 B2 | 3/2007 | Rubinstein et al. |
| 7,893,105 B2 | 2/2011 | Xiang et al. |
| 8,217,005 B2 | 7/2012 | Jenkins et al. |
| 8,497,237 B2 | 7/2013 | Jenkins et al. |
| 8,569,228 B2 | 10/2013 | Jenkins et al. |
| 8,685,916 B2 | 4/2014 | Jenkins et al. |
| 8,802,681 B2 | 8/2014 | Jenkins et al. |
| 8,921,418 B2 | 12/2014 | Jenkins et al. |
| 8,962,547 B2 | 2/2015 | Jenkins et al. |
| 2003/0035831 A1 | 2/2003 | Modi |
| 2003/0180352 A1 | 9/2003 | Patel et al. |
| 2004/0063628 A1 | 4/2004 | Piccariello et al. |
| 2005/0080012 A1 | 4/2005 | Mickle et al. |
| 2005/0176644 A1 | 8/2005 | Mickle et al. |
| 2007/0082929 A1 | 4/2007 | Gant et al. |
| 2007/0123468 A1 | 5/2007 | Jenkins et al. |
| 2007/0203055 A1 | 8/2007 | Mickle et al. |
| 2009/0136980 A1 | 5/2009 | Bebbington et al. |
| 2009/0137618 A1 | 5/2009 | Jenkins et al. |
| 2009/0192093 A1 | 7/2009 | Mickle et al. |
| 2009/0209569 A1 | 8/2009 | Arnelle et al. |
| 2010/0022792 A1 | 1/2010 | Shen |
| 2010/0035826 A1 | 2/2010 | Jenkins et al. |
| 2010/0080797 A1 | 4/2010 | Yeomans et al. |
| 2010/0092562 A1 | 4/2010 | Hollenbeck et al. |
| 2010/0227921 A1 | 9/2010 | Franklin et al. |
| 2010/0267614 A1 | 10/2010 | Jenkins |
| 2010/0286186 A1 | 11/2010 | Franklin et al. |
| 2011/0262355 A1 | 10/2011 | Jenkins et al. |
| 2011/0262359 A1 | 10/2011 | Jenkins et al. |
| 2011/0262360 A1 | 10/2011 | Jenkins et al. |
| 2012/0230916 A1 | 9/2012 | Jenkins et al. |
| 2013/0059914 A1 | 3/2013 | Jenkins et al. |
| 2014/0121152 A1 | 5/2014 | Jenkins et al. |
| 2014/0206597 A1 | 7/2014 | Jenkins et al. |
| 2015/0031635 A1 | 1/2015 | Jenkins et al. |

FOREIGN PATENT DOCUMENTS

| | | |
|---|---|---|
| WO | 2004082620 | 9/2004 |
| WO | 2005032474 | 4/2005 |
| WO | 2007120864 | 10/2007 |
| WO | 2007140272 | 12/2007 |
| WO | 2008012046 | 1/2008 |
| WO | 2007120648 | 7/2008 |
| WO | 2008101187 | 8/2008 |
| WO | 2008101202 | 8/2008 |
| WO | 2009067703 | 5/2009 |
| WO | 2010045599 | 4/2010 |
| WO | 2010100477 | 9/2010 |
| WO | 2011031350 | 3/2011 |
| WO | 2011133346 | 4/2011 |

OTHER PUBLICATIONS

Berkop-Schnurch "The use of inhibitory agents to overcome the enzymatic barrier to perorally administered therapeutic peptides and proteins" J. Control. Release (1998), vol. 50, No. 1-2, pp. 1-16.

Birk et al., "Trypsin and chymotrypsin inhibitors from soybeans" Methods in Enzymology (1976) vol. 45, pp. 700-707.

Geratz et al., "Novel bis(benzamidine) compounds with an aromatic central link. Inhibitors of thrombin, pancreatic kallikrein, trypsin, and complement" J. Med. Chem. (1976), vol. 19, pp. 634-639.

Göke et al., "Effect of a Specific Serine Protease Inhibitor on the Rat Pancreas: Systemic Administration of Camostate and Exocrine" Digestion (1984) vol. 30, pp. 171-178.

Gomes et al., "Cyclization-activated prodrugs" Molecules, (2007), vol. 12, pp. 2484-2506.

Hijikata et al., "Selective Inhibition of Trypsin by (2R,4R)-4-Phenyl-1-[Nα-(7-methoxy-2-naphthalenesulfonyl)-L-arginyl]-2-piperidinecarboxylic Acid" J. Biochem. (2000), vol. 275, pp. 18995-18999.

Kunze et al., "Effects of the serine protease inhibitors FOY and FOY 305 on phospholipase A I (EC 3.1.1.32) activity in rat—liver lysosomes" Pharm. Research Corn. (1983), vol. 15, pp. 451-459.

Lin et al., "The 0.25-nm X-ray structure of the Bowman-Birk type inhibitor from mung bean in ternary complex with porcine trypsin" Eur. J. Biochem., (1993), vol. 212, pp. 549-555.

Markwardt et al., "Comparative studies on the inhibition of trypsin, plasmin, and thrombin by derivatives of benzylamine and benzylamidine" Eur. J. Biochem, (1968), vol. 6, pp. 502-506.

Ozawa et al., "The reactive site of trypsin inhibitors" J. Biol. Chem. (1966), vol. 241, pp. 3955-3961.

Ramjee et al. "The Kinetic and Structural Characterization of the Reaction of Nafamostat with Bovine Pancreatic Trypsin" Thrmb Res. (2000), vol. 98, No. 6, pp. 559-569.

Renatus et al. "Structural and Functional Analyses of Benzamidine-Based Inhibitors in Complex with Trypsin: Implications for the Inhibition of Factor Xa, tPA, and Urokinase" J. Med. Chem., (1998), vol. 41, No. 27 pp. 5445-5456.

Tanizawa et al. "Inverse Substrates for Tryspin and Tryspin-like Enzymes" Acc. Chem. Res., (1987), vol. 20, pp. 337-343.

Testa et al, "Hydrolysis in Drug and Prodrug Metabolism" Verlag Helvetica Chimica Acta, Postfach, CH-8042, Switzerland (2003) pp. 420-534.

Tirkkonen et al., "Drug interactions with the potential to prevent prodrug activation as a common source of irrational prescribing in hospital inpatients" Clinical Pharmacology and Therapeutics, (2004) vol. 76, No. 6, pp. 639-647.

Umezawa et al., "Structure and activities of protease inhibitors of microbial origin" Methods in Enzymology (1976) vol. 45, pp. 678-695.

U.S. Appl. No. 13/686,710, filed Nov. 27, 2012, Jenkins, et al.
U.S. Appl. No. 13/708,486, filed Dec. 7, 2012, Jenkins, et al.

Pauletti, Giovanni M., et al., (1997) "Esterase-sensitive cyclic prodrugs of peptides: Evaluation of a phenylpropionic acid promoiety in a model hexapeptide", Pharmaceutical Research, 14(1):11-17.

Katragadda, Suresh, et al., (2006) "Simulataneous modulation of transport and metabolism of acyclovir prodrugs across rabbit cornea: An approach involving enzyme inhibitors", International Journal of Pharmaceuticals, 320:104-113.

Song, Xiaoping, et al., (2002) "Synthesis of a novel cyclic prodrug of RGD peptidomimetic to improve its cell membrane permeation", Bioorganic Chemistry, 30:285-301.

U.S. Appl. No. 14/593,855, filed Jan. 9, 2015, Jenkins, et al.
U.S. Appl. No. 13/415,793, filed Mar. 8, 2012, Jenkins, et al.
U.S. Appl. No. 14/551,731, filed Nov. 24, 2014, Jenkins, et al.

Gotoh et al. (2005) "The advantages of the Ussing chamber in drug absorption studies" Journal of Biomolecular Screening 10(5):517-523.

Hyams (downloaded on Nov. 21, 2014 from URL: <http://www.pediatricweb.com/webpost/iframe/MedicalConditions_465.asp?tArticleId=94>).

Nafamostat (PubChem, National Center for Biotechnology Information dated Dec. 20, 2005).

Opiois911 (downloaded on Nov. 21, 2014 from URL: <http://opioids911.org/safety.php>.

(56) References Cited

OTHER PUBLICATIONS

Pain Doctor (downloaded on Nov. 21, 2014 from URL: <http://paindoctor.com/conditions/common/phantom-limb-pain/>).

Prater et al. (2002) "Successful Pain Management for the Recovering Addicted Patient" Primary Care Companion J Clin Psychiatry 4(4):125-131.

Schanker et al. (1958) "Absorption of drugs from the rat small intestine" Journal of Pharmacology and Experimental Therapeutics 123(1):81-88.

Van Gelder et al. (2002) "Intestinal absorption enhancement of the ester prodrug tenofovir disoproxil fumarate through modulation of the biochemical barrier by defined ester mixtures" Drug Metabolism and Disposition 30(8):924-930.

Bioavailability and Bioequivalence Studies for Orally Administered Drug Products—General Considerations, Guidance for Industry, Food and Drug Administration, published on Oct. 2000.

Camostat Medilate (http://www.scbt.com/datasheet-203867-camostat-mesylate.html (downloaded on Nov. 14, 2013).

* cited by examiner c

COMPOSITIONS COMPRISING ENZYME-CLEAVABLE OPIOID PRODRUGS AND INHIBITORS THEREOF

CROSS-REFERENCE TO RELATED APPLICATION

This application is a continuation of U.S. patent application Ser. No. 12/764,877 filed on Apr. 21, 2010, now abandoned.

INTRODUCTION

Opioids are susceptible to misuse, abuse, or overdose. Use of and access to these drugs therefore needs to be controlled. The control of access to the drugs is expensive to administer and can result in denial of treatment for patients that are not able to present themselves for dosing. For example, patients suffering from acute pain may be denied treatment with an opioid unless they have been admitted to a hospital. Furthermore, control of use is often ineffective, leading to substantial morbidity and deleterious social consequences.

SUMMARY

The present disclosure provides pharmaceutical compositions, and their methods of use, where the pharmaceutical compositions comprise an opioid prodrug that provides enzymatically-controlled release of an opioid, and an enzyme inhibitor that interacts with the enzyme(s) that mediates the enzymatically-controlled release of the opioid from the prodrug so as to attenuate enzymatic cleavage of the prodrug.

According to one aspect, the embodiments include pharmaceutical compositions which comprise a gastrointestinal (GI) enzyme-cleavable opioid prodrug and a GI enzyme inhibitor. A "GI enzyme-cleavable opioid prodrug" is an opioid prodrug that comprises a promoiety comprising a GI enzyme-cleavable moiety. A GI enzyme-cleavable moiety has a site that is susceptible to cleavage by a GI enzyme.

The embodiments include compositions comprising a prodrug, wherein the prodrug comprises a drug covalently bound to a promoiety comprising a GI enzyme-cleavable moiety, wherein cleavage of the GI enzyme-cleavable moiety by the GI enzyme mediates release of the drug; and a GI enzyme inhibitor that interacts with the GI enzyme that mediates enzymatically-controlled release of the drug from the prodrug following ingestion of the composition. Such cleavage can initiate, contribute to or effect drug release.

The embodiments include dose units comprising compositions comprising a prodrug and a GI enzyme inhibitor, where the prodrug and GI enzyme inhibitor are present in the dose unit in an amount effective to provide for a pre-selected pharmacokinetic (PK) profile following ingestion. In further embodiments, the pre-selected PK profile comprises at least one PK parameter value that is less than the PK parameter value of drug released following ingestion of an equivalent dosage of prodrug in the absence of inhibitor. In further embodiments, the PK parameter value is selected from a drug Cmax value, a drug exposure value, and a (1/phenolic opioid Tmax) value.

In certain embodiments, the dose unit provides for a pre-selected PK profile following ingestion of at least two dose units. In related embodiments, the pre-selected PK profile of such dose units is modified relative to the PK profile following ingestion of an equivalent dosage of phenol-modified opioid prodrug without inhibitor. In related embodiments, such a dose unit provides that ingestion of an increasing number of the dose units provides for a linear PK profile.

In related embodiments, such a dose unit provides that ingestion of an increasing number of the dose units provides for a nonlinear PK profile. In related embodiments, the PK parameter value of the PK profile of such a dose units is selected from a drug Cmax value, a (1/drug Tmax) value, and a drug exposure value.

The embodiments include compositions comprising a container suitable for containing a composition for administration to a patient; and a dose unit as described herein disposed within the container.

The embodiments include dose units of a prodrug and a GI enzyme inhibitor wherein the dose unit has a total weight of from 1 microgram to 2 grams. The embodiments include pharmaceutical compositions of a prodrug and a GI enzyme inhibitor wherein the combined weight of prodrug and GI enzyme inhibitor is from 0.1% to 99% per gram of the composition.

The embodiments include compositions and dose units wherein prodrug is a compound of formula:

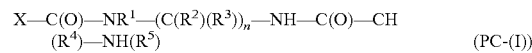

(PC-(I))

or a pharmaceutically acceptable salt thereof, wherein:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

R$^1$ represents a (1-4C)alkyl group;

R$^2$ and R$^3$ each independently represents a hydrogen atom or a (1-4C)alkyl group;

n represents 2 or 3;

R$^4$ represents —CH$_2$CH$_2$CH$_2$NH(C=NH)NH$_2$ or —CH$_2$CH$_2$CH$_2$CH$_2$NH$_2$, the configuration of the carbon atom to which R$^4$ is attached corresponding with that in an L-amino acid; and R$^5$ represents a hydrogen atom, an N-acyl group, or a residue of an amino acid, a dipeptide, or an N-acyl derivative of an amino acid or dipeptide.

The embodiments include compositions and dose units wherein the prodrug is a compound of formula PC-(IIa):

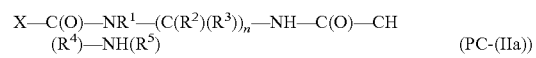

(PC-(IIa))

or a pharmaceutically acceptable salt thereof, wherein:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

R$^1$ is selected from alkyl, substituted alkyl, arylalkyl, substituted arylalkyl, aryl and substituted aryl;

each R$^2$ is independently selected from hydrogen, alkyl, substituted alkyl, aryl, substituted aryl, acyl, and aminoacyl;

each R$^3$ is independently selected from hydrogen, alkyl, substituted alkyl, aryl, substituted aryl, acyl, and aminoacyl;

or R$^2$ and R$^3$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n represents an integer from 2 to 4;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments include compositions and dose units wherein the prodrug is a compound of formula PC-(IIb):

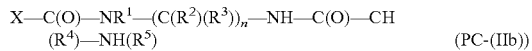

(PC-(IIb))

or a pharmaceutically acceptable salt thereof, wherein:

X represents a residue of a phenolic opioid, wherein the hydrogen atom of the phenolic hydroxyl group is replaced by a covalent bond to —C(O)—NR¹—(C(R²)(R³))ₙ—NH—C(O)—CH(R⁴)—NH(R⁵);

R¹ is selected from alkyl, substituted alkyl, arylalkyl, substituted arylalkyl, aryl and substituted aryl;

each R² is independently selected from hydrogen, alkyl, substituted alkyl, aryl, substituted aryl, acyl, and aminoacyl;

each R³ is independently selected from hydrogen, alkyl, substituted alkyl, aryl, substituted aryl, acyl, and aminoacyl;

or R² and R³ together with the carbon to which they are attached form a cycloalkyl or substituted cycloalkyl group, or two R² or R³ groups on adjacent carbon atoms, together with the carbon atoms to which they are attached, form a cycloalkyl or substituted cycloalkyl group;

n represents an integer from 2 to 4;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments include compositions and dose units wherein the prodrug is a compound of formula PC-(III):

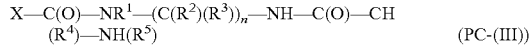

(PC-(III))

or pharmaceutically acceptable salt thereof, wherein:

X represents a residue of a phenolic opioid, wherein the hydrogen atom of the phenolic hydroxyl group is replaced by a covalent bond to —C(O)—NR¹—(C(R²)(R³))ₙ—NH—C(O)—CH(R⁴)—NH(R⁵);

R¹ represents a (1-4C)alkyl group;

R² and R³ each independently represents a hydrogen atom or a (1-4C)alkyl group;

n represents 2 or 3;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments include compositions and dose units wherein the prodrug is a compound of formula PC-(IV):

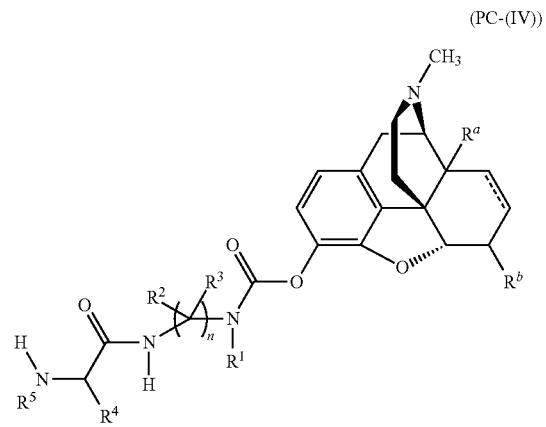

(PC-(IV))

or pharmaceutically acceptable salt thereof, wherein:

Rᵃ is hydrogen or hydroxyl;

Rᵇ is oxo (=O) or hydroxyl;

the dashed line is a double bond or single bond;

R¹ represents a (1-4C)alkyl group;

R² and R³ each independently represents a hydrogen atom or a (1-4C)alkyl group;

n represents 2 or 3;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group, or a residue of an amino acid, a dipeptide, or an N-acyl derivative of an amino acid or dipeptide.

The embodiments include compositions and dose units wherein the prodrug is a compound of formula PC-(Va):

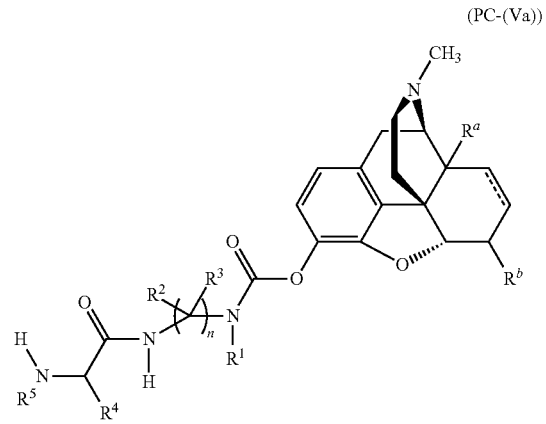

(PC-(Va))

or pharmaceutically acceptable salt thereof, wherein:

Rᵃ is hydrogen or hydroxyl;

Rᵇ is oxo (=O) or hydroxyl;

the dashed line is a double bond or single bond;

R¹ is selected from alkyl, substituted alkyl, arylalkyl, substituted arylalkyl, aryl and substituted aryl;

each R² is independently selected from hydrogen, alkyl, substituted alkyl, aryl, substituted aryl, acyl, and aminoacyl;

each R³ is independently selected from hydrogen, alkyl, substituted alkyl, aryl, substituted aryl, acyl, and aminoacyl;

or R² and R³ together with the carbon to which they are attached form a cycloalkyl, substituted cycloalkyl, aryl, or substituted aryl group, or two R² or R³ groups on adjacent carbon atoms, together with the carbon atoms to which they are attached, form a cycloalkyl, substituted cycloalkyl, aryl, or substituted aryl group;

n represents an integer from 2 to 4;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments include compositions and dose units wherein the prodrug is a compound of formula PC-(Vb):

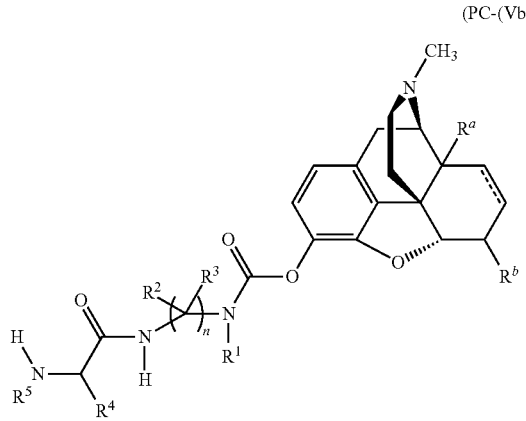

(PC-(Vb))

or pharmaceutically acceptable salt thereof, wherein:

Rᵃ is hydrogen or hydroxyl;

Rᵇ is oxo (=O) or hydroxyl;

the dashed line is a double bond or single bond;

R¹ is selected from alkyl, substituted alkyl, arylalkyl, substituted arylalkyl, aryl and substituted aryl;

each R² is independently selected from hydrogen, alkyl, substituted alkyl, aryl, substituted aryl, acyl, and aminoacyl;

each R³ is independently selected from hydrogen, alkyl, substituted alkyl, aryl, substituted aryl, acyl, and aminoacyl;

or R² and R³ together with the carbon to which they are attached form a cycloalkyl or substituted cycloalkyl group, or two R² or R³ groups on adjacent carbon atoms, together with the carbon atoms to which they are attached, form a cycloalkyl or substituted cycloalkyl group;

n represents an integer from 2 to 4;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments include compositions and dose units wherein the prodrug is a compound of formula PC-(VI):

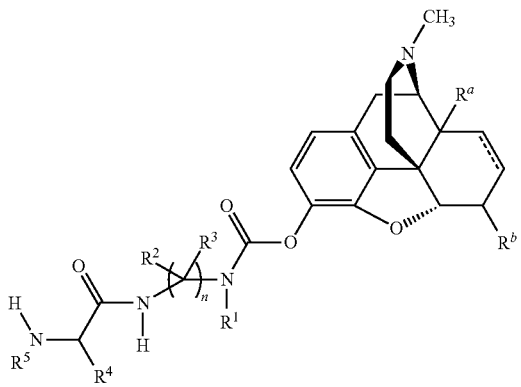

(PC-(VI))

or pharmaceutically acceptable salt thereof, wherein:

Rᵃ is hydrogen or hydroxyl;

Rᵇ is oxo (=O) or hydroxyl;

the dashed line is a double bond or single bond;

R¹ represents a (1-4C)alkyl group;

R² and R³ each independently represents a hydrogen atom or a (1-4C)alkyl group;

n represents 2 or 3;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments include compositions and dose units wherein the prodrug is a compound of formula PC-(VII):

$$X-C(O)-NR^1-(C(R^2)(R^3))_n-NH-R^6 \quad \text{(PC-(VII))}$$

or a pharmaceutically acceptable salt thereof, wherein:

X represents a residue of a phenolic opioid, wherein the hydrogen atom of the phenolic hydroxyl group is replaced by a covalent bond to —C(O)—NR¹—(C(R²)(R³))ₙ—NH—R⁶;

R¹ represents a (1-4C)alkyl group;

R² and R³ each independently represents a hydrogen atom or a (1-4C)alkyl group;

n represents 2 or 3; and

R⁶ is a trypsin-cleavable moiety.

The embodiments include compositions and dose units wherein the prodrug is a compound of formula PC-(VIII):

$$X-C(O)-NR^1-(C(R^2)(R^3))_n-NH-R^6 \quad \text{(PC-(VIII))}$$

or a pharmaceutically acceptable salt thereof, wherein:

X represents a residue of a phenolic opioid, wherein the hydrogen atom of the phenolic hydroxyl group is replaced by a covalent bond to —C(O)—NR¹—(C(R²)(R³))ₙ—NH—R⁶;

R¹ is selected from alkyl, substituted alkyl, arylalkyl, substituted arylalkyl, aryl and substituted aryl;

each R² is independently selected from hydrogen, alkyl, substituted alkyl, aryl, substituted aryl, acyl, and aminoacyl;

each R³ is independently selected from hydrogen, alkyl, substituted alkyl, aryl, substituted aryl, acyl, and aminoacyl;

or R² and R³ together with the carbon to which they are attached form a cycloalkyl, substituted cycloalkyl, aryl, or substituted aryl group, or two R² or R³ groups on adjacent carbon atoms, together with the carbon atoms to which they are attached, form a cycloalkyl, substituted cycloalkyl, aryl, or substituted aryl group;

n represents an integer from 2 to 4; and

R⁶ is a trypsin-cleavable moiety.

The embodiments include compositions and dose units wherein the prodrug is a compound of formula PC-(IX):

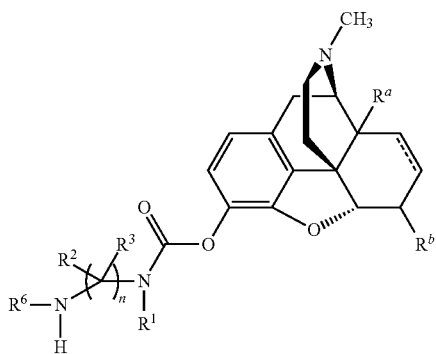

(PC-(IX))

or pharmaceutically acceptable salt thereof, wherein:
$R^a$ is hydrogen or hydroxyl;
$R^b$ is oxo (=O) or hydroxyl;
the dashed line is a double bond or single bond;
$R^1$ represents a (1-4C)alkyl group;
$R^2$ and $R^3$ each independently represents a hydrogen atom or a (1-4C)alkyl group;
n represents 2 or 3; and
$R^6$ is a trypsin-cleavable moiety.

The embodiments include compositions and dose units wherein the prodrug is a compound of formula PC-(X):

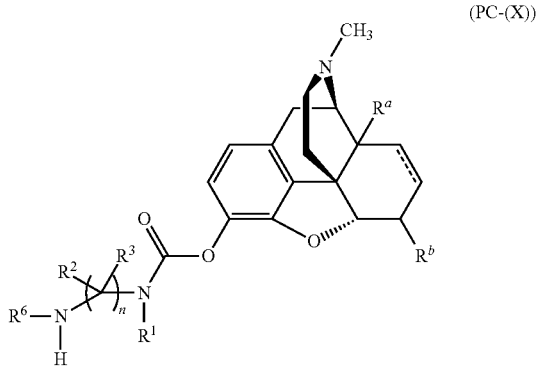

(PC-(X))

or pharmaceutically acceptable salt thereof, wherein:
$R^a$ is hydrogen or hydroxyl;
$R^b$ is oxo (=O) or hydroxyl;
the dashed line is a double bond or single bond;
$R^1$ is selected from alkyl, substituted alkyl, arylalkyl, substituted arylalkyl, aryl and substituted aryl;
each $R^2$ is independently selected from hydrogen, alkyl, substituted alkyl, aryl, substituted aryl, acyl, and aminoacyl;
each $R^3$ is independently selected from hydrogen, alkyl, substituted alkyl, aryl, substituted aryl, acyl, and aminoacyl;
or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
n represents an integer from 2 to 4; and
$R^6$ is a trypsin-cleavable moiety.

The embodiments include compositions and dose units wherein the prodrug is a compound of formula:

$$X\text{—}C(O)\text{—}NR^1\text{—}(C(R^2)(R^3))_n\text{—}NH\text{—}R^6 \quad (PC\text{-}(XI))$$

or a pharmaceutically acceptable salt thereof, in which:
X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);
$R^1$ represents a (1-4C)alkyl group;
$R^2$ and $R^3$ each independently represents a hydrogen atom or a (1-4C)alkyl group;
n represents 2 or 3; and
$R^6$ is a GI enzyme-cleavable moiety.

The embodiments include compositions and dose units wherein the prodrug is a compound of formula:

$$X\text{—}C(O)\text{—}NR^1\text{—}(C(R^2)(R^3))_n\text{—}NH\text{—}R^6 \quad (PC\text{-}(XII))$$

or a pharmaceutically acceptable salt thereof, in which:
X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);
$R^1$ is selected from alkyl, substituted alkyl, arylalkyl, substituted arylalkyl, aryl and substituted aryl;
each $R^2$ is independently selected from hydrogen, alkyl, substituted alkyl, aryl, substituted aryl, acyl, and aminoacyl;
each $R^3$ is independently selected from hydrogen, alkyl, substituted alkyl, aryl, substituted aryl, acyl, and aminoacyl;
or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
n represents an integer from 2 to 4; and
$R^6$ is a GI enzyme-cleavable moiety.

The embodiments include compositions and dose units wherein the prodrug is a compound of formula:

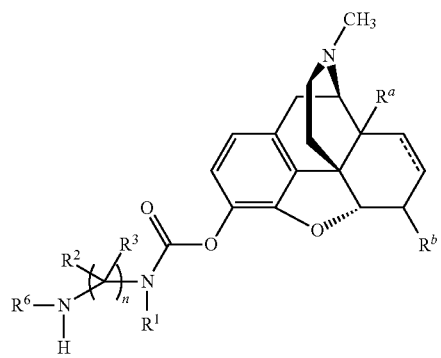

(PC-(XIII))

or pharmaceutically acceptable salt thereof, in which:
$R^a$ is hydrogen or hydroxyl;
$R^b$ is oxo (=O) or hydroxyl;
the dashed line is a double bond or single bond;
$R^1$ represents a (1-4C)alkyl group;
$R^2$ and $R^3$ each independently represents a hydrogen atom or a (1-4C)alkyl group;
n represents 2 or 3; and
$R^6$ is a GI enzyme-cleavable moiety.

The embodiments include compositions and dose units wherein the prodrug is a compound of formula:

(PC-(XIV))

or pharmaceutically acceptable salt thereof, in which:

$R^a$ is hydrogen or hydroxyl;

$R^b$ is oxo (═O) or hydroxyl;

the dashed line is a double bond or single bond;

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n represents an integer from 2 to 4; and $R^6$ is a GI enzyme-cleavable moiety.

The embodiments include compositions and dose units wherein the prodrug is a compound of formula:

(PC-(XV))

wherein:

X is a phenolic opioid, wherein the hydrogen atom of the hydroxyl group is replaced by a covalent bond to —C(O)—Y—(C($R^1$)($R^2$))$_n$—N—($R^3$)($R^6$);

Y is —$NR^5$—, —O— or —S—;

n is an integer from 1 to 4;

each $R^1$, $R^2$, $R^3$ and $R^5$ is independently hydrogen, alkyl, substituted alkyl, aryl or substituted aryl, or $R^1$ and $R^2$ together with the carbon to which they are attached form a cycloalkyl or substituted cycloalkyl group;

$R^6$ is each $R^4$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^4$ and $R^7$ together with the atoms to which they are bonded form a cycloheteroalkyl or substituted cycloheteroalkyl ring;

$R^7$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 10;

each W is independently —$NR^8$—, —O— or —S—; and each $R^8$ is independently hydrogen, alkyl, substituted alkyl, aryl or substituted aryl, or, optionally, each $R^4$ and $R^8$ independently together with the atoms to which they are bonded form a cycloheteroalkyl or substituted cycloheteroalkyl ring.

The embodiments include compositions and dose units wherein the prodrug is a compound of formula:

(PC-(XVI))

or salts, solvates or hydrates thereof wherein:

X is an opioid comprising a phenol wherein a hydrogen atom of the phenol is replaced by a covalent bond to —($CR^{12}R^{13}$)—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Y is aryl, heteroaryl or arylaryl optionally substituted with one or more —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O)_2O^-$, —$OS(O)_2R^{14}$, —$P(O)(O^-)_2$, —$P(O)(OR^{14})$($O^-$), —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ or —$C(NR^{16})NR^{15}R^{14}$;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{14}$ and $R^{15}$ together with the nitrogen atom to which they are bonded form a cycloheteroalkyl or substituted cycloheteroalkyl ring;

Z is N($R^{18}$)—, —O— or —S—;

$R^{18}$ is hydrogen, alkyl, substituted alkyl, aryl, substituted aryl, arylalkyl, substituted arylalkyl, heteroaryl, substituted heteroaryl, heteroarylalkyl or substituted heteroarylalkyl or

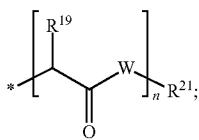

each W is independently —NR$^{20}$—, —O— or —S—;

each R$^{19}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, R$^{19}$ and R$^{20}$ together with the atoms to which they are bonded form a cycloheteroalkyl or substituted cycloheteroalkyl ring;

each R$^{20}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, R$^{20}$ and R$^{21}$ together with the atoms to which they are bonded form a cycloheteroalkyl or substituted cycloheteroalkyl ring;

R$^{21}$ is hydrogen, alkyl, substituted alkyl, aryl, substituted aryl, arylalkyl or substituted arylalkyl;

n is an integer from 0 to 5;

R$^{11}$ is

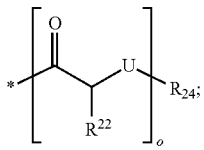

each U is independently —NR$^{23}$—, —O— or —S—;

each R$^{22}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, R$^{22}$ and R$^{23}$ together with the atoms to which they are bonded form a cycloheteroalkyl or substituted cycloheteroalkyl ring;

each R$^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, R$^{23}$ and R$^{24}$ together with the atoms to which they are bonded form a cycloheteroalkyl or substituted cycloheteroalkyl ring;

R$^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100;

provided that Z is oriented para or ortho to X—(CR$^{12}$R$^{13}$)— and that both R$^{18}$ and R$^{11}$ are not hydrogen.

The embodiments include compositions and dose units wherein the prodrug is a compound of formula:

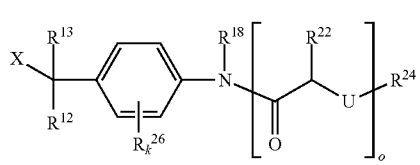
(PC-(XVII))

or salts, solvates or hydrates thereof wherein:

X is an opioid comprising a phenol, wherein X is connected by the phenol;

R$^{12}$ and R$^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

R$_k^{26}$ are each independently selected from the group consisting of one or more of —F, —Cl, —Br, —I, —R$^{14}$, —O$^-$, —OR$^{14}$, —SR$^{14}$, —S$^-$, —NR$^{14}$R$^{15}$, —CF$_3$, —CN, —OCN, —SCN, —NO, —NO$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{15}$R$^{14}$ and —C(NR$^{16}$)NR$^{15}$R$^{14}$, and k is 0, 1, 2, 3, or 4;

R$^{14}$, R$^{15}$, R$^{16}$ and R$^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally R$^4$ and R$^5$ together with the nitrogen atom to which they are bonded form a cycloheteroalkyl or substituted cycloheteroalkyl ring;

R$^{18}$ is hydrogen or methyl;

R$^{22}$ is a side chain of an amino acid or a derivative of a side chain of an amino acid;

each U is independently —NR$^{23}$—, —O— or —S—;

each R$^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, R$^{23}$ and R$^{24}$ together with the atoms to which they are bonded form a cycloheteroalkyl or substituted cycloheteroalkyl ring; and R$^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100.

The embodiments include compositions and dose units wherein the prodrug is a compound of formula:

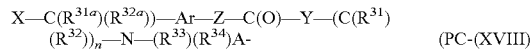
(PC-(XVIII))

or a salt, hydrate or solvate thereof wherein:

X is an opioid comprising a phenol wherein a hydrogen atom of the phenol is replaced by a covalent bond to —(C(R$^{31a}$)(R$^{32a}$)— Ar—Z—C(O)—Y—(C(R$^{31}$)(R$^{32}$))$_n$—N—(R$^{33}$)(R$^{34}$);

R$^{31a}$ and R$^{32a}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Ar is aryl, heteroaryl or arylaryl optionally substituted with one or more —F, —Cl, —Br, —I, —R$^{34a}$, —O$^-$, —OR$^{34a}$, —SR$^{34a}$, —S—, —NR$^{34a}$R$^{35a}$, —CF$_3$, —CN, —OCN, —SCN, —NO, —NO$_2$, —N$_3$, —S(O)$_2$O', —S(O)$_2$OH, —S(O)$_2$R$^{34a}$, —OS(O$_2$)O", —OS(O)$_2$R$^{34a}$, —P(0)(0")$_2$, —P(O)(OR$^{34a}$)(O"), —OP(O)(OR$^{34a}$)(OR$^{35a}$), —C(0)R$^{34a}$, —C(S)R$^{34a}$, —C(O)OR$^{34a}$, —C(O)NR$^{34a}$R$^{35a}$, —C(O)O; —C(S)OR$^{34a}$, —NR$^{36a}$C(O)NR$^{34a}$R$^{35a}$, —NR$^{36a}$C(S)NR$^{34a}$R$^{35a}$, —NR$^{37a}$C(NR$^{36a}$)NR$^{35a}$R$^{34a}$ or —C(NR$^{36a}$)NR$^{35a}$R$^{34a}$, or tethered to a polymer;

R$^{34a}$, R$^{35a}$, R$^{36a}$ and R$^{37a}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{34}$ and $R^{35}$ together with the nitrogen atom to which they are bonded form a cycloheteroalkyl or substituted cycloheteroalkyl ring;

Z is O, S or NH;

Y is —$NR^{35}$—, —O— or —S—;

n is an integer from 1 to 10;

each $R^{31}$, $R^{32}$, $R^{33}$ and $R^{35}$ is independently hydrogen, alkyl, substituted alkyl, aryl or substituted aryl, or $R^{31}$ and $R^{32}$ together with the carbon to which they are attached form a cycloalkyl or substituted cycloalkyl group, or two $R^{31}$ or $R^{32}$ groups on adjacent carbon atoms, together with the carbon atoms to which they are attached, form a cycloalkyl or substituted cycloalkyl group;

$R^{34}$ is

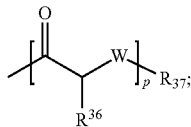

each $R^{36}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{36}$ and $R^{37}$ together with the atoms to which they are bonded form a cycloheteroalkyl or substituted cycloheteroalkyl ring;

$R^{37}$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 5;

each W is independently —$NR^{38}$—, —O— or —S—;

each $R^{38}$ is independently hydrogen, alkyl, substituted alkyl, aryl or substituted aryl, or optionally, each $R^{36}$ and $R^{38}$ independently together with the atoms to which they are bonded form a cycloheteroalkyl or substituted cycloheteroalkyl ring; and A' represents an anion.

The embodiments include compositions and dose units wherein the prodrug is a compound of formula KC-(Ia):

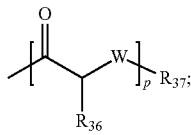

wherein:

$R^a$ is hydrogen or hydroxyl;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen;

$R^4$ is

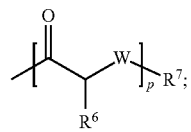

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the prodrug is a compound of formula KC-(Ib):

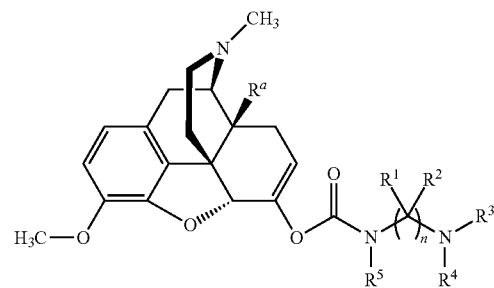

(KC-(Ib))

wherein:

$R^a$ is hydrogen or hydroxyl;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is an integer from 2 to 4;

$R^3$ is hydrogen;

$R^4$ is

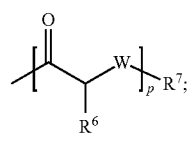

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the prodrug is a compound of formula KC-(II):

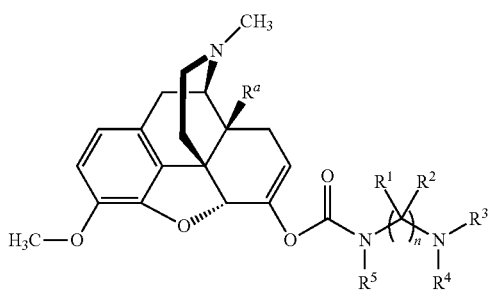

(KC-(II))

wherein:

$R^a$ is hydrogen or hydroxyl;

$R^5$ is selected from (1-6C)alkyl, (1-6C) substituted alkyl, —$(CH_2)_q(C_6H_4)$—COOH, —$(CH_2)_q(C_6H_4)$—$COOCH_3$, and —$(CH_2)_q(C_6H_4)$—$COOCH_2CH_3$, where q is an integer from one to 10;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is 2 or 3;

$R^3$ is hydrogen;

$R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof.

The embodiments include compositions and dose units wherein the prodrug is a compound of formula KC-(IIIa):

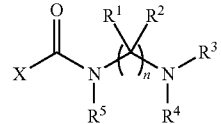

(KC-(IIIa))

wherein:

X represents a residue of a ketone-containing opioid, wherein the hydrogen atom of the corresponding enolic group of the ketone is replaced by a covalent bond to —C(O)—$NR^5$—$(C(R^1)(R^2))_n$—$NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen;

$R^4$ is

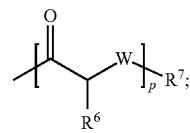

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the prodrug is a compound of formula KC-(IIIb):

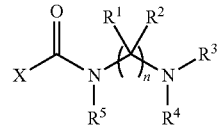

(KC-(IIIb))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl or substituted cycloalkyl group, or two R$^1$ or R$^2$ groups on adjacent carbon atoms, together with the carbon atoms to which they are attached, form a cycloalkyl or substituted cycloalkyl group;

n is an integer from 2 to 4;
R$^3$ is hydrogen;
R$^4$ is

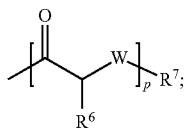

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the prodrug is a compound of formula KC-(IV):

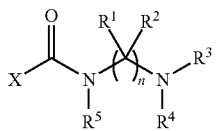

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from (1-6C)alkyl, (1-6C) substituted alkyl, —(CH$_2$)$_q$(C$_6$H$_4$)—COOH, —(CH$_2$)$_q$(C$_6$H$_4$)—COOCH$_3$, and —(CH$_2$)$_q$(C$_6$H$_4$)—COOCH$_2$CH$_3$, where q is an integer from one to 10;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl or substituted cycloalkyl group, or two R$^1$ or R$^2$ groups on adjacent carbon atoms, together with the carbon atoms to which they are attached, form a cycloalkyl or substituted cycloalkyl group;

n is 2 or 3;
R$^3$ is hydrogen;

R$^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof;

or a salt, hydrate or solvate thereof.

The embodiments include compositions and dose units wherein the prodrug is a compound of formula KC-(Va):

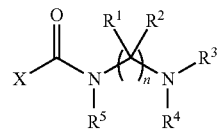

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^1$ or R$^2$ groups on adjacent carbon atoms, together with the carbon atoms to which they are attached, form a cycloalkyl, substituted cycloalkyl, aryl, or substituted aryl group;

n is an integer from 2 to 4;
R$^3$ is hydrogen;
R$^4$ is a trypsin-cleavable moiety;
or a salt, hydrate or solvate thereof.

The embodiments include compositions and dose units wherein the prodrug is a compound of formula KC-(Vb):

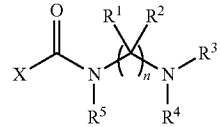

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^1$ or R$^2$ groups on adjacent carbon atoms, together with the carbon atoms to which they are attached, form a cycloalkyl, substituted cycloalkyl, aryl, or substituted aryl group;

n is an integer from 2 to 4;

R$^3$ is hydrogen;

R$^4$ is a GI enzyme-cleavable moiety;

or a salt, hydrate or solvate thereof.

The embodiments include compositions and dose units wherein the prodrug is a compound of formula:

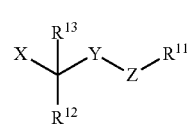

(KC-(VI))

wherein:

X represents a residue of a ketone-containing opioid, wherein the hydrogen atom of the corresponding enolic group of the ketone is replaced by a covalent bond to —C(O)—Y—(C(R$^1$)(R$^2$))$_n$—NR$^3$R$^4$;

Y is —NR$^5$—, —O— or —S—;

n is an integer from 1 to 4;

each R$^1$, R$^2$, R$^3$ and R$^5$ is independently hydrogen, alkyl, substituted alkyl, aryl or substituted aryl, or R$^1$ and R$^2$ together with the carbon to which they are attached form a cycloalkyl or substituted cycloalkyl group;

R$^4$ is

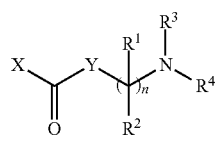

each R$^6$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, R$^6$ and R$^7$ together with the atoms to which they are bonded form a cycloheteroalkyl or substituted cycloheteroalkyl ring;

R$^7$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 10;

each W is independently —NR$^8$—, —O— or —S—; and each R$^8$ is independently hydrogen, alkyl, substituted alkyl, aryl or substituted aryl, or optionally, each R$^6$ and R$^8$ independently together with the atoms to which they are bonded form a cycloheteroalkyl or substituted cycloheteroalkyl ring.

The embodiments include compositions and dose units wherein the prodrug is a compound of formula:

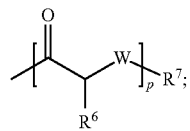

(KC-(VII))

or salts, solvates or hydrates thereof wherein:

X represents a residue of a ketone-containing opioid, wherein the hydrogen atom of the corresponding enolic group of the ketone is replaced by a covalent bond —(CR$^{12}$R$^{13}$)—Y—Z—R$^{11}$;

R$^{12}$ and R$^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Y is aryl, heteroaryl or arylaryl optionally substituted with one or more —F, —Cl, —Br, —I, —R$^{14}$, —O$^-$, —OR$^{14}$, —SR$^{14}$, —S$^-$, —NR$^{14}$R$^{15}$, —CF$_3$, —CN, —OCN, —SCN, —NO, —NO$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{15}$R$^{14}$ or —C(NR$^{16}$)NR$^{15}$R$^{14}$;

R$^{14}$, R$^{15}$, R$^{16}$ and R$^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally R$^{14}$ and R$^{15}$ together with the nitrogen atom to which they are bonded form a cycloheteroalkyl or substituted cycloheteroalkyl ring;

Z is N(R$^{18}$)—, —O— or —S—;

R$^{18}$ is hydrogen, alkyl, substituted alkyl, aryl, substituted aryl, arylalkyl, substituted arylalkyl, heteroaryl, substituted heteroaryl, heteroarylalkyl or substituted heteroarylalkyl or

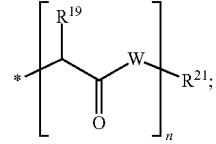

each W is independently —NR$^{20}$—, —O— or —S—;

each R$^{19}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, R$^{19}$ and R$^{20}$ together with the atoms to which they are bonded form a cycloheteroalkyl or substituted cycloheteroalkyl ring;

each R$^{20}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, R$^{20}$ and R$^{21}$ together with the atoms to which they are bonded form a cycloheteroalkyl or substituted cycloheteroalkyl ring;

$R^{21}$ is hydrogen, alkyl, substituted alkyl, aryl, substituted aryl, arylalkyl or substituted arylalkyl;

n is an integer from 0 to 5;

$R^{11}$ is

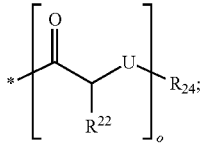

each U is independently —$NR^{23}$—, —O— or —S—;

each $R^{22}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{22}$ and $R^{23}$ together with the atoms to which they are bonded form a cycloheteroalkyl or substituted cycloheteroalkyl ring;

each $R^{23}$ is independently hydrogen, alkyl, substituted alkyl, aryl, substituted aryl, or optionally, $R^{23}$ and $R^{24}$ together with the atoms to which they are bonded form a cycloheteroalkyl or substituted cycloheteroalkyl ring;

$R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100;

provided that Z is oriented para or ortho to X—$(CR^{12}R^{13})$— and that both $R^{18}$ and $R^{11}$ are not hydrogen.

The embodiments include compositions and dose units wherein the prodrug is a compound of formula:

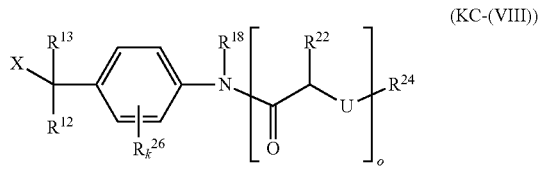

(KC-(VIII))

or salts, solvates or hydrates thereof wherein:

X represents a residue of a ketone-containing opioid, wherein the hydrogen atom of the corresponding enolic group of the ketone is replaced by a covalent bond to —$(CR^{12}R^{13})$—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

$R_k^{26}$ are each independently selected from the group consisting of one or more of —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ and —$C(NR^{16})NR^{15}R^{14}$, and k is 0, 1, 2, 3, or 4;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^4$ and $R^5$ together with the nitrogen atom to which they are bonded form a cycloheteroalkyl or substituted cycloheteroalkyl ring;

$R^{18}$ is hydrogen or methyl;

$R^{22}$ is a side chain of an amino acid or a derivative of a side chain of an amino acid;

each U is independently —$NR^{23}$—, —O— or —S—;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{23}$ and $R^{24}$ together with the atoms to which they are bonded form a cycloheteroalkyl or substituted cycloheteroalkyl ring; and $R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100.

The embodiments include compositions and dose units wherein the prodrug is a compound of formula:

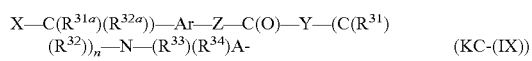

(KC-(IX))

or a salt, hydrate or solvate thereof wherein:

X represents a residue of a ketone-containing opioid, wherein the hydrogen atom of the corresponding enolic group of the ketone is replaced by a covalent bond to —$(C(R^{31a})(R^{32a})$—Ar—Z—C(O)—Y—$(C(R^{31})(R^{32}))_n$—N—$(R^{33})(R^{34})$;

$R^{31a}$ and $R^{32a}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Ar is aryl, heteroaryl or arylaryl optionally substituted with one or more —F, —Cl, —Br, —I, —$R^{34a}$, —$O^-$, —$OR^{34a}$, —$SR^{34a}$, —$S^-$, —$NR^{34a}R^{35a}$, —$CF_3$, —CN, —OCN, —SCN, —NO, —$NO_2$, —$N_3$, —$S(O)_2O^-$, —$S(O)_2OH$, —$S(O)_2R^{34a}$, —$OS(O_2)O^-$, —$OS(O)_2R^{34a}$, —$P(O)(O^-)_2$, —$P(O)(OR^{34a})(O^-)$, —$OP(O)(OR^{34a})(OR^{35a})$, —$C(O)R^{34a}$, —$C(S)R^{34a}$, —$C(O)OR^{34a}$, —$C(O)NR^{34a}R^{35a}$, —$C(O)O^-$; —$C(S)OR^{34a}$, —$NR^{36a}C(O)NR^{34a}R^{35a}$, —$NR^{36a}C(S)NR^{34a}R^{35a}$, —$NR^{37a}C(NR^{36a})NR^{35a}R^{34a}$ or —$C(NR^{36a})NR^{35a}R^{34a}$, or tethered to a polymer;

$R^{34a}$, $R^{35a}$, $R^{36a}$ and $R^{37a}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{34}$ and $R^{35}$ together with the nitrogen atom to which they are bonded form a cycloheteroalkyl or substituted cycloheteroalkyl ring;

Z is O, S or NH;

Y is —$NR^{35}$—, —O— or —S—;

n is an integer from 1 to 10;

each $R^{31}$, $R^{32}$, $R^{33}$ and $R^{35}$ is independently hydrogen, alkyl, substituted alkyl, aryl or substituted aryl, or $R^{31}$ and $R^{32}$ together with the carbon to which they are attached form a cycloalkyl or substituted cycloalkyl group, or two $R^{31}$ or $R^{32}$ groups on adjacent carbon atoms, together with the carbon atoms to which they are attached, form a cycloalkyl or substituted cycloalkyl group;

$R^{34}$ is

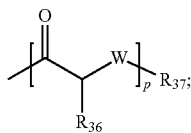

each $R^{36}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{36}$ and $R^{37}$ together with the atoms to which they are bonded form a cycloheteroalkyl or substituted cycloheteroalkyl ring;

$R^{37}$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 5;

each W is independently —$NR^{38}$—, —O— or —S—;

each $R^{38}$ is independently hydrogen, alkyl, substituted alkyl, aryl or substituted aryl, or optionally, each $R^{36}$ and $R^{38}$ independently together with the atoms to which they are bonded form a cycloheteroalkyl or substituted cycloheteroalkyl ring; and A' represents an anion.

The embodiments include compositions and dose units wherein the prodrug is a compound of formula:

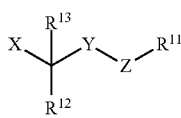

(QS-(I))

or salts, solvates or hydrates thereof wherein:

X is an opioid comprising an amine, wherein a hydrogen atom of the primary or secondary amine is replaced by a covalent bond to —$(CR^{12}R^{13})$—Y—Z—$R^{11}$ or a lone pair of electrons of a tertiary amine is replaced by a covalent bond to —$(CR^{12}R^{13})$—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Y is aryl, heteroaryl or arylaryl optionally substituted with one or more —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ or —$C(NR^{16})NR^{15}R^{14}$;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{14}$ and $R^{15}$ together with the nitrogen atom to which they are bonded form a cycloheteroalkyl or substituted cycloheteroalkyl ring;

Z is $N(R^{18})$—, —O— or —S—;

$R^{18}$ is hydrogen, alkyl, substituted alkyl, aryl, substituted aryl, arylalkyl, substituted arylalkyl, heteroaryl, substituted heteroaryl, heteroarylalkyl or substituted heteroarylalkyl or

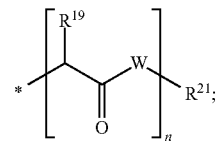

each W is independently —$NR^{20}$—, —O— or —S—;

each $R^{19}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{19}$ and $R^{20}$ together with the atoms to which they are bonded form a cycloheteroalkyl or substituted cycloheteroalkyl ring;

each $R^{20}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{20}$ and $R^{21}$ together with the atoms to which they are bonded form a cycloheteroalkyl or substituted cycloheteroalkyl ring;

$R^{21}$ is hydrogen, alkyl, substituted alkyl, aryl, substituted aryl, arylalkyl or substituted arylalkyl;

n is an integer from 0 to 5;

$R^{11}$ is

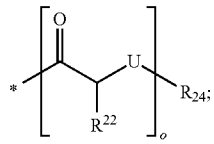

each U is independently —$NR^{23}$—, —O— or —S—;

each $R^{22}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{22}$ and $R^{23}$ together with the atoms to which they are bonded form a cycloheteroalkyl or substituted cycloheteroalkyl ring;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{23}$ and $R^{24}$ together with the atoms to which they are bonded form a cycloheteroalkyl or substituted cycloheteroalkyl ring;

$R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100;

provided that Z is oriented para or ortho to X—$(CR^{12}R^{13})$— and that both $R^{18}$ and $R^{11}$ are not hydrogen.

The embodiments include compositions and dose units wherein the prodrug is a compound of formula:

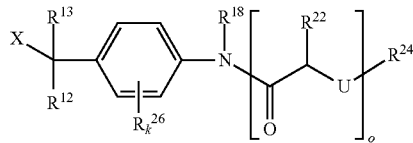 (QS-(II))

or salts, solvates or hydrates thereof wherein:

X is an opioid comprising an amine, wherein a hydrogen atom of the primary or secondary amine is replaced by a covalent bond to —$(CR^{12}R^{13})$—Y—Z—$R^{11}$ or a lone pair of electrons of a tertiary amine is replaced by a covalent bond to —$(CR^{12}R^{13})$—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

$R_k^{26}$ are each independently selected from the group consisting of one or more of —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ and —$C(NR^{16})NR^{15}R^{14}$, and k is 0, 1, 2, 3, or 4;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^4$ and $R^5$ together with the nitrogen atom to which they are bonded form a cycloheteroalkyl or substituted cycloheteroalkyl ring;

$R^{18}$ is hydrogen or methyl;

$R^{22}$ is a side chain of an amino acid or a derivative of a side chain of an amino acid;

each U is independently —$NR^{23}$—, —O— or —S—;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{23}$ and $R^{24}$ together with the atoms to which they are bonded form a cycloheteroalkyl or substituted cycloheteroalkyl ring; and $R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100.

The embodiments include compositions and dose units wherein the prodrug is a compound of formula:

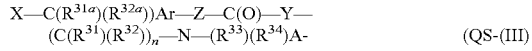 (QS-(III))

or a salt, hydrate or solvate thereof wherein:

X is a residue of an opioid wherein the lone pair of electrons of the amino nitrogen is replaced with a bond to —$(C(R^{31a})(R^{32a}))Ar$—Z—C(O)—Y—$(C(R^{31})(R^{32}))_n$—N—$(R^{33})(R^{34})$;

$R^{31a}$ and $R^{32a}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Ar is aryl, heteroaryl or arylaryl optionally substituted with one or more —F, —Cl, —Br, —I, —$R^{34a}$, —$O^-$, —$OR^{34a}$, —$SR^{34a}$, —$S^-$, —$NR^{34a}R^{35a}$, —$CF_3$, —CN, —OCN, —SCN, —NO, —$NO_2$, —$N_3$, —$S(O)_2O'$, —$S(O)_2OH$, —$S(O)_2R^{34a}$, —$OS(O_2)O''$, —$OS(O)_2R^{34a}$, —$P(O)(O'')_2$, —$P(O)(OR^{34a})(O'')$, —$OP(O)(OR^{34a})(OR^{35a})$, —$C(O)R^{34a}$, —$C(S)R^{34a}$, —$C(O)OR^{34a}$, —$C(O)NR^{34a}R^{35a}$, —$C(O)O$; —$C(S)OR^{34a}$, —$NR^{36a}C(O)NR^{34a}R^{35a}$, —$NR^{36a}C(S)NR^{34a}R^{35a}$, —$NR^{37a}C(NR^{36a})NR^{35a}R^{34a}$ or —$C(NR^{36a})NR^{35a}R^{34a}$, or tethered to a polymer;

$R^{34a}$, $R^{35a}$, $R^{36a}$ and $R^{37a}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{34}$ and $R^{35}$ together with the nitrogen atom to which they are bonded form a cycloheteroalkyl or substituted cycloheteroalkyl ring;

Z is O, S or NH;

Y is —$NR^{35}$—, —O— or —S—;

n is an integer from 1 to 10;

each $R^{31}$, $R^{32}$, $R^{33}$ and $R^{35}$ is independently hydrogen, alkyl, substituted alkyl, aryl or substituted aryl, or $R^{31}$ and $R^{32}$ together with the carbon to which they are attached form a cycloalkyl or substituted cycloalkyl group, or two $R^{31}$ or $R^{32}$ groups on adjacent carbon atoms, together with the carbon atoms to which they are attached, form a cycloalkyl or substituted cycloalkyl group;

$R^{34}$ is

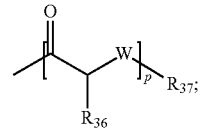

each $R^{36}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{36}$ and $R^{37}$ together with the atoms to which they are bonded form a cycloheteroalkyl or substituted cycloheteroalkyl ring;

$R^{37}$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 5;

each W is independently —$NR^{38}$—, —O— or —S—;

each $R^{38}$ is independently hydrogen, alkyl, substituted alkyl, aryl or substituted aryl, or optionally, each $R^{36}$ and $R^{38}$ independently together with the atoms to which they are bonded form a cycloheteroalkyl or substituted cycloheteroalkyl ring; and A' represents an anion.

The embodiments include compositions and dose units wherein the prodrug is a compound of formula:

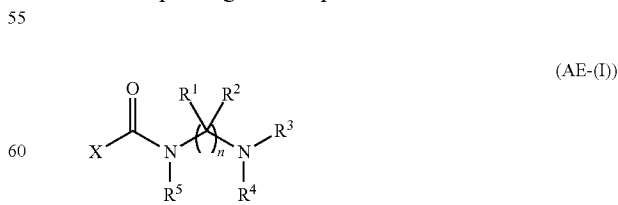 (AE-(I))

wherein:

X represents a residue of an amide-containing opioid, wherein —C(O)—$NR^5$—$(C(R^1)(R^2))_n$—$NR^3R^4$ is connected to the amide-containing opioid through the oxygen of the amide group, wherein the amide group is converted to an amide enol or an imine tautomer;

R⁵ is selected from alkyl, substituted alkyl, arylalkyl, substituted arylalkyl, aryl and substituted aryl;

each R¹ is independently selected from hydrogen, alkyl, substituted alkyl, aryl, substituted aryl, acyl, and aminoacyl;

each R² is independently selected from hydrogen, alkyl, substituted alkyl, aryl, substituted aryl, acyl, and aminoacyl;

or R¹ and R² together with the carbon to which they are attached form a cycloalkyl, substituted cycloalkyl, aryl, or substituted aryl group, or two R¹ or R² groups on adjacent carbon atoms, together with the carbon atoms to which they are attached, form a cycloalkyl, substituted cycloalkyl, aryl, or substituted aryl group;

n is an integer from 2 to 4;

R³ is hydrogen or (1-4C)alkyl;

R⁴ is

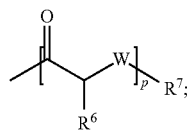

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R⁶ and R⁷ together with the atoms to which they are bonded form a cycloheteroalkyl or substituted cycloheteroalkyl ring;

each W is independently —NR⁸—, —O— or —S—;

each R⁸ is independently selected from hydrogen, alkyl, substituted alkyl, aryl and substituted aryl, or optionally, each R⁶ and R⁸ independently together with the atoms to which they are bonded form a cycloheteroalkyl or substituted cycloheteroalkyl ring;

p is an integer from one to 100; and

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the prodrug is a compound of formula:

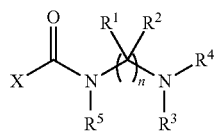

(AE-(II))

wherein:

X represents a residue of an amide-containing opioid, wherein —C(O)—NR⁵—(C(R¹)(R²))ₙ—NR³R⁴ is connected to the amide-containing opioid through the oxygen of the amide group, wherein the amide group is converted to an amide enol or an imine tautomer;

R⁵ is selected from (1-6C)alkyl, (1-6C) substituted alkyl, —(CH₂)_q(C₆H₄)—COOH, —(CH₂)_q(C₆H₄)—COOCH₃, and —(CH₂)_q(C₆H₄)—COOCH₂CH₃, where q is an integer from one to 10;

each R¹ is independently selected from hydrogen, alkyl, substituted alkyl, aryl, substituted aryl, acyl, and aminoacyl;

each R² is independently selected from hydrogen, alkyl, substituted alkyl, aryl, substituted aryl, acyl, and aminoacyl;

or R¹ and R² together with the carbon to which they are attached form a cycloalkyl, substituted cycloalkyl, aryl, or substituted aryl group, or two R¹ or R² groups on adjacent carbon atoms, together with the carbon atoms to which they are attached, form a cycloalkyl, substituted cycloalkyl, aryl, or substituted aryl group;

n is 2 or 3;

R³ is hydrogen;

R⁴ is a GI enzyme-cleavable moiety;

or a salt, hydrate or solvate thereof.

The embodiments include compositions and dose units wherein the prodrug is a compound of formula:

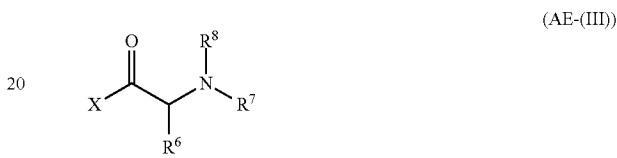

(AE-(III))

wherein:

X represents a residue of an amide-containing opioid, wherein —CO—C(R⁶)—NR⁸R⁷ is connected to the amide-containing opioid through the oxygen of the amide group, wherein the amide group is converted to an amide enol or an imine tautomer;

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R⁶ and R⁷ together with the atoms to which they are bonded form a cycloheteroalkyl or substituted cycloheteroalkyl ring;

each R⁸ is independently selected from hydrogen, alkyl, substituted alkyl, aryl and substituted aryl, or optionally, each R⁶ and R⁸ independently together with the atoms to which they are bonded form a cycloheteroalkyl or substituted cycloheteroalkyl ring;

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include methods for treating a patient comprising administering any of the compositions or dose units described herein to a patient in need thereof. The embodiments include methods to reduce side effects of a therapy comprising administering any of the compositions or dose units described herein to a patient in need thereof. The embodiments include methods of improving patient compliance with a therapy prescribed by a clinician comprising directing administration of any of the compositions or dose units described herein to a patient in need thereof. Such embodiments can provide for improved patient compliance with a prescribed therapy as compared to patient compliance with a prescribed therapy using drug and/or using prodrug without inhibitor as compared to prodrug with inhibitor.

The embodiments include methods of reducing risk of unintended overdose of a drug comprising directing administration of any of the pharmaceutical compositions or dose units described herein to a patient in need of treatment.

The embodiments include methods of making a dose unit comprising combining a prodrug and a GI enzyme inhibitor in a dose unit, wherein the prodrug and GI enzyme inhibitor are present in the dose unit in an amount effective to attenuate release of the drug from the prodrug.

The embodiments include methods of deterring misuse or abuse of multiple dose units of a prodrug comprising combining a prodrug and a GI enzyme inhibitor in a dose unit, wherein the prodrug and GI enzyme inhibitor are present in the dose unit in an amount effective to attenuate release of the drug from the prodrug such that ingestion of multiples of dose units by a patient does not provide a proportional release of the drug. In further embodiments, release of drug is decreased compared to release of drug by an equivalent dosage of prodrug in the absence of inhibitor.

One embodiment is a method for identifying a prodrug and a GI enzyme inhibitor suitable for formulation in a dose unit. Such a method can be conducted as, for example, an in vitro assay, an in vivo assay, or an ex vivo assay.

The embodiments include methods for identifying a prodrug and a GI enzyme inhibitor suitable for formulation in a dose unit comprising combining a prodrug, a GI enzyme inhibitor, and enzyme in a reaction mixture, and detecting prodrug conversion, wherein a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit.

The embodiments include methods for identifying a prodrug and a GI enzyme inhibitor suitable for formulation in a dose unit comprising administering to an animal a prodrug and a GI enzyme inhibitor and detecting prodrug conversion, wherein a decrease in drug conversion in the presence of the GI enzyme inhibitor as compared to drug conversion in the absence of the GI enzyme inhibitor indicates the prodrug and GI enzyme inhibitor are suitable for formulation in a dose unit. In certain embodiments, administering comprises administering to the animal increasing doses of inhibitor co-dosed with a selected fixed dose of prodrug. Detecting prodrug conversion can facilitate identification of a dose of inhibitor and a dose of prodrug that provides for a pre-selected pharmacokinetic (PK) profile. Such methods can be conducted as, for example, an in vivo assay or an ex vivo assay.

The embodiments include methods for identifying a prodrug and a GI enzyme inhibitor suitable for formulation in a dose unit comprising administering to an animal tissue a prodrug and a GI enzyme inhibitor and detecting prodrug conversion, wherein a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit.

BRIEF DESCRIPTION OF THE FIGURES

FIG. 10A depicts the disappearance of Compound PC-4, and FIG. 10B depicts the appearance of hydromorphone, over time under these conditions.

DEFINITIONS

Figure 1:
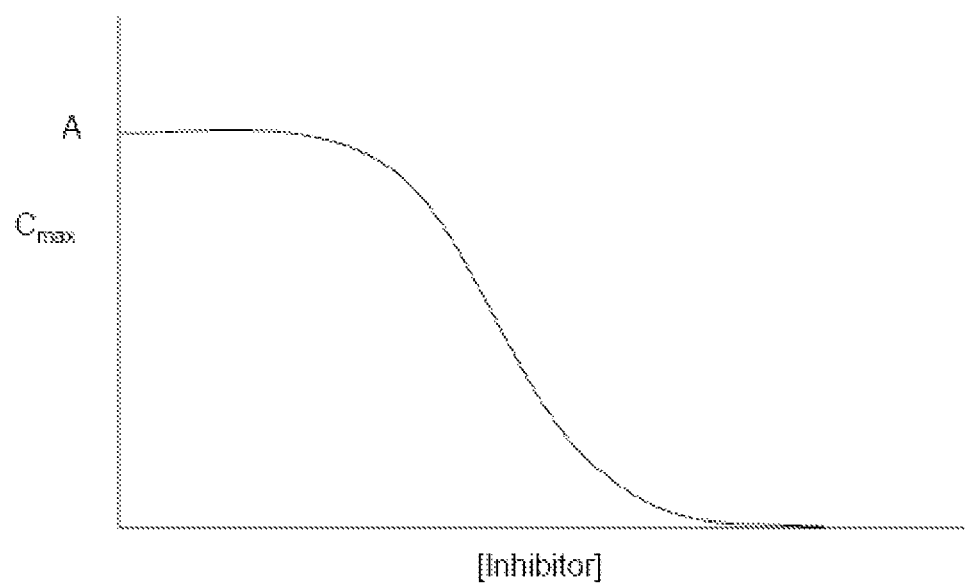
FIG. 1 is a schematic representing the effect of increasing the level of a GI enzyme inhibitor ("inhibitor", X axis) on a PK parameter (e.g., drug Cmax) (Y axis) for a fixed dose of prodrug. The effect of inhibitor upon a prodrug PK parameter can range from undetectable, to moderate, to complete inhibition (i.e., no detectable drug release).

The following terms have the following meaning unless otherwise indicated. Any undefined terms have their art recognized meanings.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —$C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is (C$_7$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$). In certain embodiments, an arylalkyl group is (C$_7$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, (C$_5$-C$_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a (C$_5$-C$_{14}$) aromatic. In certain embodiments, each aromatic ring system of an arylaryl group is independently a (C$_5$-C$_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is (C$_3$-C$_{10}$) cycloalkyl. In certain embodiments, the cycloalkyl group is (C$_3$-C$_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —R$^{60}$, —O$^-$, =O, —OR$^{60}$, —SR$^{60}$, —S$^-$, =S, NR$^{60}$R$^{61}$, NR$^{60}$, CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, NR$^{62}$C(NR$^{63}$)NR$^{60}$R$^{61}$, and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, —NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, OR$^{60}$, —C(O)NR$^{60}$R$^{61}$, C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group.

"Dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"Pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax) and side effects.

"Gastrointestinal enzyme" or "GI enzyme" refers to an enzyme located in the gastrointestinal (GI) tract, which encompasses the anatomical sites from mouth to anus. Trypsin is an example of a GI enzyme.

"Gastrointestinal enzyme-cleavable moiety" or "GI enzyme-cleavable moiety" refers to a group comprising a site susceptible to cleavage by a GI enzyme. For example, a "trypsin-cleavable moiety" refers to a group comprising a site susceptible to cleavage by trypsin.

"Gastrointestinal enzyme inhibitor" or "GI enzyme inhibitor" refers to any agent capable of inhibiting the action of a gastrointestinal enzyme on a substrate. The term also encompasses salts of gastrointestinal enzyme inhibitors. For example, a "trypsin inhibitor" refers to any agent capable of inhibiting the action of trypsin on a substrate.

"Pharmaceutical composition" refers to at least one compound and can further comprise a pharmaceutically acceptable carrier, with which the compound is administered to a patient.

"Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Pharmaceutically acceptable carrier" refers to a diluent, adjuvant, excipient or vehicle with, or in which a compound is administered.

"Preventing" or "prevention" or "prophylaxis" refers to a reduction in risk of occurrence of a condition, such as pain.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Treating" or "treatment" of any condition, such as pain, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound (e.g. prodrug) that, when administered to a patient for preventing or treating a condition such as pain, is sufficient to effect such treatment. The "therapeutically effective amount" will vary depending on the compound, the condition and its severity and the age, weight, etc., of the patient.

DETAILED DESCRIPTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a compound refers to one or more compounds. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-

1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. When possible, this nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

REPRESENTATIVE EMBODIMENTS

Reference will now be made in detail to various embodiments. It will be understood that the invention is not limited to these embodiments. To the contrary, it is intended to cover alternatives, modifications, and equivalents as may be included within the spirit and scope of the allowed claims.

The present disclosure provides pharmaceutical compositions, and their methods of use, where the pharmaceutical compositions comprise an opioid prodrug that provides enzymatically-controlled release of an opioid and an enzyme inhibitor that interacts with the enzyme(s) that mediates the enzymatically-controlled release of the opioid from the prodrug so as to attenuate enzymatic cleavage of the prodrug. The disclosure provides pharmaceutical compositions which comprise an enzyme inhibitor and an opioid prodrug that contains an enzyme-cleavable moiety that, when cleaved, facilitates release of the opioid.

According to one aspect, the embodiments include pharmaceutical compositions, which comprise a GI enzyme-cleavable opioid prodrug and a GI enzyme inhibitor. Examples of opioid prodrugs and enzyme inhibitors are described below.

Opioid Prodrugs

An "opioid" refers to a chemical substance that exerts its pharmacological action by interaction at an opioid receptor. An opioid can be a natural product, a synthetic compound or a semi-synthetic compound. In certain embodiments, an opioid is a compound with a pharmacophore that presents to the opioid receptor an aromatic group and an aliphatic amine group in an architecturally discrete way. See, for example, Foye's Principles of Medicinal Chemistry, Sixth Edition, ed. T. L. Lemke and D. A. Williams, Lippincott Williams & Wilkins, 2008, particularly Chapter 24, pages 653-678.

The disclosure provides an opioid prodrug which provides enzymatically-controlled release of an opioid. The disclosure provides a promoiety that is attached to an opioid through any structural moiety on the opioid, where the structural moiety has a reactive group. Any type of reactive group on an opioid can provide a handle for a point of attachment to a promoiety. Examples of reactive groups on an opioid include, but are not limited to, alcohol (such as phenol), ketone, amino, and amide. An alcohol (such as a phenol) on an opioid can provide a point of attachment to a promoiety by reaction to form a linkage, such as a carbamate, an ether, or an ester. A ketone on an opioid can provide a point of attachment to a promoiety by reaction to form a linkage, such as an enol carbamate. An amino group on an opioid can provide a point of attachment to a promoiety by reaction to form an amino linkage, including quaternary salts, or an amide. An amide on an opioid can provide a point of attachment to a promoiety by reaction to form a linkage, such as an amide enol or an N-acylated amide.

An alcohol-containing (such as a phenol-containing) opioid refers to a subset of the opioids that contain alcohol (such as a phenol) group. A phenolic opioid refers to a subset of the opioids that contain a phenol group. For instance, the following opioids contain an alcohol (such as a phenol group) that can be a point of attachment to a promoiety: buprenorphine, dihydroetorphine, diprenorphine, etorphine, hydromorphone, levorphanol, morphine, nalmefene, naloxone, N-methyldiprenorphine, N-methylnaloxone, naltrexone, N-methylnaltexone, oxymorphone, oripavine, ketobemidone, dezocine, pentazocine, phenazocine, butorphanol, nalbuphine, meptazinol, o-desmethyltramadol, tapentadol, and nalorphine. The following opioids also contain an alcohol (such as a phenol) that can be a point of attachment to a promoiety: benzylmorphine, codeine, dihydrocodeine, dihydromorphine, ethylmorphine, loperamide, methyldihydromorphine, normorphine, N-methylnalmefene, olmefentanyl, oxycodone, pentamorphone, pholcodine, and tramadol.

A ketone-containing opioid refers to a subset of the opioids that contain a ketone group. For instance, the following opioids contain a ketone group that can be a point of attachment to a promoiety: acetylmorphone, hydrocodone, hydromorphone, ketobemidone, methadone, naloxone, N-methylnaloxone, naltrexone, N-methylnaltrexone, oxycodone, oxymorphone, and pentamorphone.

An amino-containing opioid refers to a subset of the opioids that contain an amino group. For instance, the following opioids contain an amino group that can be a point of attachment to a promoiety as a quaternary ammonium salt: acetylmorphine, alfentanil, benzylmorphine, buprenorphine, butorphanol, carfentanil, codeine, dextropropoxyphene, diacetylhidhydromorphine, diacetylmorphine, dihydrocodeine, dihydrocodeinone enol acetate, dihydroetorphine, dihydromorphine, diphenoxylate, diprenorphine, dipropanoylmorphine, ethylmorphine, etorphine, fentanyl, hydrocodone, hydromorphone, ketobemidone, leva-α-acetylmethadol, levorphanol, lofentanil, meperidine, meptazinol, methadone, methyldihydromorphine, morphine, nalbuphine, nalmefene, nalorphine, naloxone, naltrexone, nicocodeine, nicomorphine, normorphine, olmefentanyl, oripavin, oxycodone, oxymorphone, pentamorphone, pentazocine, phenazocine, pholcodine, remifentanil, sufentanil, tapentadol, thebaine, tilidine, tramadol, and o-desmethyltramadol. For instance, the following opioid contains an amino group that can be a point of attachment to a promoiety: dezozine.

An amide-containing opioid refers to a subset of the opioids that contain an amide group. For instance, the following opioids contain an amide group that can be a point of attachment to a promoiety: alfentanil, carfentanil, fentanyl, lofentanil, loperamide, olmefentanyl, remifentanil, and sufentanil.

It is contemplated that opioids bearing at least some of the functionalities described herein will be developed; such opioids are included as part of the scope of this disclosure.

In certain embodiments, a promoiety can be attached to an alcoholic (such as phenolic) opioid via modification of the alcohol (such as phenol) moiety. Release of the opioid is mediated by enzymatic cleavage of the promoiety from the alcoholic (such as phenolic) opioid. In certain embodiments, a promoiety can be attached to a ketone-containing opioid through the enolic oxygen atom of the ketone moiety. Release of the opioid is mediated by enzymatic cleavage of the promoiety from the ketone-containing opioid. In certain embodiments, a promoiety can be attached to an amino-containing opioid through the amino moiety. Release of the opioid is mediated by enzymatic cleavage of the promoiety from the amino-containing opioid. In certain embodiments, a promoiety can be attached to an amide-containing opioid through the enolic oxygen of the amide moiety or the imine tautomer. Release of the opioid is mediated by enzymatic cleavage of the promoiety from the amide-containing opioid. In each case, the promoiety comprises an enzyme-cleavable moiety that is susceptible to cleavage by a GI enzyme. Such cleavage can initiate, contribute to or effect drug release.

Alcohol-Modified Opioid Prodrugs

The disclosure provides an alcohol-modified opioid prodrug which provides enzymatically-controlled release of an alcohol-containing opioid. In an alcohol-modified opioid prodrug, a promoiety is attached to the alcohol-containing opioid via modification of the alcohol moiety. In an alcohol-modified opioid prodrug, the hydrogen atom of the hydroxyl group of the alcohol-containing opioid is replaced by a covalent bond to a promoiety. The promoiety of an alcohol-modified opioid prodrug can be attached to an alcohol-containing opioid through the alcohol moiety, which alcohol moiety can be a phenol or can be an alcohol moiety other than phenol, including primary, secondary, and tertiary alcohol moieties.

Release of the opioid is mediated by enzymatic cleavage of the promoiety from the alcohol-containing opioid. The disclosure provides for release of the opioid through GI enzymatic cleavage (e.g, trypsin cleavage) of the promoiety from the alcohol-containing opioid. Cleavage can initiate, contribute to or effect drug release.

Examples of structures of alcohol-modified opioid prodrugs are shown in Formulae PC-(I) to PC-(XVIII), where X is an alcohol-containing opioid. The connection to the promoiety is via modification of the hydroxyl group of the opioid.

For example, in Formulae PC-(I) to PC-(VI), X represents a residue of an alcohol-containing opioid, wherein the hydrogen atom of the hydroxyl group is replaced by a covalent bond to —C(O)—NR$^1$—(C(R$^2$)(R$^3$))$_n$—NH—C(O)—CH(R$^4$)—NH(R$^5$). For example, in Formulae PC-(VII) to PC-(XIV), X represents a residue of an alcohol-containing opioid, wherein the hydrogen atom of the hydroxyl group is replaced by a covalent bond to —C(O)—NR$^1$—(C(R$^2$)(R$^3$))$_n$—NH—R$^6$. For example, in Formula PC-(XV), X is an alcohol-containing opioid, wherein the hydrogen atom of the hydroxyl group is replaced by a covalent bond to —C(O)—Y—(C(R$^1$)(R$^2$))$_n$—N—(R$^3$)(R$^4$).

For example, in Formula PC-(XVI), X is an opioid comprising a hydroxyl group wherein a hydrogen atom of the hydroxyl group is replaced by a covalent bond to —(CR$^{12}$R$^{13}$)—Y—Z—R$^{11}$. For example, in Formula PC-(XVII), X is an opioid comprising a hydroxyl group, wherein X is connected to the promoiety via modification of the hydroxyl group.

For example, in Formula PC-(XVIII), X is an opioid comprising a hydroxyl group wherein a hydrogen atom of the hydroxyl group is replaced by a covalent bond to —(C(R$^{31a}$)(R$^{32a}$)—Ar—Z—C(O)—Y—(C(R$^{31}$)(R$^{32}$))$_n$—N—(R$^{33}$)(R$^{34}$).

Examples of Alcohol-Modified Opioid Prodrugs.

Examples of certain alcohol-modified opioid prodrugs are shown below. In formulae CC-(I) to CC-(XIV), AA can represent a side chain of an amino acid. Amino acids, including amino acid variants, are discussed in a section herein.

Formula CC-(I)
A certain example is a compound of Formula CC-(I):

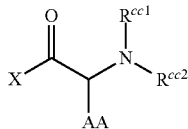

CC-(I)

wherein
X represents a residue of an alcohol-containing opioid, wherein the hydrogen atom of the hydroxyl group is replaced by a covalent bond to —C(O)—CH(AA)-NR$^{cc1}$R$^{cc2}$;
AA is a side chain of an amino acid; and
R$^{cc1}$ and R$^{cc2}$ are independently selected from hydrogen, alkyl, substituted alkyl, aryl, substituted aryl, acyl, arylalkyl, and substituted arylalkyl.

Formula CC-(II)
A certain example is a compound of formula CC-(II):

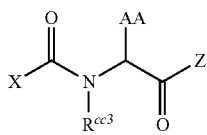

CC-(II)

wherein
X represents a residue of an alcohol-containing opioid, wherein the hydrogen atom of the hydroxyl group is replaced by a covalent bond to —C(O)—N(R$^{cc3}$)—CH(AA)-C(O)—Z;
R$^{cc3}$ is selected from selected from hydrogen, alkyl, substituted alkyl, aryl, substituted aryl, acyl, arylalkyl, and substituted arylalkyl;
AA is a side chain of an amino acid;
Z is selected from NH—R$^{cc4}$, O—R$^{cc4}$, OH, and NH$_2$; and
R$^{cc4}$ is selected from selected from hydrogen, alkyl, substituted alkyl, aryl, substituted aryl, acyl, arylalkyl, and substituted arylalkyl.

Formula CC-(III)
A certain example is a compound of formula CC-(III):

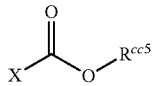

CC-(III)

wherein
X represents a residue of an alcohol-containing opioid, wherein the hydrogen atom of the hydroxyl group is replaced by a covalent bond to —C(O)—O—R$^{cc5}$; and
R$^{cc5}$ is selected from

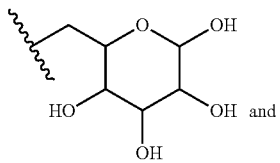

and

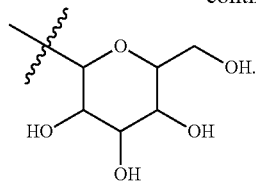

Formula CC-(IV)
A certain example is a compound of formula CC-(IV):

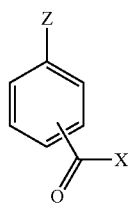

CC-(IV)

wherein
X represents a residue of an alcohol-containing opioid, wherein the hydrogen atom of the hydroxyl group is replaced by a covalent bond to the benzoyl group; and
Z is amidino or guanidino.

Formula CC-(V)
A certain example is a compound of formula CC-(V):

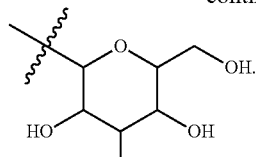

CC-(V)

wherein
X represents a residue of an alcohol-containing opioid, wherein the hydrogen atom of the hydroxyl group is replaced by a covalent bond to the carbonyl group;
R$^{cc6}$ and R$^{cc7}$ are independently selected from hydrogen, alkyl, substituted alkyl, aryl, substituted aryl, arylalkyl, and substituted arylalkyl;
n is a number from zero to 2;
Z is O or NH;
AA is a side chain of an amino acid; and
R$^{cc8}$ is selected from hydrogen, alkyl, substituted alkyl, aryl, substituted aryl, acyl, arylalkyl, and substituted arylalkyl.

Formula CC-(VI)
A certain example is a compound of formula CC-(VI):

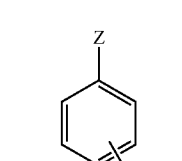

CC-(VI)

wherein
X represents a residue of an alcohol-containing opioid, wherein the hydrogen atom of the hydroxyl group is replaced by a covalent bond to the carbonyl group;
$R^{cc9}$ is selected from hydrogen, alkyl, substituted alkyl, aryl, substituted aryl, arylalkyl, and substituted arylalkyl;
Z is O or NH;
AA is a side chain of an amino acid; and
$R^{cc10}$ is selected from hydrogen, alkyl, substituted alkyl, aryl, substituted aryl, acyl, arylalkyl, and substituted arylalkyl.

Formula CC-(VII)
A certain example is a compound of formula CC-(VII):

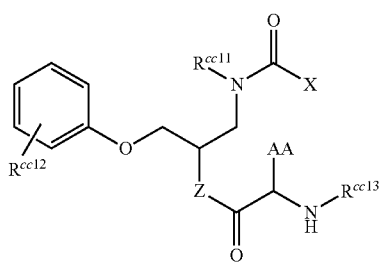

CC-(VI)

wherein
X represents a residue of an alcohol-containing opioid, wherein the hydrogen atom of the hydroxyl group is replaced by a covalent bond to the carbonyl group;
$R^{cc11}$ and $R^{cc12}$ are independently selected from hydrogen, alkyl, substituted alkyl, aryl, substituted aryl, arylalkyl, and substituted arylalkyl;
$R^{cc13}$ is selected from hydrogen, alkyl, substituted alkyl, aryl, substituted aryl, acyl, arylalkyl, and substituted arylalkyl;
Z is O or NH; and
AA is a side chain of an amino acid.

Formula CC-(VIII)
A certain example is a compound of formula CC-(VIII):

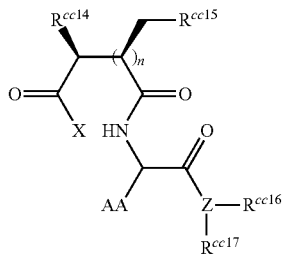

CC-(VIII)

wherein
X represents a residue of an alcohol-containing opioid, wherein the hydrogen atom of the hydroxyl group is replaced by a covalent bond to the carbonyl group;
$R^{cc14}$ and $R^{cc15}$ are independently selected from hydrogen, alkyl, substituted alkyl, aryl, substituted aryl, arylalkyl, and substituted arylalkyl;
n is a number from zero to 2;
AA is a side chain of an amino acid; and
Z is O or N;
$R^{cc16}$ and $R^{cc17}$ are independently selected from hydrogen, alkyl, substituted alkyl, aryl, substituted aryl, acyl, arylalkyl, and substituted arylalkyl, wherein if Z is O, then $R^{cc17}$ is not present.

Formula CC-(IX)
A certain example is a compound of formula CC-(IX):

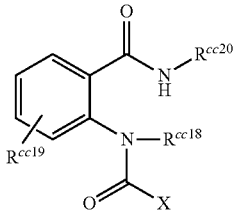

CC-(IX)

wherein
X represents a residue of an alcohol-containing opioid, wherein the hydrogen atom of the hydroxyl group is replaced by a covalent bond to the carbonyl group;
$R^{cc18}$, $R^{cc19}$, $R^{cc20}$ are independently selected from hydrogen, alkyl, substituted alkyl, aryl, substituted aryl, arylalkyl, and substituted arylalkyl.

Formula CC-(X)
A certain example is a compound of formula CC-(X):

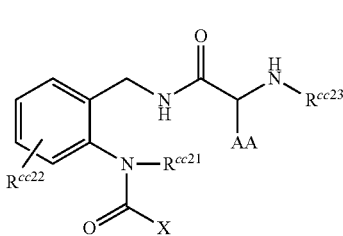

CC-(X)

wherein
X represents a residue of an alcohol-containing opioid, wherein the hydrogen atom of the hydroxyl group is replaced by a covalent bond to the carbonyl group;
$R^{cc21}$ and $R^{cc22}$ are independently selected from hydrogen, alkyl, substituted alkyl, aryl, substituted aryl, arylalkyl, and substituted arylalkyl;
$R^{cc23}$ is selected from hydrogen, alkyl, substituted alkyl, aryl, substituted aryl, acyl, arylalkyl, and substituted arylalkyl; and
AA is a side chain of an amino acid.

Formula CC-(XI)
A certain example is a compound of formula CC-(XI):

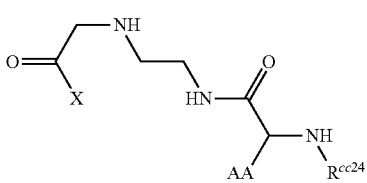

CC-(XI)

wherein
X represents a residue of an alcohol-containing opioid, wherein the hydrogen atom of the hydroxyl group is replaced by a covalent bond to the carbonyl group;
$R^{cc24}$ is selected from hydrogen, alkyl, substituted alkyl, aryl, substituted aryl, acyl, arylalkyl, and substituted arylalkyl; and
AA is a side chain of an amino acid.

47

Formula CC-(XII)
A certain example is a compound of formula CC-(XII):

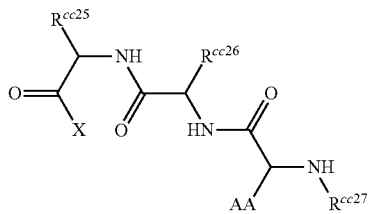

CC-(XII)

wherein
X represents a residue of an alcohol-containing opioid, wherein the hydrogen atom of the hydroxyl group is replaced by a covalent bond to the carbonyl group;
$R^{cc25}$ and $R^{cc26}$ are independently selected from hydrogen, alkyl, substituted alkyl, aryl, substituted aryl, arylalkyl, and substituted arylalkyl;
$R^{cc27}$ is selected from hydrogen, alkyl, substituted alkyl, aryl, substituted aryl, acyl, arylalkyl, and substituted arylalkyl; and
AA is a side chain of an amino acid.

Formula CC-(XIII)
A certain example is a compound of formula CC-(XIII):

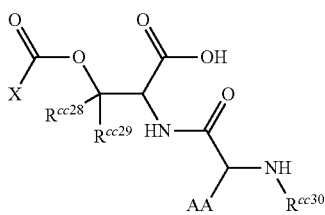

CC-(XIII)

wherein
X represents a residue of an alcohol-containing opioid, wherein the hydrogen atom of the hydroxyl group is replaced by a covalent bond to the carbonyl group;
$R^{cc28}$ and $R^{cc29}$ are independently selected from hydrogen, alkyl, substituted alkyl, aryl, substituted aryl, arylalkyl, and substituted arylalkyl;
$R^{cc30}$ is selected from hydrogen, alkyl, substituted alkyl, aryl, substituted aryl, acyl, arylalkyl, and substituted arylalkyl; and
AA is a side chain of an amino acid.

Formula CC-(XIV)
A certain example is a compound of formula CC-(XIV):

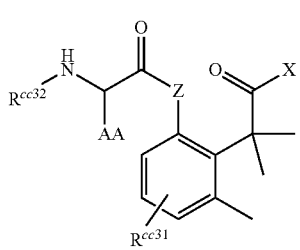

CC-(XIV)

48 wherein
X represents a residue of an alcohol-containing opioid, wherein the hydrogen atom of the hydroxyl group is replaced by a covalent bond to the carbonyl group;
$R^{cc31}$ is selected from hydrogen, alkyl, substituted alkyl, aryl, substituted aryl, arylalkyl, and substituted arylalkyl;
Z is O or NH;
$R^{cc32}$ is selected from hydrogen, alkyl, substituted alkyl, aryl, substituted aryl, acyl, arylalkyl, and substituted arylalkyl; and
AA is a side chain of an amino acid.

Phenol-Modified Opioid Prodrugs

The disclosure provides a phenol-modified opioid prodrug which provides enzymatically-controlled release of a phenolic opioid. In a phenol-modified opioid prodrug, a promoiety is attached to the phenolic opioid via modification of the phenol moiety. A phenol-modified opioid prodrug can also be referred to as a phenolic opioid prodrug. In a phenol-modified opioid prodrug, the hydrogen atom of the phenolic hydroxyl group of the phenolic opioid is replaced by a covalent bond to a promoiety.

As disclosed herein, a gastrointestinal (GI) enzyme-cleavable phenol-modified opioid prodrug is a phenol-modified opioid prodrug that comprises a promoiety comprising a GI enzyme-cleavable moiety having a site susceptible to cleavage by a GI enzyme. Such a prodrug comprises a phenolic opioid covalently bound to a promoiety comprising a GI enzyme-cleavable moiety, wherein cleavage of the GI enzyme-cleavable moiety by the GI enzyme mediates release of the drug. Cleavage can initiate, contribute to or effect drug release.

Phenol-Modified Opioid Prodrugs with Promoiety Comprising Cyclizable Spacer Leaving Group and Cleavable Moiety According to certain embodiments, there is provided a phenol-modified opioid prodrug which provides enzymatically-controlled release of a phenolic opioid. The disclosure provides for a phenol-modified opioid prodrug in which the promoiety comprises a cyclizable spacer leaving group and a cleavable moiety. In certain embodiments, the phenol-modified opioid prodrug is a corresponding compound in which the phenolic hydrogen atom has been substituted with a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide a phenolic opioid.

The enzyme capable of cleaving the enzymatically-cleavable moiety may be a peptidase, also referred to as a protease—the promoiety comprising the enzymatically-cleavable moiety being linked to the nucleophilic nitrogen through an amide (e.g. a peptide: —NHC(O)—) bond. In some embodiments, the enzyme is a digestive enzyme of a protein.

The corresponding prodrug provides post administration-activated, controlled release of the phenolic opioid. The prodrug requires enzymatic cleavage to initiate release of the phenolic opioid and thus the rate of release of the phenolic opioid depends upon both the rate of enzymatic cleavage and the rate of cyclization. Accordingly, the prodrug has reduced susceptibility to accidental overdosing or abuse, whether by deliberate overdosing, administration through an inappropriate route, such as by injection, or by chemical modification using readily available household chemicals. The prodrug is configured so that it will not provide excessively high plasma levels of the active drug if it is administered inappropriately, and cannot readily be decomposed to afford the active drug other than by enzymatic cleavage followed by controlled cyclization.

The enzyme-cleavable moiety linked to the nitrogen nucleophile through an amide bond can be, for example, a residue of an amino acid or a peptide, or an (alpha) N-acyl derivative of an amino acid or peptide (for example an N-acyl derivative of a pharmaceutically acceptable carboxylic acid). The peptide can contain, for example, up to about 100 amino acid residues. Each amino acid can advantageously be a naturally occurring amino acid, such as an L-amino acid. Examples of naturally occurring amino acids are alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. Accordingly, examples of enzyme-cleavable moieties include residues of the L-amino acids listed hereinabove and N-acyl derivatives thereof, and peptides formed from at least two of the L-amino acids listed hereinabove, and the N-acyl derivatives thereof.

The cyclic group formed when the phenolic opioid is released is conveniently pharmaceutically acceptable, in particular a pharmaceutically acceptable cyclic urea. It will be appreciated that cyclic ureas are generally very stable and have low toxicity.

Formulae PC-(I) to PC-(VI)

Examples of phenol-modified opioid prodrugs with a cyclizable spacer leaving group and cleavable moiety are shown in Formulae PC-(I) to PC-(VI) in which $R^4$ of the cleavable moiety can be a side chain of arginine or lysine. Formulae PC-(I) to PC-(VI) are now described in more detail below.

Formula PC-(I)

According to one aspect, the embodiments include pharmaceutical compositions, which comprise a compound of general formula PC-(I):

$$X—C(O)—NR^1—(C(R^2)(R^3))_n—NH—C(O)—CH(R^4)—NH(R^5) \quad (PC\text{-}(I))$$

or a pharmaceutically acceptable salt thereof, in which:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

$R^1$ represents a (1-4C)alkyl group;

$R^2$ and $R^3$ each independently represents a hydrogen atom or a (1-4C)alkyl group;

n represents 2 or 3;

$R^4$ represents —CH$_2$CH$_2$CH$_2$NH(C=NH)NH$_2$ or —CH$_2$CH$_2$CH$_2$CH$_2$NH$_2$, the configuration of the carbon atom to which $R^4$ is attached corresponding with that in an L-amino acid; and $R^5$ represents a hydrogen atom, an N-acyl group, or a residue of an amino acid, a dipeptide, or an N-acyl derivative of an amino acid or dipeptide.

The compounds of formula PC-(I) correspond with compounds disclosed in WO 2007/140272 in which the nucleophilic nitrogen atom is bound to a residue of L-arginine or L-lysine.

Examples of values for the phenolic opioid as provided in X are oxymorphone, hydromorphone, and morphine.

Examples of values for $R^1$ are methyl and ethyl groups.

Examples of values for each of $R^2$ and $R^3$ are hydrogen atoms.

An example of a value for n is 2.

In one embodiment, $R^4$ represents —CH$_2$CH$_2$CH$_2$NH(C=NH)NH$_2$.

Referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

Examples of particular values for $R^5$ are:
a hydrogen atom;
for an N-acyl group: an N-(1-4C)alkanoyl group, such as acetyl, an N-aroyl group, such as N-benzoyl, or an N-piperonyl group; and
for a residue of an amino acid, a dipeptide, or an N-acyl derivative of an amino acid or dipeptide: glycinyl or N-acetylglycinyl.

In one embodiment, $R^5$ represents N-acetyl, N-glycinyl or N-acetylglycinyl, such as N-acetyl.

An example of the group represented by —C(O)—CH(R$^4$)—NH(R$^5$) is N-acetylarginyl.

In a particular embodiment, the compound of formula PC-(I) is hydromorphone 3-(N-methyl-N-(2-N'-acetylarginylamino)) ethylcarbamate, or a pharmaceutically acceptable salt thereof. This compound is described in Example 3 of WO 2007/140272.

Formula PC-(II)

The embodiments provide a pharmaceutical composition, which comprises a compound of general formula PC-(IIa):

$$X—C(O)—NR^1—(C(R^2)(R^3))_n—NH—C(O)—CH(R^4)—NH(R^5) \quad (PC\text{-}(IIa))$$

or a pharmaceutically acceptable salt thereof, in which:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n represents an integer from 2 to 4;

$R^4$ represents —CH$_2$CH$_2$CH$_2$NH(C=NH)NH$_2$ or —CH$_2$CH$_2$CH$_2$CH$_2$NH$_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments provide a pharmaceutical composition, which comprises a compound of general formula PC-(IIb):

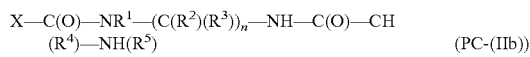

X—C(O)—NR$^1$—(C(R$^2$)(R$^3$))$_n$—NH—C(O)—CH(R$^4$)—NH(R$^5$)   (PC-(IIb))

or a pharmaceutically acceptable salt thereof, in which:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

R$^1$ is selected from alkyl, substituted alkyl, arylalkyl, substituted arylalkyl, aryl and substituted aryl;

each R$^2$ is independently selected from hydrogen, alkyl, substituted alkyl, aryl, substituted aryl, acyl, and aminoacyl;

each R$^3$ is independently selected from hydrogen, alkyl, substituted alkyl, aryl, substituted aryl, acyl, and aminoacyl;

or R$^2$ and R$^3$ together with the carbon to which they are attached form a cycloalkyl or substituted cycloalkyl group, or two R$^2$ or R$^3$ groups on adjacent carbon atoms, together with the carbon atoms to which they are attached, form a cycloalkyl or substituted cycloalkyl group;

n represents an integer from 2 to 4;

R$^4$ represents —CH$_2$CH$_2$CH$_2$NH(C=NH)NH$_2$ or —CH$_2$CH$_2$CH$_2$CH$_2$NH$_2$, the configuration of the carbon atom to which R$^4$ is attached corresponding with that in an L-amino acid; and R$^5$ represents a hydrogen atom, an N-acyl group (including N-substituted acyl), a residue of an amino acid, a dipeptide, or an N-acyl derivative (including N-substituted acyl derivative) of an amino acid or dipeptide.

Reference to formula PC-(II) is meant to include compounds of formula PC-(IIa) and PC-(IIb).

In formula PC-(II), examples of values for the phenolic opioid as provided in X are oxymorphone, hydromorphone, and morphine.

In formula PC-(II), R$^1$ can be selected from alkyl, substituted alkyl, arylalkyl, substituted arylalkyl, aryl and substituted aryl. In certain instances, R$^1$ is (1-6C)alkyl. In other instances, R$^1$ is (1-4C)alkyl. In other instances, R$^1$ is methyl or ethyl. In other instances, R$^1$ is methyl. In some instances, R$^1$ is ethyl.

In certain instances, in formula PC-(II), R$^1$ is substituted alkyl. In certain instances, R$^1$ is an alkyl group substituted with a carboxylic group such as a carboxylic acid, carboxylic ester or carboxylic amide. In certain instances, R$^1$ is —(CH$_2$)$_n$—COOH, —(CH$_2$)$_n$—COOCH$_3$, or —(CH$_2$)$_n$—COOCH$_2$CH$_3$, wherein n is a number from one to 10. In certain instances, R$^1$ is —(CH$_2$)$_5$—COOH, —(CH$_2$)$_5$—COOCH$_3$, or —(CH$_2$)$_5$—COOCH$_2$CH$_3$.

In certain instances, in formula PC-(II), R$^1$ is arylalkyl or substituted arylalkyl. In certain instances, R$^1$ is arylalkyl. In certain instances, R$^1$ is substituted arylalkyl. In certain instances, R$^1$ is an arylalkyl group substituted with a carboxylic group such as a carboxylic acid, carboxylic ester or carboxylic amide. In certain instances, R$^1$ is —(CH$_2$)$_q$(C$_6$H$_4$)—COOH, —(CH$_2$)$_q$(C$_6$H$_4$)—COOCH$_3$, or —(CH$_2$)$_q$(C$_6$H$_4$)—COOCH$_2$CH$_3$, where q is an integer from one to 10. In certain instances, R$^1$ is —CH$_2$(C$_6$H$_4$)—COOH, —CH$_2$(C$_6$H$_4$)—COOCH$_3$, or —CH$_2$(C$_6$H$_4$)—COOCH$_2$CH$_3$.

In certain instances, in formula PC-(II), R$^1$ is aryl. In certain instances, R$^1$ is substituted aryl. In certain instances, R$^1$ is an aryl group with ortho, meta or para-substituted with a carboxylic group such as a carboxylic acid, carboxylic ester or carboxylic amide. In certain instances, R$^1$ is —(C$_6$H$_4$)—COOH, —(C$_6$H$_4$)—COOCH$_3$, or —(C$_6$H$_4$)—COOCH$_2$CH$_3$.

In formula PC-(II), each R$^2$ can be independently selected from hydrogen, alkyl, substituted alkyl, aryl, substituted aryl, acyl, and aminoacyl. In certain instances, R$^2$ is hydrogen or alkyl. In certain instances, R$^2$ is hydrogen. In certain instances, R$^2$ is alkyl. In certain instances, R$^2$ is acyl. In certain instances, R$^2$ is aminoacyl.

In formula PC-(II), each R$^3$ can be independently selected from hydrogen, alkyl, substituted alkyl, aryl, substituted aryl, acyl, and aminoacyl. In certain instances, R$^3$ is hydrogen or alkyl. In certain instances, R$^3$ is hydrogen. In certain instances, R$^3$ is alkyl. In certain instances, R$^3$ is acyl. In certain instances, R$^3$ is aminoacyl.

In certain instances, R$^2$ and R$^3$ are hydrogen. In certain instances, R$^2$ and R$^3$ on the same carbon are both alkyl. In certain instances, R$^2$ and R$^3$ on the same carbon are methyl. In certain instances, R$^2$ and R$^3$ on the same carbon are ethyl.

In certain instances, R$^2$ and R$^2$ which are vicinal are both alkyl and R$^3$ and R$^3$ which are vicinal are both hydrogen. In certain instances, R$^2$ and R$^2$ which are vicinal are both ethyl and R$^3$ and R$^3$ which are vicinal are both hydrogen. In certain instances, R$^2$ and R$^2$ which are vicinal are both methyl and R$^3$ and R$^3$ which are vicinal are both hydrogen.

In certain instances, in the chain of —[C(R$^2$)(R$^3$)]$_n$— in Formula PC-(II), not every carbon is substituted. In certain instances, in the chain of —[C(R$^2$)(R$^3$)]$_n$—, there is a combination of different alkyl substituents, such as methyl or ethyl.

In certain instances, one of R$^2$ and R$^3$ is methyl, ethyl or other alkyl and R$^1$ is alkyl. In certain instances, R$^2$ and R$^2$ which are vicinal are both alkyl and R$^3$ and R$^3$ which are vicinal are both hydrogen and R$^1$ is alkyl. In certain instances, R$^2$ and R$^2$ which are vicinal are both ethyl and R$^3$ and R$^3$ which are vicinal are both hydrogen and R$^1$ is alkyl. In certain instances, R$^2$ and R$^2$ which are vicinal are both methyl and R$^3$ and R$^3$ which are vicinal are both hydrogen and R$^1$ is alkyl.

In certain instances, one of R$^2$ and R$^3$ is methyl, ethyl or other alkyl and R$^1$ is substituted alkyl. In certain instances, one of R$^2$ and R$^3$ is methyl, ethyl or other alkyl and R$^1$ is an alkyl group substituted with a carboxylic group such as a carboxylic acid, carboxylic ester or carboxylic amide. In certain instances, one of R$^2$ and R$^3$ is methyl, ethyl or other alkyl and R$^1$ is —(CH$_2$)$_q$(C$_6$H$_4$)—COOH, —(CH$_2$)$_q$(C$_6$H$_4$)—COOCH$_3$, or —(CH$_2$)$_q$(C$_6$H$_4$)—COOCH$_2$CH$_3$, where q is an integer from one to 10. In certain instances, one of R$^2$ and R$^3$ is methyl, ethyl or other alkyl and R$^1$ is carboxamide.

In formula PC-(II), R$^2$ and R$^3$ together with the carbon to which they are attached can form a cycloalkyl or substituted cycloalkyl group, or two R$^2$ or R$^3$ groups on adjacent carbon atoms, together with the carbon atoms to which they are attached, can form a cycloalkyl or substituted cycloalkyl group. In certain instances, R$^2$ and R$^3$ together with the carbon to which they are attached can form a cycloalkyl group. Thus, in certain instances, R$^2$ and R$^3$ on the same carbon form a spirocycle. In certain instances, R$^2$ and R$^3$ together with the carbon to which they are attached can form a substituted cycloalkyl group. In certain instances, two R$^2$ or R$^3$ groups on adjacent carbon atoms, together with the carbon atoms to which they are attached, can form a cycloalkyl group. In certain instances, two R$^2$ or R$^3$ groups on adjacent carbon atoms, together with the carbon atoms to which they are attached, can form a substituted cycloalkyl group.

In certain instances, R$^2$ and R$^3$ together with the carbon to which they are attached can form an aryl or substituted aryl group, or two R$^2$ or R$^3$ groups on adjacent carbon atoms, together with the carbon atoms to which they are attached, can form an aryl or substituted aryl group. In certain instances, two R$^2$ or R$^3$ groups on adjacent carbon atoms, together with the carbon atoms to which they are attached, form a phenyl ring. In certain instances, two $R^2$ or $R^3$ groups on adjacent carbon atoms, together with the carbon atoms to which they are attached, form a substituted phenyl ring. In certain instances, two $R^2$ or $R^3$ groups on adjacent carbon atoms, together with the carbon atoms to which they are attached, form a naphthyl ring.

In certain instances, one of $R^2$ and $R^3$ is aminoacyl.

In certain instances, one of $R^2$ and $R^3$ is aminoacyl comprising phenylenediamine. In certain instances, one or both of $R^2$ and $R^3$ is

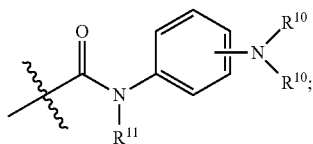

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^2$ and $R^3$ is

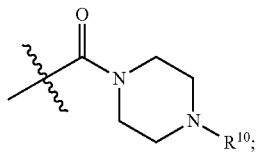

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^2$ and $R^3$ is

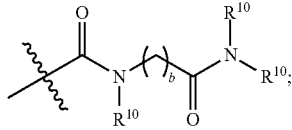

wherein each $R^{10}$ is independently hydrogen, alkyl, substituted alkyl, or acyl and b is a number from one to 5. In certain instances, one of $R^2$ and $R^3$ is

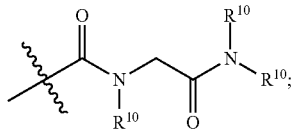

wherein each $R^{10}$ is independently hydrogen, alkyl, substituted alkyl, or acyl. In certain instances, one of $R^2$ and $R^3$ is

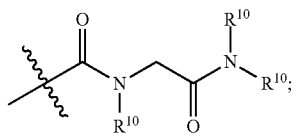

wherein $R^{10a}$ is alkyl and each $R^{10}$ is independently hydrogen, alkyl, substituted alkyl, or acyl.

In certain instances, one of $R^2$ and $R^3$ is

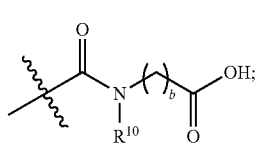

wherein $R^{10}$ is independently hydrogen, alkyl, substituted alkyl, or acyl and b is a number from one to 5. In certain instances, one of $R^2$ and $R^3$ is

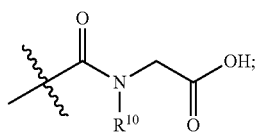

wherein $R^{10}$ is independently hydrogen, alkyl, substituted alkyl, or acyl.

In certain instances, one of $R^2$ and $R^3$ is an aminoacyl group, such as —C(O)NR$^{10a}$R$^{10b}$, wherein each $R^{10a}$ and $R^{10b}$ is independently selected from hydrogen, alkyl, substituted alkyl, and acyl. In certain instances, one of $R^2$ and $R^3$ is an aminoacyl group, such as —C(O)NR$^{10a}$R$^{10b}$, wherein $R^{10a}$ is an alkyl and $R^{10b}$ is substituted alkyl. In certain instances, one of $R^2$ and $R^3$ is an aminoacyl group, such as —C(O)NR$^{10a}$R$^{10b}$ wherein $R^{10a}$; is an alkyl and $R^{10b}$ is alkyl substituted with a carboxylic acid or carboxyl ester. In certain instances, one of $R^2$ and $R^3$ is an aminoacyl group, such as —C(O)NR$^{10a}$R$^{10b}$, wherein $R^{10a}$ is methyl and $R^{10b}$ is alkyl substituted with a carboxylic acid or carboxyl ester.

In certain instances, $R^2$ or $R^3$ can modulate a rate of intramolecular cyclization. $R^2$ or $R^3$ can speed up a rate of intramolecular cyclization, when compared to the corresponding molecule where $R^2$ and $R^3$ are both hydrogen. In certain instances, $R^2$ or $R^3$ comprise an electron-withdrawing group or an electron-donating group. In certain instances, $R^2$ or $R^3$ comprise an electron-withdrawing group. In certain instances, $R^2$ or $R^3$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (═O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, $—[C(R^2)(R^3)]_n—$ is selected from $—CH(CH_2F)CH(CH_2F)—$; $—CH(CHF_2)CH(CHF_2)—$; $—CH(CF_3)CH(CF_3)—$; $—CH_2CH(CF_3)—$; $—CH_2CH(CHF_2)—$; $—CH_2CH(CH_2F)—$; $—CH_2CH(F)CH_2—$; $—CH_2C(F_2)CH_2—$; $—CH_2CH(C(O)NR^{20}R^{21})—$; $—CH_2CH(C(O)OR^{22})—$; $—CH_2CH(C(O)OH)—$; $—CH(CH_2F)CH_2CH(CH_2F)—$; $—CH(CHF_2)CH_2CH(CHF_2)—$; $—CH(CF_3)CH_2CH(CF_3)—$; $—CH_2CH_2CH(CF_3)—$; $—CH_2CH_2CH(CHF_2)—$; $—CH_2CH_2CH(CH_2F)—$; $—CH_2CH_2CH(C(O)NR^{23}R^{24})—$; $—CH_2CH_2CH(C(O)OR^{25})—$; and $—CH_2CH_2CH(C(O)OH)—$, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formula PC-(II), n represents an integer from 2 to 4. An example of a value for n is 2. An example of a value for n is 3. An example of a value for n is 4.

In formula PC-(II), in one embodiment, $R^4$ represents $—CH_2CH_2CH_2NH(C\!=\!NH)NH_2$. In another embodiment, $R^4$ represents $—CH_2CH_2CH_2CH_2NH_2$.

In formula PC-(II), referring to $R^5$, examples of particular values are:

a hydrogen atom;

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

In formula PC-(II), examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula PC-(II), in one embodiment, $R^5$ represents N-acetyl, glycinyl or N-acetylglycinyl, such as N-acetyl.

In formula PC-(II), an example of the group represented by $—C(O)—CH(R^4)—NH(R^5)$ is N-acetylarginyl or N-acetyllysinyl.

In formula PC-(II), in certain instances, $R^5$ represents substituted acyl. In certain instances, $R^5$ can be malonyl or succinyl.

In formula PC-(II), in certain instances, the group represented by $—C(O)—CH(R^4)—NH(R^5)$ is N-malonylarginyl, N-malonyllysinyl, N-succinylarginyl and N-succinyllysinyl.

Formula PC-(III)

The embodiments provide a pharmaceutical composition, which comprises a compound of general formula PC-(III):

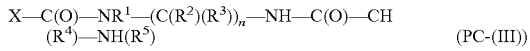

(PC-(III))

or pharmaceutically acceptable salt thereof, in which:

X represents a residue of a phenolic opioid, wherein the hydrogen atom of the phenolic hydroxyl group is replaced by a covalent bond to $—C(O)—NR^1—(C(R^2)(R^3))_n—NH—C(O)—CH(R^4)—NH(R^5)$;

$R^1$ represents a (1-4C)alkyl group;

$R^2$ and $R^3$ each independently represents a hydrogen atom or a (1-4C)alkyl group;

n represents 2 or 3;

$R^4$ represents $—CH_2CH_2CH_2NH(C\!=\!NH)NH_2$ or $—CH_2CH_2CH_2CH_2NH_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

In formula PC-(III), examples of values for the phenolic opioid as provided in X are oxymorphone, hydromorphone, and morphine.

In formula PC-(III), examples of values for $R^1$ are methyl and ethyl groups.

In formula PC-(III), examples of values for each of $R^2$ and $R^3$ are hydrogen atoms.

In formula PC-(III), an example of a value for n is 2.

In formula PC-(III), in one embodiment, $R^4$ represents $—CH_2CH_2CH_2NH(C\!=\!NH)NH_2$. In another embodiment, $R^4$ represents $—CH_2CH_2CH_2CH_2NH_2$.

In formula PC-(III), referring to $R^5$, examples of particular values are:

a hydrogen atom;

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

In formula PC-(III), examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula PC-(III), in one embodiment, $R^5$ represents N-acetyl, glycinyl or N-acetylglycinyl, such as N-acetyl.

In formula PC-(III), an example of the group represented by $—C(O)—CH(R^4)—NH(R^5)$ is N-acetylarginyl or N-acetyllysinyl.

In formula PC-(III), in certain instances, $R^5$ represents substituted acyl. In certain instances, $R^5$ can be malonyl or succinyl.

In formula PC-(III), in certain instances, the group represented by —C(O)—CH($R^4$)—NH($R^5$) is N-malonylarginyl, N-malonyllysinyl, N-succinylarginyl and N-succinyllysinyl.

Formula PC-(IV)

The embodiments provide a pharmaceutical composition, which comprises a compound of general formula PC-(IV):

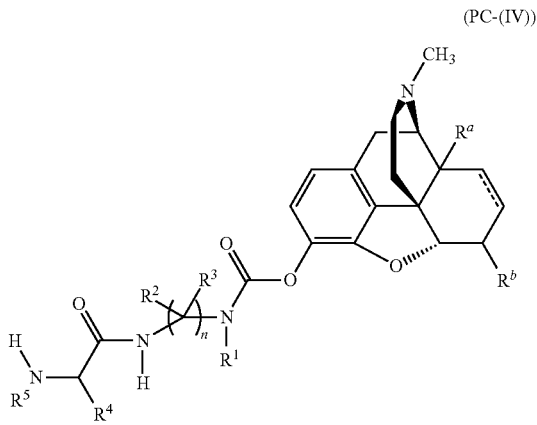

(PC-(IV))

or pharmaceutically acceptable salt thereof, in which:

$R^a$ is hydrogen or hydroxyl;

$R^b$ is oxo (=O) or hydroxyl;

the dashed line is a double bond or single bond;

$R^1$ represents a (1-4C)alkyl group;

$R^2$ and $R^3$ each independently represents a hydrogen atom or a (1-4C)alkyl group;

n represents 2 or 3;

$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group, or a residue of an amino acid, a dipeptide, or an N-acyl derivative of an amino acid or dipeptide.

In formula PC-(IV), a certain example of $R^a$ is hydrogen. In formula PC-(IV), a certain example of $R^a$ is hydroxyl.

In formula PC-(IV), a certain example of $R^b$ is oxo (=O). In formula PC-(IV), a certain example of $R^b$ is hydroxyl.

In formula PC-(IV), a certain example of the dashed line is a double bond. In formula PC-(IV), a certain example of the dashed line is a single bond.

In formula PC-(IV), examples of values for $R^1$ are methyl and ethyl groups.

In formula PC-(IV), examples of values for each of $R^2$ and $R^3$ are hydrogen atoms.

In formula PC-(IV), an example of a value for n is 2.

In formula PC-(IV), in one embodiment, $R^4$ represents —$CH_2CH_2CH_2NH(C=NH)NH_2$.

In formula PC-(IV), referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

In formula PC-(IV), examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula PC-(IV), in one embodiment, $R^5$ represents N-acetyl, glycinyl or N-acetylglycinyl, such as N-acetyl.

In formula PC-(IV), an example of the group represented by —C(O)—CH($R^4$)—NH($R^5$) is N-acetylarginyl.

Formula PC-(V)

The embodiments provide a pharmaceutical composition, which comprises a compound of general formula PC-(Va):

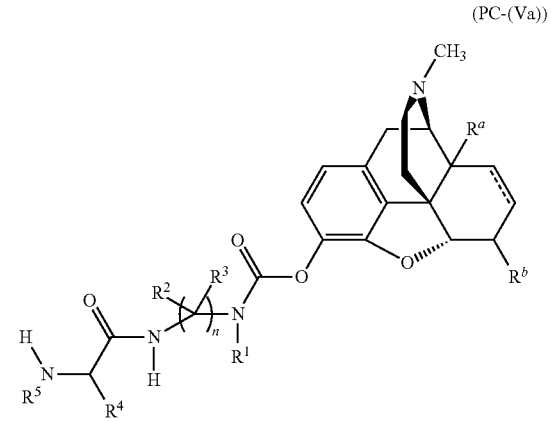

(PC-(Va))

or pharmaceutically acceptable salt thereof, in which:

$R^a$ is hydrogen or hydroxyl;

$R^b$ is oxo (=O) or hydroxyl;

the dashed line is a double bond or single bond;

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n represents an integer from 2 to 4;

$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments provide a pharmaceutical composition, which comprises a compound of general formula PC-(Vb):

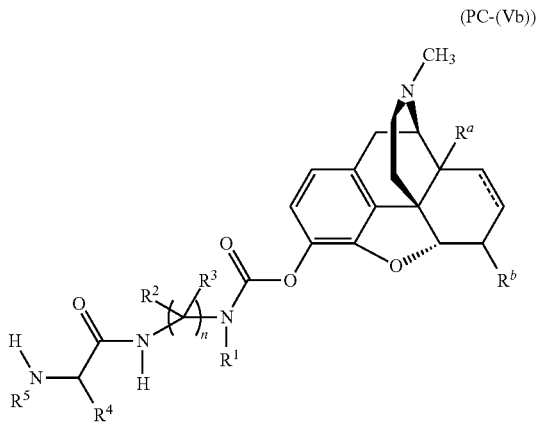

(PC-(Vb))

or pharmaceutically acceptable salt thereof, in which:
$R^a$ is hydrogen or hydroxyl;
$R^b$ is oxo (=O) or hydroxyl;
the dashed line is a double bond or single bond;
$R^1$ is selected from alkyl, substituted alkyl, arylalkyl, substituted arylalkyl, aryl and substituted aryl;
each $R^2$ is independently selected from hydrogen, alkyl, substituted alkyl, aryl, substituted aryl, acyl, and aminoacyl;
each $R^3$ is independently selected from hydrogen, alkyl, substituted alkyl, aryl, substituted aryl, acyl, and aminoacyl;
or $R^2$ and $R^3$ together with the carbon to which they are attached form a cycloalkyl or substituted cycloalkyl group, or two $R^2$ or $R^3$ groups on adjacent carbon atoms, together with the carbon atoms to which they are attached, form a cycloalkyl or substituted cycloalkyl group;
n represents an integer from 2 to 4;
$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and
$R^5$ represents a hydrogen atom, an N-acyl group (including N-substituted acyl), a residue of an amino acid, a dipeptide, or an N-acyl derivative (including N-substituted acyl derivative) of an amino acid or dipeptide.

Reference to formula PC-(V) is meant to include compounds of formula PC-(Va) and PC-(Vb).

In formula PC-(V), a certain example of $R^a$ is hydrogen. In formula PC-(V), a certain example of $R^a$ is hydroxyl.

In formula PC-(V), a certain example of $R^b$ is oxo (=O). In formula PC-(V), a certain example of $R^b$ is hydroxyl.

In formula PC-(V), a certain example of the dashed line is a double bond. In formula PC-(V), a certain example of the dashed line is a single bond.

In formula PC-(V), $R^1$ can be selected from alkyl, substituted alkyl, arylalkyl, substituted arylalkyl, aryl and substituted aryl. In certain instances, $R^1$ is (1-6C)alkyl. In other instances, $R^1$ is (1-4C)alkyl. In other instances, $R^1$ is methyl or ethyl. In other instances, $R^1$ is methyl. In some instances, $R^1$ is ethyl.

In certain instances, in formula PC-(V), $R^1$ is substituted alkyl. In certain instances, $R^1$ is an alkyl group substituted with a carboxylic group such as a carboxylic acid, carboxylic ester or carboxylic amide. In certain instances, $R^1$ is —$(CH_2)_n$—COOH, —$(CH_2)_n$—$COOCH_3$, or —$(CH_2)_n$—$COOCH_2CH_3$, wherein n is a number from one to 10. In certain instances, $R^1$ is —$(CH_2)_5$—COOH, —$(CH_2)_5$—$COOCH_3$, or —$(CH_2)_5$—$COOCH_2CH_3$.

In certain instances, in formula PC-(V), $R^1$ is arylalkyl or substituted arylalkyl. In certain instances, $R^1$ is arylalkyl. In certain instances, $R^1$ is substituted arylalkyl. In certain instances, $R^1$ is an arylalkyl group substituted with a carboxylic group such as a carboxylic acid, carboxylic ester or carboxylic amide. In certain instances, $R^1$ is —$(CH_2)_q(C_6H_4)$—COOH, —$(CH_2)_q(C_6H_4)$—$COOCH_3$, or —$(CH_2)_q(C_6H_4)$—$COOCH_2CH_3$, where q is an integer from one to 10. In certain instances, $R^1$ is —$CH_2(C_6H_4)$—COOH, —$CH_2(C_6H_4)$—$COOCH_3$, or —$CH_2(C_6H_4)$—$COOCH_2CH_3$.

In certain instances, in formula PC-(V), $R^1$ is aryl. In certain instances, $R^1$ is substituted aryl. In certain instances, $R^1$ is an aryl group ortho, meta or para-substituted with a carboxylic group such as a carboxylic acid, carboxylic ester or carboxylic amide. In certain instances, $R^1$ is —$(C_6H_4)$—COOH, —$(C_6H_4)$—$COOCH_3$, or —$(C_6H_4)$—$COOCH_2CH_3$.

In formula PC-(V), each $R^2$ can be independently selected from hydrogen, alkyl, substituted alkyl, aryl, substituted aryl, acyl, and aminoacyl. In certain instances, $R^2$ is hydrogen or alkyl. In certain instances, $R^2$ is hydrogen. In certain instances, $R^2$ is alkyl. In certain instances, $R^2$ is acyl. In certain instances, $R^2$ is aminoacyl.

In formula PC-(V), each $R^3$ can be independently selected from hydrogen, alkyl, substituted alkyl, aryl, substituted aryl, acyl, and aminoacyl. In certain instances, $R^3$ is hydrogen or alkyl. In certain instances, $R^3$ is hydrogen. In certain instances, $R^3$ is alkyl. In certain instances, $R^3$ is acyl. In certain instances, $R^3$ is aminoacyl.

In certain instances, $R^2$ and $R^3$ are hydrogen. In certain instances, $R^2$ and $R^3$ on the same carbon are both alkyl. In certain instances, $R^2$ and $R^3$ on the same carbon are methyl. In certain instances, $R^2$ and $R^3$ on the same carbon are ethyl.

In certain instances, $R^2$ and $R^2$ which are vicinal are both alkyl and $R^3$ and $R^3$ which are vicinal are both hydrogen. In certain instances, $R^2$ and $R^2$ which are vicinal are both ethyl and $R^3$ and $R^3$ which are vicinal are both hydrogen. In certain instances, $R^2$ and $R^2$ which are vicinal are both methyl and $R^3$ and $R^3$ which are vicinal are both hydrogen.

In certain instances, in the chain of —$[C(R^2)(R^3)]_n$— in Formula PC-(V), not every carbon is substituted. In certain instances, in the chain of —$[C(R^2)(R^3)]_n$—, there is a combination of different alkyl substituents, such as methyl or ethyl.

In certain instances, one of $R^2$ and $R^3$ is methyl, ethyl or other alkyl and $R^1$ is alkyl. In certain instances, $R^2$ and $R^2$ which are vicinal are both alkyl and $R^3$ and $R^3$ which are vicinal are both hydrogen and $R^1$ is alkyl. In certain instances, $R^2$ and $R^2$ which are vicinal are both ethyl and $R^3$ and $R^3$ which are vicinal are both hydrogen and $R^1$ is alkyl. In certain instances, $R^2$ and $R^2$ which are vicinal are both methyl and $R^3$ and $R^3$ which are vicinal are both hydrogen and $R^1$ is alkyl.

In certain instances, one of $R^2$ and $R^3$ is methyl, ethyl or other alkyl and $R^1$ is substituted alkyl. In certain instances, one of $R^2$ and $R^3$ is methyl, ethyl or other alkyl and $R^1$ is an alkyl group substituted with a carboxylic group such as a carboxylic acid, carboxylic ester or carboxylic amide. In certain instances, one of $R^2$ and $R^3$ is methyl, ethyl or other alkyl and $R^1$ is —$(CH_2)_q(C_6H_4)$—COOH, —$(CH_2)_q(C_6H_4)$—$COOCH_3$, or —$(CH_2)_q(C_6H_4)$—$COOCH_2CH_3$, where q is an integer from one to 10. In certain instances, one of $R^2$ and $R^3$ is methyl, ethyl or other alkyl and $R^1$ is carboxamide.

In formula PC-(V), $R^2$ and $R^3$ together with the carbon to which they are attached can form a cycloalkyl or substituted cycloalkyl group, or two $R^2$ or $R^3$ groups on adjacent carbon atoms, together with the carbon atoms to which they are attached, can form a cycloalkyl or substituted cycloalkyl group. In certain instances, R² and R³ together with the carbon to which they are attached can form a cycloalkyl group. Thus, in certain instances, R² and R³ on the same carbon form a spirocycle. In certain instances, R² and R³ together with the carbon to which they are attached can form a substituted cycloalkyl group. In certain instances, two R² or R³ groups on adjacent carbon atoms, together with the carbon atoms to which they are attached, can form a cycloalkyl group. In certain instances, two R² or R³ groups on adjacent carbon atoms, together with the carbon atoms to which they are attached, can form a substituted cycloalkyl group.

In certain instances, R² and R³ together with the carbon to which they are attached can form an aryl or substituted aryl group, or two R² or R³ groups on adjacent carbon atoms, together with the carbon atoms to which they are attached, can form an aryl or substituted aryl group. In certain instances, two R² or R³ groups on adjacent carbon atoms, together with the carbon atoms to which they are attached, form a phenyl ring. In certain instances, two R² or R³ groups on adjacent carbon atoms, together with the carbon atoms to which they are attached, form a substituted phenyl ring. In certain instances, two R² or R³ groups on adjacent carbon atoms, together with the carbon atoms to which they are attached, form a naphthyl ring.

In certain instances, one of R² and R³ is aminoacyl.

In certain instances, one of R² and R³ is aminoacyl comprising phenylenediamine. In certain instances, one or both of R² and R³ is

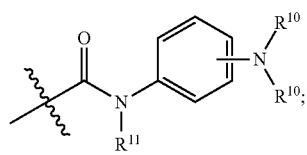

wherein each R¹⁰ is independently selected from hydrogen, alkyl, substituted alkyl, and acyl and R¹¹ is alkyl or substituted alkyl. In certain instances, at least one of R¹⁰ is acyl. In certain instances, at least one of R¹⁰ is alkyl or substituted alkyl. In certain instances, at least one of R¹⁰ is hydrogen. In certain instances, both of R¹⁰ are hydrogen.

In certain instances, one of R² and R³ is

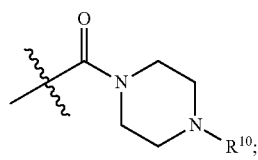

wherein R¹⁰ is hydrogen, alkyl, substituted alkyl, or acyl. In certain instances, R¹⁰ is acyl. In certain instances, R¹⁰ is alkyl or substituted alkyl. In certain instances, R¹⁰ is hydrogen.

In certain instances, one of R² and R³ is

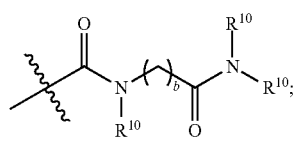

wherein each R¹⁰ is independently hydrogen, alkyl, substituted alkyl, or acyl and b is a number from one to 5. In certain instances, one of R² and R³ is

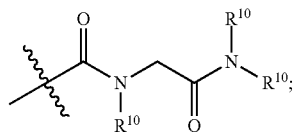

wherein each R¹⁰ is independently hydrogen, alkyl, substituted alkyl, or acyl. In certain instances, one of R² and R³ is

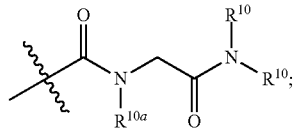

wherein $R^{10a}$ is alkyl and each R¹⁰ is independently hydrogen, alkyl, substituted alkyl, or acyl.

In certain instances, one of R² and R³ is

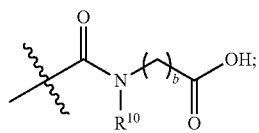

wherein R¹⁰ is independently hydrogen, alkyl, substituted alkyl, or acyl and b is a number from one to 5. In certain instances, one of R² and R³ is wherein R¹⁰ is independently hydrogen, alkyl, substituted alkyl, or acyl.

In certain instances, one of R² and R³ is an aminoacyl group, such as —C(O)NR$^{10a}$R$^{10b}$, wherein each R$^{10a}$ and R$^{10b}$ is independently selected from hydrogen, alkyl, substituted alkyl, and acyl. In certain instances, one of R² and R³ is an aminoacyl group, such as —C(O)NR$^{10a}$R$^{10b}$, wherein R$^{10a}$ is an alkyl and R$^{10b}$ is substituted alkyl. In certain instances, one of R² and R³ is an aminoacyl group, such as —C(O)NR$^{10a}$R$^{10b}$, wherein R$^{10a}$ is an alkyl and R$^{10b}$ is alkyl substituted with a carboxylic acid or carboxyl ester. In certain instances, one of R² and R³ is an aminoacyl group, such as —C(O)NR$^{10a}$R$^{10b}$, wherein R$^{10a}$ is methyl and R$^{10b}$ is alkyl substituted with a carboxylic acid or carboxyl ester.

In certain instances, R² or R³ can modulate a rate of intramolecular cyclization. R² or R³ can speed up a rate of intramolecular cyclization, when compared to the corresponding molecule where R² and R³ are both hydrogen. In certain instances, R² or R³ comprise an electron-withdrawing group or an electron-donating group. In certain instances, R² or R³ comprise an electron-withdrawing group. In certain instances, R² or R³ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, —[C($R^2$)($R^3$)]$_n$— is selected from —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$^2$OR$^{21}$)—; —CH$_2$CH(C(O)OR$^{22}$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O)NR$^{23}$R$^{24}$)—; —CH$_2$CH$_2$CH(C(O)OR$^{25}$)—; and —CH$_2$CH$_2$CH(C(O)OH)—, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formula PC-(V), n represents an integer from 2 to 4. An example of a value for n is 2. An example of a value for n is 3. An example of a value for n is 4.

In formula PC-(V), in one embodiment, $R^4$ represents —CH$_2$CH$_2$CH$_2$NH(C=NH)NH$_2$. In another embodiment, $R^4$ represents —CH$_2$CH$_2$CH$_2$CH$_2$NH$_2$.

In formula PC-(V), referring to $R^5$, examples of particular values are:
for an N-acyl group: an N-(1-4C)alkanoyl group, such as acetyl, an N-aroyl group, such as N-benzoyl, or an N-piperonyl group;
for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and
for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

In formula PC-(V), examples of particular values for $R^5$ are:
a hydrogen atom;
for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula PC-(V), in one embodiment, $R^5$ represents N-acetyl, glycinyl or N-acetylglycinyl, such as N-acetyl.

In formula PC-(V), an example of the group represented by —C(O)—CH($R^4$)—NH($R^5$) is N-acetylarginyl or N-acetyllysinyl.

In formula PC-(V), in certain instances, $R^5$ represents substituted acyl. In certain instances, $R^5$ can be malonyl or succinyl.

In formula PC-(V), in certain instances, the group represented by —C(O)—CH($R^4$)—NH($R^5$) is N-malonylarginyl, N-malonyllysinyl, N-succinylarginyl and N-succinyllysinyl.

Formula PC-(VI)

The embodiments provide a pharmaceutical composition, which comprises a compound of general formula PC-(VI):

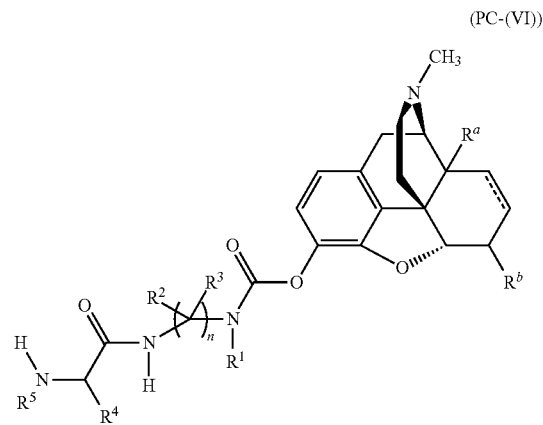

(PC-(VI))

or pharmaceutically acceptable salt thereof, in which:
$R^a$ is hydrogen or hydroxyl;
$R^b$ is oxo (=O) or hydroxyl;
the dashed line is a double bond or single bond;
$R^1$ represents a (1-4C)alkyl group;
$R^2$ and $R^3$ each independently represents a hydrogen atom or a (1-4C)alkyl group;
n represents 2 or 3;
$R^4$ represents —CH$_2$CH$_2$CH$_2$NH(C=NH)NH$_2$ or —CH$_2$CH$_2$CH$_2$NH$_2$, the configuration of the carbon atom to which $R^4$ is attached corresponding with that in an L-amino acid; and
$R^5$ represents a hydrogen atom, an N-acyl group (including N-substituted acyl), a residue of an amino acid, a dipeptide, or an N-acyl derivative (including N-substituted acyl derivative) of an amino acid or dipeptide.

In formula PC-(VI), a certain example of $R^a$ is hydrogen. In formula PC-(VI), a certain example of $R^a$ is hydroxyl.

In formula PC-(VI), a certain example of $R^b$ is oxo (=O). In formula PC-(VI), a certain example of $R^b$ is hydroxyl.

In formula PC-(VI), a certain example of the dashed line is a double bond. In formula VI, a certain example of the dashed line is a single bond.

In formula PC-(VI), examples of values for $R^1$ are methyl and ethyl groups.

In formula PC-(VI), examples of values for each of $R^2$ and $R^3$ are hydrogen atoms.

In formula PC-(VI), an example of a value for n is 2.

In formula PC-(VI), in one embodiment, $R^4$ represents —CH$_2$CH$_2$CH$_2$NH(C=NH)NH$_2$. In another embodiment, $R^4$ represents —CH$_2$CH$_2$CH$_2$CH$_2$NH$_2$.

In formula PC-(VI), referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

In formula PC-(VI), examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula PC-(VI), in one embodiment, $R^5$ represents N-acetyl, glycinyl or N-acetylglycinyl, such as N-acetyl.

In formula PC-(VI), an example of the group represented by $-C(O)-CH(R^4)-NH(R^5)$ is N-acetylarginyl or N-acetyllysinyl.

In formula PC-(VI), in certain instances, $R^5$ represents substituted acyl. In certain instances, $R^5$ can be malonyl or succinyl.

In formula PC-(VI), in certain instances, the group represented by $-C(O)-CH(R^4)-NH(R^5)$ is N-malonylarginyl, N-malonyllysinyl, N-succinylarginyl and N-succinyllysinyl.

As shown herein, Formula PC-(I) describes compounds of Formula PC-(II), in which $R^1$ is (1-4C)alkyl group; $R^2$ and $R^3$ each independently represents a hydrogen atom or a (1-4C) alkyl group; and $R^5$ represents a hydrogen atom, an N-acyl group, a residue of an amino acid, a dipeptide, or an N-acyl derivative of an amino acid or dipeptide.

Formula PC-(III) describes compounds of Formula PC-(II), in which $R^1$ is (1-4C)alkyl group; $R^2$ and $R^3$ each independently represents a hydrogen atom or a (1-4C)alkyl group; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

Formula PC-(IV) describes compounds of Formula PC-(I), wherein "X" is replaced structurally with certain phenolic opioids.

As also shown herein, Formula PC-(IV) describes compounds of Formula PC-(V), in which $R^1$ is (1-4C)alkyl group; $R^2$ and $R^3$ each independently represents a hydrogen atom or a (1-4C)alkyl group; and $R^5$ represents a hydrogen atom, an N-acyl group, a residue of an amino acid, a dipeptide, or an N-acyl derivative of an amino acid or dipeptide.

Formula PC-(VI) describes compounds of Formula PC-(V), in which $R^1$ is (1-4C)alkyl group; $R^2$ and $R^3$ each independently represents a hydrogen atom or a (1-4C)alkyl group; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

For Formulae PC-(I) to PC-(III), X represents a residue of a phenolic opioid, wherein the hydrogen atom of the phenolic hydroxyl group is replaced by a covalent bond to $-C(O)-NR^1-(C(R^2)(R^3))_n-NH-C(O)-CH(R^4)-NH(R^5)$.

Formulae PC-(VII) to PC-(X)

Examples of phenol-modified opioid prodrugs with a cyclizable spacer leaving group and a cleavable moiety are shown in Formulae PC-(VII) to PC-(X) in which $R^6$ is a trypsin-cleavable moiety. Formulae PC-(VII) to PC-(X) are now described in more detail below.

The embodiments include pharmaceutical compositions, which comprise a compound of general formula PC-(VII):

$$X-C(O)-NR^1-(C(R^2)(R^3))_n-NH-R^6 \quad \text{(PC-(VII))}$$

or a pharmaceutically acceptable salt thereof, in which:

X represents a residue of a phenolic opioid, wherein the hydrogen atom of the phenolic hydroxyl group is replaced by a covalent bond to $-C(O)-NR^1-(C(R^2)(R^3))_n-NHR^6$;

$R^1$ represents a (1-4C)alkyl group;

$R^2$ and $R^3$ each independently represents a hydrogen atom or a (1-4C)alkyl group;

n represents 2 or 3; and $R^6$ is a trypsin-cleavable moiety.

The embodiments provide a pharmaceutical composition, which comprises a compound of general formula PC-(VIII):

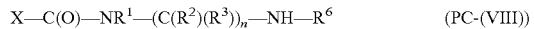

$$X-C(O)-NR^1-(C(R^2)(R^3))_n-NH-R^6 \quad \text{(PC-(VIII))}$$

or a pharmaceutically acceptable salt thereof, in which:

X represents a residue of a phenolic opioid, wherein the hydrogen atom of the phenolic hydroxyl group is replaced by a covalent bond to $-C(O)-NR^1-(C(R^2)(R^3))_n-NHR^6$;

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n represents an integer from 2 to 4; and $R^6$ is a trypsin-cleavable moiety.

The embodiments provide a pharmaceutical composition, which comprises a compound of general formula PC-(IX):

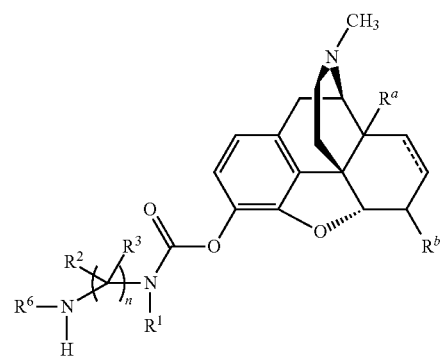

(PC-(IX))

or pharmaceutically acceptable salt thereof, in which:

$R^a$ is hydrogen or hydroxyl;

$R^b$ is oxo (=O) or hydroxyl;

the dashed line is a double bond or single bond;

$R^1$ represents a (1-4C)alkyl group;

$R^2$ and $R^3$ each independently represents a hydrogen atom or a (1-4C)alkyl group;

n represents 2 or 3; and $R^6$ is a trypsin-cleavable moiety.

The embodiments provide a pharmaceutical composition, which comprises a compound of general formula PC-(X):

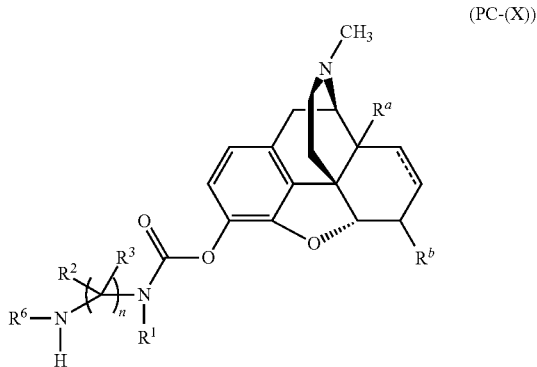

(PC-(X))

or pharmaceutically acceptable salt thereof, in which:

$R^a$ is hydrogen or hydroxyl;

$R^b$ is oxo (=O) or hydroxyl;

the dashed line is a double bond or single bond;

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n represents an integer from 2 to 4; and $R^6$ is a trypsin-cleavable moiety.

In formulae PC-(VII) to PC-(X), $R^6$ is a trypsin-cleavable moiety. A trypsin-cleavable moiety is a structural moiety that is capable of being cleaved by trypsin. In certain instances, a trypsin-cleavable moiety comprises a charged moiety that can fit into an active site of trypsin and is able to orient the prodrug for cleavage at a scissile bond. For instance, the charged moiety can be a basic moiety that exists as a charged moiety at physiological pH.

In certain embodiments, in formulae PC-(VII) to PC-(X), $R^6$ is —C(O)—CH($R^4$)—NH($R^5$), wherein $R^4$ represents a side chain of an amino acid or a derivative of a side chain of an amino acid that effects $R^6$ to be a trypsin-cleavable moiety. A derivative refers to a substance that has been altered from another substance by modification, partial substitution, homologation, truncation, or a change in oxidation state.

For example, to form a trypsin-cleavable moiety, $R^4$ can include, but is not limited to, a side chain of lysine (such as L-lysine), arginine (such as L-arginine), homolysine, homoarginine, and ornithine. Other values for $R^6$ include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines and (bicyclo[2.2.2]octan-1-yl) methanamine and derivatives thereof.

In certain instances, in formulae PC-(VII) to PC-(X), $R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid.

In formulae PC-(VII) to PC-(X), $R^5$ is selected from hydrogen, alkyl, substituted alkyl, acyl, substituted acyl, alkoxycarbonyl, substituted alkoxycarbonyl, aryl, substituted aryl, arylalkyl, and substituted arylalkyl. In certain instances, $R^5$ is an amino acid or an N-acyl derivative of an amino acid. In certain instances, $R^5$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

Formulae PC-(XI) to PC-(XIV)

Examples of phenol-modified opioid prodrugs with a cyclizable spacer leaving group and cleavable moiety are shown in Formulae PC-(XI) to PC-(XIV) in which the cleavable moiety is a GI enzyme-cleavable moiety. Formulae PC-(XI) to PC-(XIV) are now described in more detail below.

The embodiments include pharmaceutical compositions, which comprise a compound of general formula PC-(XI):

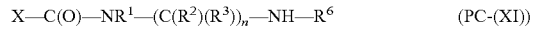

(PC-(XI))

or a pharmaceutically acceptable salt thereof, in which:

X represents a residue of a phenolic opioid, wherein the hydrogen atom of the phenolic hydroxyl group is replaced by a covalent bond to —C(O)—$NR^1$—$(C(R^2)(R^3))_n$—NH—$R^6$;

$R^1$ represents a (1-4C)alkyl group;

$R^2$ and $R^3$ each independently represents a hydrogen atom or a (1-4C)alkyl group;

n represents 2 or 3; and $R^6$ is a GI enzyme-cleavable moiety.

The embodiments provide a pharmaceutical composition, which comprises a compound of general formula PC-(XII):

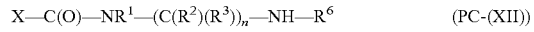

(PC-(XII))

or a pharmaceutically acceptable salt thereof, in which:

X represents a residue of a phenolic opioid, wherein the hydrogen atom of the phenolic hydroxyl group is replaced by a covalent bond to —C(O)—$NR^1$—$(C(R^2)(R^3))_n$—NH—$R^6$;

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n represents an integer from 2 to 4; and $R^6$ is a GI enzyme-cleavable moiety.

The embodiments provide a pharmaceutical composition, which comprises a compound of general formula PC-(XIII):

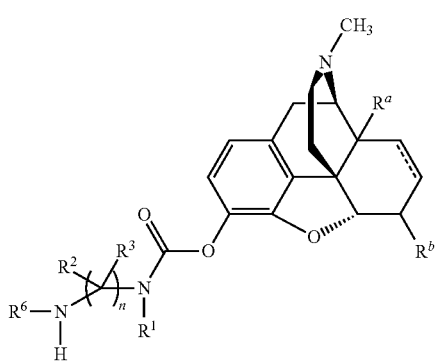

(PC-(XIII))

or pharmaceutically acceptable salt thereof, in which:

$R^a$ is hydrogen or hydroxyl;

$R^b$ is oxo (=O) or hydroxyl;

the dashed line is a double bond or single bond;

$R^1$ represents a (1-4C)alkyl group;

$R^2$ and $R^3$ each independently represents a hydrogen atom or a (1-4C)alkyl group;

n represents 2 or 3; and $R^6$ is a GI enzyme-cleavable moiety.

The embodiments provide a pharmaceutical composition, which comprises a compound of general formula PC-(XIV):

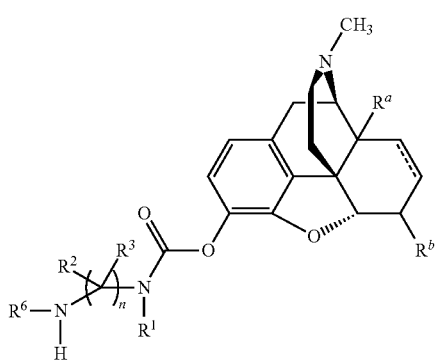

(PC-(XIV))

or pharmaceutically acceptable salt thereof, in which:

$R^a$ is hydrogen or hydroxyl;

$R^b$ is oxo (=O) or hydroxyl;

the dashed line is a double bond or single bond;

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n represents an integer from 2 to 4; and $R^6$ is a GI enzyme-cleavable moiety.

In formulae PC-(XI) to PC-(XIV), $R^6$ is a GI enzyme-cleavable moiety. A GI enzyme-cleavable moiety is a structural moiety that is capable of being cleaved by GI enzyme.

In certain embodiments, in formulae PC-(XI) to PC-(XIV), $R^6$ is —C(O)—CH($R^4$)—NH($R^5$), wherein $R^4$ represents a side chain of an amino acid or a derivative of a side chain of an amino acid that effects $R^6$ to be a GI enzyme-cleavable moiety. A derivative refers to a substance that has been altered from another substance by modification, partial substitution, homologation, truncation, or a change in oxidation state.

For example, to form a GI enzyme-cleavable moiety, $R^4$ can include, but is not limited to, a side chain of lysine (such as L-lysine), arginine (such as L-arginine), homolysine, homoarginine, and ornithine. Other values for $R^6$ include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines, and (bicyclo[2.2.2]octan-1-yl) methanamine and derivatives thereof.

In certain instances, in formulae PC-(XI) to PC-(XIV), $R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid.

In formulae PC-(XI) to PC-(XIV), $R^5$ is selected from hydrogen, alkyl, substituted alkyl, acyl, substituted acyl, alkoxycarbonyl, substituted alkoxycarbonyl, aryl, substituted aryl, arylalkyl, and substituted arylalkyl. In certain instances, $R^5$ is an amino acid or an N-acyl derivative of an amino acid. In certain instances, $R^5$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

Formula PC-(XV)

The embodiments include pharmaceutical compositions, which comprise a compound of general formula PC-(XV) or salts, solvates or hydrates thereof:

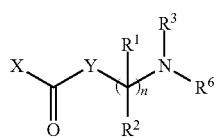

PC-(XV)

wherein:

X is a phenolic opioid, wherein the hydrogen atom of the hydroxyl group is replaced by a covalent bond to —C(O)—Y—(C($R^1$)($R^2$))$_n$—N—($R^3$)($R^6$);

Y is —$NR^5$—, —O— or —S—;

n is an integer from 1 to 4;

each $R^1$, $R^2$, $R^3$ and $R^5$ is independently hydrogen, alkyl, substituted alkyl, aryl or substituted aryl, or $R^1$ and $R^2$ together with the carbon to which they are attached form a cycloalkyl or substituted cycloalkyl group;

$R^6$ is

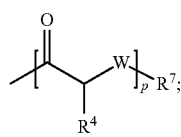

each $R^4$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^4$ and $R^7$ together with the atoms to which they are bonded form a cycloheteroalkyl or substituted cycloheteroalkyl ring;

$R^7$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 10;

each W is independently —$NR^8$—, —O— or —S—; and each $R^8$ is independently hydrogen, alkyl, substituted alkyl, aryl or substituted aryl, or optionally, each $R^4$ and $R^8$ independently together with the atoms to which they are bonded form a cycloheteroalkyl or substituted cycloheteroalkyl ring.

Compounds of Formula PC-(XV) are also described in WO 2007/140272, which is herein incorporated by reference in its entirety.

General Synthetic Procedures for Compounds of Formulae PC-(I) to PC-(XV)

Compounds of formula PC-(I) are particular prodrugs described in WO 2007/140272 and the synthesis of compounds of formula PC-(I) are described therein.

The synthetic schemes and procedure in WO 2007/140272 can also be used to synthesize compounds of formulae PC-(II) to PC-(XV). The compounds described herein may be obtained via the routes generically illustrated in Scheme PC-1.

The promoieties described herein, may be prepared and attached to drugs containing phenols by procedures known to those of skill in the art (See e.g., Green et al., "Protective Groups in Organic Chemistry," (Wiley, 2$^{nd}$ ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, (Wiley Interscience); Trost et al., "Comprehensive Organic Synthesis," (Pergamon Press, 1991); "Theilheimer's Synthetic Methods of Organic Chemistry," Volumes 1-45, (Karger, 1991); March, "Advanced Organic Chemistry," (Wiley Interscience), 1991; Larock "Comprehensive Organic Transformations," (VCH Publishers, 1989); Paquette, "Encyclopedia of Reagents for Organic Synthesis," (John Wiley & Sons, 1995), Bodanzsky, "Principles of Peptide Synthesis," (Springer Verlag, 1984); Bodanzsky, "Practice of Peptide Synthesis," (Springer Verlag, 1984). Further, starting materials may be obtained from commercial sources or via well established synthetic procedures, supra.

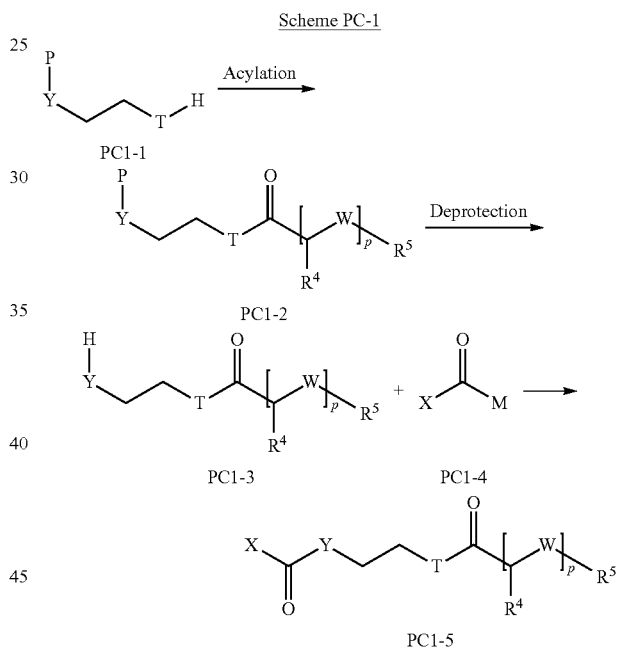

Scheme PC-1

Referring now to Scheme PC-1 and formula PC-(I), supra, where for illustrative purposes T is NH, Y is NR', W is NH, p is one, $R^1$, $R^4$, and $R^5$ are as previously defined, X is a phenolic opioid, P is a protecting group, and M is a leaving group, compound PC1-1 may be acylated with an appropriate carboxylic acid or carboxylic acid equivalent to provide compound PC1-2 which then may be deprotected to yield compound PC1-3. Compound PC1-3 is then reacted with an activated carbonic acid 'equivalent PC1-4 to provide compound PC1-5.

For compounds of formula PC-(II) to PC-(VI), —$C(R_2)(R_3))_n$— corresponds to —$(CH_2—CH_2)$— portion between Y and T. Thus, for the synthesis of compounds of formulae PC-(II) to PC-(VI), compound PC1-1 would have the appropriate entities for —$(C(R_2)(R_3))_n$— to result in the synthesis of compounds of formulae PC-(II) to PC-(VI). Compounds of formulae PC-(VII) to PC-(XV) can also be synthesized using the methods disclosed in the schemes herein.

Phenol-Modified Opioid Prodrugs with Promoiety Comprising an Electronically Decoupling Spacer and Cleavable Moiety The disclosure provides for prodrugs of phenolic opioids which are functionalized with a promoiety in which the promoiety includes a spacer group and a cleavable moiety where the spacer group may, inter alia, electronically decouple and/or physically separate the active agent from the cleavable moiety. Accordingly, a prodrug disclosed herein generally comprises an opioid attached through a heteroatom to a spacer which is further attached to a cleavable moiety. In one embodiment, the cleavable moiety is a GI enzyme cleavable moiety, such as a trypsin cleavable moiety.

A wide variety of spacers are known in the art, and include by way of example and not limitation, alkyl, heteroalkyl, acyclic heteroatomic bridges, aryl, arylaryl, arylalkyl, heteroaryl, heteroarylalkyl, alcohols, amines and the like. Thus, spacers may include, for example, single, double, triple or aromatic carbon-carbon bonds, nitrogen-nitrogen bonds, carbon-nitrogen bonds, carbon-oxygen bonds and/or carbon-sulfur bonds, and may therefore include functionalities such as carbonyls, ethers, thioethers, carboxamides, sulfonamides, ureas, urethanes, hydrazines, etc. In one embodiment, the spacers can be alcohols or amines, which can quench the quinone methide. Examples of suitable spacers include, but are not limited to, aryl, biaryl, heteroaryl, etc.

The cleavable moiety may comprise an amino acid, a peptide, an ester, a polyester, a thioester, a polythioester or any other cleavable group known to those of skill in the art. Generally, the cleavable moiety can be cleaved under physiological conditions. The cleavable moiety may be cleaved chemically (e.g., hydrolysis) or enzymatically. In some embodiments, the cleavable moiety is cleaved enzymatically. Generally, the compounds described herein are stable in aqueous solution, but not so stable that the cleavable moiety can not be cleaved chemically (e.g., hydrolysis) or enzymatically.

Formula PC-(XVI)

The embodiments provide a compound of general formula PC-(XVI):

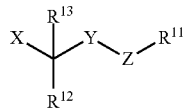

(PC-(XVI))

or salts, solvates or hydrates thereof wherein:

X is an opioid comprising a phenol wherein a hydrogen atom of the phenol is replaced by a covalent bond to —$(CR^{12}R^{13})$—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Y is aryl, heteroaryl or arylaryl optionally substituted with one or more —F, —Cl, —Br, —I, $R^{14}$, $O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ or —$C(NR^{16})NR^{15}R^{14}$;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{14}$ and $R^{15}$ together with the nitrogen atom to which they are bonded form a cycloheteroalkyl or substituted cycloheteroalkyl ring;

Z is $N(R^{18})$—, —O— or —S—;

$R^{18}$ is hydrogen, alkyl, substituted alkyl, aryl, substituted aryl, arylalkyl, substituted arylalkyl, heteroaryl, substituted heteroaryl, heteroarylalkyl or substituted heteroarylalkyl or

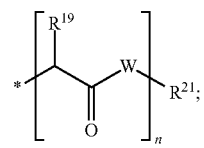

each W is independently —$NR^{20}$—, —O— or —S—;

each $R^{19}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{19}$ and $R^{20}$ together with the atoms to which they are bonded form a cycloheteroalkyl or substituted cycloheteroalkyl ring;

each $R^{20}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{20}$ and $R^{21}$ together with the atoms to which they are bonded form a cycloheteroalkyl or substituted cycloheteroalkyl ring;

$R^{21}$ is hydrogen, alkyl, substituted alkyl, aryl, substituted aryl, arylalkyl or substituted arylalkyl;

n is an integer from 0 to 5;

$R^{11}$ is

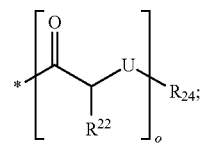

each U is independently —$NR^{23}$—, —O— or —S—;

each $R^{22}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{22}$ and $R^{23}$ together with the atoms to which they are bonded form a cycloheteroalkyl or substituted cycloheteroalkyl ring;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{23}$ and $R^{24}$ together with the atoms to which they are bonded form a cycloheteroalkyl or substituted cycloheteroalkyl ring;

$R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100;

provided that Z is oriented para or ortho to X—$(CR^{12}R^{13})$— and that both $R^{18}$ and $R^{11}$ are not hydrogen.

Formula PC-(XVII)

The embodiments provide a compound of general formula PC-(XVII):

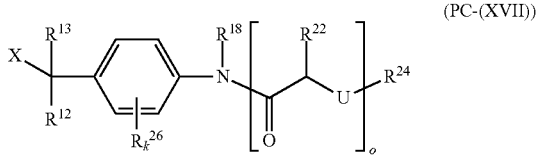

(PC-(XVII))

or salts, solvates or hydrates thereof wherein:

X is an opioid comprising a phenol, wherein X is connected by the phenol;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

$R_k^{26}$ are each independently selected from the group consisting of one or more of —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O)_2O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ and —$C(NR^{16})NR^{15}R^{14}$, and k is 0, 1, 2, 3, or 4;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^4$ and $R^5$ together with the nitrogen atom to which they are bonded form a cycloheteroalkyl or substituted cycloheteroalkyl ring;

$R^{18}$ is hydrogen or methyl;

$R^{22}$ is a side chain of an amino acid or a derivative of a side chain of an amino acid;

each U is independently —$NR^{23}$—, —O— or —S—;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{23}$ and $R^{24}$ together with the atoms to which they are bonded form a cycloheteroalkyl or substituted cycloheteroalkyl ring; and $R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100.

In formulae PC-(XVI) and PC-(XVII), $R^{22}$ can represent a side chain of an amino acid. Amino acids, including amino acid variants, are discussed in a section herein. In certain embodiments, $R^{22}$ is a derivative of a side chain of an amino acid. Such derivatives are described herein.

In certain embodiments, in formulae PC-(XVI) and PC-(XVII), $R^{22}$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, $R^{22}$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine. In certain embodiments, $R^{22}$ is a derivative of a side chain of an amino acid. Such derivatives are described herein.

In certain instances, in formulae PC-(XVI) and PC-(XVII), $R^{22}$ represents —$CH_2CH_2CH_2NH(C$=$NH)NH_2$ or —$CH_2CH_2CH_2CH_2NH_2$, the configuration of the carbon atom to which $R^{22}$ is attached corresponding with that in an L-amino acid.

In formulae PC-(XVI) and PC-(XVII), —CO—C($R^{22}$)—U—$R^{24}$ is a GI enzyme-cleavable moiety. A GI enzyme-cleavable moiety is a structural moiety that is capable of being cleaved by a GI enzyme. In certain instances, a GI enzyme-cleavable moiety comprises a charged moiety that can fit into an active site of a GI enzyme and is able to orient the prodrug for cleavage at a scissile bond. For instance, the charged moiety can be a basic moiety that exists as a charged moiety at physiological pH. For example, to form a GI enzyme-cleavable moiety, $R^{22}$ can include, but is not limited to, a side chain of lysine (such as L-lysine), a side chain of arginine (such as L-arginine), a side chain of homolysine, a side chain of homoarginine, and a side chain of ornithine. Other values for GI enzyme-cleavable moieties include, but are not limited to, arginine homologues, arginine truncates, arginine with varying oxidation states (for instance, metabolites), lysine homologues, lysine truncates, and lysine with varying oxidation states (for instance, metabolites). Examples of arginine and lysine mimics include arylguanidines, arylamidines (substituted benzamidines), benzylamines and (bicyclo[2.2.2]octan-1-yl)methanamine and derivatives thereof.

In certain instances, in formulae PC-(XVI) and PC-(XVII), $R^{24}$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

General Synthetic Procedures for Compounds of Formulae PC-(XVI) to PC-(XVII)

The compounds described herein may be obtained via the synthetic methods illustrated in Schemes PCQ-1-2. The promoieties described herein, may be prepared and attached to active agents by established procedures known to those of skill in the art (See e.g., Green et al., "Protective Groups in Organic Chemistry", (Wiley, 2nd ed. 1991); Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991;

"Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995, Bodanzsky, "Principles of Peptide Synthesis," Springer Verlag, 1984; Bodanzsky, "Practice of Peptide Synthesis," Springer Verlag, 1984).

Other methods for synthesis of the prodrugs described herein will be readily apparent to the skilled artisan and may be used to synthesize the compounds described herein. Accordingly, the methods presented in the Schemes herein are illustrative rather than comprehensive.

Scheme PCQ-1

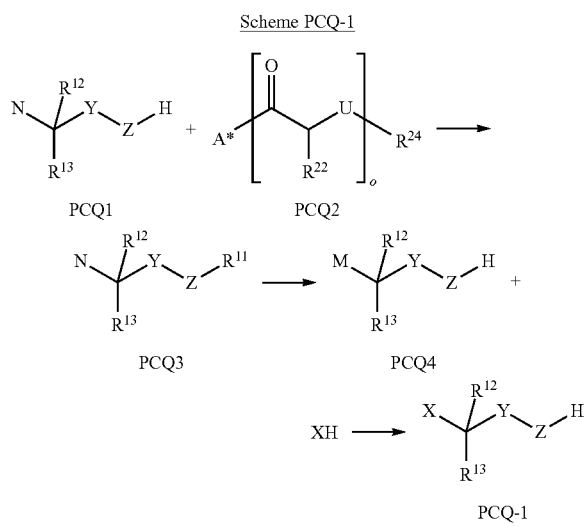

As illustrated in Scheme PCQ-1, supra, one method of synthesis of a prodrug of Formula PCQ-I. Here, compound PCQ1 where N is a capable of being converted to a leaving group, and $R^2$, $R^3$, Y and Z are as previously defined and compound PCQ2 where A, $R^{12}$, $R^{14}$, U and o are as previously defined are reacted under standard conditions to provide functionalized derivative. Compound PCQ3 is converted to compound PCQ4 under standard conditions then now reacted with active agent XH under conventional conditions to provide a prodrug of Formula PCQ-I. The active agent XH may be purchased from commercial sources or synthesized using known procedures.

Scheme PCQ-2

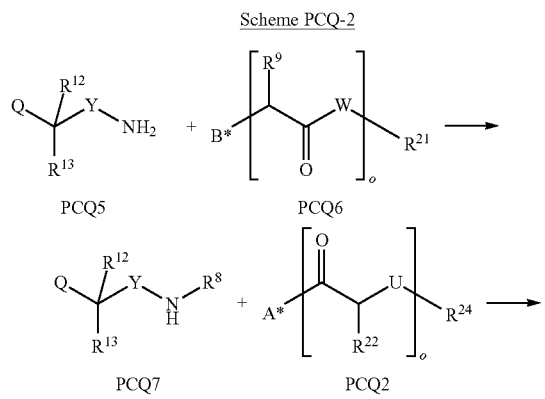

-continued

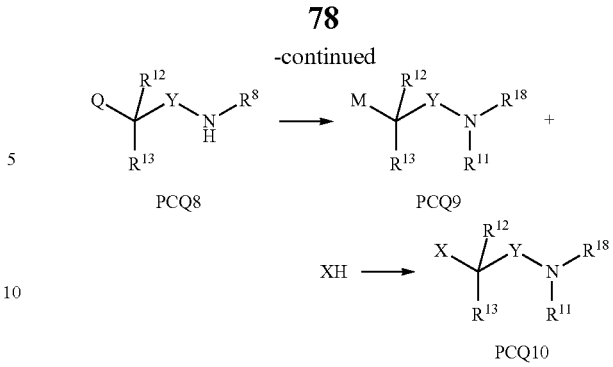

Shown above in Scheme PCQ-2 is a synthetic strategy for synthesizing compound PCQ10 where Z is $NR^1R^8$. Here, compound PCQ5 where Q is a capable of being converted to a leaving group, and $R^2$, $R^3$, and Y are as previously defined and compound PCQ6 where B, $R^{12}$, $R^{11}$, W and n are as previously defined are reacted under standard conditions to form compound PCQ7. Compound PCQ7 may be reacted under conventional conditions with compound PCQ2 to yield compound PCQ8. Compound PCQ8 is converted to compound PCQ9 under standard conditions then now reacted with active agent XH under conventional conditions to provide a prodrug of compound PCQ10.

Phenol-Modified Opioid Prodrugs with Promoiety Comprising Electronically Decoupling Spacer, Cyclizable Spacer Leaving Group, and Cleavable Moiety The embodiments provide a compound of general formula PC-(XVIII):

$$X—C(R^{31a})(R^{32a})—Ar—Z—C(O)—Y—(C(R^{31})(R^{32}))_n—N—(R^{33})(R^{34})A-$$  (PC-(XVIII))

or a salt, hydrate or solvate thereof wherein:

X is an opioid comprising a phenol wherein a hydrogen atom of the phenol is replaced by a covalent bond to —$C(R^{31a})(R^{32a})$—Ar—Z—C(O)—Y—$(C(R^{31})(R^{32}))_n$—N—$(R^{33})(R^{34})$;

$R^{31a}$ and $R^{32a}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Ar is aryl, heteroaryl or arylaryl optionally substituted with one or more —F, —Cl, —Br, —I, —$R^{34a}$, —$O^-$, —$OR^{34a}$, —$SR^{34a}$, —$S^-$, —$NR^{34a}R^{35a}$, —$CF_3$, —CN, —OCN, —SCN, —NO, —$NO_2$, —$N_3$, —$S(O)_2O'$, —$S(O)_2OH$, —$S(O)_2R^{34a}$, —$OS(O_2)O''$, —$OS(O)_2R^{34a}$, —$P(O)(O'')_2$, —$P(O)(OR^{34a})(O'')$, —$OP(O)(OR^{34a})(OR^{35a})$, —$C(O)R^{34a}$, —$C(S)R^{34a}$, —$C(O)OR^{34a}$, —$C(O)NR^{34a}R^{35a}$, —C(O)O; —$C(S)OR^{34a}$, —$NR^{36a}C(O)NR^{34a}R^{35a}$, —$NR^{36a}C(S)NR^{34a}R^{35a}$, —$NR^{37a}C(NR^{36a})NR^{35a}R^{34a}$ or —$C(NR^{36a})NR^{35a}R^{34a}$, or tethered to a polymer;

$R^{34a}$, $R^{35a}$, $R^{36a}$ and $R^{37a}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{34}$ and $R^{35}$ together with the nitrogen atom to which they are bonded form a cycloheteroalkyl or substituted cycloheteroalkyl ring;

Z is O, S or NH;

Y is —$NR^{35}$—, —O— or —S—;

n is an integer from 1 to 10;

each $R^{31}$, $R^{32}$, $R^{33}$ and $R^{35}$ is independently hydrogen, alkyl, substituted alkyl, aryl or substituted aryl, or $R^{31}$ and $R^{32}$ together with the carbon to which they are attached form a cycloalkyl or substituted cycloalkyl group, or two $R^{31}$ or $R^{32}$ groups on adjacent carbon atoms, together with the carbon atoms to which they are attached, form a cycloalkyl or substituted cycloalkyl group;

$R^{34}$ is

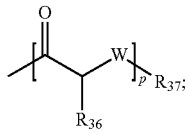

each $R^{36}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{36}$ and $R^{37}$ together with the atoms to which they are bonded form a cycloheteroalkyl or substituted cycloheteroalkyl ring;

$R^{37}$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 100;

each W is independently —$NR^{38}$—, —O— or —S—;

each $R^{38}$ is independently hydrogen, alkyl, substituted alkyl, aryl or substituted aryl, or optionally, each $R^{36}$ and $R^{38}$ independently together with the atoms to which they are bonded form a cycloheteroalkyl or substituted cycloheteroalkyl ring; and A' represents an anion.

In the compounds of formula PC-(XVIII), the phenol in an opioid has been substituted with a spacer group bearing a nitrogen nucleophile that is protected with an enzymatically-cleavable moiety ($R^{34}$), the configuration of the spacer leaving group and nitrogen nucleophile being such that, upon enzymatic cleavage of the cleavable moiety, the nitrogen nucleophile is capable of liberating the compound from the spacer leaving group so as to provide the patient with controlled release of the compound.

It will be appreciated that when the N—$R^{34}$ amide bond is cleaved enzymatically, the nitrogen nucleophile is freed and cyclises back onto the carbonyl group, forming the cyclic urea and releasing the compound, but this released compound undergoes a spontaneous 1,6-elimination to release the opioid.

General Synthetic Procedures for Compounds of Formulae PC-(XVIII)

The compounds described herein may be obtained via the routes generically illustrated in Schemes PCH-1-4.

The promoieties described herein, may be prepared and attached to compounds containing phenols by procedures known to those of skill in the art (See e.g., Green et al., "Protective Groups in Organic Chemistry," (Wiley, 2$^{nd}$ ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, (Wiley Interscience); Trost et al., "Comprehensive Organic Synthesis," (Pergamon Press, 1991); "Theilheimer's Synthetic Methods of Organic Chemistry," Volumes 1-45, (Karger, 1991); March, "Advanced Organic Chemistry," (Wiley Interscience), 1991; Larock "Comprehensive Organic Transformations," (VCH Publishers, 1989); Paquette, "Encyclopedia of Reagents for Organic Synthesis," (John Wiley & Sons, 1995), Bodanzsky, "Principles of Peptide Synthesis," (Springer Verlag, 1984); Bodanzsky, "Practice of Peptide Synthesis," (Springer Verlag, 1984). Further, starting materials may be obtained from commercial sources or via well established synthetic procedures, supra.

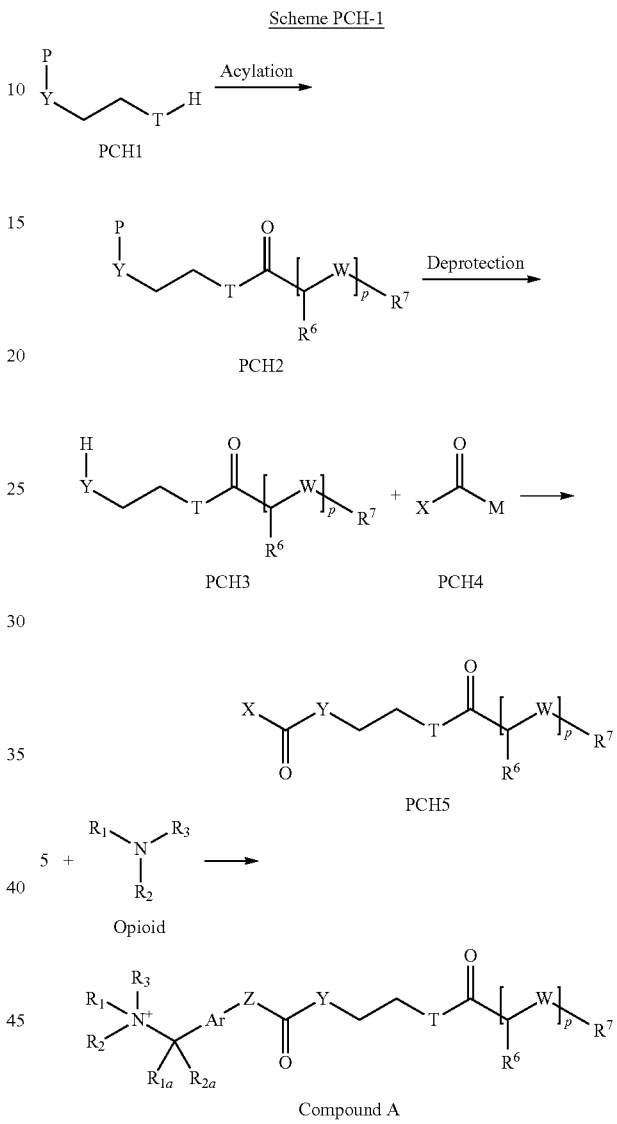

Referring now to Scheme PCH-1 and formula PC-(XXI), supra, where for illustrative purposes T is —$NR^3$, Y is $NR^5$, —O— or —S—, W is $NR^8$, —O— or —S—, n is 2, $R^1$ and $R^2$ are hydrogen, p, $R^3$, $R^5$, $R^6$, $R^7$ and $R^8$ are as previously defined, $R_1R_2R_{3N}$— represents a residue of an opioid, X is an appropriate optionally substituted phenol, optionally substituted thiol, or optionally substituted aniline (e.g. a compound of formula HO—(C(R1a)(R2a))—Ar—ZH), P is a protecting group, and M is a leaving group, compound PCH1 may be acylated with an appropriate carboxylic acid or carboxylic acid equivalent to provide compound PGH2 which then may be deprotected to yield compound PCH3. Compound PCH3 is then reacted with an activated carbonic acid equivalent PCH4 to provide desired compound PCH5. Compound PCH5 is then coupled to the tertiary nitrogen of an opioid to complete the synthesis of Compound PCH-A.

Scheme PCH-2

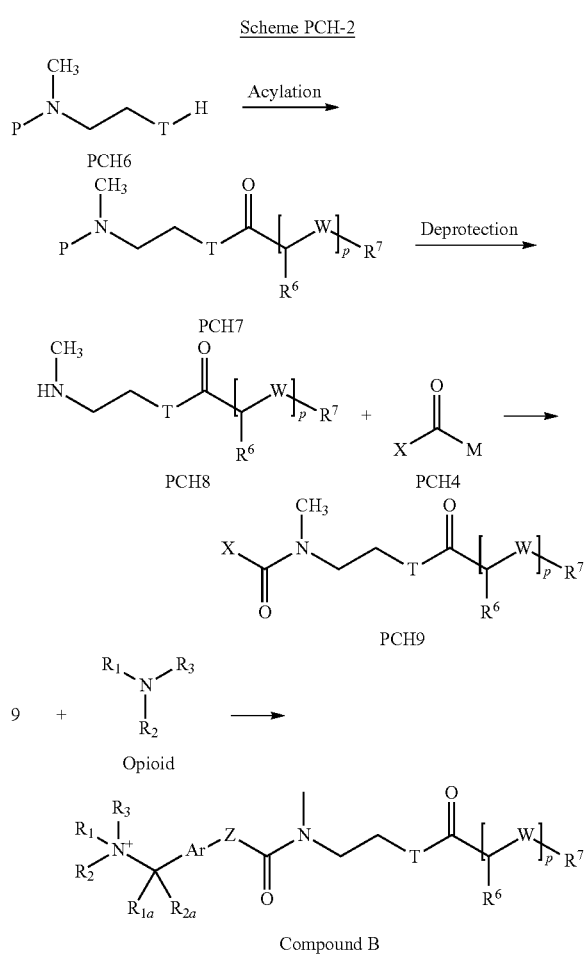

Referring now to Scheme PCH-2 and formula PC-(XXI), supra, where for illustrative purposes T is —NR$^3$, Y is NCH$_3$, W is NR$^8$, —O— or —S—, n is 2, R$^1$ and R$^2$ are hydrogen, p, R$^3$, R$^6$, R$^7$ and R$^8$ are as previously defined, R$_1$R$_2$R$_{3N}$— represents a residue of an opioid, X is an appropriately substituted phenol, optionally substituted thiol, or optionally substituted aniline, P is a protecting group, and M is a leaving group, compound PCH6 is acylated with an appropriate carboxylic acid or carboxylic acid equivalent to provide compound PCH7. Compound PCH7 is then deprotected and reacted with activated carbonic acid equivalent PCH4 to provide desired compound PCH9. Compound PCH9 is then coupled to the tertiary nitrogen of an opioid to complete the synthesis of Compound PCH-B.

Scheme PCH-3

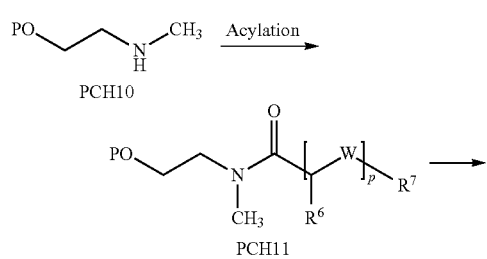

Referring now to Scheme PCH-3 and formula PC-(XXI), supra, where for illustrative purposes T is NCH$_3$, Y is NR$^5$, —O— or —S—, W is NR$^8$, —O— or —S—, n is 2, R$^1$ and R$^2$ are hydrogen, p, R$^5$, R$^6$, R$^7$ and R$^8$ are as previously defined, R$_1$R$_2$R$_{3N}$— represents a residue of an opioid, X is an appropriate optionally substituted phenol, optionally substituted thiol, or optionally substituted aniline, P is a protecting group, and M is a leaving group, compound PCH10 is acylated with an appropriate carboxylic acid or carboxylic acid equivalent to provide compound PCH11 which after deprotection and functional group intraconversion, if necessary, is converted to compound PCH12. Reaction of compound PCH12 with activated carbonic acid equivalent PCH4 provides desired compound PCH13. Compound PCH13 is then coupled to the tertiary nitrogen of an opioid to complete the synthesis of Compound PCH-C.

Scheme PCH-4

-continued

Compound D

Referring now to Scheme PCH-4 and formula PC-(XXI), supra, where for illustrative purposes T and Y are NCH$_3$, W is NR$^8$, —O— or —S—, n is 2, R$^1$ and R$^2$ are hydrogen, p, R$^6$, R$^7$ and R$^8$ are as previously defined, R$_1$R$_2$R$_{3N}$— represents a residue of an opioid, X is an appropriate optionally substituted phenol, optionally substituted thiol, or optionally substituted aniline, P is a protecting group, and M is a leaving group, compound PCH14 is acylated with an appropriate carboxylic acid or carboxylic acid equivalent to provide compound PCH15. Reaction of compound PCH15 with activated carbonic acid equivalent PCH4 provides desired compound PCH16. Compound PCH16 is then coupled to the tertiary nitrogen of an opioid to complete the synthesis of Compound PCH-D.

Examples of Phenol-modified Opioid Prodrugs.

Examples of certain phenol-modified opioid prodrugs are shown below. In formulae CC-(XV) to CC-(XXVIII), AA can represent a side chain of an amino acid. Amino acids, including amino acid variants, are discussed in a section herein.

Formula CC-(XV)
A certain example is a compound of Formula CC-(XV):

CC-(XV)

wherein
X represents a residue of a phenolic opioid, wherein the hydrogen atom of the phenol group is replaced by a covalent bond to —C(O)—CH(AA)-NR$^{cc1}$R$^{cc2}$; AA is a side chain of an amino acid; and
R$^{cc1}$ and R$^{cc2}$ are independently selected from hydrogen, alkyl, substituted alkyl, aryl, substituted aryl, acyl, arylalkyl, and substituted arylalkyl.

Formula CC-(XVI)
A certain example is a compound of formula CC-(XVI):

CC-(XVI)

wherein
X represents a residue of a phenolic opioid, wherein the hydrogen atom of the hydroxyl group is replaced by a covalent bond to —C(O)—N(R$^{cc3}$)—CH(AA)-C(O)—Z;
R$^{cc3}$ is selected from selected from hydrogen, alkyl, substituted alkyl, aryl, substituted aryl, acyl, arylalkyl, and substituted arylalkyl;
AA is a side chain of an amino acid;

Z is selected from NH—R$^{cc4}$, O—R$^{cc4}$, OH, and NH$_2$; and
R$^{cc4}$ is selected from selected from hydrogen, alkyl, substituted alkyl, aryl, substituted aryl, acyl, arylalkyl, and substituted arylalkyl.

Formula CC-(XVII)
A certain example is a compound of formula CC-(XVII):

CC-(XVII)

wherein
X represents a residue of a phenolic opioid, wherein the hydrogen atom of the phenol group is replaced by a covalent bond to —C(O)—O—R$^{cc5}$; and
R$^{cc5}$ is selected from Formula CC-(XVIII)
A certain example is a compound of formula CC-(XVIII):

CC-(XVIII)

wherein
X represents a residue of a phenolic opioid, wherein the hydrogen atom of the hydroxyl group is replaced by a covalent bond to the benzoyl group; and
Z is amidino or guanidino.

Formula CC-(XIX)
A certain example is a compound of formula CC-(XIX):

CC-(XIX)

wherein

X represents a residue of a phenolic opioid, wherein the hydrogen atom of the hydroxyl group is replaced by a covalent bond to the carbonyl group;

$R^{cc6}$ and $R^{cc7}$ are independently selected from hydrogen, alkyl, substituted alkyl, aryl, substituted aryl, arylalkyl, and substituted arylalkyl;

n is a number from zero to 2;

Z is O or NH;

AA is a side chain of an amino acid; and $R^{cc8}$ is selected from hydrogen, alkyl, substituted alkyl, aryl, substituted aryl, acyl, arylalkyl, and substituted arylalkyl.

Formula CC-(XX)

A certain example is a compound of formula CC-(XX):

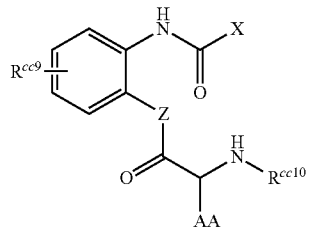

CC-(XX)

wherein

X represents a residue of a phenolic opioid, wherein the hydrogen atom of the hydroxyl group is replaced by a covalent bond to the carbonyl group;

$R^{cc9}$ is selected from hydrogen, alkyl, substituted alkyl, aryl, substituted aryl, arylalkyl, and substituted arylalkyl;

Z is O or NH;

AA is a side chain of an amino acid; and $R^{cc10}$ is selected from hydrogen, alkyl, substituted alkyl, aryl, substituted aryl, acyl, arylalkyl, and substituted arylalkyl.

Formula CC-(XXI)

A certain example is a compound of formula CC-(XXI):

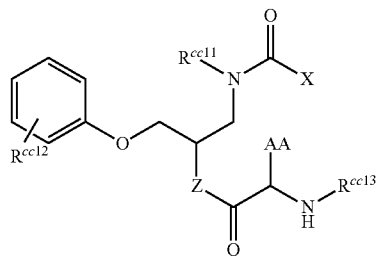

CC-(XXI)

wherein

X represents a residue of a phenolic opioid, wherein the hydrogen atom of the hydroxyl group is replaced by a covalent bond to the carbonyl group;

$R^{cc11}$ and $R^{cc12}$ are independently selected from hydrogen, alkyl, substituted alkyl, aryl, substituted aryl, arylalkyl, and substituted arylalkyl;

$R^{cc13}$ is selected from hydrogen, alkyl, substituted alkyl, aryl, substituted aryl, acyl, arylalkyl, and substituted arylalkyl;

Z is O or NH; and

AA is a side chain of an amino acid.

Formula CC-(XXII)

A certain example is a compound of formula CC-(XXII):

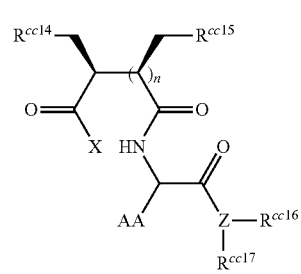

CC-(XXII)

wherein

X represents a residue of a phenolic opioid, wherein the hydrogen atom of the hydroxyl group is replaced by a covalent bond to the carbonyl group;

$R^{cc14}$ and $R^{cc15}$ are independently selected from hydrogen, alkyl, substituted alkyl, aryl, substituted aryl, arylalkyl, and substituted arylalkyl;

n is a number from zero to 2;

AA is a side chain of an amino acid; and

Z is O or N;

$R^{cc16}$ and $R^{cc17}$ are independently selected from hydrogen, alkyl, substituted alkyl, aryl, substituted aryl, acyl, arylalkyl, and substituted arylalkyl, wherein if Z is O, then $R^{cc17}$ is not present.

Formula CC-(XXIII)

A certain example is a compound of formula CC-(XXIII):

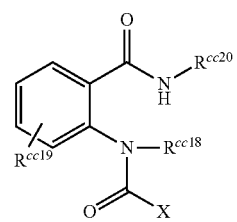

CC-(XXIII)

wherein

X represents a residue of a phenolic opioid, wherein the hydrogen atom of the hydroxyl group is replaced by a covalent bond to the carbonyl group;

$R^{cc18}$, $R^{cc19}$, $R^{cc20}$ are independently selected from hydrogen, alkyl, substituted alkyl, aryl, substituted aryl, arylalkyl, and substituted arylalkyl.

Formula CC-(XXIV)

A certain example is a compound of formula CC-(XXIV):

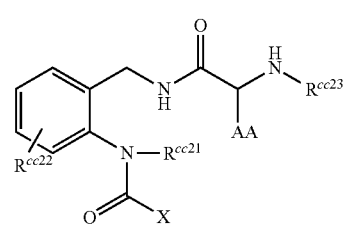

CC-(XXIV)

wherein

X represents a residue of a phenolic opioid, wherein the hydrogen atom of the hydroxyl group is replaced by a covalent bond to the carbonyl group;

$R^{cc21}$ and $R^{cc22}$ are independently selected from hydrogen, alkyl, substituted alkyl, aryl, substituted aryl, arylalkyl, and substituted arylalkyl;

$R^{cc23}$ is selected from hydrogen, alkyl, substituted alkyl, aryl, substituted aryl, acyl, arylalkyl, and substituted arylalkyl; and AA is a side chain of an amino acid.

Formula CC-(XXV)

A certain example is a compound of formula CC-(XXV):

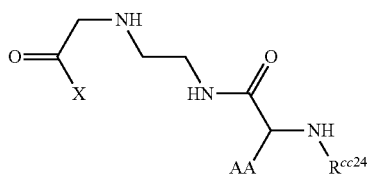

CC-(XXV)

wherein

X represents a residue of a phenolic opioid, wherein the hydrogen atom of the hydroxyl group is replaced by a covalent bond to the carbonyl group;

$R^{cc24}$ is selected from hydrogen, alkyl, substituted alkyl, aryl, substituted aryl, acyl, arylalkyl, and substituted arylalkyl; and AA is a side chain of an amino acid.

Formula CC-(XXVI)

A certain example is a compound of formula CC-(XXVI):

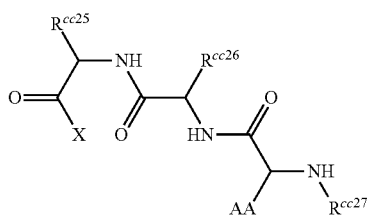

CC-(XXVI)

wherein

X represents a residue of a phenolic opioid, wherein the hydrogen atom of the hydroxyl group is replaced by a covalent bond to the carbonyl group;

$R^{cc25}$ and $R^{cc26}$ are independently selected from hydrogen, alkyl, substituted alkyl, aryl, substituted aryl, arylalkyl, and substituted arylalkyl;

$R^{cc27}$ is selected from hydrogen, alkyl, substituted alkyl, aryl, substituted aryl, acyl, arylalkyl, and substituted arylalkyl; and AA is a side chain of an amino acid.

Formula CC-(XXVII)

A certain example is a compound of formula CC-(XXVII):

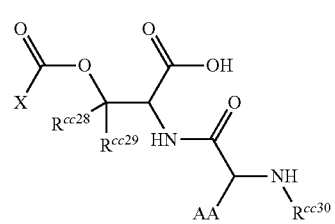

CC-(XXVII)

wherein

X represents a residue of a phenolic opioid, wherein the hydrogen atom of the hydroxyl group is replaced by a covalent bond to the carbonyl group;

$R^{cc28}$ and $R^{cc29}$ are independently selected from hydrogen, alkyl, substituted alkyl, aryl, substituted aryl, arylalkyl, and substituted arylalkyl;

$R^{cc30}$ is selected from hydrogen, alkyl, substituted alkyl, aryl, substituted aryl, acyl, arylalkyl, and substituted arylalkyl; and AA is a side chain of an amino acid.

Formula CC-(XXVIII)

A certain example is a compound of formula CC-(XXVIII):

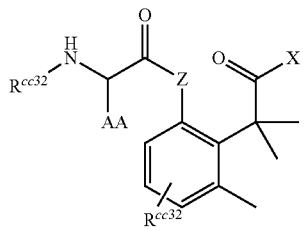

CC-(XXVIII)

wherein

X represents a residue of a phenolic opioid, wherein the hydrogen atom of the hydroxyl group is replaced by a covalent bond to the carbonyl group;

$R^{cc31}$ is selected from hydrogen, alkyl, substituted alkyl, aryl, substituted aryl, arylalkyl, and substituted arylalkyl;

Z is O or NH;

$R^{cc32}$ is selected from hydrogen, alkyl, substituted alkyl, aryl, substituted aryl, acyl, arylalkyl, and substituted arylalkyl; and AA is a side chain of an amino acid.

Ketone-Modified Opioid Prodrugs

The disclosure provides a ketone-modified opioid prodrug which provides enzymatically-controlled release of a ketone-containing opioid. As used herein, a ketone-containing opioid is an opioid containing an enolizable ketone group. In a ketone-modified opioid prodrug, a promoiety is attached to the ketone-containing opioid through the enolic oxygen atom of the ketone moiety. In a ketone-modified opioid prodrug, the hydrogen atom of the corresponding enolic group of the ketone-containing opioid is replaced by a covalent bond to a promoiety.

As disclosed herein, a trypsin-cleavable ketone-modified opioid prodrug is a ketone-modified opioid prodrug that comprises a promoiety comprising a trypsin-cleavable moiety, i.e., a moiety having a site susceptible to cleavage by trypsin.

Such a prodrug comprises a ketone-containing opioid covalently bound to a promoiety comprising a trypsin-cleavable moiety, wherein cleavage of the trypsin-cleavable moiety by trypsin mediates release of the drug. Cleavage can initiate, contribute to or effect drug release.

Ketone-Modified Opioid Prodrugs with Promoiety Comprising Cyclizable Spacer Leaving Group and Cleavable Moiety According to certain embodiments, there is provided a ketone-modified opioid prodrug which provides enzymatically-controlled release of a ketone-containing opioid. The disclosure provides for a ketone-modified opioid in which the promoiety comprises a cyclizable spacer leaving group and a cleavable moiety. In certain embodiments, the ketone-containing opioid is a corresponding compound in which the enolic oxygen atom has a substituent which is a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide a ketone-containing opioid.

The corresponding prodrug provides post administration-activated, controlled release of the ketone-containing opioid. The prodrug requires enzymatic cleavage to initiate release of the ketone-containing opioid and thus the rate of release of the ketone-containing opioid depends upon both the rate of enzymatic cleavage and the rate of cyclization. Accordingly, the prodrug has reduced susceptibility to accidental overdosing or abuse, whether by deliberate overdosing, administration through an inappropriate route, such as by injection, or by chemical modification using readily available household chemicals. The prodrug is configured so that it will not provide excessively high plasma levels of the active drug if it is administered inappropriately, and cannot readily be decomposed to afford the active drug other than by enzymatic cleavage followed by controlled cyclization.

The enzyme-cleavable moiety linked to the nitrogen nucleophile through an amide bond can be, for example, a residue of an amino acid or a peptide, or an (alpha) N-acyl derivative of an amino acid or peptide (for example an N-acyl derivative of a pharmaceutically acceptable carboxylic acid). The peptide can contain, for example, up to about 100 amino acid residues. Each amino acid can advantageously be a naturally occurring amino acid, such as an L-amino acid. Examples of naturally occurring amino acids are alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. Accordingly, examples of enzyme-cleavable moieties include residues of the L-amino acids listed hereinabove and N-acyl derivatives thereof, and peptides formed from at least two of the L-amino acids listed hereinabove, and the N-acyl derivatives thereof.

The cyclic group formed when the ketone-containing opioid is released is conveniently pharmaceutically acceptable, in particular a pharmaceutically acceptable cyclic urea. It will be appreciated that cyclic ureas are generally very stable and have low toxicity.

Formulae KC-(I) and KC-(II)

The compositions of the present disclosure include compounds of formulae KC-(I) and KC-(II) shown below. Compounds of formulae KC-(I) and KC-(II) are prodrugs of oxycodone and hydrocodone. Pharmaceutical compositions and methods of the present disclosure also contemplate compounds of formulae KC-(I) and KC-(II).

Formula KC-(I)

In one of its composition aspects, the present embodiments provide a compound of formula KC-(Ia):

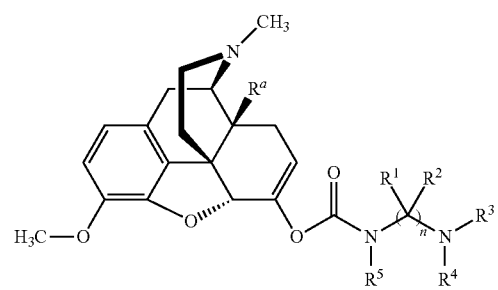

(KC-(Ia))

wherein:

$R^a$ is hydrogen or hydroxyl;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen or (1-4C)alkyl;

$R^4$ is

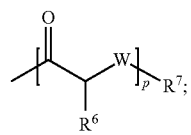

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In one of its composition aspects, the present embodiments provide a compound of formula KC-(Ib):

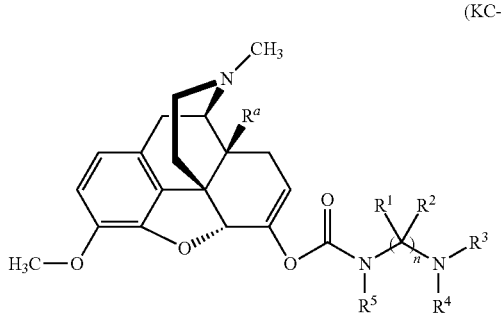

(KC-(Ib))

wherein:
R$^a$ is hydrogen or hydroxyl;
R$^5$ is selected from alkyl, substituted alkyl, arylalkyl, substituted arylalkyl, aryl and substituted aryl;
each R$^1$ is independently selected from hydrogen, alkyl, substituted alkyl, aryl, substituted aryl, acyl, and aminoacyl;
each R$^2$ is independently selected from hydrogen, alkyl, substituted alkyl, aryl, substituted aryl, acyl, and aminoacyl;
or R$^1$ and R$^2$ together with the carbon to which they are attached form a cycloalkyl or substituted cycloalkyl group, or two R$^1$ or R$^2$ groups on adjacent carbon atoms, together with the carbon atoms to which they are attached, form a cycloalkyl or substituted cycloalkyl group;
n is an integer from 2 to 4;
R$^3$ is hydrogen or (1-4C)alkyl;
R$^4$ is

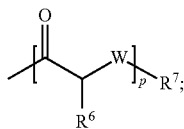

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;
each W is independently —NR$^8$—, —O— or —S—;
each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;
p is an integer from one to 100; and
R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.
Reference to formula KC-(I) is meant to include compounds of formula KC-(Ia) and KC-(IIb).
In formula KC-(I), R$^a$ can be hydrogen or hydroxyl. In certain instances, R$^a$ is hydrogen. In other instances, R$^a$ is hydroxyl.
In formula KC-(I), R$^5$ can be selected from alkyl, substituted alkyl, arylalkyl, substituted arylalkyl, aryl and substituted aryl. In certain instances, R$^5$ is (1-6C)alkyl. In other instances, R$^5$ is (1-4C)alkyl. In other instances, R$^5$ is methyl or ethyl. In other instances, R$^5$ is methyl. In certain instances, R$^5$ is ethyl.
In certain instances, R$^5$ is substituted alkyl. In certain instances, R$^5$ is an alkyl group substituted with a carboxylic group such as a carboxylic acid, carboxylic ester or carboxylic amide. In certain instances, R$^5$ is —(CH$_2$)$_n$—COOH, —(CH$_2$)$_n$—COOCH$_3$, or —(CH$_2$)$_n$—COOCH$_2$CH$_3$, wherein n is a number form one to 10. In certain instances, R$^1$ is —(CH$_2$)$_5$—COOH, —(CH$_2$)$_5$—COOCH$_3$, or —(CH$_2$)$_5$—COOCH$_2$CH$_3$.
In certain instances, in formula KC-(I), R$^5$ is arylalkyl or substituted arylalkyl. In certain instances, in formula KC-(I), R$^5$ is arylalkyl. In certain instances, R$^5$ is substituted arylalkyl. In certain instances, R$^5$ is an arylalkyl group substituted with a carboxylic group such as a carboxylic acid, carboxylic ester or carboxylic amide. In certain instances, R$^5$ is —(CH$_2$)$_q$(C$_6$H$_4$)—COOH, —(CH$_2$)$_q$(C$_6$H$_4$)—COOCH$_3$, or —(CH$_2$)$_q$(C$_6$H$_4$)—COOCH$_2$CH$_3$, where q is an integer from one to 10. In certain instances, R$^5$ is —CH$_2$(C$_6$H$_4$)—COOH, —CH$_2$(C$_6$H$_4$)—COOCH$_3$, or —CH$_2$(C$_6$H$_4$)—COOCH$_2$CH$_3$.
In certain instances, in formula KC-(I), R$^5$ is aryl. In certain instances, R$^5$ is substituted aryl. In certain instances, R$^5$ is an aryl group ortho, meta or para-substituted with a carboxylic group such as a carboxylic acid, carboxylic ester or carboxylic amide. In certain instances, R$^5$ is —(C$_6$H$_4$)—COOH, —(C$_6$H$_4$)—COOCH$_3$, or —(C$_6$H$_4$)—COOCH$_2$CH$_3$.
In formula KC-(I), each R$^1$ can be independently selected from hydrogen, alkyl, substituted alkyl, aryl, substituted aryl, acyl, and aminoacyl. In certain instances, R$^1$ is hydrogen or alkyl. In certain instances, R$^1$ is hydrogen. In certain instances, R$^1$ is alkyl. In certain instances, R$^1$ is acyl. In certain instances, R$^1$ is aminoacyl.
In formula KC-(I), each R$^2$ can be independently selected from hydrogen, alkyl, substituted alkyl, aryl, substituted aryl, acyl, and aminoacyl. In certain instances, R$^2$ is hydrogen or alkyl. In certain instances, R$^2$ is hydrogen. In certain instances, R$^2$ is alkyl. In certain instances, R$^2$ is acyl. In certain instances, R$^2$ is aminoacyl.
In certain instances, R$^1$ and R$^2$ are hydrogen. In certain instances, R$^1$ and R$^2$ on the same carbon are both alkyl. In certain instances, R$^1$ and R$^2$ on the same carbon are methyl. In certain instances, R$^1$ and R$^2$ on the same carbon are ethyl.
In certain instances, R$^1$ and R$^1$ which are vicinal are both alkyl and R$^2$ and R$^2$ which are vicinal are both hydrogen. In certain instances, R$^1$ and R$^1$ which are vicinal are both ethyl and R$^2$ and R$^2$ which are vicinal are both hydrogen. In certain instances, R$^1$ and R$^1$ which are vicinal are both methyl and R$^2$ and R$^2$ which are vicinal are both hydrogen.
In certain instances, in the chain of —[C(R$^1$)(R$^2$)]$_n$— in Formula KC-(I), not every carbon is substituted. In certain instances, in the chain of —[C(R$^1$)(R$^2$)]$_n$—, there is a combination of different alkyl substituents, such as methyl or ethyl.
In certain instances, one of R$^1$ and R$^2$ is methyl, ethyl or other alkyl and R$^5$ is alkyl. In certain instances, R$^1$ and R$^1$ which are vicinal are both alkyl and R$^2$ and R$^2$ which are vicinal are both hydrogen and R$^5$ is alkyl. In certain instances, R$^1$ and R$^1$ which are vicinal are both ethyl and R$^2$ and R$^2$ which are vicinal are both hydrogen and R$^5$ is alkyl. In certain instances, R$^1$ and R$^1$ which are vicinal are both methyl and R$^2$ and R$^2$ which are vicinal are both hydrogen and R$^5$ is alkyl.
In certain instances, one of R$^1$ and R$^2$ is methyl, ethyl or other alkyl and R$^5$ is substituted alkyl. In certain instances, one of R$^1$ and R$^2$ is methyl, ethyl or other alkyl and R$^5$ is an alkyl group substituted with a carboxylic group such as a carboxylic acid, carboxylic ester or carboxylic amide. In certain instances, one of $R^1$ and $R^2$ is methyl, ethyl or other alkyl and $R^5$ is —$(CH_2)_q(C_6H_4)$—COOH, —$(CH_2)_q(C_6H_4)$—COOCH$_3$, or —$(CH_2)_q(C_6H_4)$—COOCH$_2$CH$_3$, where q is an integer from one to 10. In certain instances, one of $R^1$ and $R^2$ is methyl, ethyl or other alkyl and $R^5$ is an alkyl group substituted with carboxamide.

In formula KC-(I), $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group. In certain instances, $R^1$ and $R^2$ together with the carbon to which they are attached can form a cycloalkyl group. Thus, in certain instances, $R^1$ and $R^2$ on the same carbon form a spirocycle. In certain instances, $R^1$ and $R^2$ together with the carbon to which they are attached can form a substituted cycloalkyl group. In certain instances, two $R^1$ or $R^2$ groups on adjacent carbon atoms, together with the carbon atoms to which they are attached, can form a cycloalkyl group. In certain instances, two $R^1$ or $R^2$ groups on adjacent carbon atoms, together with the carbon atoms to which they are attached, can form a substituted cycloalkyl group.

In formula KC-(I), $R^1$ and $R^2$ together with the carbon to which they are attached can form an aryl or substituted aryl group, or two $R^1$ or $R^2$ groups on adjacent carbon atoms, together with the carbon atoms to which they are attached, can form an aryl or substituted aryl group. In certain instances, two $R^1$ or $R^2$ groups on adjacent carbon atoms, together with the carbon atoms to which they are attached, form a phenyl ring. In certain instances, two $R^1$ or $R^2$ groups on adjacent carbon atoms, together with the carbon atoms to which they are attached, form a substituted phenyl ring. In certain instances, two $R^1$ or $R^2$ groups on adjacent carbon atoms, together with the carbon atoms to which they are attached, form a naphthyl ring.

In certain instances, one of $R^1$ and $R^2$ is aminoacyl.

In certain instances, one or both of $R^1$ and $R^2$ is aminoacyl comprising phenylenediamine. In certain instances, one of $R^1$ and $R^2$ is

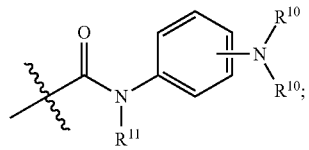

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^1$ and $R^2$ is

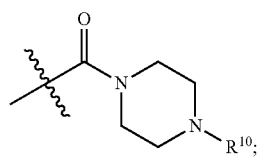

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^1$ and $R^2$ is

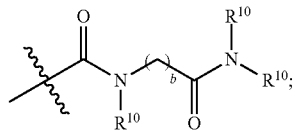

wherein each $R^{10}$ is independently hydrogen, alkyl, substituted alkyl, or acyl and b is a number from one to 5. In certain instances, one of $R^1$ and $R^2$ is

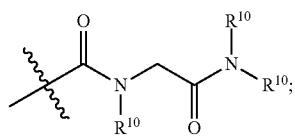

wherein each $R^{10}$ is independently hydrogen, alkyl, substituted alkyl, or acyl. In certain instances, one of $R^1$ and $R^2$ is

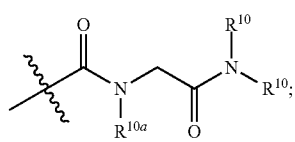

wherein $R^{10a}$ is alkyl and each $R^{10}$ is independently hydrogen, alkyl, substituted alkyl, or acyl.

In certain instances, one of $R^1$ and $R^2$ is

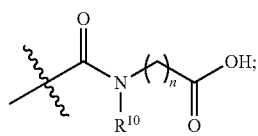

wherein $R^{10}$ is independently hydrogen, alkyl, substituted alkyl, or acyl and b is a number from one to 5. In certain instances, one of $R^1$ and $R^2$ is

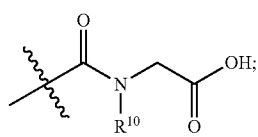

wherein $R^{10}$ is independently hydrogen, alkyl, substituted alkyl, or acyl.

In certain instances, one of $R^1$ and $R^2$ is an aminoacyl group, such as —C(O)NR$^{10a}$R$^{10b}$, wherein each $R^{10a}$ and $R^{10b}$ is independently selected from hydrogen, alkyl, substituted alkyl, and acyl. In certain instances, one of $R^1$ and $R^2$ is an aminoacyl group, such as —C(O)NR$^{10a}$R$^{10b}$, wherein $R^{10a}$ is an alkyl and $R^{10b}$ is substituted alkyl. In certain instances, one of $R^1$ and $R^2$ is an aminoacyl group, such as —C(O)NR$^{10a}$R$^{10b}$, wherein $R^{10a}$ is an alkyl and $R^{10b}$ is alkyl substituted with a carboxylic acid or carboxyl ester. In certain instances, one of $R^1$ and $R^2$ is an aminoacyl group, such as —C(O)NR$^{10a}$R$^{10b}$, wherein R$^{10a}$ is methyl and R$^{10b}$ is alkyl substituted with a carboxylic acid or carboxyl ester.

In certain instances, $R^1$ or $R^2$ can modulate a rate of intramolecular cyclization. $R^1$ or $R^2$ can speed up a rate of intramolecular cyclization, when compared to the corresponding molecule where $R^1$ and $R^2$ are both hydrogen. In certain instances, $R^1$ or $R^2$ comprise an electron-withdrawing group or an electron-donating group. In certain instances, $R^1$ or $R^2$ comprise an electron-withdrawing group. In certain instances, $R^1$ or $R^2$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (═O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, —[C(R$^1$)(R$^2$)]$_n$— is selected from —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$^{20}$OR$^{21}$)—; —CH$_2$CH(C(O)OR$^{22}$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O)NR$^{23}$R$^{24}$)—; —CH$_2$CH$_2$CH(C(O)OR$^{25}$)—; and —CH$_2$CH$_2$CH(C(O)OH)—, in which R$^{20}$, R$^{21}$, R$^{22}$ and R$^{23}$ each independently represents hydrogen or (1-6C)alkyl, and R$^{24}$ and R$^{25}$ each independently represents (1-6C)alkyl.

In formula KC-(I), n can be an integer from 2 to 4. In certain instances, n is two. In other instances, n is three. In other instances, n is four.

In formula KC-(I), $R^3$ can be hydrogen or (1-4C)alkyl. In certain instances, $R^3$ is hydrogen or methyl. In certain instances, $R^3$ is hydrogen. In certain instances, $R^3$ is methyl. In certain instances, $R^3$ is ethyl. In certain instances, $R^3$ is propyl or butyl.

In formula KC-(I), $R^4$ can be a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof. Such a peptide can be from 2 to about 100 amino acids in length. Examples of N-acyl derivatives include acetyl, benzoyl, malonyl, piperonyl or succinyl derivatives.

In certain instances, $R^4$ is a residue of L-arginine or L-lysine, or a residue of an N-acyl derivative of L-arginine or L-lysine.

In certain instances, in formula KC-(I), when p is greater than one, then the $R^4$ adjacent to the nitrogen of —N(R$^3$)(R$^4$) is a residue of L-arginine or L-lysine. In certain instances, when p is greater than one, the $R^4$ adjacent to the nitrogen of —N(R$^3$)(R$^4$) is a residue of L-arginine or L-lysine and the first residue is joined to at least one additional L-amino acid residue selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. The terminal residue of the peptide can be an N-acyl derivative of any of such L-amino acids. In certain instances $R^4$ is a dipeptide or an N-acyl derivative thereof. In certain instances R is a tripeptide or an N-acyl derivative thereof.

In formula KC-(I), $R^4$ is

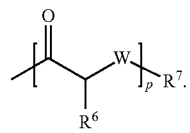

In formula KC-(I), each $R^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring.

In certain instances, in formula KC-(I), $R^6$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^6$ is selected from hydrogen, alkyl, substituted alkyl, arylalkyl, substituted arylalkyl, heteroarylalkyl, and substituted heteroarylalkyl. In certain instances, $R^6$ is hydrogen. In certain instances, $R^6$ is alkyl. In certain instances, $R^6$ is substituted alkyl. In certain instances, $R^6$ is arylalkyl or substituted arylalkyl. In certain instances, $R^6$ is heteroarylalkyl or substituted heteroarylalkyl.

In certain instances, $R^6$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, $R^6$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine.

In certain instances, $R^6$ is —CH$_2$CH$_2$CH$_2$NH(C═NH)NH$_2$ or —CH$_2$CH$_2$CH$_2$CH$_2$NH$_2$.

In formula KC-(I), each W can be independently —NR$^8$—, —O— or —S—. In certain instances, W is —NR$^8$—. In certain instances, W is —O—. In certain instances, W is —S—.

In formula KC-(I), each $R^8$ can be independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

In certain instances, in formula KC-(I), $R^8$ is hydrogen or alkyl. In certain instances, $R^8$ is hydrogen. In certain instances, $R^8$ is alkyl. In certain instances, $R^8$ is aryl. In certain instances, $R^6$ and $R^8$ independently together with the atoms to which they are bonded form a cycloheteroalkyl or substituted cycloheteroalkyl ring.

In formula KC-(I), p can be an integer from one to 100 and each $R^6$ can be selected independently from a side chain of any amino acid. In certain instances, p is an integer from one to 50. In certain instances, p is an integer from one to 90, 80, 70, 60, 50, 40, 30, 20, or 10. In certain instances, p is about 100. In certain instances, p is about 75. In certain instances, p is about 50. In certain instances, p is about 25. In certain instances, p is about 20. In certain instances, p is about 15. In certain instances, p is about 10. In certain instances, p is about 9. In certain instances, p is about 8. In certain instances, p is about 7. In certain instances, p is about 6. In certain instances, p is about 5. In certain instances, p is about 4. In certain instances, p is about 3. In certain instances, p is about 2. In certain instances, p is about one.

In certain instances, the $R^6$ of $R^4$ adjacent to the nitrogen of —$N(R^3)(R^4)$ is —$CH_2CH_2CH_2NH(C=NH)NH_2$ or —$CH_2CH_2CH_2CH_2NH_2$, and any additional $R^6$ can be a side chain of any amino acid independently selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine.

In formula KC-(I), $R^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl.

In certain instances, $R^7$ is hydrogen, alkyl, acyl, or substituted acyl. In certain instances, $R^7$ is hydrogen. In certain instances, $R^7$ is alkyl. In certain instances, $R^7$ is acyl or substituted acyl. In certain instances, $R^7$ is acyl. In certain instances, $R^7$ is substituted acyl. In certain instances, $R^7$ can be acetyl, benzoyl, malonyl, piperonyl or succinyl.

Formula KC-(II)

Compounds of formula KC-(II) are compounds of formula KC-(I) in which $R^5$ is selected from (1-6C) alkyl, (1-6C) substituted alkyl, —$(CH_2)_q(C_6H_4)$—COOH, —$(CH_2)_q(C_6H_4)$—COOCH$_3$, and —$(CH_2)_q(C_6H_4)$—COOCH$_2$CH$_3$, where q is an integer from one to 10; n is 2 or 3; $R^3$ is hydrogen; $R^4$ is an L-amino acid or peptide, where the peptide can be comprised of L-amino acids. In one of its composition aspects, the present embodiments provide a compound of formula KC-(II):

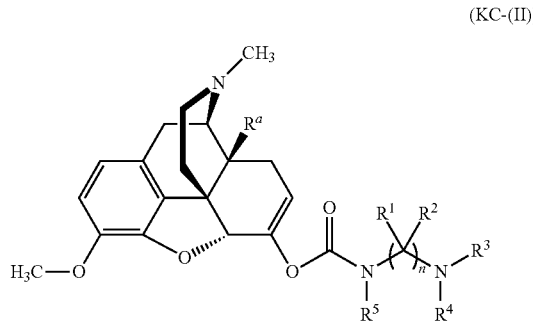

(KC-(II))

wherein:
$R^a$ is hydrogen or hydroxyl;
$R^5$ is selected from (1-6C)alkyl, (1-6C) substituted alkyl, —$(CH_2)_q(C_6H_4)$—COOH, —$(CH_2)_q(C_6H_4)$—COOCH$_3$, and —$(CH_2)_q(C_6H_4)$—COOCH$_2$CH$_3$, where q is an integer from one to 10;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;
n is 2 or 3;
$R^3$ is hydrogen;
$R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof.

In certain embodiments in Formula KC-(II), $R^4$ is a residue of an L-amino acid selected from arginine and lysine.

In certain instances, in formula KC-(II), when $R^4$ is a peptide comprising more than one amino acid, then the $R^4$ adjacent to the nitrogen of —$N(R^3)(R^4)$ is a residue of L-arginine or L-lysine. In certain instances $R^4$ is a dipeptide or an N-acyl derivative thereof. In certain instances $R^4$ is a tripeptide or an N-acyl derivative thereof.

In certain embodiments in Formula KC-(II), $R^4$ is a residue of an N-acyl derivative thereof. In certain instances, $R^4$ is a residue of an N-acyl derivative thereof, where the N-acyl derivative is substituted, such as, but not limited to, malonyl and succinyl.

Formulae KC-(III) to KC-(V)

The compositions of the present disclosure include compounds of formulae KC-(III) to KC-(V) shown below. Pharmaceutical compositions and methods of the present disclosure also contemplate compounds of formulae KC-(III) to KC-(V).

Formula KC-(III)

In one of its composition aspects, the present embodiments provide a compound of formula KC-(IIIa):

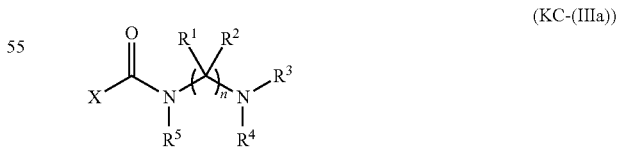

(KC-(IIIa))

wherein:
X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;
$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 2 to 4;
$R^3$ is hydrogen;
$R^4$ is

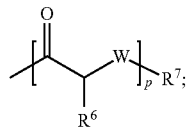

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In one of its composition aspects, the present embodiments provide a compound of formula KC-(IIIb):

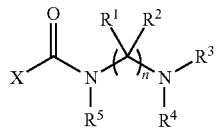

(KC-(IIIb))

wherein:

X represents a residue of a ketone-containing opioid, wherein the hydrogen atom of the corresponding enolic group of the ketone is replaced by a covalent bond to —C(O)—$NR^5$—$(C(R^1)(R^2))_n$—$NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is an integer from 2 to 4;
$R^3$ is hydrogen;
$R^4$ is

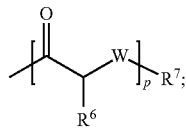

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Reference to formula KC-(III) is meant to include compounds of formula KC-(IIIa) and KC-(IIIb).

In formula KC-(III), $R^5$ can be selected from alkyl, substituted alkyl, arylalkyl, substituted arylalkyl, aryl and substituted aryl. In certain instances, $R^5$ is (1-6C)alkyl. In other instances, $R^5$ is (1-4C)alkyl. In other instances, $R^5$ is methyl or ethyl. In other instances, $R^5$ is methyl. In certain instances, $R^5$ is ethyl.

In certain instances, $R^5$ is substituted alkyl. In certain instances, $R^5$ is an alkyl group substituted with a carboxylic group such as a carboxylic acid, carboxylic ester or carboxylic amide. In certain instances, $R^5$ is —$(CH_2)_n$—COOH, —$(CH_2)_n$—$COOCH_3$, or —$(CH_2)_n$—$COOCH_2CH_3$, wherein n is a number form one to 10. In certain instances, $R^1$ is —$(CH_2)_5$—COOH, —$(CH_2)_5$—$COOCH_3$, or —$(CH_2)_5$—$COOCH_2CH_3$.

In certain instances, in formula KC-(III), $R^5$ is arylalkyl or substituted arylalkyl. In certain instances, in formula KC-(III), $R^5$ is arylalkyl. In certain instances, $R^5$ is substituted arylalkyl. In certain instances, $R^5$ is an arylalkyl group substituted with a carboxylic group such as a carboxylic acid, carboxylic ester or carboxylic amide. In certain instances, $R^5$ is —$(CH_2)_q(C_6H_4)$—COOH, —$(CH_2)_q(C_6H_4)$—$COOCH_3$, or —$(CH_2)_q(C_6H_4)$—$COOCH_2CH_3$, where q is an integer from one to 10. In certain instances, $R^5$ is —$CH_2(C_6H_4)$—COOH, —$CH_2(C_6H_4)$—$COOCH_3$, or —$CH_2(C_6H_4)$—$COOCH_2CH_3$.

In certain instances, in formula KC-(III), $R^5$ is aryl. In certain instances, $R^5$ is substituted aryl. In certain instances, $R^5$ is an aryl group ortho, meta or para-substituted with a carboxylic group such as a carboxylic acid, carboxylic ester or carboxylic amide. In certain instances, $R^5$ is —$(C_6H_4)$—COOH, —$(C_6H_4)$—$COOCH_3$, or —$(C_6H_4)$—$COOCH_2CH_3$.

In formula KC-(III), each $R^1$ can be independently selected from hydrogen, alkyl, substituted alkyl, aryl, substituted aryl, acyl, and aminoacyl. In certain instances, $R^1$ is hydrogen or alkyl. In certain instances, $R^1$ is hydrogen. In certain instances, $R^1$ is alkyl. In certain instances, $R^1$ is acyl. In certain instances, $R^1$ is aminoacyl.

In formula KC-(III), each $R^2$ can be independently selected from hydrogen, alkyl, substituted alkyl, aryl, substituted aryl, acyl, and aminoacyl. In certain instances, $R^2$ is hydrogen or alkyl. In certain instances, $R^2$ is hydrogen. In certain instances, $R^2$ is alkyl. In certain instances, $R^2$ is acyl. In certain instances, $R^2$ is aminoacyl.

In certain instances, $R^1$ and $R^2$ are hydrogen. In certain instances, $R^1$ and $R^2$ on the same carbon are both alkyl. In certain instances, $R^1$ and $R^2$ on the same carbon are methyl. In certain instances, $R^1$ and $R^2$ on the same carbon are ethyl.

In certain instances, $R^1$ and $R^1$ which are vicinal are both alkyl and $R^2$ and $R^2$ which are vicinal are both hydrogen. In certain instances, $R^1$ and $R^1$ which are vicinal are both ethyl and $R^2$ and $R^2$ which are vicinal are both hydrogen. In certain instances, $R^1$ and $R^1$ which are vicinal are both methyl and $R^2$ and $R^2$ which are vicinal are both hydrogen.

In certain instances, in the chain of $-[C(R^1)(R^2)]_n-$ in Formula KC-(III), not every carbon is substituted. In certain instances, in the chain of $-[C(R^1)(R^2)]_n-$, there is a combination of different alkyl substituents, such as methyl or ethyl.

In certain instances, one of $R^1$ and $R^2$ is methyl, ethyl or other alkyl and $R^5$ is alkyl. In certain instances, $R^1$ and $R^1$ which are vicinal are both alkyl and $R^2$ and $R^2$ which are vicinal are both hydrogen and $R^5$ is alkyl. In certain instances, $R^1$ and $R^1$ which are vicinal are both ethyl and $R^2$ and $R^2$ which are vicinal are both hydrogen and $R^5$ is alkyl. In certain instances, $R^1$ and $R^1$ which are vicinal are both methyl and $R^2$ and $R^2$ which are vicinal are both hydrogen and $R^5$ is alkyl.

In certain instances, one of $R^1$ and $R^2$ is methyl, ethyl or other alkyl and $R^5$ is substituted alkyl. In certain instances, one of $R^1$ and $R^2$ is methyl, ethyl or other alkyl and $R^5$ is an alkyl group substituted with a carboxylic group such as a carboxylic acid, carboxylic ester or carboxylic amide. In certain instances, one of $R^1$ and $R^2$ is methyl, ethyl or other alkyl and $R^5$ is $-(CH_2)_q(C_6H_4)-COOH$, $-(CH_2)_q(C_6H_4)-COOCH_3$, or $-(CH_2)_q(C_6H_4)-COOCH_2CH_3$, where q is an integer from one to 10. In certain instances, one of $R^1$ and $R^2$ is methyl, ethyl or other alkyl and $R^5$ is an alkyl group substituted with carboxamide.

In formula KC-(III), $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group. In certain instances, $R^1$ and $R^2$ together with the carbon to which they are attached can form a cycloalkyl group. Thus, in certain instances, $R^1$ and $R^2$ on the same carbon form a spirocycle. In certain instances, $R^1$ and $R^2$ together with the carbon to which they are attached can form a substituted cycloalkyl group. In certain instances, two $R^1$ or $R^2$ groups on adjacent carbon atoms, together with the carbon atoms to which they are attached, can form a cycloalkyl group. In certain instances, two $R^1$ or $R^2$ groups on adjacent carbon atoms, together with the carbon atoms to which they are attached, can form a substituted cycloalkyl group.

In certain instances, $R^1$ and $R^2$ together with the carbon to which they are attached can form an aryl or substituted aryl group, or two $R^1$ or $R^2$ groups on adjacent carbon atoms, together with the carbon atoms to which they are attached, can form an aryl or substituted aryl group. In certain instances, two $R^1$ or $R^2$ groups on adjacent carbon atoms, together with the carbon atoms to which they are attached, form a phenyl ring. In certain instances, two $R^1$ or $R^2$ groups on adjacent carbon atoms, together with the carbon atoms to which they are attached, form a substituted phenyl ring. In certain instances, two $R^1$ or $R^2$ groups on adjacent carbon atoms, together with the carbon atoms to which they are attached, form a naphthyl ring.

In certain instances, one of $R^1$ and $R^2$ is aminoacyl.

In certain instances, one or both of $R^1$ and $R^2$ is aminoacyl comprising phenylenediamine. In certain instances, one of $R^1$ and $R^2$ is

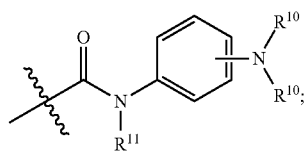

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^1$ and $R^2$ is

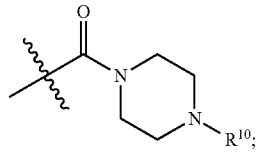

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^1$ and $R^2$ is

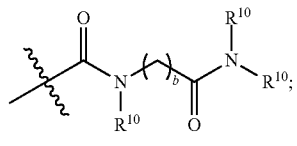

wherein each $R^{10}$ is independently hydrogen, alkyl, substituted alkyl, or acyl and b is a number from one to 5. In certain instances, one of $R^1$ and $R^2$ is

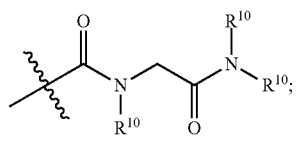

wherein each $R^{10}$ is independently hydrogen, alkyl, substituted alkyl, or acyl. In certain instances, one of $R^1$ and $R^2$ is

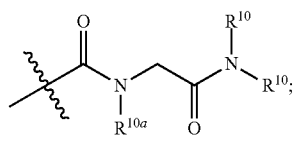

wherein $R^{10a}$ is alkyl and each $R^{10}$ is independently hydrogen, alkyl, substituted alkyl, or acyl.

In certain instances, one of $R^1$ and $R^2$ is

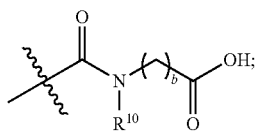

wherein $R^{10}$ is independently hydrogen, alkyl, substituted alkyl, or acyl and b is a number from one to 5. In certain instances, one of $R^1$ and $R^2$ is

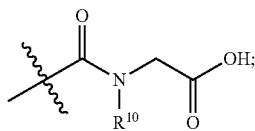

wherein $R^{10}$ is independently hydrogen, alkyl, substituted alkyl, or acyl.

In certain instances, one of $R^1$ and $R^2$ is an aminoacyl group, such as $-C(O)NR^{10a}R^{10b}$, wherein each $R^{10a}$ and $R^{10b}$ is independently selected from hydrogen, alkyl, substituted alkyl, and acyl. In certain instances, one of $R^1$ and $R^2$ is an aminoacyl group, such as $-C(O)NR^{10a}R^{10b}$, wherein $R^{10a}$ is an alkyl and $R^{10b}$ is substituted alkyl. In certain instances, one of $R^1$ and $R^2$ is an aminoacyl group, such as $-C(O)NR^{10a}R^{10b}$, wherein $R^{10a}$ is an alkyl and $R^{10b}$ is alkyl substituted with a carboxylic acid or carboxyl ester. In certain instances, one of $R^1$ and $R^2$ is an aminoacyl group, such as $-C(O)NR^{10a}R^{10b}$, wherein $R^{10a}R^{10a}$ is methyl and $R^{10b}$ is alkyl substituted with a carboxylic acid or carboxyl ester.

In certain instances, $R^1$ or $R^2$ can modulate a rate of intramolecular cyclization. $R^1$ or $R^2$ can speed up a rate of intramolecular cyclization, when compared to the corresponding molecule where $R^1$ and $R^2$ are both hydrogen. In certain instances, $R^1$ or $R^2$ comprise an electron-withdrawing group or an electron-donating group. In certain instances, $R^1$ or $R^2$ comprise an electron-withdrawing group. In certain instances, $R^1$ or $R^2$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, $-[C(R^1)(R^2)]_n-$ is selected from $-CH(CH_2F)CH(CH_2F)-$; $-CH(CHF_2)CH(CHF_2)-$; $-CH(CF_3)CH(CF_3)-$; $-CH_2CH(CF_3)-$; $-CH_2CH(CHF_2)-$; $-CH_2CH(CH_2F)-$; $-CH_2CH(CH_2F)CH_2-$; $-CH_2C(F_2)CH_2-$; $-CH_2CH(C(O)NR^{20}OR^{21})-$; $-CH_2CH(C(O)OR^{22})-$; $-CH_2CH(C(O)OH)-$; $-CH(CH_2F)CH_2CH(CH_2F)-$; $-CH(CHF_2)CH_2CH(CHF_2)-$; $-CH(CF_3)CH_2CH(CF_3)-$; $-CH_2CH_2CH(CF_3)-$; $-CH_2CH_2CH(CHF_2)-$; $-CH_2CH_2CH(CH_2F)-$; $-CH_2CH_2CH(C(O)NR^{23}R^{24})-$; $-CH_2CH_2CH(C(O)OR^{25})-$; and $-CH_2CH_2CH(C(O)OH)-$, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formula KC-(III), n can be an integer from 2 to 4. In certain instances, n is two. In other instances, n is three. In other instances, n is four.

In formula KC-(III), $R^3$ can be hydrogen or (1-4C)alkyl. In certain instances, $R^3$ is hydrogen or methyl. In certain instances, $R^3$ is hydrogen. In certain instances, $R^3$ is methyl. In certain instances, $R^3$ is ethyl. In certain instances, $R^3$ is propyl or butyl.

In formula KC-(III), $R^4$ can be a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof. Such a peptide can be from 2 to about 100 amino acids in length. Examples of N-acyl derivatives include acetyl, benzoyl, malonyl, piperonyl or succinyl derivatives.

In certain instances, $R^4$ is a residue of L-arginine or L-lysine, or a residue of an N-acyl derivative of L-arginine or L-lysine.

In certain instances, in formula KC-(III), when p is greater than one, then the $R^4$ adjacent to the nitrogen of $-N(R^3)(R^4)$ is a residue of L-arginine or L-lysine. In certain instances, when p is greater than one, the $R^4$ adjacent to the nitrogen of $-N(R^3)(R^4)$ is a residue of L-arginine or L-lysine and the first residue is joined to at least one additional L-amino acid residue selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. The terminal residue of the peptide can be an N-acyl derivative of any of such amino acids. In certain instances $R^4$ is a dipeptide or an N-acyl derivative thereof. In certain instances R is a tripeptide or an N-acyl derivative thereof. In formula KC-(III), $R^4$ is

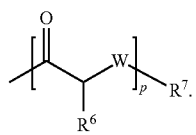

In formula KC-(III), each $R^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring.

In certain instances, in formula KC-(III), $R^6$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^6$ is selected from hydrogen, alkyl, substituted alkyl, arylalkyl, substituted arylalkyl, heteroarylalkyl, and substituted heteroarylalkyl. In certain instances, $R^6$ is hydrogen. In certain instances, $R^6$ is alkyl. In certain instances, $R^6$ is substituted alkyl. In certain instances, $R^6$ is arylalkyl or substituted arylalkyl. In certain instances, $R^6$ is heteroarylalkyl or substituted heteroarylalkyl.

In certain instances, $R^6$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, $R^6$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine.

In certain instances, $R^6$ is —$CH_2CH_2CH_2NH(C=NH)NH_2$ or —$CH_2CH_2CH_2CH_2NH_2$.

In formula KC-(III), each W can be independently —$NR^8$—, —O— or —S—. In certain instances, W is —$NR^8$—. In certain instances, W is —O—. In certain instances, W is —S—.

In formula KC-(III), each $R^8$ can be independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

In certain instances, in formula KC-(III), $R^8$ is hydrogen or alkyl. In certain instances, $R^8$ is hydrogen. In certain instances, $R^8$ is alkyl. In certain instances, $R^8$ is aryl. In certain instances, $R^6$ and $R^8$ independently together with the atoms to which they are bonded form a cycloheteroalkyl or substituted cycloheteroalkyl ring.

In formula KC-(III), p can be an integer from one to 100 and each $R^6$ can be selected independently from a side chain of any amino acid. In certain instances, p is an integer from one to 50. In certain instances, p is an integer from one to 90, 80, 70, 60, 50, 40, 30, 20, or 10. In certain instances, p is about 100. In certain instances, p is about 75. In certain instances, p is about 50. In certain instances, p is about 25. In certain instances, p is about 20. In certain instances, p is about 15. In certain instances, p is about 10. In certain instances, p is about 9. In certain instances, p is about 8. In certain instances, p is about 7. In certain instances, p is about 6. In certain instances, p is about 5. In certain instances, p is about 4. In certain instances, p is about 3. In certain instances, p is about 2. In certain instances, p is about one.

In certain instances, the $R^6$ of $R^4$ adjacent to the nitrogen of —$N(R^3)(R^4)$ is —$CH_2CH_2CH_2NH(C=NH)NH_2$ or —$CH_2CH_2CH_2CH_2NH_2$, and any additional $R^6$ can be a side chain of any amino acid independently selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine.

In formula KC-(III), $R^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl.

In certain instances, $R^7$ is hydrogen, alkyl, acyl, or substituted acyl. In certain instances, $R^7$ is hydrogen. In certain instances, $R^7$ is alkyl. In certain instances, $R^7$ is acyl or substituted acyl. In certain instances, $R^7$ is acyl. In certain instances, $R^7$ is substituted acyl. In certain instances, $R^7$ can be acetyl, benzoyl, malonyl, piperonyl or succinyl.

Formula KC-(IV)

Compounds of formula KC-(IV) are compounds of formula KC-(III) in which $R^5$ is selected from (1-6C) alkyl, (1-6C) substituted alkyl, —$(CH_2)_q(C_6H_4)$—COOH, —$(CH_2)_q(C_6H_4)$—$COOCH_3$, and —$(CH_2)_q(C_6H_4)$—$COOCH_2CH_3$, where q is an integer from one to 10; n is 2 or 3; $R^3$ is hydrogen; $R^4$ is an L-amino acid or peptide, where the peptide can be comprised of L-amino acids. In one of its composition aspects, the present embodiments provide a compound of formula KC-(IV):

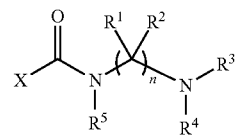

(KC-(IV))

wherein:

X represents a residue of a ketone-containing opioid, wherein the hydrogen atom of the corresponding enolic group of the ketone is replaced by a covalent bond to —C(O)—$NR^5$—$(C(R^1)(R^2))_n$—$NR^3R^4$;

$R^5$ is selected from (1-6C)alkyl, (1-6C) substituted alkyl, —$(CH_2)_q(C_6H_4)$—COOH, —$(CH_2)_q(C_6H_4)$—$COOCH_3$, and —$(CH_2)_q(C_6H_4)$—$COOCH_2CH_3$, where q is an integer from one to 10;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is 2 or 3;

$R^3$ is hydrogen;

$R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof;

or a salt, hydrate or solvate thereof.

In certain embodiments in Formula KC-(IV), $R^4$ is a residue of an L-amino acid selected from arginine and lysine.

In certain instances, in formula KC-(IV), when $R^4$ is a peptide comprising more than one amino acid, then the $R^4$ adjacent to the nitrogen of —$N(R^3)(R^4)$ is a residue of L-arginine or L-lysine. In certain instances $R^4$ is a dipeptide or an N-acyl derivative thereof. In certain instances $R^4$ is a tripeptide or an N-acyl derivative thereof.

In certain embodiments in Formula KC-(IV), $R^4$ is a residue of an N-acyl derivative thereof. In certain instances, $R^4$ is a residue of an N-acyl derivative thereof, where the N-acyl derivative is substituted, such as, but not limited to, malonyl and succinyl.

Formulae KC-(V)

Compounds of formula KC-(Va) are compounds of formula KC-(III) in which $R^4$ is a trypsin-cleavable moiety.

In one of its composition aspects, the present embodiments provide a compound of formula KC-(Va):

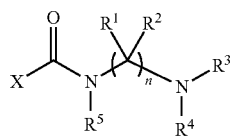

(KC-(Va))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen;

$R^4$ is a trypsin-cleavable moiety;

or a salt, hydrate or solvate thereof.

In formula KC-(Va), $R^4$ is a trypsin-cleavable moiety. A trypsin-cleavable moiety is a structural moiety that is capable of being cleaved by trypsin. In certain instances, a trypsin-cleavable moiety comprises a charged moiety that can fit into an active site of trypsin and is able to orient the prodrug for cleavage at a scissile bond. For instance, the charged moiety can be a basic moiety that exists as a charged moiety at physiological pH.

In certain embodiments, in formula KC-(Va), $R^4$ is —C(O)—CH(R$^{6a}$)—NH(R$^{7a}$), wherein R$^{6a}$ represents a side chain of an amino acid or a derivative of a side chain of an amino acid that effects $R^4$ to be a trypsin-cleavable moiety. A derivative refers to a substance that has been altered from another substance by modification, partial substitution, homologation, truncation, or a change in oxidation state.

For example, to form a trypsin-cleavable moiety, R$^{6a}$ can include, but is not limited to, a side chain of lysine (such as L-lysine), arginine (such as L-arginine), homolysine, homoarginine, and ornithine. Other values for $R^4$ include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines, and (bicyclo[2.2.2]octan-1-yl) methanamine and derivatives thereof.

In certain instances, in formula KC-(Va), R$^{6a}$ represents —CH$_2$CH$_2$CH$_2$NH(C=NH)NH$_2$ or —CH$_2$CH$_2$CH$_2$CH$_2$NH$_2$, the configuration of the carbon atom to which $R^4$ is attached corresponding with that in an L-amino acid.

In formula KC-(Va), R$^{7a}$ is selected from hydrogen, alkyl, substituted alkyl, acyl, substituted acyl, alkoxycarbonyl, substituted alkoxycarbonyl, aryl, substituted aryl, arylalkyl, and substituted arylalkyl. In certain instances, R$^{7a}$ is an amino acid or an N-acyl derivative of an amino acid. In certain instances, R$^{7a}$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

Formulae KC-(Vb)

Compounds of formula KC-(Vb) are compounds of formula KC-(III) in which $R^4$ is a GI enzyme-cleavable moiety.

In one of its composition aspects, the present embodiments provide a compound of formula KC-(Vb):

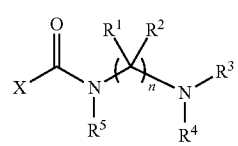

(KC-(Vb))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen;

$R^4$ is a GI enzyme-cleavable moiety;

or a salt, hydrate or solvate thereof.

In formulae KC-(Vb), $R^4$ is a GI enzyme-cleavable moiety. A GI enzyme-cleavable moiety is a structural moiety that is capable of being cleaved by GI enzyme.

In certain embodiments, in formulae KC-(Vb), $R^4$ is —C(O)—CH($R^6$)—NH($R^5$), wherein $R^6$ represents a side chain of an amino acid or a derivative of a side chain of an amino acid that effects $R^4$ to be a GI enzyme-cleavable moiety. A derivative refers to a substance that has been altered from another substance by modification, partial substitution, homologation, truncation, or a change in oxidation state.

For example, to form a GI enzyme-cleavable moiety, $R^6$ can include, but is not limited to, a side chain of lysine (such as L-lysine), arginine (such as L-arginine), homolysine, homoarginine, and ornithine. Other values for $R^4$ include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines, and (bicyclo[2.2.2]octan-1-yl) methanamine and derivatives thereof.

In certain instances, in formulae KC-(Vb), $R^6$ represents —CH$_2$CH$_2$CH$_2$NH(C=NH)NH$_2$ or —CH$_2$CH$_2$CH$_2$CH$_2$NH$_2$, the configuration of the carbon atom to which $R^6$ is attached corresponding with that in an L-amino acid.

In formulae KC-(Vb), $R^5$ is selected from hydrogen, alkyl, substituted alkyl, acyl, substituted acyl, alkoxycarbonyl, substituted alkoxycarbonyl, aryl, substituted aryl, arylalkyl, and substituted arylalkyl. In certain instances, $R^5$ is an amino acid or an N-acyl derivative of an amino acid. In certain instances, $R^5$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

Formula KC-(VI)

In one of its composition aspects, the present embodiments provide a compound of formula KC-(VI):

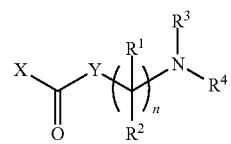

KC-(VI)

wherein:

X represents a residue of a ketone-containing opioid, wherein the hydrogen atom of the corresponding enolic group of the ketone is replaced by a covalent bond to —C(O)—Y—(C($R^1$)($R^2$))$_n$—NR$^3$R$^4$;

Y is —NR$^5$—, —O— or —S—;

n is an integer from 1 to 4;

each $R^1$, $R^2$, $R^3$ and $R^5$ is independently hydrogen, alkyl, substituted alkyl, aryl or substituted aryl, or $R^1$ and $R^2$ together with the carbon to which they are attached form a cycloalkyl or substituted cycloalkyl group;

$R^4$ is

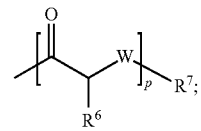

each $R^6$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^6$ and $R^7$ together with the atoms to which they are bonded form a cycloheteroalkyl or substituted cycloheteroalkyl ring;

$R^7$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 10;

each W is independently —NR$^8$—, —O— or —S—; and each $R^8$ is independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

Particular compounds of interest, and salts or solvates or stereoisomers thereof, include:

oxycodone 6-(N-methyl-N-(2-N'-acetylarginylamino))ethylcarbamate:

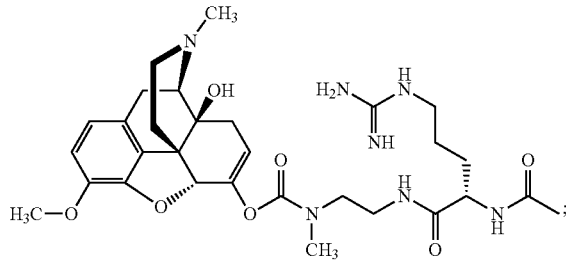

hydrocodone 6-(N-methyl-N-(2-N'-acetylarginylamino))ethylcarbamate:

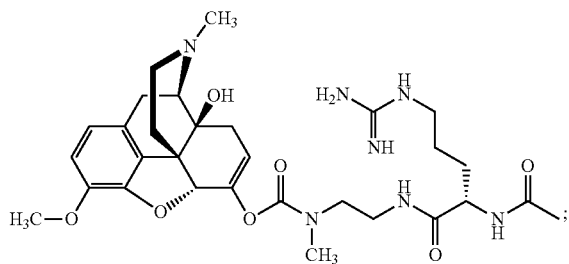

oxycodone 6-(N-methyl-N-(2-N'-malonylarginylamino))ethylcarbamate:

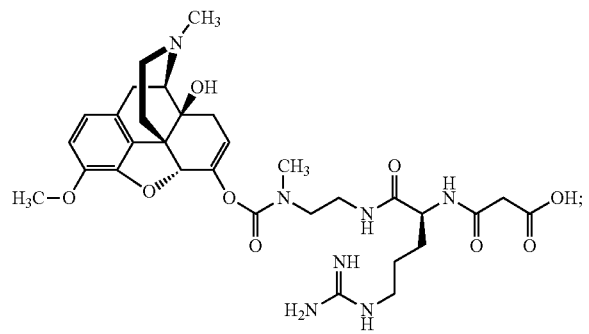

oxycodone 6-(N-5'-carboxypentyl-N-(2-N'-acetylarginylamino))ethylcarbamate:

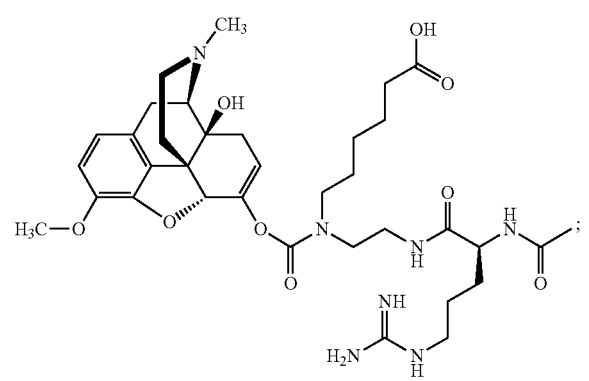

hydrocodone 6-(N-methyl-N-(2-N'-malonylarginylamino))ethylcarbamate:

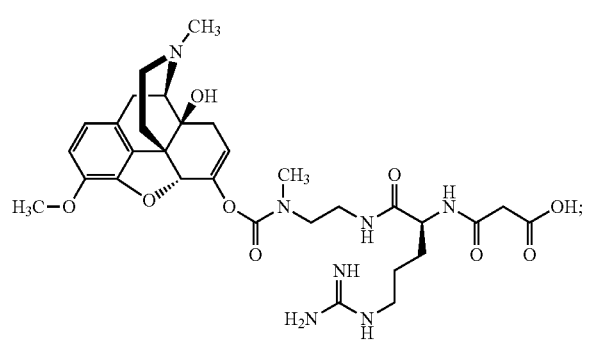

oxycodone 6-(N-methyl-N-(2-N'-acetylarginylamino-2-(N-methyl-N-carboxymethyl-acetamido))ethylcarbamate:

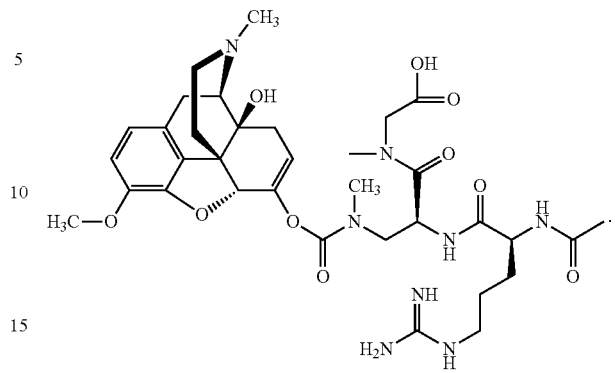

wherein the amino acid residue is of the L configuration.

The embodiments provide a pharmaceutical composition, which comprises a compound of general Formula KC-(I) to KC-(II), or a pharmaceutically acceptable salt thereof.

The embodiments provide a pharmaceutical composition, which comprises a compound of general Formulae KC-(III) to KC-(V), or a pharmaceutically acceptable salt thereof.

The embodiments provide a pharmaceutical composition, which comprises a compound disclosed herein other than a compound of general Formulae KC-(I) to KC-(II), or a pharmaceutically acceptable salt thereof.

General Synthetic Procedures for Formulae KC-(I) to KC-(VI)

A representative synthesis for compounds of Formulae KC-(I) and KC-(II) is shown in the following schemes. Compounds of Formulae KC-(III) to KC-(VI) can also be synthesized by using the disclosed methods. A representative synthesis for Compound KC203 is shown in Scheme KC-1. In Scheme KC-1, the terms $R^1$, $R^2$, $R^5$, and n are defined herein. The terms $PG^1$ and $PG^2$ are amino protecting groups.

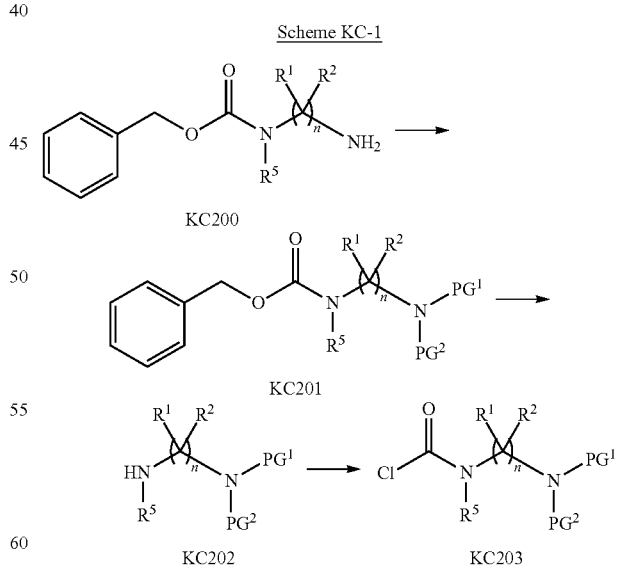

In Scheme KC-1, Compound KC200 is a commercially available starting material. Alternatively, Compound KC200 can be synthesized via a variety of different synthetic routes using commercially available starting materials and/or starting materials prepared by conventional synthetic methods.

With continued reference to Scheme KC-1, Compound KC200 is protected at the amino group to form Compound KC201, wherein PG$^1$ and PG$^2$ are amino protecting groups. Amino protecting groups can be found in T. W. Greene and P. G. M. Wuts, "*Protective Groups in Organic Synthesis*", Fourth edition, Wiley, New York 2006. Representative amino-protecting groups include, but are not limited to, formyl groups; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

In certain embodiments, PG$^1$ and PG$^2$ are Boc groups. Conditions for forming Boc groups on Compound KC201 can be found in Greene and Wuts. One method is reaction of Compound KC200 with di-tert-butyl dicarbonate. The reaction can optionally be run in the presence of an activating agent, such as DMAP.

With continued reference to Scheme KC-1, the carboxybenzyl group on Compound KC201 is deprotected to form Compound KC202. Conditions to remove the carboxybenzyl group can be found in Greene and Wuts. Methods to remove the carboxybenzyl group include hydrogenolysis of Compound KC201 or treatment of Compound KC201 with HBr. One method to remove the carboxybenzyl group is reaction of Compound KC201 with hydrogen and palladium.

With continued reference to Scheme KC-1, Compound KC202 is reacted with phosgene to form Compound KC203. Reaction with phosgene forms an acyl chloride on the amino group of Compound KC202. Other reagents can act as substitutes for phosgene, such as diphosgene or triphosgene.

A representative synthesis for Compound KC302 is shown in Scheme KC-2. In Scheme 2, the terms R$^a$, R$^1$, R$^2$, R$^5$, and n are defined herein. The terms PG$^1$ and PG$^2$ are amino protecting groups.

Scheme KC-2

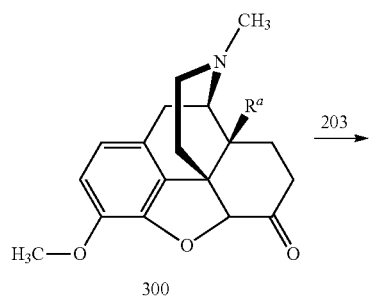

300

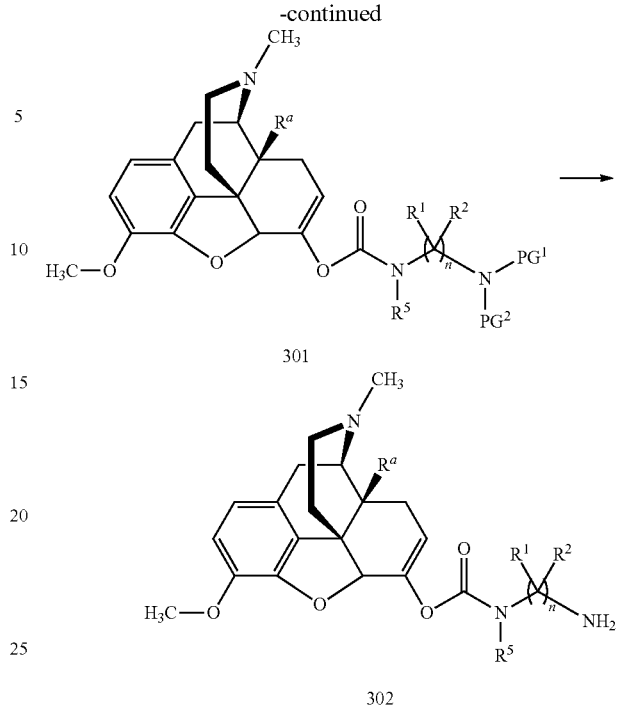

In Scheme KC-2, Compound KC300 is a commercially available starting material. Alternatively, Compound KC300 can be synthesized via a variety of different synthetic routes using commercially available starting materials and/or starting materials prepared by conventional synthetic methods.

With continued reference to Scheme KC-2, Compound KC300 is reacted with Compound KC203 to form Compound KC301. In this reaction, the enolate of Compound KC300 reacts with the acyl chloride of Compound KC203 to form a carbamate.

With continued reference to Scheme KC-2, the protecting groups PG$^1$ and PG$^2$ are removed from Compound KC301 to form Compound KC302. Conditions to remove amino groups can be found in Greene and Wuts. When PG$^1$ and PG$^2$ are Boc groups, the protecting groups can be removed with acidic conditions, such as treatment with trifluoroacetic acid.

A representative synthesis for Compound KC402 is shown in Scheme KC-3. In Scheme KC-3, the terms R$^a$, R$^1$, R$^2$, R$^5$, R$^6$, R$^7$ and n are defined herein. The term PG$^3$ is an amino protecting group.

Scheme KC-3

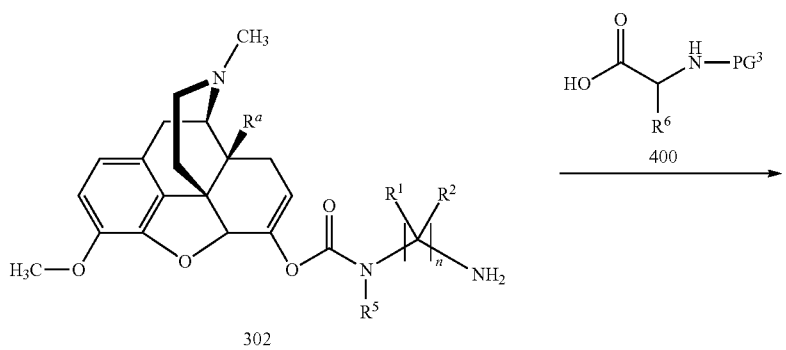

302

-continued

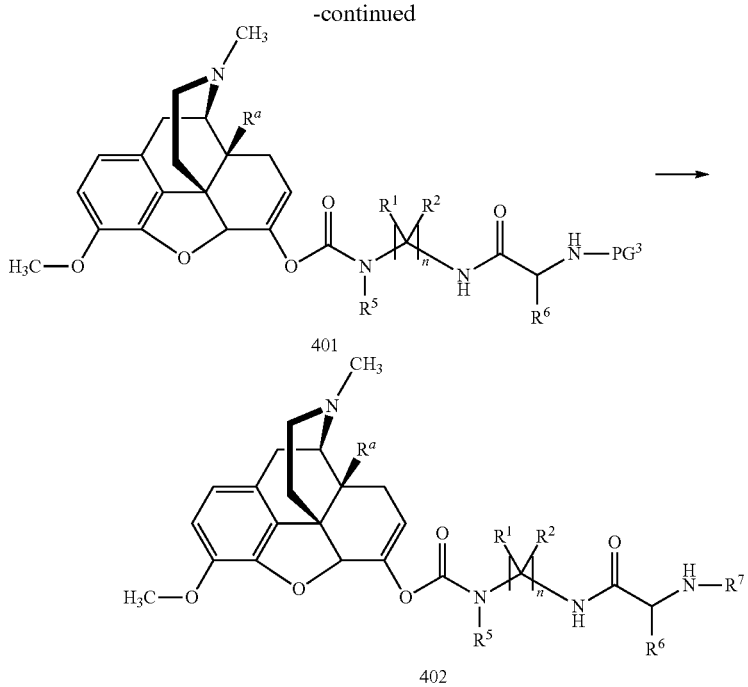

In Scheme KC-3, Compound KC400 is a commercially available starting material. Alternatively, Compound KC400 can be synthesized via a variety of different synthetic routes using commercially available starting materials and/or starting materials prepared by conventional synthetic methods.

With continued reference to Scheme KC-3, Compound KC302 reacts with Compound KC400 to form Compound KC401 in a peptide coupling reaction. A peptide coupling reaction typically employs a conventional peptide coupling reagent and is conducted under conventional coupling reaction conditions, typically in the presence of a trialkylamine, such as ethyldiisopropylamine or diisopropylethylamine (DIEA). Suitable coupling reagents for use include, by way of example, carbodiimides, such as ethyl-3-(3-dimethylamino) propylcarbodiimide (EDC), dicyclohexylcarbodiimide (DCC), diisopropylcarbodiimide (DIC) and the like, and other well-known coupling reagents, such as N,N'-carbonyl-diimidazole, 2-ethoxy-1-ethoxycarbonyl-1,2-dihydroquinoline (EEDQ), benzotriazol-1-yloxy-tris(dimethylamino) phosphonium hexafluorophosphate (BOP), O-(7-azabenzotriazol-1-yl)-N,N,N',N'-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound KC302 reacts with Compound KC400 to form Compound KC401 in the presence of HATU and DIEA in DMF.

With continued reference to Scheme KC-3, Compound KC401 is transformed into Compound KC402 with removal of the amino protecting group and addition of $R^7$ group. In certain cases, the amino protecting group is $R^7$ and removal of the amino protecting group is optional.

As disclosed herein, representative amino-protecting groups include, but are not limited to, formyl groups; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like. In certain embodiments, $PG^3$ is a Boc group. When $PG^3$ is a Boc group, the protecting group can be removed with acidic conditions, such as treatment with trifluoroacetic acid.

In certain instances, the $R^7$ group is added to Compound KC401. Conditions for addition of $R^7$ depend on the identity of $R^7$ and are known to those skilled in the art. In certain instances $R^7$ is an acyl group, such as acetyl, benzoyl, malonyl, piperonyl or succinyl.

N-Acyl derivatives of the compounds of formula KC-(I) may conveniently be prepared by acylating a corresponding compound of formula KC-(I) using an appropriate acylating agent, for example an anhydride, such as acetic anhydride (to prepare an N-acetyl compound) or an acid halide. The reaction is conveniently performed in the presence of a non-reactive base, for example a tertiary amine, such as triethylamine. Convenient solvents include amides, such as dimethyl formamide. The temperature at which the reaction is performed is conveniently in the range of from 0 to 100° C., such as at ambient temperature.

With continued reference to Scheme KC-3, removal of other protecting groups can be performed if other protecting groups were used, such as protecting groups present on the $R^6$ moiety. Conditions for removal of other protecting groups depend on the identity of the protecting group and are known to those skilled in the art. The conditions can also be found in Greene and Wuts.

As described in more detail herein, the disclosure provides processes and intermediates useful for preparing compounds of the present disclosure or a salt or solvate or stereoisomer thereof. Accordingly, the present disclosure provides a process of preparing a compound of the present disclosure, the process involves:
contacting a compound of formula:

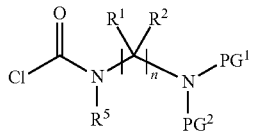

with a compound of formula

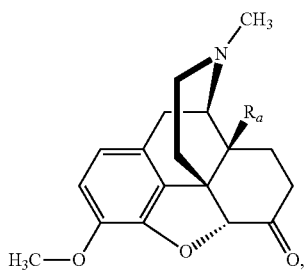

wherein $PG^1$ and $PG^2$ are amino protecting groups.

Accordingly and as described in more detail herein, the present disclosure provides a process of preparing a compound of the present disclosure, the process involves:
contacting a compound of formula:

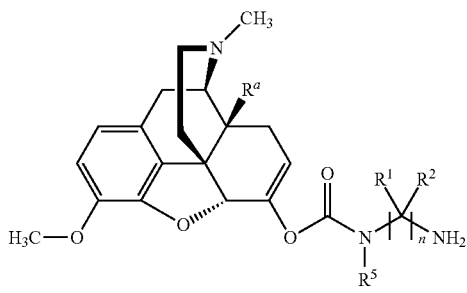

with a compound of formula

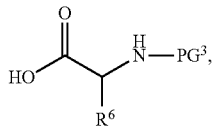

wherein $PG^3$ is an amino protecting group.

In one instance, the above process further involving the step of forming a salt of a compound of the present disclosure. Embodiments are directed to the other processes described herein; and to the product prepared by any of the processes described herein.

Ketone-Modified Opioid Prodrugs with Promoiety Comprising Electronically Decoupling Spacer and Cleavable Moiety The disclosure provides for prodrugs of ketone-containing opioids which are functionalized with a promoiety in which the promoiety includes a spacer group and a cleavable moiety where the spacer group may, inter alia, electronically decouple and/or physically separate the active agent from the cleavable moiety. Accordingly, a prodrug disclosed herein generally comprises an opioid attached through a heteroatom to a spacer which is further attached to a cleavable moiety. In one embodiment, the cleavable moiety is a GI enzyme moiety, such as a trypsin-cleavable moiety.

A wide variety of spacers are known in the art, and include by way of example and not limitation, alkyl, heteroalkyl, acyclic heteroatomic bridges, aryl, arylaryl, arylalkyl, heteroaryl, heteroarylalkyl and the like. Thus, spacers may include, for example, single, double, triple or aromatic carbon-carbon bonds, nitrogen-nitrogen bonds, carbon-nitrogen bonds, carbon-oxygen bonds and/or carbon-sulfur bonds, and may therefore include functionalities such as carbonyls, ethers, thioethers, carboxamides, sulfonamides, ureas, urethanes, hydrazines, etc. In one embodiment, the spacers can be alcohols or amines, which can quench the quinone methide. Examples of suitable spacers include, but are not limited to, aryl, biaryl, heteroaryl, etc.

The cleavable moiety may comprise an amino acid, a peptide, an ester, a polyester, a thioester, a polythioester or any other cleavable group known to those of skill in the art. Generally, the cleavable moiety can be cleaved under physiological conditions. The cleavable moiety may be cleaved chemically (e.g., hydrolysis) or enzymatically. In some embodiments, the cleavable moiety is cleaved enzymatically. Generally, the compounds described herein are stable in aqueous solution, but not so stable that the cleavable moiety can not be cleaved chemically (e.g., hydrolysis) or enzymatically.

Formula KC-(VII)

The embodiments provide a compound of general formula KC-(VII):

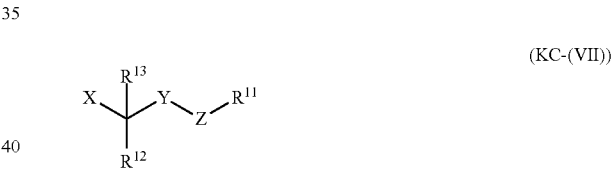

(KC-(VII))

or salts, solvates or hydrates thereof wherein:

X represents a residue of a ketone-containing opioid, wherein the hydrogen atom of the corresponding enolic group of the ketone is replaced by a covalent bond —$(CR^{12}R^{13})$—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Y is aryl, heteroaryl or arylaryl optionally substituted with one or more —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ or —$C(NR^{16})NR^{15}R^{14}$;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{14}$ and $R^{15}$ together with the nitrogen atom to which they are bonded form a cycloheteroalkyl or substituted cycloheteroalkyl ring;

Z is N($R^{18}$)—, —O— or —S—;

$R^{18}$ is hydrogen, alkyl, substituted alkyl, aryl, substituted aryl, arylalkyl, substituted arylalkyl, heteroaryl, substituted heteroaryl, heteroarylalkyl or substituted heteroarylalkyl or

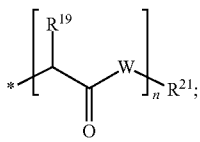

each W is independently —$NR^{20}$—, —O— or —S—;

each $R^{19}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{19}$ and $R^{20}$ together with the atoms to which they are bonded form a cycloheteroalkyl or substituted cycloheteroalkyl ring;

each $R^{20}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{20}$ and $R^{21}$ together with the atoms to which they are bonded form a cycloheteroalkyl or substituted cycloheteroalkyl ring;

$R^{21}$ is hydrogen, alkyl, substituted alkyl, aryl, substituted aryl, arylalkyl or substituted arylalkyl;

n is an integer from 0 to 5;

$R^{11}$ is

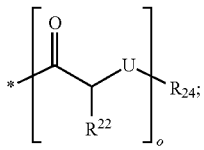

each U is independently —$NR^{23}$—, —O— or —S—;

each $R^{22}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{22}$ and $R^{23}$ together with the atoms to which they are bonded form a cycloheteroalkyl or substituted cycloheteroalkyl ring;

each $R^{23}$ is independently hydrogen, alkyl, substituted alkyl, aryl, substituted aryl, or optionally, $R^{23}$ and $R^{24}$ together with the atoms to which they are bonded form a cycloheteroalkyl or substituted cycloheteroalkyl ring;

$R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100;

provided that Z is oriented para or ortho to X—($CR^{12}R^{13}$)— and that both $R^{18}$ and $R^{11}$ are not hydrogen.

Formula KC-(VIII)

The embodiments provide a compound of general formula KC-(VIII):

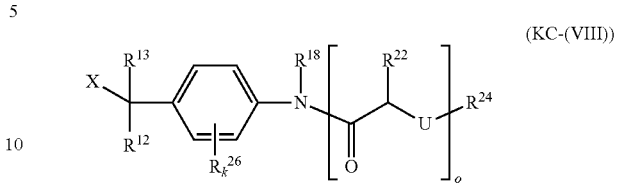

or salts, solvates or hydrates thereof wherein:

X represents a residue of a ketone-containing opioid, wherein the hydrogen atom of the corresponding enolic group of the ketone is replaced by a covalent bond to —($CR^{12}R^{13}$)—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

$R_k^{26}$ are each independently selected from the group consisting of one or more of —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ and —$C(NR^{16})NR^{15}R^{14}$, and k is 0, 1, 2, 3, or 4;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^4$ and $R^5$ together with the nitrogen atom to which they are bonded form a cycloheteroalkyl or substituted cycloheteroalkyl ring;

$R^{18}$ is hydrogen or methyl;

$R^{22}$ is a side chain of an amino acid or a derivative of a side chain of an amino acid;

each U is independently —$NR^{23}$—, —O— or —S—;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{23}$ and $R^{24}$ together with the atoms to which they are bonded form a cycloheteroalkyl or substituted cycloheteroalkyl ring; and $R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100.

In formulae KC-(VII) and KC-(VIII), $R^{22}$ can represent a side chain of an amino acid. Amino acids, including amino acid variants, are discussed in a section herein. In certain embodiments, $R^{22}$ is a derivative of a side chain of an amino acid. Such derivatives are described herein.

In certain embodiments, in formulae KC-(VII) and KC-(VIII), $R^{22}$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, $R^{22}$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine. In certain embodiments, $R^{22}$ is a derivative of a side chain of an amino acid. Such derivatives are described herein.

In certain instances, in formulae KC-(VII) and KC-(VIII), $R^{22}$ represents —$CH_2CH_2CH_2NH(C=NH)NH_2$ or —$CH_2CH_2CH_2CH_2NH_2$, the configuration of the carbon atom to which $R^{22}$ is attached corresponding with that in an L-amino acid.

In formulae KC-(VII) and KC-(VIII), —CO—C($R^{22}$)—U—$R^{24}$ is a GI enzyme-cleavable moiety. A GI enzyme-cleavable moiety is a structural moiety that is capable of being cleaved by a GI enzyme. In certain instances, a GI enzyme-cleavable moiety comprises a charged moiety that can fit into an active site of a GI enzyme and is able to orient the prodrug for cleavage at a scissile bond. For instance, the charged moiety can be a basic moiety that exists as a charged moiety at physiological pH. For example, to form a GI enzyme-cleavable moiety, $R^{22}$ can include, but is not limited to, a side chain of lysine (such as L-lysine), a side chain of arginine (such as L-arginine), a side chain of homolysine, a side chain of homoarginine, and a side chain of ornithine. Other values for GI enzyme-cleavable moieties include, but are not limited to, arginine homologues, arginine truncates, arginine with varying oxidation states (for instance, metabolites), lysine homologues, lysine truncates, and lysine with varying oxidation states (for instance, metabolites). Examples of arginine and lysine mimics include arylguanidines, arylamidines (substituted benzamidines), benzylamines and (bicyclo[2.2.2]octan-1-yl)methanamine and derivatives thereof.

In certain instances, in formulae KC-(VII) and KC-(VIII), —[CO—C($R^{22}$)—U]$_o$—$R^{24}$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

General Synthetic Procedures for Compounds of Formulae KC-(VII) to KC-(VIII)

The synthetic schemes and procedures disclosed herein for formulae PC-(XVI) to PC-(XVII) can also be used to synthesize compounds of formulae KC-(VII) to KC-(VIII).

Ketone-Modified Opioid Prodrugs with Promoiety Comprising Electronically Decoupling Spacer, Cyclizable Spacer Leaving Group, and Cleavable Moiety The embodiments provide a compound of general formula KC-(IX):

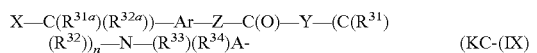

(KC-(IX))

or a salt, hydrate or solvate thereof wherein:

X represents a residue of a ketone-containing opioid, wherein the hydrogen atom of the corresponding enolic group of the ketone is replaced by a covalent bond to —(C($R^{31a}$)($R^{32a}$))—Ar—Z—C(O)—Y—(C($R^{31}$)($R^{32}$))$_n$—N—($R^{33}$)($R^{34}$);

$R^{31a}$ and $R^{32a}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Ar is aryl, heteroaryl or arylaryl optionally substituted with one or more —F, —Cl, —Br, —I, —$R^{34a}$, —$O^-$, —$OR^{34a}$, —$SR^{34a}$, —$S^-$, —$NR^{34a}R^{35a}$, —$CF_3$, —CN, —OCN, —SCN, —NO, —$NO_2$, —$N_3$, —$S(O)_2O'$, —$S(O)_2OH$, —$S(O)_2R^{34a}$, —$OS(O_2)O''$, —$OS(O)_2R^{34a}$, —$P(0)(0'')_2$, —$P(O)(OR^{34a})(O'')$, —$OP(O)(OR^{34a})(OR^{35a})$, —$C(0)R^{34a}$, —$C(S)R^{34a}$, —$C(O)OR^{34a}$, —$C(O)NR^{34a}R^{35a}$, —C(O)O; —$C(S)OR^{34a}$, —$NR^{36a}C(O)NR^{34a}R^{35a}$, —$NR^{36a}C(S)NR^{34a}R^{35a}$, —$NR^{37a}C(NR^{36a})NR^{35a}R^{34a}$ or —$C(NR^{36a})NR^{35a}R^{34a}$, or tethered to a polymer;

$R^{34a}$, $R^{35a}$, $R^{36a}$ and $R^{37a}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{34}$ and $R^{35}$ together with the nitrogen atom to which they are bonded form a cycloheteroalkyl or substituted cycloheteroalkyl ring;

Z is O, S or NH;

Y is —$NR^{35}$—, —O— or —S—;

n is an integer from 1 to 10;

each $R^{31}$, $R^{32}$, $R^{33}$ and $R^{35}$ is independently hydrogen, alkyl, substituted alkyl, aryl or substituted aryl, or $R^{31}$ and $R^{32}$ together with the carbon to which they are attached form a cycloalkyl or substituted cycloalkyl group, or two $R^{31}$ or $R^{32}$ groups on adjacent carbon atoms, together with the carbon atoms to which they are attached, form a cycloalkyl or substituted cycloalkyl group;

$R^{34}$ is

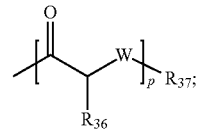

each $R^{36}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{36}$ and $R^{37}$ together with the atoms to which they are bonded form a cycloheteroalkyl or substituted cycloheteroalkyl ring;

$R^{37}$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 5;

each W is independently —$NR^{38}$—, —O— or —S—;

each $R^{38}$ is independently hydrogen, alkyl, substituted alkyl, aryl or substituted aryl, or optionally, each $R^{36}$ and $R^{38}$ independently together with the atoms to which they are bonded form a cycloheteroalkyl or substituted cycloheteroalkyl ring; and A' represents an anion.

In the compounds of formula KC-(IX), the enolic oxygen of the corresponding ketone in an opioid has been substituted with a spacer group bearing a nitrogen nucleophile that is protected with an enzymatically-cleavable moiety ($R^{34}$), the configuration of the spacer leaving group and nitrogen nucleophile being such that, upon enzymatic cleavage of the cleavable moiety, the nitrogen nucleophile is capable of liberating the compound from the spacer leaving group so as to provide the patient with controlled release of the compound.

It will be appreciated that when the N—$R^{34}$ amide bond is cleaved enzymatically, the nitrogen nucleophile is freed and cyclises back onto the carbonyl group, forming the cyclic urea and releasing the compound, but this released compound undergoes a spontaneous 1,6-elimination to release the opioid.

General Synthetic Procedures for Compounds of Formula KC-(IX)

The synthetic schemes and procedures disclosed herein for formula PC-(XVIII) can also be used to synthesize compounds of formulae KC-(IX).

Examples of Ketone-Modified Opioid Prodrugs

Examples of certain ketone-modified opioid prodrugs are shown below. In formulae CC-(XXIX) to CC-(XXXXIII), AA can represent a side chain of an amino acid. Amino acids, including amino acid variants, are discussed in a section herein.

Formula CC-(XXIX)

A certain example is a compound of Formula CC-(XXIX):

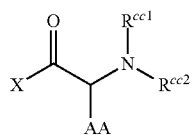

CC-(XXIX)

wherein

X represents a residue of a ketone-containing opioid, wherein the hydrogen atom of the corresponding enolic group of the ketone is replaced by a covalent bond to —C(O)—CH(AA)-$NR^{cc1}R^{cc2}$;

AA is a side chain of an amino acid; and $R^{cc1}$ and $R^{cc2}$ are independently selected from hydrogen, alkyl, substituted alkyl, aryl, substituted aryl, acyl, arylalkyl, and substituted arylalkyl.

Formula CC-(XXX)

A certain example is a compound of formula CC-(XXX):

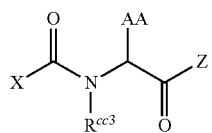

CC-(XXX)

wherein

X represents a residue of a ketone-containing opioid, wherein the hydrogen atom of the corresponding enolic group of the ketone is replaced by a covalent bond to —C(O)—N($R^{cc3}$)—CH(AA)-C(O)—Z;

$R^{cc3}$ is selected from selected from hydrogen, alkyl, substituted alkyl, aryl, substituted aryl, acyl, arylalkyl, and substituted arylalkyl;

AA is a side chain of an amino acid;

Z is selected from NH—$R^{cc4}$, O—$R^{cc4}$, OH, and $NH_2$; and $R^{cc4}$ is selected from selected from hydrogen, alkyl, substituted alkyl, aryl, substituted aryl, acyl, arylalkyl, and substituted arylalkyl.

Formula CC-(XXXI)

A certain example is a compound of formula CC-(XXXI):

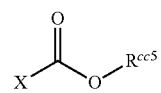

CC-(XXXI)

wherein

X represents a residue of a ketone-containing opioid, wherein the hydrogen atom of the corresponding enolic group of the ketone is replaced by a covalent bond to —C(O)—O—$R^{cc5}$; and $R^{cc5}$ is selected from

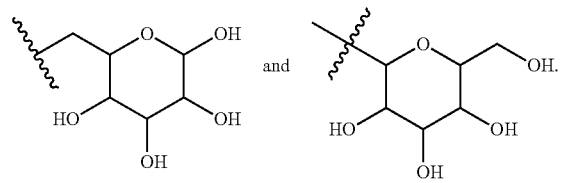 [SMILES: *CC1OC(O)C(O)C(O)C1O ; "and" ; *C1OC(CO)C(O)C(O)C1O]

Formula CC-(XXXII)

A certain example is a compound of formula CC-(XXXII):

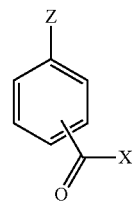

CC-(XXXII)

wherein

X represents a residue of a ketone-containing opioid, wherein the hydrogen atom of the corresponding enolic group of the ketone is replaced by a covalent bond to the benzoyl group; and Z is amidino or guanidino.

Formula CC-(XXXIII)

A certain example is a compound of formula CC-(XXXIII):

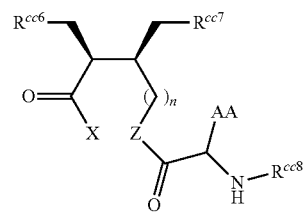

CC-(XXXIII)

wherein

X represents a residue of a ketone-containing opioid, wherein the hydrogen atom of the corresponding enolic group of the ketone is replaced by a covalent bond to the carbonyl group;

$R^{cc6}$ and $R^{cc7}$ are independently selected from hydrogen, alkyl, substituted alkyl, aryl, substituted aryl, arylalkyl, and substituted arylalkyl;

n is a number from zero to 2;

Z is O or NH;

AA is a side chain of an amino acid; and $R^{cc8}$ is selected from hydrogen, alkyl, substituted alkyl, aryl, substituted aryl, acyl, arylalkyl, and substituted arylalkyl.

Formula CC-(XXXIV)

A certain example is a compound of formula CC-(XXXIV):

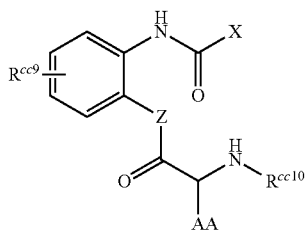

CC-(XXXIV)

wherein

X represents a residue of a ketone-containing opioid, wherein the hydrogen atom of the corresponding enolic group of the ketone is replaced by a covalent bond to the carbonyl group;

$R^{cc9}$ is selected from hydrogen, alkyl, substituted alkyl, aryl, substituted aryl, arylalkyl, and substituted arylalkyl;

Z is O or NH;

AA is a side chain of an amino acid; and $R^{cc10}$ is selected from hydrogen, alkyl, substituted alkyl, aryl, substituted aryl, acyl, arylalkyl, and substituted arylalkyl.

Formula CC-(XXXV)

A certain example is a compound of formula CC-(XXXV):

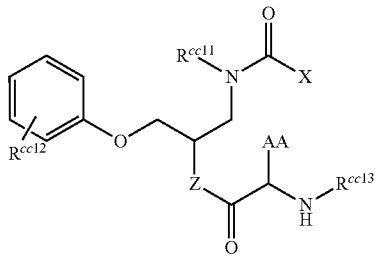

CC-(XXXV)

wherein

X represents a residue of a ketone-containing opioid, wherein the hydrogen atom of the corresponding enolic group of the ketone is replaced by a covalent bond to the carbonyl group;

$R^{cc11}$ and $R^{cc12}$ are independently selected from hydrogen, alkyl, substituted alkyl, aryl, substituted aryl, arylalkyl, and substituted arylalkyl;

$R^{cc13}$ is selected from hydrogen, alkyl, substituted alkyl, aryl, substituted aryl, acyl, arylalkyl, and substituted arylalkyl;

Z is O or NH; and

AA is a side chain of an amino acid.

Formula CC-(XXXVI)

A certain example is a compound of formula CC-(XXXVI):

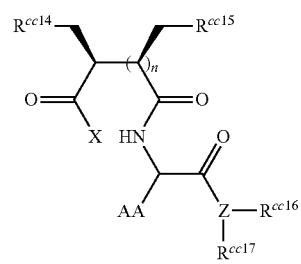

CC-(XXXVI)

wherein

X represents a residue of a ketone-containing opioid, wherein the hydrogen atom of the corresponding enolic group of the ketone is replaced by a covalent bond to the carbonyl group;

$R^{cc14}$ and $R^{cc15}$ are independently selected from hydrogen, alkyl, substituted alkyl, aryl, substituted aryl, arylalkyl, and substituted arylalkyl;

n is a number from zero to 2;

AA is a side chain of an amino acid; and

Z is O or N;

$R^{cc16}$ and $R^{cc17}$ are independently selected from hydrogen, alkyl, substituted alkyl, aryl, substituted aryl, acyl, arylalkyl, and substituted arylalkyl, wherein if Z is O, then $R^{cc17}$ is not present.

Formula CC-(XXXVII)

A certain example is a compound of formula CC-(XXXVII):

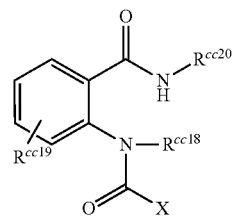

CC-(XXXVII)

wherein

X represents a residue of a ketone-containing opioid, wherein the hydrogen atom of the corresponding enolic group of the ketone is replaced by a covalent bond to the carbonyl group;

$R^{cc18}$, $R^{cc19}$, $R^{cc20}$ are independently selected from hydrogen, alkyl, substituted alkyl, aryl, substituted aryl, arylalkyl, and substituted arylalkyl.

Formula CC-(XXXVIII)

A certain example is a compound of formula CC-(XXXVIII):

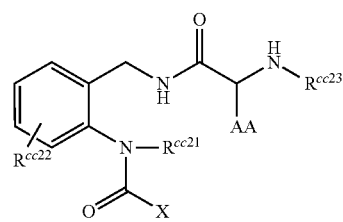

CC-(XXXVIII)

wherein

X represents a residue of a ketone-containing opioid, wherein the hydrogen atom of the corresponding enolic group of the ketone is replaced by a covalent bond to the carbonyl group;

$R^{cc21}$ and $R^{cc22}$ are independently selected from hydrogen, alkyl, substituted alkyl, aryl, substituted aryl, arylalkyl, and substituted arylalkyl;

$R^{cc23}$ is selected from hydrogen, alkyl, substituted alkyl, aryl, substituted aryl, acyl, arylalkyl, and substituted arylalkyl; and AA is a side chain of an amino acid.

Formula CC-(XXXIX)

A certain example is a compound of formula CC-(XXXIX):

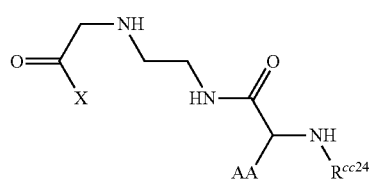

CC-(XXXIX)

wherein

X represents a residue of a ketone-containing opioid, wherein the hydrogen atom of the corresponding enolic group of the ketone is replaced by a covalent bond to the carbonyl group;

$R^{cc24}$ is selected from hydrogen, alkyl, substituted alkyl, aryl, substituted aryl, acyl, arylalkyl, and substituted arylalkyl; and AA is a side chain of an amino acid.

Formula CC-(XXXX)

A certain example is a compound of formula CC-(XXXX):

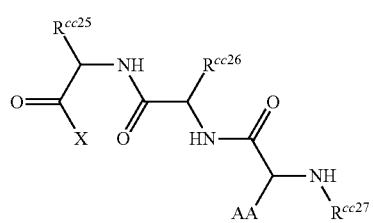

CC-(XXXX)

wherein

X represents a residue of a ketone-containing opioid, wherein the hydrogen atom of the corresponding enolic group of the ketone is replaced by a covalent bond to the carbonyl group;

$R^{cc25}$ and $R^{cc26}$ are independently selected from hydrogen, alkyl, substituted alkyl, aryl, substituted aryl, arylalkyl, and substituted arylalkyl;

$R^{cc27}$ is selected from hydrogen, alkyl, substituted alkyl, aryl, substituted aryl, acyl, arylalkyl, and substituted arylalkyl; and AA is a side chain of an amino acid.

Formula CC-(XXXXI)

A certain example is a compound of formula CC-(XXXXI):

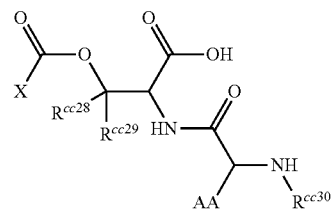

CC-(XXXXI)

wherein

X represents a residue of a ketone-containing opioid, wherein the hydrogen atom of the corresponding enolic group of the ketone is replaced by a covalent bond to the carbonyl group;

$R^{cc28}$ and $R^{cc29}$ are independently selected from hydrogen, alkyl, substituted alkyl, aryl, substituted aryl, arylalkyl, and substituted arylalkyl;

$R^{cc30}$ is selected from hydrogen, alkyl, substituted alkyl, aryl, substituted aryl, acyl, arylalkyl, and substituted arylalkyl; and AA is a side chain of an amino acid.

Formula CC-(XXXXII)

A certain example is a compound of formula CC-(XXXXII):

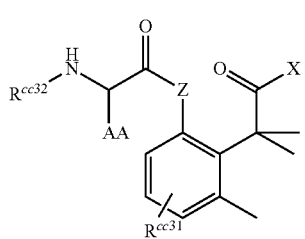

CC-(XXXXII)

wherein

X represents a residue of a ketone-containing opioid, wherein the hydrogen atom of the corresponding enolic group of the ketone is replaced by a covalent bond to the carbonyl group;

$R^{cc31}$ is selected from hydrogen, alkyl, substituted alkyl, aryl, substituted aryl, arylalkyl, and substituted arylalkyl;

Z is O or NH;

$R^{cc32}$ is selected from hydrogen, alkyl, substituted alkyl, aryl, substituted aryl, acyl, arylalkyl, and substituted arylalkyl; and AA is a side chain of an amino acid.

Amino-Modified Opioid Prodrugs

The disclosure provides an amino-modified opioid prodrug which provides enzymatically-controlled release of an amino-containing opioid. In an amino-modified opioid prodrug, a promoiety is attached via modification of the amino moiety, such as through a quaternary ammonium salt, or as an amide. Release of the opioid is mediated by enzymatic cleavage of the promoiety from the amino-containing opioid. The disclosure provides for release of the opioid through enzyme cleavage of the promoiety from the amino-containing opioid.

Amino-Modified Opioid Prodrugs with Promoiety Comprising Electronically Decoupling Spacer and Cleavable Moiety The disclosure provides for prodrugs of opioids with amino groups which are functionalized with a promoiety in which the promoiety includes a spacer group and a cleavable moiety where the spacer group may, inter alia, electronically decouple and/or physically separate the active agent from the cleavable moiety. Accordingly, a prodrug disclosed herein generally comprises an opioid attached through a heteroatom to a spacer which is further attached to a cleavable moiety. In certain embodiments, the opioid is attached to the promoiety via modification of an amino group as a quaternary ammonium salt. In one embodiment, the cleavable moiety is a GI enzyme cleavable moiety, such as a trypsin cleavable moiety. Such cleavage can initiate, contribute to or effect drug release.

A wide variety of spacers are known in the art, and include by way of example and not limitation, alkyl, heteroalkyl, acyclic heteroatomic bridges, aryl, arylaryl, arylalkyl, heteroaryl, heteroarylalkyl and the like. Thus, spacers may include, for example, single, double, triple or aromatic carbon-carbon bonds, nitrogen-nitrogen bonds, carbon-nitrogen bonds, carbon-oxygen bonds and/or carbon-sulfur bonds, and may therefore include functionalities such as carbonyls, ethers, thioethers, carboxamides, sulfonamides, ureas, urethanes, hydrazines, etc. In one embodiment, the spacers can be alcohols or amines, which can quench the quinone methide. Examples of suitable spacers include, but are not limited to, aryl, biaryl, heteroaryl, etc.

The cleavable moiety may comprise an amino acid, a peptide, an ester, a polyester, a thioester, a polythioester or any other cleavable group known to those of skill in the art. Generally, the cleavable moiety can be cleaved under physiological conditions. The cleavable moiety may be cleaved chemically (e.g., hydrolysis) or enzymatically. In some embodiments, the cleavable moiety is cleaved enzymatically. Generally, the compounds described herein are stable in aqueous solution, but not so stable that the cleavable moiety can not be cleaved chemically (e.g., hydrolysis) or enzymatically.

Formula QS-(I)

The present disclosure provides amino-modified opioid prodrugs in which the promoiety is attached through an amino group as a quaternary ammonium salt. The disclosure provides compounds of the general formula QS-(I):

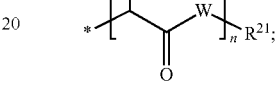

(QS-(I))

or salts, solvates or hydrates thereof wherein:

X is an opioid comprising an amine, wherein a hydrogen atom of the primary or secondary amine is replaced by a covalent bond to —$(CR^{12}R^{13})$—Y—Z—$R^{11}$ or a lone pair of electrons of a tertiary amine is replaced by a covalent bond to —$(CR^{12}R^{13})$—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Y is aryl, heteroaryl or arylaryl optionally substituted with one or more —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ or —$C(NR^{16})NR^{15}R^{14}$;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{14}$ and $R^{15}$ together with the nitrogen atom to which they are bonded form a cycloheteroalkyl or substituted cycloheteroalkyl ring;

Z is N($R^{18}$)—, —O— or —S—;

$R^{18}$ is hydrogen, alkyl, substituted alkyl, aryl, substituted aryl, arylalkyl, substituted arylalkyl, heteroaryl, substituted heteroaryl, heteroarylalkyl or substituted heteroarylalkyl or

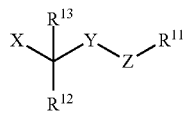

each W is independently —$NR^{20}$—, —O— or —S—;

each $R^{19}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{19}$ and $R^{20}$ together with the atoms to which they are bonded form a cycloheteroalkyl or substituted cycloheteroalkyl ring;

each $R^{20}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{20}$ and $R^{21}$ together with the atoms to which they are bonded form a cycloheteroalkyl or substituted cycloheteroalkyl ring;

$R^{21}$ is hydrogen, alkyl, substituted alkyl, aryl, substituted aryl, arylalkyl or substituted arylalkyl;

n is an integer from 0 to 5;

$R^{11}$ is

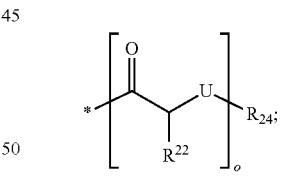

each U is independently —$NR^{23}$—, —O— or —S—;

each $R^{22}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{22}$ and $R^{23}$ together with the atoms to which they are bonded form a cycloheteroalkyl or substituted cycloheteroalkyl ring;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{23}$ and $R^{24}$ together with the atoms to which they are bonded form a cycloheteroalkyl or substituted cycloheteroalkyl ring;

$R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100;

provided that Z is oriented para or ortho to X—(CR$^{12}$R$^{13}$)— and that both R$^{18}$ and R$^{11}$ are not hydrogen.

Formula QS-(II)

The disclosures provide compounds of the general formula QS-(II):

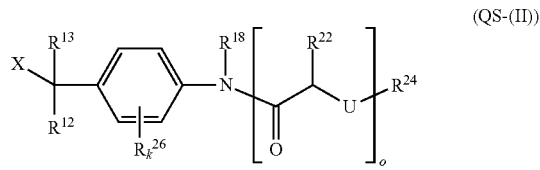

(QS-(II))

or salts, solvates or hydrates thereof wherein:

X is an opioid comprising an amine, wherein a hydrogen atom of the primary or secondary amine is replaced by a covalent bond to —(CR$^{12}$R$^{13}$)—Y—Z—R$^{11}$ or a lone pair of electrons of a tertiary amine is replaced by a covalent bond to —(CR$^{12}$R$^{13}$)—Y—Z—R$^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

$R_k^{26}$ are each independently selected from the group consisting of one or more of —F, —Cl, —Br, —I, —R$^{14}$, —O$^-$, —OR$^{14}$, —SR$^{14}$, —S$^-$, —NR$^{14}$R$^{15}$, —CF$_3$, —CN, —OCN, —SCN, —NO, —NO$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{15}$R$^{14}$ and —C(NR$^{16}$)NR$^{15}$R$^{14}$, and k is 0, 1, 2, 3, or 4;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally R$^4$ and R$^5$ together with the nitrogen atom to which they are bonded form a cycloheteroalkyl or substituted cycloheteroalkyl ring;

$R^{18}$ is hydrogen or methyl;

$R^{22}$ is a side chain of an amino acid or a derivative of a side chain of an amino acid;

each U is independently —NR$^{23}$—, —O— or —S—;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, R$^{23}$ and R$^{24}$ together with the atoms to which they are bonded form a cycloheteroalkyl or substituted cycloheteroalkyl ring; and $R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100.

In formulae QS-(I) and QS-(II), R$^{22}$ can represent a side chain of an amino acid. Amino acids, including amino acid variants, are discussed in a section herein. In certain embodiments, R$^{22}$ is a derivative of a side chain of an amino acid. Such derivatives are described herein.

In certain embodiments, in formulae QS-(I) and QS-(II) R$^{22}$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, R$^{22}$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine. In certain embodiments, R$^{22}$ is a derivative of a side chain of an amino acid. Such derivatives are described herein.

In certain instances, in formulae QS-(I) and QS-(II), R$^{22}$ represents —CH$_2$CH$_2$CH$_2$NH(C=NH)NH$_2$ or —CH$_2$CH$_2$CH$_2$CH$_2$NH$_2$, the configuration of the carbon atom to which R$^{22}$ is attached corresponding with that in an L-amino acid.

In formulae QS-(I) and QS-(II), —CO—C(R$^{22}$)—U—R$^{24}$ is a GI enzyme-cleavable moiety. A GI enzyme-cleavable moiety is a structural moiety that is capable of being cleaved by a GI enzyme. In certain instances, a GI enzyme-cleavable moiety comprises a charged moiety that can fit into an active site of a GI enzyme and is able to orient the prodrug for cleavage at a scissile bond. For instance, the charged moiety can be a basic moiety that exists as a charged moiety at physiological pH. For example, to form a GI enzyme-cleavable moiety, R$^{22}$ can include, but is not limited to, a side chain of lysine (such as L-lysine), a side chain of arginine (such as L-arginine), a side chain of homolysine, a side chain of homoarginine, and a side chain of ornithine. Other values for GI enzyme-cleavable moieties include, but are not limited to, arginine homologues, arginine truncates, arginine with varying oxidation states (for instance, metabolites), lysine homologues, lysine truncates, and lysine with varying oxidation states (for instance, metabolites). Examples of arginine and lysine mimics include arylguanidines, arylamidines (substituted benzamidines), benzylamines and (bicyclo[2.2.2]octan-1-yl)methanamine and derivatives thereof.

In certain instances, in formula QS-(I) and QS-(II), —[CO—C(R$^{22}$)—U]$_o$—R$^{24}$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

General Synthetic Procedures for Compounds of Formulae QS-(I) to QS-(II)

The synthetic schemes and procedures disclosed herein for formulae PC-(XVI) to PC-(XVII) can also be used to synthesize compounds of formulae QS-(I) to QS-(II).

Amino-Modified Opioid Prodrugs with Promoiety Comprising Electronically Decoupling Spacer, Cyclizable Spacer Leaving Group, and Cleavable Moiety The embodiments provide a compound of general formula QS-(III):

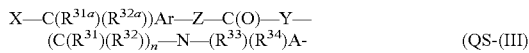

(QS-(III))

or a salt, hydrate or solvate thereof wherein:

X is a residue of an opioid wherein the lone pair of electrons of the amino nitrogen is replaced with a bond to —C($R^{31a}$)($R^{32a}$)Ar—Z—C(O)—Y—(C($R^{31}$)($R^{32}$))$_n$—N—($R^{33}$)($R^{34}$);

$R^{31a}$ and $R^{32a}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Ar is aryl, heteroaryl or arylaryl optionally substituted with one or more —F, —Cl, —Br, —I, —$R^{34a}$, —O⁻, —$OR^{34a}$, —$SR^{34a}$, —S⁻, —$NR^{34a}R^{35a}$, —$CF_3$, —CN, —OCN, —SCN, —NO, —$NO_2$, —$N_3$, —$S(O)_2O'$, —$S(O)_2OH$, —$S(O)_2R^{34a}$, —$OS(O_2)O''$, —$OS(O)_2R^{34a}$, —$P(O)(O'')_2$, —$P(O)(OR^{34a})(O'')$, —$OP(O)(OR^{34a})(OR^{35a})$, —$C(O)R^{34a}$, —$C(S)R^{34a}$, —$C(O)OR^{34a}$, —$C(O)NR^{34a}R^{35a}$, —C(O)O; —$C(S)OR^{34a}$, —$NR^{36a}C(O)NR^{34a}R^{35a}$, —$NR^{36a}C(S)NR^{34a}R^{35a}$, —$NR^{37a}C(NR^{36a})NR^{35a}R^{34a}$ or —$C(NR^{36a})NR^{35a}R^{34a}$, or tethered to a polymer;

$R^{34a}$, $R^{35a}$, $R^{36a}$ and $R^{37a}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{34}$ and $R^{35}$ together with the nitrogen atom to which they are bonded form a cycloheteroalkyl or substituted cycloheteroalkyl ring;

Z is O, S or NH;

Y is —$NR^{35}$—, —O— or —S—;

n is an integer from 1 to 10;

each $R^{31}$, $R^{32}$, $R^{33}$ and $R^{35}$ is independently hydrogen, alkyl, substituted alkyl, aryl or substituted aryl, or $R^{31}$ and $R^{32}$ together with the carbon to which they are attached form a cycloalkyl or substituted cycloalkyl group, or two $R^{31}$ or $R^{32}$ groups on adjacent carbon atoms, together with the carbon atoms to which they are attached, form a cycloalkyl or substituted cycloalkyl group;

$R^{34}$ is

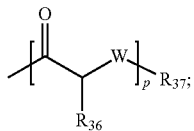

each $R^{36}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{36}$ and $R^{37}$ together with the atoms to which they are bonded form a cycloheteroalkyl or substituted cycloheteroalkyl ring;

$R^{37}$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 100;

each W is independently —$NR^{38}$—, —O— or —S—;

each $R^{38}$ is independently hydrogen, alkyl, substituted alkyl, aryl or substituted aryl, or optionally, each $R^{36}$ and $R^{38}$ independently together with the atoms to which they are bonded form a cycloheteroalkyl or substituted cycloheteroalkyl ring; and A' represents an anion.

In the compounds of formula QS-(III), the amino group in an opioid has been substituted with a spacer group bearing a nitrogen nucleophile that is protected with an enzymatically-cleavable moiety ($R^{34}$), the configuration of the spacer leaving group and nitrogen nucleophile being such that, upon enzymatic cleavage of the cleavable moiety, the nitrogen nucleophile is capable of liberating the compound from the spacer leaving group so as to provide the patient with controlled release of the compound.

It will be appreciated that when the N—$R^{34}$ amide bond is cleaved enzymatically, the nitrogen nucleophile is freed and cyclises back onto the carbonyl group, forming the cyclic urea and releasing the compound, but this released compound undergoes a spontaneous 1,6-elimination to release the opioid.

General Synthetic Procedures for Compounds of Formulae QS-(III)

The synthetic schemes and procedures disclosed herein for formula PC-(XVIII) can also be used to synthesize compounds of formula QS-(III).

Examples of Amino-Modified Opioid Prodrugs

Examples of certain amino-modified opioid prodrugs are shown below. In formulae CC-(XXXXIII) to CC-(XXXXIV), AA can represent a side chain of an amino acid. Amino acids, including amino acid variants, are discussed in a section herein.

Formula CC-(XXXXIII)

A certain example is a compound of Formula CC-(XXXXIII):

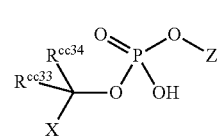

CC-(XXXXIII)

wherein

X is a residue of an opioid wherein the lone pair of electrons of the amino nitrogen is replaced with a bond to —C($R^{cc33}R^{cc34}$)—O—P(O)(OH)—OZ;

$R^{cc33}$ and $R^{cc34}$ are independently selected from hydrogen, halide, alkyl, and cycloalkyl or $R^{cc33}$ and $R^{cc34}$ can be combined with the carbon to which they are connected to form a cycloalkyl group; and Z is hydrogen or alkyl.

A certain formula of CC-(XXXXIII) is shown below:

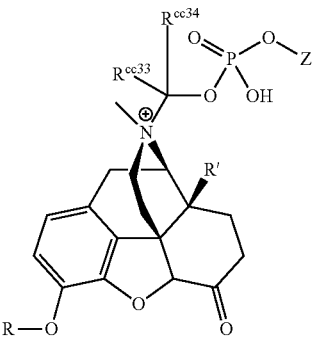

wherein $R^{cc33}$ and $R^{cc34}$ are independently selected from hydrogen, halide, alkyl, and cycloalkyl or $R^{cc33}$ and $R^{cc34}$ can be combined with the carbon to which they are connected to form a cycloalkyl group;

Z is hydrogen or alkyl;

R is hydrogen or methyl; and

R' is hydrogen or hydroxyl.

Formula CC-(XXXXIV)

A certain example is a compound of Formula CC-(XXXXIV):

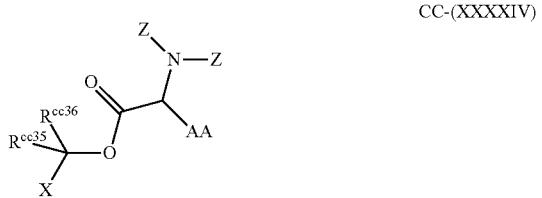

wherein

X is a residue of an opioid wherein the lone pair of electrons of the amino nitrogen is replaced with a bond to —C($R^{cc33}R^{cc34}$)—O—C(O)—C(AA)-NZZ; $R^{cc35}$ and $R^{cc36}$ are independently selected from hydrogen, halide, alkyl, and cycloalkyl or $R^{cc35}$ and $R^{cc36}$ can be combined with the carbon to which they are connected to form a cycloalkyl group;

AA is a side chain of an amino acid; and

Z is hydrogen, alkyl, or acyl.

A certain formula of CC-(XXXXIV) is shown below:

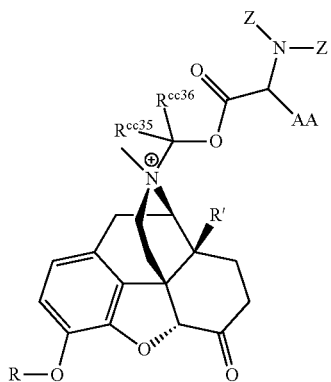

wherein $R^{cc35}$ and $R^{cc36}$ are independently selected from hydrogen, halide, alkyl, and cycloalkyl or $R^{cc35}$ and $R^{cc36}$ can be combined with the carbon to which they are connected to form a cycloalkyl group;

AA is a side chain of an amino acid;

Z is hydrogen, alkyl, or acyl; and

R is hydrogen or methyl; and

R' is hydrogen or hydroxyl.

Amide-Modified Opioid Prodrugs

The disclosure provides an amide-modified opioid prodrug which provides enzymatically-controlled release of an amide-containing opioid. In an amide-modified opioid prodrug, a promoiety is attached to the amide-containing opioid through the enolic oxygen atom of the amide enol moiety or through the oxygen of the imine tautomer. In an amide-modified opioid prodrug, the hydrogen atom of the corresponding enolic group of the amide enol or the imine tautomer of the amide-containing opioid is replaced by a covalent bond to a promoiety. In certain embodiments, the promoiety that replaces the hydrogen atom of the corresponding enolic group of the amide enol or the imine tautomer of the amide-containing opioid contains an acyl group as the point of connection.

Release of the opioid is mediated by enzymatic cleavage of the promoiety from the amide-containing opioid. The promoiety comprises an enzyme-cleavable moiety. In one embodiment, the cleavable moiety is a GI enzyme cleavable moiety, such as a trypsin cleavable moiety. Such cleavage can initiate, contribute to or effect drug release.

Amide-Modified Opioid Prodrugs with Promoiety Comprising Cyclizable Spacer Leaving Group and Cleavable Moiety According to certain embodiments, there is provided an amide-modified opioid prodrug which provides enzymatically-controlled release of an amide-containing opioid. The amide-containing opioid is a corresponding compound in which the enolic oxygen atom of the amide enol moiety or the oxygen of the imine tautomer has a substituent which is a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide an amide-containing opioid.

The corresponding compound (prodrug in accordance with the present disclosure) provides post administration-activated, controlled release of the amide-containing opioid, because it requires enzymatic cleavage to initiate release of the compound, and because the rate of release of the amide-containing opioid depends upon both the rate of enzymatic cleavage and the rate of cyclization. Accordingly, the prodrug has reduced susceptibility to accidental overdosing or abuse, whether by deliberate overdosing, administration through an inappropriate route, such as by injection, or by chemical modification using readily available household chemicals. The prodrug is configured so that it will not provide excessively high plasma levels of the active drug if it is administered inappropriately, and cannot readily be decomposed to afford the active drug other than by enzymatic cleavage followed by controlled cyclization.

The enzyme-cleavable moiety linked to the nitrogen nucleophile through an amide bond can be, for example, a residue of an amino acid or a peptide, or an (alpha) N-acyl derivative of an amino acid or peptide (for example an N-acyl derivative of a pharmaceutically acceptable carboxylic acid). The peptide can contain, for example, up to about 100 amino acid residues. Each amino acid can advantageously be a naturally occurring amino acid, such as an L-amino acid. Examples of naturally occurring amino acids are alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. Accordingly, examples of enzyme-cleavable moieties include residues of the L-amino acids listed hereinabove and N-acyl derivatives thereof, and peptides formed from at least two of the L-amino acids listed hereinabove, and the N-acyl derivatives thereof.

The cyclic group formed when the amide-containing opioid is released is conveniently pharmaceutically acceptable, in particular a pharmaceutically acceptable cyclic urea. It will be appreciated that cyclic ureas are generally very stable and have low toxicity.

Formula AE-(I)

In one of its composition aspects, the present embodiments provide a compound of formula AE-(I):

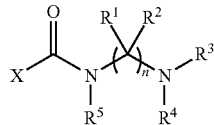

(AE-(I))

wherein:

X represents a residue of an amide-containing opioid, wherein —C(O)—NR$^5$—(C(R$^1$)(R$^2$))$_n$—NR$^3$R$^4$ is connected to the amide-containing opioid through the oxygen of the amide group, wherein the amide group is converted to an amide enol or an imine tautomer;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^1$ or R$^2$ groups on adjacent carbon atoms, together with the carbon atoms to which they are attached, form a cycloalkyl, substituted cycloalkyl, aryl, or substituted aryl group;

n is an integer from 2 to 4;

R$^3$ is hydrogen or (1-4C)alkyl;

R$^4$ is

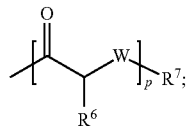

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Formula AE-(II)

Compounds of formula AE-(II) are compounds of formula AE-(I) in which R$^5$ is selected from (1-6C) alkyl, (1-6C) substituted alkyl, —(CH$_2$)$_q$(C$_6$H$_4$)—COOH, —(CH$_2$)$_q$(C$_6$H$_4$)—COOCH$_3$, and —(CH$_2$)$_q$(C$_6$H$_4$)—COOCH$_2$CH$_3$, where q is an integer from one to 10; n is 2 or 3; R$^3$ is hydrogen; R$^4$ is an amino acid or peptide, where the peptide can be comprised of amino acids. In one of its composition aspects, the present embodiments provide a compound of formula AE-(II):

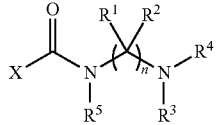

(AE-(II))

wherein:

X represents a residue of an amide-containing opioid, wherein —C(O)—NR$^5$—(C(R$^1$)(R$^2$))$_n$—NR$^3$R$^4$ is connected to the amide-containing opioid through the oxygen of the amide group, wherein the amide group is converted to an amide enol or an imine tautomer;

R$^5$ is selected from (1-6C)alkyl, (1-6C) substituted alkyl, —(CH$_2$)$_q$(C$_6$H$_4$)—COOH, —(CH$_2$)$_q$(C$_6$H$_4$)—COOCH$_3$, and —(CH$_2$)$_q$(C$_6$H$_4$)—COOCH$_2$CH$_3$, where q is an integer from one to 10;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^1$ or R$^2$ groups on adjacent carbon atoms, together with the carbon atoms to which they are attached, form a cycloalkyl, substituted cycloalkyl, aryl, or substituted aryl group;

n is 2 or 3;

R$^3$ is hydrogen;

R$^4$ is a GI enzyme-cleavable moiety;

or a salt, hydrate or solvate thereof.

In formula AE-(II), R$^4$ is a GI enzyme-cleavable moiety. A GI enzyme-cleavable moiety is a structural moiety that is capable of being cleaved by GI enzyme.

In certain embodiments, in formula AE-(II), R$^4$ is —C(O)—CH(R$^6$)—NH(R$^5$), wherein R$^6$ represents a side chain of an amino acid or a derivative of a side chain of an amino acid that effects R$^4$ to be a GI enzyme-cleavable moiety. A derivative refers to a substance that has been altered from another substance by modification, partial substitution, homologation, truncation, or a change in oxidation state.

For example, to form a GI enzyme-cleavable moiety, R$^6$ can include, but is not limited to, lysine (such as L-lysine), arginine (such as L-arginine), homolysine, homoarginine, and ornithine. Other values for a GI enzyme cleavable moiety include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines, and (bicyclo[2.2.2] octan-1-yl)methanamine and derivatives thereof.

In certain instances, in formula AE-(II), R$^6$ represents —CH$_2$CH$_2$CH$_2$NH(C═NH)NH$_2$ or —CH$_2$CH$_2$CH$_2$CH$_2$NH$_2$, the configuration of the carbon atom to which R$^6$ is attached corresponding with that in an L-amino acid.

In formula AE-(II), R$^5$ is selected from hydrogen, alkyl, substituted alkyl, acyl, substituted acyl, alkoxycarbonyl, substituted alkoxycarbonyl, aryl, substituted aryl, arylalkyl, and substituted arylalkyl. In certain instances, R$^5$ is an amino acid or an N-acyl derivative of an amino acid. In certain instances, $R^5$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

General Synthetic Procedures for Compounds of Formulae AE-(I) to AE-(II)

The synthetic schemes and procedures disclosed herein for formulae PC-(I) to PC-(XV) can also be used to synthesize compounds of formulae AE-(I) to AE-(II).

Amide-Modified Opioid Prodrugs with Attachment to Amino Acid Promoiety

According to certain embodiments, there is provided an amide-modified opioid prodrug which provides enzymatically-controlled release of an amide-containing opioid. The amide-containing opioid is a corresponding compound in which the lone pair of electrons of the nitrogen of the amide group is replaced with a bond to a promoiety.

In one of its composition aspects, the present embodiments provide a compound of formula AE-(III):

(AE-(III))

wherein:

X represents a residue of an amide-containing opioid, wherein —CO—C($R^6$)—N$R^8R^7$ is connected to the amide-containing opioid through the oxygen of the amide group, wherein the amide group is converted to an amide enol or an imine tautomer;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl; or a salt, hydrate or solvate thereof.

General Synthetic Procedures for Compounds of Formula AE-(III)

Compounds of formula AE-(III) can be made with standard peptide coupling chemistry.

Amino Acids Found in Prodrugs

"Amino acid" means a building block of a polypeptide. As used herein, "amino acid" includes the 20 common naturally occurring L-amino acids and all amino acids variants. In certain embodiments, an amino acid is a cleavable substrate for a gastrointestinal enzyme.

"Naturally occurring amino acids" means the 20 common naturally occurring L-amino acids, that is, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

"Amino acid variants" means an amino acid other than any of the 20 common naturally occurring L-amino acids that is hydrolysable by a protease in a manner similar to the ability of a protease to hydrolyze a naturally occurring L-amino acid. Amino acid variants, thus, include amino acids or analogs of amino acids other than the 20 naturally-occurring amino acids. Amino acid variants include synthetic amino acids. Amino acid variants also include amino acid derivatives. A derivative refers to a substance that has been altered from another substance by modification, partial substitution, homologation, truncation, or a change in oxidation state while retaining the ability to be cleaved by a GI enzyme.

Certain examples of amino acid variants include, but are not limited to: 2-aminoindane-2-carboxylic acid, 2-aminoisobutyric acid, 4-amino-phenylalanine, 5-hydroxylysine, biphenylalanine, citrulline, cyclohexylalanine, cyclohexylglycine, diethylglycine, dipropylglycine, homoarginine, homocitrulline, homophenylalanine, homoproline, homoserine, homotyrosine, hydroxyproline, lanthionine, naphthylalanine, norleucine, ornithine, phenylalanine(4-fluoro), phenylalanine(4-nitro), phenylglycine, pipecolic acid, tert-butylalanine, tert-butylglycine, tert-leucine, tetrahydroisoquinoline-3-carboxylic acid, α-aminobutyric acid, γ-amino butyric acid, 2,3-diaminoproprionic acid, phenylalanine(2,3,4,5,6 pentafluoro), aminohexanoic acid and derivatives thereof.

Certain examples of amino acid variants include, but are not limited to, N-methyl amino acids. For example, N-methyl-alanine, N-methyl aspartic acid, N-methyl-glutamic acid, N-methyl-glycine (sarcosine) are N-methyl amino acids.

Certain examples of amino acid variants include, but are not limited to: dehydroalanine, ethionine, hypusine, lanthionine, pyrrolysine, α-aminoisobutyric acid, selenomethionine and derivatives thereof.

Certain examples of amino acid variants include, but are not limited to: (3,2-amino benzoic acid, 2-amino methyl benzoic acid, 2-amino-3-guanidinopropionic acid, 2-amino-3-methoxy benzoic acid, 2-amino-3-ureidopropionic acid, 3-amino benzoic acid, 4-amino benzoic acid, 4-amino methyl benzoic acid, 4-nitroanthranillic acid, 5-acetamido-2-aminobenzoic acid, butanoic acid (HMB), glutathione, homocysteine, statine, taurine, β-alanine, 2-hydroxy-4-(methylthio), (3,4)-diamino benzoic acid, (3,5)-diamino benzoic acid and derivatives thereof.

Certain examples of amino acid variants include, but are not limited to: (2 amino ethyl) cysteine, 2-amino-3-ethyoxybutanoic acid, buthionine, cystathion, cysteic acid, ethionine, ethoxytheorine, methylserine, N-ε-ε-dimethyl-lysine, N-ω-nitro-arginine, saccharopine, isoserine derivatives thereof, and combinations thereof.

Certain examples of amino acid variants include, but are not limited to: l-carnitine, selenocysteine, l-sarcosine, l-lysinol, benzoic acid, citric acid, choline, EDTA or succinic acid and derivatives thereof.

Certain examples of amino acid variants are amino alcohols. Examples of amino alcohols include, but are not limited to: alaminol, indano, norephedrine, asparaginol, aspartimol, glutamol, leucinol, methioninol, phenylalaminol, prolinol, tryptophanol, valinol, isoleucinol, argininol, serinol, tyrosinol, threoninol, cysteinol, lysinol, histidinol and derivatives thereof.

Enzyme Inhibitors

The enzyme capable of cleaving the enzymatically-cleavable moiety of an opioid prodrug can be a peptidase, also called a protease. In certain embodiments, the enzyme is an enzyme located in the gastrointestinal (GI) tract, i.e., a gastrointestinal enzyme, or a GI enzyme. The enzyme can be a digestive enzyme such as a gastric, intestinal, pancreatic or brush border enzyme or enzyme of GI microbial flora, such as those involved in peptide hydrolysis. Examples include a pepsin, such as pepsin A or pepsin B; a trypsin; a chymotrypsin; an elastase; a carboxypeptidase, such as carboxypeptidase A or carboxypeptidase B; an aminopeptidase (such as aminopeptidase N or aminopeptidase A; an endopeptidase; an exopeptidase; a dipeptidylaminopeptidase such as dipeptidylaminopeptidase IV; a dipeptidase; a tripeptidase; or an enteropeptidase. In certain embodiments, the enzyme is a cytoplasmic protease located on or in the GI brush border. In certain embodiments, the enzyme is trypsin. Accordingly, in certain embodiments, the corresponding composition is administered orally to the patient.

The disclosure provides for a composition comprising a GI enzyme inhibitor. Such an inhibitor can inhibit at least one of any of the GI enzymes disclosed herein. An example of a GI enzyme inhibitor is a protease inhibitor, such as a trypsin inhibitor.

As used herein, the term "GI enzyme inhibitor" refers to any agent capable of inhibiting the action of a GI enzyme on a substrate. The ability of an agent to inhibit a GI enzyme can be measured using assays well known in the art.

In certain embodiments, the GI enzyme capable of cleaving the enzymatically-cleavable moiety may be a protease—the promoiety comprising the enzymatically-cleavable moiety being linked to the opioid or prodrug through an amide (e.g. a peptide: —NHC(O)—) bond. The disclosure provides for inhibitors of proteases.

Proteases can be classified as exopeptidases or endopeptidases. Examples of exopeptidases include aminopeptidase and carboxypeptidase (A, B, or Y). Examples of endopeptidases include trypsin, chymotrypsin, elastase, pepsin, and papain. The disclosure provides for inhibitors of exopeptidase and endopeptidase.

In some embodiments, the enzyme is a digestive enzyme of a protein. The disclosure provides for inhibitors of digestive enzymes. A gastric phase involves stomach enzymes, such as pepsin. An intestinal phase involves enzymes in the small intestine duodenum, such as trypsin, chymotrypsin, elastase, carboxypeptidase A, and carboxypeptidase B. An intestinal brush border phase involves enzymes in the small intestinal brush border, such as aminopeptidase N, aminopeptidase A, endopeptidases, dipeptidases, dipeptidylaminopeptidase, and dipeptidylaminopeptidase IV. An intestinal intracellular phase involves intracellular peptidases, such as dipeptidases (i.e. iminopeptidase) and aminopeptidase.

In certain embodiments, the enzyme inhibitor in the disclosed compositions is a peptidase inhibitor or protease inhibitor. In certain embodiments, the enzyme is a digestive enzyme such as a gastric, pancreatic or brush border enzyme, such as those involved in peptide hydrolysis. Examples include pepsin, trypsin, chymotrypsin, colipase, elastase, aminopeptidase N, aminopeptidase A, dipeptidylaminopeptidase IV, tripeptidase or enteropeptidase.

Proteases can be inhibited by naturally occurring peptide or protein inhibitors, or by small molecule naturally occurring or synthetic inhibitors. Examples of protein or peptide inhibitors that are protease inhibitors include, but are not limited to, α1-antitrypsin from human plasma, aprotinin, trypsin inhibitor from soybean (SBTI), Bowman-Birk Inhibitor from soybean (BBSI), trypsin inhibitor from egg white (ovomucoid), chromostatin, and potato-derived carboxypeptidase inhibitor. Examples of small molecule irreversible inhibitors that are protease inhibitors include, but are not limited to, TPCK (1-chloro-3-tosylamido-4-phenyl-2-butanone), TLCK (1-chloro-3-tosylamido-7-amino-2-heptone), and PMSF (phenylmethyl sulfonyl floride). Examples of small molecule irreversible inhibitors that are protease inhibitors include, but are not limited to benzamidine, apixaban, camostat, 3,4-dichloroisocoumarin, ε-aminocaprionic acid, amastatin, lysianadioic acid, 1,10-phenanthroline, cysteamine, and bestatin. Other examples of small molecule inhibitors are Compound 101, Compound 102, Compound 103, Compound 104, Compound 105, Compound 106, Compound 107, Compound 108, Compound 109 and Compound 110.

The following table shows examples of gastrointestinal (GI) proteases, examples of their corresponding substrates, and examples of corresponding inhibitors.

Table of Examples of GI Proteases and Corresponding Susbtrates and Inhibitors

| GI Protease | Substrates | Inhibitors |
| --- | --- | --- |
| Trypsin | $R_{n-1}$ = Arg, Lys, positively charged residues | TLCK, Benzamidine, Apixaban, Bowman Birk |
| Chymotrypsin | $R_{n-1}$ = Phe, Tyr, Trp, bulky hydrophobic residues | ε-Aminocaprionic TPCK Bowman-Birk |
| Pepsin | $R_n$ = Leu, Phe, Trp, Tyr | Pepstatin, PMSF |
| Carboypeptidase B | $R_n$ = Arg, Lys | Potato-derived inhibitor, Lysianadioic acid |
| Carboypeptidase A | $R_n$ not = Arg, Lys | Potato-derived inhibitor, 1,10-phenanthroline |

Table of Examples of GI Proteases and Corresponding Susbtrates and Inhibitors

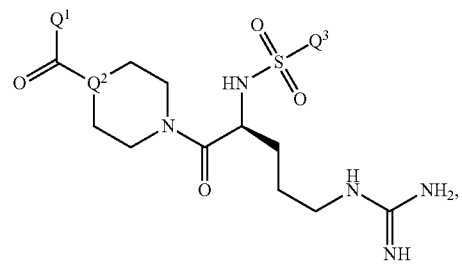

Endopeptidase Substrates     Exopeptidase Substrates

| GI Protease | Substrates | Inhibitors |
|---|---|---|
| Elastase | $R_{n-1}$ = Ala, Gly, Ser, small neutral residues | α1-antitrypsin, 3,4-dichlorocoumarin |
| Aminopeptidase | All free N-terminal AA | Bestatin, Amastatin |

Trypsin Inhibitors

As used herein, the term "trypsin inhibitor" refers to any agent capable of inhibiting the action of trypsin on a substrate. The term "trypsin inhibitor" also encompasses salts of trypsin inhibitors. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241, 3955 and Y. Birk, 1976, Meth. Enzymol. 45, 700. In certain instances, a trypsin inhibitor can interact with an active site of trypsin, such as the 51 pocket and the S3/4 pocket. The 51 pocket has an aspartate residue which has affinity for positively charged moiety. The S3/4 pocket is a hydrophobic pocket. The disclosure provides for specific trypsin inhibitors and non-specific serine protease inhibitors.

There are many trypsin inhibitors known in the art, both those specific to trypsin and those that inhibit trypsin and other proteases such as chymotrypsin. The disclosure provides for trypsin inhibitors that are proteins, peptides, and small molecules. The disclosure provides for trypsin inhibitors that are irreversible inhibitors or reversible inhibitors. The disclosure provides for trypsin inhibitors that are competitive inhibitors, non-competitive inhibitors, or uncompetitive inhibitors. The disclosure provides for natural, synthetic or semi-synthetic trypsin inhibitors.

Trypsin inhibitors can be derived from a variety of animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678.

In one embodiment, the trypsin inhibitor is derived from soybean. Trypsin inhibitors derived from soybean (*Glycine max*) are readily available and are considered to be safe for human consumption. They include, but are not limited to, SBTI, which inhibits trypsin, and Bowman-Birk inhibitor, which inhibits trypsin and chymotrypsin. Such trypsin inhibitors are available, for example from Sigma-Aldrich, St. Louis, Mo., USA.

A trypsin inhibitor can be an arginine mimic or lysine mimic, either natural or synthetic compound. In certain embodiments, the trypsin inhibitor is an arginine mimic or a lysine mimic, wherein the arginine mimic or lysine mimic is a synthetic compound. As used herein, an arginine mimic or lysine mimic can include a compound capable of binding to the $P^1$ pocket of trypsin and/or interfering with trypsin active site function. The arginine or lysine mimic can be a cleavable or non-cleavable moiety.

Examples of trypsin inhibitors, which are arginine mimics and/or lysine mimics, include, but not limited to, arylguanidine, benzamidine, 3,4-dichloroisocoumarin, diisopropylfluorophosphate, gabexate mesylate, and phenylmethanesulfonyl fluoride, or substituted versions or analogs thereof. In certain embodiments, trypsin inhibitors comprise a covalently modifiable group, such as a chloroketone moiety, an aldehyde moiety, or an epoxide moiety. Other examples of trypsin inhibitors are aprotinin, camostat and pentamidine.

Other examples of trypsin inhibitors include compounds of formula:

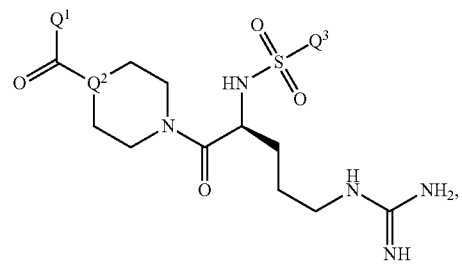

wherein:
$Q^1$ is selected from —O-$Q^4$ or -$Q^4$-COOH, where $Q^4$ is $C_1$-$C_4$ alkyl;
$Q^2$ is N or CH; and
$Q^3$ is aryl or substituted aryl.

Certain trypsin inhibitors include compounds of formula:

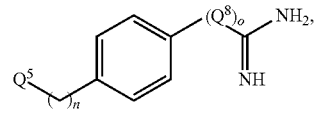

wherein:
$Q^5$ is —C(O)—COOH or —NH-$Q^6$-$Q^7$-$SO_2$—$C_6H_5$, where
$Q^6$ is —$(CH_2)_p$—COOH;
$Q^7$ is —$(CH_2)_r$—$C_6H_5$;
$Q^8$ is NH;
n is a number from zero to two;
o is zero or one;
p is an integer from one to three; and
r is an integer from one to three.

Other examples of trypsin inhibitors include compounds of formula:

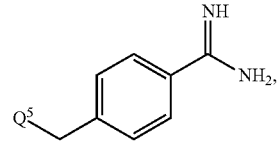

wherein:
$Q^5$ is —C(O)—COOH or —NH-$Q^6$-$Q^7$-$SO_2$—$C_6H_5$, where
$Q^6$ is —$(CH_2)_p$—COOH;
$Q^7$ is —$(CH_2)_r$—$C_6H_5$; and
p is an integer from one to three; and
r is an integer from one to three.

Certain trypsin inhibitors include the following:

Compound 101 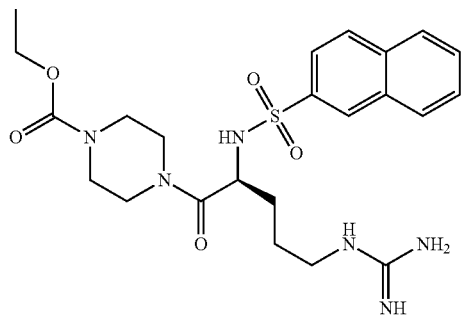 [SMILES: CCOC(=O)N1CCN(C(=O)[C@H](CCCNC(=N)N)NS(=O)(=O)c2ccc3ccccc3c2)CC1] (S)-ethyl 4-(5-guanidino-2-(naphthalene-2-sulfonamido)pentanoyl)piperazine-1-carboxylate Compound 102 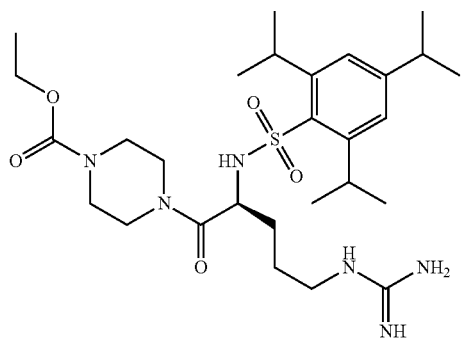 (S)-ethyl 4-(5-guanidino-2-(2,4,6-triisopropylphenylsulfonamido)pentanoyl)piperazine-1-carboxylate Compound 103 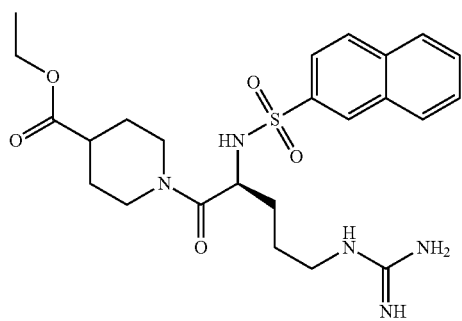 (S)-ethyl 1-(5-guanidino-2-(naphthalene-2-sulfonamido)pentanoyl)piperidine-4-carboxylate Compound 104 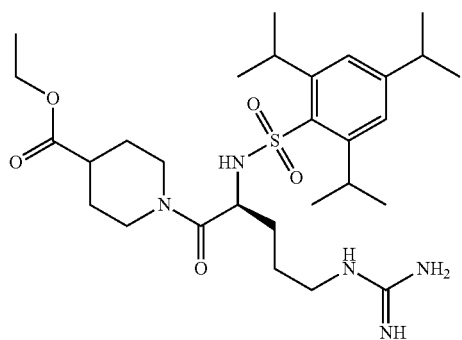 [SMILES: CCOC(=O)C1CCN(C(=O)[C@H](CCCNC(=N)N)NS(=O)(=O)c2c(C(C)C)cc(C(C)C)cc2C(C)C)CC1] (S)-ethyl 1-(5-guanidino-2-(2,4,6-triisopropylphenylsulfonamido)pentanoyl)piperidine-4-carboxylate -continued

| | | |
|---|---|---|
| Compound 105 | 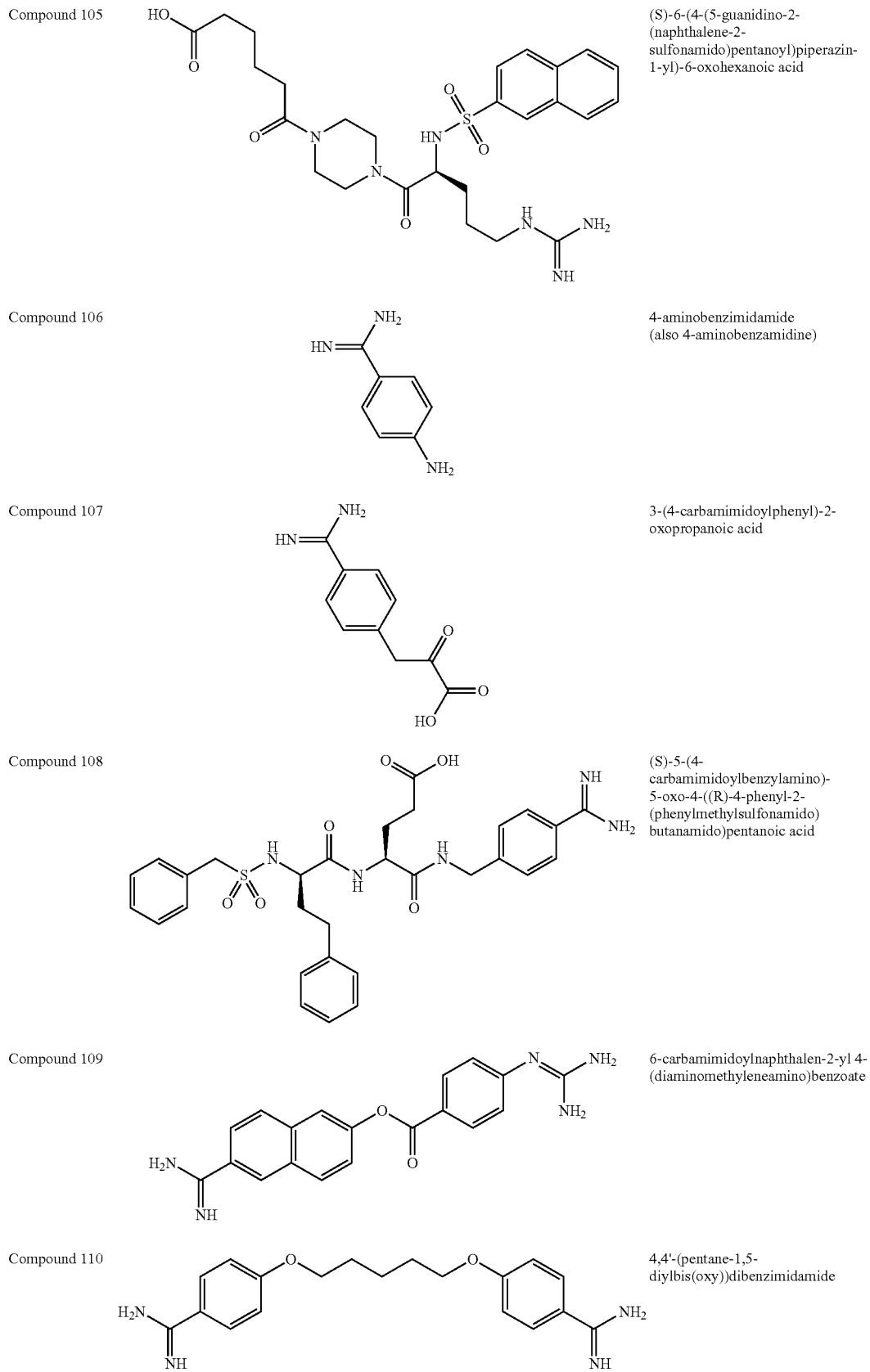 | (S)-6-(4-(5-guanidino-2-(naphthalene-2-sulfonamido)pentanoyl)piperazin-1-yl)-6-oxohexanoic acid |
| Compound 106 | | 4-aminobenzimidamide (also 4-aminobenzamidine) |
| Compound 107 | | 3-(4-carbamimidoylphenyl)-2-oxopropanoic acid |
| Compound 108 | | (S)-5-(4-carbamimidoylbenzylamino)-5-oxo-4-((R)-4-phenyl-2-(phenylmethylsulfonamido)butanamido)pentanoic acid |
| Compound 109 | | 6-carbamimidoylnaphthalen-2-yl 4-(diaminomethyleneamino)benzoate |
| Compound 110 | | 4,4'-(pentane-1,5-diylbis(oxy))dibenzimidamide |

In certain embodiments, the trypsin inhibitor is SBTI, BBSI, Compound 101, Compound 106, Compound 108, Compound 109, or Compound 110. In certain embodiments, the trypsin inhibitor is camostat.

In certain embodiments, the trypsin inhibitor is a compound of formula T-I:

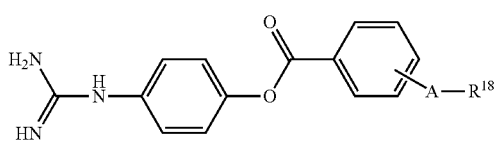

(T-I)

wherein

A represents a group of the following formula:

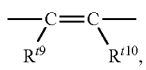

$R^{t9}$ and $R^{t10}$ each represents independently a hydrogen atom or a $C_{1-4}$ alkyl group, $R^{t8}$ represents a group selected from the following formulae:

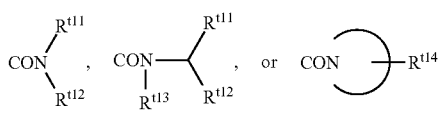

wherein $R^{t11}$, $R^{t12}$ and $R^{t13}$ each represents independently
(1) a hydrogen atom,
(2) a phenyl group,
(3) a $C_{1-4}$ alkyl group substituted by a phenyl group,
(4) a $C_{1-10}$ alkyl group,
(5) a $C_{1-10}$ alkoxyl group,
(6) a $C_{2-10}$ alkenyl group having 1 to 3 double bonds,
(7) a $C_{2-10}$ alkynyl group having 1 to 2 triple bonds,
(8) a group of formula: $R^{t15}$—C(O)X$R^{t16}$,
wherein $R^{t15}$ represents a single bond or a $C_{1-8}$ alkylene group,
X represents an oxygen atom or an NH-group, and
$R^{t16}$ represents a hydrogen atom, a $C_{1-4}$ alkyl group, a phenyl group or a $C_{1-4}$ alkyl group substituted by a phenyl group, or
(9) a $C_{3-7}$ cycloalkyl group;
the structure

represents a 4-7 membered monocyclic hetero-ring containing 1 to 2 nitrogen or oxygen atoms, $R^{t14}$ represents a hydrogen atom, a $C_{1-4}$ alkyl group substituted by a phenyl group or a group of formula: COO$R^{t17}$, wherein $R^{t17}$ represents a hydrogen atom, a $C_{1-4}$ alkyl group or a $C_{1-4}$ alkyl group substituted by a phenyl group;

provided that $R^{t11}$, $R^{t12}$ and $R^{t13}$ do not represent simultaneously hydrogen atoms;

or nontoxic salts, acid addition salts or hydrates thereof.

In certain embodiments, the trypsin inhibitor is a compound selected from the following:

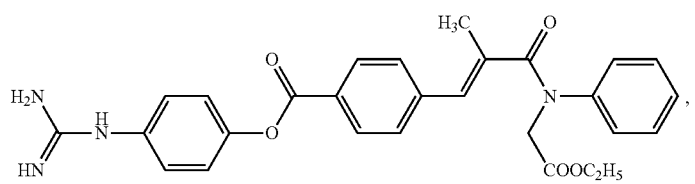

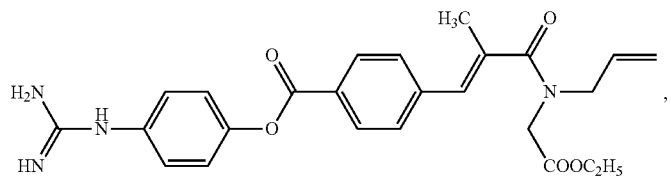

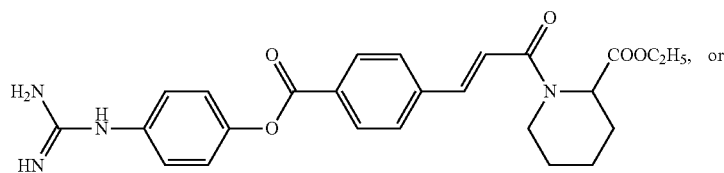

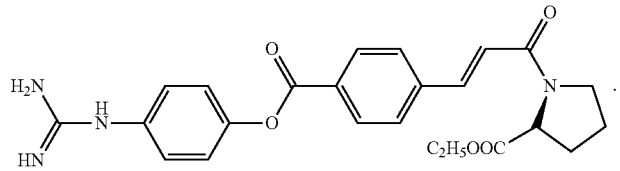

In certain embodiments, the trypsin inhibitor is a compound of formula T-II:

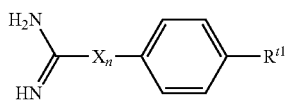

(T-II)

wherein

X is NH;

n is zero or one; and $R^{t1}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —$(CH_2)_m$—C(O)—O—$(CH_2)_m$—C(O)—N—$R^{n1}R^{n2}$, wherein each m is independently zero to 2; and $R^{n1}$ and $R^{n2}$ are independently selected from hydrogen and $C_{1-4}$ alkyl.

In certain embodiments, in formula T-II, $R^{t1}$ is guanidino or amidino.

In certain embodiments, in formula T-II, $R^{t1}$ is —$(CH_2)_m$—C(O)—O—$(CH_2)_m$—C(O)—N—$R^{n1}R^{n2}$, wherein m is one and $R^{n1}$ and $R^{n2}$ are methyl.

In certain embodiments, the trypsin inhibitor is a compound of formula T-III:

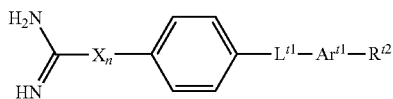

(T-III)

wherein

X is NH;

n is zero or one;

$L^{t1}$ is selected from —C(O)—O—; —O—C(O)—; —O—$(CH_2)_m$—O—; —OCH$_2$—Ar$^{t2}$—CH$_2$O—; —C(O)—NR$^{t3}$—; and —NR$^{t3}$—C(O)—;

$R^{t3}$ is selected from hydrogen, $C_{1-6}$ alkyl, and substituted $C_{1-6}$ alkyl;

Ar$^{t1}$ and Ar$^{t2}$ are independently a substituted or unsubstituted aryl group;

m is a number from 1 to 3; and $R^{t2}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —$(CH_2)_m$—C(O)—O—$(CH_2)_m$—C(O)—N—$R^{n1}R^{n2}$, wherein each m is independently zero to 2; and $R^{n1}$ and $R^{n2}$ are independently selected from hydrogen and $C_{1-4}$ alkyl.

In certain embodiments, in formula T-III, $R^{t2}$ is guanidino or amidino.

In certain embodiments, in formula T-III, $R^{t2}$ is —$(CH_2)_m$—C(O)—O—$(CH_2)_m$—C(O)—N—$R^{n1}R^{n2}$, wherein m is one and $R^{n1}$ and $R^{n2}$ are methyl.

In certain embodiments, the trypsin inhibitor is a compound of formula T-IV:

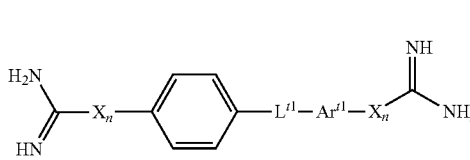

(T-IV)

wherein each X is NH;

each n is independently zero or one;

$L^{t1}$ is selected from —C(O)—O—; —O—C(O)—; —O—$(CH_2)_m$—O—; —OCH$_2$—Ar$^{t2}$—CH$_2$O—; —C(O)—NR$^{t3}$—; and —NR$^{t3}$—C(O)—;

$R^{t3}$ is selected from hydrogen, $C_{1-6}$ alkyl, and substituted $C_{1-6}$ alkyl;

Ar$^{t1}$ and Ar$^{t2}$ are independently a substituted or unsubstituted aryl group; and m is a number from 1 to 3.

In certain embodiments, in formula T-IV, Ar$^{t1}$ or Ar$^{t2}$ is phenyl.

In certain embodiments, in formula T-IV, Ar$^{t1}$ or Ar$^{t2}$ is naphthyl.

In certain embodiments, the trypsin inhibitor is Compound 109.

In certain embodiments, the trypsin inhibitor is

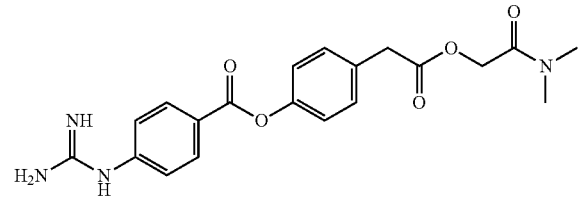 [SMILES: CN(C)C(=O)COC(=O)Cc1ccc(OC(=O)c2ccc(NC(=N)N)cc2)cc1]

In certain embodiments, the trypsin inhibitor is Compound 110 or a bis-arylamidine variant thereof; see, for example, J. D. Geratz, M. C.-F. Cheng and R. R. Tidwell (1976) J Med. Chem. 19, 634-639.

It will be appreciated that the pharmaceutical composition according to the embodiments may further comprise one or more additional trypsin inhibitors.

It is to be appreciated that the invention also includes inhibitors of other enzymes involved in protein assimilation that can be used in combination with a prodrug disclosed herein comprising an amino acid of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine or amino acid variants thereof.

Combinations of Prodrugs and Enzyme Inhibitors

As discussed above, the present disclosure provides pharmaceutical compositions which comprise a trypsin inhibitor and an opioid prodrug that contains a trypsin-cleavable moiety that, when cleaved, facilitates release of an opioid.

Combinations of Alcohol-Modified Opioid Prodrug and Enzyme Inhibitor

Examples of compositions containing an alcohol-modified opioid prodrug (e.g., a phenol-modified opioid prodrug) and an enzyme inhibitor (e.g., a trypsin inhibitor) are described below.

Combinations of Formulae PC-(I) to PC-(VI) and Enzyme Inhibitor

The embodiments provide a pharmaceutical composition, which comprises an enzyme inhibitor and a compound of general Formula PC-(I), or a pharmaceutically acceptable salt thereof.

The embodiments provide a pharmaceutical composition, which comprises an enzyme inhibitor and a compound of general Formulae PC-(II) to PC-(VI), or a pharmaceutically acceptable salt thereof.

The embodiments provide a pharmaceutical composition, which comprises a compound of Formulae T-I to T-IV and a compound of general Formulae PC-(I) to PC-(VI), or a pharmaceutically acceptable salt thereof. The embodiments provide a pharmaceutical composition, which comprises Compound 109 and a compound of general Formulae PC-(I) to PC-(VI), or a pharmaceutically acceptable salt thereof.

The embodiments provide a pharmaceutical composition, which comprises an enzyme inhibitor and a compound disclosed herein other than a compound of general Formula PC-(I), or a pharmaceutically acceptable salt thereof.

The embodiments provide a pharmaceutical composition, which comprises an enzyme inhibitor and a compound disclosed herein other than a compound of general Formula PC-(II) to PC-(VI), or a pharmaceutically acceptable salt thereof.

Certain embodiments provide for a combination of a compound of Formula PC-(I) and an enzyme inhibitor, in which the phenolic opioid of Formula PC-(I) and the enzyme inhibitor are shown in the following table.

Examples of Combinations of:
Prodrug of Formula PC-(I) Having Phenolic Opioid
As Indicated Below; and Enzyme Inhibitor

| | | | |
|---|---|---|---|
| Oxymorphone | Hydromorphone | Morphine | Tapentadol |
| SBTI | SBTI | SBTI | SBTI |
| Oxymorphone | Hydromorphone | Morphine | Tapentadol |
| BBSI | BBSI | BBSI | BBSI |
| Oxymorphone | Hydromorphone | Morphine | Tapentadol |
| Compound 101 | Compound 101 | Compound 101 | Compound 101 |
| Oxymorphone | Hydromorphone | Morphine | Tapentadol |
| Compound 106 | Compound 106 | Compound 106 | Compound 106 |
| Oxymorphone | Hydromorphone | Morphine | Tapentadol |
| Compound 108 | Compound 108 | Compound 108 | Compound 108 |
| Oxymorphone | Hydromorphone | Morphine | Tapentadol |
| Compound 109 | Compound 109 | Compound 109 | Compound 109 |
| Oxymorphone | Hydromorphone | Morphine | Tapentadol |
| Compound 110 | Compound 110 | Compound 110 | Compound 110 |

Certain embodiments provide for a combination of a compound of formula PC-(II) and enzyme inhibitor, in which the phenolic opioid of formula PC-(II) and the enzyme inhibitor are shown in the following table.

Examples of Combinations of:
Prodrug of Formula PC-(II) Having Phenolic Opioid
As Indicated Below; and Enzyme Inhibitor

| | | | |
|---|---|---|---|
| Oxymorphone | Hydromorphone | Morphine | Tapentadol |
| SBTI | SBTI | SBTI | SBTI |
| Oxymorphone | Hydromorphone | Morphine | Tapentadol |
| BBSI | BBSI | BBSI | BBSI |
| Oxymorphone | Hydromorphone | Morphine | Tapentadol |
| Compound 101 | Compound 101 | Compound 101 | Compound 101 |
| Oxymorphone | Hydromorphone | Morphine | Tapentadol |
| Compound 106 | Compound 106 | Compound 106 | Compound 106 |
| Oxymorphone | Hydromorphone | Morphine | Tapentadol |
| Compound 108 | Compound 108 | Compound 108 | Compound 108 |
| Oxymorphone | Hydromorphone | Morphine | Tapentadol |
| Compound 109 | Compound 109 | Compound 109 | Compound 109 |
| Oxymorphone | Hydromorphone | Morphine | Tapentadol |
| Compound 110 | Compound 110 | Compound 110 | Compound 110 |

Certain embodiments provide for a combination of a compound of formula PC-(III) and enzyme inhibitor, in which the phenolic opioid of formula PC-(III) and the enzyme inhibitor are shown in the following table.

Examples of Combinations of:
Prodrug of Formula PC-(III) Having Phenolic Opioid As
Indicated Below; and Enzyme Inhibitor

| | | | |
|---|---|---|---|
| Oxymorphone | Hydromorphone | Morphine | Tapentadol |
| SBTI | SBTI | SBTI | SBTI |
| Oxymorphone | Hydromorphone | Morphine | Tapentadol |
| BBSI | BBSI | BBSI | BBSI |
| Oxymorphone | Hydromorphone | Morphine | Tapentadol |
| Compound 101 | Compound 101 | Compound 101 | Compound 101 |
| Oxymorphone | Hydromorphone | Morphine | Tapentadol |
| Compound 106 | Compound 106 | Compound 106 | Compound 106 |
| Oxymorphone | Hydromorphone | Morphine | Tapentadol |
| Compound 108 | Compound 108 | Compound 108 | Compound 108 |
| Oxymorphone | Hydromorphone | Morphine | Tapentadol |
| Compound 109 | Compound 109 | Compound 109 | Compound 109 |
| Oxymorphone | Hydromorphone | Morphine | Tapentadol |
| Compound 110 | Compound 110 | Compound 110 | Compound 110 |

Certain embodiments provide for a combination of Compound PC-1 and an enzyme inhibitor, Compound PC-2 and an enzyme inhibitor, Compound PC-3 and an enzyme inhibitor, Compound PC-4 and an enzyme inhibitor, Compound PC-5 and an enzyme inhibitor, and/or Compound PC-6 and an enzyme inhibitor, in which the enzyme inhibitor is shown in the following table. Compound PC-1 is hydromorphone 3-(N-methyl-N-(2-N'-acetylarginylamino)) ethylcarbamate (which can be produced as described in PCT International Publication No. WO 2007/140272, published 6 Dec. 2007, Example 3). Compound PC-2, Compound PC-3, Compound PC-4, Compound PC-5, and Compound PC-6 are each described in the Examples. Examples of combinations of such compounds and an enzyme inhibitor are provided in the following table.

Examples of Combinations of:
Compound PC-1, -2, -3, -4, -5, and -6;
and Enzyme Inhibitor

| | | | | | |
|---|---|---|---|---|---|
| PC-1; | PC-2; | PC-3; | PC-4; | PC-5; | PC-6; |
| SBTI | SBTI | SBTI | SBTI | SBTI | SBTI |
| PC-1; | PC-2; | PC-3; | PC-4; | PC-5; | PC-6; |
| BBSI | BBSI | BBSI | BBSI | BBSI | BBSI |
| PC-1; | PC-2; | PC-3; | PC-4; | PC-5; | PC-6; |
| Compound 101 | Compound 101 | Compound 101 | Compound 101 | Compound 101 | Compound 101 |

Examples of Combinations of:
Compound PC-1, -2, -3, -4, -5, and -6;
and Enzyme Inhibitor

| PC-1; Compound 106 | PC-2; Compound 106 | PC-3; Compound 106 | PC-4; Compound 106 | PC-5; Compound 106 | PC-6; Compound 106 |
|---|---|---|---|---|---|
| PC-1; Compound 108 | PC-2; Compound 108 | PC-3; Compound 108 | PC-4; Compound 108 | PC-5; Compound 108 | PC-6; Compound 108 |
| PC-1; Compound 109 | PC-2; Compound 109 | PC-3; Compound 109 | PC-4; Compound 109 | PC-5; Compound 109 | PC-6; Compound 109 |
| PC-1; Compound 110 | PC-2; Compound 110 | PC-3; Compound 110 | PC-4; Compound 110 | PC-5; Compound 110 | PC-6; Compound 110 |

Combinations of Formulae PC-(VII) to PC-(X) and Enzyme Inhibitor

The embodiments provide a pharmaceutical composition, which comprises an enzyme inhibitor and a compound of general Formulae PC-(VII) to PC-(X), or a pharmaceutically acceptable salt thereof.

The embodiments provide a pharmaceutical composition, which comprises a compound of Formulae T-I to T-IV and a compound of general Formulae PC-(VII) to PC-(X), or a pharmaceutically acceptable salt thereof. The embodiments provide a pharmaceutical composition, which comprises Compound 109 and a compound of general Formulae PC-(VII) to PC-(X), or a pharmaceutically acceptable salt thereof.

The embodiments provide a pharmaceutical composition, which comprises an enzyme inhibitor and a compound disclosed herein other than a compound of general Formulae PC-(I) to PC-(VI), or a pharmaceutically acceptable salt thereof.

Certain embodiments provide for a combination of a compound of Formula PC-(VII) and an enzyme inhibitor, in which the phenolic opioid of Formula PC-(VII) and the enzyme inhibitor are shown in the following table.

Examples of Combinations of:
Prodrug of Formula PC-(VII) Having Phenolic Opioid As Indicated Below; and Enzyme Inhibitor

| Oxymorphone | Hydromorphone | Morphine | Tapentadol |
|---|---|---|---|
| SBTI | SBTI | SBTI | SBTI |
| Oxymorphone | Hydromorphone | Morphine | Tapentadol |
| BBSI | BBSI | BBSI | BBSI |
| Oxymorphone | Hydromorphone | Morphine | Tapentadol |
| Compound 101 | Compound 101 | Compound 101 | Compound 101 |
| Oxymorphone | Hydromorphone | Morphine | Tapentadol |
| Compound 106 | Compound 106 | Compound 106 | Compound 106 |
| Oxymorphone | Hydromorphone | Morphine | Tapentadol |
| Compound 108 | Compound 108 | Compound 108 | Compound 108 |
| Oxymorphone | Hydromorphone | Morphine | Tapentadol |
| Compound 109 | Compound 109 | Compound 109 | Compound 109 |
| Oxymorphone | Hydromorphone | Morphine | Tapentadol |
| Compound 110 | Compound 110 | Compound 110 | Compound 110 |

Certain embodiments provide for a combination of a compound of Formula PC-(VIII) and an enzyme inhibitor, in which the phenolic opioid of Formula PC-(VIII) and the enzyme inhibitor are shown in the following table.

Examples of Combinations of:
Prodrug of Formula PC-(VIII) Having Phenolic Opioid As Indicated Below; and Enzyme Inhibitor

| Oxymorphone | Hydromorphone | Morphine | Tapentadol |
|---|---|---|---|
| SBTI | SBTI | SBTI | SBTI |
| Oxymorphone | Hydromorphone | Morphine | Tapentadol |
| BBSI | BBSI | BBSI | BBSI |
| Oxymorphone | Hydromorphone | Morphine | Tapentadol |
| Compound 101 | Compound 101 | Compound 101 | Compound 101 |
| Oxymorphone | Hydromorphone | Morphine | Tapentadol |
| Compound 106 | Compound 106 | Compound 106 | Compound 106 |
| Oxymorphone | Hydromorphone | Morphine | Tapentadol |
| Compound 108 | Compound 108 | Compound 108 | Compound 108 |
| Oxymorphone | Hydromorphone | Morphine | Tapentadol |
| Compound 109 | Compound 109 | Compound 109 | Compound 109 |
| Oxymorphone | Hydromorphone | Morphine | Tapentadol |
| Compound 110 | Compound 110 | Compound 110 | Compound 110 |

Combinations of Ketone-Modified Opioid Prodrug and Enzyme Inhibitor

Examples of compositions containing a ketone-modified opioid prodrug and an enzyme inhibitor (e.g., a trypsin inhibitor) are described below.

Combinations of Formulae KC-(I) to KC-(II) and Enzyme Inhibitor

The embodiments provide a pharmaceutical composition, which comprises an enzyme inhibitor and a compound of general Formulae KC-(I) to KC-(II), or a pharmaceutically acceptable salt thereof. The embodiments provide a pharmaceutical composition, which comprises a compound of Formulae T-I to T-VI and a compound of general Formulae KC-(I) to KC-(II), or a pharmaceutically acceptable salt thereof. The embodiments provide a pharmaceutical composition, which comprises Compound 109 and a compound of general Formulae KC-(I) to KC-(II), or a pharmaceutically acceptable salt thereof.

Certain embodiments provide for a combination of a compound of Formula KC-(I) and an enzyme inhibitor, in which the ketone-containing opioid of Formula KC-(I) and the enzyme inhibitor are shown in the following table. Certain embodiments provide for a combination of a compound of Formula KC-(II) and an enzyme inhibitor, in which the ketone-containing opioid of Formula KC-(II) and the enzyme inhibitor are also shown in the following table.

| Prodrug of Formula KC-(I) Having Indicated Opioid; and Enzyme Inhibitor | | Prodrug of Formula KC-(II) Having Indicated Opioid; and Enzyme Inhibitor | |
|---|---|---|---|
| Oxycodone; SBTI | Hydrocodone; SBTI | Oxycodone; SBTI | Hydrocodone; SBTI |
| Oxycodone; BBSI | Hydrocodone; BBSI | Oxycodone; BBSI | Hydrocodone; BBSI | the ketone-containing opioid of Formula KC-(III) and the enzyme inhibitor are shown in the table below. Certain embodiments provide for a combination of a compound of Formula KC-(IV) and an enzyme inhibitor, in which the ketone-containing opioid of Formula KC-(IV) and the enzyme inhibitor are shown in the table below. Certain embodiments provide for a combination of a compound of Formula KC-(V) and an enzyme inhibitor, in which the ketone-containing opioid of Formula KC-(V) and the enzyme inhibitor are shown in the following table.

| Prodrug of Formula KC-(III) Having Indicated Opioid; and Enzyme Inhibitor | | Prodrug of Formula KC-(IV) Having Indicated Opioid; and Enzyme Inhibitor | | Prodrug of Formula KC-(V) Having Indicated Opioid; and Enzyme Inhibitor | |
|---|---|---|---|---|---|
| Oxycodone; SBTI | Hydrocodone; SBTI | Oxycodone; SBTI | Hydrocodone; SBTI | Oxycodone; SBTI | Hydrocodone; SBTI |
| Oxycodone; BBSI | Hydrocodone; BBSI | Oxycodone; BBSI | Hydrocodone; BBSI | Oxycodone; BBSI | Hydrocodone; BBSI |
| Oxycodone; Compound 101 | Hydrocodone; Compound 101 | Oxycodone; Compound 101 | Hydrocodone; Compound 101 | Oxycodone; Compound 101 | Hydrocodone; Compound 101 |
| Oxycodone; Compound 106 | Hydrocodone; Compound 106 | Oxycodone; Compound 106 | Hydrocodone; Compound 106 | Oxycodone; Compound 106 | Hydrocodone; Compound 106 |
| Oxycodone; Compound 108 | Hydrocodone; Compound 108 | Oxycodone; Compound 108 | Hydrocodone; Compound 108 | Oxycodone; Compound 108 | Hydrocodone; Compound 108 |
| Oxycodone; Compound 109 | Hydrocodone; Compound 109 | Oxycodone; Compound 109 | Hydrocodone; Compound 109 | Oxycodone; Compound 109 | Hydrocodone; Compound 109 |
| Oxycodone; Compound 110 | Hydrocodone; Compound 110 | Oxycodone; Compound 110 | Hydrocodone; Compound 110 | Oxycodone; Compound 110 | Hydrocodone; Compound 110 |

-continued

| Prodrug of Formula KC-(I) Having Indicated Opioid; and Enzyme Inhibitor | | Prodrug of Formula KC-(II) Having Indicated Opioid; and Enzyme Inhibitor | |
|---|---|---|---|
| Oxycodone; Compound 101 | Hydrocodone; Compound 101 | Oxycodone; Compound 101 | Hydrocodone; Compound 101 |
| Oxycodone; Compound 106 | Hydrocodone; Compound 106 | Oxycodone; Compound 106 | Hydrocodone; Compound 106 |
| Oxycodone; Compound 108 | Hydrocodone; Compound 108 | Oxycodone; Compound 108 | Hydrocodone; Compound 108 |
| Oxycodone; Compound 109 | Hydrocodone; Compound 109 | Oxycodone; Compound 109 | Hydrocodone; Compound 109 |
| Oxycodone; Compound 110 | Hydrocodone; Compound 110 | Oxycodone; Compound 110 | Hydrocodone; Compound 110 |

Combinations of Formulae KC-(III) to KC-(V) and Enzyme Inhibitor

The embodiments provide a pharmaceutical composition, which comprises an enzyme inhibitor and a compound of general Formulae KC-(III) to KC-(V), or a pharmaceutically acceptable salt thereof. The embodiments provide a pharmaceutical composition, which comprises a compound of Formulae T-I to T-VI and a compound of general Formulae KC-(III) to KC-(V), or a pharmaceutically acceptable salt thereof. The embodiments provide a pharmaceutical composition, which comprises Compound 109 and a compound of general Formulae KC-(III) to KC-(V), or a pharmaceutically acceptable salt thereof.

The embodiments provide a pharmaceutical composition, which comprises an enzyme inhibitor and a compound disclosed herein other than a compound of general Formulae KC-(I) to KC-(II), or a pharmaceutically acceptable salt thereof.

Certain embodiments provide for a combination of a compound of Formula KC-(III) and an enzyme inhibitor, in which Combinations of Compound KC-2 and Enzyme Inhibitor Certain embodiments provide for a combination of Compound KC-2 and an enzyme inhibitor, in which the enzyme inhibitor is shown in the following table.

| Compound | Enzyme inhibitor |
|---|---|
| Compound KC-2 | SBTI |
| Compound KC-2 | BBSI |
| Compound KC-2 | Compound 101 |
| Compound KC-2 | Compound 106 |
| Compound KC-2 | Compound 108 |
| Compound KC-2 | Compound 109 |
| Compound KC-2 | Compound 110 |

Combinations of Opioid Prodrugs and Other Drugs

The disclosure provides for an opioid prodrug and a further prodrug or drug included in a pharmaceutical composition. Such a prodrug or drug would provide additional analgesia or other benefits. Examples include opioids, acetaminophen, non-steroidal anti-inflammatory drugs (NSAIDs) and other analgesics. In one embodiment, an opioid agonist prodrug or drug would be combined with an opioid antagonist prodrug or drug. Other examples include drugs or prodrugs that have benefits other than, or in addition to, analgesia. The embodiments provide a pharmaceutical composition, which comprises an opioid prodrug and acetaminophen and optionally comprises an enzyme inhibitor. Also included are pharmaceutically acceptable salts thereof.

In certain embodiments, the enzyme inhibitor is selected from SBTI, BBSI, Compound 101, Compound 106, Compound 108, Compound 109, and Compound 110. In certain embodiments, the enzyme inhibitor is camostat.

In certain embodiments, a pharmaceutical composition can comprise an opioid prodrug, a non-opioid drug and at least one opioid or opioid prodrug.

Pharmaceutical Compositions and Methods of Use

The pharmaceutical composition according to the embodiments can further comprise a pharmaceutically acceptable carrier. The composition is conveniently formulated in a form suitable for oral (including buccal and sublingual) administration, for example as a tablet, capsule, thin film, powder, suspension, solution, syrup, dispersion or emulsion. The composition can contain components conventional in pharmaceutical preparations, e.g. one or more carriers, binders, lubricants, excipients (e.g., to impart controlled release characteristics), pH modifiers, sweeteners, bulking agents, coloring agents or further active agents.

Patients can be humans, and also other mammals, such as livestock, zoo animals and companion animals, such as a cat, dog or horse.

In another aspect, the embodiments provide a pharmaceutical composition as described hereinabove for use in the treatment of pain. The pharmaceutical composition according to the embodiments is useful, for example, in the treatment of a patient suffering from, or at risk of suffering from, pain. Accordingly, the present disclosure provides methods of treating or preventing pain in a subject, the methods involving administering to the subject a disclosed composition. The present disclosure provides for a disclosed composition for use in therapy or prevention or as a medicament. The present disclosure also provides the use of a disclosed composition for the manufacture of a medicament, especially for the manufacture of a medicament for the treatment or prevention of pain.

The compositions of the present disclosure can be used in the treatment or prevention of pain including, but not limited to include, acute pain, chronic pain, neuropathic pain, acute traumatic pain, arthritic pain, osteoarthritic pain, rheumatoid arthritic pain, muscular skeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, muscular skeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain.

The present disclosure provides use of an opioid prodrug and a trypsin inhibitor in the treatment of pain. The present disclosure provides use of an opioid prodrug and a trypsin inhibitor in the prevention of pain.

The present disclosure provides use of an opioid prodrug and a trypsin inhibitor in the manufacture of a medicament for treatment of pain. The present disclosure provides use of an opioid prodrug and a trypsin inhibitor in the manufacture of a medicament for prevention of pain.

In another aspect, the embodiments provide a method of treating pain in a patient requiring treatment, which comprises administering an effective amount of a pharmaceutical composition as described hereinabove. In another aspect, the embodiments provides method of preventing pain in a patient requiring treatment, which comprises administering an effective amount of a pharmaceutical composition as described hereinabove.

The amount of composition disclosed herein to be administered to a patient to be effective (i.e. to provide blood levels of phenolic opioid sufficient to be effective in the treatment or prophylaxis of pain) will depend upon the bioavailability of the particular composition, the susceptibility of the particular composition to enzyme activation in the gut, the amount and potency of trypsin inhibitor present in the composition, as well as other factors, such as the species, age, weight, sex, and condition of the patient, manner of administration and judgment of the prescribing physician. In general, the composition dose can be such that the opioid prodrug is in the range of from 0.01 milligrams prodrug per kilogram to 20 milligrams prodrug per kilogram (mg/kg) body weight. For example, a composition comprising a residue of an opioid can be administered at a dose equivalent to administering free opioid in the range of from 0.02 to 0.5 mg/kg body weight or 0.01 mg/kg to 10 mg/kg body weight or 0.01 to 2 mg/kg body weight. In one embodiment wherein the composition comprises an opioid prodrug, the composition can be administered at a dose such that the level of an opioid achieved in the blood is in the range of from 0.5 ng/ml to 200 ng/ml.

The amount of a trypsin inhibitor to be administered to the patient to be effective (i.e. to attenuate release of an opioid when administration of an opioid prodrug disclosed herein alone would lead to overexposure of the opioid) will depend upon the effective dose of the particular prodrug and the potency of the particular inhibitor, as well as other factors, such as the species, age, weight, sex and condition of the patient, manner of administration and judgment of the prescribing physician. In general, the dose of inhibitor can be in the range of from 0.05 mg to 50 mg per mg of prodrug disclosed herein. In a certain embodiment, the dose of inhibitor can be in the range of from 0.001 mg to 50 mg per mg of prodrug disclosed herein. In one embodiment, the dose of inhibitor can be in the range of from 0.01 nanomoles to 100 micromoles per micromole of prodrug disclosed herein.

Dose Units of Prodrug and Inhibitor Having a Desired Pharmacokinetic Profile

The present disclosure provides dose units of prodrug and inhibitor that can provide for a desired pharmacokinetic (PK) profile. Dose units can provide a modified PK profile compared to a reference PK profile as disclosed herein. It will be appreciated that a modified PK profile can provide for a modified pharmacodynamic (PD) profile. Ingestion of multiples of such a dose unit can also provide a desired PK profile.

Unless specifically stated otherwise, "dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

As used herein, a "PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile".) A PK profile is characterized by PK parameters.

As used herein, a "PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

For purposes of describing the features of dose units of the present disclosure, "PK parameter values" that define a PK profile include drug Cmax (e.g., phenolic opioid Cmax), total drug exposure (e.g., area under the curve) (e.g., phenolic opioid exposure) and 1/(drug Tmax) (such that a decreased 1/Tmax is indicative of a delay in Tmax relative to a reference Tmax) (e.g., 1/phenolic opioid Tmax). Thus a decrease in a PK parameter value relative to a reference PK parameter value can indicate, for example, a decrease in drug Cmax, a decrease in drug exposure, and/or a delayed Tmax.

Dose units of the present disclosure can be adapted to provide for a modified PK profile, e.g., a PK profile that is different from that achieved from dosing a given dose of prodrug in the absence of inhibitor (i.e., without inhibitor). For example, dose units can provide for at least one of decreased drug Cmax, delayed drug Tmax and/or decreased drug exposure compared to ingestion of a dose of prodrug in the same amount but in the absence of inhibitor. Such a modification is due to the inclusion of an inhibitor in the dose unit.

As used herein, "a pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax), and side effects.

FIG. 1 is a schematic illustrating an example of the effect of increasing inhibitor concentrations upon the PK parameter drug Cmax for a fixed dose of prodrug. At low concentrations of inhibitor, there may be no detectable effect on drug release, as illustrated by the plateau portion of the plot of drug Cmax (Y axis) versus inhibitor concentration (X axis). As inhibitor concentration increases, a concentration is reached at which drug release from prodrug is attenuated, causing a decrease in, or suppression of, drug Cmax. Thus, the effect of inhibitor upon a prodrug PK parameter for a dose unit of the present disclosure can range from undetectable, to moderate, to complete inhibition (i.e., no detectable drug release).

A dose unit can be adapted to provide for a desired PK profile (e.g., a concentration-time PK profile) following ingestion of a single dose. A dose unit can be adapted to provide for a desired PK profile (e.g., a concentration-dose PK profile) following ingestion of multiple dose units (e.g., at least 2, at least 3, at least 4 or more dose units).

Dose Units Providing Modified PK Profiles

A combination of a prodrug and an inhibitor in a dose unit can provide a desired (or "pre-selected") PK profile (e.g., a concentration-time PK profile) following ingestion of a single dose. The PK profile of such a dose unit can be characterized by one or more of a pre-selected drug Cmax, a pre-selected drug Tmax or a pre-selected drug exposure. The PK profile of the dose unit can be modified compared to a PK profile achieved from the equivalent dosage of prodrug in the absence of inhibitor (i.e., a dose that is the same as the dose unit except that it lacks inhibitor).

A modified PK profile can have a decreased PK parameter value relative to a reference PK parameter value (e.g., a PK parameter value of a PK profile following ingestion of a dosage of prodrug that is equivalent to a dose unit except without inhibitor). For example, a dose unit can provide for a decreased drug Cmax, decreased drug exposure, and/or delayed drug Tmax.

Figure 2:
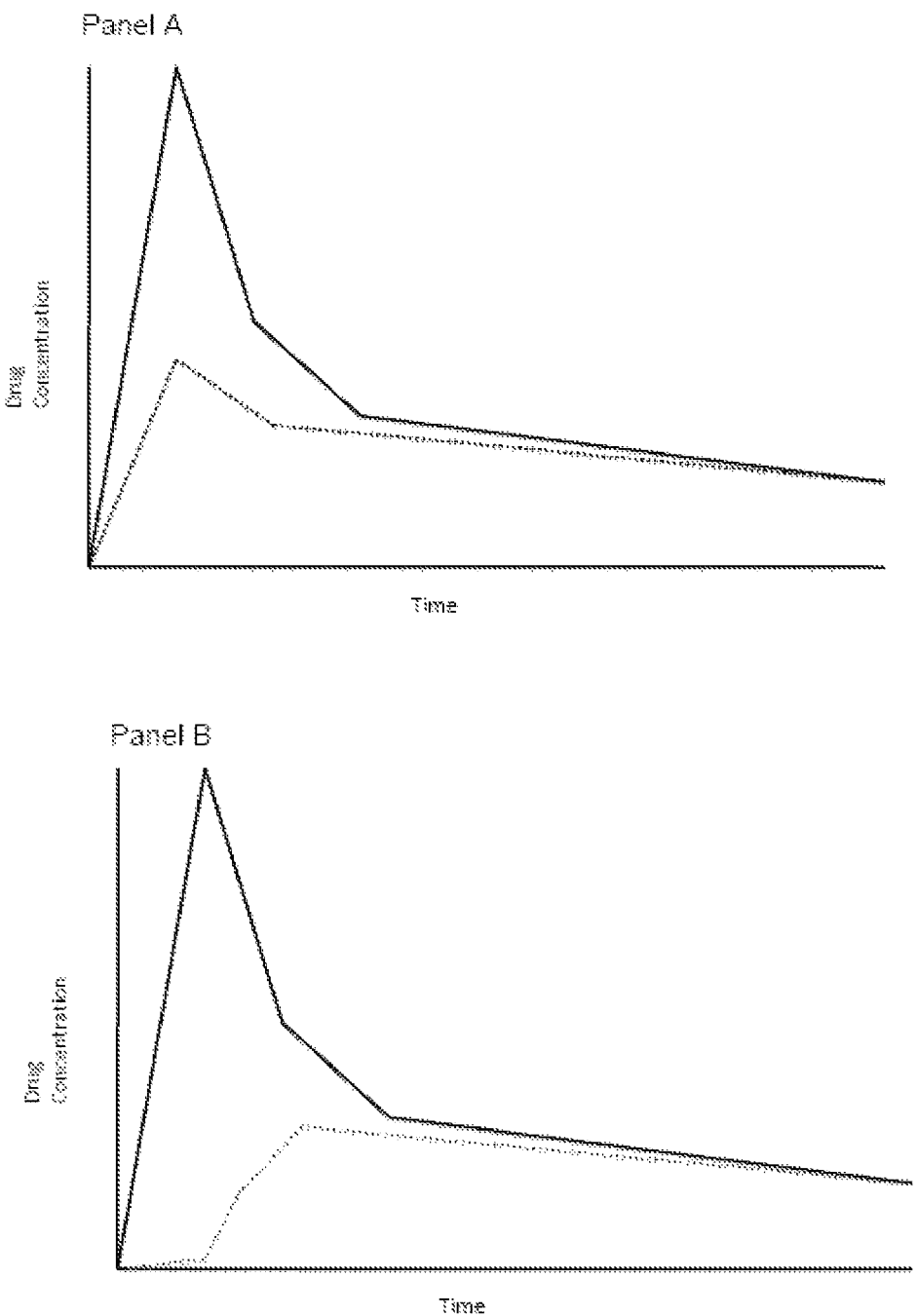
FIG. 2 provides schematics of drug concentration in plasma (Y axis) over time (X axis). Panel A is a schematic of a pharmacokinetic (PK) profile following ingestion of prodrug with a GI enzyme inhibitor (dashed line) where the drug Cmax is modified relative to that of prodrug without inhibitor (solid line). Panel B is a schematic of a PK profile following ingestion of prodrug with inhibitor (dashed line) where drug Cmax and drug Tmax are modified relative to that of prodrug without inhibitor (solid line). Panel C is a schematic of a PK profile following ingestion of prodrug with inhibitor (dashed line) where drug Tmax is modified relative to that of prodrug without inhibitor (solid line).
Figure 2:
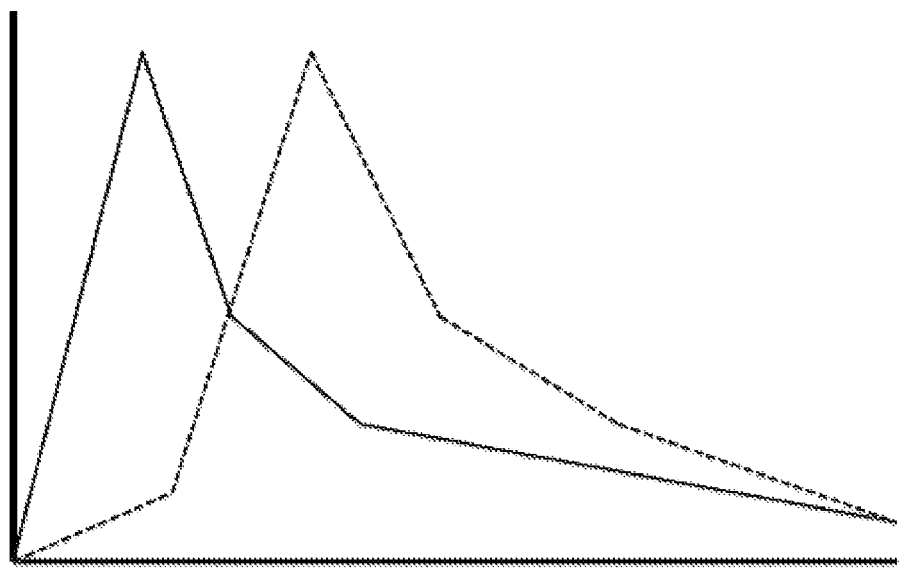

FIG. 2 presents schematic graphs showing examples of modified concentration-time PK profiles of a single dose unit. Panel A is a schematic of drug concentration in blood or plasma (Y axis) following a period of time (X axis) after ingestion of prodrug in the absence or presence of inhibitor. The solid, top line in Panel A provides an example of drug concentration following ingestion of prodrug without inhibitor. The dashed, lower line in Panel A represents drug concentration following ingestion of the same dose of prodrug with inhibitor. Ingestion of inhibitor with prodrug provides for a decreased drug Cmax relative to the drug Cmax that results from ingestion of the same amount of prodrug in the absence of inhibitor. Panel A also illustrates that the total drug exposure following ingestion of prodrug with inhibitor is also decreased relative to ingestion of the same amount of prodrug without inhibitor.

Panel B of FIG. 2 provides another example of a dose unit having a modified concentration-time PK profile. As in Panel A, the solid top line represents drug concentration over time in blood or plasma following ingestion of prodrug without inhibitor, while the dashed lower line represents drug concentration following ingestion of the same amount of prodrug with inhibitor. In this example, the dose unit provides a PK profile having a decreased drug Cmax, decreased drug exposure, and a delayed drug Tmax (i.e., decreased (1/drug Tmax) relative to ingestion of the same dose of prodrug without inhibitor.

Panel C of FIG. 2 provides another example of a dose unit having a modified concentration-time PK profile. As in Panel A, the solid line represents drug concentration over time in blood or plasma following ingestion of prodrug without inhibitor, while the dashed line represents drug concentration following ingestion of the same amount of prodrug with inhibitor. In this example, the dose unit provides a PK profile having a delayed drug Tmax (i.e., decreased (1/drug Tmax) relative to ingestion of the same dose of prodrug without inhibitor.

Dose units that provide for a modified PK profile (e.g., a decreased drug Cmax and/or delayed drug Tmax as compared to, a PK profile of drug or a PK profile of prodrug without inhibitor), find use in tailoring of drug dose according to a patient's needs (e.g., through selection of a particular dose unit and/or selection of a dosage regimen), reduction of side effects, and/or improvement in patient compliance (as compared to side effects or patient compliance associated with drug or with prodrug without inhibitor). As used herein, "patient compliance" refers to whether a patient follows the direction of a clinician (e.g., a physician) including ingestion of a dose that is neither significantly above nor significantly below that prescribed. Such dose units also reduce the risk of misuse, abuse or overdose by a patient as compared to such risk(s) associated with drug or prodrug without inhibitor. For example, dose units with a decreased drug Cmax provide less reward for ingestion than does a dose of the same amount of drug, and/or the same amount of prodrug without inhibitor.

Dose Units Providing Modified PK Profiles Upon Ingestion of Multiple Dose Units

A dose unit of the present disclosure can be adapted to provide for a desired PK profile (e.g., a concentration-time PK profile or concentration-dose PK profile) following ingestion of multiples of a dose unit (e.g., at least 2, at least 3, at least 4, or more dose units). A concentration-dose PK profile refers to the relationship between a selected PK parameter and a number of single dose units ingested. Such a profile can be dose proportional, linear (a linear PK profile) or nonlinear (a nonlinear PK profile). A modified concentration-dose PK profile can be provided by adjusting the relative amounts of prodrug and inhibitor contained in a single dose unit and/or by using a different prodrug and/or inhibitor.

Figure 3:
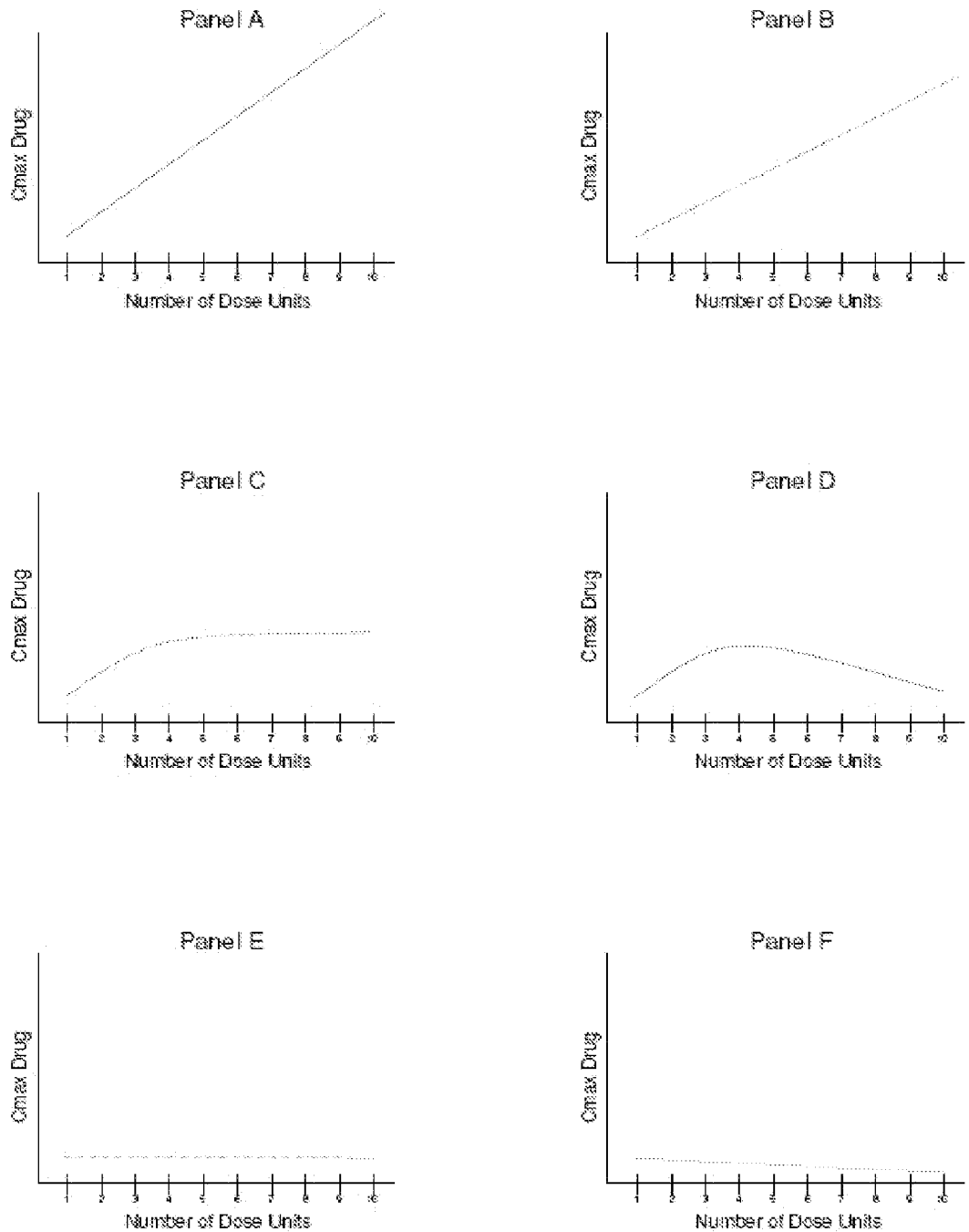
FIG. 3 provides schematics representing differential concentration-dose PK profiles that can result from the dosing of multiples of a dose unit (X axis) of the present disclosure. Different PK profiles (as exemplified herein for a representative PK parameter, drug Cmax (Y axis)) can be provided by adjusting the relative amount of prodrug and GI enzyme inhibitor contained in a single dose unit or by using a different prodrug or inhibitor in the dose unit.

FIG. 3 provides schematics of examples of concentration-dose PK profiles (exemplified by drug Cmax, Y axis) that can be provided by ingestion of multiples of a dose unit (X axis) of the present disclosure. Each profile can be compared to a concentration-dose PK profile provided by increasing doses of drug alone, where the amount of drug in the blood or plasma from one dose represents a therapeutically effective amount equivalent to the amount of drug released into the blood or plasma by one dose unit of the disclosure. Such a "drug alone" PK profile is typically dose proportional, having a forty-five degree angle positive linear slope. It is also to be appreciated that a concentration-dose PK profile resulting from ingestion of multiples of a dose unit of the disclosure can also be compared to other references, such as a concentration-dose PK profile provided by ingestion of an increasing number of doses of prodrug without inhibitor wherein the amount of drug released into the blood or plasma by a single dose of prodrug in the absence of inhibitor represents a therapeutically effective amount equivalent to the amount of drug released into the blood or plasma by one dose unit of the disclosure.

As illustrated by the relationship between prodrug and inhibitor concentration in FIG. 1, a dose unit can include inhibitor in an amount that does not detectably affect drug release following ingestion. Ingestion of multiples of such a dose unit can provide a concentration-dose PK profile such that the relationship between number of dose units ingested and PK parameter value is linear with a positive slope, which is similar to, for example, a dose proportional PK profile of increasing amounts of prodrug alone. Panel A of FIG. 3 depicts such a profile. Dose units that provide a concentration-dose PK profile having such an undetectable change in drug Cmax in vivo compared to the profile of prodrug alone can find use in thwarting enzyme conversion of prodrug from a dose unit that has sufficient inhibitor to reduce or prevent in vitro cleavage of the enzyme-cleavable prodrug by its respective enzyme.

Panel B in FIG. 3 represents a concentration-dose PK profile such that the relationship between the number of dose units ingested and a PK parameter value is linear with positive slope, where the profile exhibits a reduced slope relative to panel A. Such a dose unit provides a profile having a decreased PK parameter value (e.g., drug Cmax) relative to a reference PK parameter value exhibiting dose proportionality.

Concentration-dose PK profiles following ingestion of multiples of a dose unit can be non-linear. Panel C in FIG. 3 represents an example of a non-linear, biphasic concentration-dose PK profile. In this example, the biphasic concentration-dose PK profile contains a first phase over which the concentration-dose PK profile has a positive rise, and then a second phase over which the relationship between number of dose units ingested and a PK parameter value (e.g., drug Cmax) is relatively flat (substantially linear with zero slope). For such a dose unit, for example, drug Cmax can be increased for a selected number of dose units (e.g., 2, 3, or 4 dose units). However, ingestion of additional dose units does not provide for a significant increase in drug Cmax.

Panel D in FIG. 3 represents another example of a non-linear, biphasic concentration-dose PK profile. In this example, the biphasic concentration-dose PK profile is characterized by a first phase over which the concentration-dose PK profile has a positive rise and a second phase over which the relationship between number of dose units ingested and a PK parameter value (e.g., drug Cmax) declines. Dose units that provide this concentration-dose PK profile provide for an increase in drug Cmax for a selected number of ingested dose units (e.g., 2, 3, or 4 dose units). However, ingestion of further additional dose units does not provide for a significant increase in drug Cmax and instead provides for decreased drug Cmax.

Panel E in FIG. 3 represents a concentration-dose PK profile in which the relationship between the number of dose units ingested and a PK parameter (e.g., drug Cmax) is linear with zero slope. Such dose units do not provide for a significant increase or decrease in drug Cmax with ingestion of multiples of dose units.

Panel F in FIG. 3 represents a concentration-dose PK profile in which the relationship between number of dose units ingested and a PK parameter value (e.g., drug Cmax) is linear with a negative slope. Thus drug Cmax decreases as the number of dose units ingested increases.

Dose units that provide for concentration-dose PK profiles when multiples of a dose unit are ingested find use in tailoring of a dosage regimen to provide a therapeutic level of released drug while reducing the risk of overdose, misuse, or abuse. Such reduction in risk can be compared to a reference, e.g., to administration of drug alone or prodrug alone. In one embodiment, risk is reduced compared to administration of a drug or prodrug that provides a proportional concentration-dose PK profile. A dose unit that provides for a concentration-dose PK profile can reduce the risk of patient overdose through inadvertent ingestion of dose units above a prescribed dosage. Such a dose unit can reduce the risk of patient misuse (e.g., through self-medication). Such a dose unit can discourage abuse through deliberate ingestion of multiple dose units. For example, a dose unit that provides for a biphasic concentration-dose PK profile can allow for an increase in drug release for a limited number of dose units ingested, after which an increase in drug release with ingestion of more dose units is not realized. In another example, a dose unit that provides for a concentration-dose PK profile of zero slope can allow for retention of a similar drug release profile regardless of the number of dose units ingested.

Ingestion of multiples of a dose unit can provide for adjustment of a PK parameter value relative to that of ingestion of multiples of the same dose (either as drug alone or as a prodrug) in the absence of inhibitor such that, for example, ingestion of a selected number (e.g., 2, 3, 4 or more) of a single dose unit provides for a decrease in a PK parameter value compared to ingestion of the same number of doses in the absence of inhibitor.

Pharmaceutical compositions include those having an inhibitor to provide for protection of a therapeutic compound from degradation in the GI tract. Inhibitor can be combined with a drug (i.e., not a prodrug) to provide for protection of the drug from degradation in the GI system. In this example, the composition of inhibitor and drug provide for a modified PK profile by increasing a PK parameter. Inhibitor can also be combined with a prodrug that is susceptible to degradation by a GI enzyme and has a site of action outside the GI tract. In this composition, the inhibitor protects ingested prodrug in the GI tract prior to its distribution outside the GI tract and cleavage at a desired site of action.

Methods Used to Define Relative Amounts of Prodrug and Inhibitor in a Dose Unit

Dose units that provide for a desired PK profile, such as a desired concentration-time PK profile and/or a desired concentration-dose PK profile, can be made by combining a prodrug and an inhibitor in a dose unit in relative amounts effective to provide for release of drug that provides for a desired drug PK profile following ingestion by a patient.

Prodrugs can be selected as suitable for use in a dose unit by determining the GI enzyme-mediated drug release competency of the prodrug. This can be accomplished in vitro, in vivo or ex vivo.

In vitro assays can be conducted by combining a prodrug with a GI enzyme (e.g., trypsin) in a reaction mixture. The GI enzyme can be provided in the reaction mixture in an amount sufficient to catalyze cleavage of the prodrug. Assays are conducted under suitable conditions, and optionally may be under conditions that mimic those found in a GI tract of a subject, e.g., human. "Prodrug conversion" refers to release of drug from prodrug. Prodrug conversion can be assessed by detecting a level of a product of prodrug conversion (e.g., released drug) and/or by detecting a level of prodrug that is maintained in the presence of the GI enzyme. Prodrug conversion can also be assessed by detecting the rate at which a product of prodrug conversion occurs or the rate at which prodrug disappears. An increase in released drug, or a decrease in prodrug, indicate prodrug conversion has occurred. Prodrugs that exhibit an acceptable level of prodrug conversion in the presence of the GI enzyme within an acceptable period of time are suitable for use in a dose unit in combination with an inhibitor of the GI enzyme that is shown to mediate prodrug conversion.

In vivo assays can assess the suitability of a prodrug for use in a dose unit by administration of the prodrug to an animal (e.g., a human or non-human animal, e.g., rat, dog, pig, etc.). Such administration can be enteral (e.g., oral administration). Prodrug conversion can be detected by, for example, detecting a product of prodrug conversion (e.g., released drug or a metabolite of released drug) or detecting prodrug in blood or plasma of the animal at a desired time point(s) following administration.

Ex vivo assays, such as a gut loop or inverted gut loop assay, can assess the suitability of a prodrug for use in a dose unit by, for example, administration of the prodrug to a ligated section of the intestine of an animal. Prodrug conversion can be detected by, for example, detecting a product of prodrug conversion (e.g., released drug or a metabolite of released drug) or detecting prodrug in the ligated gut loop of the animal at a desired time point(s) following administration.

Inhibitors are generally selected based on, for example, activity in interacting with the GI enzyme(s) that mediate release of drug from a prodrug with which the inhibitor is to be co-dosed. Such assays can be conducted in the presence of enzyme either with or without prodrug. Inhibitors can also be selected according to properties such as half-life in the GI system, potency, avidity, affinity, molecular size and/or enzyme inhibition profile (e.g., steepness of inhibition curve in an enzyme activity assay, inhibition initiation rate). Inhibitors for use in prodrug-inhibitor combinations can be selected through use of in vitro, in vivo and/or ex vivo assays.

One embodiment is a method for identifying a prodrug and a GI enzyme inhibitor suitable for formulation in a dose unit wherein the method comprises combining a prodrug (e.g., a phenol-modified opioid prodrug), a GI enzyme inhibitor (e.g., a trypsin inhibitor), and a GI enzyme (e.g., trypsin) in a reaction mixture and detecting prodrug conversion. Such a combination is tested for an interaction between the prodrug, inhibitor and enzyme, i.e., tested to determine how the inhibitor will interact with the enzyme that mediates enzymatically-controlled release of the drug from the prodrug. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit. Such a method can be an in vitro assay.

One embodiment is a method for identifying a prodrug and a GI enzyme inhibitor suitable for formulation in a dose unit wherein the method comprises administering to an animal a prodrug (e.g., a phenol-modified opioid prodrug) and a GI enzyme inhibitor (e.g., a trypsin inhibitor) and detecting prodrug conversion. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit. Such a method can be an in vivo assay; for example, the prodrug and GI enzyme inhibitor can be administered orally. Such a method can also be an ex vivo assay; for example, the prodrug and GI enzyme inhibitor can be administered orally or to a tissue, such as an intestine, that is at least temporarily exposed. Detection can occur in the blood or plasma or respective tissue. As used herein, tissue refers to the tissue itself and can also refer to contents within the tissue.

One embodiment is a method for identifying a prodrug and a GI enzyme inhibitor suitable for formulation in a dose unit wherein the method comprises administering a prodrug and a gastrointestinal (GI) enzyme inhibitor to an animal tissue that has removed from an animal and detecting prodrug conversion. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit.

In vitro assays can be conducted by combining a prodrug, an inhibitor and a GI enzyme in a reaction mixture. The GI enzyme can be provided in the reaction mixture in an amount sufficient to catalyze cleavage of the prodrug, and assays conducted under suitable conditions, optionally under conditions that mimic those found in a GI tract of a subject, e.g., human. Prodrug conversion can be assessed by detecting a level of a product of prodrug conversion (e.g., released drug) and/or by detecting a level of prodrug maintained in the presence of the GI enzyme. Prodrug conversion can also be assessed by detecting the rate at which a product of prodrug conversion occurs or the rate at which prodrug disappears. Prodrug conversion that is modified in the presence of inhibitor as compared to a level of prodrug conversion in the absence of inhibitor indicates the inhibitor is suitable for attenuation of prodrug conversion and for use in a dose unit. Reaction mixtures having a fixed amount of prodrug and increasing amounts of inhibitor, or a fixed amount of inhibitor and increasing amounts of prodrug, can be used to identify relative amounts of prodrug and inhibitor which provide for a desired modification of prodrug conversion.

In vivo assays can assess combinations of prodrugs and inhibitors by co-dosing of prodrug and inhibitor to an animal. Such co-dosing can be enteral. "Co-dosing" refers to administration of prodrug and inhibitor as separate doses or a combined dose (i.e., in the same formulation). Prodrug conversion can be detected by, for example, detecting a product of prodrug conversion (e.g., released drug or drug metabolite) or detecting prodrug in blood or plasma of the animal at a desired time point(s) following administration. Combinations of prodrug and inhibitor can be identified that provide for a prodrug conversion level that yields a desired PK profile as compared to, for example, prodrug without inhibitor.

Combinations of relative amounts of prodrug and inhibitor that provide for a desired PK profile can be identified by dosing animals with a fixed amount of prodrug and increasing amounts of inhibitor, or with a fixed amount of inhibitor and increasing amounts of prodrug. One or more PK parameters can then be assessed, e.g., drug Cmax, drug Tmax, and drug exposure. Relative amounts of prodrug and inhibitor that provide for a desired PK profile are identified as amounts of prodrug and inhibitor for use in a dose unit. The PK profile of the prodrug and inhibitor combination can be, for example, characterized by a decreased PK parameter value relative to prodrug without inhibitor. A decrease in the PK parameter value of an inhibitor-to-prodrug combination (e.g., a decrease in drug Cmax, a decrease in 1/drug Tmax (i.e., a delay in drug Tmax) or a decrease in drug exposure) relative to a corresponding PK parameter value following administration of prodrug without inhibitor can be indicative of an inhibitor-to-prodrug combination that can provide a desired PK profile. Assays can be conducted with different relative amounts of inhibitor and prodrug.

In vivo assays can be used to identify combinations of prodrug and inhibitor that provide for dose units that provide for a desired concentration-dose PK profile following ingestion of multiples of the dose unit (e.g., at least 2, at least 3, at least 4 or more). Ex vivo assays can be conducted by direct administration of prodrug and inhibitor into a tissue and/or its contents of an animal, such as the intestine, including by introduction by injection into the lumen of a ligated intestine (e.g., a gut loop, or intestinal loop, assay, or an inverted gut assay). An ex vivo assay can also be conducted by excising a tissue and/or its contents from an animal and introducing prodrug and inhibitor into such tissues and/or contents.

For example, a dose of prodrug that is desired for a single dose unit is selected (e.g., an amount that provides an efficacious plasma drug level). A multiple of single dose units for which a relationship between that multiple and a PK parameter to be tested is then selected. For example, if a concentration-dose PK profile is to be designed for ingestion of 2, 3, 4, 5, 6, 7, 8, 9 or 10 dose units, then the amount of prodrug equivalent to ingestion of that same number of dose units is determined (referred to as the "high dose"). The multiple of dose units can be selected based on the number of ingested pills at which drug Cmax is modified relative to ingestion of the single dose unit. If, for example, the profile is to provide for abuse deterrence, then a multiple of 10 can be selected, for example. A variety of different inhibitors (e.g., from a panel of inhibitors) can be tested using different relative amounts of inhibitor and prodrug. Assays can be used to identify suitable combination(s) of inhibitor and prodrug to obtain a single dose unit that is therapeutically effective, wherein such a combination, when ingested as a multiple of dose units, provides a modified PK parameter compared to ingestion of the same multiple of drug or prodrug alone (wherein a single dose of either drug or prodrug alone releases into blood or plasma the same amount of drug as is released by a single dose unit).

Increasing amounts of inhibitor are then co-dosed to animals with the high dose of prodrug. The dose level of inhibitor that provides a desired drug Cmax following ingestion of the high dose of prodrug is identified and the resultant inhibitor-to-prodrug ratio determined.

Prodrug and inhibitor are then co-dosed in amounts equivalent to the inhibitor-to-prodrug ratio that provided the desired result at the high dose of prodrug. The PK parameter value of interest (e.g., drug Cmax) is then assessed. If a desired PK parameter value results following ingestion of the single dose unit equivalent, then single dose units that provide for a desired concentration-dose PK profile are identified. For example, where a zero dose linear profile is desired, the drug Cmax following ingestion of a single dose unit does not increase significantly following ingestion of a multiple number of the single dose units.

Methods for Manufacturing, Formulating, and Packaging Dose Units

Dose units of the present disclosure can be made using manufacturing methods available in the art and can be of a variety of forms suitable for enteral (including oral, buccal and sublingual) administration, for example as a tablet, capsule, thin film, powder, suspension, solution, syrup, dispersion or emulsion. The dose unit can contain components conventional in pharmaceutical preparations, e.g. one or more carriers, binders, lubricants, excipients (e.g., to impart controlled release characteristics), pH modifiers, flavoring agents (e.g., sweeteners), bulking agents, coloring agents or further active agents. Dose units of the present disclosure can include can include an enteric coating or other component(s) to facilitate protection from stomach acid, where desired.

Dose units can be of any suitable size or shape. The dose unit can be of any shape suitable for enteral administration, e.g., ellipsoid, lenticular, circular, rectangular, cylindrical, and the like.

Dose units provided as dry dose units can have a total weight of from about 1 microgram to about 1 gram, and can be from about 5 micrograms to 1.5 grams, from about 50 micrograms to 1 gram, from about 100 micrograms to 1 gram, from 50 micrograms to 750 milligrams, and may be from about 1 microgram to 2 grams.

Dose units can comprise components in any relative amounts. For example, dose units can be from about 0.1% to 99% by weight of active ingredients (i.e., prodrug and inhibitor) per total weight of dose unit (0.1% to 99% total combined weight of prodrug and inhibitor per total weight of single dose unit). In some embodiments, dose units can be from 10% to 50%, from 20% to 40%, or about 30% by weight of active ingredients per total weight dose unit.

Dose units can be provided in a variety of different forms and optionally provided in a manner suitable for storage. For example, dose units can be disposed within a container suitable for containing a pharmaceutical composition. The container can be, for example, a bottle (e.g., with a closure device, such as a cap), a blister pack (e.g., which can provide for enclosure of one or more dose units per blister), a vial, flexible packaging (e.g., sealed Mylar or plastic bags), an ampule (for single dose units in solution), a dropper, thin film, a tube and the like.

Containers can include a cap (e.g., screw cap) that is removably connected to the container over an opening through which the dose units disposed within the container can be accessed.

Containers can include a seal which can serve as a tamper-evident and/or tamper-resistant element, which seal is disrupted upon access to a dose unit disposed within the container. Such seal elements can be, for example, a frangible element that is broken or otherwise modified upon access to a dose unit disposed within the container. Examples of such frangible seal elements include a seal positioned over a container opening such that access to a dose unit within the container requires disruption of the seal (e.g., by peeling and/or piercing the seal). Examples of frangible seal elements include a frangible ring disposed around a container opening and in connection with a cap such that the ring is broken upon opening of the cap to access the dose units in the container.

Dry and liquid dose units can be placed in a container (e.g., bottle or package, e.g., a flexible bag) of a size and configuration adapted to maintain stability of dose units over a period during which the dose units are dispensed into a prescription.

For example, containers can be sized and configured to contain 10, 20, 30, 40, 50, 60, 70, 80, 90, 100 or more single dry or liquid dose units. The containers can be sealed or resealable. The containers can be packaged in a carton (e.g., for shipment from a manufacturer to a pharmacy or other dispensary). Such cartons can be boxes, tubes, or of other configuration, and may be made of any material (e.g., cardboard, plastic, and the like). The packaging system and/or containers disposed therein can have one or more affixed labels (e.g., to provide information such as lot number, dose unit type, manufacturer, and the like).

The container can include a moisture barrier and/or light barrier, e.g., to facilitate maintenance of stability of the active ingredients in the dose units contained therein. Where the dose unit is a dry dose unit, the container can include a desiccant pack which is disposed within the container. The container can be adapted to contain a single dose unit or multiples of a dose unit. The container can include a dispensing control mechanism, such as a lock out mechanism that facilitates maintenance of dosing regimen.

The dose units can be provided in solid or semi-solid form, and can be a dry dose unit. "Dry dose unit" refers to a dose unit that is in other than in a completely liquid form. Examples of dry dose units include, for example, tablets, capsules (e.g., solid capsules, capsules containing liquid), thin film, microparticles, granules, powder and the like. Dose units can be provided as liquid dose units, where the dose units can be provided as single or multiple doses of a formulation containing prodrug and inhibitor in liquid form. Single doses of a dry or liquid dose unit can be disposed within a sealed container, and sealed containers optionally provided in a packaging system, e.g., to provide for a prescribed number of doses, to provide for shipment of dose units, and the like.

Dose units can be formulated such that the prodrug and inhibitor are present in the same carrier, e.g., solubilized or suspended within the same matrix. Alternatively, dose units can be composed of two or more portions, where the prodrug and inhibitor can be provided in the same or different portions, and can be provided in adjacent or non-adjacent portions.

Dose units can be provided in a container in which they are disposed, and may be provided as part of a packaging system (optionally with instructions for use). For example, dose units containing different amounts of prodrug can be provided in separate containers, which containers can be disposed within a larger container (e.g., to facilitate protection of dose units for shipment). For example, one or more dose units as described herein can be provided in separate containers, where dose units of different composition are provided in separate containers, and the separate containers disposed within package for dispensing.

In another example, dose units can be provided in a double-chambered dispenser where a first chamber contains a prodrug formulation and a second chamber contains an inhibitor formulation. The dispenser can be adapted to provide for mixing of a prodrug formulation and an inhibitor formulation prior to ingestion. For example, the two chambers of the dispenser can be separated by a removable wall (e.g., frangible wall) that is broken or removed prior to administration to allow mixing of the formulations of the two chambers. The first and second chambers can terminate into a dispensing outlet, optionally through a common chamber. The formulations can be provided in dry or liquid form, or a combination thereof. For example, the formulation in the first chamber can be liquid and the formulation in the second chamber can be dry, both can be dry, or both can be liquid.

Dose units that provide for controlled release of prodrug, of inhibitor, or of both prodrug and inhibitor are contemplated by the present disclosure, where "controlled release" refers to release of one or both of prodrug and inhibitor from the dose unit over a selected period of time and/or in a pre-selected manner.

Methods of Use of Dose Units

Dose units are advantageous because they find use in methods to reduce side effects and/or improve tolerability of drugs to patients in need thereof by, for example, limiting a PK parameter as disclosed herein. The present disclosure thus provides methods to reduce side effects by administering a dose unit of the present disclosure to a patient in need so as to provide for a reduction of side effects as compared to those associated with administration of drug and/or as compared to administration of prodrug without inhibitor. The present disclosure also provides methods to improve tolerability of drugs by administering a dose unit of the present disclosure to a patient in need so as to provide for improvement in tolerability as compared to administration of drug and/or as compared to administration of prodrug without inhibitor.

Dose units find use in methods for increasing patient compliance of a patient with a therapy prescribed by a clinician, where such methods involve directing administration of a dose unit described herein to a patient in need of therapy so as to provide for increased patient compliance as compared to a therapy involving administration of drug and/or as compared to administrations of prodrug without inhibitor. Such methods can help increase the likelihood that a clinician-specified therapy occurs as prescribed.

Dose units can provide for enhanced patient compliance and clinician control. For example, by limiting a PK parameter (e.g., such as drug Cmax or drug exposure) when multiples (e.g., two or more, three or more, or four or more) dose units are ingested, a patient requiring a higher dose of drug must seek the assistance of a clinician. The dose units can provide for control of the degree to which a patient can readily "self-medicate", and further can provide for the patient to adjust dose to a dose within a permissible range. Dose units can provide for reduced side effects, by for example, providing for delivery of drug at an efficacious dose but with a modified PK profile over a period of treatment, e.g., as defined by a decreased PK parameter (e.g., decreased drug Cmax, decreased drug exposure).

Dose units find use in methods to reduce the risk of unintended overdose of drug that can follow ingestion of multiple doses taken at the same time or over a short period of time. Such methods of the present disclosure can provide for reduction of risk of unintended overdose as compared to risk of unintended overdose of drug and/or as compared to risk of unintended overdose of prodrug without inhibitor. Such methods involve directing administration of a dosage described herein to a patient in need of drug released by conversion of the prodrug. Such methods can help avoid unintended overdosing due to intentional or unintentional misuse of the dose unit.

The present disclosure provides methods to reduce misuse and abuse of a drug, as well as to reduce risk of overdose, that can accompany ingestion of multiples of doses of a drug, e.g., ingested at the same time. Such methods generally involve combining in a dose unit a prodrug and an inhibitor of a GI enzyme that mediates release of drug from the prodrug, where the inhibitor is present in the dose unit in an amount effective to attenuate release of drug from the prodrug, e.g., following ingestion of multiples of dose units by a patient. Such methods provide for a modified concentration-dose PK profile while providing therapeutically effective levels from a single dose unit, as directed by the prescribing clinician. Such methods can provide for, for example, reduction of risks that can accompany misuse and/or abuse of a prodrug, particularly where conversion of the prodrug provides for release of a narcotic or other drug of abuse (e.g., opioid). For example, when the prodrug provides for release of a drug of abuse, dose units can provide for reduction of reward that can follow ingestion of multiples of dose units of a drug of abuse.

Dose units can provide clinicians with enhanced flexibility in prescribing drug. For example, a clinician can prescribe a dosage regimen involving different dose strengths, which can involve two or more different dose units of prodrug and inhibitor having different relative amounts of prodrug, different amounts of inhibitor, or different amounts of both prodrug and inhibitor. Such different strength dose units can provide for delivery of drug according to different PK parameters (e.g., drug exposure, drug Cmax, and the like as described herein). For example, a first dose unit can provide for delivery of a first dose of drug following ingestion, and a second dose unit can provide for delivery of a second dose of drug following ingestion. The first and second prodrug doses of the dose units can be different strengths, e.g., the second dose can be greater than the first dose. A clinician can thus prescribe a collection of two or more, or three or more dose units of different strengths, which can be accompanied by instructions to facilitate a degree of self-medication, e.g., to increase delivery of an opioid drug according to a patient's needs to treat pain.

Thwarting Tampering by Enzyme Mediated Release of an Opioid from Prodrugs

The disclosure provides for a composition comprising a compound disclosed herein and an enzyme inhibitor that reduces drug abuse potential. An enzyme inhibitor can thwart the ability of a user to apply an enzyme to effect the release of an opioid from the opioid prodrug in vitro. For example, if an abuser attempts to incubate an enzyme with a composition of the embodiments that includes an opioid prodrug and an enzyme inhibitor, the enzyme inhibitor can reduce the action of the added enzyme, thereby thwarting attempts to release an opioid for purposes of abuse.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Synthesis of Small Molecule Trypsin Inhibitors

Example 1

Synthesis of (S)-ethyl 4-(5-guanidino-2-(naphthalene-2-sulfonamido)pentanoyl)piperazine-1-carboxylate (Compound 101)

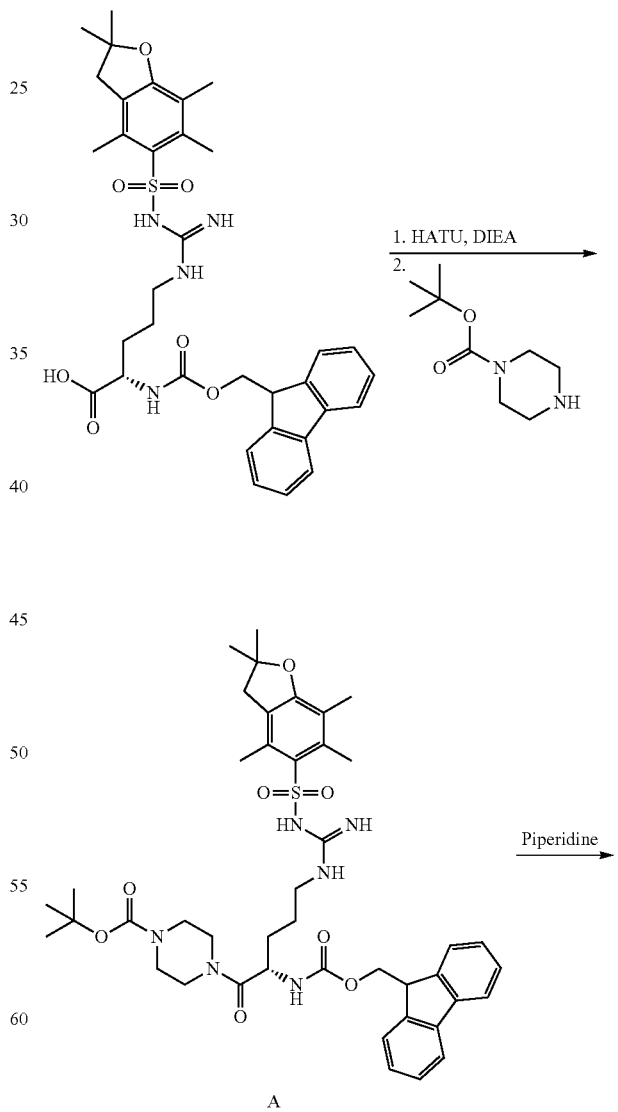

A

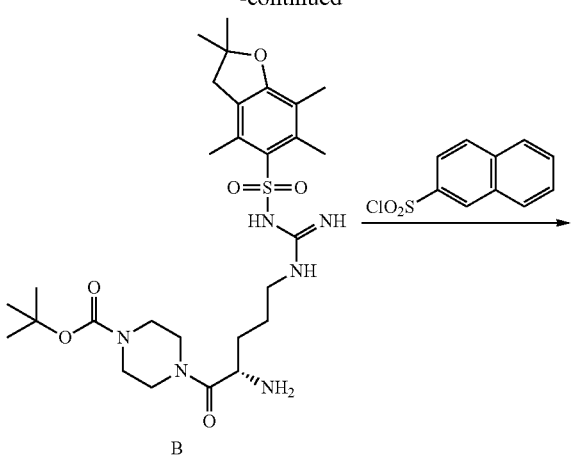

B

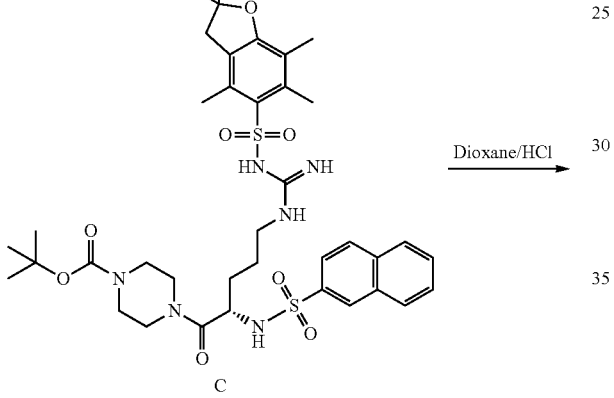

C

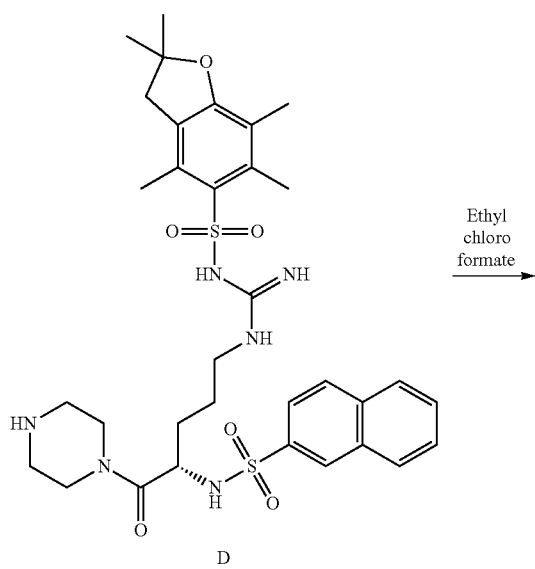

D

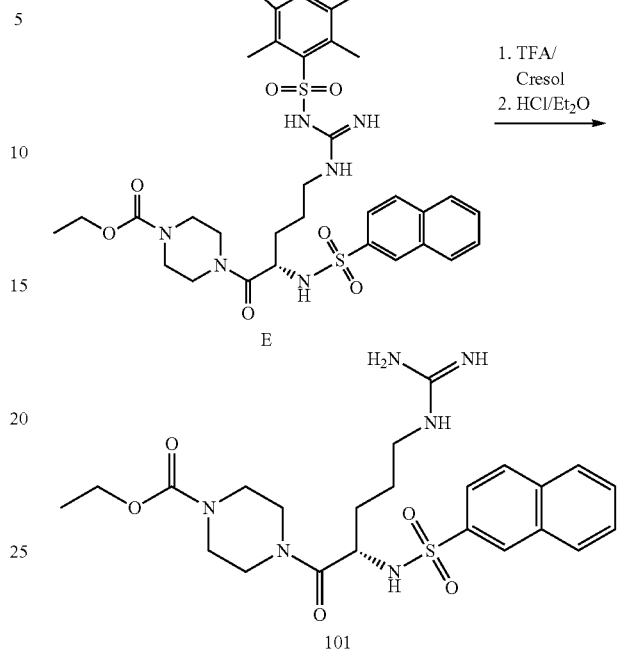

E

101

Preparation 1: Synthesis of 4-[(S)-5-({Amino-[(E)-2,2,4,6,7-pentamethyl-2,3-dihydro-benzofuran-5-sulfonylimino]-methyl}-amino)-2-(9H-fluoren-9-yl-methoxycarbonylamino)-pentanoyl]-piperazine-1-carboxylic acid tert-butyl ester (A)

To a solution of Fmoc-Arg(Pbf)-OH 1 (25.0 g, 38.5 mmol) in DMF (200 mL) at room temperature was added DIEA (13.41 mL, 77.1 mmol). After stirring at room temperature for 10 min, the reaction mixture was cooled to ~5° C. To the reaction mixture was added HATU (16.11 g, 42.4 mmol) in portions and stirred for 20 min and a solution of tert-butyl-1-piperazine carboxylate (7.18 g, 38.5 mmol) in DMF (50 mL) was added dropwise. The reaction mixture was stirred at ~5° C. for 5 min. The mixture reaction was then allowed to warm to room temperature and stirred for 2 h. Solvent was removed in vacuo and the residue was dissolved in EtOAc (500 mL), washed with water (2×750 mL), 1% $H_2SO_4$ (300 mL) and brine (750 mL). The organic layer was separated, dried over $Na_2SO_4$ and solvent removed in vacuo to a total volume of 100 mL. Compound A was taken to the next step as EtOAc solution (100 mL). LC-MS [M+H] 817.5 ($C_{43}H_{56}N_6O_8S$+H, calc: 817.4).

Preparation 2: Synthesis of 4-[(S)-2-Amino-5-({amino-[(E)-2,2,4,6,7-pentamethyl-2,3-dihydro-benzofuran-5-sulfonylimino]-methyl}-amino)-pentanoyl]-piperazine-1-carboxylic acid tert-butyl ester (B)

To a solution of compound A (46.2 mmol) in EtOAc (175 mL) at room temperature was added piperidine (4.57 mL, 46.2 mmol) and the reaction mixture was stirred for 18 h at room temperature. Next the solvent was removed in vacuo and the resulting residue dissolved in minimum amount of EtOAc (~50 mL) and hexane (~1 L) was added. Precipitated crude product was filtered off and recrystallised again with EtOAc (~30 mL) and hexane (~750 mL). The precipitate was filtered off, washed with hexane and dried in vacuo to afford compound B (28.0 g, 46.2 mmol). LC-MS [M+H] 595.4 ($C_{28}H_{46}N_6O_6S$+H, calc: 595.3).

Preparation 3: Synthesis of 4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazine-1-carboxylic acid tert-butyl ester (C)

To a solution of compound B (28.0 g, 46.2 mmol) in THF (250 mL) was added aqueous 1N NaOH (171 mL). The reaction mixture was cooled to ~5° C., a solution of 2-naphthalene sulfonylchloride (26.19 g, 115.6 mmol) in THF (125 mL) was added dropwise. The reaction mixture was stirred at ~5° C. for 10 min, with stirring continued at room temperature for 2 h. The reaction mixture was diluted with EtOAc (1 L), washed with aqueous 1N NaOH (1 L), water (1 L) and brine (1 L). The organic layer was separated, dried over $Na_2SO_4$ and removal of the solvent in vacuo to afford compound C (36.6 g, 46.2 mmol). LC-MS [M+H] 785.5 ($C_{38}H_{52}N_6O_8S_2$+H, calc: 785.9).

Preparation 4: Synthesis of 2,2,4,6,7-Pentamethyl-2,3-dihydro-benzofuran-5-sulfonic acid 1-amino-1-[(S)-4-(naphthalene-2-sulfonylamino)-5-oxo-5-piperazin-1-yl-pentylamino]-meth-(E)-ylideneamide (D)

To a solution of compound C (36.6 g, 46.2 mmol) in dioxane (60 mL) was added 4M HCl in dioxane (58 mL) dropwise. The reaction mixture was stirred at room temperature for 1.5 h. $Et_2O$ (600 mL) was added to the reaction mixture, precipitated product was filtered off, washed with $Et_2O$ and finally dried under vacuum to afford compound D (34.5 g, 46.2 mmol). LC-MS [M+H] 685.4 ($C_{33}H_{44}N_6O_6S_2$+H, calc: 685.9). Compound D was used without further purification.

Preparation 5: Synthesis of 4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazine-1-carboxylic acid ethyl ester (E)

To a solution of compound D (8.0 g, 11.1 mmol) in $CHCl_3$ (50 ml) was added DIEA (4.1 mL, 23.3 mmol) at room temperature and stirred for 15 min. The mixture was cooled to ~5° C., ethyl chloroformate (1.06 mL, 11.1 mmol) was added drop wise. After stirring at room temperature overnight (~18 h), solvent removed in vacuo. The residue was dissolved in MeOH (~25 ml) and Et2O (~500 mL) was added. The precipitated crude product was filtered off, washed with $Et_2O$ and dried under vacuo to afford compound E (8.5 g, 11.1 mmol). LC-MS [M+H] 757.6 ($C_{36}H_{48}N_6O_8S_2$+H, calc: 757.9). Compound E was used without further purification.

Synthesis of (S)-ethyl 4-(5-guanidino-2-(naphthalene-2-sulfonamido)pentanoyl)piperazine-1-carboxylate (Compound 101)

A solution of 5% m-cresol/TFA (50 ml) was added to compound E (8.5 g, 11.1 mmol) at room temperature. After stirring for 1 h, the reaction mixture was precipitated with $Et_2O$ (~500 mL). The precipitate was filtered and washed with $Et_2O$ and dried under vacuo to afford the crude product.

The crude product was purified by preparative reverse phase HPLC. [Column: VARIAN, LOAD & LOCK, L&L 4002-2, Packing: MicrosoRb 100-10 C18, Injection, Volume: ~15 mL×2, Injection flow rate: 20 mL/min, 100% A, (water/0.1% TFA), Flow rate: 100 mL/min, Fraction: 30 Sec (50 mL), Method: 0% B (MeCN/0.1% TFA)-60% B/60 min/100 ml/min/254 nm]. Solvents were removed from pure fractions in vacuo. Trace of water was removed by co-evaporation with 2×i-PrOH (50 ml). The residue was dissolved in a minimum amount of i-PrOH and product was precipitated with 2 M HCl in $Et_2O$. Product was filtered off and washed with $Et_2O$ and dried under vacuo to afford Compound 101 as HCl salt 7 (3.78 g, 63% yield, 99.4% purity). LC-MS [M+H] 505.4 ($C_{38}H_{52}N_6O_8S_2$+H, calc: 505.6).

Example 2

Synthesis of (S)-ethyl 4-(5-guanidino-2-(2,4,6-triisopropylphenylsulfonamido)pentanoyl)piperazine-1-carboxylate (Compound 102)

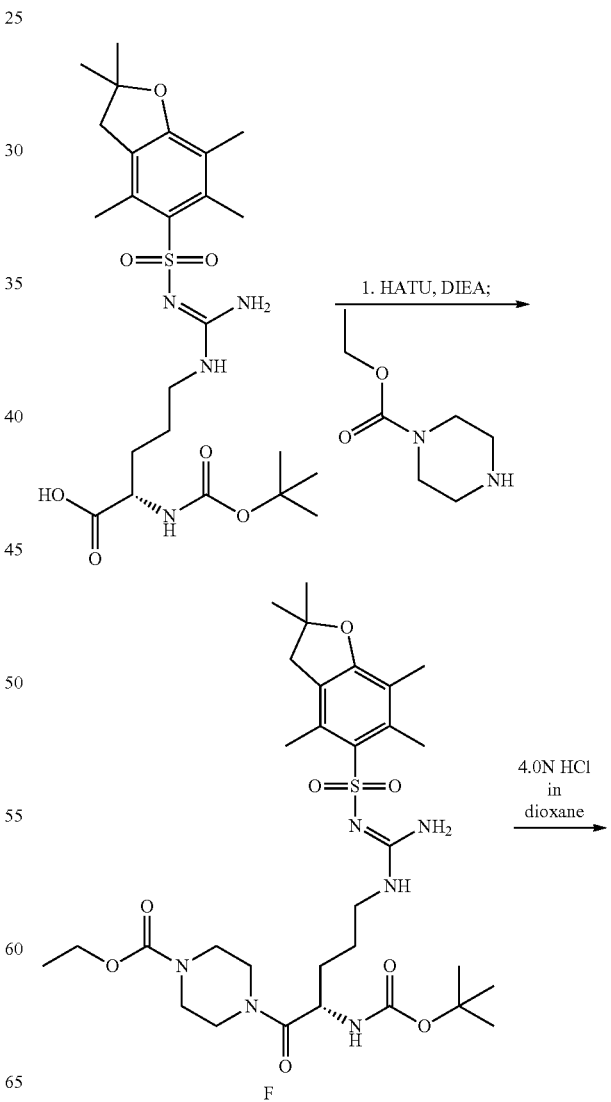

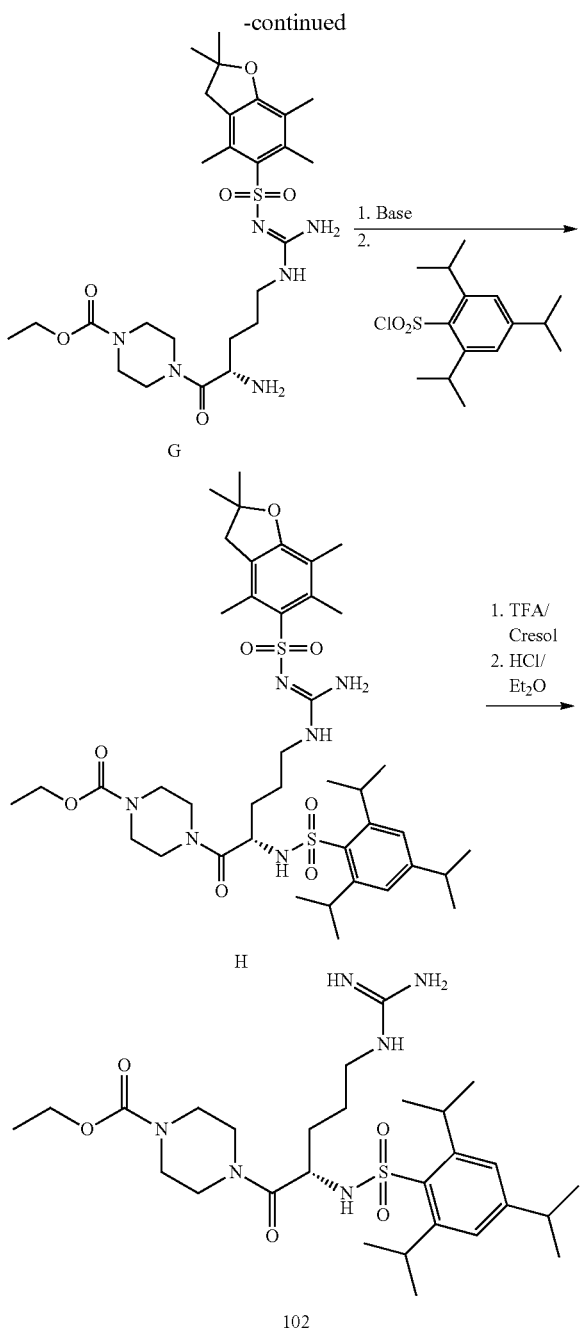

Preparation 6: Synthesis of 4-[(S)-5-({Amino-[(E)-2,2,4,6,7-pentamethyl-2,3-dihydro-benzofuran-5-sulfonylimino]-methyl}-amino)-2-tert-butoxycarbonylamino-pentanoyl]-piperazine-1-carboxylic acid ethyl ester (F)

To a solution of Boc-Arg(Pbf)-OH (13.3 g, 25.3 mmol) in DMF (10 mL) was added DIEA (22.0 mL, 126.5 mmol) at room temperature and stirred for 15 min. The reaction mixture was then cooled to ~5° C. and HATU (11.5 g, 30.3 mmol) was added in portions and stirred for 30 min, followed by the dropwise addition of ethyl-1-piperazine carboxylate (4.0 g, 25.3 mmol) in DMF (30 mL). After 40 min, the reaction mixture was diluted with EtOAc (400 mL) and poured in to $H_2O$ (1 L). Extracted with EtOAc (2×400 mL) and washed with $H_2O$ (800 mL), 2% $H_2SO_4$ (500 mL), $H_2O$ (2×800 mL) and brine (800 mL). Organic layer was separated, dried over $MgSO_4$ and solvent removed in vacuo. The resultant oily residue was dried in vacuo to afford compound F (16.4 g, 24.5 mmol) as foamy solid. LC-MS [M+H] 667.2 ($C_{31}H_{50}N_6O_8S$+H, calc: 667.8). Compound F was used without further purification.

Preparation 7: Synthesis of 4-[(S)-2-Amino-5-({amino-[(E)-2,2,4,6,7-pentamethyl-2,3-dihydro-benzofuran-5 sulfonylimino]-methyl}-amino)-pentanoyl]-piperazine-1-carboxylic acid ethyl ester (G)

A solution of compound F (20.2 g, 30.2 mmol) in dichloromethane (90 mL) was treated with 4.0 N HCl in 1,4-dioxane (90 mL, 363.3 mmol) and stirred at room temperature for 2 h. Next most of the dichloromethane was removed in vacuo and $Et_2O$ (~1 L) was added. The resultant precipitate was filtered off and washed with $Et_2O$ and dried in vacuo to afford compound G (17.8 g, 30.2 mmol). LC-MS [M+H] 567.8 ($C_{26}H_{42}N_6O_6S$+H, calc: 567.8).

Preparation 8: Synthesis of 4-[(S)-5-({Amino-[(E)-2,2,4,6,7-pentamethyl-2,3-dihydro-benzofuran-5-sulfonylimino]-methyl}-amino)-2-(2,4,6-triisopropyl-benzenesulfonylamino)-pentanoyl]-piperazine-1-carboxylic acid ethyl ester (H)

To a solution of compound G (1.0 g, 1.8 mmol) in THF (7 mL) was added 3.1N aqueous NaOH (4.0 mL) and stirred for 5 min. The reaction mixture was cooled to ~5° C., and then a solution of tripsyl chloride added drop wise (2.2 g, 7.3 mmol) in THF (5 mL) and stirred at room temperature overnight (~18 h). The reaction mixture was diluted with $H_2O$ (130 mL), acidified with 2% $H_2SO_4$ (15 mL) and extracted with EtOAc (3×80 mL). Organic layer were combined and washed with $H_2O$ (2×400 mL), saturated $NaHCO_3$ (100 mL), $H_2O$ (200 mL) and brine (200 mL). The organic layer was separated dried over $MgSO_4$ and solvent removed in vacuo to afford (2.9 g) of crude product. This was purified by normal phase flash chromatography (5-10% MeOH/DCM) to afford compound H (0.52 g, 1.0 mmol). LC-MS [M+H] 833.8 ($C_{41}H_{64}N_6O_8S_2$+H, calc: 834.1).

Synthesis of (S)-ethyl 4-(5-guanidino-2-(2,4,6-triisopropylphenylsulfonamido)pentanoyl)piperazine-1-carboxylate (Compound 102)

A solution of 5% m-cresol/TFA (40 ml) was added to compound H (3.73 g, 3.32 mmol) at room temperature. After stirring for 45 min, solvents were removed in vacuo. Residue was dissolved in dichloromethane (100 ml), washed with $H_2O$ (3×200 mL) and brine (200 mL). The organic layer was separated, dried over $MgSO_4$ and then the solvent removed in vacuo. The residue was dissolved in dichloromethane (~5 mL) and then hexane (~250 mL) was added and a precipitate was formed. This was washed with hexane and dried under vacuo to afford the crude product (1.95 g). The crude product was purified by reverse phase HPLC [Column: VARIAN, LOAD & LOCK, L&L 4002-2, Packing: Microsorb 100-10 C18, Injection Volume: ~15 mL, Injection flow rate: 20 mL/min, 100% A, (water/0.1% TFA), Flow rate: 100 mL/min, Fraction: Sec (50 mL), Method: 25% B (MeCN/0.1% TFA)/70% B/98 min/100 ml/min/254 nm]. Solvents were removed from pure fractions in vacuo. Trace of water was removed by co-evaporation with 2×i-PrOH (50 ml). The residue was dissolved in a minimum amount of i-PrOH and product was precipitated with 2 M HCl in $Et_2O$. Product was filtered off and washed with $Et_2O$ and dried under vacuo to afford the product as HCl salt of Compound 102 (0.72 g, 35% yield, 99.8% purity). LC-MS [M+H] 581.6 ($C_{28}H_{48}N_6O_5S$+H, calc: 581.7).

Example 3

Synthesis of (S)-ethyl 1-(5-guanidino-2-(naphthalene-2-sulfonamido)pentanoyl)piperidine-4-carboxylate HCl salt (Compound 103)

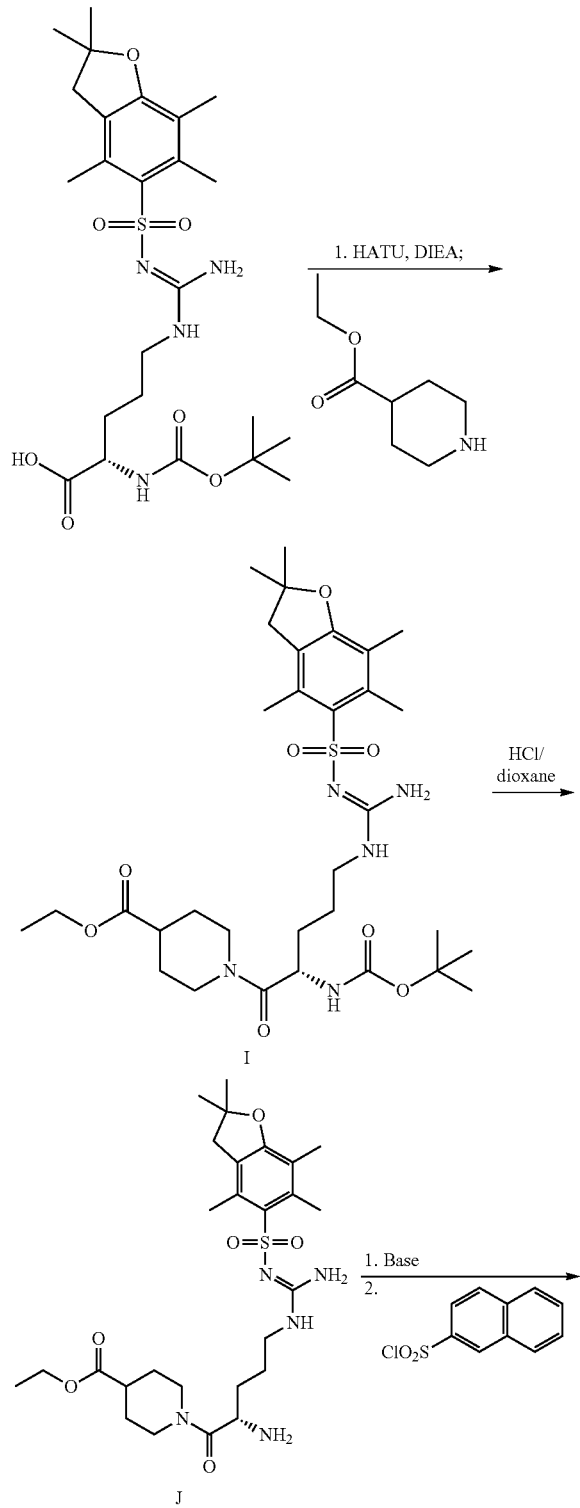

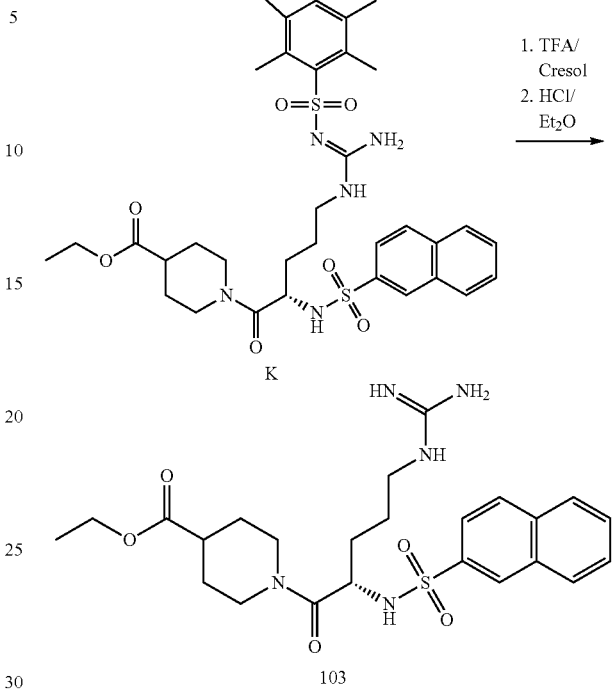

Preparation 9: Synthesis of 1-[boc-Arg(Pbf)]-piperidine-4-carboxylic acid ethyl ester (I)

To a solution of Boc-Arg(Pbf)-OH (3.4 g, 6.36 mmol) and HATU (2.9 g, 7.63 mmol) in DMF (15 mL) was added DIEA (7.4 mL, 42.4 mmol) and the reaction mixture was stirred for 10 min at room temperature. A solution of ethyl isonipecotate (1.0 g, 6.36 mmol) in DMF (6 mL) was added to the reaction mixture dropwise. The reaction mixture was stirred at room temperature for 1 h, then diluted with ethyl acetate (150 mL) and poured into water (500 mL). The product was extracted with ethyl acetate (2×100 mL). Organic layer was washed with aqueous 0.1 N HCl (200 mL), 2% aqueous sodium bicarbonate (200 mL), water (200 mL) and brine (200 mL). The organic layer was dried over sodium sulfate, filtered, and then evaporated in vacuo. The resultant oily product was dried in vacuo overnight to give compound I (3.7 g, 5.57 mmol) as a viscous solid. LC-MS [M+H] 666.5 ($C_{32}H_{51}N_5O_8S$+H, calc: 666.7). Compound I was used without further purification.

Preparation 10: Synthesis of 1-[Arg(Pbf)]-piperidine-4-carboxylic acid ethyl ester HCl salt (J)

To a solution of compound I (4.7 g, 7.07 mmol) in dichloromethane (25 mL) was added 4N HCl in dioxane (25.0 mL, 84.84 mmol), and the reaction mixture was stirred at room temperature for 2 h. The reaction mixture was concentrated in vacuo to ~20 mL of solvent, and then diluted with diethyl ether (250 mL) to produce a white fine precipitate. The reaction mixture was stirred for 1 h and the solid was washed with ether (50 mL) and dried in a high vacuum overnight to give compound J (4.3 g, 7.07 mmol) as a fine powder. LC-MS [M+H] 566.5 ($C_{27}H_{43}N_5O_6S$+H, calc: 566.7).

181

Preparation 11: Synthesis of 1-[5(S)—(N'-Pbf-guanidino)-2-(naphthalene-2-sulfonylamino)-pentanoyl]-piperidine-4-carboxylic acid ethyl ester (K)

To a solution of compound J (1.1 g, 1.6 mmol) and NaOH (260 mg, 5.9 mmol) in a mixture of THF (5 mL) and water (3 mL) was added a solution of 2-naphthalosulfonyl chloride (0.91 g, 2.5 mmol) in THF (10 mL) dropwise with stirring at ~5° C. The reaction mixture was stirred at room temperature for 1 h, then diluted with water (5 mL). Aqueous 1N HCl (5 mL) was added to obtain pH ~3. Additional water was added (20 mL), and the product was extracted with ethyl acetate (3×50 mL). The organic layer was removed and then washed with 2% aqueous sodium bicarbonate (50 mL), water (50 mL) and brine (50 mL). The extract was dried over anhydrous sodium sulfate, filtered, and was evaporated in vacuo. The formed oily product was dried in vacuo overnight to give compound K (1.3 g, 1.6 mmol) as an oily foaming solid. LC-MS [M+H] 756.5 ($C_{37}H_{49}N_5O_8S_2$+H, calc: 756.7).

Synthesis of (S)-ethyl 1-(5-guanidino-2-(naphthalene-2-sulfonamido)pentanoyl)piperidine-4-carboxylate HCl salt (Compound 103)

To a flask, was added compound K (1.3 g, 1.6 mmol) and then treated with 5% m-cresol/TFA (10 mL). The reaction mixture was stirred at room temperature for 1 h. Next, the reaction mixture was concentrated in vacuo to a volume 5 mL. Diethyl ether (200 mL) was then added to the residue, and formed fine white precipitate. The precipitate was filtered off and washed with ether (2×25 mL). The resultant solid was dried in vacuo overnight to give a crude material, which was purified by preparative reverse phase HPLC. [Nanosyn-Pack Microsorb (100-10) C-18 column (50×300 mm); flow rate=100 ml/min; injection volume 12 ml (DMSO-water, 1:1, v/v); mobile phase A: 100% water, 0.1% TFA; mobile phase B: 100% ACN, 0.1% TFA; gradient elution from 25% B to 55% B in 90 min, detection at 254 nm]. Fractions containing desired compound were combined and concentrated in vacuo. The residue was dissolved in i-PrOH (50 ml) and evaporated in vacuum (repeated twice). The residue was next dissolved in i-PrOH (5 ml) and treated with 2 N HCl/ether (100 ml, 200 mmol) to give a white precipitate. It was dried in vacuo overnight to give Compound 103 (306 mg, 31% yield, 95.7% purity) as a white solid. LC-MS [M+H] 504.5 ($C_{24}H_{33}N_5O_5S$+H, calc: 504.6).

Example 4

Synthesis of (S)-ethyl 1-(5-guanidino-2-(2,4,6-triisopropylphenylsulfonamido)pentanoyl)piperidine-4-carboxylate HCl salt (Compound 104)

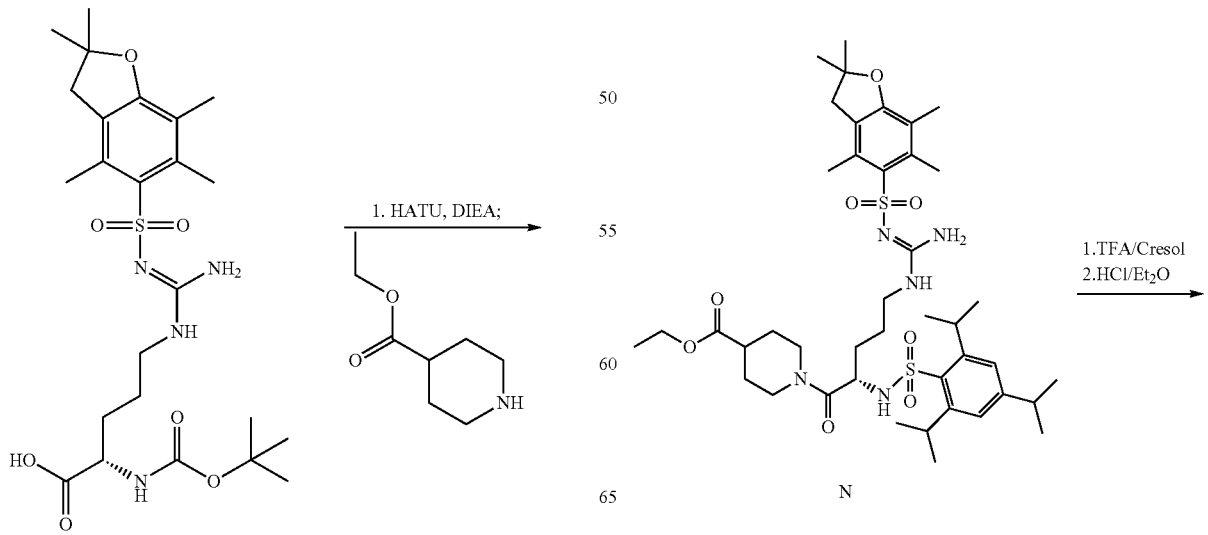

-continued

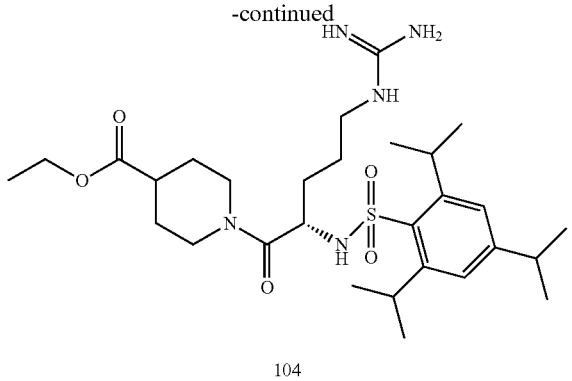

104

Preparation 12: Synthesis of 1-[5(S)—(N'-Pbf-guanidino)-2-(2,4,6-triisopropyl-benzenesulfonylamino)-pentanoyl]-piperidine-4-carboxylic acid ethyl ester (N)

To a solution of compound J (1.0 g, 1.6 mmol) and NaOH (420.0 mg, 10.4 mmol) in a mixture of THF (5 mL) and water (4 mL) was added a solution of 2,4,6-triisopropyl-benzenesulfonyl chloride (2.4 g, 8.0 mmol) drop wise with stirring and maintained at ~5° C. The reaction mixture was then stirred at room temperature for 1 h, monitoring the reaction progress, then diluted with water (20 mL), and acidified with aqueous 1 N HCl (5 mL) to pH ~3. Additional water was added (30 mL), and the product was extracted with ethyl acetate (3×50 mL). The organic layer was washed with 2% aqueous sodium bicarbonate (50 mL), water (50 mL) and brine (50 mL). The organic layer was dried over anhydrous sodium sulfate, filtered, and was evaporated in vacuo. Formed oily residue was dried in a vacuo overnight to give compound N (1.0 g, 1.2 mmol) as an oily material. LC-MS [M+H] 832.8 ($C_{42}H_{65}N_5O_8S_2$+H, calc: 832.7).

Synthesis of (S)-ethyl 1-(5-guanidino-2-(2,4,6-triisopropylphenylsulfonamido)pentanoyl)piperidine-4-carboxylate HCl salt (Compound 104)

To a flask was added compound N (2.3 g, 2.8 mmol) and then treated with 5% m-cresol/TFA (16 mL). The reaction mixture was stirred at room temperature for 1 h. The reaction mixture was then concentrated in vacuo to a volume of 5 mL. Hexane (200 mL) was added to the residue and decanted off to give an oily precipitate. The product was purified by preparative reverse phase HPLC. [Nanosyn-Pack Microsorb (100-10) C-18 column (50×300 mm); flow rate=100 ml/min; injection volume 15 ml (DMSO-water, 1:1, v/v); mobile phase A: 100% water, 0.1% TFA; mobile phase B: 100% ACN, 0.1% TFA; gradient elution from 35% B to 70% B in 90 min, detection at 254 nm]. Fractions containing desired compound were combined and concentrated in vacuo. The residue was dissolved in i-PrOH (100 ml) and evaporated in vacuo (repeated twice). The residue was dissolved in i-PrOH (5 ml) and treated with 2 N HCl/ether (100 ml, 200 mmol) to give an oily residue. It was dried in vacuo overnight to give Compound 104 (1.08 g, 62.8%) as a viscous solid. LC-MS [M+H] 580.6 ($C_{29}H_{49}N_5O_5S$+H, calc: 580.8).

Example 5

Synthesis of (S)-6-(4-(5-guanidino-2-(naphthalene-2-sulfonamido)pentanoyl)piperazin-1-yl)-6-oxohexanoic acid (Compound 105)

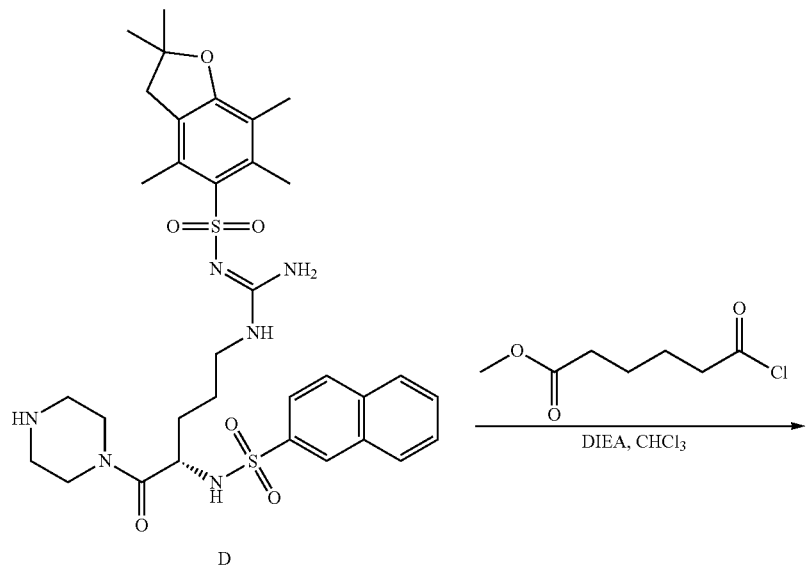

D

-continued
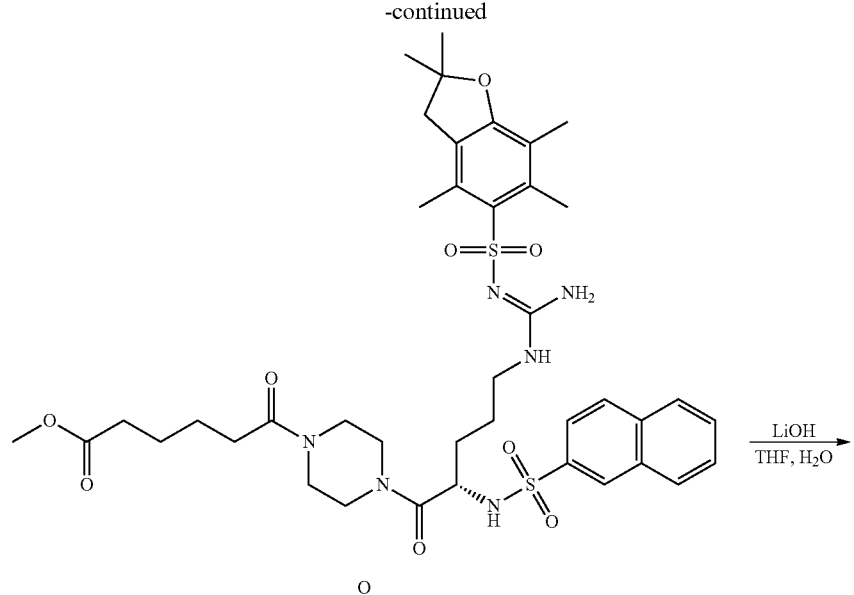
LiOH
THF, H₂O
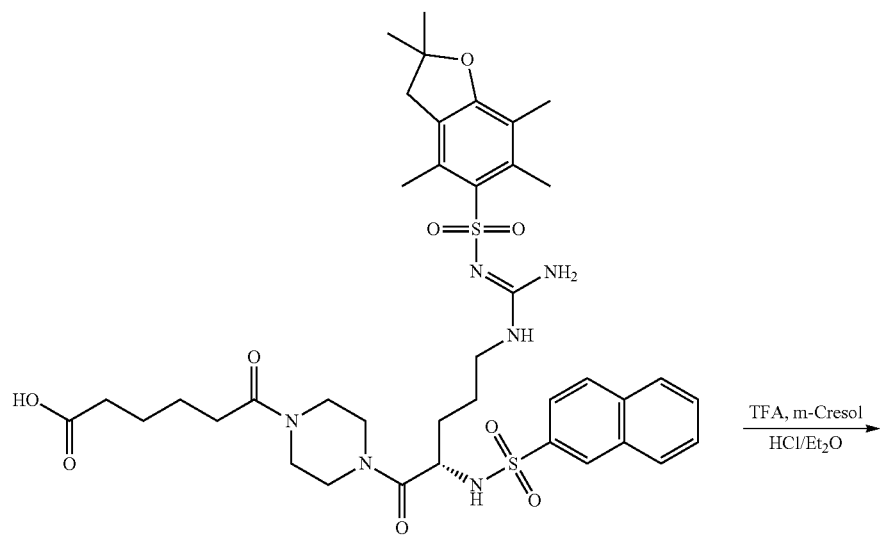
TFA, m-Cresol
HCl/Et₂O
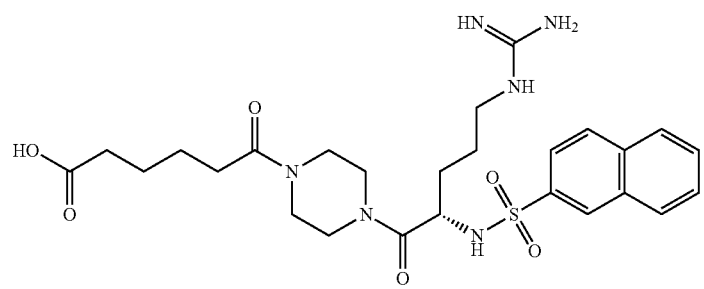
105

Preparation 13: Synthesis of 6-{4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazin-1-yl}-6-oxo-hexanoic acid methyl ester (O)

To a solution of compound D (1.5 g, 2.08 mmol) in CHCl$_3$ (50 mL) was added DIEA (1.21 mL, 4.16 mmol) followed by adipoyl chloride (0.83 mL, 6.93 mmol) dropwise. The reaction mixture was stirred at room temperature overnight (~18 h). Solvents were removed in vacuo and the residue was dried under vacuo to afford the compound O (2.1 g, amount exceeds quantative). LC-MS [M+H] 827.5 ($C_{40}H_{54}N_6O_9S_2$+H, calc: 827.3). Compound O was used without further purification.

Preparation 14: Synthesis of 6-{4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazin-1-yl}-6-oxohexanoic acid (P)

To a solution of compound O (2.1 g, 2.08 mmol) in THF (5 mL), H$_2$O (5 mL) was added 2 M aq LiOH (6 mL). The reaction mixture was stirred at room temperature for 2 h. Solvents were removed in vacuo, then the residue was dissolved in water (~50 mL), acidified with saturated aqueous NaHSO$_4$ (~100 ml) and extracted with EtOAc (2×100 ml). The organic layer was dried over Na$_2$SO$_4$ and removal of the solvent gave compound P (1.72 g, 2.08 mmol). LC-MS [M+H] 813.5 ($C_{39}H_{52}N_6O_9S_2$+H, calc: 813.3). Compound P was used without further purification.

Synthesis of (S)-6-(4-(5-guanidino-2-(naphthalene-2-sulfonamido)pentanoyl)piperazin-1-yl)-6-oxohexanoic acid (Compound 105)

A solution of 5% m-cresol/TFA (25 ml) was added to compound P (1.72 g, 2.08 mmol) at room temperature. After stirring for 30 min, the reaction mixture was precipitated with addition of Et$_2$O (~200 mL). The precipitate was filtered and washed with Et$_2$O and dried under vacuo to afford the crude product. The crude product was purified by preparative reverse phase HPLC [Column: VARIAN, LOAD & LOCK, L&L 4002-2, Packing: Microsorb 100-10 C18, Injection Volume: ~25 mL, Injection flow rate: 20 mL/min, 95% A, (water/ 0.1% TFA), Flow rate: 100 mL/min, Fraction: 30 Sec (50 mL), Method: 5% B (MeCN/0.1% TFA)/5 min/25% B/20 min/25% B/15 min/50% B/25 min/100 ml/min/254 nm]. Solvents were removed from pure fractions in vacuo. Trace of water was removed by co-evaporation with i-PrOH (25 ml) (repeated twice). The residue was dissolved in a minimum amount of i-PrOH, then 2 M HCl in Et$_2$O (~50 mL) was added and diluted with Et$_2$O (~250 mL). Precipitate formed was filtered off and washed with Et$_2$O and dried under vacuo to afford the product as HCl salt Compound 105 (0.74 g, 59% yield, 98.9% purity). LC-MS [M+H] 561.4 ($C_{26}H_{36}N_6O_6S$+H, calc: 561.2).

Example 6

Synthesis of 3-(4-carbamimidoylphenyl)-2-oxopropanoic acid (Compound 107)

Compound 107, i.e., 3-(4-carbamimidoylphenyl)-2-oxopropanoic acid can be produced using methods known to those skilled in the art, such as that described by Richter P et al, Pharmazie, 1977, 32, 216-220 and references contained within. The purity of Compound 107 used herein was estimated to be 76%, an estimate due low UV absorbance of this compound via HPLC. Mass spec data: LC-MS [M+H] 207.0 (C10H10N2O3+H, calc: 207.1).

Example 7

Synthesis of (S)-5-(4-carbamimidoylbenzylamino)-5-oxo-4-((R)-4-phenyl-2-(phenylmethylsulfonamido)butanamido)pentanoic acid (Compound 108)

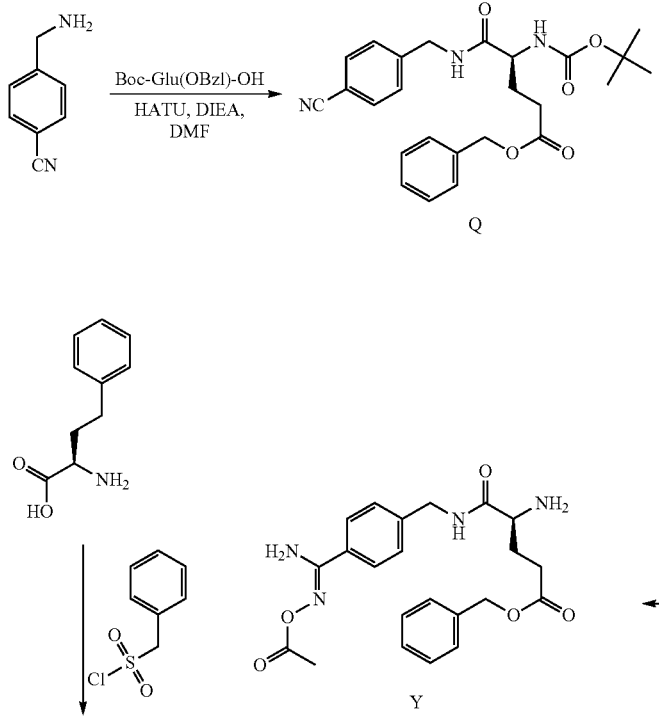

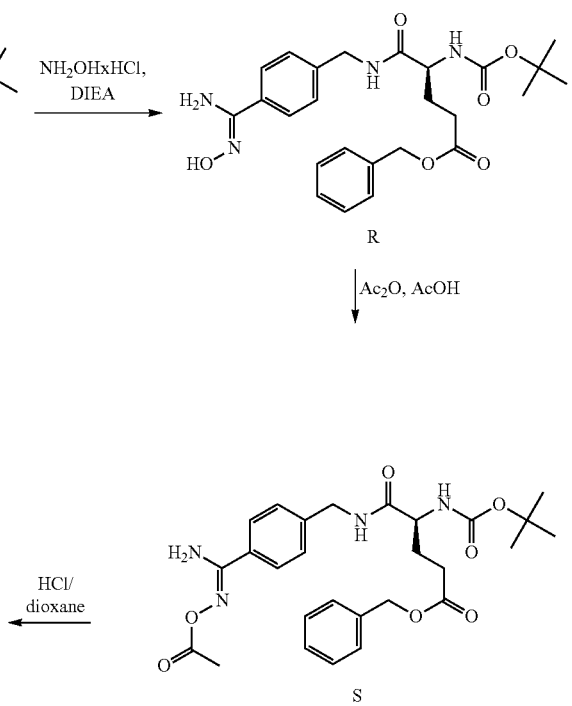

-continued
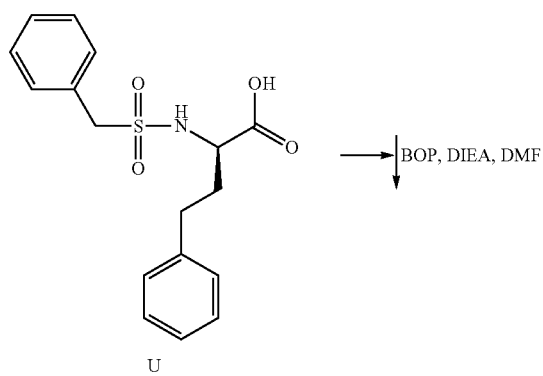
U
→ BOP, DIEA, DMF
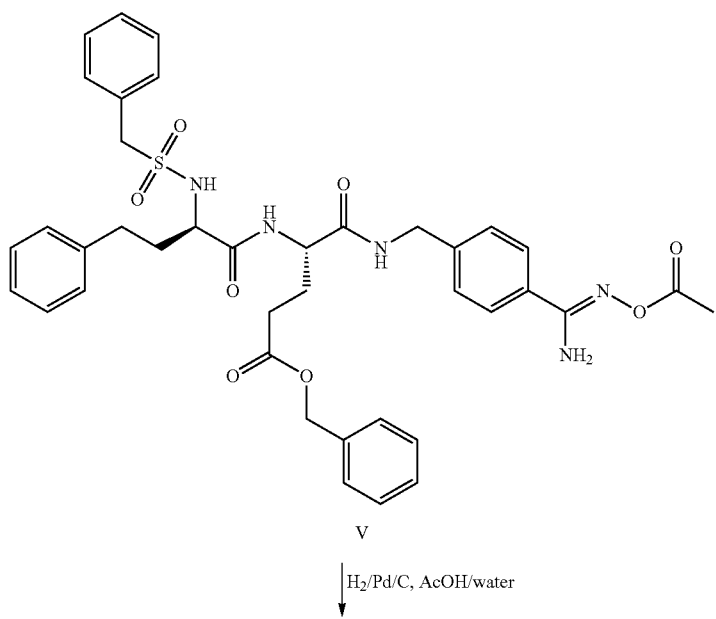
V
↓ H₂/Pd/C, AcOH/water
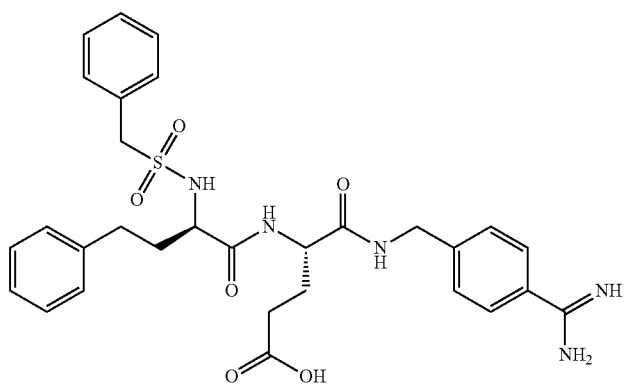
108

Preparation 15: Synthesis of (S)-4-tert-butoxycarbonylamino-4-(4-cyano-benzylcarbamoyl)-butyric acid benzyl ester (Q)

A solution of Boc-Glu(OBzl)-OH (7.08 g, 21.0 mmol), BOP (9.72 g, 22.0 mmol) and DIEA (12.18 ml, 70.0 mmol) in DMF (50 ml) was maintained at room temperature for 20 min, followed by the addition of 4-(aminomethyl)benzonitrile hydrochloride (3.38 g, 20.0 mmol). The reaction mixture was stirred at room temperature for an additional 1 h and diluted with EtOAc (500 ml). The obtained solution was extracted with water (100 ml), 5% aq. NaHCO$_3$ (100 ml) and water (2×100 ml). The organic layer was dried over MgSO$_4$, evaporated and dried in vacuo to provide compound Q (9.65 g, yield exceeded quantitative) as yellowish oil. LC-MS [M+H] 452.0 (C$_{25}$H$_{29}$N$_3$O$_5$+H, calc: 452.4). Compound Q was used without further purification.

Preparation 16: Synthesis of (5)-4-tert-butoxycarbonylamino-4-[4-(N-hydroxycarbamimidoyl)-benzyl carbamoyl]-butyric acid benzyl ester (R)

A solution of compound Q (9.65 g, 20.0 mmol), hydroxylamine hydrochloride (2.10 g, 30.0 mmol) and DIEA (5.22 ml, 30.0 mmol) in ethanol (abs., 150 ml) was refluxed for 6 h. The reaction mixture was allowed to cool to room temperature and stirred for additional 16 h, then the solvents were evaporated in vacuo. The resultant residue was dried in vacuo to provide compound R (14.8 g, yield exceeded quantitative) as yellowish oil. LC-MS [M+H] 485.5 (C$_{25}$H$_{32}$N$_4$O$_6$+H, calc: 485.8). Compound R was used without further purification.

Preparation 17: Synthesis of (S)-4-tert-butoxycarbonylamino-4-[4-(N-acetylhydroxycarbamimidoyl)-benzyl carbamoyl]-butyric acid benzyl ester (S)

A solution of compound R (14.8 g, 20.0 mmol) and acetic anhydride (5.7 ml, 60.0 mmol) in acetic acid (100 ml) was stirred at room temperature for 45 min, and then solvent was evaporated in vacuo. The resultant residue was dissolved in EtOAc (300 ml) and extracted with water (2×75 ml) and brine (75 ml). The organic layer was then dried over MgSO$_4$, evaporated and dried in vacuo to provide compound S (9.58 g, 18.2 mmol) as yellowish solid. LC-MS [M+H] 527.6 (C$_{27}$H$_{34}$N$_4$O$_7$+H, calc: 527.9). Compound S was used without further purification.

Preparation 18: Synthesis of (S)-4-[4-(N-acetylhydroxycarbamimidoyl)-benzyl carbamoyl]-butyric acid benzyl ester (T)

Compound S (9.58 g, 18.2 mmol) was dissolved in 1,4-dioxane (50 ml) and treated with 4 N HCl/dioxane (50 ml, 200 mmol) at room temperature for 1 h. Next, the solvent was evaporated in vacuo. The resultant residue was triturated with ether (200 ml). The obtained precipitate was filtrated, washed with ether (100 ml) and hexane (50 ml) and dried in vacuo to provide compound T (9.64 g, yield exceeded quantitative) as off-white solid. LC-MS [M+H] 426.9 (C$_{22}$H$_{26}$N$_4$O$_5$+H, calc: 427.3). Compound T was used without further purification.

Preparation 19: Synthesis of (R)-4-phenyl-2-phenylmethanesulfonylamino-butyric acid (U)

A solution of D-homo-phenylalanine (10.0 g, 55.9 mmol) and NaOH (3.35 g, 83.8 mmol) in a mixture of 1,4-dioxane (80 ml) and water (50 ml) was cooled to ~5° C., followed by alternate addition of α-toluenesulfonyl chloride (16.0 g, 83.8 mmol; 5 portions by 3.2 g) and 1.12 M NaOH (50 ml, 55.9 mmol; 5 portions by 10 ml) maintaining pH>10. The reaction mixture was acidified with 2% aq. H$_2$SO$_4$ to pH=~2. The obtained solution was extracted with EtOAc (2×200 ml). The organic layer was washed with water (3×75 ml), dried over MgSO$_4$ and then the solvent was evaporated in vacuo. The resultant residue was dried in vacuo to provide compound U (12.6 g, 37.5 mmol) as white solid. LC-MS [M+H] 334.2 (C$_{17}$H$_{19}$NO$_4$S+H, calc: 333.4). Compound U was used without further purification.

Preparation 20: Synthesis of (S)-4-[4-(N-acetylhydroxycarbamimidoyl)-benzylcarbamoyl]-4-((R)-4-phenyl-2-phenylmethanesulfonylamino-butyrylamino)-butyric acid benzyl ester (V)

A solution of compound U (5.9 g, 17.8 mmol), compound T di-hydrochloride (18.0 mmol), BOP (8.65 g, 19.6 mmol) and DIEA (10.96 ml, 19.6 mmol) in DMF (250 ml) was stirred at room temperature for 2 h. The reaction mixture was diluted with EtOAc (750 ml) and extracted with water (200 ml). The formed precipitate was filtrated, washed with EtOAc (200 ml) and water (200 ml) and dried at room temperature overnight (~18 h) to provide compound V (8.2 g, 11.0 mmol) as off-white solid. LC-MS [M+H] 743.6 (C$_{39}$H$_{43}$N$_5$O$_8$S+H, calc: 743.9). Compound V was used without further purification.

Synthesis of (S)-5-(4-carbamimidoylbenzylamino)-5-oxo-4-((R)-4-phenyl-2-(phenylmethylsulfonamido)butanamido)pentanoic acid (Compound 108)

Compound V (8.0 g, 10.77 mmol) was dissolved in acetic acid (700 ml) followed by the addition of Pd/C (5% wt, 3.0 g) as a suspension in water (50 ml). Reaction mixture was subjected to hydrogenation (Parr apparatus, 5 psi) at room temperature for 3 h. The catalyst was filtered over a pad of Celite on sintered glass filter and washed with methanol. Filtrate was evaporated in vacuo to provide compound 108 as colorless oil. LC-MS [M+H] 594.2 (C$_{30}$H$_{35}$N$_5$O$_6$S+H, calc: 594). Obtained oil was dissolved in water (150 ml) and subjected to HPLC purification. [Nanosyn-Pack YMC-ODS-A (100-10) C-18 column (75×300 mm); flow rate=250 ml/min; injection volume 150 ml; mobile phase A: 100% water, 0.1% TFA; mobile phase B: 100% acetonitrile, 0.1% TFA; isocratic elution at 10% B in 4 min., gradient elution to 24% B in 18 min, isocratic elution at 24% B in 20 min, gradient elution from 24% B to 58% B in 68 min; detection at 254 nm]. Fractions containing desired compound were combined and concentrated in vacuo. Residue was dissolved in i-PrOH (75 ml) and evaporated in vacuo (procedure was repeated twice) to provide Compound 108 (4.5 g, 70% yield, 98.0% purity) as white solid. LC-MS [M+H] 594.2 (C$_{30}$H$_{35}$N$_5$O$_6$S+H, calc: 594). Retention time*: 3.55 min.

*—[Chromolith SpeedRod RP-18e C18 column (4.6×50 mm); flow rate 1.5 ml/min; mobile phase A: 0.1% TFA/water; mobile phase B 0.1% TFA/acetonitrile; gradient elution from 5% B to 100% B over 9.6 min, detection 254 nm]

Synthesis of Phenolic Opioid Prodrugs
Example 8
Synthesis of [2-((S)-2-amino-5-guanidino-pentanoylamino)-ethyl]-methyl-carbamic acid hydromorphyl ester (Compound PC-2)
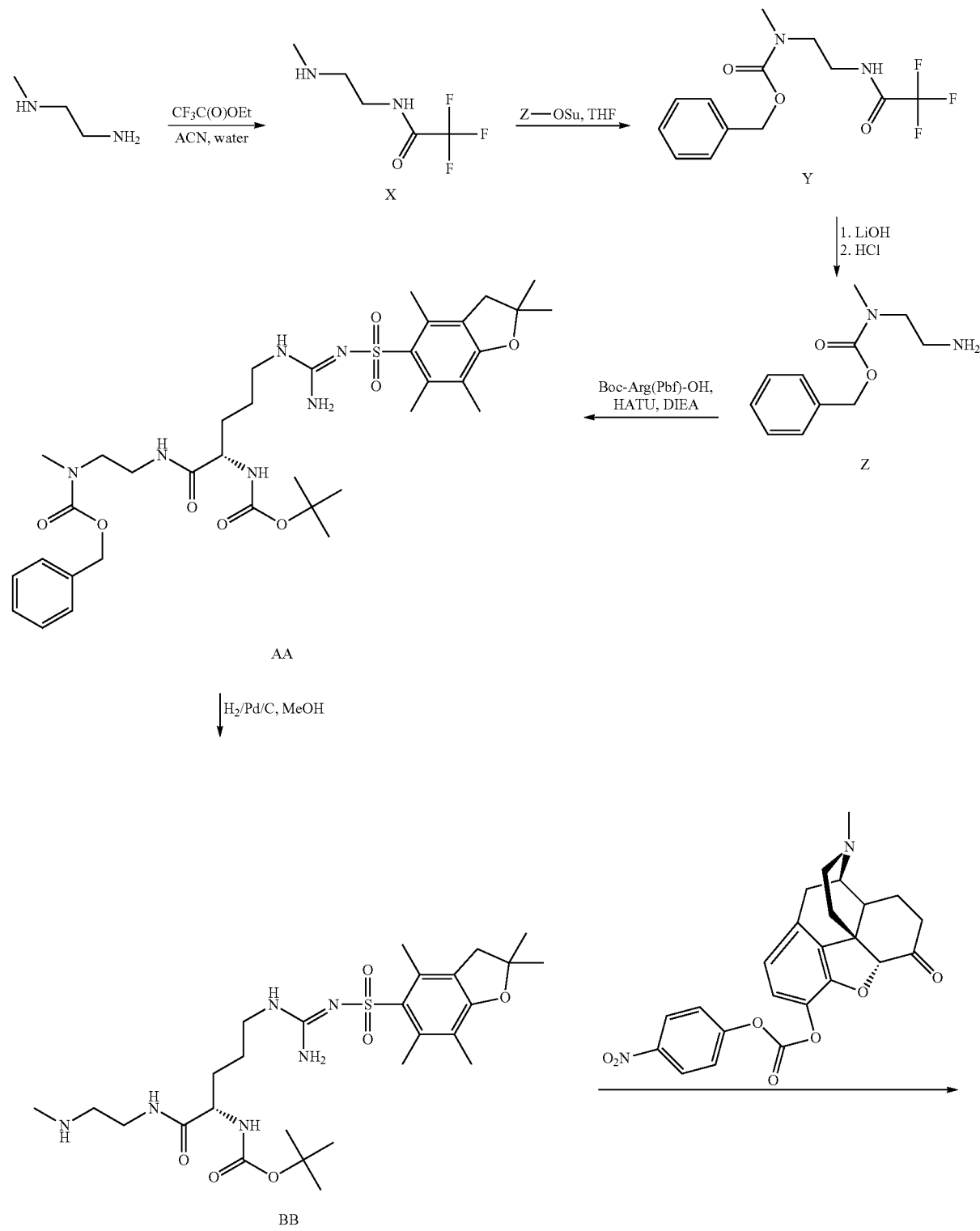

-continued

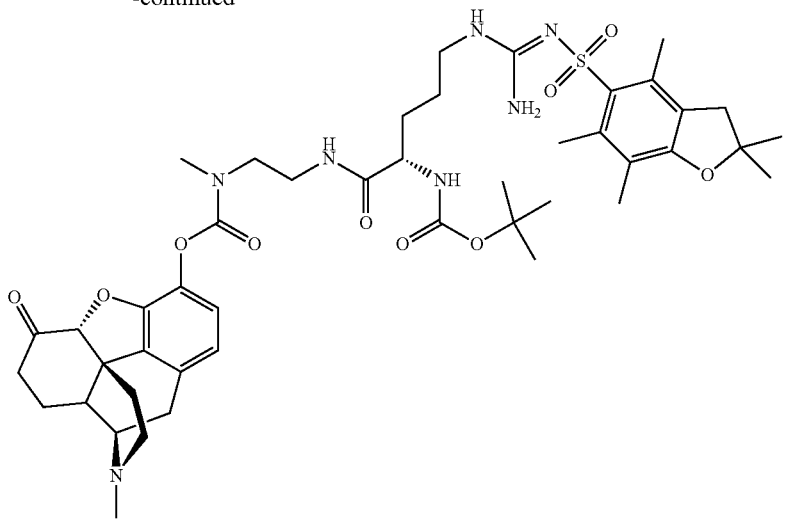

CC

1. TFA, 5% m-cresol
2. 2M HCl/ether

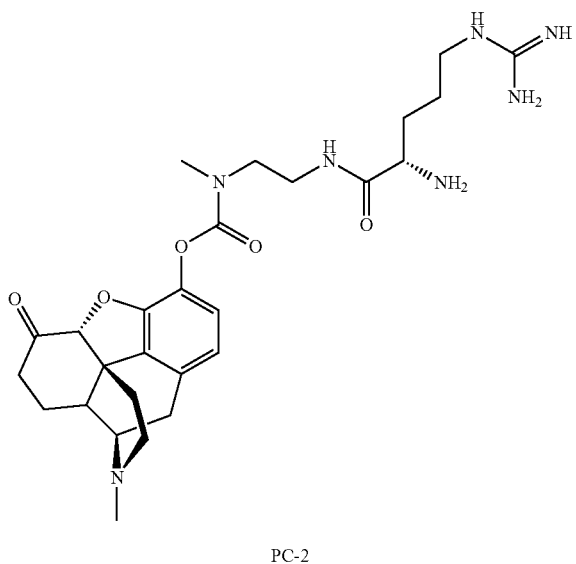

PC-2

Preparation 21: Synthesis of 2,2,2-trifluoro-N-(2-methylamino-ethyl)-acetamide (X)

A solution of N-methylethylenediamine (27.0 g, 364.0 mmol) and ethyl trifluoroacetate (96.6 mL, 838.0 mmol) in a mixture of acetonitrile (350 mL) and water (7.8 mL, 436 mmol) was refluxed overnight with stirring. Next the solvents were evaporated in vacuo. Residue was re-evaporated with isopropanol (3×100 mL). Residue was dissolved in dichloromethane (500 mL) and left overnight at room temperature. The formed crystals were filtered, washed with dichloromethane and dried in vacuo to provide compound X (96.8 g, 94%) as white solid powder.

Preparation 22: Synthesis of methyl-[2-(2,2,2-trifluoro-acetylamino)-ethyl]carbamic acid benzyl ester (Y)

A solution of compound X (96.8 g, 340.7 mmol) and DIEA (59.3 mL, 340.7 mmol) in THF (350 mL) was cooled to ~5° C., followed by addition of a solution of N-(benzyloxycarbonyl)succinimide (84.0 g, 337.3 mmol) in THF (150 mL) dropwise over the period of 20 min. The temperature of reaction mixture was raised to room temperature and stirring was continued for an additional 30 min, followed by the solvents being evaporated. The resultant residue was dissolved in EtOAc (600 mL). EtOAc was extracted with 5% aq. NaHCO$_3$ (2×150 mL) and brine (150 mL). The organic layer was separated and evaporated to provide compound Y as yellowish oil (103.0 g, 340.7 mmol). LC-MS [M+H] 305.3 ($C_{13}H_{15}F_3N_2O_3$+H, calc: 305.3). Compound Y was used without further purification.

Preparation 23: Synthesis of
(2-amino-ethyl)-methyl-carbamic acid benzyl ester
(Z)

To a solution of compound Y (103.0 g, 340.7 mmol) in MeOH (1200 mL) was added a solution of LiOH (16.4 g, 681.4 mmol) in water (120 mL). The reaction mixture was stirred at room temperature for 3 h. Solvents were evaporated to ¾ of initial volume followed by dilution with water (400 mL). Solution was extracted with EtOAc (2×300 mL). The organic layer was washed with brine (200 mL), dried over $MgSO_4$ and evaporated in vacuo. The resultant residue was dissolved in ether (300 mL) and treated with 2 N HCl/ether (200 mL). The formed precipitate was filtered, washed with ether and dried in vacuo to provide hydrochloric salt of compound Z (54.5 g, 261.2 mmol) as white solid. LC-MS [M+H] 209.5 ($C_{11}H_{16}N_2O_2$+H, calc: 209.3).

Preparation 24: Synthesis of {(S)-4-({amino-[(E)-2,
2,4,6,7-pentamethyl-2,3-dihydro-benzofuran-5-sul-
fonylimino]-methyl}-amino)-1-[2-(benzyloxycarbo-
nyl-methyl-amino)-ethyl carbamoyl]-butyl}-
carbamic acid tert-butyl ester (AA)

A solution of Boc-Arg(Pbf)-OH (3.33 g, 6.32 mmol), HATU (2.88 g, 7.58 mmol) and DIEA (7.4 mL, 31.6 mmol) in DMF (40 mL) was maintained at room temperature for 20 min, followed by the addition of compound C hydrochloride (1.45 g, 6.95 mmol). Stirring was continued for additional 1 h. The reaction mixture was diluted with EtOAc (500 mL) and extracted with water (3×75 mL) and brine (75 mL). The organic layer was dried over $MgSO_4$ and then evaporated to provide compound AA (4.14 g, 5.77 mmol) as yellowish amorphous solid. LC-MS [M+H] 717.6 ($C_{35}H_{52}N_6O_8S$+H, calc: 717.9). Compound AA was used without further purification.

Preparation 25: Synthesis of (S)-2-amino-5-({amino-
[(E)-2,2,4,6,7-pentamethyl-2,3-dihydro-benzofuran-
5-sulfonylimino]-methyl}-amino)-pentanoic acid
(2-methylamino-ethyl)-amide (BB)

Compound AA (4.14 g, 5.77 mmol) and AcOH (330 µl, 5.77 mmol) were dissolved in methanol (40 mL) followed by the addition of Pd/C (5% wt, 880 mg) suspension in water (5 mL). The reaction mixture was subjected to hydrogenation (Parr apparatus, 75 psi) at room temperature for 2.5 h. The catalyst was filtered over a pad of Celite on sintered glass funnel and washed with methanol. Filtrate was evaporated in vacuo to provide compound BB (1.96 g, 3.2 mmol) as yellowish amorphous solid. LC-MS [M+H] 483.2 ($C_{22}H_{38}N_6O_4S$+H, calc: 483.2). Compound BB was used without further purification.

Preparation 26: Synthesis of {(S)-4-({amino-[(E)-2,
2,4,6,7-pentamethyl-2,3-dihydro-benzofuran-5-sul-
fonylimino]-methyl}-amino)-1-[2-(hydromorphyl-
carbonyl-methyl-amino)-ethyl carbamoyl]-butyl}-
carbamic acid tert-butyl ester (CC)

A suspension of hydromorphone hydrochloride (332 mg, 1.03 mmol) and DIEA (179 µl, 1.03 mmol) in chloroform (4 mL) was sonicated in an ultrasonic bath at room temperature for 1 h. This was followed by the addition of 4-nitrophenyl chloroformate (162 mg, 0.80 mmol). The reaction mixture was sonicated in an ultrasonic bath at room temperature for additional 1 h, followed by the addition of solution of compound BB (400 mg, 0.67 mmol) and 1-hydroxybenzo-triazole (154 mg, 1.14 mmol) in DMF (4 mL). The reaction mixture was stirred overnight (~18 h) at room temperature, followed by the solvents being evaporated in vacuo. The residue was dissolved in MeOH (5 mL) and precipitated with addition of ether (500 mL). The formed precipitate was filtered and dried in vacuo to provide compound CC (520 mg, yield exceeded quantitative) as off-white solid. LC-MS [M+H] 894.6 ($C_{45}H_{63}N_7O_{10}S$+H, calc: 894.9). Compound CC was used without further purification.

Synthesis of [2-((S)-2-amino-5-guanidino-pentanoy-
lamino)-ethyl]-methyl-carbamic acid hydromorphyl
ester (Compound PC-2)

Compound CC (679 mg, 0.76 mmol) was dissolved in the mixture of 5% m-cresol/TFA (10 mL). The reaction mixture was maintained at room temperature for 1 h, followed by the dilution with ether (500 mL). Formed precipitate was filtered, washed with ether (100 mL) and dried in vacuo to provide crude compound PC-2 (441 mg, yield exceeded quantitative) as off-white solid. LC-MS [M+H] 542.4 ($C_{27}H_{39}N_7O_5$+H, calc: 542).

Crude compound PC-2 was dissolved in water (10 mL) and subjected to preparative reverse phase HPLC purification. [Nanosyn-Pack Microsorb (100-10) C-18 column (50×300 mm); flow rate: 100 mL/min; injection volume 10 mL; mobile phase A: 100% water, 0.1% TFA; mobile phase B: 100% acetonitrile, 0.1% TFA; isocratic elution at 0% B in 5 min., gradient elution to 6% B in 6 min, isocratic elution at 6% B in 23 min, gradient elution from 6% B to 55% B in 66 min; detection at 254 nm]. Fractions containing the desired compound were combined and concentrated in vacuo. Residue was dissolved in i-PrOH (20 mL) and evaporated in vacuo (procedure was repeated twice). Residue was dissolved in i-PrOH (2 mL) and treated with 2 N HCl/ether (100 mL, 200 mmol) to provide the hydrochloride salt of Compound PC-2 (80 mg, 17% yield, 98% purity) as white solid. LC-MS [M+H] 542.0 ($C_{27}H_{39}N_7O_5$+H, calc: 542.9). Retention time*: 2.04 min.

*—[Chromolith SpeedRod RP-18e C18 column (4.6×50 mm); flow rate 1.5 mL/min; mobile phase A: 0.1% TFA/water; mobile phase B 0.1% TFA/ACN; gradient elution from 5% B to 100% B over 9.6 min, detection 254 nm]

Example 9
Synthesis of (S)-2-Acetylamino-6-amino-hexanoic acid (2-methylamino-ethyl)-amide hydromorphone ester (Compound PC-3)
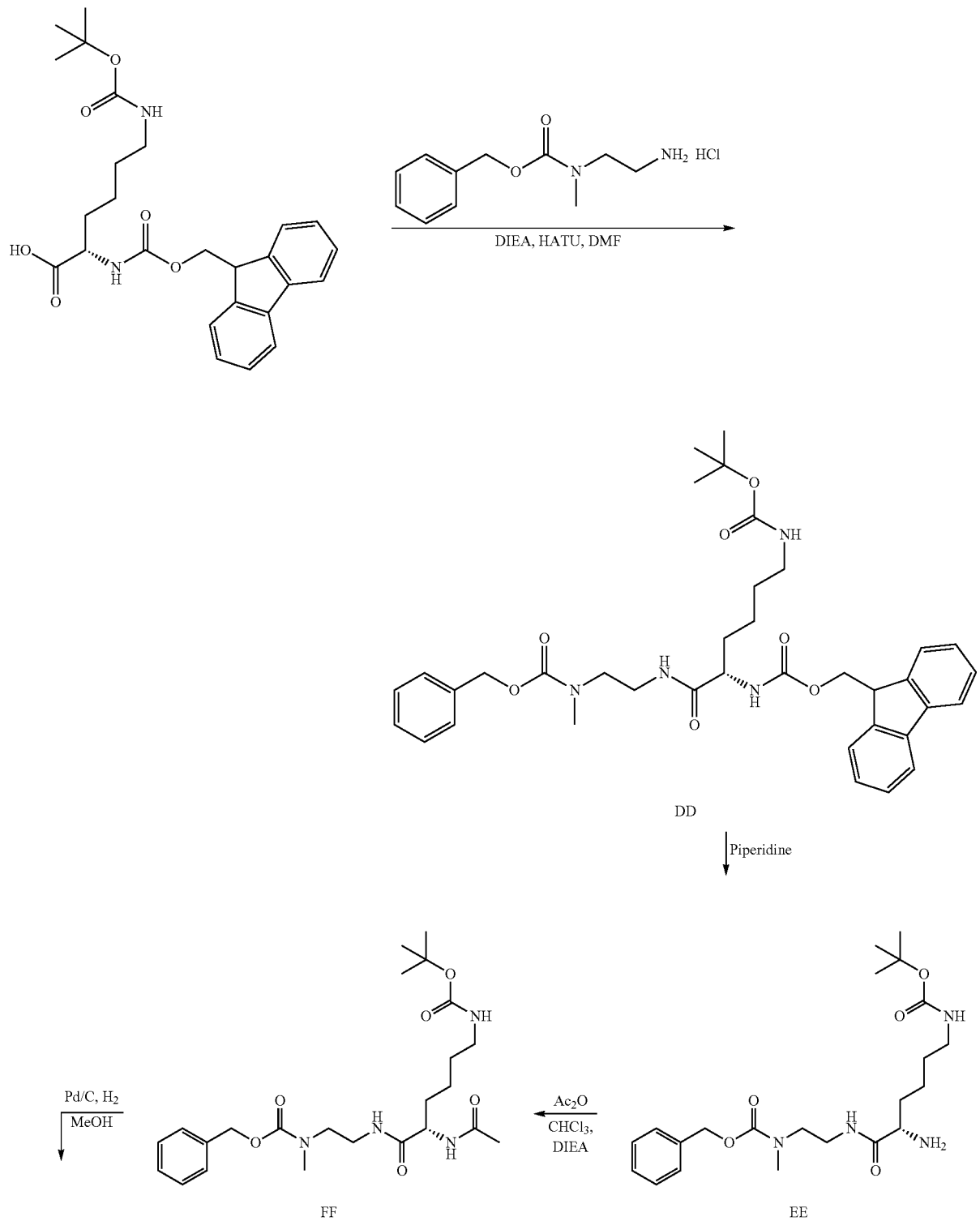

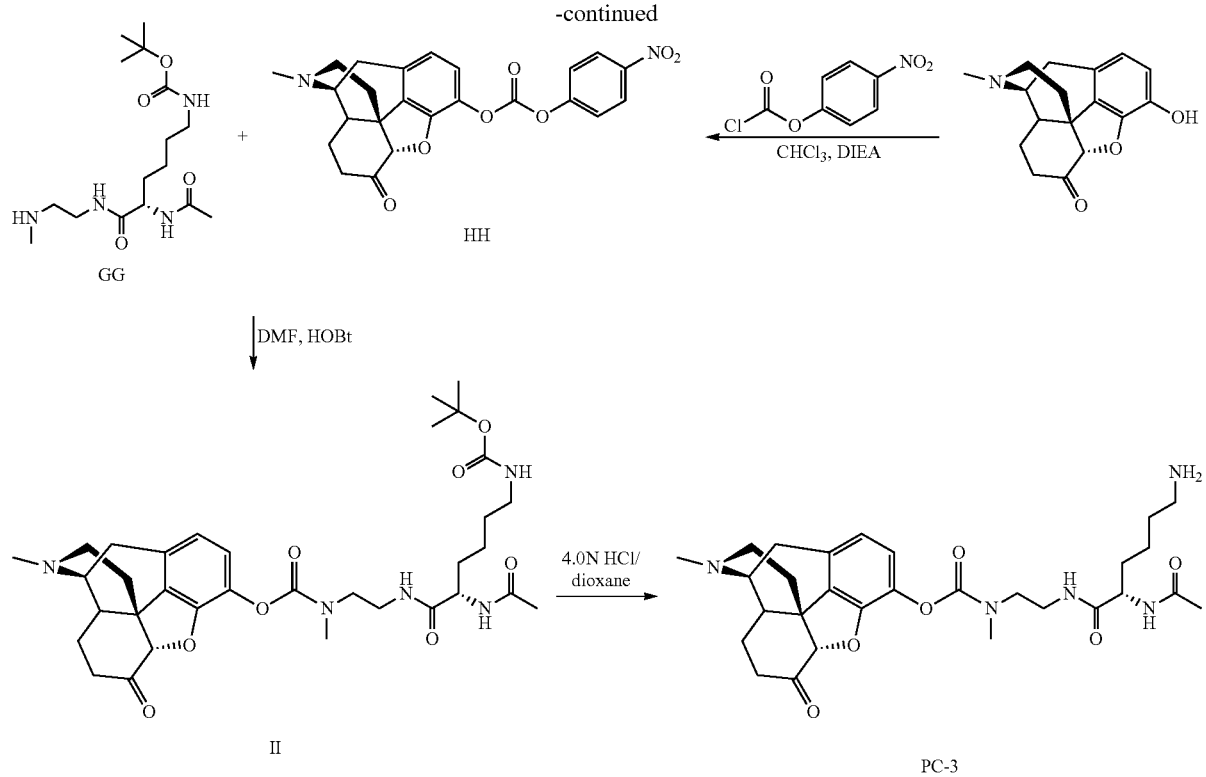

Preparation 27: Synthesis of {(S)-1-[2-(Benzyloxy-carbonyl-methyl-amino)-ethylcarbamoyl]-5-tert-butoxycarbonylamino-pentyl}-carbamic acid 9H-fluoren-9-ylmethyl ester (DD)

To a solution of Fmoc-Lys(Boc)-OH (2.0 g, 4.26 mmol) in DMF (50 mL) was added DIEA (2.38 mL, 13.65 mmol) and stirred for 15 min at room temperature. The reaction mixture was then cooled to ~5° C., followed by addition of HATU (1.95 g, 5.12 mmol) added in portions and stirred for 30 min. The CBZ-diamine (1.05 g, 4.26 mmol) was added to the reaction mixture and stirred at room temperature for 2 h. The reaction mixture was diluted with EtOAc (250 mL), washed with water (250 mL) and brine (250 mL). The organic layer was separated, dried over $Na_2SO_4$, and removal of the solvent in vacuo afforded compound DD (2.3 g, 82%). LC-MS [M+H] 659.6 ($C_{37}H_{46}N_4O_7$+H, calc: 659.7). Compound DD was used without further purification.

Preparation 28: Synthesis of {(S)-5-Amino-5-[2-(benzyloxycarbonyl-methyl-amino)-ethylcarbamoyl]-pentyl}-carbamic acid tert-butyl ester (EE)

To a solution of compound DD (2.3 g, 3.49 mmol) in EtOAC (50 mL) was added piperidine (0.34 mL, 3.49 mmol). The reaction mixture was stirred for 18 h at room temperature and then the solvents were removed in vacuo. The residue was dissolved in a minimum amount of EtOAc, and then was precipitated with $Et_2O$. Precipitate was filtered off and washed with $Et_2O$ and dried to afford compound EE (1.4 g, 94%). LC-MS [M+H] 437.6 ($C_{22}H_{36}N_4O_5$+H, calc: 437.5). Compound EE was used without further purification.

Preparation 29: Synthesis of {(S)-5-Acetylamino-5-[2-(benzyloxycarbonyl-methyl-amino)-ethyl carbamoyl]-pentyl}-carbamic acid isopropyl ester (FF)

To a solution of compound EE (1.4 g, 3.21 mmol) in $CHCl_3$ (10 mL) at room temperature was added DIEA (2.6 mL, 15 mmol) followed by $Ac_2O$ (0.85 mL, 9.0 mmol). The reaction mixture was stirred at room temperature for 2 h. Solvents were removed in vacuo and then the residue was dissolved in DCM (100 mL). The organic layer was washed with 10% citric acid (75 mL), saturated $NaHCO_3$ (75 mL) and brine (75 mL). The organic layer was separated, dried over $Na_2SO_4$ and solvent removed in vacuo to afford compound FF (1.45 g, 99%). LC-MS [M+H] 479.5 ($C_{24}H_{38}N_4O_6$+H, calc: 479.5). Compound FF was used without further purification.

Preparation 30: Synthesis of [(S)-5-Acetylamino-5-(2-methylamino-ethylcarbamoyl)-pentyl]-carbamic acid tert-butyl ester (GG)

To a solution of compound FF (1.4 g, 3.00 mmol) in MeOH (40 mL) was added 5% Pd/C (300 mg). This reaction mixture was subjected to hydrogenation at 70 psi for 2 h. Next, the reaction mixture was filtered through a celite pad, MeOH was removed in a rotary evaporator to afford compound GG (1.02 g, 98%). LC-MS [M+H] 344.9 ($C_{16}H_{32}N_4O_4$+H, calc: 345.4). Compound GG was used without further purification.

Preparation 31: [(S)-5-Acetylamino-5-(2-methylamino-ethylcarbamoyl)-pentyl]-carbamic acid tert-butyl-hydromorphone-di-ester (II)

Hydromorphone HCl salt (1.24 g, 3.86 mmol) and DIEA (0.67 mL, 3.86 mmol) were suspended in $CHCl_3$ (12 mL) and sonicated for 1 h at room temperature. 4-Nitro phenylchloroformate (600 mg, 2.97 mmol) was added to the reaction mixture and was then sonicated for 100 min. To the activated hydromorphone reaction mixture was added a solution of compound GG (1.02 g, 2.97 mmol) and HOBt (0.52 g, 3.86 mmol) in DMF (12 mL) dropwise and stirred at room temperature overnight (~18 h). Solvents were then removed in vacuo and the residue was dissolved in a minimum amount of MeOH and precipitated with an excess of $Et_2O$. The precipitate was filtered off, washed with $Et_2O$ and dried in vacuo to afford compound II. LC-MS [M+H] 656.9 ($C_{34}H_{49}N_5O_8$+H, calc: 656.7). This crude product was purified by preparative reverse phase HPLC. [Column: VARIAN, LOAD & LOCK, L&L 4002-2 packing: Microsorb 100-10 C18, Injection Volume: ~15 mL, Injection flow rate: 20 mL/min, 100% A, (water/0.1% TFA), Flow rate: 100 mL/min, Fraction: 30 Sec (50 mL) Method: 0% B (MeCN/0.1% TFA)/2 min/75% B/96 min/100 mL/min/254 nm]. Pure fractions were combined, solvents were removed in vacuo. Residue was dried via co-evaporation with i-PrOH (4×100 mL) to afford compound II as yellow oil (0.90 g, 46%).

Synthesis of (S)-2-Acetylamino-6-amino-hexanoic acid (2-methylamino-ethyl)-amide hydromorphone ester (Compound PC-3)

Compound II (0.90 g, 1.37 mmol) was suspended in dioxane (~2 mL), sonicated and treated with 4.0 N HCl/dioxane (~20 mL) at room temperature. White precipitate was formed immediately. Next the mixture was diluted with $Et_2O$ (200 mL), hexane (20 mL) and the precipitate was filtered off and washed with $Et_2O$ (100 mL), hexane (100 mL) and dried in vacuo to afford Compound PC-3 (0.67 g, 78% yield, 97.5% purity). LC-MS [M+H] 556.3 ($C_{29}H_{41}N_5O_6$+H, calc: 556.6).

Example 10

Synthesis of [2-((S)-2-Acetylamino-5-guanidino-pentanoylamino)-ethyl]-ethyl-carbamic acid hydromorphone ester (Compound PC-4)

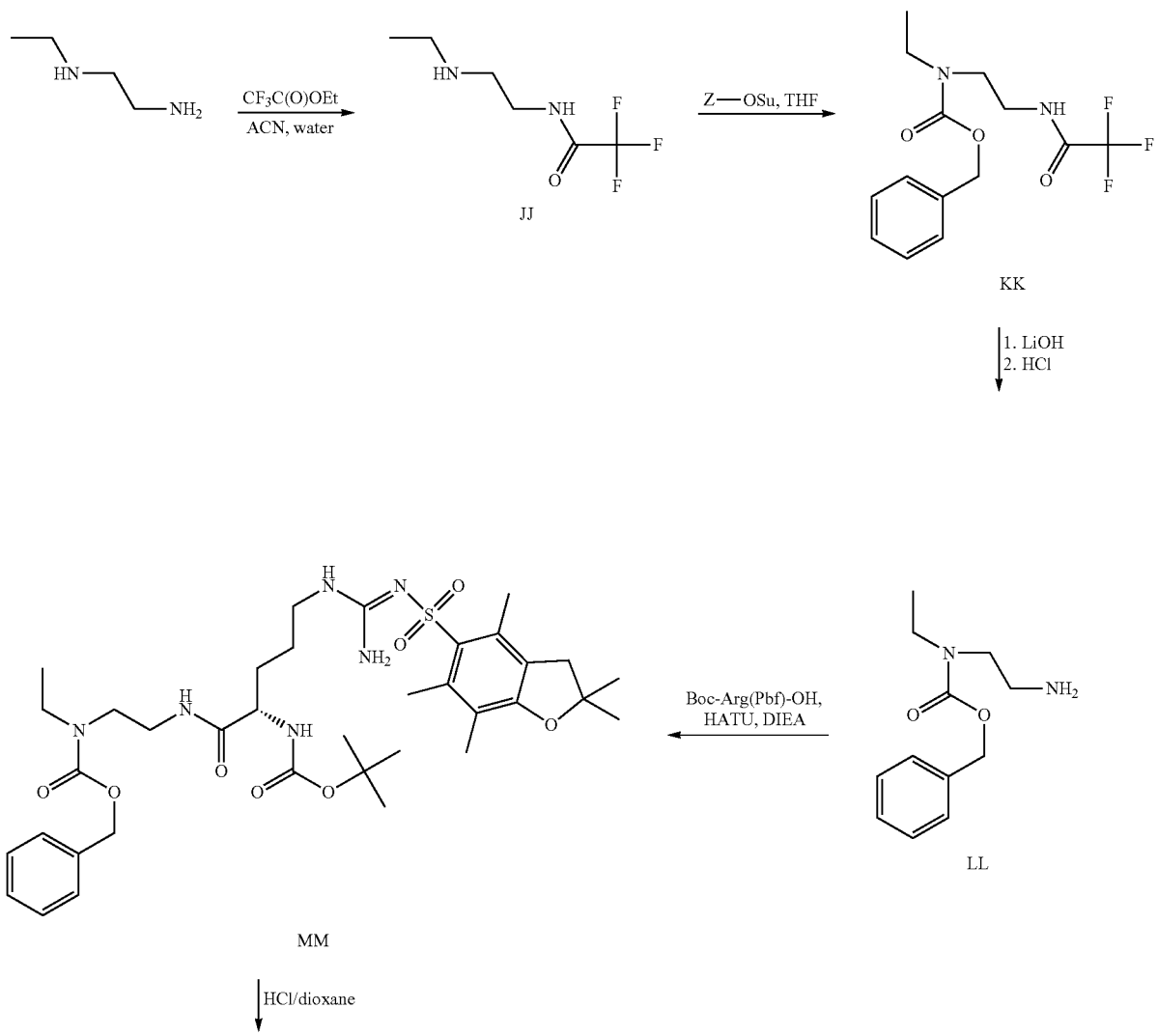

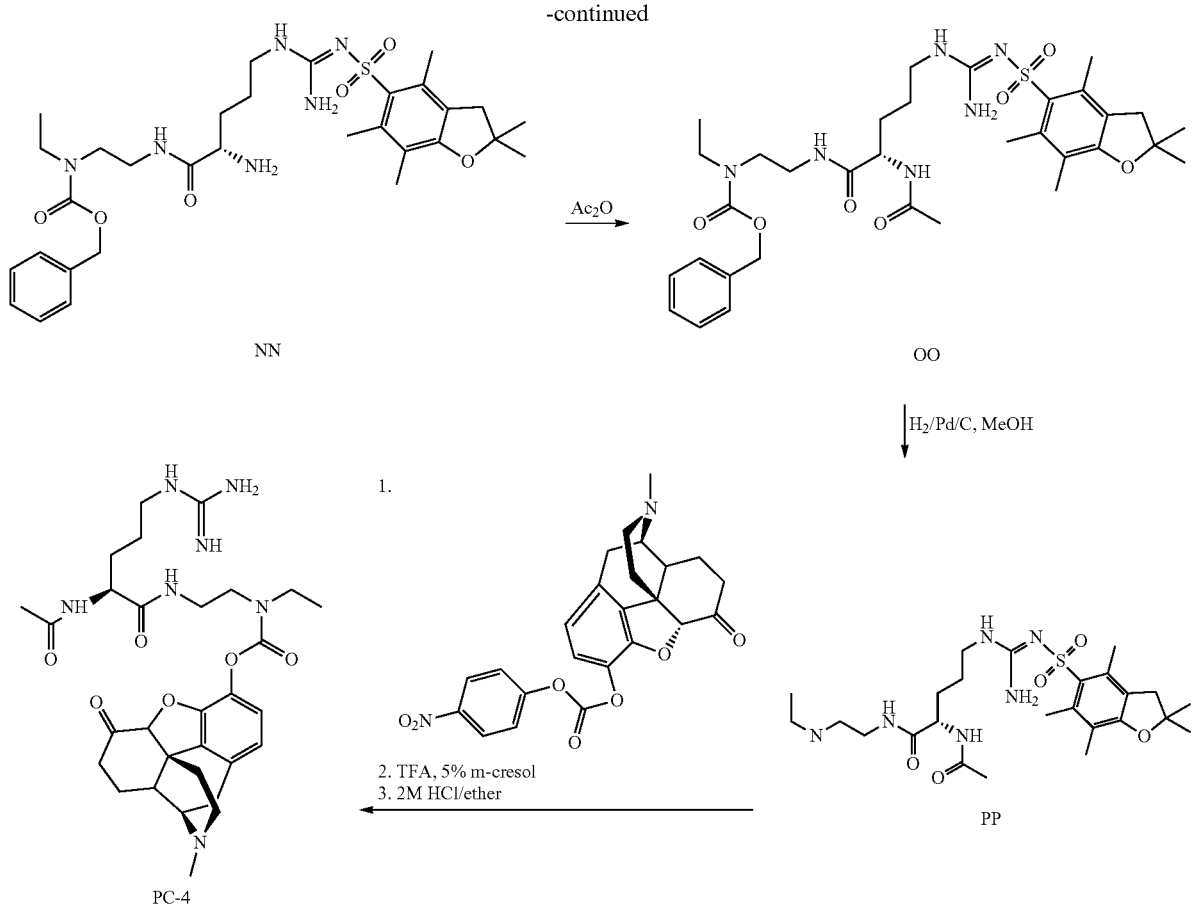

Preparation 32: Synthesis of 2,2,2-trifluoro-N-(2-ethylamino-ethyl)-acetamide (JJ)

A solution of N-ethylethylenediamine (10.0 g, 113.4 mmol) and ethyl trifluoroacetate (32.0 mL, 261 mmol) in the mixture of acetonitrile (110 mL) and water (2.5 mL, 139 mmol) was refluxed with stirring overnight (~18 h). Solvents were evaporated in vacuo. Residue was re-evaporated with i-PrOH (3×100 mL). Residue was dissolved in dichloromethane (500 mL) and left overnight at room temperature. The formed crystals were filtered, washed with dichloromethane (100 mL) and dried in vacuo to provide compound JJ (24.6 g, 82.4 mmol) as white solid powder.

Preparation 33: Synthesis of {ethyl-[2-(2,2,2-trifluoro-acetylamino)-ethyl]-carbamic acid benzyl ester (KK)

A solution of compound JJ (24.6 g, 82.4 mmol) and DIEA (14.3 mL, 82.4 mmol) in THF (100 mL) was cooled to ~5° C., followed by the addition of a solution of N-(benzyloxycarbonyl)succinimide (20.3 g, 81.6 mmol) in THF (75 mL) dropwise over 20 min. The temperature of the reaction mixture was raised to room temperature and stirring was continued for an additional 30 min. Solvents were evaporated and the residue was dissolved in EtOAc (500 mL). The organic layer was extracted with 5% aqueous $NaHCO_3$ (2×100 mL) and brine (100 mL). The organic layer was evaporated to provide compound KK (24.9 g, 78.2 mmol) as yellowish oil. LC-MS [M+H] 319.0 ($C_{14}H_{17}F_3N_2O_3$+H, calc: 319.2). Compound KK was used without further purification.

Preparation 34: Synthesis of (2-Amino-ethyl)-ethyl-carbamic acid benzyl ester (LL)

To a solution of compound KK (24.9 g, 78.2 mmol) in MeOH (300 mL) was added a solution of LiOH (3.8 g, 156 mmol) in water (30 mL). The reaction mixture was stirred at room temperature for 5 h. Next the solvents were evaporated to ¾ of initial volume followed by the dilution with water (200 mL). The solution was extracted with EtOAc (200 mL×2) and the organic layer was washed with brine (100 mL), dried over $MgSO_4$ and evaporated in vacuo. Residue was dissolved in ether (200 mL) and treated with 2 N HCl/ether (200 mL). The formed precipitate was filtered, washed with ether and dried in vacuo to provide hydrochloride salt of compound LL (12.1 g, 46.7 mmol) as white solid. LC-MS [M+H] 222.9 ($C_{12}H_{18}N_2O_2$+H, calc: 223.2).

Preparation 35: Synthesis of {2-[boc-Arg(Pbf)]-aminoethyl}-ethyl-carbamic acid benzyl ester (MM)

A solution of Boc-Arg(Pbf)-OH (3.0 g, 5.69 mmol), compound LL (1.62 g, 6.26 mmol), DIEA (3.17 mL, 18.21 mmol) and HATU (2.59 g, 6.83 mmol) in DMF (20 mL) was stirred at room temperature for 1 h. The reaction mixture was diluted with EtOAc (300 mL) and extracted with water (3×75 mL) and brine (75 mL). The organic layer was dried over $MgSO_4$, filtered and then evaporated to provide compound MM (5.97 g, yield exceeded quantitative) as yellowish oil. LC-MS [M+H] 731.5 ($C_{36}H_{54}N_6O_8S$+H, calc: 731.7). Compound MM was used without further purification.

Preparation 36: Synthesis of {2-[H-Arg(Pbf)]-aminoethyl}-ethyl-carbamic acid benzyl ester (NN)

Compound MM (5.69 mmol) was dissolved in dioxane (20 mL) and treated with 4 N HCl/dioxane (100 mL, 70 mmol) at room temperature for 1 h. The solvent was then removed in vacuo, followed by suspension in i-PrOH (50 mL) and finally, the solvent was evaporated to remove residual solvents (procedure was repeated twice). The crude reaction mixture was dried in vacuo to provide compound NN (5.97, yield exceeded quantitative) as yellowish solid. LC-MS [M+H] 631.5 ($C_{31}H_{46}N_6O_6S$+H, calc: 631.2). Compound NN was used without further purification.

Preparation 37: Synthesis of {2-[Ac-Arg(Pbf)]-aminoethyl}-ethyl-carbamic acid benzyl ester (OO)

A solution of compound NN (5.69 mmol), $Ac_2O$ (649 μl, 6.83 mmol) and DIEA (2.97 mL, 17.07 mmol) in chloroform (20 mL) was stirred at room temperature for 1 h. This was followed by addition of 2M $EtNH_2$/THF (1.71 mL, 3.41 mmol). The reaction mixture was stirred at room temperature for an additional 30 min, followed by the dilution with EtOAc (300 mL). The organic layer was extracted with water (75 mL), 2% aq. $H_2SO_4$ (75 mL), water (3×75 mL) and brine (75 mL). The organic layer was then dried over $MgSO_4$ and evaporated to provide compound OO (3.99 g, yield exceeded quantitative) as yellowish solid. LC-MS [M+H] 673.6 ($C_{33}H_{48}N_6O_7S$+H, calc: 672.9). Compound OO was used without further purification.

Preparation 38: Synthesis of N—[Ac-Arg(Pbf)]-N'-ethyl-ethane-1,2-diamine (PP)

Compound OO (5.69 mmol) was dissolved in methanol (50 mL) followed by addition of Pd/C (5% wt, 1 g) suspension in water (5 mL). Reaction mixture was subjected to hydrogenation (Parr apparatus, 80 psi) at room temperature for 1 h. Upon completion, the catalyst was filtered over pad of Celite on sintered glass funnel and washed with methanol. The filtrate was evaporated in vacuo to provide the compound PP (3.06 g, quantitative yield) as colorless oil. LC-MS [M+H] 539.5 ($C_{25}H_{42}N_6O_5S$+H, calc: 539.9). Compound PP was used without further purification.

Synthesis of [2-(2-Acetylamino-5-guanidino-pentanoylamino)-ethyl]-ethyl-carbamic acid hydromorphone ester (Compound PC-4)

A suspension of hydromorphone hydrochloride (2.75 g, 8.54 mmol) and DIEA (1.49 mL, 8.54 mmol) in chloroform (8 mL) was sonicated in an ultrasonic bath at room temperature for 1 h, followed by addition of 4-nitrophenyl chloroformate (1.38 g, 6.83 mmol). The reaction mixture was sonicated in an ultrasonic bath at room temperature for additional 1 h, followed by the addition of solution of compound PP (3.06 g, 5.69 mmol) and 1-hydroxybenzotriazole (1.31 g, 9.67 mmol) in DMF (8 mL). The reaction mixture was stirred overnight (~18 h) at room temperature, followed by solvents being evaporated in vacuo. The crude reaction mixture was dissolved in MeOH (10 mL) and precipitated with ether (500 mL). The formed precipitate was filtered and dried in vacuo to provide Pbf protected compound PC-4 (6.96 g yield exceeded quantitative) as off-white solid. LC-MS [M+H] 850.6 ($C_{43}H_{59}N_7O_9S$+H, calc: 850.2).

Pbf protected compound PC-4 was dissolved in a mixture of 5% m-cresol/TFA (100 mL). The reaction mixture was maintained at room temperature for 1 h, followed by dilution with ether (2 L). A precipitate was formed and subsequently filtered over sintered glass funnel, washed with ether (200 mL) and dried in vacuo to provide crude compound PC-4 (5.2 g, 97%) as off-white solid. Crude compound PC-4 (5.2 g, 5.54 mmol) was dissolved in water (50 mL) and subjected to HPLC purification. [Nanosyn-Pack Microsorb (100-10) C-18 column (50×300 mm); flow rate: 100 mL/min; injection volume 50 mL; mobile phase A: 100% water, 0.1% TFA; mobile phase B: 100% acetonitrile, 0.1% TFA; isocratic elution at 0% B in 5 min., gradient elution to 6% B in 6 min, isocratic elution at 6% B in 13 min, gradient elution from 6% B to 55% B in 76 min; detection at 254 nm]. Fractions containing the desired compound were combined and concentrated in vacuo. The residue was dissolved in i-PrOH (50 mL) and evaporated in vacuo (procedure was repeated twice). The residue was dissolved in i-PrOH (50 mL) and treated with 2 N HCl/ether (200 mL, 400 mmol) to provide hydrochloride salt of Compound PC-4 (1.26 g, 32% yield, 95.7% purity) as white solid. LC-MS [M+H] 598.4 ($C_{30}H_{43}N_7O_6$+H, calc: 598.7). Retention time*: 2.53 min

*—[Chromolith SpeedRod RP-18e C18 column (4.6×50 mm); flow rate 1.5 mL/min; mobile phase A: 0.1% TFA/water; mobile phase B 0.1% TFA/ACN; gradient elution from 5% B to 100% B over 9.6 min, detection 254 nm]

Example 11

Synthesis of [2-((S)-2-malonylamino-4-amino-pentanoyl amino)-ethyl]-ethyl-carbamic acid hydromorphone ester (Compound PC-5)

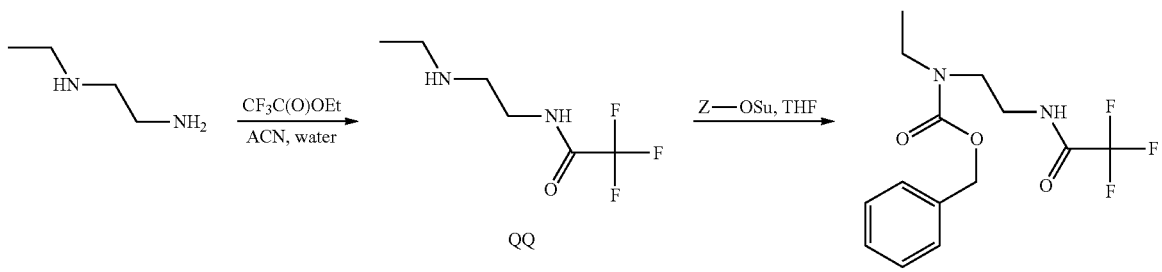

209
210
-continued
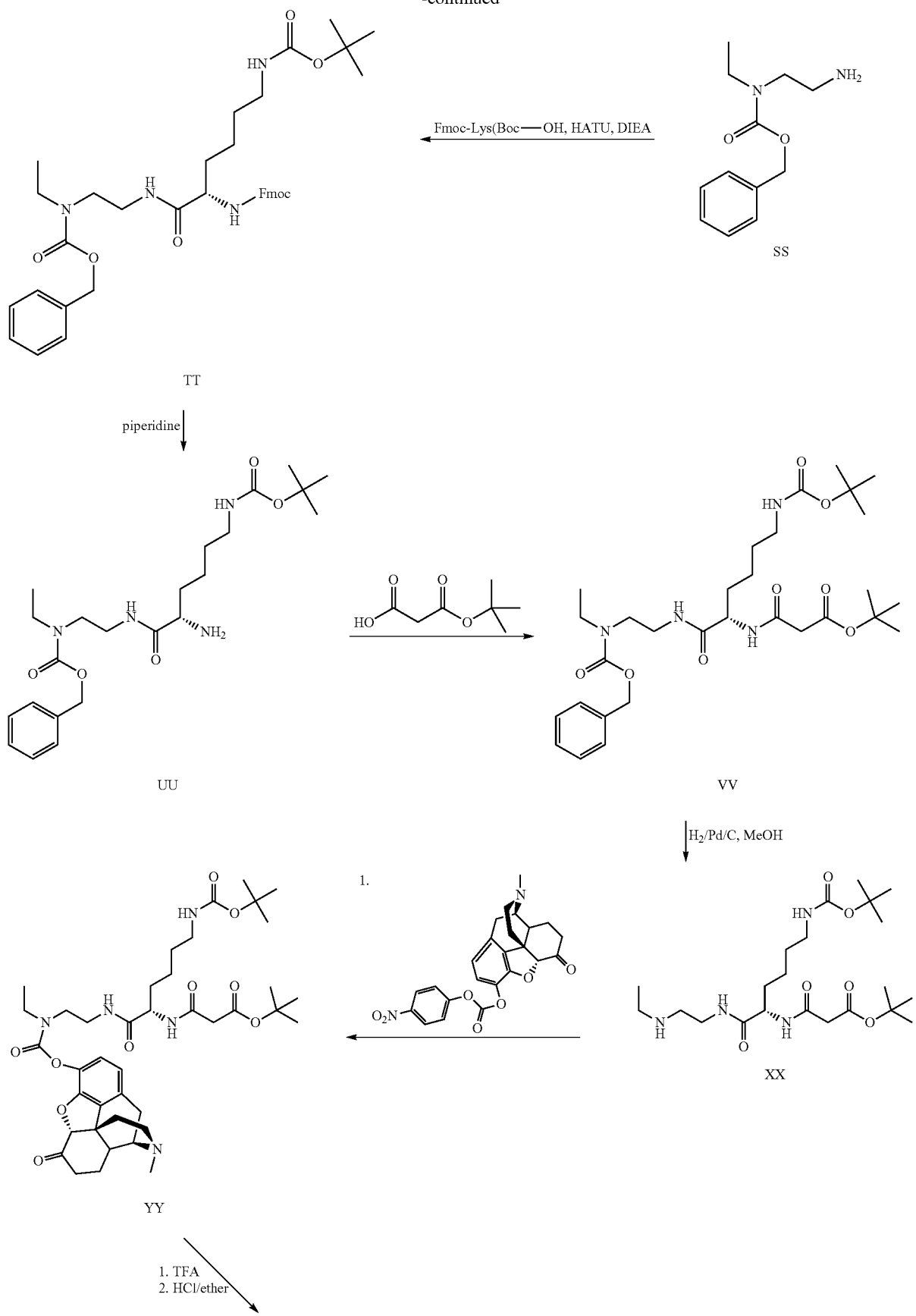

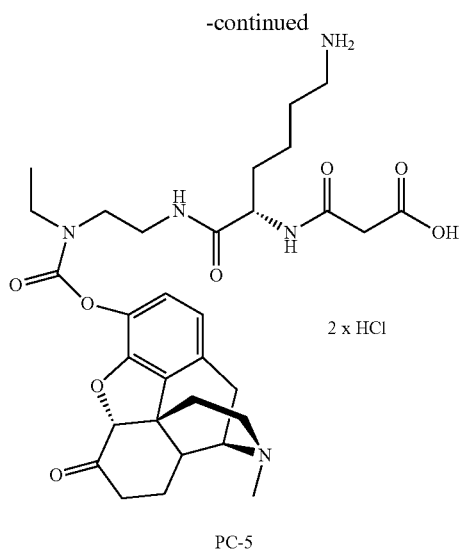

PC-5

Preparation 39: Synthesis of 2,2,2-trifluoro-N-(2-ethylamino-ethyl)-acetamide (QQ)

A solution of N-ethylethylenediamine (10.0 g, 113.4 mmol) and ethyl trifluoroacetate (32.0 mL, 261 mmol) in a mixture of acetonitrile (110 mL) and water (2.5 mL, 139 mmol) was refluxed with stirring overnight (~18 hours (hr, h)). Solvents were evaporated in vacuo. Residue was re-evaporated with isopropanol (3×100 mL). Residue was dissolved in dichloromethane (500 mL) and left overnight at room temperature (rt). The formed crystals were filtered, washed with dichloromethane (100 mL) and dried in vacuo to provide compound QQ (24.6 g, 82.4 mmol) as a white solid powder.

Preparation 40: Synthesis of ethyl-[2-(2,2,2-trifluoro-acetylamino)-ethyl]carbamic acid benzyl ester (RR)

A solution of compound QQ (24.6 g, 82.4 mmol) and DIEA (14.3 mL, 82.4 mmol) in THF (100 mL) was cooled to ~5° C., followed by the addition a solution of N-(benzyloxy-carbonyl)succinimide (20.3 g, 81.6 mmol) in THF (75 mL) dropwise over 20 min. The temperature of the reaction mixture was raised to room temperature and stirring was continued for an additional 30 minutes (min). Solvents were evaporated and the residue was dissolved in ethyl acetate (500 mL). The organic layer was extracted with 5% aq. NaHCO$_3$ (2×100 mL) and brine (100 mL). The organic layer was evaporated to provide compound RR (24.9 g, 78.2 mmol) as a yellowish oil. LC-MS [M+H] 319.0 (C$_{14}$H$_{17}$F$_3$N$_2$O$_3$+H, calc: 319.2). Compound RR was used without further purification.

Preparation 41: Synthesis of (2-Amino-ethyl)-ethyl-carbamic acid benzyl ester (SS)

To a solution of compound RR (24.9 g, 78.2 mmol) in methanol (300 mL) was added a solution of LiOH (3.8 g, 156 mmol) in water (30 mL). The reaction mixture was stirred at room temperature for 5 h. Next the solvents were evaporated to 75% of initial volume followed by dilution with water (200 mL). The solution was extracted with ethyl acetate (200 mL×2) and the organic layer was washed with brine (100 mL), dried over MgSO$_4$ and evaporated in vacuo. Residue was dissolved in ether (200 mL) and treated with 2 N HCl/ether (200 mL). The formed precipitate was filtered, washed with ether and dried in vacuo to provide the hydrochloric salt of compound SS (12.1 g, 46.7 mmol) as a white solid. LC-MS [M+H] 222.9 (C$_{12}$H$_{18}$N$_2$O$_2$+H, calc: 223.2). Purity >95% (UV/254 nm).

Preparation 42: Synthesis of {2-[Fmoc-Lys(Boc)]-aminoethyl}-ethyl-carbamic acid benzyl ester (TT)

To a solution of Fmoc-Lys(Boc)-OH (25.02 g, 53.4 mmol, 1 eq), compound SS (13.82 g, 53.4 mmol, 1 eq) and HATU (22.3 g, 58.7 mmol, 1.1 eq) in DMF (300 mL) was added a solution of DIEA (28 mL, 160.2 mmol, 3.0 eq), cooled with an ice/water bath and stirring for 30 min. The reaction mixture was stirred at ambient temperature for 2 h. Upon completion, the reaction mixture was diluted with EtOAc (1 L) and extracted with water (2×2.5 L) and brine (500 mL). The organic layer was dried over anhydrous Na$_2$SO$_4$, filtered and then evaporated to give an oily residue, which was dried overnight in vacuo (120 mbar) to give compound TT (39.5 g) as a yellow-brown viscous solid. LC-MS [M+H] 672.5 (C$_{38}$H$_{48}$N$_4$O$_7$+H, calc: 672.7). Purity >95% (UV/254 nm). Compound TT was used without purification.

Preparation 43: Synthesis of {2-[H-Lys(Boc)]-aminoethyl}-ethyl-carbamic acid benzyl ester (UU)

Compound TT (18.5 g, 25 mmol, 1 eq) and piperidine (3.1 mL, 31 mmol, 1.2 eq) was dissolved in ethyl acetate (125 mL), using sonication and stirring to assist in dissolving all components. The reaction mixture was stirred at ambient temperature for 5 h, monitoring the reaction progress by LC/MS. Upon completion, the solvent was then removed in vacuo to ~15 mL, then the product was triturated with hexane (250 mL) to give an oily residue. Hexane was decanted and the residue was washed further with hexane (100 mL). The product was dried overnight in vacuo to provide compound UU (13.5 g) as a yellowish solid. LC-MS [M+H] 451.3 ($C_{23}H_{438}N_4O_5$+H, calc: 451.3). Purity >95% (UV/254 nm). Compound UU was used without purification.

Preparation 44: Synthesis of {2-[t-Boc-malonyl-Lys(Boc)]-aminoethyl}-ethyl-carbamic acid benzyl ester (VV)

Compound UU (12.5 g, 25.0 mmol, 1 eq), DIEA (10.9 mL, 27.5 mmol, 2.5 eq) and BOP (12.2 g, 27.5 mmol, 1.1 eq) were dissolved in DMF (20 mL), and a solution of mono-t-butyl-malonate (4.5 g, 27.5 mmol, 1.1 eq) in DMF (20 mL) was added to the reaction mixture with cooling with an ice/water bath and stirring over 30 min. The reaction was complete in 2 h, and the solvent was removed in vacuo. The residue was dissolved in ethyl acetate (700 mL) and washed with water (1.2 L) and then brine (500 mL). The organic layer was separated, and the aqueous phase was reextracted with ethyl acetate (400 mL). The combined organic phase was dried over anhydrous $Na_2SO_4$, and solvent was evaporated in vacuo to give an oily residue. The product was dried overnight in vacuo to give compound VV (19.2 g) as a pale yellow oil. LC-MS [M+H] 593.7 ($C_{30}H_{48}N_4O_8$+H, calc: 593.4). Compound VV was used without purification. Purity >95% (UV/254 nm).

Preparation 45: Synthesis of N—[t-Boc-malonyl-Lys(Boc)] N'-ethyl-ethane-1,2-diamine (XX)

Compound VV (19.2 g, 25 mmol) was suspended in methanol (500 mL) and filtered off from inorganic salts. A Pd/C (5% wt, 2.4 g) suspension in water (10 mL) was added, and the reaction mixture was hydrogenated (Parr apparatus, 80 psi) at ambient temperature for 2 h. Upon reaction completion, the catalyst was filtered through a pad of Celite® on sintered glass frit and washed with methanol (2×50 mL). The filtrate was evaporated in vacuo to give an oily residue. The product was dried overnight in vacuo to give compound XX (17.3 g) as a pale yellow oil. LC-MS [M+H] 459.4 ($C_{22}H_{42}N_4O_6$+H, calc: 459.3). Compound XX was used without purification. Purity >95% (UV/254 nm).

Preparation 46: Synthesis of [t-Boc-malonyl-Lys(Boc)]-ethyl-carbamic acid hydromorphone ester (YY)

A suspension of hydromorphone hydrochloride (10.5 g, 32.5 mmol, 1.3 eq) and DIPEA (5.7 mL, 32.5 mmol) in chloroform (70 mL) was sonicated in an ultrasonic bath at ambient temperature for 1 h, followed by addition of 4-nitrophenyl chloroformate (5.05 g, 25 mmol, 1 eq). The reaction mixture was sonicated in an ultrasonic bath at ambient temperature for additional 1 h, followed by the addition of a solution of compound XX (17.3 g, 25 mmol, 1 eq) and 1-hydroxybenzotriazole (5.06 g, 37.5 mmol, 1.5 eq) in DMF (50 mL). The reaction mixture was stirred overnight (~18 h) at ambient temperature. Next, the reaction mixture was filtered through a glass frit and the solvents were evaporated in vacuo. The crude reaction mixture was dissolved in methanol (50 mL) and precipitated with ether (500 mL) to give an oily yellow residue. It was re-precipitated from methanol/ether (50 mL/500 mL) to form a viscous product, which was dried in vacuo overnight to provide crude compound YY (18.8 g, 98% yield) as a foaming pale yellow solid. LC-MS [M+H-Boc] 670.1 ($C_{40}H_{59}N_5O_{10}$+H-boc, calc: 670.2). Purity ~50% (UV/254 nm).

Crude product YY (5.2 g, 5.54 mmol) was dissolved in a mixture DMSO/AcOH (10 mL/40 mL) and diluted with water (50 mL). The solution was subjected to HPLC purification: Nanosyn-Pack Microsorb (100-10) C-18 column (50× 300 mm); flow rate: 100 mL/min; injection volume 50 mL; mobile phase A: 100% water, 0.1% TFA; mobile phase B: 100% ACN, 0.1% TFA; isocratic elution at 10% B in 4 min, gradient elution from 10% to 28% B in 27 min, isocratic elution at 28% B in 30 min, gradient elution from 28% B to 42% B in 29 min; detection at 254 nm. Fractions containing the desired compound were combined and concentrated in vacuo. The residue was dissolved in isopropanol (100 mL) and co-evaporated in vacuo (procedure repeated twice). The resulting solid was dried in vacuo overnight to provide compound YY (10.2 g, 48% yield) as a foaming white solid. LC-MS [M+H-Boc] 670.1 ($C_{40}H_{59}N_5O_{10}$+H-boc, calc: 670.2). Purity >95% (UV/254 nm).

Synthesis of [2-((S)-2-malonylamino-4-amino-pentanoyl amino)-ethyl]ethyl-carbamic acid hydromorphone ester (Compound PC-5)

Compound YY (10.2 g, 11.5 mmol) was dissolved in DCM (20 mL) and treated with TFA (50 mL). The reaction mixture was stirred at ambient temperature for 1 h, monitoring the reaction progress by LC/MS. Upon reaction completion, the solvent was evaporated in vacuo to afford a pale yellow oil. It was dissolved in isopropanol (20 mL) and treated with 2 N HCl/ether (100 mL, 200 mmol) to give immediately a thick white precipitate. It was diluted with ether (500 mL) and filtered off. The solid was washed with ether (2×50 mL) and hexane (2×50 mL). The solid was dried in vacuo to yield Compound PC-5: (6.8 g, 86.1% yield, 96.8% purity) by 254 nm/UV) as a white solid. LC-MS [M+H] 614.2 ($C_{31}H_{43}N_5O_8$+H, calc: 614.3). Retention time*: 1.93 min *—[Chromolith SpeedRod RP-18e C18 column (4.6×50 mm); flow rate 1.5 mL/min; mobile phase A: 0.1% TFA/water; mobile phase B 0.1% TFA/ACN; gradient elution from 5% B to 100% B over 9.6 min, detection 254 nm]

Example 12
Synthesis of [2-(2-Malonyl-5-guanidino-pentanoylamino)-ethyl]-ethyl-carbamic acid hydromorphone ester (Compound PC-6)
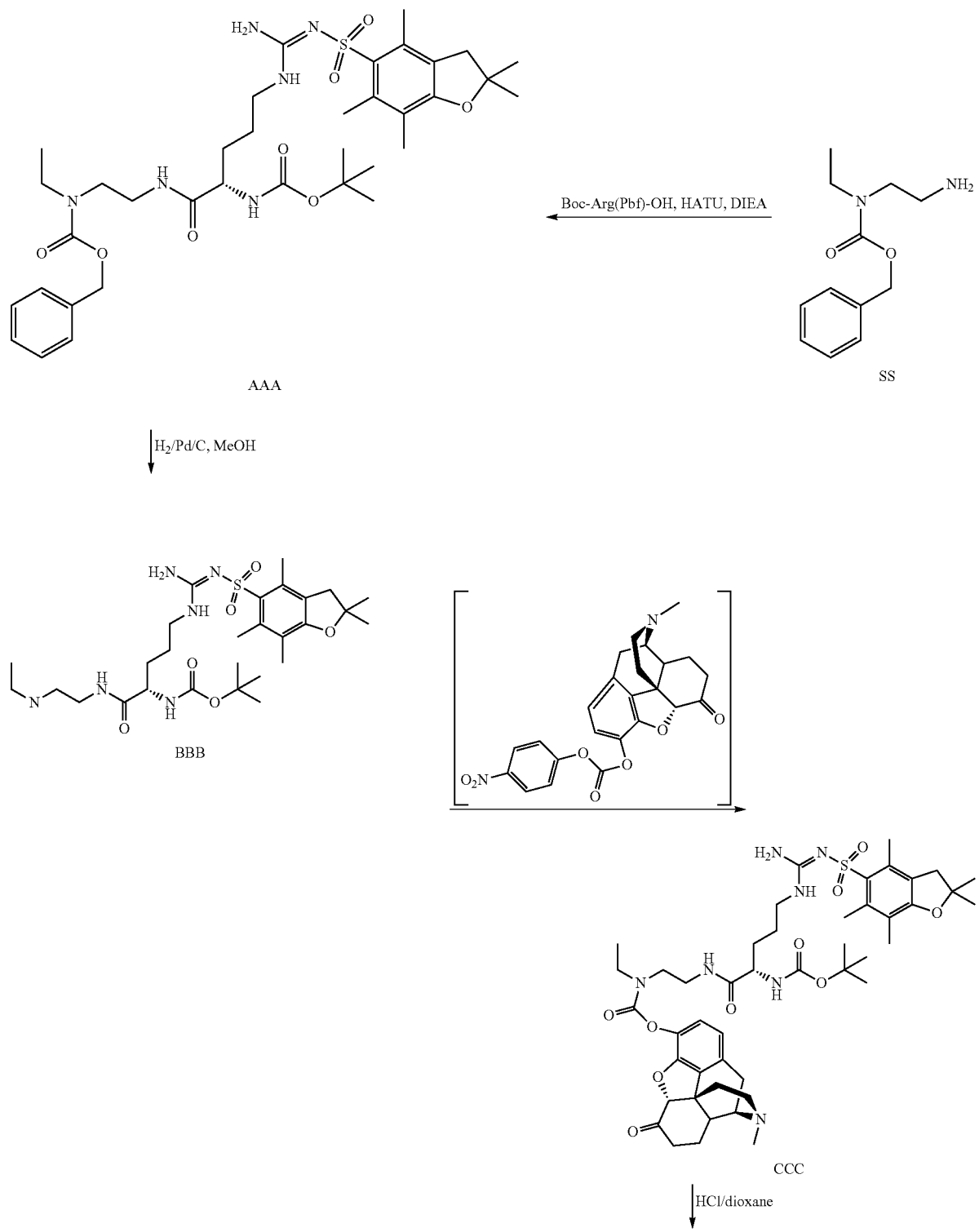

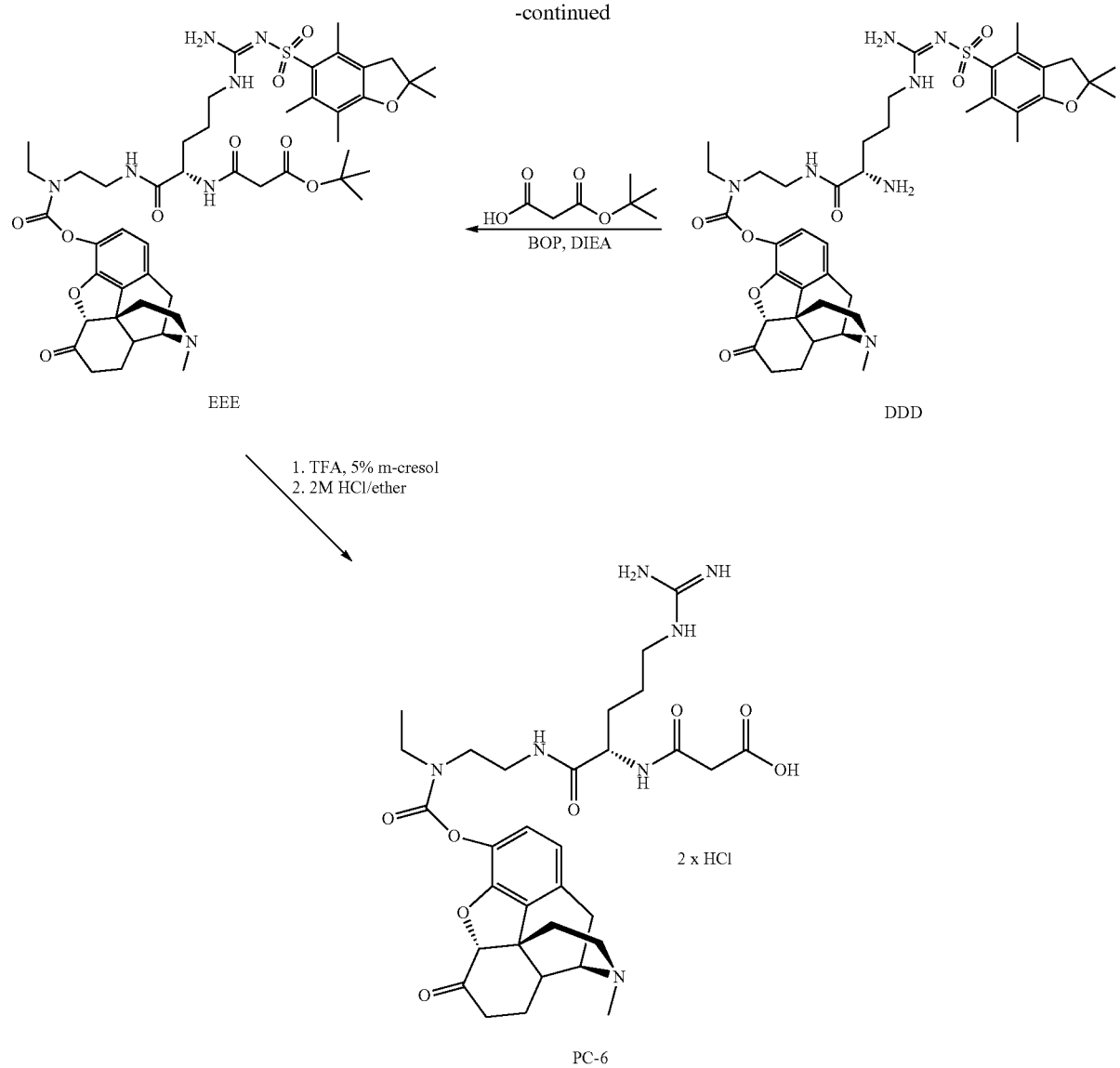

Preparation 47: Synthesis of {2-[Boc-Arg(Pbf)]-aminoethyl}-ethyl-carbamic acid benzyl ester (AAA)

To a solution of Boc-Arg(Pbf)-OH (10.0 g, 18.98 mmol) and DIPEA (10.6 mL, 60.74 mmol) in DMF (100 mL) was added HATU (7.21 g, 18.98 mmol); the mixture was stirred at 5° C. for 15 min. To this reaction mixture, compound SS (5.40 g, 24.32 mmol), produced as described herein (Preparation 41) was added and stirred at ambient temperature for 2 h. Next, the reaction mixture was diluted with ethyl acetate (750 mL) and extracted with water (2×500 mL) and brine (500 mL). The organic layer was dried over anhydrous $Na_2SO_4$, filtered and then evaporated to give an oily residue, which was dried overnight in vacuo to give compound AAA (20.0 g) as an off-white solid. LC-MS [M+H] 731.9 ($C_{36}H_{54}N_6O_8S$+H, calc: 731.3). Purity >95% (UV/254 nm). Compound AAA was used without purification.

Preparation 48: Synthesis of N-[Boc-Arg(Pbf)]-N'-ethyl-ethane-1,2-diamine (BBB)

Compound AAA (20.0 g, 18.98 mmol) was dissolved in methanol (250 mL) followed by addition of Pd/C (5% wt, 2.0 g) suspension in water (5 mL). The reaction mixture was subjected to hydrogenation (Parr apparatus, 70 psi) at ambient temperature for 1.5 h. Upon completion, the catalyst was filtered over a pad of Celite® on sintered glass funnel and washed with methanol. The filtrate was evaporated in vacuo to provide compound BBB (11.53 g, quantitative yield) as a foamy solid. LC-MS [M+H] 597.6 ($C_{28}H_{48}N_6O_6S$+H, calc: 597.3). Compound BBB was used without purification.

Preparation 49: Synthesis of [N-Boc-Arg(Pbf)]-ethyl-carbamic acid hydromorphone ester (CCC)

A suspension of hydromorphone hydrochloride (7.94 g, 24.67 mmol, 1.3 eq) and DIPEA (4.29 mL, 24.67 mmol) in chloroform (30 mL) was sonicated in an ultrasonic bath at ambient temperature for 1 h, followed by addition of 4-nitrophenyl chloroformate (4.21 g, 20.88 mmol, 1.1 eq). The reaction mixture was sonicated at ambient temperature for an additional 1 h, followed by the addition of a solution of compound BBB (11.53 g, 18.98 mmol, 1 eq) and 1-hydroxybenzotriazole (3.33 g, 24.67 mmol, 1.3 eq) in DMF (50 mL). The reaction mixture was stirred overnight at ambient temperature. Next, the reaction mixture was filtered through a glass frit and the solvents were evaporated in vacuo. The crude reaction mixture was dissolved in methanol (50 mL) and precipitated with ether (500 mL). Precipitate was filtered off, washed with ether and dried in vacuo overnight to provide crude compound CCC (23.0 g) as a pale yellow solid. LC-MS [M+H] 908.8 ($C_{46}H_{65}N_7O_{10}S$+H, calc: 908.45). Purity ~60% (UV/254 nm). Compound CCC was used without purification.

Preparation 50: Synthesis of {2-[H-Arg(Pbf)]-aminoethyl}-ethyl-carbamic acid hydromorphone ester (DDD)

Compound CCC (23.0 g, 20.88 mmol) was dissolved in dioxane (75 mL) and treated with 4 N HCl/dioxane (45.0 mL, 180 mmol) at ambient temperature for 1 h. The solvent was then removed in vacuo to ~50 mL, followed by precipitation with ether (~500 mL). Precipitate was filtered off, washed with ether and dried in vacuo overnight to provide crude compound DDD (22.6 g) as a pale yellow solid. LC-MS [M+H] 808.8 ($C_{41}H_{57}N_7O_8S$+H, calc: 808.4). Purity ~60% (UV/254 nm).

Crude product DDD (22.6 g) was dissolved in water (70 mL). The solution was subjected to HPLC purification: Nano-syn-Pack Microsorb (100-10) C-18 column (50×300 mm); flow rate: 100 mL/min; injection volume 15 mL; mobile phase A: 100% water, 0.1% TFA; mobile phase B: 100% ACN, 0.1% TFA; isocratic elution at 0% B in 5 min, gradient elution from 0% to 30% B in 30 min, isocratic elution at 30% B in 20 min, gradient elution from 30% B to 50% B in 40 min; detection at 254 nm. Fractions containing the desired compound were combined and concentrated in vacuo. The residue was dissolved in isopropanol (100 mL) and co-evaporated in vacuo (procedure repeated twice). The residue was dissolved in ~25 mL isopropanol, 2.0 M HCl in ether (100 mL) was added. The resulting solid was filtered, washed with ether (2×100 mL) and dried in vacuo overnight to provide compound DDD (10.0 g, 60% yield) as a white solid. LC-MS [M+H] 808.8 ($C_{41}H_{57}N_7O_8S$+H, calc: 808.4). Purity >95% (UV/254 nm).

Preparation 51: Synthesis of [2-(2-tert-Butyl-malonyl-Arg(Pbf)]-aminoethyl]-ethyl-carbamic acid hydromorphone ester (EEE)

To a solution of mono-tert-butyl malonate (182 mg, 1.13 mmol) and DIEA (0.592 mL, 3.40 mmol) in DMF (20 mL) was added BOP (502 mg, 1.13 mmol); the mixture was stirred at 5° C. for 15 min. To this reaction mixture, compound DDD (1 g, 1.13 mmol) was added and stirred at ambient temperature for 3 h. Upon completion, solvent was then removed in vacuo to ~5 mL, followed by precipitation with ether (150 mL). The precipitate was filtered off, washed with ether and dried in vacuo overnight to provide crude compound EEE (1.64 g) as a pale yellow solid. LC-MS [M+H] 950.4 ($C_{48}H_{67}N_7O_{11}S$, calc: 950.4). Purity ~60% (UV/254 nm). Compound EEE was used without purification.

Synthesis of [2-(2-Malonyl-5-guanidino-pentanoylamino)-ethyl]-ethyl-carbamic acid hydromorphone ester (Compound PC-6)

Compound EEE (1.64 g, 1.13 mmol) was treated with 5% m-cresol in TFA for 1 h at ambient temperature. Upon completion, the reaction mixture was precipitated with ether (100 mL). Precipitate was filtered off, washed with ether and dried in vacuo overnight to provide crude compound PC-6 (1.7 g) as a pale yellow solid. LC-MS [M+H] 642.7 ($C_{31}H_{43}N_7O_8$, calc: 642.3). Purity ~60% (UV/254 nm).

Crude Compound PC-6 (1.7 g) was dissolved in water (15 mL). The solution was subjected to HPLC purification: Nano-syn-Pack Microsorb (100-10) C-18 column (50×300 mm); flow rate: 100 mL/min; injection volume 15 mL; mobile phase A: 100% water, 0.1% TFA; mobile phase B: 100% ACN, 0.1% TFA; isocratic elution at 0% B in 5 min, gradient elution from 0% to 12% B in 12 min, isocratic elution at 12% B in 20 min, gradient elution from 12% B to 40% B in 43 min; detection at 254 nm. Fractions containing the desired product were combined and concentrated in vacuo. The residue was dissolved in isopropanol (50 mL) and co-evaporated in vacuo (procedure repeated twice). The residue was dissolved in ~5 mL isopropanol, and 2.0 M HCl in ether (50 mL) was added. The product was precipitated as a HCl salt. The resulting solid was filtered, washed with ether (2×50 mL) and dried in vacuo overnight to provide Compound PC-6 (468 mg, 62% yield) as a white solid. LC-MS [M+H] 642.7 ($C_{31}H_{43}N_7O_8$, calc: 642.3). Purity 98.8% (UV/254 nm).

Biological Data of Phenol-Modified Opioid Prodrugs

Example 13

Oral Administration of Compound PC-1 and SBTI Trypsin Inhibitor to Rats

Hydromorphone 3-(N-methyl-N-(2-N'-acetylarginylamino)) ethylcarbamate (which can be produced as described in PCT International Publication No. WO 2007/140272, published 6 Dec. 2007, Example 3, hereinafter referred to as Compound PC-1) and SBTI (trypsin inhibitor from *Glycine max* (soybean) (Catalog No. 93620, ~10,000 units per mg, Sigma-Aldrich) were each dissolved in saline.

Saline solutions of Compound PC-1 and SBTI were dosed as indicated in Table 1 via oral gavage into jugular vein-cannulated male Sprague Dawley rats that had been fasted for 16-18 hr prior to oral dosing; 4 rats were dosed per group. When SBTI was dosed, it was administered 5 minutes (min) prior to Compound PC-1. At specified time points, blood samples were drawn, quenched into methanol, centrifuged at 14,000 rpm @ 4° C., and stored at −80° C. until analysis by high performance liquid chromatography/mass spectrometry (HPLC/MS).

Table 1 indicates the results for rats administered a constant amount of Compound PC-1 and variable amounts of SBTI. Results are reported as maximum blood concentration of hydromorphone (average±standard deviation) for each group of 4 rats.

TABLE 1

Maximum concentration (Cmax) of hydromorphone in rat blood

| Compound PC-1 (mg/kg) | SBTI (mg/kg) | Cmax (ng/mL HM) |
|---|---|---|
| 20 | 0 | 16.5 ± 5.3 |
| 20 | 10 | 8.9 ± 1.8 |
| 20 | 100 | 6.0 ± 4.0 |
| 20 | 500 | <5 |
| 20 | 1000 | <5 |

Lower limit of quantitation was 1 nanogram per milliliter (ng/mL) for the first group and 5 ng/mL for the other groups.

The results in Table 1 indicate that SBTI attenuates Compound PC-1's ability to release hydromorphone in a dose-dependent manner that can approach approximately 100% attenuation at higher SBTI concentrations.

Figure 4:
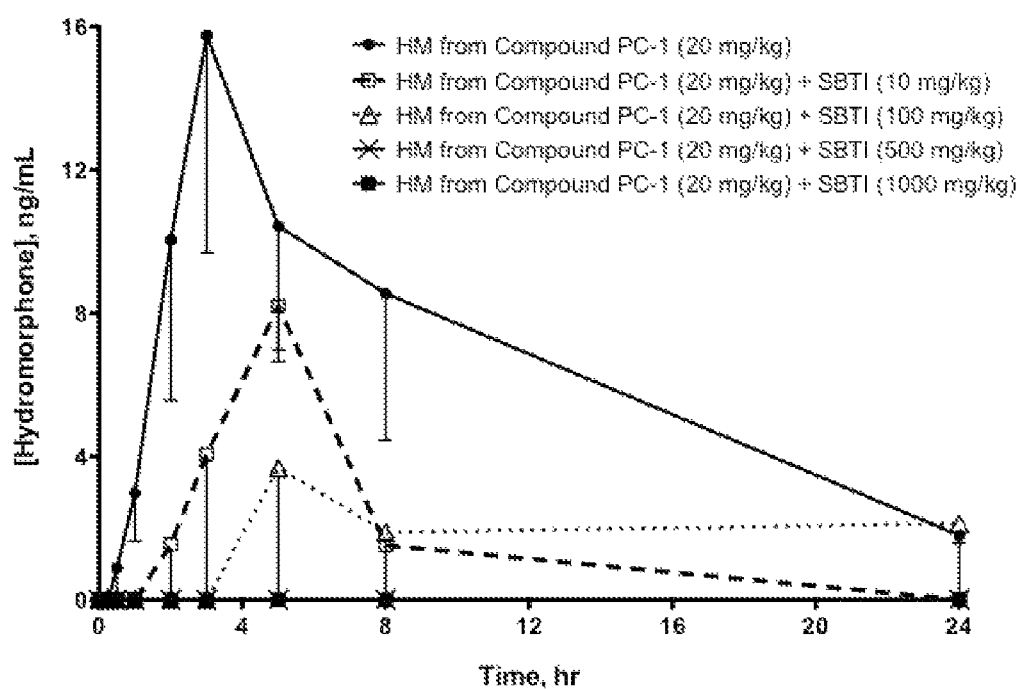
FIG. 4 is a graph that compares mean blood concentrations over time of hydromorphone (HM) following PO administration to rats of Compound PC-1 alone and Compound PC-1 with various amounts of trypsin inhibitor from *Glycine max* (soybean) (SBTI).

Data obtained from the rats represented in Table 1 are also provided in FIG. 4 which compares mean blood concentrations (± standard deviations) over time of hydromorphone following PO administration to rats of 20 mg/kg Compound PC-1 (a) alone (solid line with closed circle symbols), (b) with 10 mg/kg SBTI (dashed line with open square symbols), (c) with 100 mg/kg SBTI (dotted line with open triangle symbols), (d) with 500 mg/kg SBTI (solid line with X symbols) or (e) with 1000 mg/kg SBTI (solid line with closed square symbols). The results in FIG. 4 indicate that SBTI attenuation of Compound PC-1's ability to release hydromorphone suppresses Cmax and delays Tmax of such hydromorphone release into the blood of rats administered Compound PC-1 and 10, 100, 500 or 1000 mg/kg SBTI.

Example 14

Oral Administration of Compound PC-1 and SBTI Trypsin Inhibitor, in the Presence of Ovalbumin, to Rats In an effort to understand the role of SBTI, ovalbumin was used as a non-trypsin inhibitor protein control. Albumin from chicken egg white (ovalbumin) (Catalog No. A7641, Grade VII, lyophilized powder, Sigma-Aldrich) was dissolved in saline.

Saline solutions of Compound PC-1 and SBTI (as described in Example 13) and of ovalbumin were combined and dosed as indicated in Table 2 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (µl) plasma transferred from each sample into a fresh tube containing 1 µl of formic acid. The tubes were vortexed for 5-10 seconds, immediately placed in dry ice and then stored until analysis by HPLC/MS.

Table 2 indicates the results for rats administered Compound PC-1 with or without various amounts of ovalbumin (OVA) and/or SBTI as indicated. Results are reported as maximum plasma concentration of hydromorphone (average±standard deviation) for each group of 4 rats.

TABLE 2

Maximum concentration (Cmax) of hydromorphone in rat plasma

| Compound PC-1 (mg/kg) | OVA (mg/kg) | SBTI (mg/kg) | Cmax (ng/mL HM) |
|---|---|---|---|
| 20 | 0 | 0 | 13.3 ± 3.7 |
| 20 | 20 | 0 | 11.0 ± 5.4 |
| 20 | 100 | 0 | 9.7 ± 3.1 |
| 20 | 500 | 0 | 11.6 ± 2.5 |
| 20 | 1000 | 0 | 10.3 ± 3.5 |
| 20 | 500 | 500 | 1.9 ± 0.9 |

Lower limit of quantitation was 12.5 picograms/mL (pg/mL) for the first group, 25 pg/mL for the last group, and 100 pg/mL for the other groups.

The results in Table 2 indicate that ovalbumin does not significantly affect Compound PC-1's ability to release hydromorphone or SBTI's ability to attenuate such release.

Figure 5:
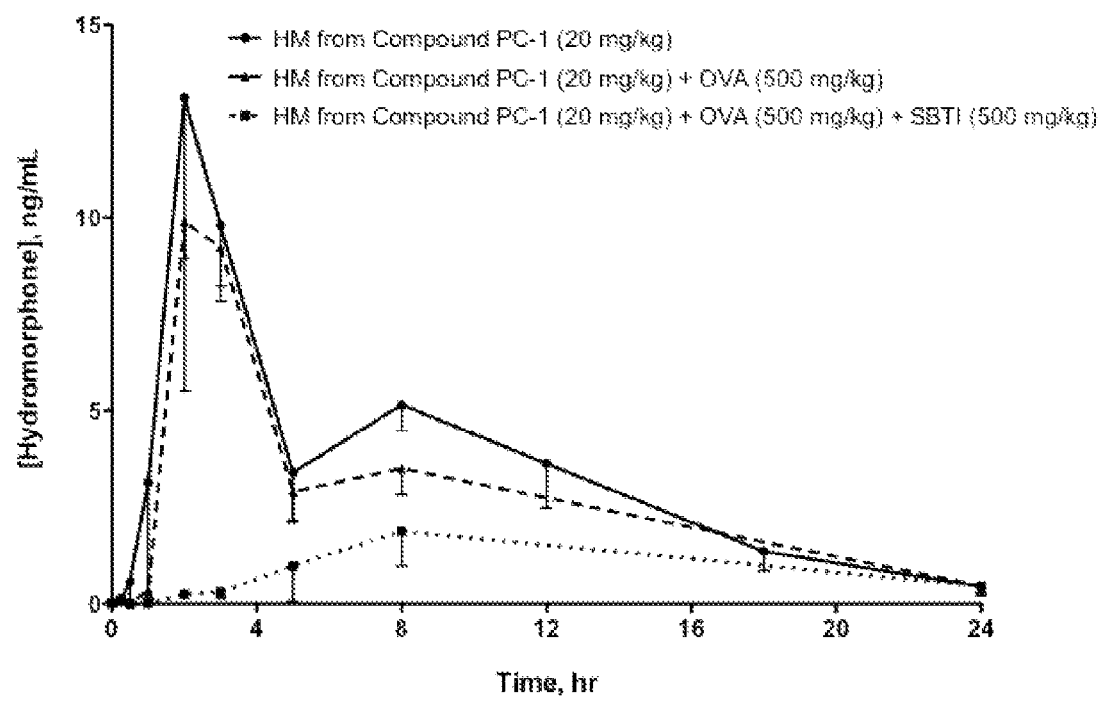
FIG. 5 is a graph that compares mean plasma concentrations over time of hydromorphone (HM) following PO administration to rats of Compound PC-1 alone, Compound PC-1 with ovalbumin (OVA), and Compound PC-1 with ovalbumin and SBTI.

Data obtained from the rats represented in rows 1, 4 and 6 of Table 2 are also provided in FIG. 5 which compares mean plasma concentrations (± standard deviations) over time of hydromorphone following PO administration to rats of 20 mg/kg Compound PC-1 (a) alone (solid line with circle symbols), (b) with 500 mg/kg OVA (dashed line with triangle symbols) or (c) with 500 mg/kg OVA and 500 mg/kg SBTI (dotted line with square symbols). The results in FIG. 5 indicate that SBTI attenuation of Compound PC-1's ability to release hydromorphone suppresses Cmax and delays Tmax of such hydromorphone in plasma, even in the presence of ovalbumin. Rats administered 20 mg/kg Compound PC-1 with 500 mg/kg OVA and 500 mg/kg SBTI displayed a plasma Tmax of 8.0 hr, whereas rats administered 20 mg/kg Compound PC-1 alone displayed a plasma Tmax of 2.3 hr. The results in Table 2 and FIG. 5 also indicate that SBTI is acting specifically by inhibiting trypsin rather than in a non-specific manner.

Example 15

Oral Administration of Compound PC-1 and BBSI Inhibitor to Rats

Compound PC-1 and BBSI (Bowman-Birk trypsin-chymotrypsin inhibitor from *Glycine max* (soybean), Catalog No. T9777, Sigma-Aldrich) were each dissolved in saline.

Saline solutions of Compound PC-1 and BBSI were dosed as indicated in Table 3. Dosing, sampling and analysis procedures were as described in Example 13.

Table 3 indicates the results for rats administered Compound PC-1 with or without BBSI. Results are reported as maximum blood concentration of hydromorphone (average±standard deviation) for each group of 4 rats (n=4) as well as for 3 of the 4 rats administered Compound PC-1 and BBSI (n=3).

TABLE 3

Maximum concentration (Cmax) of hydromorphone in rat blood

| Compound PC-1 (mg/kg) | BBSI (mg/kg) | Cmax (ng/mL HM) | Number of Rats (n) |
|---|---|---|---|
| 20 | 0 | 16.5 ± 5.3 | n = 4 |
| 20 | 100 | 10.6 ± 5.9 | n = 3 |
| 20 | 100 | 18.7 ± 17.0 | n = 4 |

Lower limit of quantitation was 1 ng/mL for both groups. Cmax of rat not included in n = 3 analysis was 43 ng/mL; range of other rats was 6.8-17 ng/mL.

The results in Table 3 indicate that BBSI can attenuate Compound PC-1's ability to release hydromorphone.

Figure 6:
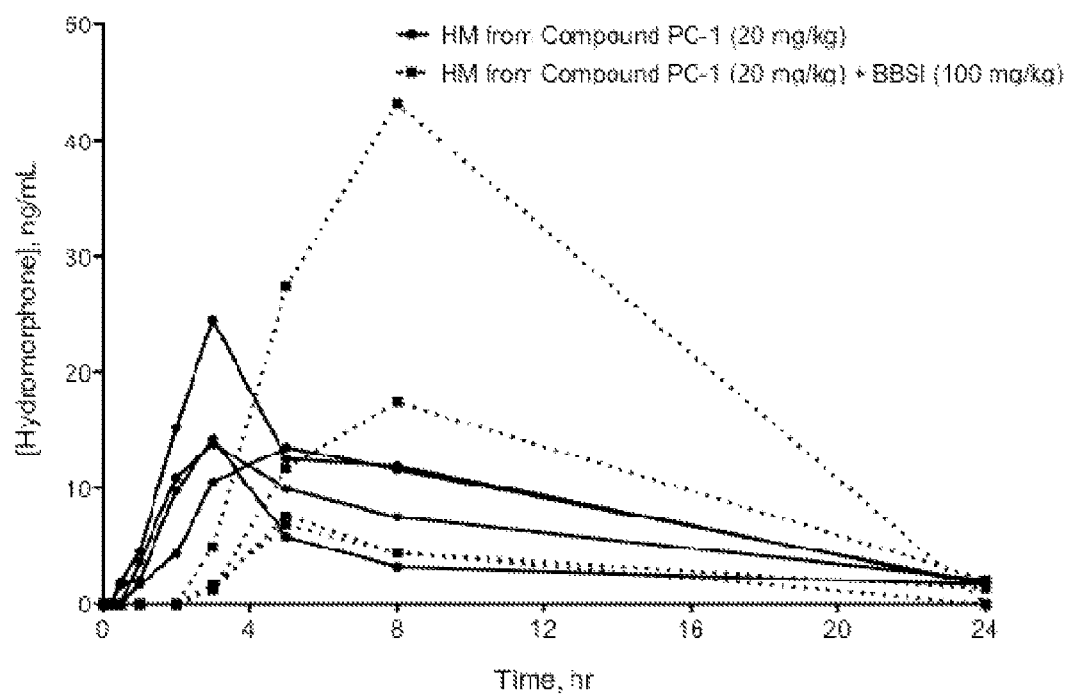
FIG. 6 is a graph that compares individual blood concentrations over time of hydromorphone (HM) following PO administration to rats of Compound PC-1 alone and Compound PC-1 with Bowman-Birk trypsin-chymotrypsin inhibitor (BBSI).

Data obtained from the individual rats represented in Table 3, rows 1 and 3 are provided in FIG. 6 which compares individual blood concentrations over time of hydromorphone following PO administration to rats of 20 mg/kg Compound PC-1 (a) alone (solid lines) or (b) with 100 mg/kg BBSI (dotted lines). The results in FIG. 6 indicate that BBSI attenuation of Compound PC-1's ability to release hydromorphone suppresses Cmax and delays Tmax of such hydromorphone in blood, at least for 3 of the 4 rats administered Compound PC-1 and BBSI.

Example 16

Oral Administration of Compound PC-2 and SBTI Trypsin Inhibitor to Rats

Saline solutions of Compound PC-2 and SBTI were dosed as indicated in Table 4 via oral gavage into jugular vein-cannulated male Sprague Dawley rats (4 per group) that had been fasted for 16-18 hr prior to oral dosing. When SBTI was dosed, it was administered 5 min prior to Compound PC-2. At specified time points, blood samples were drawn, processed and analyzed as described in Example 14.

Figure 7:
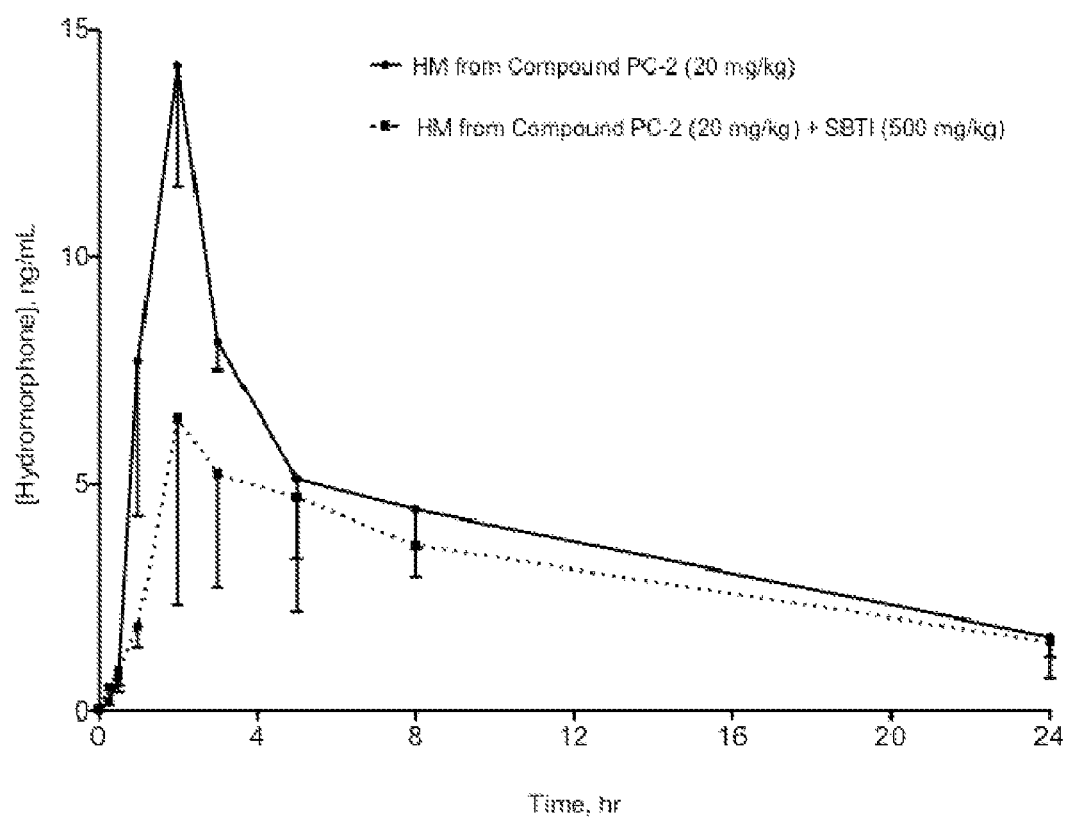
FIG. 7 is a graph that compares mean plasma concentrations over time of hydromorphone (HM) release following PO administration of Compound PC-2 alone and Compound PC-2 with SBTI to rats.

Table 4 and FIG. 7 provide results for rats administered 20 mg/kg of Compound PC-2 with or without 500 mg/kg of SBTI as indicated. Results in Table 4 are reported, for each group of 4 rats, as (a) maximum plasma concentration (Cmax) of hydromorphone (HM) (average±standard deviation) and (b) time after administration of Compound PC-2, with or without SBTI, to reach maximum hydromorphone concentration (Tmax).

TABLE 4

Cmax and Tmax of hydromorphone in rat plasma

| Compound PC-2 (mg/kg) | SBTI (mg/kg) | Cmax (ng/mL HM) | Tmax (hr) |
|---|---|---|---|
| 20 | 0 | 14.2 ± 2.6 | 2.0 |
| 20 | 500 | 7.3 ± 3.5 | 3.5 |

Lower limit of quantitation was 0.0125 ng/mL for both groups.

FIG. 7 compares mean plasma concentrations (± standard deviations) over time of hydromorphone release following PO administration of 20 mg/kg Compound PC-2 alone (solid line) or with 500 mg/kg SBTI (dotted line) to rats.

The results in Table 4 and FIG. 7 indicate that SBTI attenuates Compound PC-2's ability to release hydromorphone, both with respect to suppressing Cmax and delaying Tmax.

Example 17

Oral Administration of Compound PC-3 and SBTI Trypsin Inhibitor to Rats

Saline solutions of Compound PC-3 and SBTI were dosed as indicated in Table 5. Dosing, sampling and analysis procedures were as described in Example 16.

Figure 8:
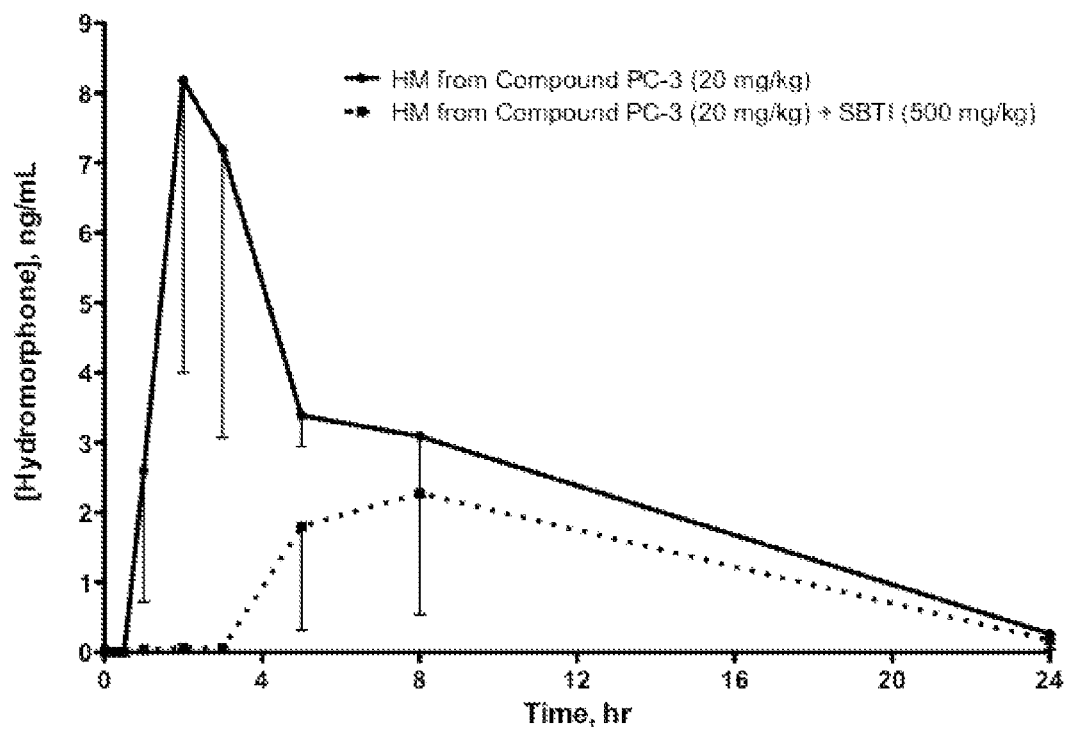
FIG. 8 is a graph that compares mean plasma concentrations over time of hydromorphone (HM) release following PO administration of Compound PC-3 alone and Compound PC-3 with SBTI to rats.

Table 5 and FIG. 8 provide results for rats administered 20 mg/kg of Compound PC-3 with or without 500 mg/kg of SBTI as indicated. Results in Table 5 are reported as Cmax and Tmax of hydromorphone in plasma for each group of 4 rats.

TABLE 5

Cmax and Tmax of hydromorphone in rat plasma

| Compound PC-3 (mg/kg) | SBTI (mg/kg) | Cmax (ng/mL HM) | Tmax (hr) |
|---|---|---|---|
| 20 | 0 | 9.0 ± 3.1 | 2.3 |
| 20 | 500 | 2.3 ± 1.7 | 7.3 |

Lower limit of quantitation was 0.100 ng/mL for both groups.

FIG. 8 compares mean plasma concentrations (± standard deviations) over time of hydromorphone release following PO administration of 20 mg/kg Compound PC-3 alone (solid line) or with 500 mg/kg SBTI (dotted line) to rats.

The results in Table 5 and FIG. 8 indicate that SBTI attenuates Compound PC-3's ability to release hydromorphone, both with respect to suppressing Cmax and delaying Tmax.

Example 18

Oral Administration of Compound PC-4 and SBTI Trypsin Inhibitor to Rats

Saline solutions of Compound PC-4 and SBTI were dosed as indicated in Table 6. Dosing, sampling and analysis procedures were as described in Example 16, except that Compound PC-4 without inhibitor was administered to 7 rats.

Figure 9:
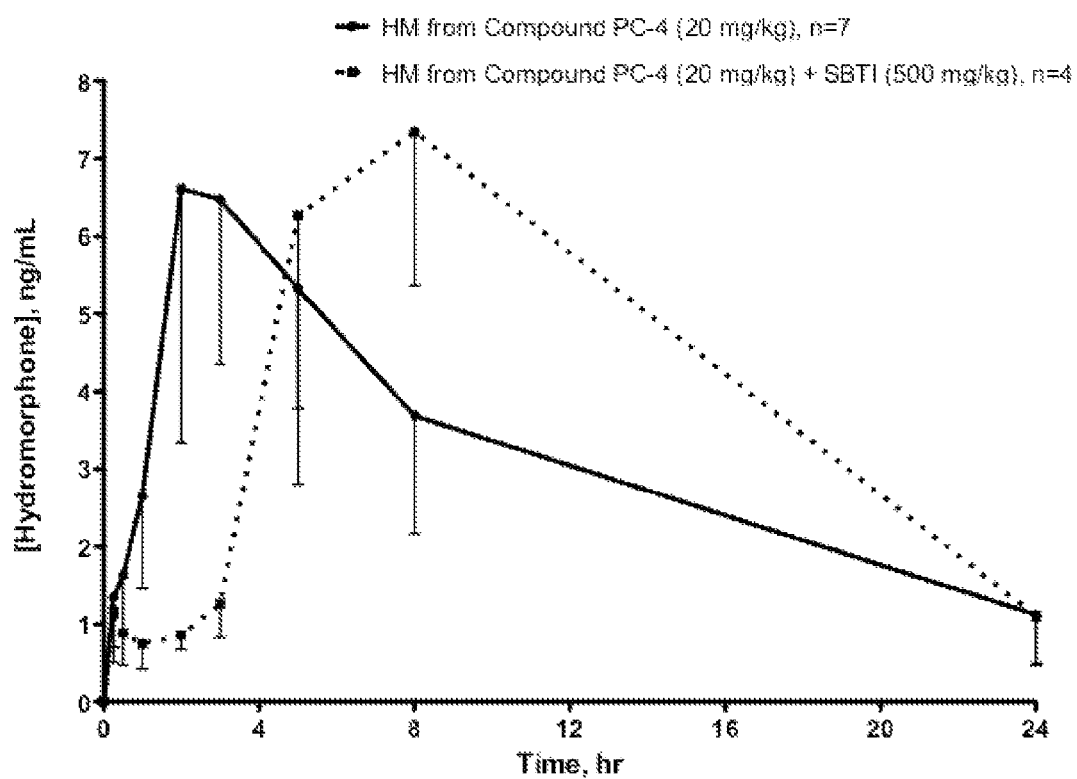
FIG. 9 is a graph that compares mean plasma concentrations over time of hydromorphone (HM) release following PO administration of Compound PC-4 alone and Compound PC-4 with SBTI to rats.

Table 6 and FIG. 9 provide results for rats administered 20 mg/kg of Compound PC-4 with or without 500 mg/kg of SBTI as indicated. Results in Table 6 are reported as Cmax and Tmax of hydromorphone in plasma for each group of 4 rats.

TABLE 6

Cmax and Tmax of HM in rat plasma

| Compound PC-4 (mg/kg) | SBTI (mg/kg) | Cmax (ng/mL HM) | Tmax (hr) | Number of rats (n) |
|---|---|---|---|---|
| 20 | 0 | 7.7 ± 2.3 | 2.3 | 7 |
| 20 | 500 | 7.5 ± 2.1 | 6.5 | 4 |

Lower limit of quantitation was 0.500 ng/mL for both groups.

FIG. 9 compares mean plasma concentrations (± standard deviations) over time of hydromorphone release following PO administration of 20 mg/kg Compound PC-4 alone (solid line) or with 500 mg/kg SBTI (dotted line) to rats.

The results in Table 6 and FIG. 9 indicate that SBTI attenuates Compound PC-4's ability to release hydromorphone, at least with respect to delaying Tmax.

Example 19

In Vitro IC50 Data

Several candidate trypsin inhibitors, namely Compounds 101-105, 107 and 108 were produced as described herein. Compound 106 (also known as 4-aminobenzamidine), Compound 109 and Compound 110 are available from Sigma-Aldrich (St. Louis, Mo.).

The half maximal inhibitory concentration (IC50 or $IC_{50}$) values of each of Compounds 101-110 as well as of SBTI and BBSI were determined using a modified trypsin assay as described by Bergmeyer, H U et al, 1974, Methods of Enzymatic Analysis Volume 1, $2^{nd}$ edition, 515-516, Bergmeyer, HU, ed., Academic Press, Inc. New York, N.Y.

Table 7 indicates the IC50 values for each of the designated trypsin inhibitors.

TABLE 7

IC50 values of certain trypsin inhibitors

| Compound | IC50 value |
|---|---|
| 101 | 2.0E−5 |
| 102 | 7.5E−5 |
| 103 | 2.3E−5 |
| 104 | 2.7E−5 |
| 105 | 4.1E−5 |
| 106 | 2.4E−5 |
| 107 | 1.9E−6 |
| 108 | 8.8E−7 |
| 109 | 9.1E−7 |
| 110 | 1.8E−5 |
| SBTI | 2.7E−7 |
| BBSI | 3.8E−7 |

The results of Table 7 indicate that each of Compounds 101-110 exhibits trypsin inhibition activity.

Example 20

Effect of Trypsin Inhibitors on In Vitro Trypsin-Mediated Trypsin Release of Hydromorphone from Compound PC-4

Compound PC-4 was incubated with trypsin from bovine pancreas (Catalog No. T8003, Type I, ~10,000 BAEE units/mg protein, Sigma-Aldrich) in the absence or presence of one of the following trypsin inhibitors: SBTI, Compound 107, Compound 108 or Compound 109. When a trypsin inhibitor was part of the incubation mixture, Compound PC-4 was added 5 min after the other incubation components. The reactions were conducted at 37° C. for 24 hr. Samples were collected at specified time points, transferred into 0.5% formic acid in acetonitrile to stop trypsin activity and stored at less than −70° C. until analysis by LC-MS/MS.

The final incubation mixtures consisted of the following components:

| | Incubation Components | | | | |
|---|---|---|---|---|---|
| Compound | Inhibitor | Tris pH 8 | CaCl$_2$ | Trypsin | Compound PC-4 |
| Control | 0 | 40 mM | 22.5 mM | 0.0228 mg/mL | 0.51 mg/mL |
| 107 | 1.67 mg/mL | 20 mM | 22.5 mM | 0.0228 mg/mL | 0.51 mg/mL |
| 108 | 1.67 mg/mL | 20 mM | 22.5 mM | 0.0228 mg/mL | 0.51 mg/mL |
| 109 | 1.67 mg/mL | 20 mM | 22.5 mM | 0.0228 mg/mL | 0.51 mg/mL |
| SBTI | 10 mg/mL | 20 mM | 22.5 mM | 0.0228 mg/mL | 0.51 mg/mL |

Figure 10A:
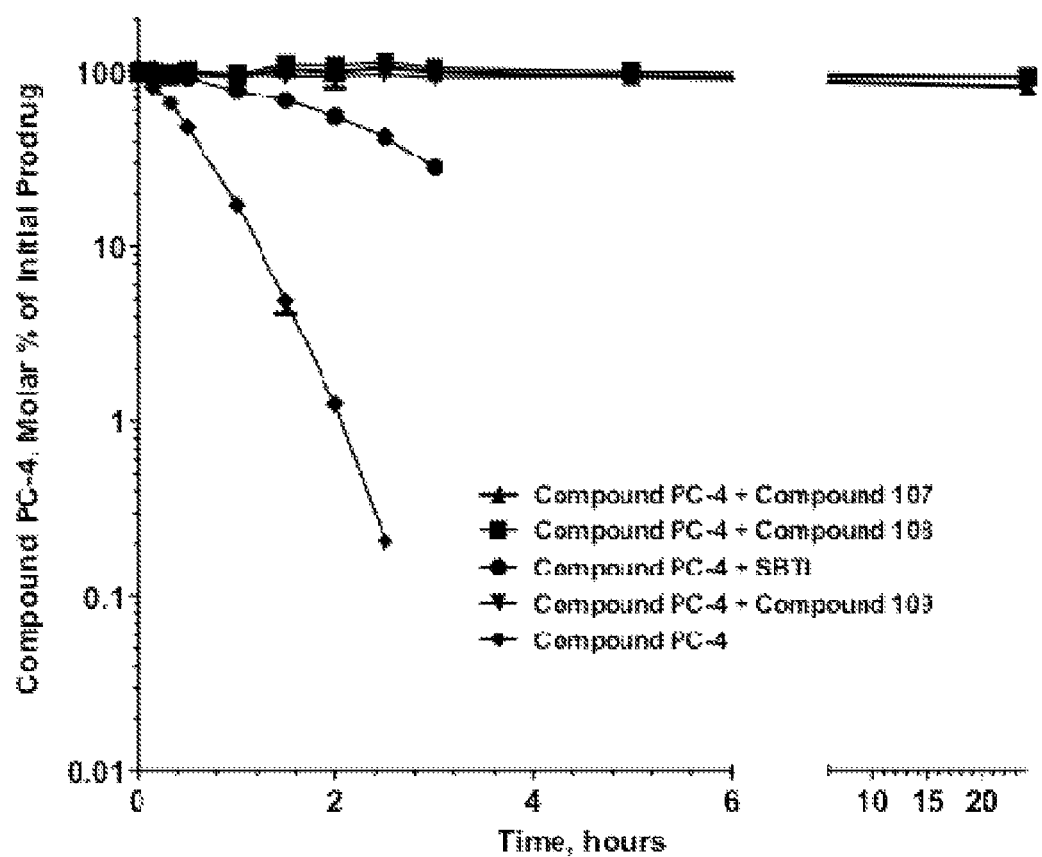
FIGS. 10A and 10B are graphs that indicate the in vitro results of exposure of a certain combination of Compound PC-4 and trypsin, in the absence of any trypsin inhibitor or in the presence of SBTI, Compound 107, Compound 108, or Compound 109.
Figure 10B:
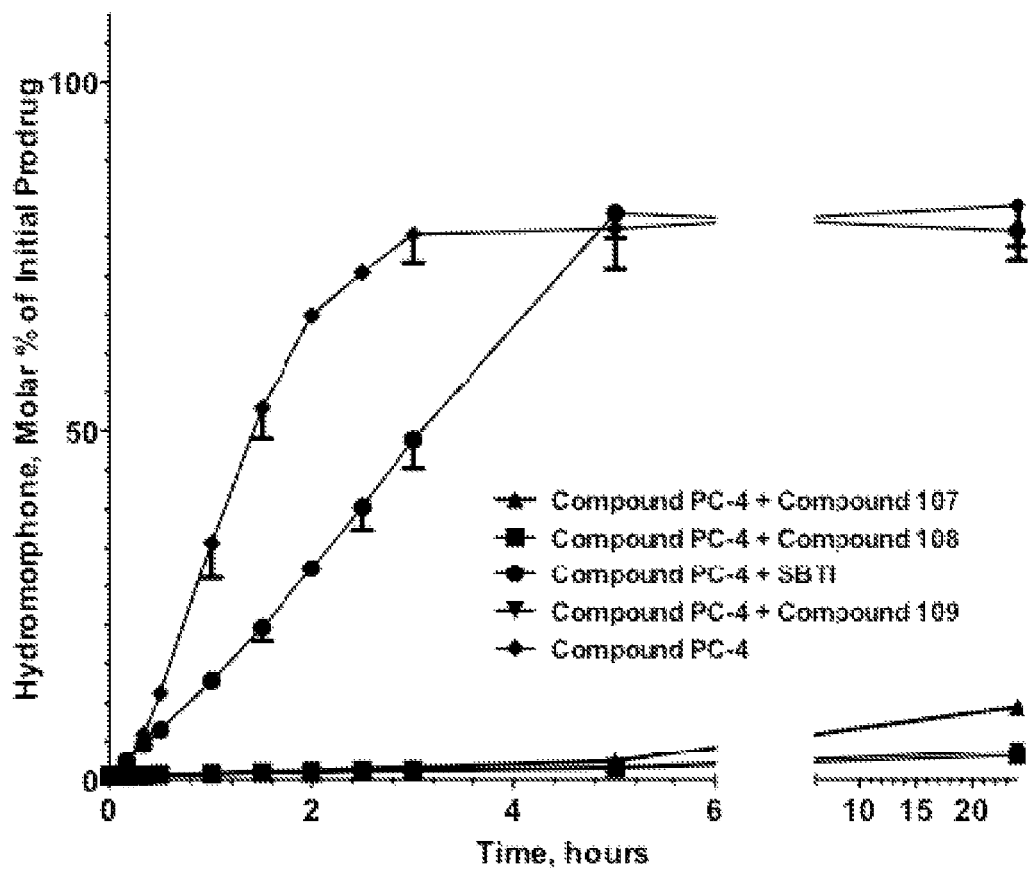

FIGS. 10A and 10B indicate the results of exposure of 0.51 mg/mL Compound PC-4 to 22.8 ng/mL trypsin in the absence of any trypsin inhibitor (diamond symbols) or in the presence of 10 mg/mL SBTI (circle symbols), 1.67 mg/mL Compound 107 (upward-pointing triangle symbols), 1.67 mg/mL Compound 108 (square symbols) or 1.67 mg/mL Compound 109 (downward-pointing triangles symbols). Specifically, FIG. 10A depicts the disappearance of Compound PC-4, and FIG. 10B depicts the appearance of hydromorphone, over time under these conditions.

The results in FIGS. 10A and 10B indicate that a trypsin inhibitor of the embodiments can thwart the ability of a user to apply trypsin to effect the release of hydromorphone from Compound PC-4.

Example 21

Oral Administration of Compound PC-3 and Compound 101 Trypsin Inhibitor to Rats

Saline solutions of Compound PC-3 and Compound 101 were dosed as indicated in Table 8. Dosing, sampling and analysis procedures were as described in Example 16, except that Compound PC-3 and Compound 101 were combined for dosing.

Figure 11:
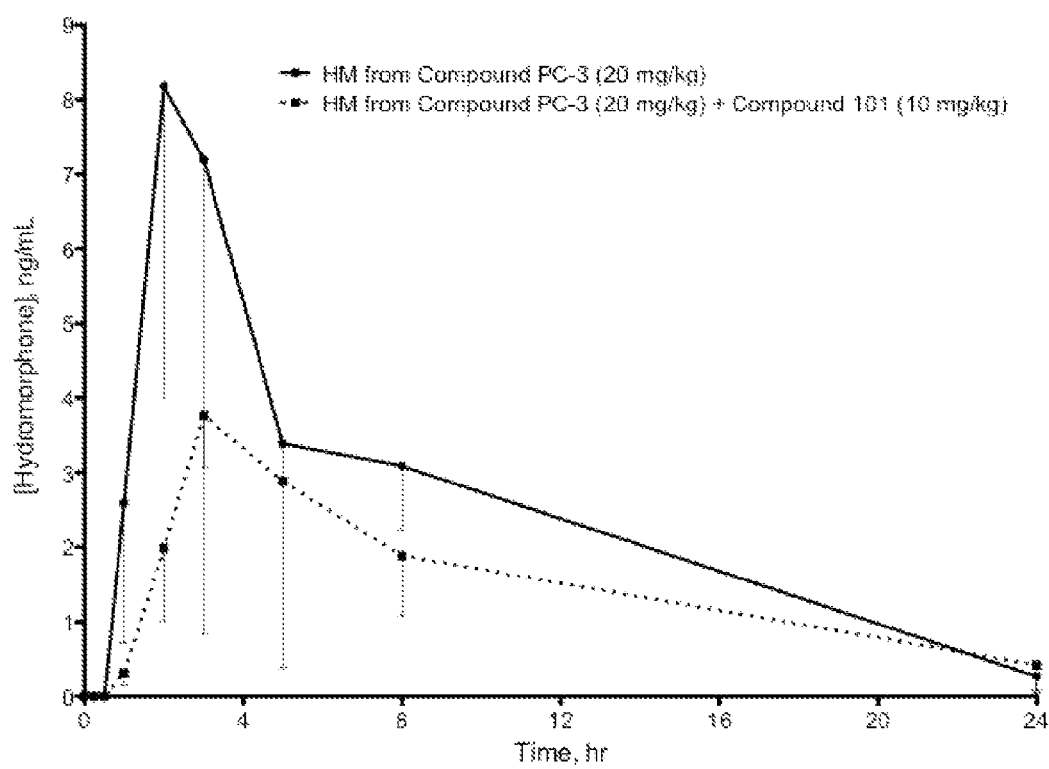
FIG. 11 is a graph that compares mean plasma concentrations over time of hydromorphone (HM) release following PO administration of Compound PC-3 alone and Compound PC-3 with Compound 101 to rats.

Table 8 and FIG. 11 provide results for rats administered 20 mg/kg of Compound PC-3 with or without 10 mg/kg of Compound 101 as indicated. Results in Table 8 are reported as Cmax and Tmax of hydromorphone in plasma for each group of 4 rats.

TABLE 8

Cmax and Tmax of HM in rat plasma

| Compound PC-3 (mg/kg) | Compound 101 (mg/kg) | Cmax (ng/mL HM) | Tmax (hr) |
|---|---|---|---|
| 20 | 0 | 9.0 ± 3.1 | 2.3 |
| 20 | 10 | 3.8 ± 2.9 | 3.5 |

Lower limit of quantitation was 0.100 ng/mL for the first group and 0.500 ng/mL for the second group.

FIG. 11 compares mean plasma concentrations (± standard deviations) over time of hydromorphone release following PO administration of 20 mg/kg Compound PC-3 alone (solid line) or with 10 mg/kg Compound 101 (dotted line) to rats.

The results in Table 8 and FIG. 11 indicate that Compound 101 attenuates Compound PC-3's ability to release hydromorphone, both with respect to suppressing Cmax and delaying Tmax.

Example 22

Oral Administration of Compound PC-4 and Compound 101 Trypsin Inhibitor to Rats

Saline solutions of Compound PC-4 and Compound 101 were dosed as indicated in Table 9. Dosing, sampling and analysis procedures were as described in Example 16, except that Compound PC-4 and Compound 101 were combined for dosing, and Compound PC-4 without inhibitor was administered to 7 rats.

Figure 12:
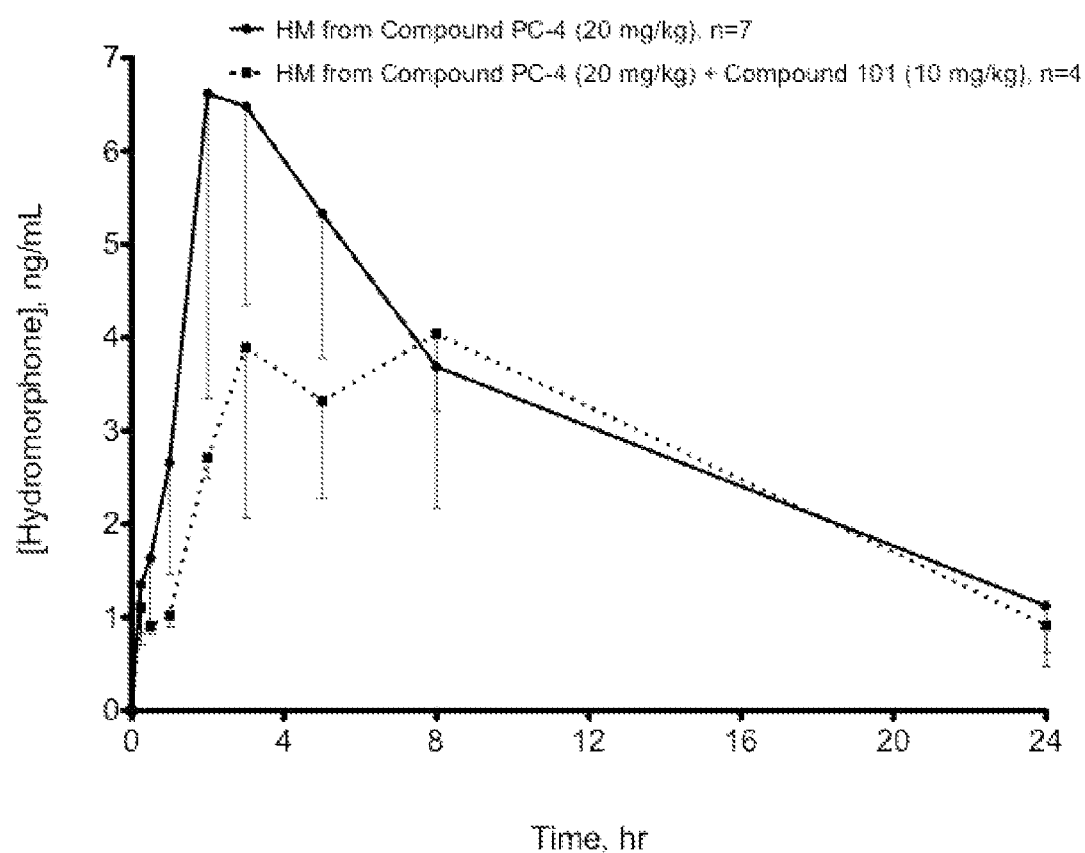
FIG. 12 is a graph that compares mean plasma concentrations over time of hydromorphone (HM) release following PO administration of Compound PC-4 alone and Compound PC-4 with Compound 101 to rats.

Table 9 and FIG. 12 provide results for rats administered 20 mg/kg of Compound PC-4 with or without 10 mg/kg of Compound 101 as indicated. Results in Table 9 are reported as Cmax and Tmax of hydromorphone in plasma for each group of 4 rats.

TABLE 9

Cmax and Tmax of HM in rat plasma

| Compound PC-4 (mg/kg) | Compound 101 (mg/kg) | Cmax (ng/mL HM) | Tmax (hr) | Number of rats (n) |
|---|---|---|---|---|
| 20 | 0 | 7.7 ± 2.3 | 2.3 | 7 |
| 20 | 10 | 4.8 ± 1.4 | 6.0 | 4 |

Lower limit of quantitation was 0.500 ng/mL for both groups.

FIG. 12 compares mean plasma concentrations (± standard deviations) over time of hydromorphone release following PO administration of 20 mg/kg Compound PC-4 alone (solid line) or with 10 mg/kg Compound 101 (dotted line) to rats.

The results in Table 9 and FIG. 12 indicate that Compound 101 attenuates Compound PC-4's ability to release hydromorphone, both with respect to suppressing Cmax and delaying Tmax.

Example 23

In Vitro Trypsin Conversion of Prodrugs to Hydromorphone and Inhibition by Trypsin Inhibitor This Example demonstrates trypsin conversion of prodrugs to hydromorphone. Compound PC-1, Compound PC-4, Compound PC-5 and Compound PC-6 were each incubated with trypsin from bovine pancreas (Catalog No. T8003, Type I, ~10,000 BAEE units/mg protein, Sigma-Aldrich. Compound PC-4 was also incubated with trypsin as above in the presence of trypsin inhibitor, Compound 109 (Catalog No. 3081, Tocris Bioscience); in this study, Compound 109 and trypsin were pre-incubated for 5 min at 37° C. prior to the addition of Compound PC-4. Specifically, the reactions included 0.761 mM Compound PC-1•2 HCl, Compound PC-4•2HCl, Compound PC-5•2HCl or Compound PC-6•2HCl in the presence of 0.02 to 0.0228 mg/mL trypsin, 17.5 to 22.5 mM calcium chloride, Tris pH 8 at 40 to 172 mM, and either 0.25% DMSO or Compound 109 as indicated in Table 11, depending on whether inhibitor was included in the incubation. The reactions were conducted at 37° C. for 24 hr. Samples were collected at specified time points, transferred into 0.5% formic acid in acetonitrile to stop trypsin activity and stored at less than −70° C. until analysis by LC-MS/MS.

Table 10 indicates the results of exposure of Compound PC-1, Compound PC-4, Compound PC-5, and Compound PC-6 to trypsin in the absence of any trypsin inhibitor, and Table 11 indicates the results for Compound PC-4 in the presence of trypsin inhibitor. The results are expressed as half-life of prodrug when exposed to trypsin (i.e., Prodrug trypsin half-life) in hours and rate of formation of HM per unit of trypsin.

The results in Tables 10 and 11 indicate that trypsin can release hydromorphone from the respective compounds and that a trypsin inhibitor of the embodiments can attenuate trypsin-mediated release of hydromorphone.

TABLE 10

In vitro trypsin conversion of prodrugs to hydromorphone

| | | No trypsin inhibitor |
| --- | --- | --- |
| Prodrug | Prodrug trypsin half-life, h Average ± sd | Rate of HM formation, umols/h/umol trypsin Average ± sd |
| Compound PC-1 | 0.61 ± 0.02 | 230 ± 8 |
| Compound PC-4 | 0.411 ± na* (n = 1) | 322 ± na (n = 1) |
| Compound PC-4 | 0.435 ± 0.009 | 243 ± 1 |
| Compound PC-5 | 2.81 ± 0.23 | 106 ± 2 |
| Compound PC-6 | 0.574 ± 0.063 | 262 ± 11 |

*na = not available

TABLE 11

In vitro trypsin conversion of prodrugs to hydromorphone and inhibition by trypsin inhibitor

| | | With trypsin inhibitor | |
| --- | --- | --- | --- |
| Prodrug | Trypsin inhibitor | Prodrug trypsin half-life, h Average ± sd | Rate of HM formation, umols/h/umol trypsin Average ± sd |
| Compound PC-4 | 2.78 uM Compound 109 | 12.2 ± na (n = 1) | nd* |
| Compound PC-4 | 3,089 uM Compound 109 | 721 ± 230 | 3.27 ± 1.87 |

*na = not available;
nd = not detectable

Example 24

Pharmacokinetics of Compound PC-5 Following PO Administration to Rats

Saline solutions of Compound PC-5 were dosed as indicated in Table 12A and Table 12B via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 13A:
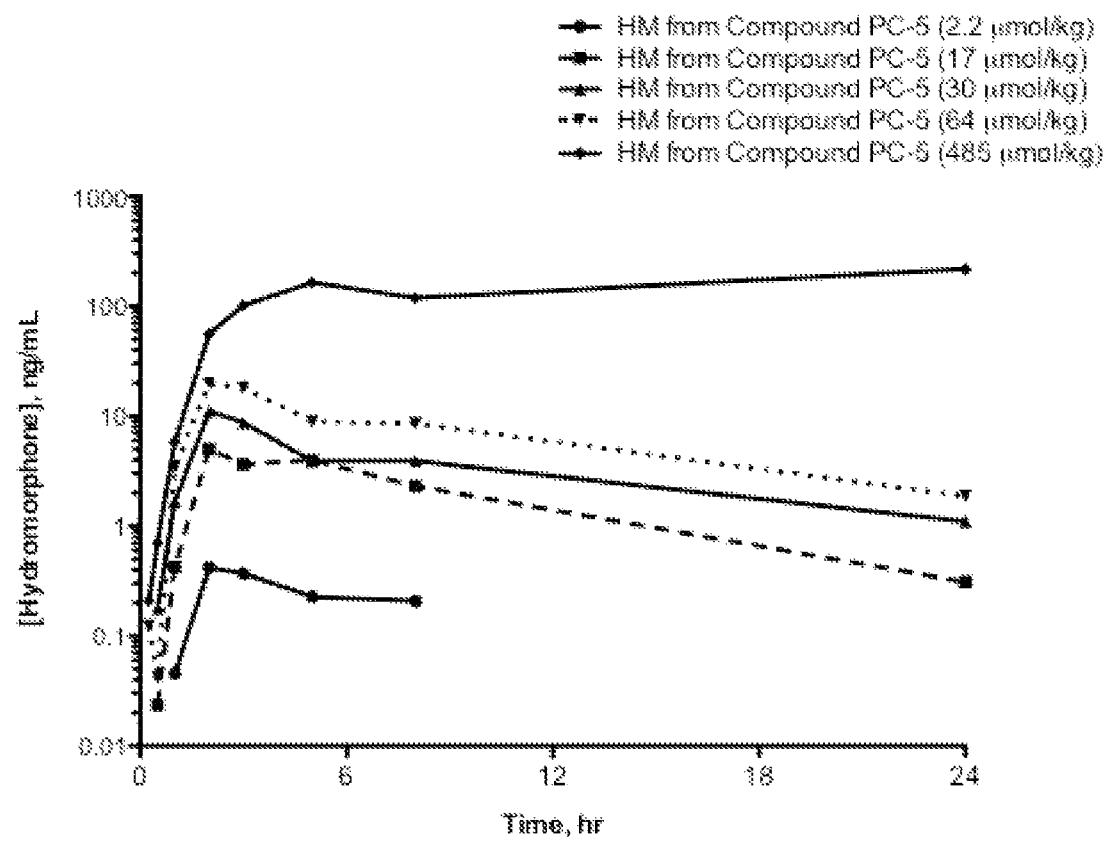
FIG. 13A and FIG. 13B compare mean plasma concentrations over time of hydromorphone release following PO administration of increasing doses of prodrug Compound PC-5 to rats.
Figure 13B:
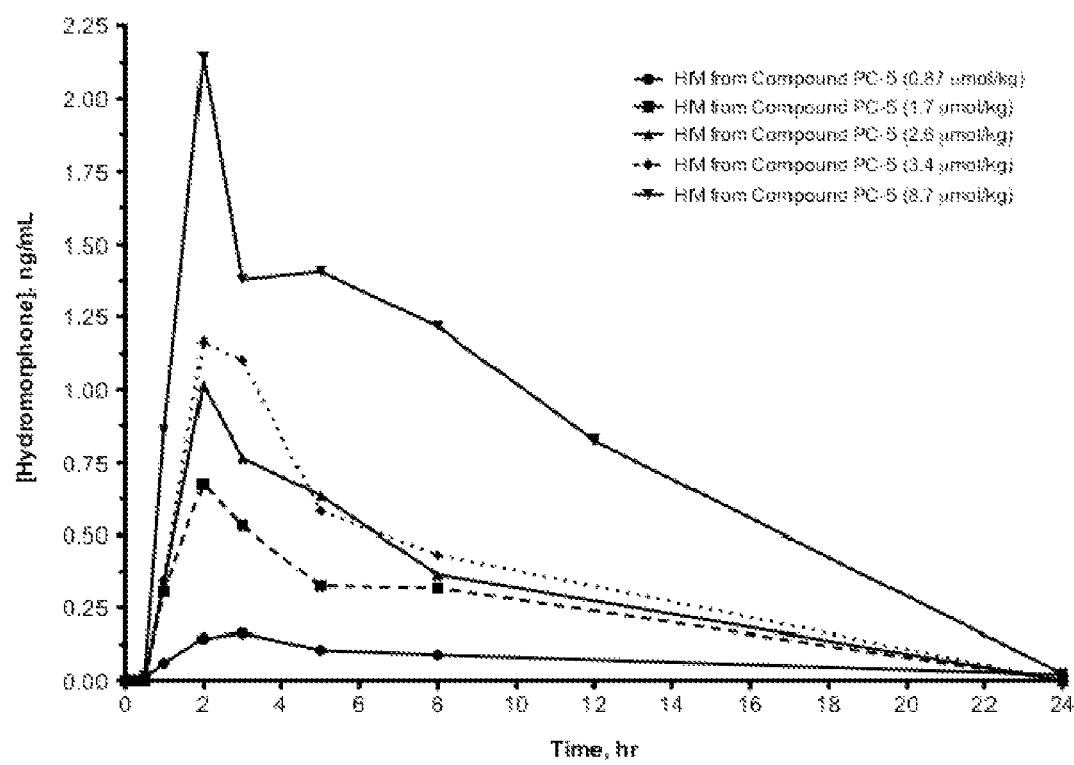

Table 12A, Table 12B, FIG. 13A and FIG. 13B provide hydromorphone exposure results for rats administered different doses of Compound PC-5. Results in Table 12A and Table 12B are reported, for each group of 4 rats, as (a) maximum plasma concentration (Cmax) of hydromorphone (HM) (average±standard deviation), (b) time after administration of Compound PC-5 to reach maximum hydromorphone concentration (Tmax) (average±standard deviation) and (c) area under the curve (AUC) from 0 to 24 hr for all doses except for the 1.5 mg/kg Compound PC-5 dose where the AUC was calculated from 0 to 8 hr.

TABLE 12A

Cmax, Tmax and AUC values of hydromorphone in rat plasma

| Compound | Dose, mg/kg | Dose μmol/kg | HM Cmax ± sd, ng/mL | Tmax ± sd, hr | AUC ± sd, ng × hr/mL |
| --- | --- | --- | --- | --- | --- |
| PC-5 | 1.5 | 2.2 | 0.363 ± 0.15 | 3.25 ± 1.3 | 1.58 ± 0.53 |
| PC-5 | 12 | 17 | 5.89 ± 2.4 | 3.50 ± 1.7 | 45.2 ± 11 |
| PC-5 | 21 | 30 | 11.4 ± 1.3 | 2.25 ± 0.50 | 81.1 ± 5.2 |
| PC-5 | 44 | 64 | 20.0 ± 5.2 | 2.25 ± 0.50 | 168 ± 26 |
| PC-5 | 333 | 485 | 404 ± 280 | 25.3 ± 17 | 8580 ± 6100 |

Lower limit of quantitation was 0.0500 ng/mL.

TABLE 12B

Cmax, Tmax and AUC values of hydromorphone in rat plasma

| Compound | Dose, mg/kg | Dose μmol/kg | HM Cmax ± sd, ng/mL | Tmax ± sd, hr | AUC ± sd, ng × hr/mL |
| --- | --- | --- | --- | --- | --- |
| PC-5 | 0.6 | 0.87 | 0.196 ± 0.11 | 3.75 ± 2.9 | 1.33 ± 0.84 |
| PC-5 | 1.2 | 1.7 | 0.720 ± 0.28 | 2.25 ± 0.50 | 3.07 ± 0.74 |

TABLE 12B-continued

Cmax, Tmax and AUC values of hydromorphone in rat plasma

| Compound | Dose, mg/kg | Dose μmol/kg | HM Cmax ± sd, ng/mL | Tmax ± sd, hr | AUC ± sd, ng × hr/mL |
|---|---|---|---|---|---|
| PC-5 | 1.8 | 2.6 | 1.04 ± 0.33 | 2.25 ± 0.50 | 4.64 ± 1.3 |
| PC-5 | 2.4 | 3.4 | 1.34 ± 0.73 | 2.25 ± 0.50 | 5.24 ± 2.3 |
| PC-5 | 6 | 8.7 | 2.17 ± 0.50 | 2.75 ± 1.5 | 15.8 ± 4.1 |

Lower limit of quantitation was 0.0500 ng/mL, except 0.87 μmol/kg dose was 0.0250 ng/mL FIG. 13A and FIG. 13B compared mean plasma concentrations over time of hydromorphone release following PO administration of increasing doses of Compound PC-5 for the studies reported in Table 12A and Table 12B, respectively.

The results in Table 12A, Table 12B, FIG. 13A and FIG. 13B indicate that plasma concentrations of hydromorphone increase proportionally with Compound PC-5 dose.

Example 25

Oral Administration of Compound PC-5 Co-Dosed with Trypsin Inhibitor Compound 109 to Rats Saline solutions of Compound PC-5 were dosed with increasing co-doses of Compound 109 (Catalog No. 3081, Tocris Bioscience, Ellisville, Mo., USA or Catalog WS38665, Waterstone Technology, Carmel, Ind., USA) as indicated in Table 13 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 14:
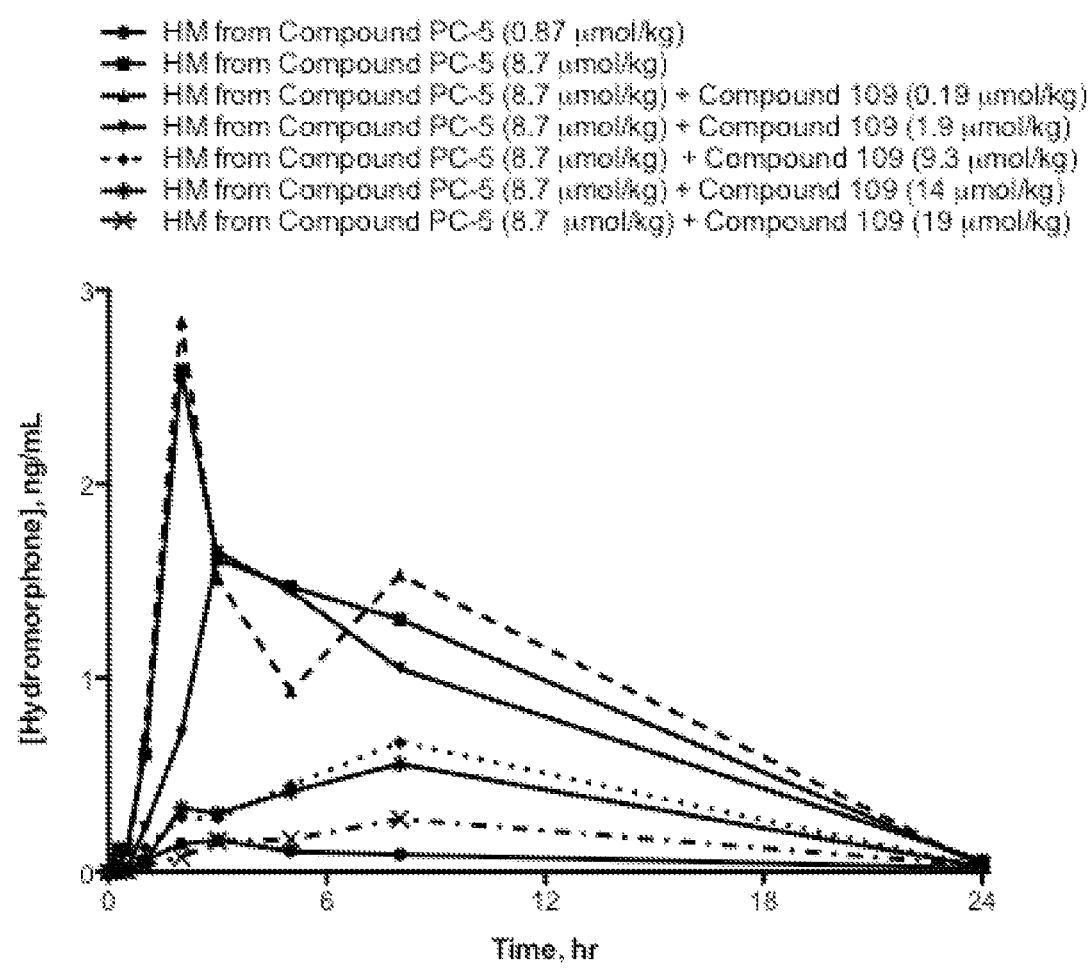
FIG. 14 compares mean plasma concentrations over time of hydromorphone release following PO administration of prodrug Compound PC-5 with increasing amounts of co-dosed trypsin inhibitor Compound 109 to rats.

Table 13 and FIG. 14 provide hydromorphone exposure results for rats administered Compound PC-5 and increasing doses of trypsin inhibitor. Results in Table 13 are reported, for each group of 4 rats, as (a) maximum plasma concentration (Cmax) of hydromorphone (HM) (average±standard deviation), (b) time after administration of Compound PC-5 to reach maximum hydromorphone concentration (Tmax) (average±standard deviation) and (c) area under the curve (AUC) from 0 to 24 hr.

The results in Table 13 and FIG. 14 indicate Compound 109's ability to attenuate Compound PC-5's ability to release hydromorphone in a dose dependent manner, both by suppressing Cmax and AUC and by delaying Tmax.

Example 26

Oral Administration of a Single Dose Unit and of Multiple Dose Units of a Composition Comprising Prodrug Compound PC-5 and Trypsin Inhibitor Compound 109 in Rats A saline solution of a composition comprising 0.87 μmol/kg (0.6 mg/kg) Compound PC-5 and 1.9 μmol/kg (1 mg/kg) Compound 109, representative of a single dose unit, was administered via oral gavage into a group of 4 rats. It is to be noted that the mole-to-mole ratio of trypsin inhibitor-to-prodrug (109-to-PC-5) is 2.2-to-1 as such this dose unit is referred to herein as a 109-to-PC-5 (2.2-to-1) dose unit. Saline solutions representative of (a) 2 dose units (i.e., a composition comprising 1.7 μmol/kg (1.2 mg/kg) Compound PC-5 and 3.8 μmol/kg (2 mg/kg) Compound 109), (b) 3 dose units (i.e., a composition comprising 2.6 μmol/kg (1.8 mg/kg) Compound PC-5 and 5.7 μmol/kg (3 mg/kg) Compound 109), and (c) 10 dose units (i.e., a composition comprising 8.7 μmol/kg (6 mg/kg) Compound PC-5 and 19 μmol/kg (10 mg/kg) Compound 109) of the 109-to-PC-5 (2.2-to 1) dose unit were similarly administered to additional groups of 4 rats. All rats were jugular vein-cannulated male Sprague Dawley rats that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 15A:
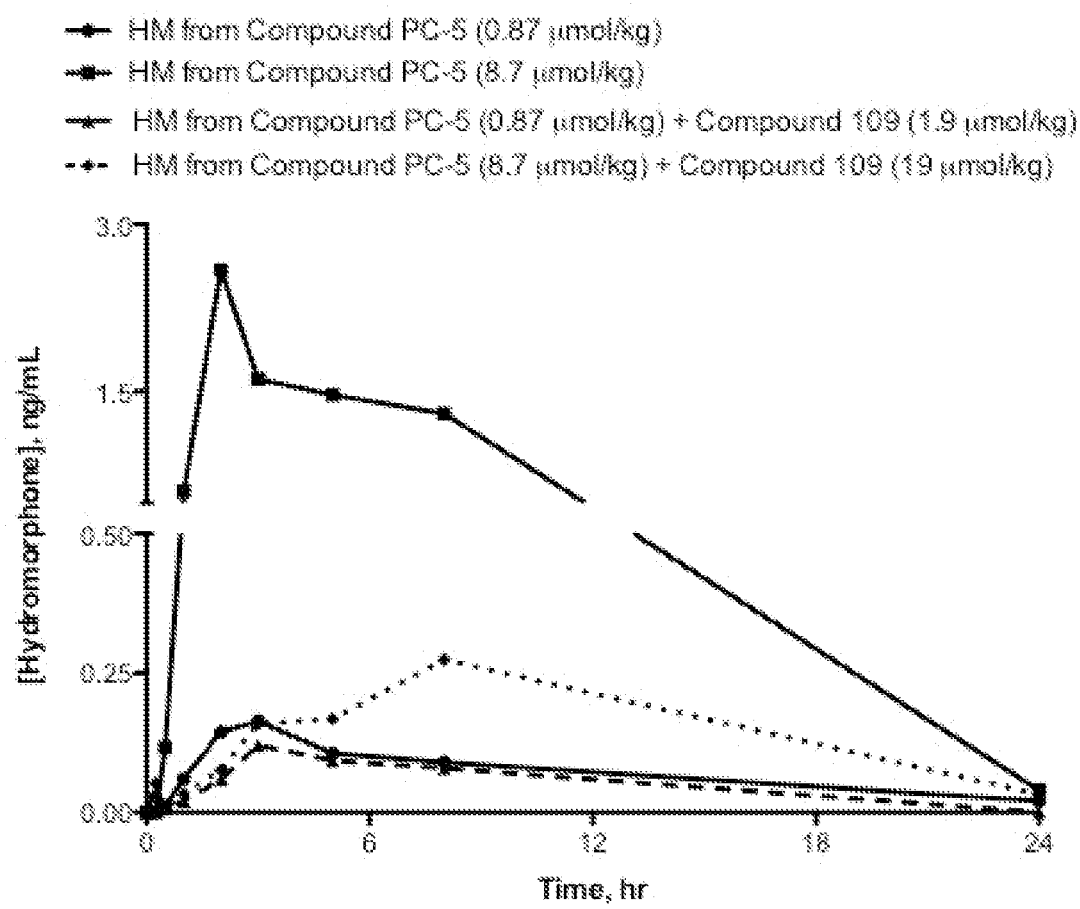
FIG. 15A and FIG. 15B compare mean plasma concentrations over time of hydromorphone release following PO administration of a single dose unit and of multiple dose units of a composition comprising prodrug Compound PC-5 and trypsin inhibitor Compound 109 to rats.
Figure 15B:
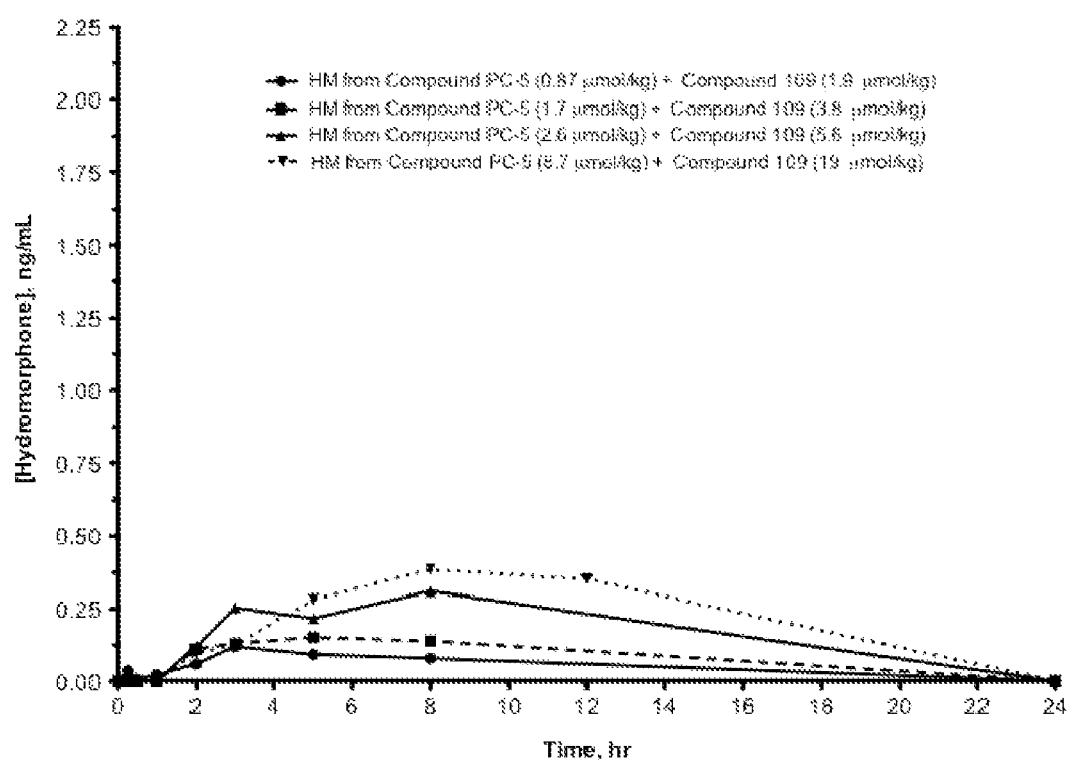

Table 14A and FIG. 15A provide hydromorphone exposure results for rats administered a single dose unit or 10 dose units of the 109-to-PC-5 (2.2-to 1) dose unit. Also provided are results, obtained as described in Example 25, for rats administered 0.87 μmol/kg (0.6 mg/kg) or 8.7 μmol/kg (6 mg/kg) of Compound PC-5 without trypsin inhibitor. Table 14B and FIG. 15B compare hydromorphone exposure results for rats administered 1, 2, 3 or 10 dose units of the 109-to-PC-5 (2.2-to 1) dose unit. Results in Table 14A and Table 14B are reported, for each group of 4 rats, as (a) maximum plasma concentration (Cmax) of hydromorphone (HM)

TABLE 13

Cmax, Tmax and AUC values of hydromorphone in rat plasma

| PC-5 Dose, mg/kg | PC-5 Dose, μmol/kg | Compound 109 Dose, mg/kg | Compound 109 Dose, μmol/kg | HM Cmax ± sd, ng/mL | Tmax ± sd, hr | AUC ± sd, ng × hr/mL |
|---|---|---|---|---|---|---|
| 0.6 | 0.87 | 0 | 0 | 0.196 ± 0.11 | 3.75 ± 2.9 | 1.33 ± 0.84 |
| 6 | 8.7 | 0 | 0 | 2.68 ± 1.2 | 2.50 ± 0.58 | 19.4 ± 5.7 |
| 6 | 8.7 | 0.1 | 0.19 | 2.84 ± 1.8 | 2.00 ± 0.0 | 19.3 ± 4.3 |
| 6 | 8.7 | 1 | 1.9 | 1.75 ± 1.0 | 3.25 ± 1.3 | 17.4 ± 8.4 |
| 6 | 8.7 | 5 | 9.3 | 0.669 ± 0.15 | 8.00 ± 0.0 | 7.54 ± 4.0 |
| 6 | 8.7 | 7.5 | 14 | 0.584 ± 0.18 | 4.56 ± 4.0 | 6.57 ± 3.5 |
| 6 | 8.7 | 10 | 19 | 0.295 ± 0.063 | 6.06 ± 3.9 | 2.29 ± 1.3 |

Lower limit of quantitation was 0.0250 ng/mL.

FIG. 14 compares mean plasma concentrations over time of hydromorphone release following PO administration of Compound PC-5 with increasing amounts of co-dosed trypsin inhibitor Compound 109.

(average±standard deviation), (b) time after administration of Compound PC-5 to reach maximum hydromorphone concentration (Tmax) (average±standard deviation) and (c) area under the curve (AUC) from 0 to 24 hr.

TABLE 14A

Cmax, Tmax and AUC values of hydromorphone in rat plasma

| PC-5 Dose, mg/kg | PC-5 Dose, μmol/kg | Compound 109 Dose, mg/kg | Compound 109 Dose, μmol/kg | HM Cmax ± sd, ng/mL | Tmax ± sd, hr | AUC ± sd, ng × hr/mL |
|---|---|---|---|---|---|---|
| 0.6 | 0.87 | 1 | 1.9 | 0.131 ± 0.027 | 4.25 ± 2.5 | 0.596 ± 0.24 |
| 6 | 8.7 | 10 | 19 | 0.295 ± 0.063 | 6.06 ± 3.9 | 2.29 ± 1.3 |
| 0.6 | 0.87 | 0 | 0 | 0.196 ± 0.11 | 3.75 ± 2.9 | 1.33 ± 0.84 |
| 6 | 8.7 | 0 | 0 | 2.68 ± 1.2 | 2.50 ± 0.58 | 19.4 ± 5.7 |

Lower limit of quantitation was 0.0500 ng/mL for both groups.

TABLE 14B

Cmax, Tmax and AUC values of hydromorphone in rat plasma

| PC-5 Dose, mg/kg | PC-5 Dose, μmol/kg | Compound 109 Dose, mg/kg | Compound 109 Dose, μmol/kg | HM Cmax ± sd, ng/mL | Tmax ± sd, hr | AUC ± sd, ng × hr/mL |
|---|---|---|---|---|---|---|
| 0.6 | 0.87 | 1 | 1.9 | 0.131 ± 0.027 | 4.25 ± 2.5 | 0.596 ± 0.24 |
| 1.2 | 1.7 | 2 | 3.8 | 0.165 ± 0.061 | 5.00 ± 2.4 | 0.918 ± 0.32 |
| 1.8 | 2.6 | 3 | 5.6 | 0.343 ± 0.18 | 5.50 ± 2.9 | 1.64 ± 0.80 |
| 6 | 8.7 | 10 | 19 | 0.438 ± 0.21 | 9.25 ± 3.4 | 3.05 ± 1.7 |

Lower limit of quantitation was 0.0500 ng/mL, except 0.87 μmol/kg dose was 0.0250 ng/mL FIG. 15A and FIG. 15B compare mean plasma concentrations over time of hydromorphone release following PO administration of a single dose unit and of multiple dose units of a composition comprising prodrug Compound PC-5 and trypsin inhibitor Compound 109.

The results in Table 14A, Table 14B, FIG. 15A and FIG. 15B indicate that administration of multiple dose units (as exemplified by 2, 3 and 10 dose units of the 109-to-PC-5 (2.2-to 1) dose unit) results in a plasma hydromorphone concentration-time PK profile that was not dose proportional to the plasma hydromorphone concentration-time PK profile of the single dose unit. In addition, the PK profile of the multiple dose units was modified compared to the PK profile of the equivalent dosage of prodrug in the absence of trypsin inhibitor.

Example 27

Pharmacokinetics of Compound PC-6 Following PO Administration to Rats

Saline solutions of Compound PC-6 were dosed as indicated in Table 15 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 16:
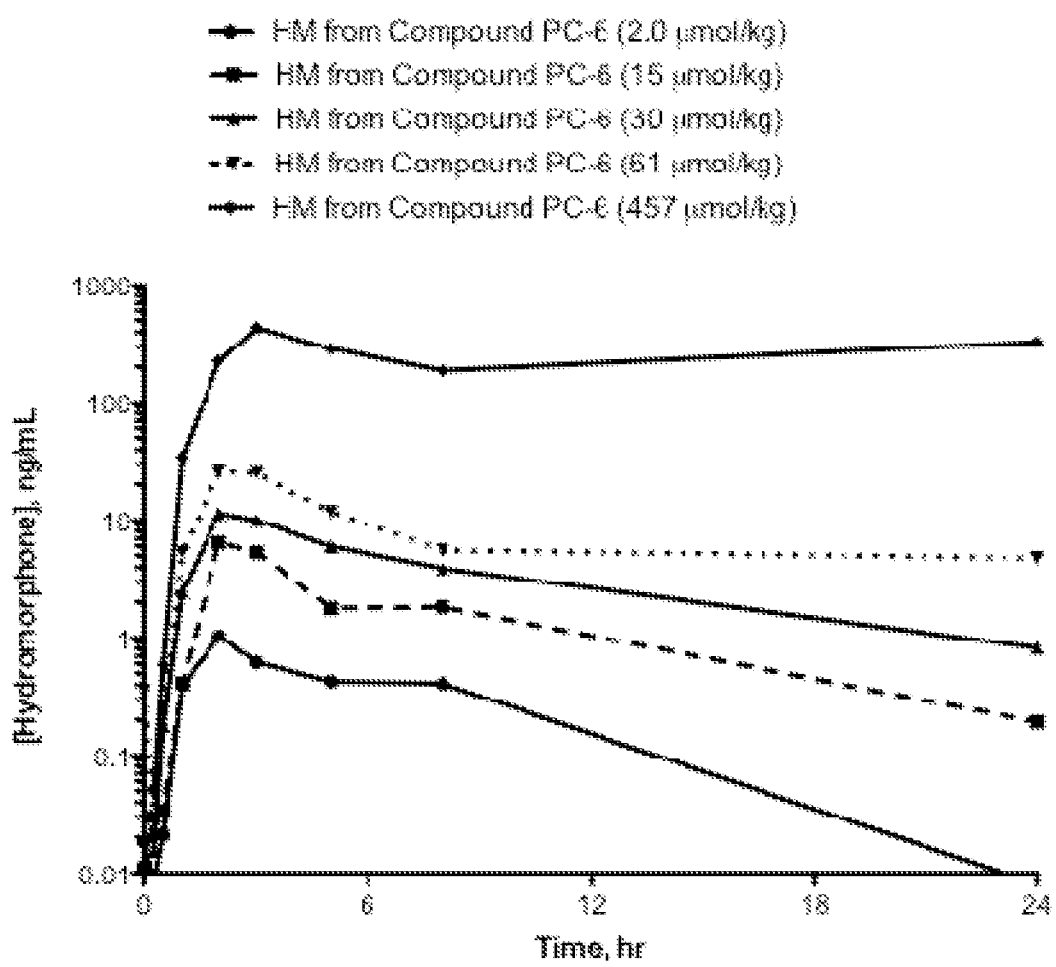
FIG. 16 compares mean plasma concentrations over time of hydromorphone release following PO administration of increasing doses of prodrug Compound PC-6 to rats.

Table 15 and FIG. 16 provide hydromorphone exposure results for rats administered different doses of Compound PC-6. Results in Table 15 are reported, for each group of 4 rats, as (a) maximum plasma concentration (Cmax) of hydromorphone (HM) (average±standard deviation), (b) time after administration of Compound PC-6 to reach maximum hydromorphone concentration (Tmax) (average±standard deviation) and (c) area under the curve (AUC) from 0 to 24 hr.

TABLE 15

Cmax, Tmax and AUC values of hydromorphone in rat plasma

| Compound | Dose, mg/kg | Dose μmol/kg | HM Cmax ± sd, ng/mL | Tmax ± sd, hr | AUC ± sd, ng × hr/mL |
|---|---|---|---|---|---|
| PC-6 | 1.4 | 2.0 | 1.05 ± 0.38* | 2.25 ± 0.5 | 4.78 ± 1.1 |
| PC-6 | 11 | 15 | 6.76 ± 5.3* | 3.50 ± 3 | 38.3 ± 17 |
| PC-6 | 22 | 30 | 11.9 ± 3.2* | 2.25 ± 0.50 | 87.4 ± 20 |
| PC-6 | 44 | 61 | 29.6 ± 15.0* | 2.25 ± 0.50 | 188 ± 41 |
| PC-6 | 327 | 457 | 633 ± 150^ | 30.5 ± 22 | 16200 ± 5600 |

*Lower limit of quantitation was 0.0250 ng/mL.
^Lower limit of quantitation was 0.0500 ng/mL.

FIG. 16 compares mean plasma concentrations over time of hydromorphone release following PO administration of increasing doses of Compound PC-6.

The results in Table 15 and FIG. 16 indicate that plasma concentrations of hydromorphone increase proportionally with Compound PC-6 dose.

Example 28

Oral Administration of Compound PC-6 Co-Dosed with Trypsin Inhibitor Compound 109 to Rats Saline solutions of Compound PC-6 were dosed with increasing co-doses of Compound 109 (Catalog No. 3081, Tocris Bioscience or Catalog No. WS38665, Waterstone Technology) as indicated in Table 16 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 17:
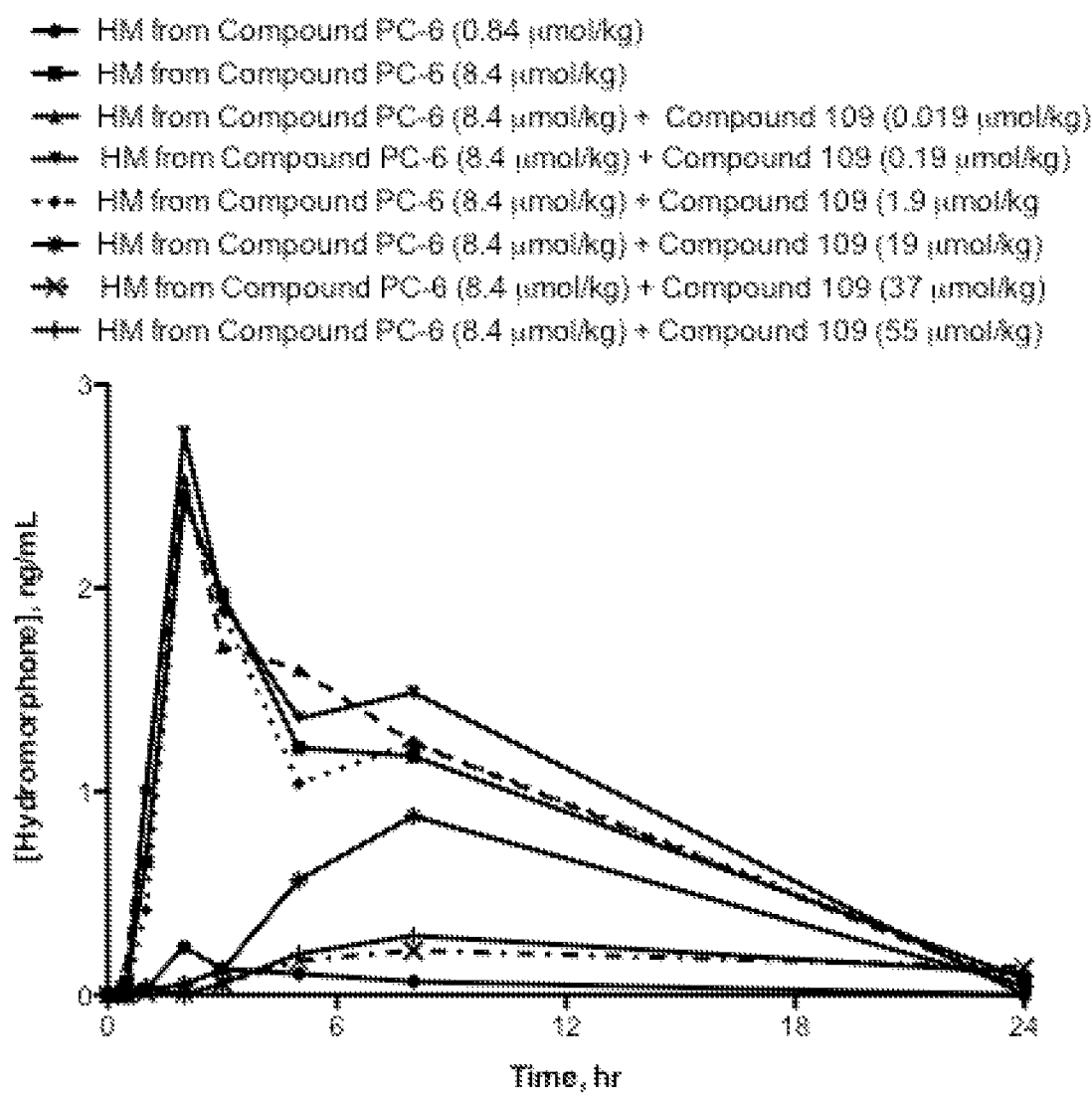
FIG. 17 compares mean plasma concentrations over time of hydromorphone release following PO administration of prodrug Compound PC-6 with increasing amounts of co-dosed trypsin inhibitor Compound 109 to rats.

Table 16 and FIG. 17 provide hydromorphone exposure results for rats administered Compound PC-6 and increasing doses of trypsin inhibitor. Results in Table 16 are reported, for each group of 4 rats, as (a) maximum plasma concentration (Cmax) of hydromorphone (HM) (average±standard deviation), (b) time after administration of Compound PC-6 to reach maximum hydromorphone concentration (Tmax) (average±standard deviation) and (c) area under the curve (AUC) from 0 to 24 hr.

TABLE 16

Cmax, Tmax and AUC values of hydromorphone in rat plasma

| PC-6 Dose mg/kg | PC-6 Dose µmol/kg | Compound 109 Dose, mg/kg | Compound 109 Dose, µmol/kg | HM Cmax ± sd, ng/mL | Tmax ± sd, hr | AUC ± sd, ng × hr/mL |
|---|---|---|---|---|---|---|
| 0.6 | 0.84 | 0 | 0* | 0.235 ± 0.093 | 2.00 ± 0.0 | 0.787 ± 0.31 |
| 6 | 8.4 | 0 | 0* | 2.51 ± 0.67 | 2.25 ± 0.50 | 18.8 ± 8.3 |
| 6 | 8.4 | 0.01 | 0.019* | 2.74 ± 0.42 | 2.75 ± 1.5 | 14.2 ± 5.2 |
| 6 | 8.4 | 0.1 | 0.19* | 2.76 ± 1.2 | 2.00 ± 0.0 | 12.0 ± 5.0 |
| 6 | 8.4 | 1 | 1.9* | 2.95 ± 0.44 | 2.25 ± 0.50 | 15.4 ± 6.1 |
| 6 | 8.4 | 10 | 19* | 0.880 ± 0.31 | 8.00 ± 0.0 | 6.75 ± 4.9 |
| 6 | 8.4 | 20 | 37^ | 0.326 ± 0.11 | 16.0 ± 9.2 | 3.75 ± 1.6 |
| 6 | 8.4 | 30 | 55^ | 0.350 ± 0.066 | 12.0 ± 8.0 | 2.94 ± 1.8 |

*Lower limit of quantitation was 0.050 ng/mL.
^Lower limit of quantitation was 0.0125 ng/mL.

FIG. 17 compares mean plasma concentrations over time of hydromorphone release following PO administration of Compound PC-6 with increasing amounts of co-dosed trypsin inhibitor.

The results in Table 16 and FIG. 17 indicate Compound 109's ability to attenuate Compound PC-6's ability to release hydromorphone in a dose dependent manner, both by suppressing Cmax and AUC and by delaying Tmax.

Example 29

Oral Administration of a Single Dose Unit and of Multiple Dose Units of a Composition Comprising Prodrug Compound PC-6 and Trypsin Inhibitor Compound 109 in Rats A saline solution of a composition comprising 0.84 µmol/kg (0.6 mg/kg) Compound PC-6 and 5.5 µmol/kg (3 mg/kg) Compound 109, representative of a single dose unit, was administered via oral gavage into a group of 4 rats. It is to be noted that the mole-to-mole ratio of trypsin inhibitor-to-prodrug (109-to-PC-6) is 6.5-to-1; as such this dose unit is referred to herein as a 109-to-PC-6 (6.5-to-1) dose unit. A saline solution of a composition representative of 10 dose units (i.e., a composition comprising 8.4 µmol/kg (6 mg/kg) Compound PC-6 and 55 tmol/kg (30 mg/kg) Compound 109) of the 109-to-PC-6 (6.5-to-1) dose unit, was similarly administered to a second group of 4 rats. All rats were jugular vein-cannulated male Sprague Dawley rats that had been fasted for 16-18 hr prior to oral dosing. At specified time points, blood samples were drawn, harvested for plasma via centrifugation at 5,400 rpm at 4° C. for 5 min, and 100 microliters (µl) plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 18:
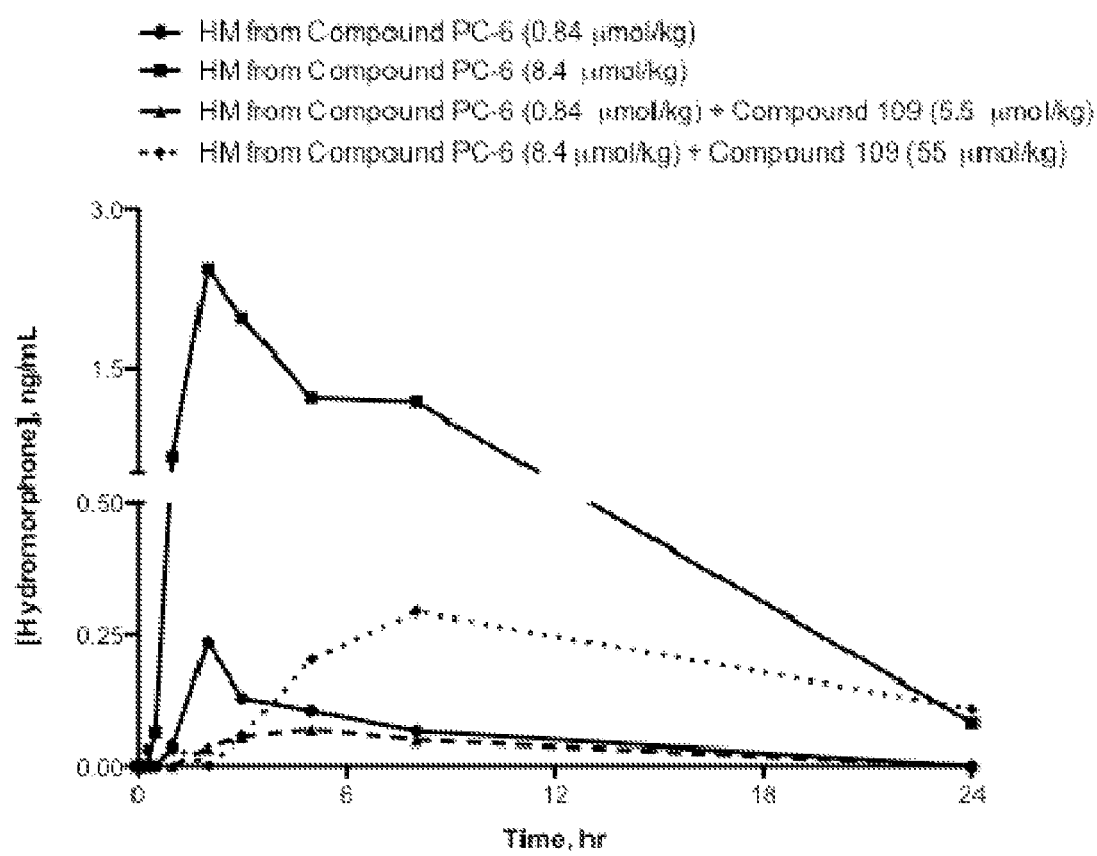
FIG. 18 compares mean plasma concentrations over time of hydromorphone release following PO administration of a single dose unit and of multiple dose units of a composition comprising prodrug Compound PC-6 and trypsin inhibitor Compound 109 to rats.

Table 17 and FIG. 18 provide hydromorphone exposure results for rats administered a single dose unit or 10 dose units of the 109-to-PC-6 (6.5-to-1) dose unit. Also provided are results, obtained as described in Example 28, for rats administered 0.84 µmol/kg (0.6 mg/kg) or 8.4 µmol/kg (6 mg/kg) of Compound PC-6 without trypsin inhibitor. Results in Table 17 are reported, for each group of 4 rats, as (a) maximum plasma concentration (Cmax) of hydromorphone (HM) (average±standard deviation), (b) time after administration of Compound PC-6 to reach maximum hydromorphone concentration (Tmax) (average±standard deviation) and (c) area under the curve (AUC) from 0 to 24 hr.

TABLE 17

Cmax, Tmax and AUC values of hydromorphone in rat plasma

| PC-6 Dose, mg/kg | PC-6 Dose, µmol/kg | Compound 109 Dose, mg/kg | Compound 109 Dose, µmol/kg | HM Cmax ± sd, ng/mL | Tmax ± sd, hr | AUC ± sd, ng × hr/mL |
|---|---|---|---|---|---|---|
| 0.6 | 0.84 | 3 | 5.5 | 0.0756 ± 0.043 | 3.75 ± 1.5 | 0.488 ± 0.11 |
| 6 | 8.4 | 30 | 55 | 0.350 ± 0.066 | 12.0 ± 8.0 | 2.94 ± 1.8 |
| 0.6 | 0.84 | 0 | 0 | 0.235 ± 0.093 | 2.00 ± 0.0 | 0.787 ± 0.31 |
| 6 | 8.4 | 0 | 0 | 2.51 ± 0.67 | 2.25 ± 0.50 | 18.8 ± 8.3 |

Lower limit of quantitation was 0.0500 ng/mL for both groups.

FIG. 18 compares mean plasma concentrations over time of hydromorphone release following PO administration of a single dose unit and of multiple dose units of a composition comprising prodrug Compound PC-6 and trypsin inhibitor Compound 109.

The results in Table 17 and FIG. 18 indicate that administration of multiple dose units (as exemplified by 10 dose units of the 109-to-PC-6 (6.5-to-1) dose unit) results in a plasma hydromorphone concentration-time PK profile that was not dose proportional to the plasma hydromorphone concentration-time PK profile of the single dose unit. In addition, the PK profile of the multiple dose units was modified compared to the PK profile of the equivalent dosage of prodrug in the absence of trypsin inhibitor.

Synthesis of Ketone-modified Opioid Prodrugs

Example 30

Synthesis of N,N-Bis(tert-butyl)N'-2-(chlorocarbonyl (methyl)amino)ethylcarbamate

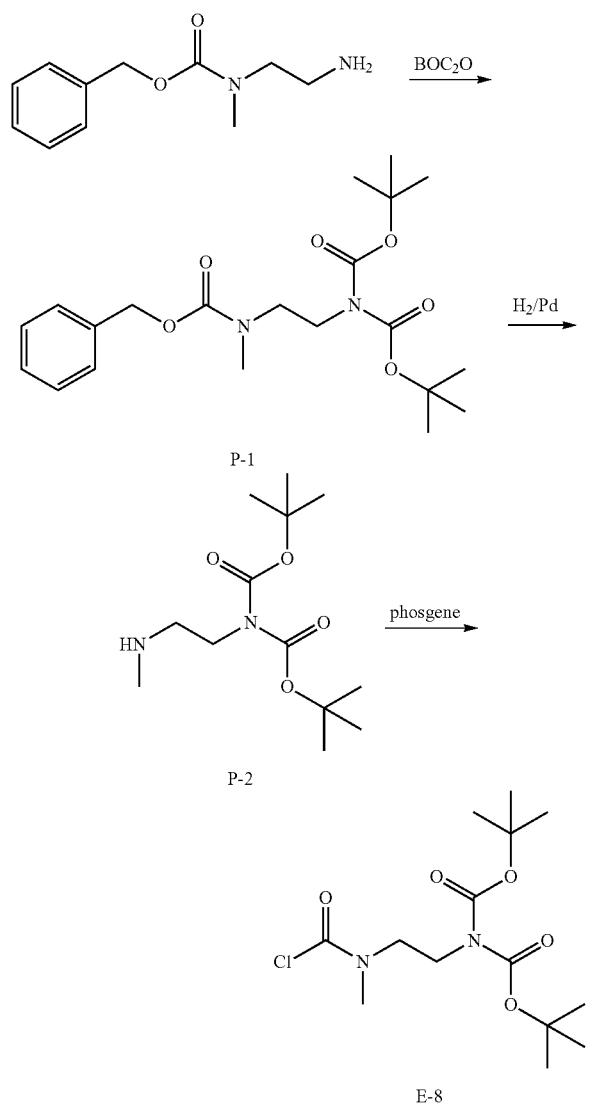

Synthesis of [2-(Benzyloxycarbonyl-methyl-amino)-ethyl]-dicarbamic acid tert-butyl ester (P-1)

2-(Aminoethyl)-methyl-carbamic acid benzyl ester (2.0 g, 9.6 mmol) was dissolved in dichloroethene (DCE) (20 mL) at room temperature. Triethyl amine (NEt₃) (1.40 mL, 11.5 mmol) was added, followed by di-tert-butyl dicarbonate (BOC₂O) (10.5 g, 48 mmol) and dimethylaminopyridine (DMAP) (120 mg). The reaction mixture was stirred at room temperature under nitrogen (N₂) for 2 h and then heated at 60° C. for 16 h. The reaction mixture was then concentrated. The residue was purified by silica gel chromatography, using 4/1 hexanes/EtOAc, to give P-1 in 86% yield (3.4 g, 8.3 mmol). MS: (m/z) calc: 408.2, observed (M+Na⁺) 431.9.

Synthesis of N1, N1-bis-BOC-N2-methylethane-1,2-diamine (P-2)

P-1 (1.3 g, 3.18 mmol) was dissolved in methanol/EtOAc (10 mL/3 mL respectively). The mixture was degassed and saturated with N₂. Palladium on carbon (Pd/C) (330 mg, 5% on carbon) was added. The mixture was shaken in a Parr hydrogenator flask (50 psi H₂) for 4 h. The mixture was then filtered through a celite pad and the filtrate was concentrated to give P-2 (1.08 g, yield exceeded quantative). P-2 was used without further purification.

Synthesis of N,N-Bis(tert-butyl)N'-2-(chlorocarbonyl (methyl)amino)ethylcarbamate (E-8)

P-2 (500 mg, 1.82 mmol) and NEt₃ (0.4 mL, 2.74 mmol) was mixed together in dichloromethane (4 mL). The mixture was added to a pre-chilled to 0° C. solution of phosgene (5.5 mL, 0.5 M in toluene). The reaction mixture was stirred at 0° C. for 1 h, followed by dilution with ether (20 mL) and filtered through filter paper. The filtrate was concentrated and passed through a short silica gel column (10 cm×3 cm), eluted with 3/1 hexanes/EtOAc. The fractions were concentrated to give N,N-Bis(tert-butyl) N'-2-(chlorocarbonyl(methyl)amino) ethylcarbamate (E-8) as a colorless solid in quantative yield (615 mg, 1.82 mmol). MS: (m/z) calc: 336.1, observed (M+Na⁺) 359.8.

Example 31

Synthesis of Oxycodone 6-(N-methyl-N-(2-amino)ethylcarbamate-2TFA

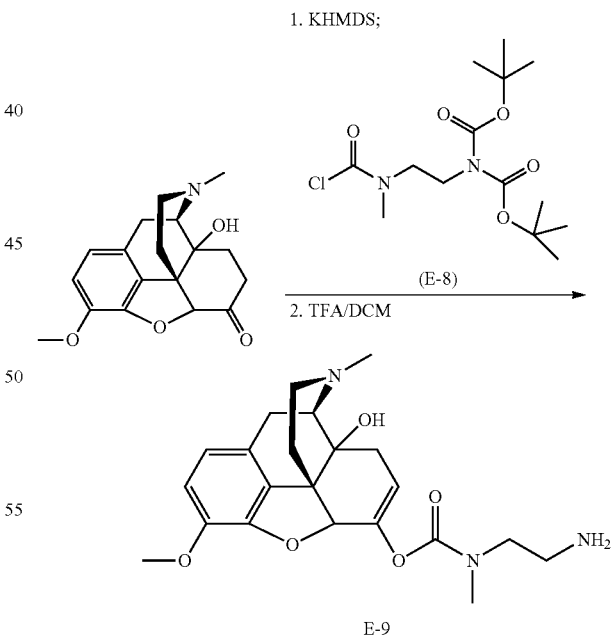

Synthesis of oxycodone 6-(N-methyl-N-(2-amino) ethylcarbamate-2TFA (E-9)

Oxycodone free base (6.5 g, 20.6 mmol) was dissolved in dry, degassed tetrahydrofuran (120 mL), and the mixture was cooled to −10° C. using dry ice/acetone bath. Potassium bis(trimethylsilyl)amide (KHMDS) (103.0 mL, 51.6 mmol, 0.5 M in toluene) was added via cannula. The mixture was stirred under $N_2$ at below −5° C. for 30 min. N,N-Bis(tert-butyl)N'-2-(chlorocarbonyl(methyl)amino)ethylcarbamate (8.0 g, 23.7 mmol), (E-8) prepared as described in the Example herein, in THF (30 mL) was then added via cannula over 15 min. The mixture was stirred at −5° C. for 30 min. Another portion of carbamoyl chloride (4.0 g, 11.9 mmol) in THF (10 mL) was added. The reaction was stirred at room temperature for 2 h. Sodium bicarbonate (10 mL, sat. aq.) was added. The mixture was concentrated in vacuo to half of its initial volume. EtOAc (50 mL) was added and layers were separated. The organic phase was further washed with water (3×20 mL), brine (40 mL) and then was concentrated. The residue was purified by silica gel chromatography, using DCM/MeOH (gradient 100/1 to 100/15) to afford a white foam in 55% yield (7.0 g, 13.4 mmol). This material was dissolved in a 1:1 mixture of DCM/trifluoroacetic acid (TFA) (20 mL/20 mL) at room temperature and stirred for 1 h. The solution was then concentrated in vacuo to afford oxycodone 6-(N-methyl-N-(2-amino)ethylcarbamate-2TFA as a thick oil (7.3 g, 11.4 mmol, 99% purity). MS: (m/z) calc: 415.2, observed (M+H$^+$) 416.5. The oxycodone 6-(N-methyl-N-(2-amino)ethylcarbamate-2TFA (E-9) was used without further purification.

Example 32

Synthesis of Oxycodone 6-(N-methyl-N-(2-N'-acetylarginylamino)) ethylcarbamate (Compound KC-2)

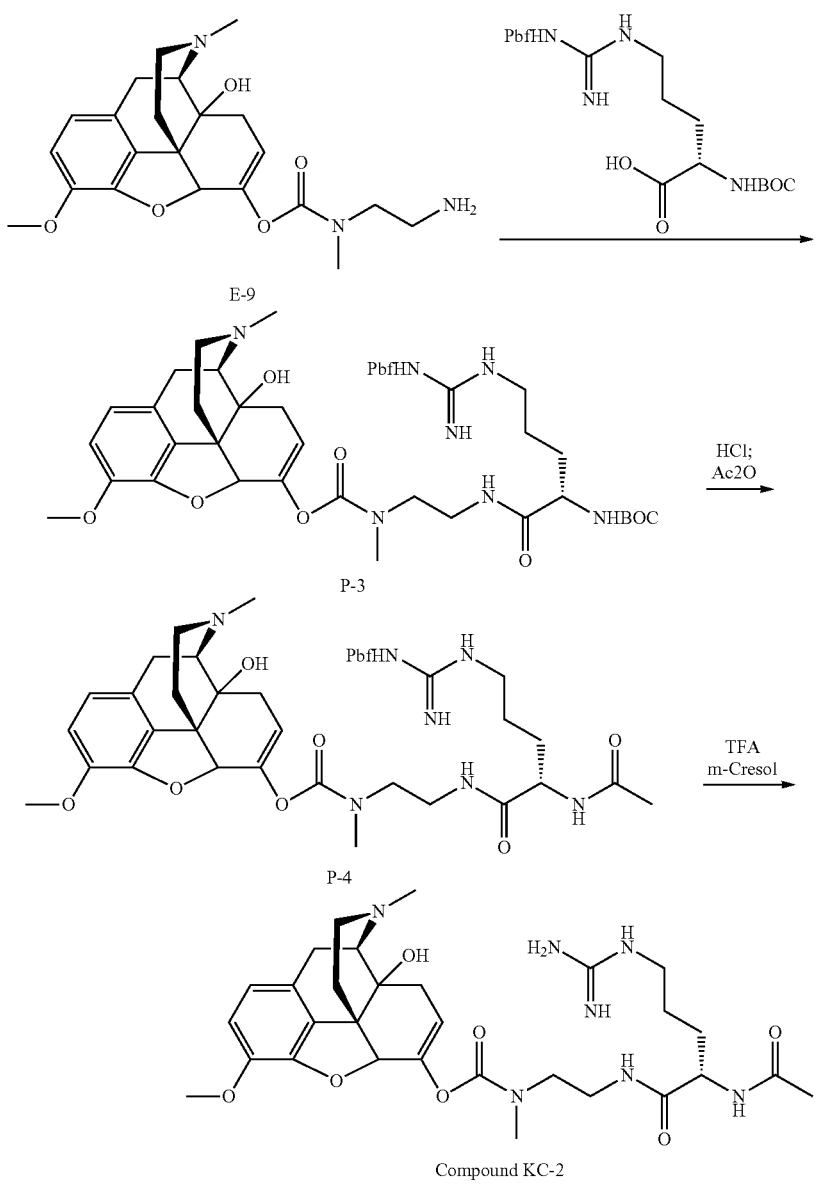

Compound KC-2

Preparation 52: Synthesis of oxycodone 6-(N-methyl-N-(2-N'-Boc-arginyl(Pbf)amino))ethylcarbamate (P-3)

Oxycodone 6-(N-methyl-N-(2-amino)ethylcarbamate-2TFA (7.3 g, 11.4 mmol), (E-9) prepared as described in the Example herein, was dissolved in dimethylformamide (DMF) (60 mL). Boc-Arg(Pbf)-OH (6.0 g, 11.4 mmol), HATU (4.75 g, 12.5 mmol) and diisopropylethylamine (DIPEA) (6.0 mL, 34.4 mmol) were added in this order. The reaction was stirred at room temperature for 2 h. The mixture was then concentrated in vacuo and the residue was partitioned between EtOAc/water (100 mL/60 mL). The organic layer was washed with water (60 mL), brine (50 mL), dried over $Na_2SO_4$ and concentrated to afford crude P-3 (11.0 g). P-3 was used without further purification.

Preparation 53: Synthesis of oxycodone 6-(N-methyl-N-(2-N'-acetylarginyl(Pbf)amino))ethylcarbamate (P-4)

P-3 (11.0 g), prepared as described above, was dissolved into dioxane (10 mL) and cooled to 0° C. A hydrochloric acid (HCl) solution in dioxane (4 N, 30 mL) was added. The mixture was stirred at room temperature for 3 h and then concentrated in vacuo. 10 g of the crude mixture was dissolved in a mixture of DIPEA (5.0 mL 28.5 mmol) in DCM (60 mL). Acetic anhydride (1.4 mL, 14.3 mmol) was added drop wise. The reaction mixture was stirred at room temperature for 2 h. $NaHCO_3$ (30 mL, sat. aq.) was then added. The layers were separated and the DCM layer was dried over $Na_2SO_4$, filtered and concentrated to afford P-4 (8.5 g). P-4 was used without further purification.

Synthesis of oxycodone 6-(N-methyl-N-(2-N'-acetylarginylamino))ethylcarbamate, as the bis-TFA salt (Compound KC-2)

P-4 (8.5 g) was dissolved in a mixture of m-cresol (3 mL) in TFA (30 mL). The mixture was stirred at room temperature for 3 h. TFA was then removed in vacuo. The residue was dissolved into MeOH (10 mL) and added drop wise to a stirred HCl solution in ether (40 mL, 2 M). The white solid was filtered and washed with ethyl ether (4×30 mL). The white solid was further purified by prep HPLC (*RP-18e C18 column (4.6×50 mm); flow rate 1.5 mL/min; mobile phase A: 0.1% TFA/water; mobile phase B 0.1% TFA/acetonitrile ($CH_3CN$); gradient elution), yielding Compound KC-2 (3.5 g, 4.1 mmol, 96.6% purity). MS: (m/z) calc: 613.7, observed ($M+H^+$) 614.5.

Example 33

Synthesis of N-{(S)-4-guanidino-1-[2-(methyl-[(5R,9R,13S,14S)-4,5a-epoxy-6,7-didehydro-14-hydroxy-3-methoxy-17-methylmorphinan-6-oxy]carbonyl-amino)-ethylcarbamoyl]-butyl}-malonamic acid (Compound KC-3)

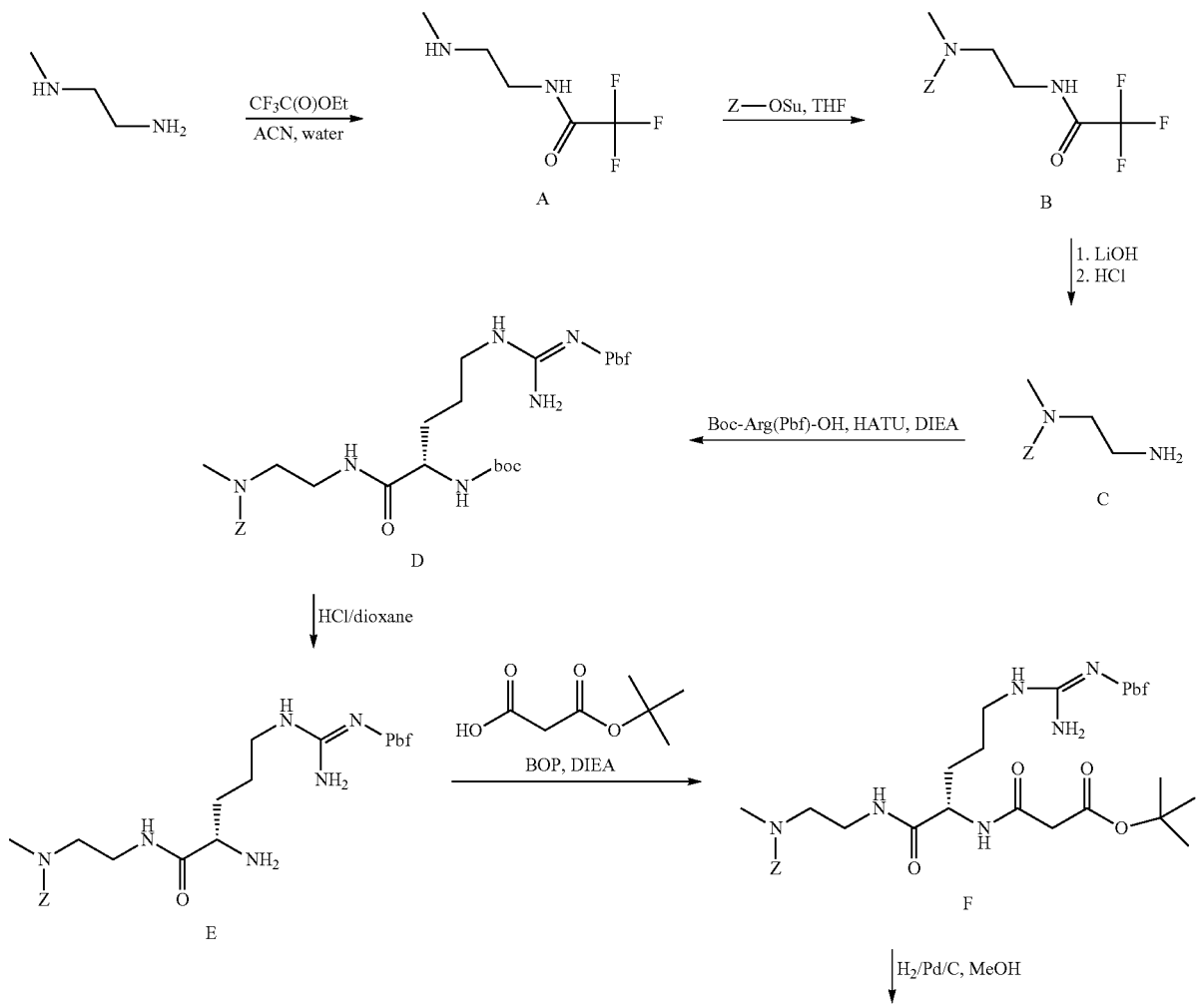

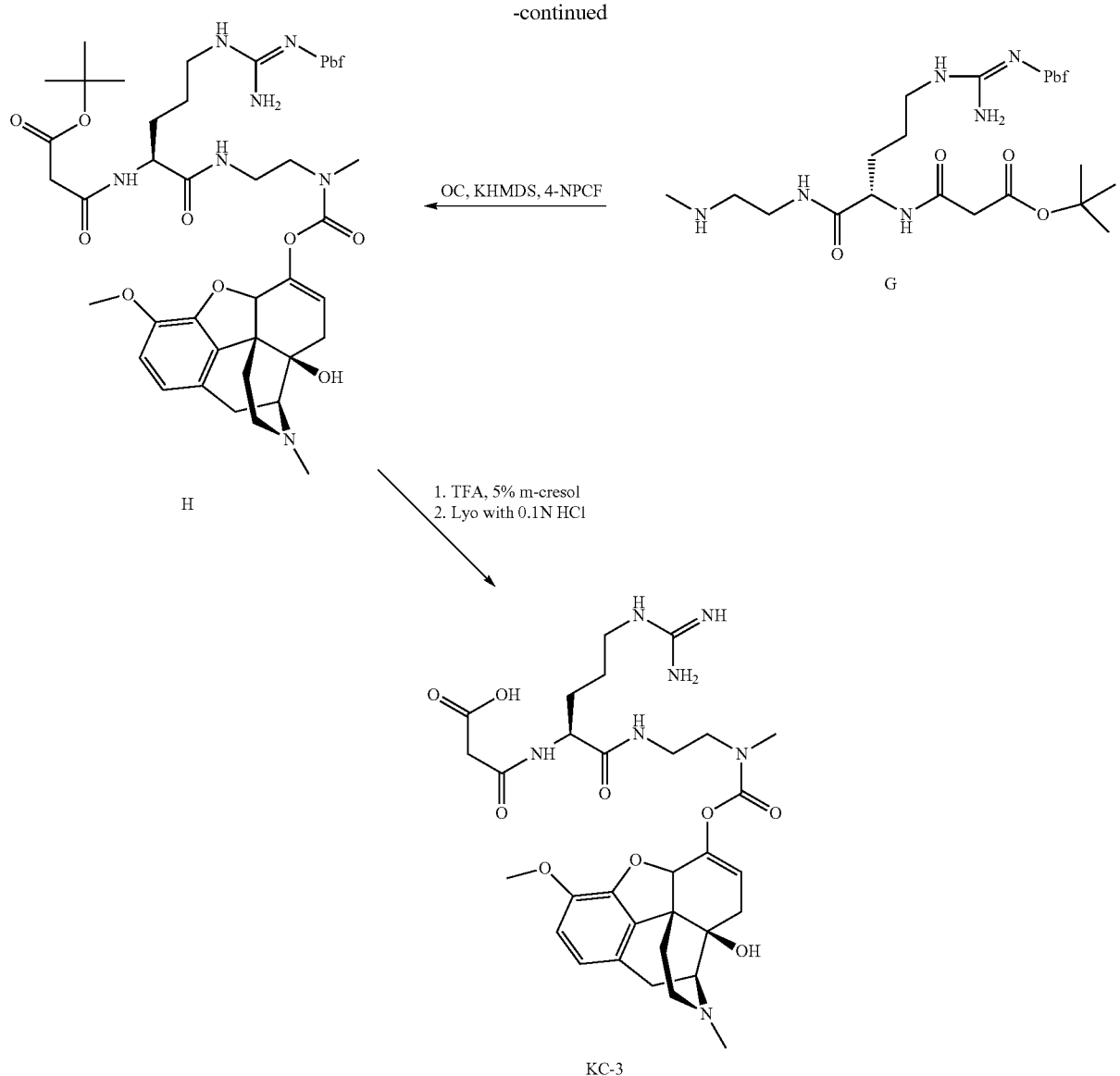

Preparation 54: Synthesis of 2,2,2-trifluoro-N-(2-methylamino-ethyl)-acetamide (A)

A solution of N-methylethylenediamine (27.0 g, 364 mmol) and ethyl trifluoroacetate (96.6 mL, 812 mmol) in a mixture of ACN (350 mL) and water (7.8 mL, 436 mmol) was refluxed with stirring overnight. Solvents were evaporated in vacuo. The residue was re-evaporated with i-PrOH (3×100 mL), followed by heat-cool crystallization from DCM (500 mL). Formed crystals were filtered, washed with DCM and dried in vacuo to provide compound A (88.3 g, 85%) as white solid powder.

Preparation 55: Synthesis of methyl-[2-(2,2,2-trifluoro-acetylamino)-ethyl]carbamic acid benzyl ester (B)

A solution of compound A (88.2 g, 311 mmol) and DIEA (54.1 mL, 311 mmol) in THF (350 mL) was cooled in an ice bath, followed by the addition of a solution of N-(benzyloxycarbonyl)succinimide (76.6 g, 307 mmol) in THF (150 mL) drop wise over the period of 20 min. The temperature of the reaction mixture was raised to ambient temperature and stirring was continued for an additional 30 min. Solvents were then evaporated and the resulting residue was dissolved in EtOAc (600 mL). The organic layer was extracted with 5% aq. NaHCO$_3$ (2×150 mL) and brine (150 mL). The organic layer was evaporated to provide compound B as yellowish oil. LC-MS [M+H] 305.1 (C$_{13}$H$_{15}$F$_3$N$_2$O$_3$+H, calc: 305.3). Compound B was used directly in the next reaction without purification as a MeOH solution.

Preparation 56: Synthesis of (2-amino-ethyl)-methyl-carbamic acid benzyl ester (C)

To a solution of compound B (~311 mmol) in MeOH (1.2 L) was added a solution of LiOH (14.9 g, 622 mmol) in water (120 mL). The reaction mixture was stirred at ambient temperature for 3 h. Solvents were evaporated to 75% of the initial volume followed by dilution with water (400 mL). The solution was extracted with EtOAc (2×300 mL). The organic layer was washed with brine (200 mL), dried over MgSO$_4$ and evaporated in vacuo. The residue was dissolved in ether (300 mL) and treated with 2 N HCl/ether (200 mL). Formed precipitate was filtrated, washed with ether and dried in vacuo to provide the hydrochloric salt of compound C (67.8 g, 89%) as a white solid. LC-MS [M+H] 209.0 (C$_{11}$H$_{16}$N$_2$O$_2$+H, calc: 209.3). Compound C was used directly in the next reaction without purification as a DMF solution.

Preparation 57: Synthesis of {2-[boc-Arg(Pbf)]-aminoethyl}-methyl-carbamic acid benzyl ester (D)

A solution of Boc-Arg(Pbf)-OH (16.0 g, ~30.4 mmol), compound C hydrochloride (8.2 g, 33.4 mmol) and DIEA (16.9 mL, 97.2 mmol) in DMF (150 mL) was cooled in an ice bath followed by the addition of a solution of HATU (13.8 g, 36.4 mmol) drop wise over 20 min. The temperature of the reaction mixture was raised to ambient temperature and stirring was continued for an additional 1 h. The reaction mixture was diluted with EtOAc (1 L) and extracted with water (3×200 mL) and brine (200 mL). The organic layer was dried over MgSO$_4$ and evaporated to provide compound D (24.4 g, yield exceeded quantitative) as a yellowish oil. LC-MS [M+H] 717.4 (C$_{35}$H$_{52}$N$_6$O$_8$S+H, calc: 717.9). Compound D was used directly in the next reaction without purification as a dioxane solution.

Preparation 58: Synthesis of {2-[H-Arg(Pbf)]-aminoethyl}-methyl-carbamic acid benzyl ester (E)

Compound D (24.4 g, ~30.4 mmol) was dissolved in dioxane (150 mL) and treated with 4 N HCl/dioxane (150 mL, 600 mmol) at ambient temperature for 1 h. The solvent was then evaporated. The residue was suspended in i-PrOH (100 mL) and the mixture was evaporated (procedure was repeated twice). The residue was then dried in vacuo to provide compound E (21.1 g, yield exceeded quantitative) as a yellowish solid. LC-MS [M+H] 617.5 (C$_{30}$H$_{44}$N$_6$O$_6$S+H, calc: 617.8). Compound E was used directly in the next reaction without purification as a DMF solution.

Preparation 59: Synthesis of {2-[2-tert-butylmalonyl-Arg(Pbf)]-aminoethyl}-methyl-carbamic acid benzyl ester (F)

A solution of compound E (21.1 g, ~30.4 mmol), mono-tert-butyl malonate (5.9 mL, 36.7 mmol), BOP (16.2 g, 36.7 mmol) and DIEA (14.9 mL, 83.5 mmol) in DMF (100 mL) was maintained at ambient temperature for 1 h. The reaction mixture was diluted with EtOAc (1 L) and extracted with water (500 mL), 5% aq. NaHCO$_3$ (500 mL), water (3×500 mL) and brine (500 mL). The organic layer was dried over MgSO$_4$, filtered, and then evaporated to provide compound F (24.5 g, 97%) as a yellowish amorphous solid. LC-MS [M+H] 759.6 (C$_{37}$H$_{54}$N$_6$O$_9$S+H, calc: 759.9). Compound F was used without further purification.

Preparation 60: Synthesis of N-{2-[2-tert-butylmalonyl-Arg(Pfb)]}—N'-methyl-ethane-1,2-diamine (G)

Compound F (12.3 g, 16.7 mmol) was dissolved in methanol (100 mL) followed by the addition of a Pd/C (5% wt, 2.0 g) suspension in water (2 mL). The reaction mixture was subjected to hydrogenation (Parr apparatus, 70 psi H$_2$) at ambient temperature for 1 h. The catalyst was filtered and washed with methanol. The filtrate was evaporated in vacuo to provide compound G (10.0 g, 99%) as a colorless amorphous solid. LC-MS [M+H] 625.5 (C$_{29}$H$_{48}$N$_6$O$_7$S+H, calc: 625.8). Compound G was used without further purification.

Preparation 61: Oxycodone free base

Oxycodone hydrochloride (10.0 g, 28.5 mmol) was dissolved in chloroform (150 mL) and washed with 5% aq. NaHCO$_3$ (50 mL). The organic layer was dried over MgSO$_4$ and evaporated. The residue was dried in vacuo overnight to provide oxycodone free base (8.3 g, 93%) as a white solid.

Preparation 62: Synthesis of N-{(S)-4-(2,2,4,6,7-pentamethyldihydrobenzofuran-5-sulfonyl-guanidino)-1-[2-(methyl-[(5R,9R,13S,14S)-4,5a-epoxy-6,7-didehydro-14-hydroxy-3-methoxy-17-methylmorphinan-6-oxy]carbonyl-amino)-ethylcarbamoyl]-butyl}-malonamic acid tert-butyl ester (H)

A solution of oxycodone free base (6.6 g, 21.0 mmol) in THF (400 mL) was cooled to −20° C., followed by addition of a 0.5 M solution of KHMDS in toluene (46.3 mL, 23.1 mmol). The obtained solution was then added to a solution of 4-nitro-phenyl chloroformate (4.3 g, 21.0 mmol) in THF (100 mL) drop wise over the period of 20 min at −20° C. The reaction was maintained at −20° C. for an additional 1 h, followed by addition of a solution of compound G (10.0 g, 16.1 mmol) in THF (200 mL) at −20° C. The reaction mixture was allowed to warm to ambient temperature and stirred overnight. Solvents were evaporated in vacuo. The resulting residue was dissolved in EtOAc (20 mL) and precipitated with ether (1 L). The formed precipitate was filtrated, washed with ether and dried in vacuo to provide compound H (13.6 g, 87%) as an off-white solid. LC-MS [M+H] 966.9 (C$_{48}$H$_{67}$N$_7$O$_{12}$S+H, calc: 966.2).

Synthesis of N-{(S)-4-guanidino-1-[2-(methyl-[(5R,9R,13S,14S)-4,5a-epoxy-6,7-didehydro-14-hydroxy-3-methoxy-17-methylmorphinan-6-oxy]carbonyl-amino)-ethylcarbamoyl]-butyl}-malonamic acid (Compound KC-3)

Compound H (13.6 g, 14.1 mmol) was dissolved in a mixture of 5% m-cresol/TFA (100 mL). The reaction mixture was maintained at ambient temperature for 1 h, followed by dilution with ethyl ether (1 L). The formed precipitate was filtered, washed with ether and hexane, and dried in vacuo to provide a TFA salt of Compound KC-3 (11.4 g, 81%) as an off-white solid. LC-MS [M+H] 658.6 (C$_{31}$H$_{43}$N$_7$O$_9$+H, calc: 658.7).

The TFA salt of crude Compound KC-3 (11.4 g, 11.4 mmol) was dissolved in water (50 mL). The obtained solution was subjected to HPLC purification. [Nanosyn-Pack YMC-GEL-ODS A (100-10) C-18 column (75×500 mm); flow rate: 250 mL/min; injection volume 50 mL; mobile phase A: 100% water, 0.1% TFA; mobile phase B: 100% ACN, 0.1% TFA; isocratic elution at 0% B in 4 min, gradient elution from 0% to 10% B in 20 min, isocratic elution at 10% B in 30 min, gradient elution from 10% B to 30% B in 41 min; detection at 254 nm]. Fractions containing Compound KC-3 were combined and concentrated in vacuo. The TFA counterion of the latter was replaced with an HCl counterion via lyophilization using 0.1N HCl to provide a HCl salt of Compound KC-3 (4.2 g, 41% yield) as a white solid. LC-MS [M+H] 658.6 (C$_{31}$H$_{43}$N$_7$O$_9$+H, calc: 658.7).

Example 34
Synthesis of N—((S)-1-{2-[(Dihydrocodein-6-eny-loxycarbonyl)-methylamino]-ethylcarbamoyl-4-guanidino}-butyl)-malonamic acid (Compound KC-4)
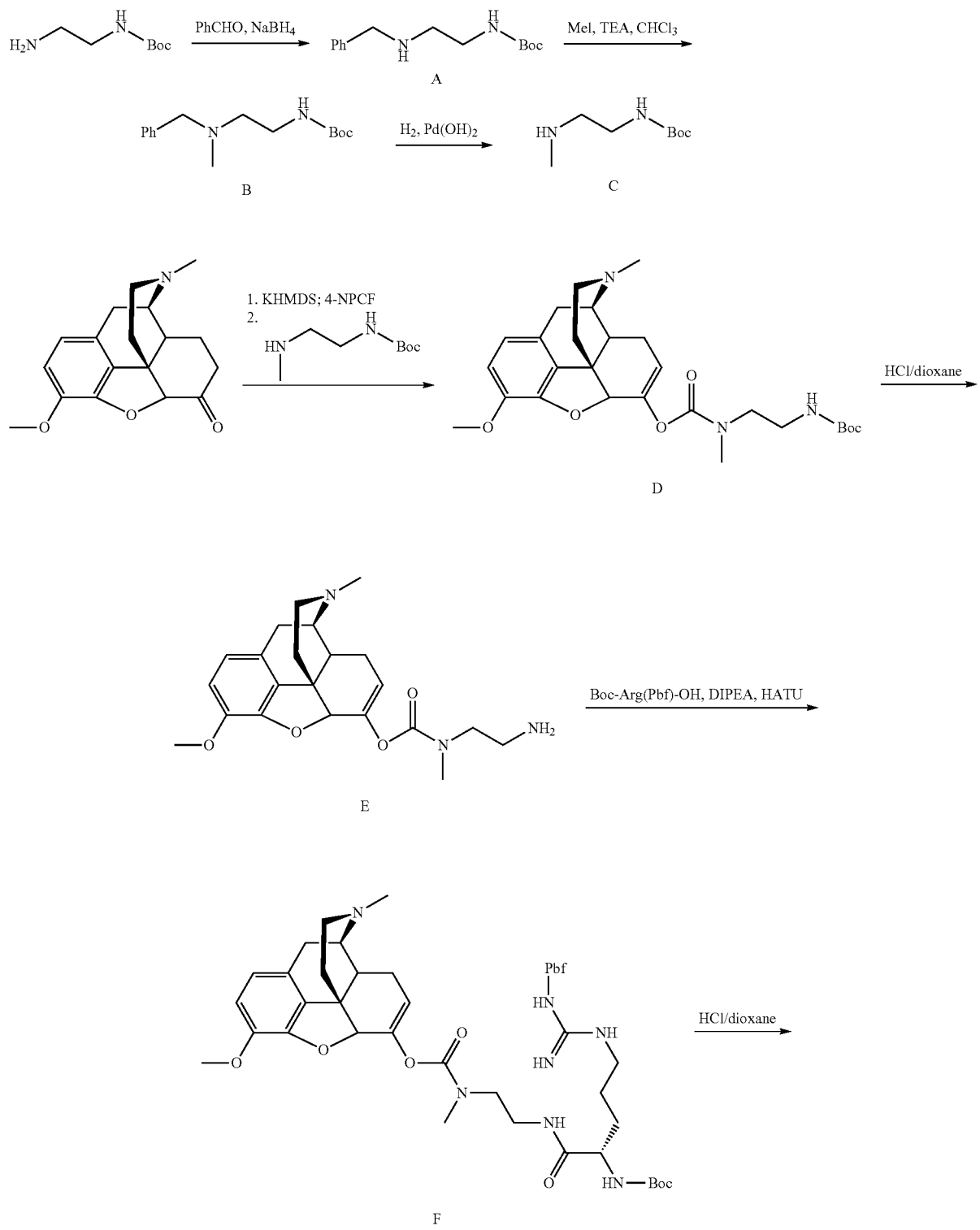

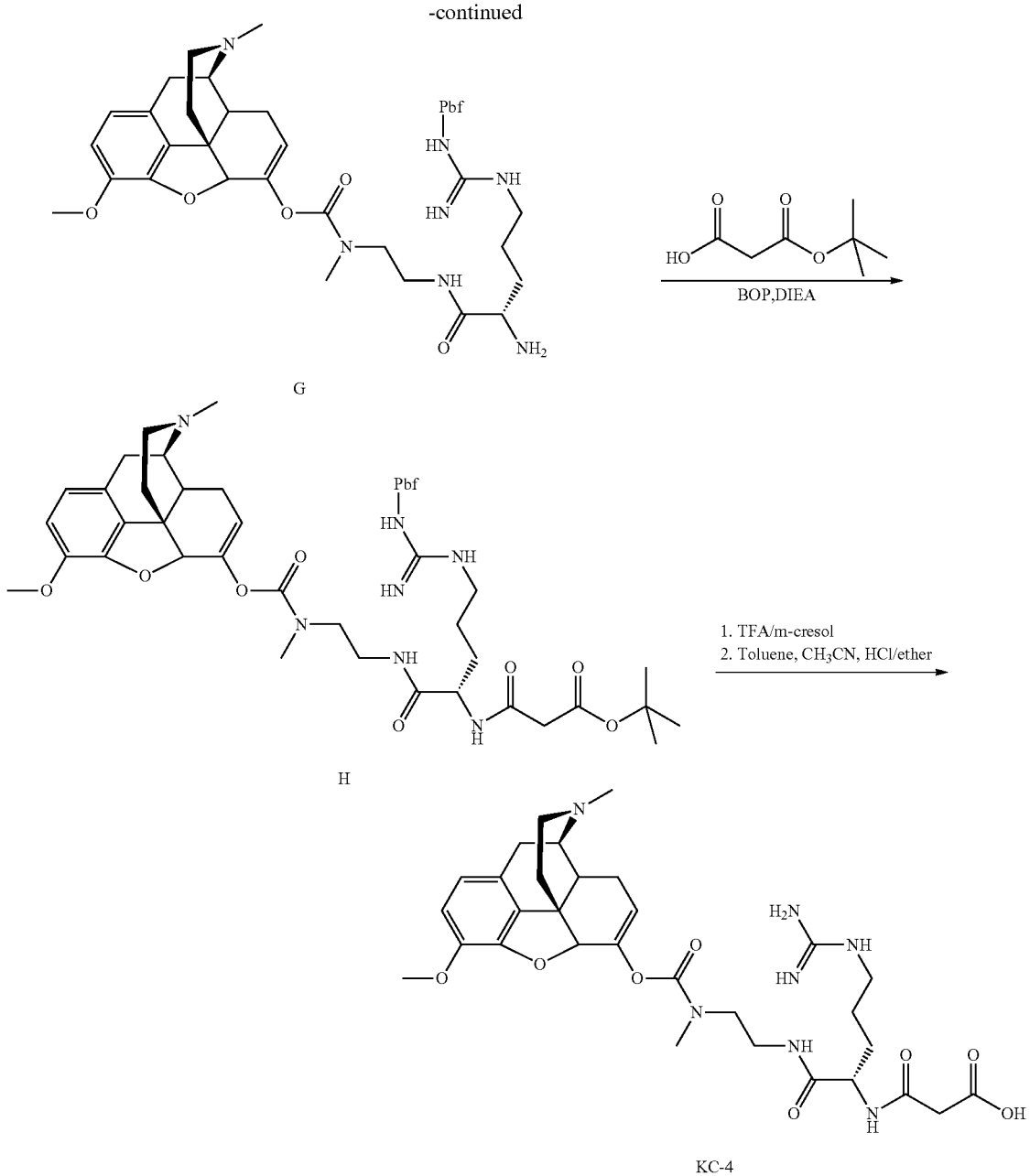

Preparation 63: Synthesis of tert-butyl 2-(benzylamino)ethylcarbamate (A)

To a solution of tert-butyl 2-aminoethylcarbamate (6.4 g, 40.0 mmol) in methanol (60 mL) was added benzaldehyde (4.7 g, 44.0 mmol) and molecular sieve 3 Å. After stirring at ambient temperature overnight, the mixture was cooled down to ca. −10° C. (ice/salt bath) and treated portion wise with NaBH$_4$ (9.1 g, 240.0 mmol) over 30 min. After complete addition, the bath was removed and the reaction mixture stirred at ambient temperature for 16 h. The solvent was evaporated and the residue taken into EtOAc (150 mL) and poured into water (100 mL). The organic layer was extracted with 0.5 N HCl (3×100 mL). The combined aqueous solution was cooled to 0° C., basified with sat. NaHCO$_3$ and extracted with CHCl$_3$ (3×100 mL). The combined organic layers were washed with brine (200 mL). After drying over MgSO$_4$ and filtering, the solvent was evaporated in vacuo to give compound A (9.2 g, 36.8 mmol, 92%) as a colorless oil. LC-MS [M+H] 251.2 (C$_{14}$H$_{22}$N$_2$O$_2$+H, calc: 251.3). TLC R$_f$(DCM/MeOH 9:1): 0.30. Compound A was used without further purification.

Preparation 64: Synthesis of tert-butyl 2-(N-benzyl-N-methylamino)ethylcarbamate (B)

To a cooled (~5° C.) solution of compound A (6.2 g, 25.0 mmol) and TEA (3.0 g, 29.7 mmol, 4.13 mL) in chloroform (50 mL) was added iodomethane (4.2 g, 29.7 mmol, 1.85 mL). The pressure tube was sealed, and the mixture stirred at ambient temperature for 20 h. The mixture was then precipitated with ether (300 mL); the white solid was filtered off and washed with ether (50 mL). The filtrate was concentrated and the residual yellow oil (5.2 g) was purified by silica gel column chromatography (2-10% MeOH gradient in DCM) to give compound B (3.3 g, 12.5 mmol, 50%) as a colorless oil. TLC $R_f$ (DCM/MeOH 9:1): 0.55. LC-MS [M+H] 264.3 ($C_{15}H_{24}N_2O_2$+H, calc: 264.4).

Preparation 65: Synthesis of tert-butyl 2-(methylamino)ethylcarbamate (C)

To a flask was added 20% $Pd(OH)_2$ on carbon (3.1 g), compound B (3.3 g, 12.5 mmol) in MeOH (200 mL) and water (10 mL), while being exposed to $H_2$ (40 psi). After 2.5 h, the reaction mixture was filtered through celite and concentrated in vacuo. Water was then added (50 mL) and the mixture brought to pH 12 (by addition of 1 N NaOH) and extracted with DCM (3×50 mL). The combined organic layers were dried over $MgSO_4$, filtered, and concentrated in vacuo to give compound C (2.0 g, 11.7 mmol, 94%) as a colorless oil. LC-MS [M+H] 686.5 ($C_{35}H_{51}N_5O_7S$+H, calc: 685.9). Compound C was used without further purification.

Preparation 66: Synthesis of [2-(N-dihydrocodein-6-enyloxycarbonyl-N-methylamino)ethyl]carbamic acid tert-butyl ester (D)

To a cooled (−5° C.) solution of hydrocodone (2.9 g, 9.8 mmol, free base) in anhydrous THF (150 mL) was added drop wise, a 0.5 M solution of KHMDS in toluene (11.6 mmol, 23.3 mL) over 20 min. The yellow solution was stirred at this temperature for 30 min. The solution was added through a cannula to a cooled solution (−30° C.) of 4-nitrophenyl chloroformate (1.9 g, 9.5 mmol) in anhydrous THF (40 mL) over 15 min. The bath was removed and the mixture stirred at ambient temperature for 15 min until treated drop wise with a solution of compound C (2.3 g, 11.6 mmol) in anhydrous THF (15 mL) over 10 min. After stirring at ambient temperature for 18 h, the reaction mixture was quenched with sat. $NaHCO_3$ solution (7 mL). The resulting precipitate was filtered, washed with EtOAc (30 mL) and the filtrate concentrated in vacuo. The residue was taken into EtOAc (300 mL) and washed with a mixture of water (100 mL) and 2% aq. $H_2SO_4$ (30 mL). The aqueous layer was basified with 2 N NaOH to pH 12 and extracted with EtOAc (2×200 mL). The combined organic layers were washed with water (2×400 mL) and brine (300 mL), dried over $MgSO_4$, filtered and concentrated in vacuo to give a yellowish foamy solid (5.9 g), which was purified by HPLC. [Nanosyn-Pack Microsorb (100-10) C-18 column (50×300 mm); flow rate: 100 mL/min; injection volume: 65 mL; mobile phase A: 100% water, 0.1% TFA; mobile phase B: 100% acetonitrile, 0.1% TFA; isocratic elution at 10% B in 5 min, gradient elution to 18% B in 8 min, isocratic elution at 18% B in 20 min, gradient elution from 18% B to 40% B in 44 min; detection at UV 254 nm]. Fractions containing the desired compound were combined and concentrated in vacuo. Traces of water were removed by treating the residue with toluene (30 mL) followed by evaporation in vacuo (procedure was repeated twice). The isolated fractions are a 1:1 mixture of compound D and the boc deprotected compound E (4.37 g, 7.85 mmol, 83%). LC-MS [M+H] 500.2 ($C_{27}H_{37}N_3O_6$+H, calc: 500.6). Retention time [Chromolith SpeedRod RP-18e C18 column (4.6×50 mm); flow rate: 1.5 ml/min; mobile phase A: 0.1% TFA/water; mobile phase B 0.1% TFA/ACN; gradient elution from 5% B to 100% B over 9.6 min, detection 254 nm]: 3.52 min (compound D), 1.82 (compound E).

Preparation 67: Synthesis of dihydrocodein-6-enyl-2-aminoethylmethylcarbamate (E)

A solution of compound D (4.4 g, 8.8 mmol) in DCM (40 mL) was treated with 4 M HCl in dioxane (105 mmol, 26 mL), leading to some precipitate formation. The mixture was homogenized by addition of acetonitrile (20 mL) and stirred at ambient temperature for 45 min. Ether (400 mL) was added and the resulting white precipitate filtered, washed with ether (50 mL) and hexane (50 mL) and then dried in vacuo to give compound E as an off-white solid (2.4 g, 4.7 mmol, 58%). LC-MS [M+H] 400.3 ($C_{22}H_{29}N_3O_4$+H, calc: 400.5). Compound E was used without further purification.

Preparation 68: Synthesis of {2-[boc-Arg(Pbf)]-aminomethyl}-ethyl carbamic acid hydrocodone ester (F)

Compound E (2.0 g, 4.0 mmol), Boc-Arg(Pbf)-OH (2.0 g, 3.8 mmol) and HATU (1.7 g, 4.3 mmol) were dissolved in DMF (40 mL), brought to ~5° C. and treated drop wise with DIPEA (3.2 mL, 18.1 mmol) over 10 min. The reaction mixture was stirred at ~5° C. for an additional 10 min and then warmed to ambient temperature, followed by stirring for 30 min. The reaction was then diluted with EtOAc (200 mL) and poured into water (250 mL). The layers were separated, the aqueous extracted with EtOAc (2×150 mL) and the combined organic layers washed with 2% aq. $H_2SO_4$ (30 mL), water (2×250 mL) and brine (250 mL). The organic layer was dried over $MgSO_4$, filtered and concentrated in vacuo to give compound F (3.0 g, 3.2 mmol, 83%) as a yellowish foamy solid. LC-MS [M+H] 908.7 ($C_{46}H_{65}N_7O_{10}S$+H, calc: 909.1). Compound F was used without further purification.

Preparation 69: Synthesis of {2-[H-Arg(Pbf)]-aminomethyl}-ethyl carbamic acid hydrocodone ester (G)

A solution of compound F (3.0 g, 3.3 mmol) in DCM (20 mL) was treated with 4 M HCl in dioxane (39 mmol, 9.8 mL) and stirred at ambient temperature for 30 min. Ether (500 mL) was added and the resulting white precipitate was filtered, washed with ether (50 mL) and hexane (50 mL) and then dried in vacuo to give compound G as an off-white solid (2.7 g, 3.0 mmol, 93%). LC-MS [M+H] 808.7 ($C_{41}H_{57}N_7O_8S$+H, calc: 809.0). Compound G was used without further purification.

Preparation 70: Synthesis of N—((S)-1-{2-[(Dihydrocodein-6-enyloxycarbonyl)-methylamino]-ethyl-carbamoyl-4-guanidino(Pbf))-butyl}-malonamic acid tert-butyl ester (H)

To a cooled solution (~5° C.) of compound G (2.7 g, 3.0 mmol) was added mono tert-Butyl malonate (474 mg, 3.0 mmol, 438 µL) in DMF (25 mL) followed by BOP (1.4 g, 3.2 mmol) over 5 min and finally by DIEA (1.6 g, 12.1 mmol, 2.1 mL) drop wise over 10 min. After an additional 15 min, the ice bath was removed and the mixture stirred at ambient temperature. After 45 min, the reaction mixture was diluted with EtOAc (300 mL) and poured into water (200 mL). The layers were separated and the aqueous layer extracted with EtOAc (2×250 mL). The combined organic layers were washed with water (500 mL), 2% aq. $H_2SO_4$ (100 mL), water (3×500 mL) and brine (2×500 mL). After drying over $MgSO_4$, the solvent was evaporated in vacuo and the residue dried under high vacuum to give H (1.7 g, 1.8 mmol, 58%) as a yellowish solid. LC-MS [M+H] 950.8 ($C_{48}H_{67}N_7O_{11}S$+H, calc: 951.2). Compound H was used without further purification.

Synthesis of N—((S)-1-{2-[(Dihydrocodein-6-enyloxycarbonyl)-methylamino]-ethylcarbamoyl-4-guanidino-butyl)-malonamic acid (Compound KC-4)

A solution of compound H (1.7 g, 1.8 mmol) in 5% m-cresol/TFA (45 mL) was stirred at ambient temperature. After 1 h, the mixture was diluted with ether (300 mL). The resulting fine suspension was filtered, the solid washed with ether (30 mL) and hexane (30 mL) and dried in vacuo for 15 min. The crude material was dissolved in water (35 mL) and purified by HPLC [Nanosyn-Pack Microsorb (100-10) C-18 column (50×300 mm); flow rate: 100 mL/min; injection volume: 35 mL; mobile phase A: 100% water, 0.1% TFA; mobile phase B: 100% acetonitrile, 0.1% TFA; gradient elution 0 to 10% B in 10 min, isocratic elution at 10% B in 20 min, gradient elution from 10% B to 42% B in 60 min; detection at UV 254 nm]. Fractions containing the desired compound were combined and concentrated in vacuo. The residue was treated with toluene (50 mL) to remove traces of water and co-evaporated in vacuo (procedure repeated twice). The residue was dissolved in acetonitrile (5 mL), treated with 2.0 M HCl in ether (20 mL), followed by dilution with ether (100 mL). The resulting solid was filtered, washed with ether (20 mL) and hexane (20 mL) and dried in vacuo overnight to provide Compound KC-4 (1.1 g, 86% yield) as a white solid, hydrochloride salt. LC-MS [M+H] 642.5 ($C_{31}H_{43}N_7O_8$+H, calc: 642.7). Purity >95% (UV/254 nm). Retention time [Chromolith SpeedRod RP-18e C18 column (4.6×50 mm); flow rate: 1.5 ml/min; mobile phase A: 0.1% TFA/water; mobile phase B 0.1% TFA/ACN; gradient elution from 5% B to 100% B over 9.6 min, detection 254 nm]: 2.24 min.

Example 35

Synthesis of 6-{[2-(2-Acetylamino-5-guanidino-pentanoylamino)-ethyl]-[(5R,9R,13S,14S)-4,5a-epoxy-6,7-didehydro-14-hydroxy-3-methoxy-17-methylmorphinan-6-oxy]-1-enyloxycarbonyl-amino}-hexanoic acid (Compound KC-5)

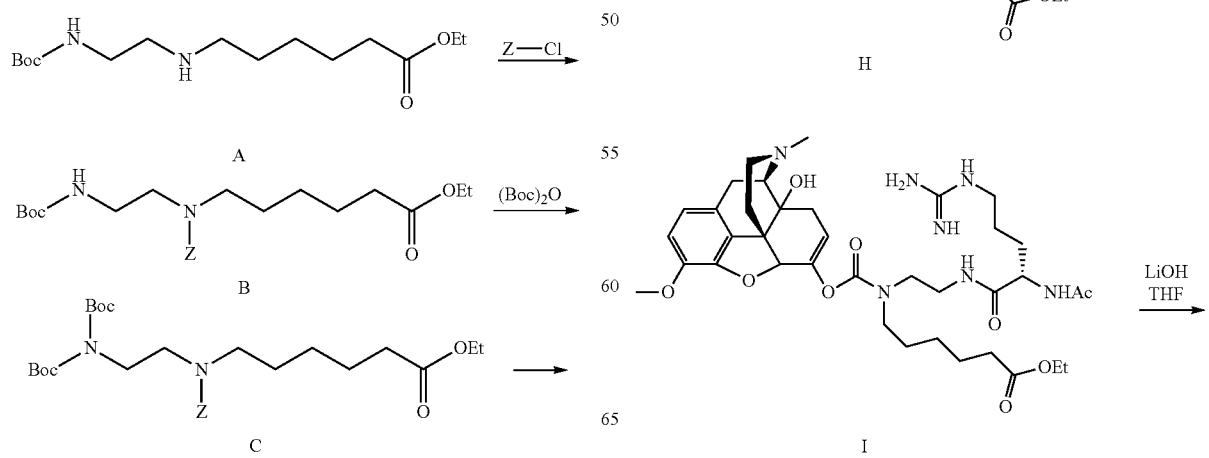

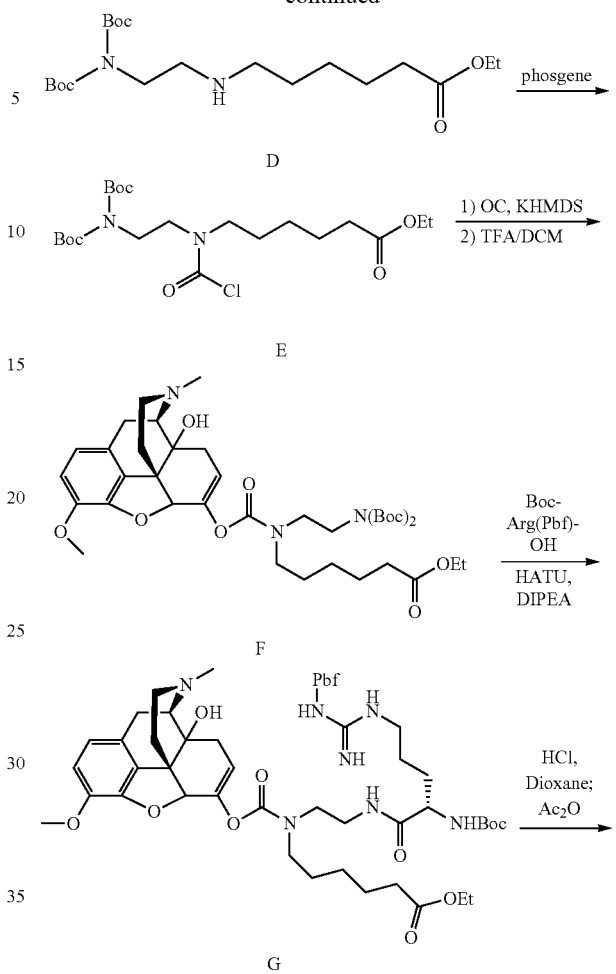

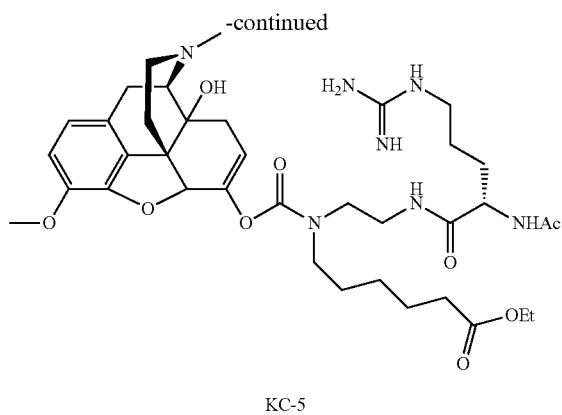

KC-5

Preparation 71: Synthesis of 6-[Benzyloxycarbonyl-(2-tert-Butoxycarbonylamino-ethyl)-amino]-hexanoic acid ethyl ester (B)

Compound A (26.8 g, 88.6 mmol) was dissolved in DCM (200 mL) at ambient temperature. $NEt_3$ (12.5 mL, 88.6 mmol) was added, followed by Cbz-Cl (Z—Cl) (12.5 mL, 88.6 mmol). The reaction mixture was stirred at ambient temperature under $N_2$ for 2 h. The reaction mixture was treated with $NaHCO_3$ (30 mL, aq. sat.). The layers were separated and the organic layer was dried over $MgSO_4$, filtered and concentrated. The residue was purified by silica gel chromatography, using 4/1 hexanes/EtOAc, to give compound B as a colorless oil (22.5 g, 66.5 mmol, 75%).

Preparation 72: Synthesis of Intermediate (C)

Compound B (22.0 g, 50.4 mmol) was dissolved in DCE (100 mL) at ambient temperature. $NEt_3$ (8.5 mL, 61 mmol) was added, followed by $(Boc)_2O$ (33.0 g, 151.2 mmol) and DMAP (615 mg, 5.0 mmol). The reaction mixture was stirred at ambient temperature under $N_2$ for 2 h and then heated at 60° C. for 16 h. The reaction mixture was concentrated, and the residue was purified by silica gel chromatography, using 4/1 hexanes/EtOAc, to give compound C as a colorless oil (23.2 g, 41.9 mmol, 86%). MS: (m/z) calc: 536.6, observed (M+Na$^+$) 560.1.

Preparation 73: Synthesis of Intermediate (D)

Compound C (22.5 g, 41.9 mmol) was dissolved in EtOH (50 mL). The mixture was degassed and saturated with $N_2$. Pd/C (500 mg, 5% on carbon) was added. The mixture was shaken in a Parr hydrogenator flask under 2 atm $H_2$ for 2 h. The mixture was then filtered through a celite pad and the filtrate was concentrated to give crude compound D as a colorless oil (21.0 g, 52.2 mmol, crude). This material was used without further purification.

Preparation 74: Synthesis of Intermediate (E)

Compound D (21.0 g, 52.2 mmol, crude) and $NEt_3$ (11.0 mL, 78.3 mmol) were mixed together with DCM (150 mL). The mixture was added to a pre-chilled (ice/water bath) phosgene solution in toluene (41.2 mL, 20% wt in toluene, ~83.3 mmol). The reaction mixture was stirred at 0° C. for 2 h. The mixture was then concentrated to one-third of its original volume and diluted with ether (50 mL). The mixture was filtered through filter paper. The filtrate was concentrated to give compound E as a white solid (20.0 g, 43.1 mmol, 82%) MS: (m/z) calc: 464.2, observed (M+Na$^+$) 487.7. Compound E was used without further purification.

Preparation 75: Synthesis of Intermediate (F)

Oxycodone free base (1.0 g, 3.2 mmol) was dissolved in dry THF (degassed) (15 mL) and the mixture was cooled to −10° C. using a dry ice/acetone bath. KHMDS (7.6 mL, 3.8 mmol, 0.5 M in toluene) was added via syringe. The mixture was stirred under $N_2$ at a temperature below −5° C. for 30 min. Compound E (1.5 g, 3.2 mmol) in THF (10 mL) was then added via syringe over 5 min. The mixture was stirred at −5° C. for 30 min. The reaction was continued at ambient temperature for 2 h. $NaHCO_3$ (10 mL, sat. aq.) was added. The mixture was then concentrated in vacuo to half of its initial volume. EtOAc (20 mL) was added and the layers were separated. The organic phase was further washed with water (20 mL) and brine (20 mL), followed by concentration with the resulting residue purified by silica gel chromatography (DCM/MeOH (gradient 100/1 to 100/15)) to afford a colorless oil (~1.7 g, 3.1 mmol, 97%). This material was dissolved in a mixture of DCM/TFA (5 mL/5 mL) at ambient temperature and stirred for 1 h. It was then concentrated in vacuo to afford compound F as its TFA salt (1.8 g, 2.7 mmol, 88%). MS: (m/z) calc: 543.7, observed (M+H$^+$) 545.2. Compound F was used without further purification.

Preparation 76: Synthesis of Intermediate (G)

Compound F (1.8 g, 2.6 mmol) was dissolved in DMF (20 mL) with stirring. Boc-Arg(Pbf)-OH (1.4 g, 2.7 mmol), HATU (1.1 g, 2.9 mmol) and DIPEA (1.4 mL, 8.0 mmol) were added with stirring. The reaction was continued at ambient temperature for 2 h. The mixture was then concentrated, and the residue was partitioned between EtOAc and water (30 mL/20 mL). The organic layer was separated, washed with water (20 mL), brine (20 mL), dried over $Na_2SO_4$ and concentrated to afford crude compound G (1.5 g, 1.4 mmol, 54%). MS: (m/z) calc: 1052.3, observed (M+H$^+$) 1053.9. Compound G was used without further purification.

Preparation 77: Synthesis of Intermediate (H)

Crude compound G (1.5 g, 1.4 mmol)) was taken into dioxane (3 mL) and cooled in an ice/water bath. An HCl solution in dioxane (4 N, 10 mL, 40 mmol) was added and the mixture was stirred at ambient temperature for 3 h and then concentrated in vacuo to afford a white foam. This material was dissolved in a mixture of DIPEA (0.8 mL 4.3 mmol) in DCM (20 mL). Acetic anhydride (0.2 mL, 2.1 mmol) was added. The reaction mixture was stirred at ambient temperature for 2 h. $NaHCO_3$ (20 mL, sat. aq.) was added. The layers were separated and the DCM layer was dried over $Na_2SO_4$, filtered and concentrated to afford intermediate compound H (0.85 g, crude). Compound H was used without further purification.

Synthesis of 6-{[2-(2-Acetylamino-5-guanidino-pentanoylamino)-ethyl]-[(5R,9R,13S,14S)-4,5a-epoxy-6,7-didehydro-14-hydroxy-3-methoxy-17-methylmorphinan-6-oxy]-1-enyloxycarbonyl-amino}-hexanoic acid (Compound KC-5)

Compound H (0.85 g, crude) was dissolved in a mixture of m-Cresol (0.5 mL) in TFA (20 mL). The mixture was stirred at ambient temperature for 2 h. The mixture was concentrated in vacuo. The residue was taken into MeOH (3 mL) and added drop wise to a stirred HCl solution in ether (20 mL, 2 M, 40 mmol). The resulting white solid (compound I) was filtered and washed with ether (3×10 mL). Compound I was then dissolved in a mixture of THF/H$_2$O (2 mL/2 mL) at ambient temperature. LiOH (41 mg, 1.7 mmol) was added in one portion. The mixture was stirred for 4 h. The mixture was then acidified by adding AcOH until pH ~6. The mixture was then concentrated and the residue was purified by prep HPLC, using RP-18e C18 column (4.6×50 mm); flow rate: 1.5 ml/min; mobile phase A: 0.1% TFA/water; mobile phase B 0.1% TFA/CH$_3$CN; gradient elution. Lyophilization of the collected fractions afforded Compound KC-5 (TFA salt) as a white solid. The solid was treated with 0.1 N HCl (aq.) and lyophilized to give the corresponding HCl salt of Compound KC-5 as a white foam (406 mg, 38% from compound E, 100% purity). MS: (m/z) calc: 713.8, observed (M+H$^+$) 714.5.

Example 36

({(S)-2-(S)-2-Acetylamino-5-guanidino-pentanoylamino)-3-[(oxycodone-enyloxycarbonyl)-methylamino]-propionyl}-methyl-amino)-acetic acid (Compound KC-6)

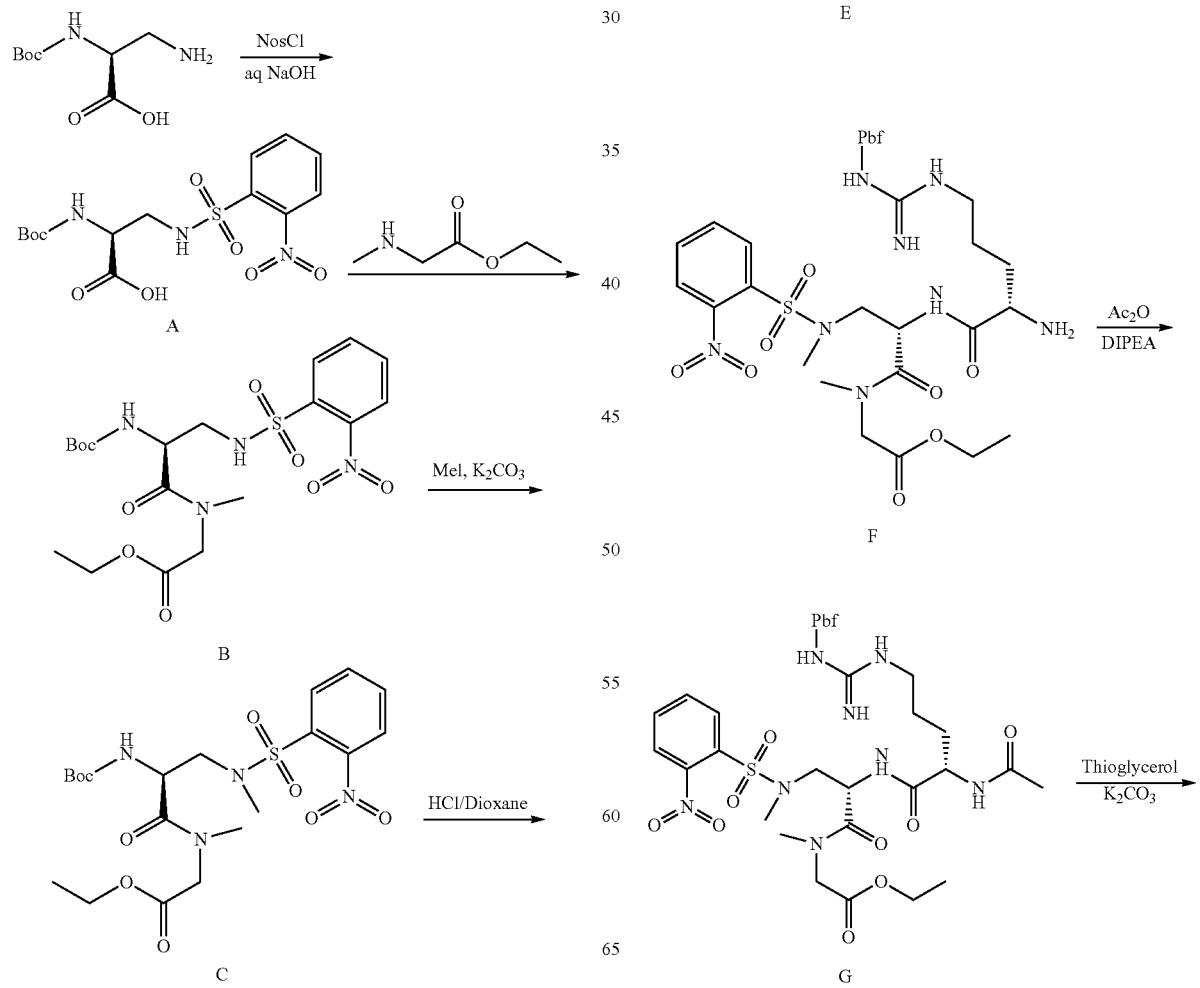

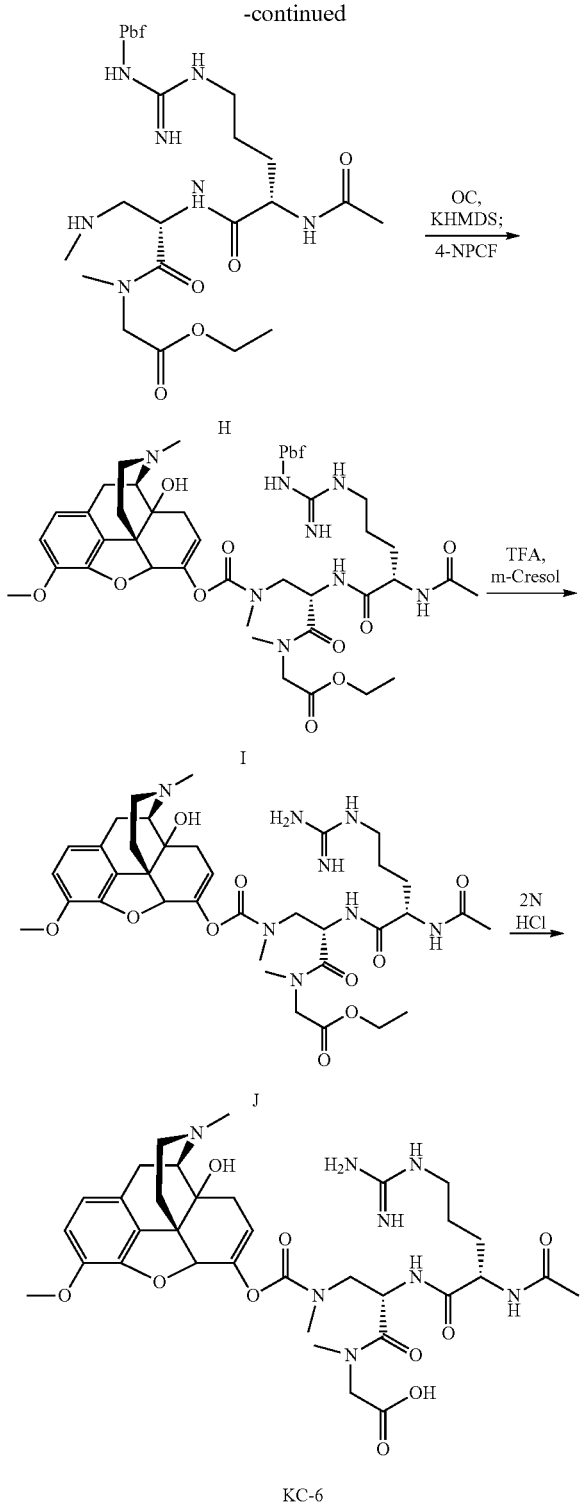

Preparation 78: (S)-2-tert-Butoxycarbonylamino-3-(2-nitro-benzenesulfonylamino)-propionic acid (A)

(S)-2-tert-Butoxycarbonylamino-3-amino-propionic acid (14.9 g, 73.2 mmol) was dissolved in a mixture of THF (45 mL) and 3 N aq. NaOH (45 mL). The reaction mixture was cooled to −10° C. and nosyl chloride (17.9 g, 80.5 mmol) was added as a THF solution (75 mL) drop wise over 30 min. The reaction mixture was stirred at −10° C. for 45 min followed by stirring at ambient temperature for 30 min. The reaction mixture was diluted with water (150 mL), acidified with 2% aqueous $H_2SO_4$ (to pH ~2) and diluted with additional water (450 mL). The product was extracted with EtOAc (600 mL total) and washed with water (3×400 mL) and brine (100 mL). The organic layer was separated, dried over $Na_2SO_4$, filtered and condensed in vacuo to afford compound A (20.0 g, 70% yield) as a cream solid. LC-MS [M+H-Boc] 290.3 ($C_{14}H_{19}N_3O_8S$+H, calc: 390.4). Purity >95% (UV/254 nm). Compound A was used without further purification.

Preparation 79: {[(S)-2-tert-Butoxycarbonylamino-3-(2-nitro-benzenesulfonylamino)-propionyl]-methyl-amino}-acetic acid ethyl ester (B)

Free basing procedure of Sarcosine ethyl ester: Sarcosine ethyl ester hydrochloride (39.3 g, 256.8 mmol) was dissolved in water (300 mL), washed with $Et_2O$ (2×100 mL), pH adjusted to ~pH 8, extracted with $CHCl_3$ (3×100 mL) and dried over $Na_2SO_4$ and finally filtered.

To a solution of compound A (10.0 g, 25.7 mmol) in DMF (100 mL) was added HOBt (5.2 g, 38.5 mmol) and the reaction mixture was cooled to −10° C. To this reaction mixture, EDC-HCl (5.4 g, 28.2 mmol) was added in portions over 10 min and stirred at −10° C. for 20 min. To the reaction mixture, Sarcosine ethyl ester (256.8 mmol) in $CHCl_3$ (300 mL) was added drop wise over 30 min. The reaction mixture was stirred at this temperature for 30 min followed by stirring at ambient temperature overnight. Solvents were then removed in vacuo, and the residue was dissolved in EtOAc (500 mL), washed with water (3×300 mL), saturated aqueous $NaHCO_3$ (2×300 mL) and brine (100 mL). The organic layer was separated, dried over $Na_2SO_4$ and concentrated in vacuo to afford compound B (11.5 g, 91%) as a cream solid. LC-MS [M+H] 489.5 ($C_{19}H_{28}N_4O_9S$+H, calc: 489.3). Purity >95% (UV/254 nm). Compound B was used without further purification.

Preparation 80: ({(S)-2-tert-Butoxycarbonylamino-3-[methyl-(2-nitro-benzenesulfonyl)-amino]-propionyl}-methyl-amino)-acetic acid ethyl ester (C)

Compound B (8.0 g, 16.3 mmol) was dissolved in DMF (40 mL) and the reaction mixture was cooled to −10° C. To the reaction mixture was added $K_2CO_3$ (6.8 g, 49.1 mmol) followed by addition of MeI (5.1 mL, 81.9 mmol) drop wise and stirred at 0° C. for 1 h. The reaction mixture was filtered and washed with EtOAc. Solvents removed in vacuo and the residue was dissolved in EtOAc (250 mL) and poured into water (500 mL), extracted with EtOAc (2×250 mL), and washed with water (250 mL) and brine (100 mL). The organic layer was dried over $Na_2SO_4$, filtered, and then concentrated in vacuo, to afford compound C (8.1 g, 98% yield) as a cream solid. LC-MS [M+H] 503.1 ($C_{20}H_{30}N_4O_9S$+H, calc: 503.5). Purity >95% (UV/254 nm). Compound C was used without further purification.

Preparation 81: ({(S)-2-Amino-3-[methyl-(2-nitro-benzenesulfonyl)-amino]-propionyl}methyl-amino)-acetic acid ethyl ester (D)

Compound C (6.9 g, 13.8 mmol) was dissolved in DCM (45 mL) and then treated with 4 M HCl in dioxane (40 mL) at ambient temperature. The reaction mixture was stirred at ambient temperature for 90 min. The mixture was concentrated in vacuo to a total volume of ~25 mL, and $Et_2O$ (400 mL) was added. The precipitated product was filtered off, washed with Et$_2$O (250 mL), and hexane (250 mL) and finally dried in vacuo to afford compound D (6.3 g, 100% yield) as a cream solid. LC-MS [M+H] 403.3 (C$_{15}$H$_{22}$N$_4$O$_7$S+H, calc: 403.4). Purity >95% (UV/254 nm). Compound D was used without further purification.

Preparation 82: ({(S)-2-[(S)-5-({Amino-[(Z)-2,2,4,6,7-pentamethyl-2,3-dihydro-benzofuran-5-sulfonylimino]-methyl}-amino)-2-tert-butoxycarbonylamino-pentanoylamino]-3-[methyl-(2-nitro-benzenesulfonyl)-amino]-propionyl}-methyl-amino)-acetic acid ethyl ester (E)

To a solution of Boc-Arg(Pbf)-OH (7.3 g, 13.8 mmol), DIPEA (7.7 mL, 44.2 mmol) in DMF (35 mL) was added HATU (5.8 g, 15.2 mmol) and stirred at 5° C. for 15 min. To this reaction mixture, compound D (6.3 g, 13.8 mmol) was added and stirred at ambient temperature for 1 h. DMF was then removed in vacuo to a total volume of ~15 mL. The reaction mixture was diluted with EtOAc (250 mL) and poured into water (500 mL), extracted with EtOAc (2×250 mL), and washed with 2% aqueous H$_2$SO$_4$ (150 mL), water (150 mL) and brine (150 mL). The organic layer was dried over anhydrous Na$_2$SO$_4$, filtered and then evaporated to give an oily residue, which was dried overnight under high vacuum to give compound E (7.4 g, 59%) as an off-white solid. LC-MS [M+H] 911.5 (C$_{39}$H$_{58}$N$_8$O$_{13}$S+H, calc: 912.05). Purity >95% (UV/254 nm). Compound E was used without further purification.

Preparation 83: ({(S)-2-[(S)-2-Amino-5-({amino-[(Z)-2,2,4,6,7-pentamethyl-2,3-dihydro-benzofuran-5-sulfonylimino]-methyl}-amino)-pentanoylamino]-3-[methyl-(2-nitro-benzenesulfonyl)-amino]-propionyl}-methyl-amino)-acetic acid ethyl ester (F)

Compound E (7.4 g, 8.2 mmol) in DCM (24 mL) was treated with 4 M HCl in dioxane (24 mL) at ambient temperature. The reaction mixture was stirred at ambient temperature for 1 h. DCM and most of the dioxane were removed in vacuo to a total volume of ~15 mL, and Et$_2$O (300 mL) was added. Precipitated product was filtered off, washed with Et$_2$O (150 mL) and hexane and finally dried in vacuo to afford compound F (6.34 g, 100% yield) as a cream solid. LC-MS [M+H] 811.4 (C$_{34}$H$_{50}$N$_8$O$_{11}$S$_2$+H, calc: 811.94). Purity >95% (UV/254 nm). Compound F was used without further purification.

Preparation 84: ({(S)-2-[(S)-2-Acetylamino-5-({amino-[(Z)-2,2,4,6,7-pentamethyl-2,3-dihydro-benzofuran-5-sulfonylimino]-methyl}-amino)-pentanoylamino]-3-[methyl-(2-nitro-benzenesulfonyl)-amino]-propionyl}-methyl-amino)-acetic acid ethyl ester (G)

To a solution of compound F (6.6 g, 7.8 mmol) in CHCl$_3$ (50 mL) at 5° C. was added DIPEA (4.8 mL, 27.4 mmol) followed by Ac$_2$O (0.9 mL, 9.4 mmol). The reaction mixture was stirred at ambient temperature for 30 min. Solvents were removed in vacuo, and then the residue was diluted with water (500 mL) and EtOAc (500 mL). The organic layer was separated and washed with water (300 mL), 2% aqueous H$_2$SO$_4$ (200 mL), water (2×300 mL) and brine (100 mL). The organic layer was separated, dried over Na$_2$SO$_4$ and solvent removed in vacuo to afford compound G (5.5 g, 82%). LC-MS [M+H] 853.4 (C$_{36}$H$_{52}$N$_8$O$_{12}$S$_2$+H, calc: 853.9). Purity >95% (UV/254 nm). Compound G was used without further purification.

Preparation 85: ({(S)-2-[(S)-2-Acetylamino-5-({amino-[(Z)-2,2,4,6,7-pentamethyl-2,3-dihydro-benzofuran-5-sulfonylimino]-methyl}-amino)-pentanoylamino]-3-methylamino-propionyl}-methyl-amino)-acetic acid ethyl ester (H)

To a solution of compound G (5.5 g, 6.5 mmol) in DMF (21 mL) at ambient temperature was added K$_2$CO$_3$ (8.9 g, 64.5 mmol) followed by thioglycerol (5.6 mL, 64.5 mmol). The reaction mixture was stirred at ambient temperature for 1 h, filtered off and DMF was removed in vacuo. The residue was diluted with water (500 mL) and extracted with EtOAc (2×300 mL) and CHCl$_3$ (2×300 mL). Combined organic layers were dried and removal of the solvents in vacuo afforded the crude product. The crude product was purified by flash chromatography eluting with EtOAc followed by 10% MeOH in CHCl$_3$ to afford compound H (1.3 g, 30%). LC-MS [M+H] 668.3 (C$_{30}$H$_{49}$N$_7$O$_8$S+H, calc: 667.8). Purity >95% (UV/254 nm).

Preparation 86: ({(S)-2-[(S)-2-Acetylamino-5-({amino-[(Z)-2,2,4,6,7-pentamethyl-2,3-dihydro-benzofuran-5-sulfonylimino]-methyl}-amino)-pentanoylamino]-3-[(oxycodone-enyloxycarbonyl)-methyl-amino]-propionyl}methyl-amino)-acetic acid ethyl ester (I)

To a solution of oxycodone free base (2.0 g, 6.3 mmol) in THF (100 mL) at −60° C. was added 0.5 M KHMDS (13.9 mL, 7.0 mmol) drop wise. The reaction mixture was stirred for 30 min and then transferred to a solution of 4-nitrophenyl chloroformate (1.3 g) in THF (100 mL) at −60° C. and stirred for 30 min. A solution of amine compound H (3.2 g, 4.9 mmol) was added as a THF (20 mL) solution to the reaction mixture. After stirring at −60° C. for 15 min, the cooling bath was removed and the reaction was stirred at ambient temperature overnight. Another portion (1.0 g, 3.2 mmol) of oxycodone free base was activated using the above procedure and added to the reaction mixture as above, and stirring continued overnight. The reaction was determined to be complete by LC-MS. The solvents were removed, and the residue was dissolved in MeOH (~25 mL) and precipitated with Et$_2$O (400 mL). The precipitate was washed with Et$_2$O and hexane and dried in vacuo. The product was dissolved in water and DMSO and purified by HPLC. [Nanosyn-Pack Microsorb (100-10) C-18 column (50×300 mm); flow rate: 100 mL/min; injection volume 15 mL; mobile phase A: 100% water, 0.1% TFA; mobile phase B: 100% ACN, 0.1% TFA; gradient elution from 0% to 33% B in 33 min, isocratic elution at 33% B in 30 min, gradient elution from 33% B to 50% B in 33 min; detection at 254 nm]. Desired fractions were combined and dried in vacuo to afford compound I (5 g, 92% yield)). LC-MS [M+H] 979.6 (C$_{48}$H$_{66}$N$_8$O$_{12}$S+H, calc: 980.15). Purity >95% (UV/254 nm).

Preparation 87: ({(S)-2-((S)-2-Acetylamino-5-guanidino-pentanoylamino)-3-[(oxycodone-enyloxycarbonyl)-methyl-amino]-propionyl}-methyl-amino)-acetic acid ethyl ester (J)

Compound I (5 g, 4.5 mmol) was treated with 5% m-cresol in TFA (25 mL). After 1 h, ether (400 mL) was added to the reaction mixture. The precipitated product was filtered off, washed with Et$_2$O and hexane and dried in vacuo to afford compound J (3.2 g, 65% yield). LC-MS [M+H] 757.7 ($C_{36}H_{52}N_8O_{10}$+H, calc: 757.9). Purity >95% (UV/254 nm). Compound J was used without further purification.

({(S)-2-(S)-2-Acetylamino-5-guanidino-pentanoylamino)-3-[(oxycodone-enyloxycarbonyl)-methylamino]-propionyl}-methyl-amino)-acetic acid (Compound KC-6)

Compound J was treated with 2 N aq. HCl (75 mL) and heated at 55° C. for 6.5 h. Heating was removed and the reaction mixture was cooled to ~5° C. and pH was adjusted to pH 6 with aqueous saturated $NaHCO_3$. Most of the water was removed in vacuo to a total volume of ~50 mL. This solution was subjected to HPLC purification. [Nanosyn-Pack Microsorb (100-10) C-18 column (50×300 mm); flow rate: 100 mL/min; injection volume 15 mL; mobile phase A: 100% water, 0.1% TFA; mobile phase B: 100% ACN, 0.1% TFA; isocratic elution at 0% B in 2 min, gradient elution from 0% to 8% B in 14 min, isocratic elution at 8% B in 30 min, gradient elution from 8% B to 33% B in 55 min; detection at 254 nm]. Desired fractions were combined and dried in vacuo, followed by lyophilization using 0.1 N HCl to afford Compound KC-6 as a HCl salt (1.5 g, 48% yield). LC-MS [M+H] 729.6 ($C_{34}H_{48}N_8O_{10}$+H, calc: 729.8). Purity >95% (UV/254 nm).

Biological Data

Example 37

Pharmacokinetics of Oxycodone Prodrug Following PO Administration to Rats

This Example compares the plasma concentrations of oxycodone in rats following oral (PO) administration of oxycodone 6-(N-methyl-N-(2-N'-acetylarginylamino)) ethylcarbamate (produced as described in the Example herein and also referred to as Compound KC-2) or oxycodone.

Compound KC-2 and oxycodone were each dissolved in saline and dosed at equimolar doses (20 mg/kg and 10 mg/kg, respectively) via oral gavage into jugular vein-cannulated male Sprague Dawley rats; four rats were dosed per group. At specified time points, blood samples were drawn, harvested for plasma via centrifugation at 5,400 rpm at 4° C. for 5 min, and 100 microliters (µl) plasma transferred from each sample into a fresh tube containing 1 µl of formic acid. The tubes were vortexed for 5-10 seconds, immediately placed in dry ice and then stored until analysis by high performance liquid chromatography/mass spectrometry (HPLC/MS).

Table 18 indicates plasma $C_{max}$ (maximum plasma concentration) and $T_{max}$ (time after administration when the maximum plasma concentration was reached) values of oxycodone (average±standard deviation) for each group of 4 rats. Also indicated are the $C_{max}$ and $T_{max}$ values for oxymorphone, a metabolite of oxycodone.

TABLE 18

Plasma $C_{max}$ and $T_{max}$ values of oxycodone (OC) and oxymorphone (OM) in rats dosed PO with oxycodone or Compound KC-2

| Compound administered | $C_{max}$ OC (ng/mL OC) | $T_{max}$ OC (hr) | $C_{max}$ OM (ng/mL OM) | $T_{max}$ OM (hr) |
|---|---|---|---|---|
| Oxycodone | 14.7 ± 6.5 | 0.63 ± 0.43 | 18.4 ± 10.0 | 0.50 ± 0.35 |
| Compound KC-2 | 3.8 ± 1.1 | 3.8 ± 1.5 | 3.9 ± 1.6 | 3.8 ± 1.5 |

Figure 19:
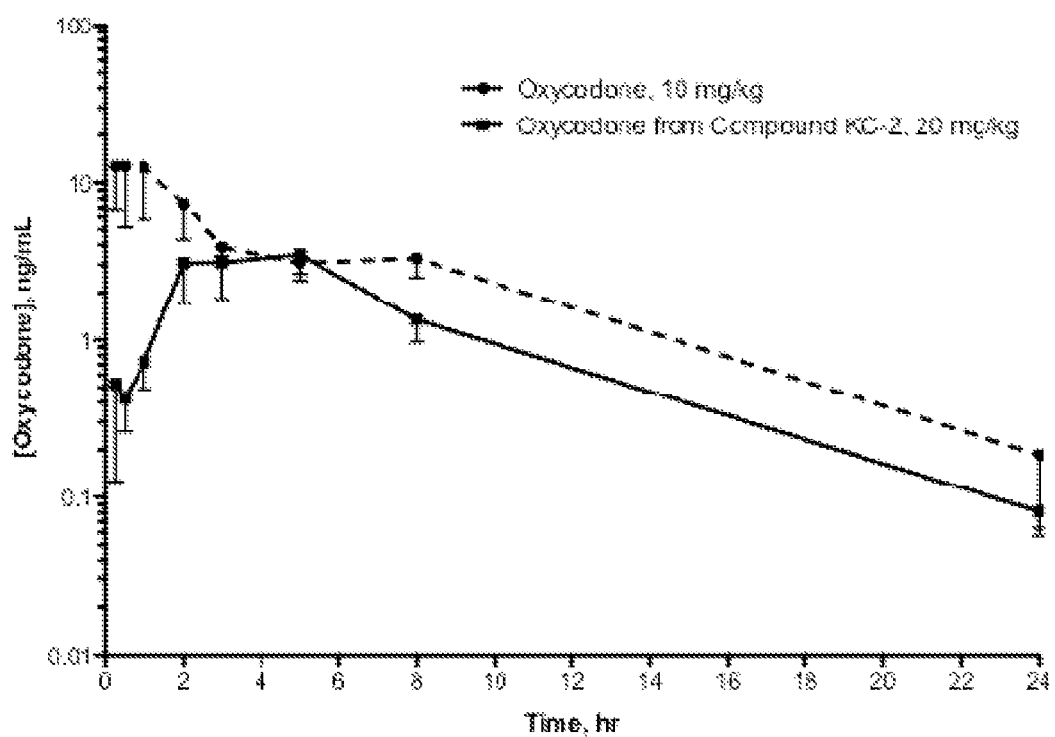
FIG. 19 shows a plasma concentration time course of the production of oxycodone following oral (PO) dosing of an oxycodone prodrug in rats.

FIG. 19 compares mean plasma concentrations (± standard deviations) over time of oxycodone following PO administration of 20 mg/kg Compound KC-2 (solid line) or 10 mg/kg oxycodone (dashed line) to rats.

The results in Table 18 and FIG. 19 indicate that administration of Compound KC-2 yields oxycodone plasma concentrations that exhibit a suppressed $C_{max}$ and delayed $T_{max}$ compared to administration of oxycodone.

Example 38

Pharmacokinetics of Oxycodone Prodrug Following IV Administration to Rats

This Example compares the plasma concentrations of prodrug and oxycodone in rats following intravenous (IV) administration of oxycodone 6-(N-methyl-N-(2-N'-acetylarginylamino)) ethylcarbamate (produced as described in the Example herein and also referred to as Compound KC-2).

Compound KC-2 was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 microliters (µl) plasma transferred from each sample into a fresh tube containing 1 µl of formic acid. The tubes were vortexed for 5-10 seconds, immediately placed in dry ice and then stored until analysis by high performance liquid chromatography/mass spectrometry (HPLC/MS).

Table 19 indicates plasma $C_{max}$ values (average±standard deviation) of Compound KC-2, oxycodone and oxymorphone (a metabolite of oxycodone).

TABLE 19

Plasma $C_{max}$ values of Compound KC-2, oxycodone and oxymorphone in rats dosed IV with Compound KC-2

| Compound in plasma measured | Cmax (ng/mL) |
|---|---|
| Compound KC-2 | 2680 ± 755 |
| Oxycodone | 0.798 ± 0.1 |
| Oxymorphone | 0.118 ± 0.1 |

Figure 20:
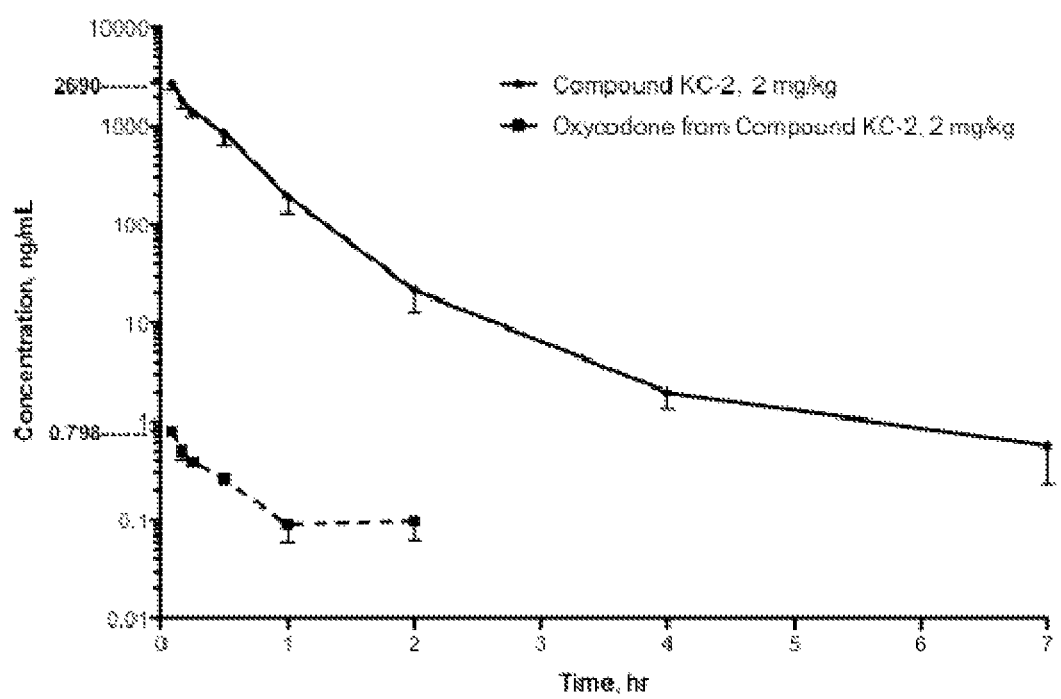
FIG. 20 shows a plasma concentration time course of the production of oxycodone following intravenous (IV) dosing of an oxycodone prodrug in rats.

FIG. 20 compares mean plasma concentrations (± standard deviations) over time of Compound KC-2 (solid line) and oxycodone (dashed line) following IV administration of 2 mg/kg Compound KC-2 to rats. Numbers on the Y-axis also depict the Cmax values of Compound KC-2 and oxycodone, respectively.

Table 19 and FIG. 20 demonstrate that the plasma concentration of oxycodone in rats administered Compound KC-2 IV is only 0.03% of the plasma concentration of Compound KC-2, indicating that IV administration of Compound KC-2 does not lead to significant release of oxycodone.

Example 39

In Vitro Stability of Oxycodone Prodrug

This Example demonstrates the stability of oxycodone 6-(N-methyl-N-(2-N'-acetylarginylamino)) ethylcarbamate (produced as described in the Example herein and also referred to as Compound KC-2) to a variety of readily available household chemicals and enzyme preparations.

Compound KC-2 was exposed at room temperature (RT) or 80° C. for either 1 or 24 hours (hr) to the following household chemicals: vodka (40% alcohol), baking soda (saturated sodium bicarbonate solution, pH 9), WINDEX® with Ammonia-D (pH11) and vinegar (5% acetic acid). Compound KC-2 was also exposed to the following enzyme-containing compositions at RT for 1 or 24 hr: GNC® Super Digestive (2 capsules of GNC Super Digestive Enzymes dissolved in 5 mL of water), tenderizer (Adolf's meat tenderizer, primarily papain, dissolved in water to a concentration of 0.123 g/mL to approximate the concentration of a marinade given on the bottle label), and subtilisn (8 tablets of ULTRA-ZYME® contact lens cleaner (Advanced Medical Optics) dissolved in 4 mL water). Samples were incubated as described and aliquots removed at 1 hr and 24 hr and stabilized by adding each to a solution of 50% or 100% of 85% phosphoric acid solution to achieve a final pH of less than or equal to pH 4. The stabilized aliquots were then diluted 4- to 6-fold with water, vortex-mixed and applied to HPLC.

Figure 21:
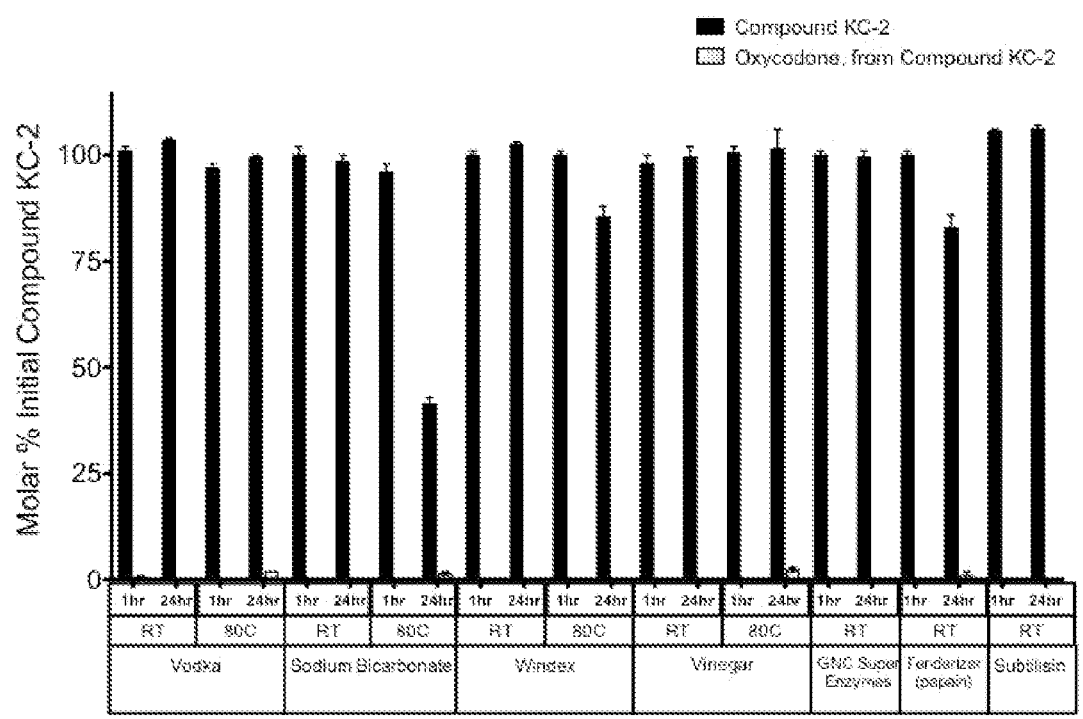
FIG. 21 shows release of oxycodone from an oxycodone prodrug exposed to a variety of readily available household chemicals or enzyme preparations.

FIG. 21 demonstrates the release of oxycodone when Compound KC-2 was exposed to the various household chemicals and enzyme-containing compositions described above. The percentage of Compound KC-2 remaining after exposure is indicated by the solid black bars and percentage conversion of Compound KC-2 to oxycodone is indicated by the lightly shaded bars with a black outline. These results indicate that exposure of Compound KC-2 to these various conditions leads to substantially less than 10% conversion to oxycodone.

Example 40

In Vitro IC50 Data of Several Candidate Trypsin Inhibitors

Several candidate trypsin inhibitors, namely Compounds 101-105, 107 and 108 were produced as described in the Examples herein. Compound 106 (also known as 4-aminobenzamidine), Compound 109 and Compound 110 are available from Sigma-Aldrich (St. Louis, Mo.).

The half maximal inhibitory concentration (IC50 or $IC_{50}$) values of each of Compounds 101-110 as well as of SBTI and BBSI were determined using a modified trypsin assay as described by Bergmeyer, H U et al, 1974, Methods of Enzymatic Analysis Volume 1, $2^{nd}$ edition, 515-516, Bergmeyer, HU, ed., Academic Press, Inc. New York, N.Y.

Table 20 indicates the IC50 values for each of the designated trypsin inhibitors.

TABLE 20

IC50 values of certain trypsin inhibitors

| Compound | IC50 value |
|---|---|
| 101 | 2.0E−5 |
| 102 | 7.5E−5 |
| 103 | 2.3E−5 |
| 104 | 2.7E−5 |
| 105 | 4.1E−5 |
| 106 | 2.4E−5 |
| 107 | 1.9E−6 |
| 108 | 8.8E−7 |
| 109 | 9.1E−7 |
| 110 | 1.8E−5 |
| SBTI | 2.7E−7 |
| BBSI | 3.8E−7 |

The results of Table 20 indicate that each of Compounds 101-110 exhibits trypsin inhibition activity.

Example 41

Effect of Trypsin Inhibition on In Vitro Trypsin-Mediated Trypsin Release of Oxycodone from Compound KC-2

Compound KC-2 (which can be prepared as described in the Example herein) was incubated with trypsin from bovine pancreas (Catalog No. T8003, Type I, ~10,000 BAEE units/mg protein, Sigma-Aldrich), in the absence or presence of Compound 109 (Catalog No. N0289, Sigma-Aldrich). When Compound 109 was part of the incubation mixture, Compound KC-2 was added 5 min after the other incubation components. Specifically, the reactions included 0.761 mM Compound KC-2•2HCl, 0.0228 mg/mL trypsin, 22.5 mM calcium chloride, 40 to 172 mM Tris pH 8 and 0.00108 mg/mL (2 µM) Compound 109 or 0.25% DMSO depending on whether inhibitor was included in the incubation. The reactions were conducted at 37° C. for 24 hr. Samples were collected at specified time points, transferred into 0.5% formic acid in acetonitrile to stop trypsin activity and stored at less than −70° C. until analysis by LC-MS/MS.

Figure 22:
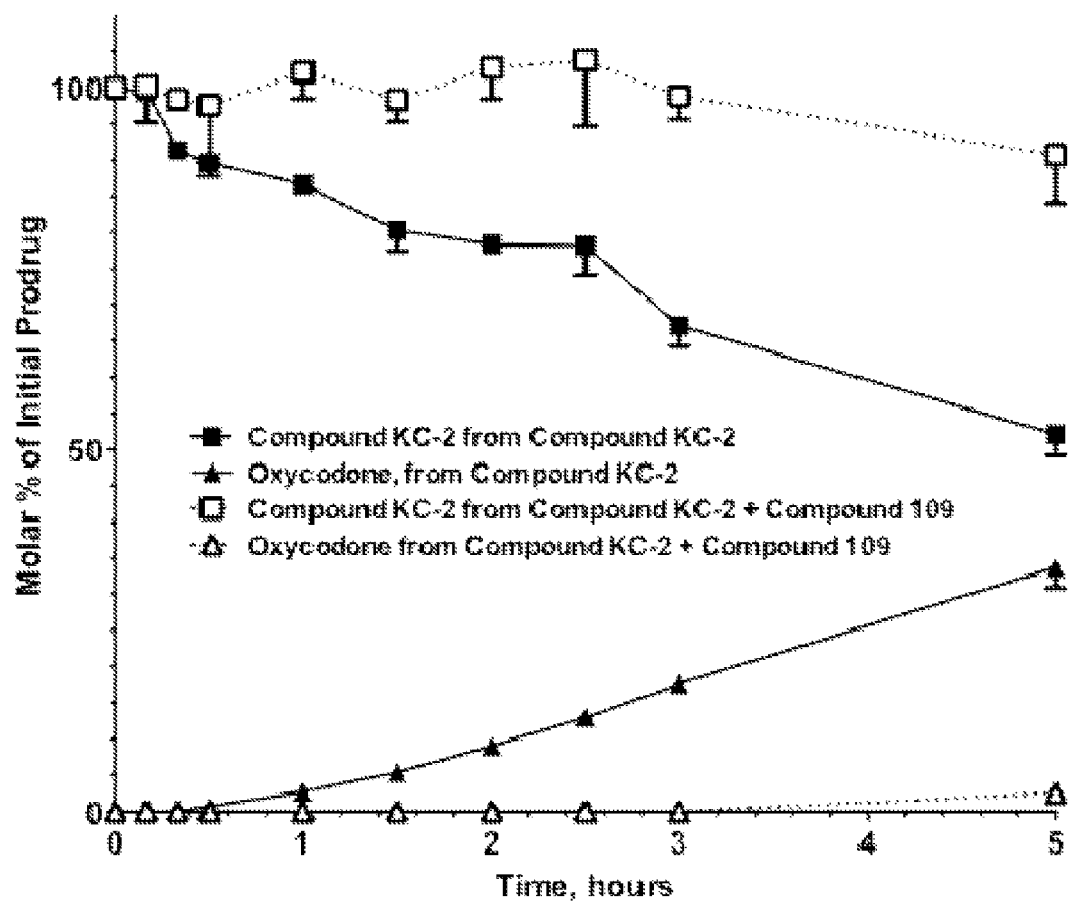
FIG. 22 shows disappearance of an oxycodone prodrug and appearance of oxycodone following in vitro incubation of the prodrug and trypsin, in the absence or presence of a trypsin inhibitor.

FIG. 22 indicates the results of exposure of Compound KC-2 to trypsin in the absence of any trypsin inhibitor (solid symbols) or in the presence of Compound 109 (open symbols). The square symbols indicate the disappearance of Compound KC-2, and the triangle symbols depict the appearance of oxycodone, over time under the conditions described in this Example.

The results in FIG. 22 indicate that a trypsin inhibitor of the embodiments can attenuate trypsin-mediated release of oxycodone from Compound KC-2. In addition, such a trypsin inhibitor can thwart the ability of a user to apply trypsin to effect the release of oxycodone from Compound KC-2.

Table 21 indicates the results of exposure of Compound KC-2 to trypsin in the absence and presence of Compound 109. The results are expressed as half-life of prodrug when exposed to trypsin (i.e., Prodrug trypsin half-life) in hours and rate of formation of oxycodone per unit to trypsin.

TABLE 21

In Vitro Trypsin Conversion of Compound KC-2 to Oxycodone

| | No trypsin inhibitor | | With trypsin inhibitor | |
|---|---|---|---|---|
| Prodrug | Pro-drug trypsin half-life, h Average ± sd | Rate of oxycodone formation, umols/h/ umol trypsin Average ± sd | Compound 109 | Pro-drug trypsin half-life, h Average ± sd | Rate of oxycodone formation, umols/h/ umol trypsin Average ± sd |
| KC-2 | 5.64 ± 0.26 | 37.4 ± 0.9 | 2 uM | 116 ± 118 | nd* |

*nd = not detectable

The results in Table 21 indicate that trypsin can effect release of oxycodone from a prodrug of the embodiments and that a trypsin inhibitor of the embodiments can attenuate trypsin-mediated release of oxycodone.

Example 42

Oral Administration of Compound KC-2 and Trypsin Inhibitor Compound 109 to Rats

Saline solutions of Compound KC-2 (which can be prepared as described in the Example herein) were dosed at 8.7

μmol/kg (6 mg/kg) with or without a co-dose of 55 μmol/kg (30 mg/kg) Compound 109 (Catalog No. 3081, Tocris Bioscience, Ellisville, Mo., USA or Catalog No. WS38665, Waterstone Technology, Carmel, Ind., USA) as indicated in Table 22 via oral gavage into jugular vein-cannulated male Sprague Dawley rats (4 per groups) that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 23:
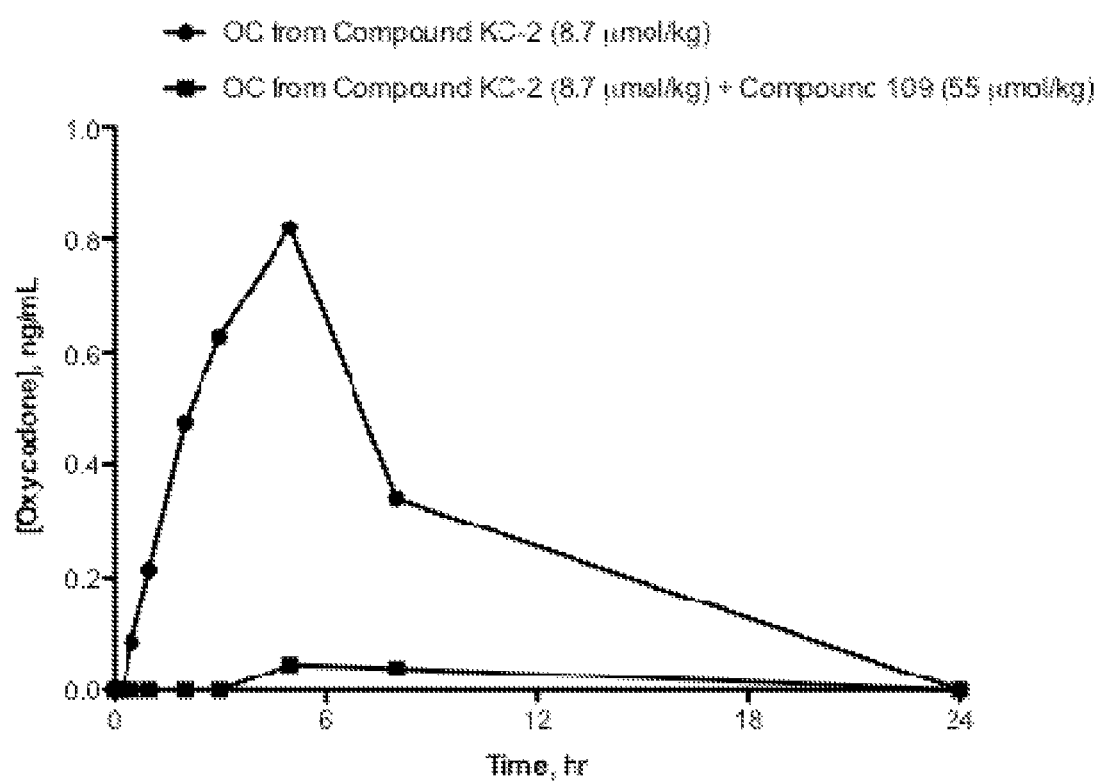
FIG. 23 compares mean plasma concentrations over time of oxycodone release following PO administration of prodrug Compound KC-2 alone and Compound KC-2 with trypsin inhibitor Compound 109 to rats.

Table 22 and FIG. 23 provide oxycodone exposure results for rats administered with Compound KC-2 in the absence or presence of trypsin inhibitor. Results in Table 22 are reported as (a) maximum plasma concentration (Cmax) of oxycodone (OC) (average±standard deviation) and (b) time after administration of Compound KC-2 to reach maximum oxycodone concentration (Tmax) (average±standard deviation).

TABLE 22

Cmax and Tmax values of oxycodone in rat plasma

| KC-2 Dose, mg/kg | KC-2 Dose, μmol/kg | Compound 109 Dose, mg/kg | Compound 109 Dose, μmol/kg | OC Cmax ± sd, ng/mL | Tmax ± sd, hr |
|---|---|---|---|---|---|
| 6 | 8.7 | 0 | 0 | 0.863 ± 0.69 | 3.00 ± 1.4 |
| 6 | 8.7 | 30 | 55 | 0.0468 ± 0.094 | 5.00 ± nc |

Lower limit of quantitation was 0.100 ng/mL;
nc = not calculated

FIG. 23 compares mean plasma concentrations over time of oxycodone release following PO administration of Compound KC-2 with or without a co-dose of trypsin inhibitor.

The results in Table 22 and FIG. 23 indicate that Compound 109 attenuates Compound KC-2's ability to release oxycodone, both by suppressing Cmax and by delaying Tmax.

Example 43

Pharmacokinetics of Compound KC-2 Following PO Administration to Rats

Saline solutions of Compound KC-2 (which can be prepared as described in the Example herein) were dosed as indicated in Table 23 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 24:
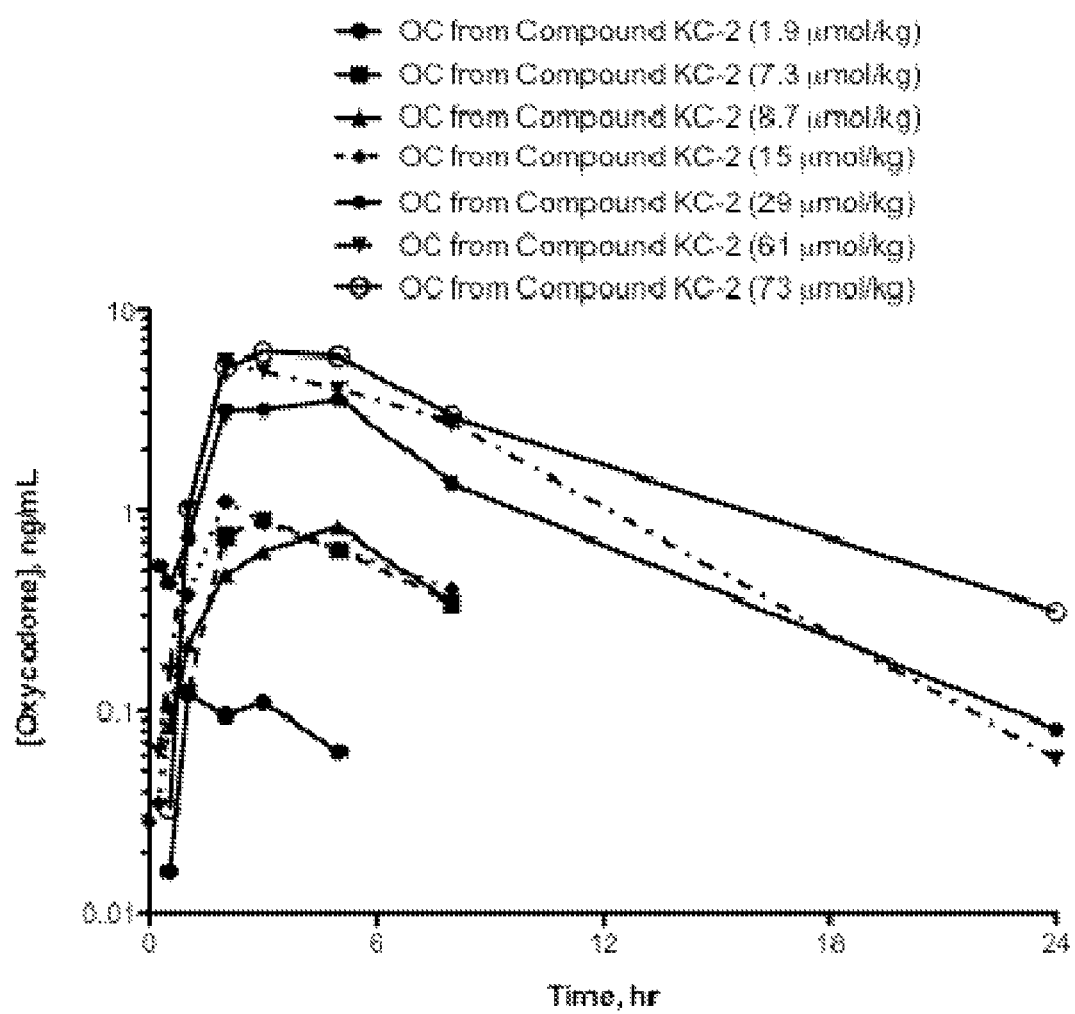
FIG. 24 compares mean plasma concentrations over time of oxycodone release following PO administration of increasing doses of prodrug Compound KC-2 to rats.

Table 23 and FIG. 24 provide oxycodone exposure results for rats administered with different doses of Compound KC-2. Results in Table 23 are reported, for each group of rats, as (a) maximum plasma concentration (Cmax) of oxycodone (OC) (average+standard deviation), (b) time after administration of Compound KC-2 to reach maximum oxycodone concentration (Tmax) (average±standard deviation) and (c) area under the curve (AUC) from 0 to 24 hr (average±standard deviation).

TABLE 23

Rat dosing PO with Compound KC-2

| Dose, mg/kg | Dose μmol/kg | OC Cmax ± sd, ng/mL | Tmax ± sd, hr | AUC ± sd, ng * hr/mL |
|---|---|---|---|---|
| 1.3 | 1.9 | 0.144 ± 0.018 | 1.50 ± 0.58 | 0.445 ± 0.13 |
| 5 | 7.3 | 0.918 ± 0.30 | 2.75 ± 0.5 | 4.30 ± 1.1 |
| 6 | 8.7 | 0.863 ± 0.69 | 3.00 ± 1.4 | 4.29 ± 2.6 |
| 10 | 15 | 1.13 ± 0.75 | 3.75 ± 2.9 | 4.94 ± 2.2 |
| 20 | 29 | 3.84 ± 1.1 | 3.75 ± 1.5 | 30.9 ± 6.3 |
| 42 | 61 | 6.00 ± 2.4 | 3.00 ± 1.4 | 39.6 ± 18 |
| 50 | 73 | 7.03 ± 2.3 | 3.75 ± 1.5 | 59.9 ± 14 |

Lower limit of concentration was 0.0500 ng/mL except 20 mg/kg dose was 0.0250 ng/mL FIG. 24 compares mean plasma concentrations over time of oxycodone release following PO administration of increasing doses of Compound KC-2.

The results in FIG. 24 and Table 23 indicate that plasma concentrations of oxycodone increase proportionally with Compound KC-2 dose.

Example 44

Oral Administration of Compound KC-2 Co-Dosed with Trypsin Inhibitor Compound 109 to Rats Saline solutions of Compound KC-2 were dosed at 7.3 μmol/kg (5 mg/kg) and 73 tmol/kg (50 mg/kg). The higher dose was co-dosed with increasing concentrations of Compound 109 (Catalog No. 3081, Tocris Bioscience or Catalog No. WS38665, Waterstone Technology) as indicated in Table 24 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 25:
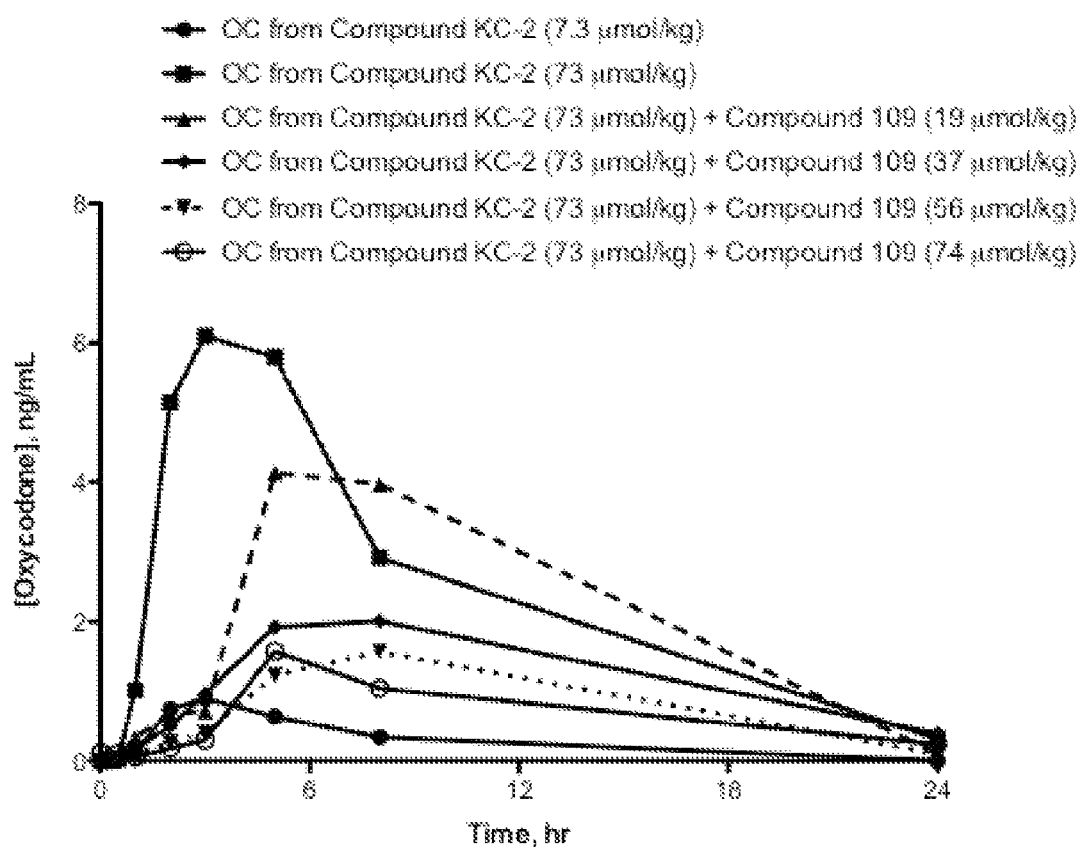
FIG. 25 compares mean plasma concentrations over time of oxycodone release following PO administration of prodrug Compound KC-2 with increasing amounts of co-dosed trypsin inhibitor Compound 109 to rats.

Table 24 and FIG. 25 provide oxycodone exposure results for rats administered with different doses of Compound KC-2. Results in Table 24 are reported, for each group of rats, as (a) maximum plasma concentration (Cmax) of oxycodone (OC) (average+standard deviation), (b) time after administration of Compound KC-2 to reach maximum oxycodone concentration (Tmax) (average±standard deviation) and (c) area under the curve (AUC) from 0 to 24 hr (average±standard deviation).

TABLE 24

Rat dosing PO with Compound KC-2 in the absence or presence of Compound 109

| KC-2 Dose, mg/kg | KC-2 Dose, μmol/kg | Compound 109 Dose, mg/kg | Compound 109 Dose, μmol/kg | OC Cmax ± sd, ng/mL | Tmax ± sd, hr | AUC ± sd, ng*hr/mL |
|---|---|---|---|---|---|---|
| 5 | 7.3 | 0 | 0 | 0.918 ± 0.30 | 2.75 ± 0.5 | 4.30 ± 1.1 |
| 50 | 73 | 0 | 0 | 7.03 ± 2.3 | 3.75 ± 1.5 | 59.9 ± 14 |
| 50 | 73 | 10 | 19 | 4.44 ± 1.5 | 6.50 ± 1.7 | 51.0 ± 16 |
| 50 | 73 | 20 | 37 | 2.25 ± 0.89 | 7.25 ± 1.5 | 29.2 ± 8.9 |
| 50 | 73 | 30 | 56 | 1.77 ± 0.57 | 6.50 ± 1.7 | 19.8 ± 7.6 |
| 50 | 73 | 40 | 74 | 1.64 ± 0.96 | 5.75 ± 1.5 | 16.5 ± 5.9 |

Lower limit of quantitations were 0.0250 ng/ml

FIG. 25 compares mean plasma concentrations over time of oxycodone release following PO administration of Compound KC-2 with increasing amounts of co-dosed trypsin inhibitor Compound 109.

The results in Table 24 and FIG. 25 indicate Compound 109's ability to attenuate Compound KC-2's ability to release oxycodone in a dose dependent manner, both by suppressing Cmax and AUC and by delaying Tmax.

Example 45

In Vitro Human μ-Opioid Receptor Binding Assay

This example measures the affinity of compound KC-2 for the mu (μ)-opioid receptor expressed in recombinant HEK-293 cells.

The general procedure follows the protocol described by Wang, J.-B., Johnson, P. S., Perscio, A. M., Hawkins, A. L., Griffin, C. A. and Uhl, G. R. (1994). FEBS Lett., 338: 217-222. More specifically, the assays included, as appropriate, oxycodone or Compound KC-2 (which can be prepared as described in Example 10) as well as recombinant HEK-293 cells expressing the human μ-opioid receptor on their cell surfaces, reference compound [d-Ala$^2$,N-Me-Phe$^4$,Gly$^5$-ol]-enkephalin (DAMGO), radioligand [$^3$H]DAMGO (0.5 nM) and non-specific ligand naloxone (10 uM). The reaction mixtures were incubated at 22° C. for 2 hr. The samples were then submitted to scintillation counting.

In these assays, the specific binding of a test compound to the receptors is defined as the difference between the total binding and the non-specific binding determined in the presence of an excess of unlabelled ligand. Results are expressed as a percent of control specific binding and as a percent inhibition of control specific binding obtained in the presence of test compounds. The IC$_{50}$ values (concentration of competing ligand required for 50% inhibition of [$^3$H]DAMGO binding), and Hill coefficients (nH) were determined by non-linear regression analysis of competition curves using Hill equation curve fitting.

Table 25 shows the IC$_{50}$ values for oxycodone and Compound KC-2.

TABLE 25

IC$_{50}$ values

| Compound | IC$_{50}$ Human μ-opioid receptor |
|---|---|
| Oxycodone | 1.2E-08 |
| Compound KC-2 | 2.2E-08 |

These data demonstrate that Compound KC-2 binds to the μ-opioid receptor with an affinity about 2-fold less than that of oxycodone.

Example 46

In Vitro Human μ-Opioid Receptor Agonist Cellular Functional Assay

This Example measures the ability of certain compounds of the present disclosure to effect an agonist response when exposed to recombinant human μ-opioid receptor expressed in CHO cells.

The general procedure follows the protocol described by Wang, J.-B., Johnson, P. S., Perscio, A. M., Hawkins, A. L., Griffin, C. A. and Uhl, G. R. (1994). FEBS Lett., 338: 217-222. More specifically, the assays included each of the compounds indicated in Table 26 and recombinant Chinese hamster ovary (CHO) cells expressing the human μ-opioid receptor on their cell surfaces. The control reaction included 1 μM DAMGO. The reaction mixtures were incubated at 37° C. for 10 min, and the reaction product was cyclic AMP (cAMP). The samples were submitted to homogeneous time resolved fluorescence (HTRF®). EC$_{50}$ values (concentration producing a half-maximal specific response) were determined by non-linear regression fit using the Hillplot software.

Table 26 shows results from three separate experiments. EC$_{50}$ values are provided for Compound KC-2, Compound KC-3, Compound KC-5, and Compound KC-6 (each of which can be prepared as described in the Examples herein) and compared to the EC$_{50}$ value for oxycodone, measured in the same respective experiments. Also shown are the EC$_{50}$ values for Compound KC-4 (which can be prepared as described in Example 12) and hydrocodone, measured in the same experiment. Table 26 also provides the drug-to-prodrug (drug/prodrug) relative potency (i.e., EC$_{50}$ at the human μ-opioid receptor) of oxycodone or hydrocodone to a prodrug of that respective drug.

TABLE 26

EC$_{50}$ values

| Experiment # | Compound | EC$_{50}$ Human μ-opioid receptor | Drug/prodrug relative potency |
|---|---|---|---|
| 1 | Oxycodone | 1.2E-7 | |
| 1 | Compound KC-2 | 4.9E-7 | 4.1 |
| 2 | Oxycodone | 4.0E-8 | |
| 2 | Compound KC-3 | 1.6E-6 | 40 |
| 2 | Compound KC-5 | 2.0E-6 | 50 |
| 3 | Hydrocodone | 8.8E-8 | |
| 3 | Compound KC-4 | 1.3E-6 | 15 |
| 3 | Oxycodone | 7.8E-8 | |
| 3 | Compound KC-6 | 1.8E-6 | 23 |

The results of Table 26 show that prodrugs of the embodiments exhibit a drug/prodrug relative potency greater than 1;

thus, prodrugs of the embodiments are less potent at the human μ-opioid receptor than are the respective drugs they release.

Example 47

Pharmacokinetics Following IV Administration of Compound KC-2 or Oxycodone to Rats: Plasma and Cerebrospinal Fluid Penetration This Example compares the plasma and cerebrospinal fluid (CSF) concentrations of prodrug Compound KC-2 and oxycodone following intravenous (IV) administration of the respective compounds to rats. Plasma/CSF partitioning coefficients are predictive of the ability of a compound to penetrate the blood-brain barrier.

Compound KC-2 (which can be prepared as described in the Example herein), at a dose of 10 mg/kg, or an equimolar dose of oxycodone each was dissolved in saline and injected into the tail vein of 4 male Sprague Dawley rats. After 15 minutes, the rats were anesthetized by carbon dioxide asphyxiation and blood samples were drawn, harvested for plasma via centrifugation at 5,400 rpm at 4° C. for 5 min, and 100 microliters (μl) plasma transferred from each sample into a fresh tube containing 2 μl of 50% formic acid. The CSF fluid was collected using a 22×1 inch gauge needle connected to polyurethane catheter type MRE-040 tubing (Braintree Scientific, Inc., Braintree, Mass.). The needle was inserted just below the nuchal crest at the area of the foramen magnum; clear CSF fluid was collected into the catheter and transferred into a collection tube. The CSF samples were centrifuged at 5,400 rpm at 4° C. for 5 min, and 100 μl CSF fluid transferred from each sample into a fresh tube. The plasma and CSF samples were immediately placed in dry ice and then stored in a −80° C. freezer until analysis by high performance liquid chromatography/mass spectrometry (HPLC/MS).

Results in Table 27 are reported, for each group of 4 rats as mean concentrations of the indicated compounds in plasma or CSF. Table 27 also provides the plasma-to-CSF (plasma/CSF) partitioning coefficient, i.e., the ratio of concentration in the plasma to concentration in the CSF of the indicated compounds.

TABLE 27

Mean plasma and CSF concentration values and partitioning coefficients of Compound KC-2 and oxycodone

| Compound | Compound conc. in Plasma, ng/mL | Compound conc. in CSF, ng/mL | Plasma/CSF partitioning coefficient |
|---|---|---|---|
| Compound KC-2 | 27,200 | 61.9 | 439 |
| OC | 3,257 | 863 | 3.8 |

The results in Table 27 indicate that the relative plasma/CSF partitioning coefficient of Compound KC-2 to oxycodone is about 116 (i.e., 439/3.8); that is, Compound KC-2 is about 116-fold less CSF penetrant than oxycodone. In addition, as shown in the Example herein, the drug/prodrug relative potency of Compound KC-2 is about 4.1. Thus, Compound KC-2, when administered intravenously in equimolar amounts would be expected to be about 475-fold (i.e., 116× 4.1) less effective at CNS mu-opioid receptors than oxycodone.

Example 48

Pharmacokinetics of Compound KC-3 following PO Administration to Rats

This Example compares the pharmacokinetics of several concentrations of Compound KC-3 administered orally (PO) to rats.

Saline solutions of Compound KC-3 (which can be prepared as described in the Example herein) were dosed as indicated in Table 28 via oral gavage into jugular vein-cannulated male Sprague Dawley rats (4 per group, except dose 46 mg/kg KC-3 where 3 rats were used) that had been fasted for 16-18 hr prior to oral dosing. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 26:
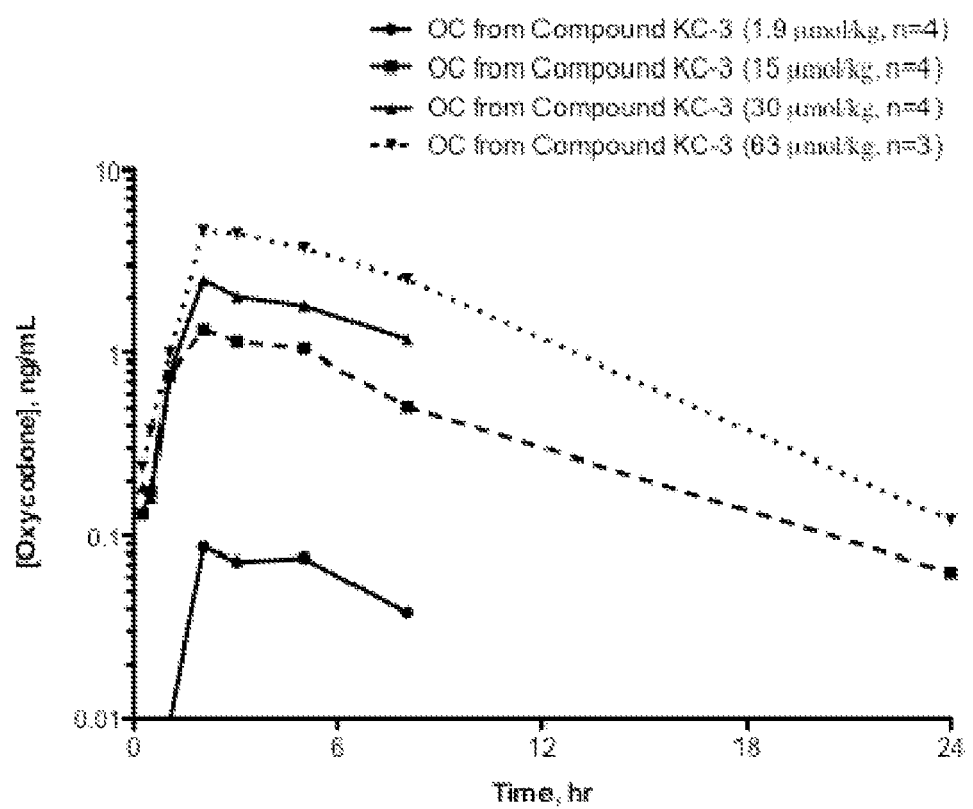
FIG. 26 compares mean plasma concentrations over time of oxycodone release following PO administration of increasing doses of Compound KC-3. to rats.

Table 28 and FIG. 26 provide oxycodone exposure results for rats administered with different doses of Compound KC-3. Results in Table 28 are reported, for each group of rats, as (a) maximum plasma concentration (Cmax) of oxycodone (OC) (average+standard deviation), (b) time after administration of Compound KC-3 to reach maximum oxycodone concentration (Tmax) (average±standard deviation) and (c) area under the curve (AUC) from 0 to 24 hr for all doses except for the 1.4 mg/kg and 22 mg/kg doses where the AUC values were calculated from 0 to 8 hr (average±standard deviation).

TABLE 28

Cmax, Tmax and AUC values of oxycodone in rat plasma

| Compound | Dose, mg/kg | Dose μmol/kg | OC Cmax ± sd, ng/mL | Tmax ± sd, hr | AUC ± sd (ng × hr)/mL |
|---|---|---|---|---|---|
| KC-3 | 1.4 | 1.9 | 0.0992 ± 0.0084 | 2.25 ± 0.5 | 0.376 ± 0.14 |
| KC-3 | 11 | 15 | 1.34 ± 0.31 | 2.00 ± 0.0 | 8.96 ± 4.9 |
| KC-3 | 22 | 30 | 2.54 ± 0.34 | 2.00 ± 0.0 | 12.6 ± 1.9 |
| KC-3 | 46 | 63 | 5.19 ± 0.76 | 3.33 ± 1.5 | 40.5 ± 17 |

Lower limit of quantitation was 0.05 ng/mL

FIG. 26 compares mean plasma concentrations over time of oxycodone release following PO administration of increasing doses of Compound KC-3.

The results in Table 28 and FIG. 26 indicate that plasma concentrations of oxycodone increase proportionally with Compound KC-3 dose.

Example 49

Pharmacokinetics of Compound KC-3 Following IV Administration to Rats

This Example compares the plasma concentrations of prodrug and oxycodone in rats following intravenous (IV) administration of Compound KC-3.

Compound KC-3 (which can be prepared as described in the Example herein) was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by high performance liquid chromatography/mass spectrometry (HPLC/MS).

Figure 27:
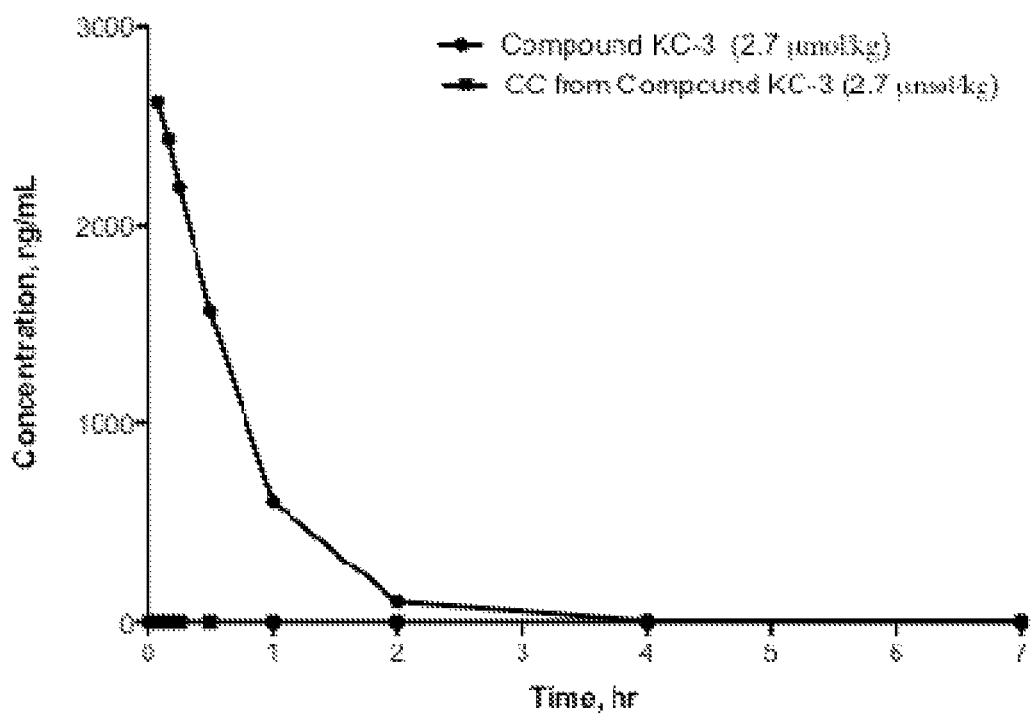
FIG. 27 shows a plasma concentration time course of the production of oxycodone following intravenous (IV) dosing of prodrug Compound KC-3 in rats.

Table 29 and FIG. 27 provide Compound KC-3 and oxycodone exposure results for the group of rats administered Compound KC-3 intravenously. Results in Table 29 are reported as maximum plasma concentration (Cmax) of Compound KC-3 and oxycodone (OC), respectively (average±standard deviation).

TABLE 29

Cmax values of Compound KC-3 and oxycodone in rat plasma

| KC-3 Dose, mg/kg | KC-3 Dose, μmol/kg | KC-3 Cmax ± sd, ng/mL | OC Cmax ± sd, ng/mL |
|---|---|---|---|
| 2 | 2.7 | 2620 ± 85 | 1.14 ± 0.48 |

Lower limit of quantitation was 0.05 ng/mL

Table 29 and FIG. 27 demonstrate that the plasma concentration of oxycodone in rats administered Compound KC-3 intravenously is only 0.04% of the plasma concentration of Compound KC-3, indicating that IV administration of Compound KC-3 does not lead to significant release of oxycodone into plasma.

Example 50

Effect of Trypsin Inhibition on In Vitro Trypsin-Mediated Trypsin Release of Drug from Ketone-Modified Opioid Prodrugs This Example demonstrates the ability of trypsin to cleave a prodrug of the embodiments and the effect of trypsin inhibitors on such cleavage.

Compound KC-3, Compound KC-4, Compound KC-5, or Compound KC-6 was each incubated with trypsin from bovine pancreas (Catalog No. T8003, Type I, ~10,000 BAEE units/mg protein, Sigma-Aldrich). Specifically, the reactions included 0.761 mM of Compound KC-3•2HCl, Compound KC-5•2HCl, Compound KC-4•2HCl, or Compound KC-6•2HCl, 22.5 mM calcium chloride, 40-172 mM Tris pH 8 and 0.25% DMSO with variable activities of trypsin as indicated in Table 30A. The reactions were conducted at 37° C. for 24 hr. Samples were collected at specified time points, transferred into 0.5% formic acid in acetonitrile to stop trypsin activity and stored at less than −70° C. until analysis by LC-MS/MS.

Compound KC-3 was also incubated in the presence of 2 micromolar (μM) trypsin inhibitor Compound 109. In that case, Compound KC-3 was added 5 min after the other incubation components. Other reaction and sample treatment conditions were as described above.

Tables 30A and 30B indicate the results of exposure of the tested compounds to trypsin in the absence or presence of trypsin inhibitor. The results are expressed as half-life of prodrug when exposed to trypsin (i.e., Prodrug trypsin half-life) in hours and rate of oxycodone or hydrocodone formation in umoles per hour per BAEE unit (umol/h/BAEE U) trypsin.

TABLE 30A

In vitro trypsin conversion of prodrugs to oxycodone or hydrocodone

| Pro-drug | BAEE U trypsin/mL | Pro-drug trypsin half-life, h Average ± sd | Rate of oxycodone formation, umol/h/BAEE U Average ± sd | Rate of hydrocodone formation, umol/h/BAEE U Average ± sd |
|---|---|---|---|---|
| KC-3 | 241 | 8.92 ± 1.91 | 0.0684 ± 0.0009 | na |
| KC-5 | 241 | 1.2 ± 0.04 | 0.135 ± 0.005 | na |
| KC-4 | 241 | 6.35 ± 0.13 | na | 0.0911 ± 0.015 |
| KC-4 | 4815 | 0.315 ± 0.004 | na | 0.0137 ± 0.0014 |
| KC-6 | 241 | nc | 0.0118 ± 0.0042 | na |
| KC-6 | 4815 | nc | 0.00571 ± 0.0002 | na | nc = not calculable;
na = not applicable

TABLE 30B

Inhibition of in vitro trypsin conversion of Compound KC-3 to oxycodone by Compound 109

| | | With trypsin inhibitor | |
|---|---|---|---|
| Prodrug | Compound 109 | Pro-drug trypsin half-life, h Average ± sd | Rate of oxycodone formation, umol/h/BAEE U Average ± sd |
| KC-3 | 2 uM | 43.338 ± 40.637 | nc | nc = not calculable

The results in Table 30A indicate that trypsin can mediate release of oxycodone or hydrocodone from a prodrug of the embodiments. The results in Table 30B indicate that a trypsin inhibitor of the embodiments can attenuate trypsin-mediated release of drug from a ketone-modified opioid prodrug of the embodiments.

Example 51

Oral Administration of Compound KC-3 and Trypsin Inhibitor Compound 109 to Rats

This Example demonstrates the ability of a trypsin inhibitor of the embodiments to affect drug release into plasma from Compound KC-3 administered orally.

Saline solutions of Compound KC-3 (which can be prepared as described in the Example herein) were dosed at 6.8 μmol/kg (5 mg/kg) and 68 μmol/kg (50 mg/kg) Compound KC-3 with or without a co-dose of increasing concentrations of Compound 109 (Catalog No. 3081, Tocris Bioscience or Catalog No. WS38665, Waterstone Technology) as indicated in Table 31 via oral gavage into jugular vein-cannulated male Sprague Dawley rats (4 per groups) that had been fasted for 16-18 hr prior to oral dosing. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 28:
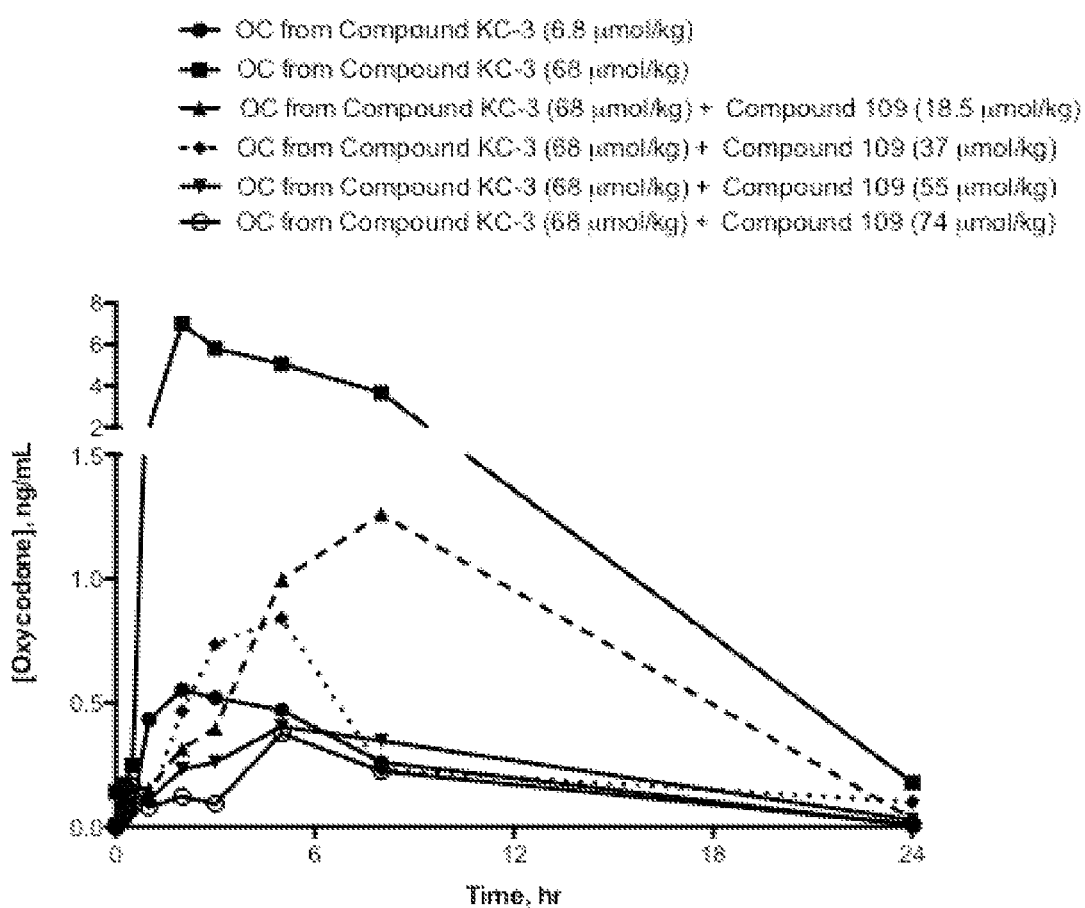
FIG. 28 compares mean plasma concentrations over time of oxycodone release following PO administration of prodrug Compound KC-3 with increasing amounts of co-dosed trypsin inhibitor Compound 109 to rats.

Table 31 and FIG. 28 provide oxycodone exposure results for rats administered with Compound KC-3 in the absence or presence of trypsin inhibitor. Results in Table 31 are reported as (a) maximum plasma concentration (Cmax) of oxycodone (OC) (average±standard deviation), (b) time after administration of Compound KC-3 to reach maximum oxycodone concentration (Tmax) (average±standard deviation) and (c) area under the curve (AUC) from 0 to 24 hr (average±standard deviation).

TABLE 31

Cmax, Tmax and AUC values of oxycodone in rat plasma

| KC-3 Dose, mg/kg | KC-3 Dose, μmol/kg | Compound 109 Dose, mg/kg | Compound 109 Dose, μmol/kg | OC Cmax ± sd, ng/mL | Tmax ± sd, hr | AUC ± sd (ng × hr)/mL |
|---|---|---|---|---|---|---|
| 5 | 6.8 | 0 | 0 | 0.611 ± 0.10 | 3.00 ± 1.4 | 3.95 ± 1.6 |
| 50 | 68 | 0 | 0 | 7.08 ± 2.6 | 3.00 ± 1.4 | 59.1 ± 23 |
| 50 | 68 | 10 | 18.5 | 1.26 ± 0.34 | 8.00 ± 0.0 | 12.3 ± 2.9 |
| 50 | 68 | 20 | 37 | 1.05 ± 0.61 | 3.75 ± 1.5 | 10.5 ± 5.4 |
| 50 | 68 | 30 | 55 | 0.49 ± 0.19 | 4.50 ± 2.6 | 2.82 ± 1.3 |
| 50 | 68 | 40 | 74 | 0.47 ± 0.36 | 4.63 ± 3.1 | 2.71 ± 3.7 |

Lower limit of quantitation was 0.025 ng/mL

FIG. 28 compares mean plasma concentrations over time of oxycodone release following PO administration of Compound KC-3 with or without a co-dose of trypsin inhibitor.

The results in Table 31 and FIG. 28 indicate that Compound 109 attenuates Compound KC-3's ability to release oxycodone, both by suppressing Cmax and AUC and by delaying Tmax.

Example 52

Pharmacokinetics Following IV Administration of Compound KC-3 or Oxycodone to Rats: Plasma and Cerebrospinal Fluid Penetration This Example compares the plasma and cerebrospinal fluid (CSF) concentrations of prodrug Compound KC-3 and oxycodone following intravenous (IV) administration of the respective compounds to rats. Plasma/CSF partitioning coefficients are predictive of the ability of a compound to penetrate the blood-brain barrier.

Compound KC-3 (which can be prepared as described in the Example herein), at a dose of 10 mg/kg, or an equimolar dose of oxycodone each was dissolved in saline and injected into the tail vein of 4 male Sprague Dawley rats. After 2 minutes, the rats were anesthetized by carbon dioxide asphyxiation and blood samples were drawn, harvested for plasma via centrifugation at 5,400 rpm at 4° C. for 5 min, and 100 μl plasma transferred from each sample into a fresh tube containing 2 μl of 50% formic acid. The CSF fluid was collected using a 22×1 inch gauge needle connected to polyurethane catheter type MRE-040 tubing (Braintree Scientific, Inc.). The needle was inserted just below the nuchal crest at the area of the foramen magnum; clear CSF fluid was collected into the catheter and transferred into a collection tube. The CSF samples were centrifuged at 5,400 rpm at 4° C. for 5 min, and 100 μl CSF fluid transferred from each sample into a fresh tube. The plasma and CSF samples were immediately placed in dry ice and then stored in a −80° C. freezer until analysis by high performance liquid chromatography/mass spectrometry (HPLC/MS). In order to study Compound KC-3 and oxycodone plasma and CSF penetration over time, additional groups of 4 rats were administered compounds as described above and anesthetized at specified time points. Plasma and CSF were collected and analyzed as described above. Results from these rats indicated that equilibrium was quickly reached in the plasma and CSF compartments after dosing and that the extent of partitioning between CSF and plasma was consistent across time points. Thus, only the 2-minute time point data are reported in Table 32.

Results in Table 32 are reported, for each group of 4 rats as mean concentrations of the indicated compounds in plasma or CSF. Table 32 also provides the plasma-to-CSF (plasma/CSF) partitioning coefficient, i.e., the ratio of concentration in the plasma to concentration in the CSF of the indicated compounds.

TABLE 32

Mean plasma and CSF concentration values and partitioning coefficients of Compound KC-3 and oxycodone

| Compound | Compound conc. in Plasma, ng/mL | Compound conc. in CSF, ng/mL | Plasma/CSF partitioning coefficient |
|---|---|---|---|
| Compound KC-3 | 59,225 | 34.1 | 1,737 |
| OC | 10,300 | 2158 | 4.8 |

The results in Table 32 indicate that the relative plasma/CSF partitioning coefficient of Compound KC-3 to oxycodone is about 364 (i.e., 1,737/4.8); that is, Compound KC-3 is about 364-fold less CSF penetrant than oxycodone. In addition, as shown in the Example herein, the drug/prodrug relative potency of Compound KC-3 is about 40. Thus, Compound KC-3, when administered intravenously in equimolar amounts would be expected to be about 14,500-fold (i.e., 364×40) less effective at CNS mu-opioid receptors than oxycodone.

Example 53

In Vivo Tolerability of Compound KC-3 in Rats

This Example demonstrates that Compound KC-3 was tolerated when administered intravenously to rats.

Male naïve Sprague-Dawley rats, 4 per dose, were used in the study. Rats were weighed, and then placed under a heat lamp for 15-20 minutes to dilate the lateral tail veins. Dose volumes were based on the body weights (1 mL/kg); dosing of Compound KC-3 (which can be prepared as described in the Example herein) was as indicated in Table 33. Before dosing, rats were placed in Broome restrainers and the drug was introduced into one of the tail veins using a syringe and needle. After dosing, the timer was set and rats were observed for clinical signs. Blood samples were collected 5 minutes post-dose via the saphenous vein. The rats were observed up to 24 hours. Results are shown in Table 33.

TABLE 33

In vivo tolerability of Compound KC-3 in rats

| Compound | Dose, mg/kg | Dose, μmol/kg | Number of Rats dosed | Clinical observations |
|---|---|---|---|---|
| KC-3 | 71 | 97 | 4 | 2 normal and 2 with ataxia which resolved by 2 minutes |

The results in Table 33 indicate that rats tolerate a dose of 97 μmol/kg of Compound KC-3 and recover to normal activity within 2 minutes.

Example 54

In Vitro Stability of Oxycodone Prodrug Compound KC-3

This Example demonstrates the stability of Compound KC-3 to a variety of readily available household chemicals and enzyme preparations.

Compound KC-3 (which can be prepared as described in the Example herein) was exposed at room temperature (RT) or 80° C. for either 1 or 24 hours (hr) to the following household chemicals: vodka (40% alcohol), baking soda (saturated sodium bicarbonate solution, pH 9), WINDEX® with Ammonia-D (pH11) and vinegar (5% acetic acid). Compound KC-3 was also exposed to the following enzyme-containing compositions at RT for 1 or 24 hr: GNC® Super Digestive (2 capsules of GNC Super Digestive Enzymes dissolved in 5 mL of water), tenderizer (Adolf's meat tenderizer, primarily papain, dissolved in water to a concentration of 0.123 g/mL to approximate the concentration of a marinade given on the bottle label), and subtilisn (8 tablets of ULTRA-ZYME® contact lens cleaner (Advanced Medical Optics) dissolved in 4 mL water). Samples were incubated as described. Aliquots were removed at 1 hr and 24 hr and stabilized by adding each to a solution of 50% or 100% of 85% phosphoric acid solution to achieve a final pH of less than or equal to pH 4. The stabilized aliquots were then diluted 4- to 6-fold with water, vortex-mixed and applied to HPLC.

Figure 29:
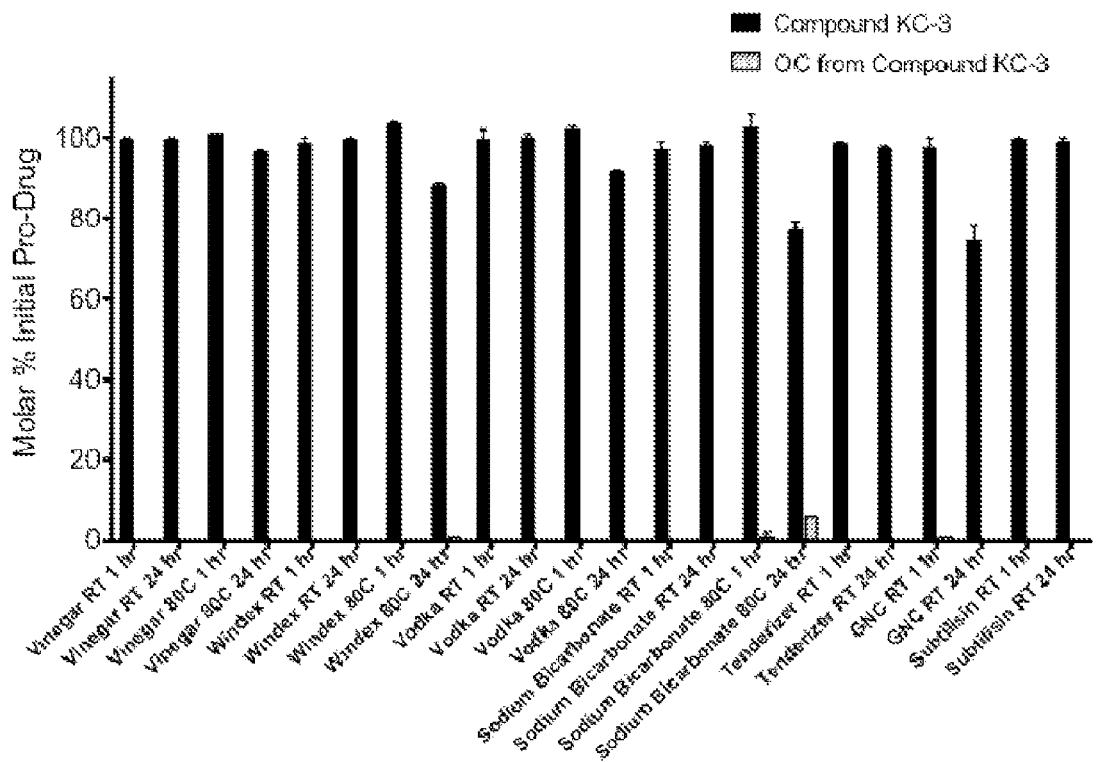
FIG. 29 demonstrates the release of oxycodone from prodrug Compound KC-3 exposed to a variety of household chemicals and enzyme preparations.

FIG. 29 demonstrates the release of oxycodone when Compound KC-3 was exposed to the various household chemicals and enzyme-containing compositions described above. The percentage of Compound KC-3 remaining after exposure is indicated by the solid black bars and percentage conversion of Compound KC-3 to oxycodone is indicated by the lightly shaded bars with a black outline. These results indicate that exposure of Compound KC-3 to these various conditions leads to substantially less than 10% conversion to oxycodone.

Example 55

Pharmacokinetics of Compound KC-4 Following PO Administration to Rats

This Example demonstrates the release of hydrocodone into plasma when Compound KC-4 is administered orally (PO) to rats.

Saline solutions of Compound KC-4 (which can be prepared as described in the Example herein) were dosed as indicated in Table 34) via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Table 34 provides hydrocodone exposure results for rats administered Compound KC-4 orally. Results in Table 34 are reported as (a) maximum plasma concentration (Cmax) of hydrocodone (OC) (average±standard deviation), (b) time after administration of Compound KC-4 to reach maximum hydrocodone concentration (Tmax) (average±standard deviation) and (c) area under the curve (AUC) from 0 to 24 hr (average±standard deviation).

TABLE 34

Cmax, Tmax and AUC values of hydrocodone in rat plasma

| Compound | Dose, mg/kg | Dose μmol/kg | HC Cmax ± sd, ng/mL | Tmax ± sd, hr | AUC ± sd (ng × hr)/mL |
|---|---|---|---|---|---|
| KC-4 | 6 | 8.4 | 0.0667 ± 0.019 | 4.5 ± 2.6 | 0.315 ± 0.063 |

Lower limit of quantitation was 0.025 ng/mL

The results in Table 34 indicate that oral administration of Compound KC-4 leads to release of hydrocodone by a hydrocodone prodrug of the embodiments.

Example 56

Pharmacokinetics of Compound KC-4 Following IV Administration to Rats

This Example compares the plasma concentrations of prodrug and hydrocodone in rats following intravenous (IV) administration of Compound KC-4.

Compound KC-4 (which can be prepared as described in the Example herein) was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by high performance liquid chromatography/mass spectrometry (HPLC/MS).

Figure 30:
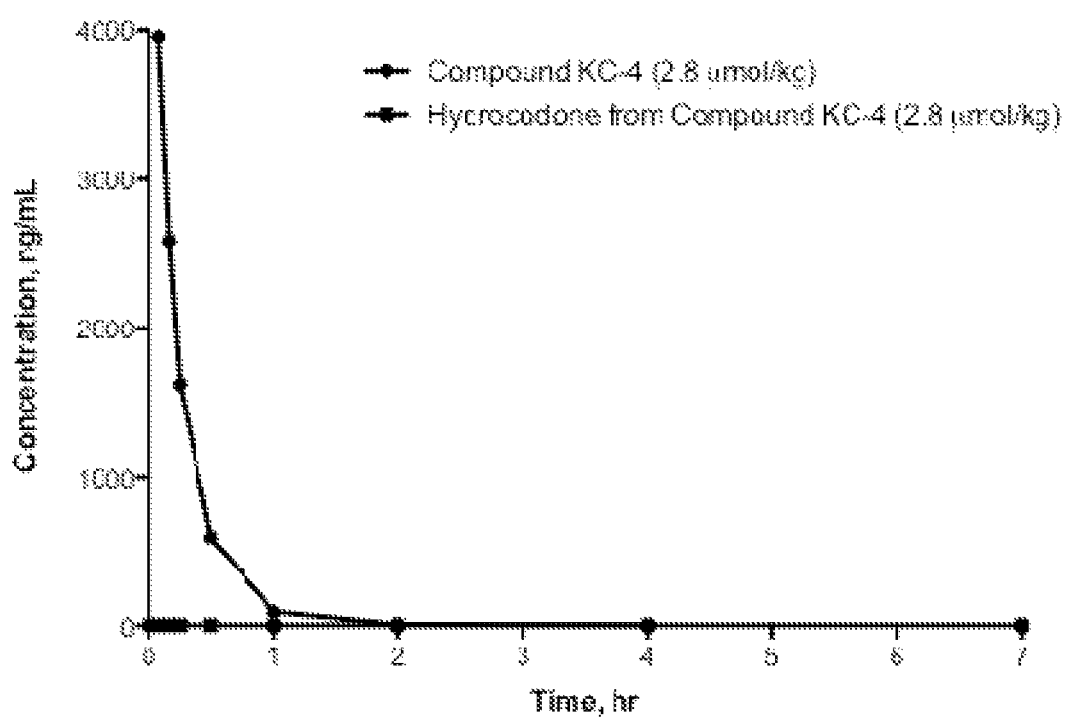
FIG. 30 shows a plasma concentration time course of the production of oxycodone following intravenous (IV) dosing of prodrug Compound KC-4 in rats.

Table 35 and FIG. 30 provide Compound KC-4 and hydrocodone exposure results for rats administered Compound KC-4 intravenously. Results in Table 35 are reported as maximum plasma concentration (Cmax) of Compound KC-4 and hydrocodone (HC), respectively, (average±standard deviation).

TABLE 35

Cmax values of Compound KC-4 and hydrocodone in rat plasma

| KC-4 Dose, mg/kg | KC-4 Dose, μmol/kg | KC-4 Cmax ± sd, ng/mL* | HC Cmax ± sd, ng/mL˜ |
|---|---|---|---|
| 2 | 2.8 | 3960 ± 570 | 0.224 ± 0.020 |

*Lower limit of quantitation was 0.05 ng/mL
˜Lower limit of quantitation was 0.025 ng/mL Table 35 and FIG. 30 demonstrate that the plasma concentration of hydrocodone in rats administered Compound KC-4 intravenously is only 0.006% of the plasma concentration of Compound KC-4, indicating that IV administration of Compound KC-4 does not lead to significant release of hydrocodone into plasma.

Example 57

Oral Administration of Compound KC-4 and Trypsin Inhibitor Compound 109 to Rats This Example demonstrates the ability of a trypsin inhibitor of the embodiments to affect drug release into plasma from Compound KC-4 administered orally.

Saline solutions of Compound KC-4 (which can be prepared as described in the Example herein) were dosed at 8.4 µmol/kg (6 mg/kg) with or without a co-dose of 55 µmol/kg (30 mg/kg) Compound 109 (Catalog No. 3081, Tocris Bioscience or Catalog No. WS38665, Waterstone Technology) as indicated in Table 36 via oral gavage into jugular vein-cannulated male Sprague Dawley rats (4 per groups) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 31:
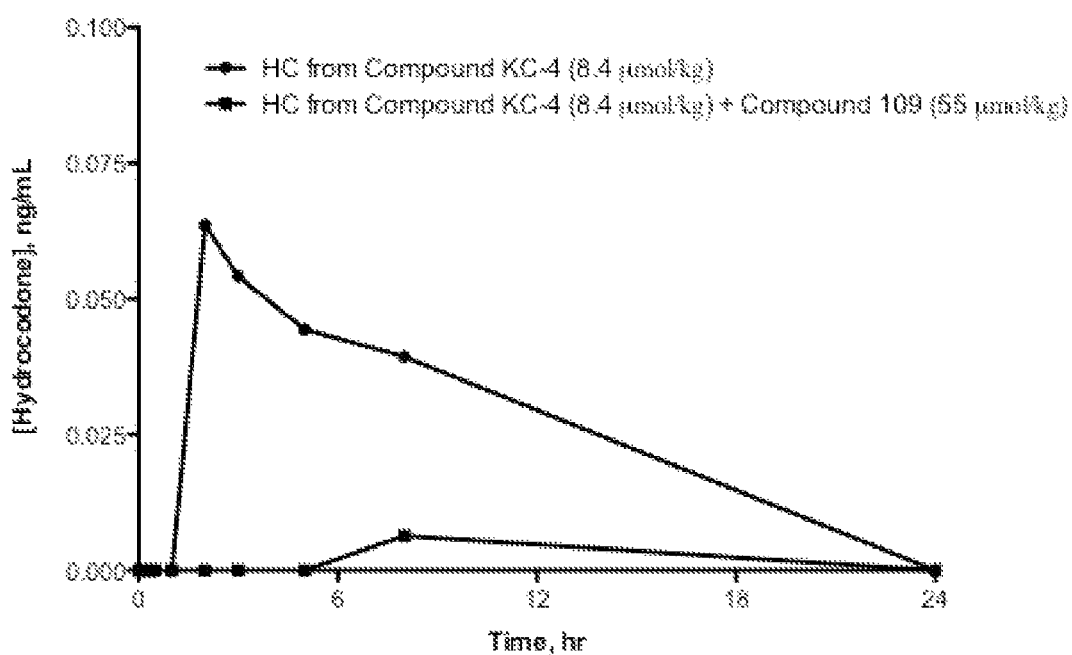
FIG. 31 compares mean plasma concentrations over time of hydrocodone release following PO administration of prodrug Compound KC-4 with or without a co-dose of trypsin inhibitor to rats.

Table 36 and FIG. 31 provide hydrocodone exposure results for rats administered with Compound KC-4 in the absence or presence of trypsin inhibitor. Results in Table 36 are reported as (a) maximum plasma concentration (Cmax) of hydrocodone (HC) (average±standard deviation), (b) time after administration of Compound KC-4 to reach maximum hydrocodone concentration (Tmax) (average±standard deviation) and (c) area under the curve from 0 to 24 hr (average±standard deviation).

TABLE 36

Cmax, Tmax and AUC values of hydrocodone in rat plasma

| KC-4 Dose, mg/kg | KC-4 Dose, µmol/kg | Compound 109 Dose, mg/kg | Compound 109 Dose, µmol/kg | HC Cmax ± sd, ng/mL | Tmax ± sd, hr | AUC ± sd (ng × hr)/mL |
|---|---|---|---|---|---|---|
| 6 | 8.4 | 0 | 0 | 0.0667 ± 0.019 | 4.5 ± 2.6 | 0.315 ± 0.063 |
| 6 | 8.4 | 30 | 55 | 0.0064 ± 0.013 | 8.0 ± 0.0 | 0.016 ± 0.032 |

Lower limit of quantitation was 0.025 ng/mL

FIG. 31 compares mean plasma concentrations over time of hydrocodone release following PO administration of Compound KC-4 with or without a co-dose of trypsin inhibitor.

The results in Table 36 and FIG. 31 indicate that Compound 109 attenuates Compound KC-4's ability to release hydrocodone, both by suppressing Cmax and AUC and by delaying Tmax.

Example 58

Pharmacokinetics of Compound KC-5 Following PO Administration to Rats

This Example demonstrates the release of oxycodone into plasma when Compound KC-5 is administered orally (PO) to rats.

Saline solutions of Compound KC-5 (which can be prepared as described in the Example herein) were dosed as indicated in Table 37 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 32:
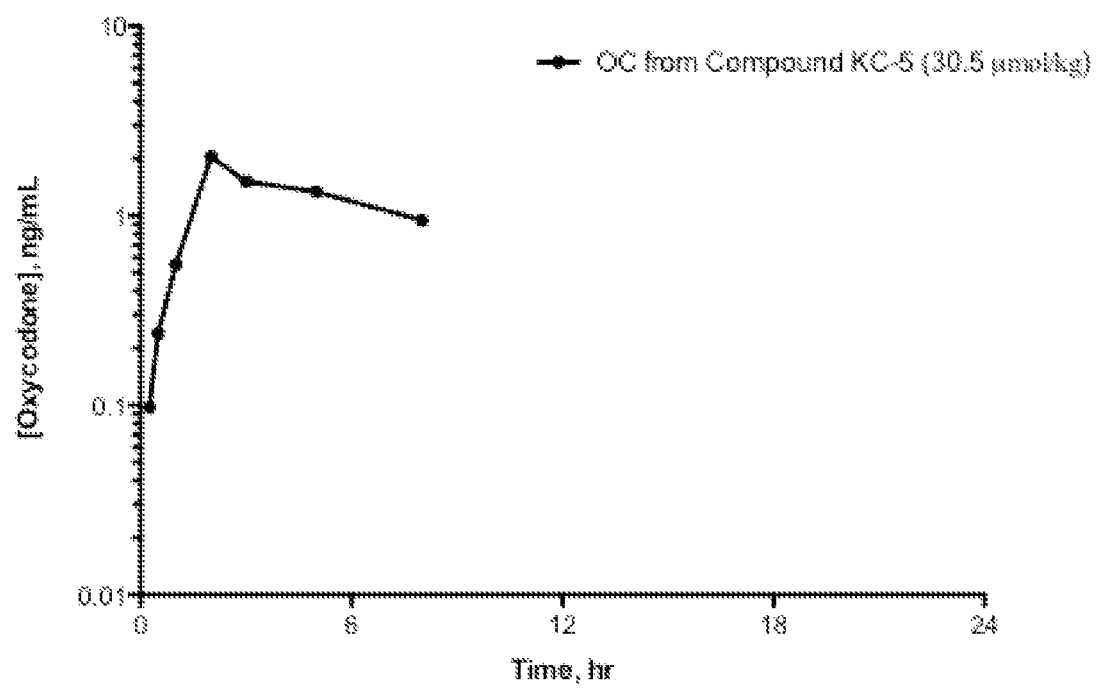
FIG. 32 demonstrates mean plasma concentrations over time of oxycodone release following PO administration of Compound KC-5.

Table 37 and FIG. 32 provide oxycodone exposure results for rats administered Compound KC-5 orally. Results in Table 37 are reported as (a) maximum plasma concentration (Cmax) of oxycodone (OC) (average±standard deviation), (b) time after administration of Compound KC-5 to reach maximum oxycodone concentration (Tmax) (average±standard deviation) and (c) area under the curve (AUC) (ng×hr)/mL from 0 to 8 hr (average±standard deviation).

TABLE 37

Cmax, Tmax and AUC values of oxycodone (OC) in rat plasma

| Compound | Dose, mg/kg | Dose, µmol/kg | OC Cmax ± sd, ng/mL | Tmax ± sd, hr | AUC ± sd (ng × hr)/mL |
|---|---|---|---|---|---|
| KC-5 | 24 | 30.5 | 2.06 ± 0.45 | 2.0 ± 0.0 | 9.61 ± 1.4 |

Lower limit of quantitation was 0.025 ng/mL

FIG. 32 demonstrates mean plasma concentrations over time of oxycodone release following PO administration of Compound KC-5.

The results in Table 37 and FIG. 32 indicate that oral administration of Compound KC-5 yields oxycodone plasma concentrations that exhibit a suppressed Cmax and AUC and delayed Tmax compared to administration of oxycodone (see Example herein).

Example 59

Pharmacokinetics of Compound KC-5 Following IV Administration to Rats

This Example compares the plasma concentrations of prodrug and oxycodone in rats following intravenous (IV) administration of Compound KC-5.

Compound KC-5 (which can be prepared as described in the Example herein) was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by high performance liquid chromatography/mass spectrometry (HPLC/MS).

Figure 33:
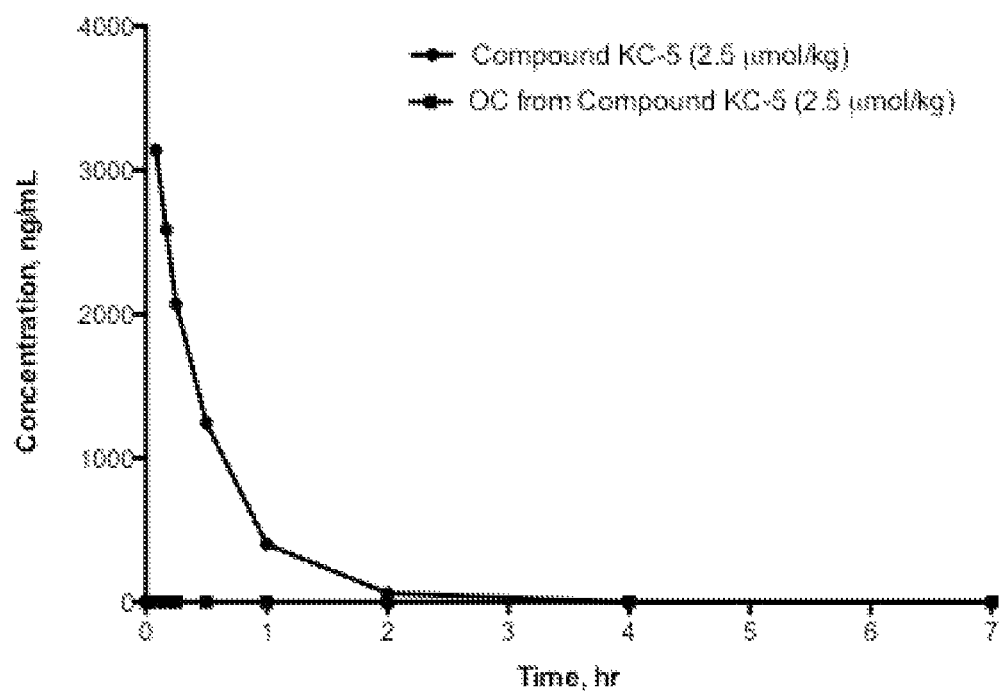
FIG. 33 shows a plasma concentration time course of the production of oxycodone following intravenous (IV) dosing of prodrug Compound KC-5 in rats.

Table 38 and FIG. 33 provide Compound KC-5 and oxycodone exposure results for rats administered Compound KC-5 intravenously. Results in Table 38 are reported as maximum plasma concentration (Cmax) of Compound KC-5 and oxycodone (OC), respectively (average±standard deviation).

TABLE 38

| Cmax values of Compound KC-5 and oxycodone in rat plasma | | | |
|---|---|---|---|
| KC-5 Dose, mg/kg | KC-5 Dose, μmol/kg | KC-5 Cmax ± sd, ng/mL* | OC Cmax ± sd, ng/mL^ |
| 2 | 2.5 | 3140 ± 270 | 0.878 ± 0.78 |

*Lower limit of quantitation was 0.100 ng/mL
^Lower limit of quantitation was 0.0125 ng/mL Table 38 and FIG. 33 demonstrate that the plasma concentration of oxycodone in rats administered Compound KC-5 IV is only 0.028% of the plasma concentration of Compound KC-5, indicating that IV administration of Compound KC-5 does not lead to significant release of oxycodone into plasma.

Example 60

Pharmacokinetics Following IV Administration of Compound KC-5 or Oxycodone to Rats: Plasma and Cerebrospinal Fluid Penetration This Example compares the plasma and cerebrospinal fluid (CSF) concentrations of prodrug Compound KC-5 and oxycodone following intravenous (IV) administration of the respective compounds to rats. Plasma/CSF partitioning coefficients are predictive of the ability of a compound to penetrate the blood-brain barrier.

Compound KC-5 (which can be prepared as described in the Example herein), at a dose of 10 mg/kg, or an equimolar dose of oxycodone each was dissolved in saline and injected into the tail vein of 4 male Sprague Dawley rats. After 2 minutes, the rats were anesthetized by carbon dioxide asphyxiation and blood samples were drawn, harvested for plasma via centrifugation at 5,400 rpm at 4° C. for 5 min, and 100 μl plasma transferred from each sample into a fresh tube containing 2 μl of 50% formic acid. The CSF fluid was collected using a 22×1 inch gauge needle connected to polyurethane catheter type MRE-040 tubing (Braintree Scientific, Inc.). The needle was inserted just below the nuchal crest at the area of the foramen magnum and clear CSF fluid was collected into the catheter and transferred into a collection tube. The CSF samples were centrifuged at 5,400 rpm at 4° C. for 5 min, and 100 μl CSF fluid transferred from each sample into a fresh tube. The plasma and CSF samples were immediately placed in dry ice and then stored in a −80° C. freezer until analysis by high performance liquid chromatography/mass spectrometry (HPLC/MS). In order to study Compound KC-5 and oxycodone plasma and CSF penetration over time, additional groups of 4 rats were administered compounds as described above and anesthetized at specified time points. Plasma and CSF were collected and analyzed as described above. Results from these rats indicated that equilibrium was quickly reached in the plasma and CSF compartments after dosing and that the extent of partitioning between CSF and plasma was consistent across time points. Thus, only the 2-minute time point data are reported in Table 39.

Results in Table 39 are reported, for each group of 4 rats as mean concentrations of the indicated compounds in plasma or CSF. Table 39 also provides the plasma-to-CSF (plasma/CSF) partitioning coefficient, i.e., the ratio of concentration in the plasma to concentration in the CSF of the indicated compounds.

TABLE 39

| Mean plasma and CSF concentration values and partitioning coefficients of Compound KC-5 and oxycodone | | | |
|---|---|---|---|
| Compound | Compound conc. in Plasma, ng/mL | Compound conc. in CSF, ng/mL | Plasma/CSF partitioning coefficient |
| Compound KC-5 | 54,900 | 36.4 | 1,508 |
| OC | 10,300 | 2,158 | 4.8 |

The results in Table 39 indicate that the relative plasma/CSF partitioning coefficient of Compound KC-5 to oxycodone is about 316 (i.e., 1,508/4.8); that is, Compound KC-5 is about 316-fold less CSF penetrant than oxycodone. In addition, as shown in the Example herein, the drug/prodrug relative potency of Compound KC-5 is about 50. Thus, Compound KC-5, when administered intravenously in equimolar amounts would be expected to be about 15,800-fold (i.e., 316×50) less effective at CNS mu-opioid receptors than oxycodone.

Example 61

Pharmacokinetics of Compound KC-6 Following PO Administration to Rats

This Example demonstrates the release of oxycodone into plasma when Compound KC-6 is administered orally (PO) to rats.

Saline solutions of Compound KC-6 (which can be prepared as described in the Example herein) were dosed as indicated in Table 40 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 34:
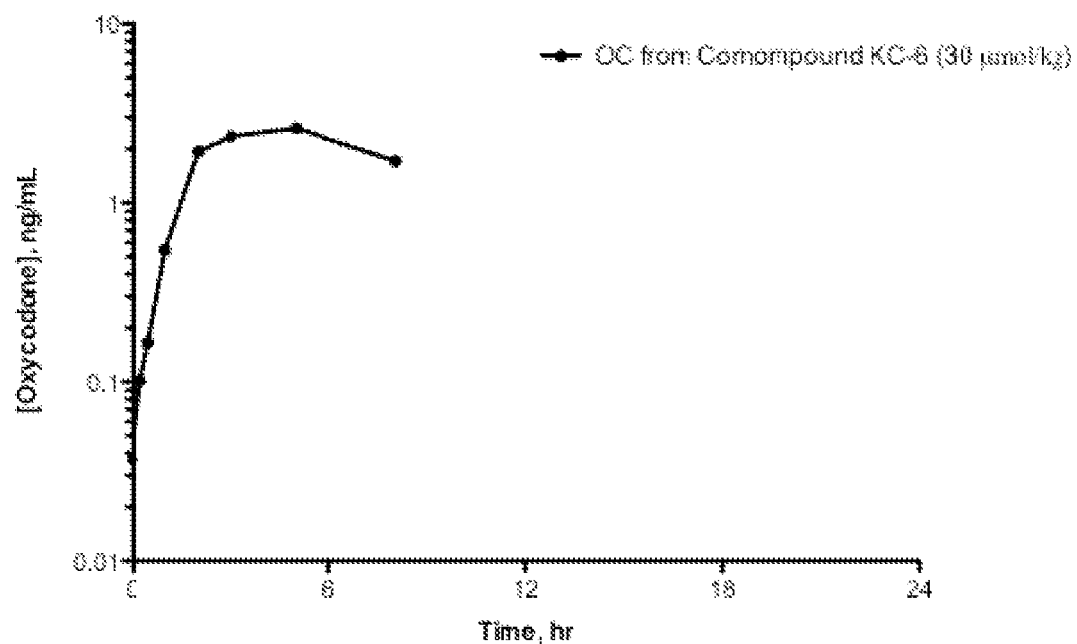
FIG. 34 demonstrates mean plasma concentrations over time of oxycodone release following PO administration of Compound KC-6 to rats.

Table 40 and FIG. 34 provide oxycodone exposure results for rats administered Compound KC-6 orally. Results in Table 40 are reported as (a) maximum plasma concentration (Cmax) of oxycodone (OC) (average±standard deviation), (b) time after administration of Compound KC-6 to reach maximum oxycodone concentration (Tmax) (average±standard deviation) and (c) area under the curve (AUC) (ng×hr)/mL from 0 to 8 hr (average±standard deviation).

TABLE 40

| Cmax, Tmax and AUC values of oxycodone in rat plasma | | | | | |
|---|---|---|---|---|---|
| Compound | Dose, mg/kg | Dose μmol/kg | OC Cmax ± sd, ng/mL | Tmax ± sd, hr | AUC ± sd (ng × hr)/mL |
| KC-6 | 24 | 30 | 2.72 ± 0.18 | 4.25 ± 1.5 | 15.1 ± 0.75 |

Lower limit of quantitation was 0.025 ng/mL

FIG. 34 demonstrates mean plasma concentrations over time of oxycodone release following PO administration of Compound KC-6.

The results in Table 40 and FIG. 34 indicate that oral administration of Compound KC-6 yields oxycodone plasma concentrations that exhibit a suppressed Cmax and AUC and delayed Tmax compared to administration of oxycodone (see Example herein).

Example 62

Pharmacokinetics of Compound KC-6 Following IV Administration to Rats

This Example compares the plasma concentrations of pro-drug and oxycodone in rats following intravenous (IV) administration of Compound KC-6.

Compound KC-6 (which can be prepared as described in the Example herein) was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by high performance liquid chromatography/mass spectrometry (HPLC/MS).

Figure 35:
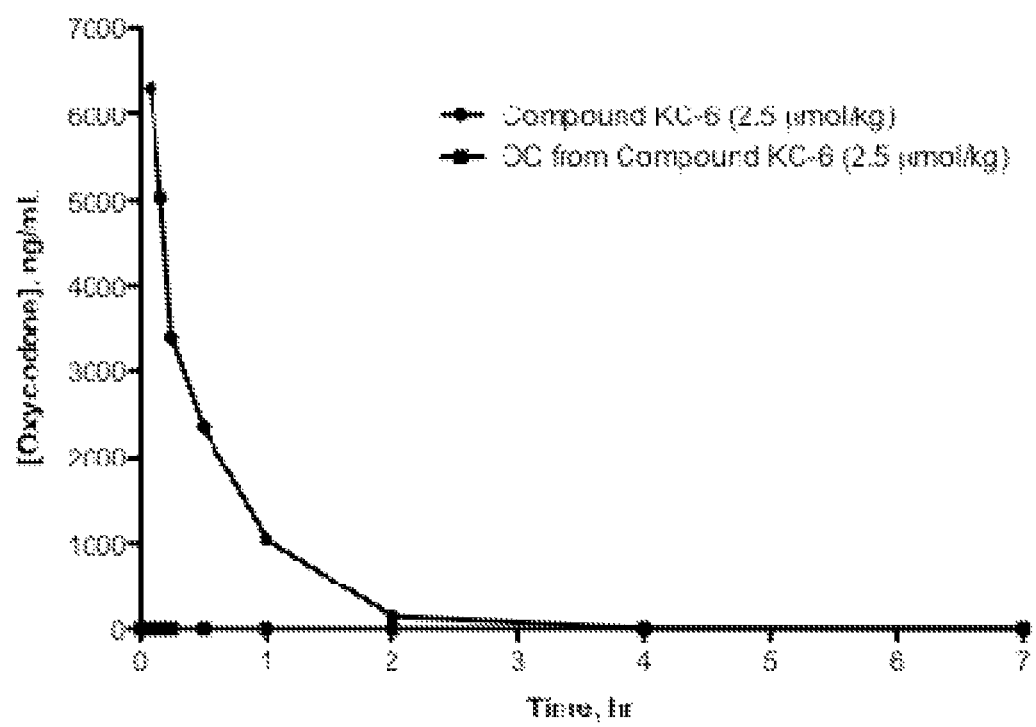
FIG. 35 shows a plasma concentration time course of the production of oxycodone following intravenous (IV) dosing of prodrug Compound KC-6 in rats.

Table 41 and FIG. 35 provide Compound KC-6 and oxycodone exposure results for rats administered Compound KC-6 intravenously. Results in Table 41 are reported as maximum plasma concentration (Cmax) of Compound KC-6 and oxycodone (OC), respectively, (average±standard deviation).

TABLE 41

Cmax values of Compound KC-6 and oxycodone in rat plasma

| KC-6 Dose, mg/kg | KC-6 Dose, μmol/kg | KC-6 Cmax ± sd, ng/mL | OC Cmax ± sd, ng/mL |
|---|---|---|---|
| 2 | 2.5 | 6360 ± 2300* | 0.960 ± 0.22^ |

*Lower limit of quantitation was 0.05 ng/mL
^Lower limit of quantitation was 0.1 ng/mL Table 41 and FIG. 35 demonstrate that the plasma concentration of oxycodone in rats administered Compound KC-6 intravenously is only 0.015% of the plasma concentration of Compound KC-6, indicating that IV administration of Compound KC-6 does not lead to significant release of oxycodone into plasma.

Example 63

Pharmacokinetics Following IV Administration of Compound KC-6 to Rats Plasma and Cerebrospinal Fluid Penetration This Example compares the plasma and cerebrospinal fluid (CSF) concentrations of prodrug Compound KC-6 and oxycodone following intravenous (IV) administration of the respective compounds to rats. Plasma/CSF partitioning coefficients are predictive of the ability of a compound to penetrate the blood-brain barrier.

Compound KC-6 (which can be prepared as described in the Example herein), at a dose of 7.5 mg/kg, and oxycodone at a dose of 7.5 mg/kg, each was dissolved in saline and injected into the tail vein of 4 male Sprague Dawley rats. After 2 minutes, the rats were anesthetized by carbon dioxide asphyxiation and blood samples were drawn, harvested for plasma via centrifugation at 5,400 rpm at 4° C. for 5 min, and 100 μl plasma transferred from each sample into a fresh tube containing 2 μl of 50% formic acid. The CSF fluid was collected using a 22×1 inch gauge needle connected to polyurethane catheter type MRE-040 tubing (Braintree Scientific, Inc.). The needle was inserted just below the nuchal crest at the area of the foramen magnum and clear CSF fluid was collected into the catheter and transferred into a collection tube. The CSF samples were centrifuged at 5,400 rpm at 4° C. for 5 min, and 100 μl CSF fluid transferred from each sample into a fresh tube. The plasma and CSF samples were immediately placed in dry ice and then stored in a −80° C. freezer until analysis by high performance liquid chromatography/mass spectrometry (HPLC/MS). In order to study Compound KC-6 and oxycodone plasma and CSF penetration over time, additional groups of 4 rats were administered compounds as described above and anesthetized at specified time points. Plasma and CSF were collected and analyzed as described above. Results from these rats indicated that equilibrium was quickly reached in the plasma and CSF compartments after dosing and that the extent of partitioning between CSF and plasma was consistent across time points. Thus, only the 2-minute time point data are reported in Table 42.

Results in Table 42 are reported, for each group of 4 rats as mean concentrations of the indicated compounds in plasma or CSF. Table 42 also provides the plasma-to-CSF (plasma/CSF) partitioning coefficient, i.e., the ratio of concentration in the plasma to concentration in the CSF of the indicated compounds.

TABLE 42

Mean plasma and CSF concentration values and partitioning coefficients of Compound KC-6 and oxycodone

| Compound | Compound conc. in Plasma, ng/mL | Compound conc. in CSF, ng/mL | Plasma/CSF partitioning coefficient |
|---|---|---|---|
| Compound KC-6 | 60,400 | 74.1 | 815 |
| OC | 10,300 | 2,158 | 4.8 |

The results in Table 42 indicate that the relative plasma/CSF partitioning coefficient of Compound KC-6 to oxycodone is about 171 (i.e., 815/4.8); that is, Compound KC-6 is about 171-fold less CSF penetrant than oxycodone. In addition, as shown in the Example herein, the drug/prodrug relative potency of Compound KC-6 is about 23. Thus, Compound KC-6, when administered intravenously in equimolar amounts would be expected to be about 3,940-fold (i.e., 171× 23) less effective at CNS mu-opioid receptors than oxycodone.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A composition comprising:
    an opioid prodrug comprising a ketone-containing opioid covalently bound to a promoiety comprising a GI enzyme-cleavable moiety wherein the hydrogen atom of the corresponding enolic group of the ketone is replaced by a covalent bond to the GI enzyme-cleavable moiety, and wherein cleavage of the GI enzyme-cleavable moiety by a GI enzyme mediates release of the opioid; and
a GI enzyme inhibitor that interacts with the GI enzyme that mediates enzymatically-controlled release of the opioid from the opioid prodrug following ingestion of the composition.

2. A composition comprising:
a container suitable for containing a composition for administration to a patient; and
a dose unit comprising the composition of claim 1 disposed within the container.

3. The composition of claim 1, wherein the composition is a dose unit having a total weight of from 1 microgram to 2 grams.

4. The composition of claim 1, wherein the composition has a combined weight of opioid prodrug and GI enzyme inhibitor of from 0.1% to 99% per gram of the composition.

5. The composition of claim 1, wherein the opioid prodrug is a compound of formula KC-(Ia):

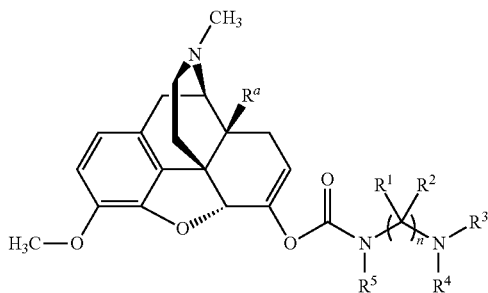

(KC-(Ia))

wherein:
$R^a$ is hydrogen or hydroxyl;
$R^5$ is selected from alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;
n is an integer from 2 to 4;
$R^3$ is hydrogen or (1-4C)alkyl;
$R^4$ is

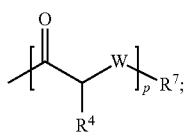

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;
each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;
p is an integer from one to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

6. The composition of claim 1, wherein the opioid prodrug is a compound of formula KC-(Ib):

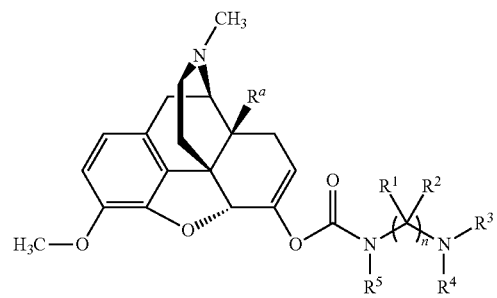

(KC-(Ib))

wherein:
$R^a$ is hydrogen or hydroxyl;
$R^5$ is selected from alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;
n is an integer from 2 to 4;
$R^3$ is hydrogen or (1-4C)alkyl;
$R^4$ is

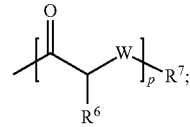

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;

each R⁸ is independently selected from hydrogen, alkyl, substituted alkyl, aryl and substituted aryl, or optionally, each R⁶ and R⁸ independently together with the atoms to which they are bonded form a cycloheteroalkyl or substituted cycloheteroalkyl ring;

p is an integer from one to 100; and

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

7. The composition of claim 1, wherein the opioid prodrug is a compound of formula KC-(II):

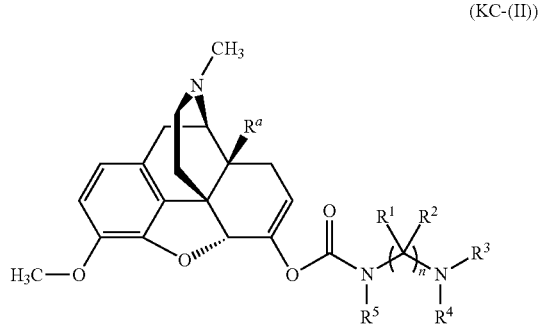

(KC-(II))

wherein:

Rᵃ is hydrogen or hydroxyl;

R⁵ is selected from (1-6C)alkyl, (1-6C) substituted alkyl, —(CH₂)$_q$(C₆H₄)—COOH, —(CH₂)$_q$(C₆H₄)—COOCH₃, and —(CH₂)$_q$(C₆H₄)—COOCH₂CH₃, where q is an integer from one to 10;

each R¹ is independently selected from hydrogen, alkyl, substituted alkyl, aryl, substituted aryl, acyl, and aminoacyl;

each R² is independently selected from hydrogen, alkyl, substituted alkyl, aryl, substituted aryl, acyl, and aminoacyl;

or R¹ and R² together with the carbon to which they are attached form a cycloalkyl or substituted cycloalkyl group, or two R¹ or R² groups on adjacent carbon atoms, together with the carbon atoms to which they are attached, form a cycloalkyl or substituted cycloalkyl group;

n is 2 or 3;

R³ is hydrogen;

R⁴ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof.

8. The composition of claim 1, wherein the opioid prodrug is a compound of formula KC-(IIIa):

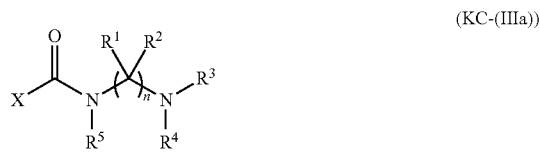

(KC-(IIIa))

wherein:

X represents a residue of a ketone-containing opioid, wherein the hydrogen atom of the corresponding enolic group of the ketone is replaced by a covalent bond to —C(O)—NR⁵—(C(R¹)(R²))$_n$—NR³R⁴;

R⁵ is selected from alkyl, substituted alkyl, arylalkyl, substituted arylalkyl, aryl and substituted aryl;

each R¹ is independently selected from hydrogen, alkyl, substituted alkyl, aryl, substituted aryl, acyl, and aminoacyl;

each R² is independently selected from hydrogen, alkyl, substituted alkyl, aryl, substituted aryl, acyl, and aminoacyl;

or R¹ and R² together with the carbon to which they are attached form a cycloalkyl, substituted cycloalkyl, aryl, or substituted aryl group, or two R² or R³ groups on adjacent carbon atoms, together with the carbon atoms to which they are attached, form a cycloalkyl, substituted cycloalkyl, aryl, or substituted aryl group;

n is an integer from 2 to 4;

R³ is hydrogen or (1-4C) alkyl;

R⁴ is

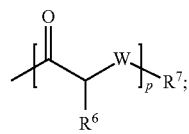

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R⁶ and R⁷ together with the atoms to which they are bonded form a cycloheteroalkyl or substituted cycloheteroalkyl ring;

each W is independently —NR⁸—, —O— or —S—;

each R⁸ is independently selected from hydrogen, alkyl, substituted alkyl, aryl and substituted aryl, or optionally, each R⁶ and R⁸ independently together with the atoms to which they are bonded form a cycloheteroalkyl or substituted cycloheteroalkyl ring;

p is an integer from one to 100; and

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

9. The composition of claim 1, wherein the opioid prodrug is a compound of formula KC-(IIIb):

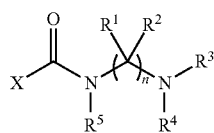

(KC-(IIIb))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl or substituted cycloalkyl group, or two R$^1$ or R$^2$ groups on adjacent carbon atoms, together with the carbon atoms to which they are attached, form a cycloalkyl or substituted cycloalkyl group;

n is an integer from 2 to 4;

R$^3$ is hydrogen or (1-4C) alkyl;

R$^4$ is

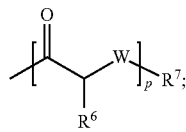

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

10. The composition of claim 1, wherein the opioid prodrug is a compound of formula KC-(IV):

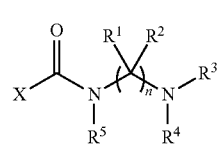

(KC-(IV))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from (1-6C)alkyl, (1-6C) substituted alkyl, —(CH$_2$)$_q$(C$_6$H$_4$)—COOH, —(CH$_2$)$_q$(C$_6$H$_4$)—COOCH$_3$, and —(CH$_2$)$_q$(C$_6$H$_4$)—COOCH$_2$CH$_3$, where q is an integer from one to 10;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl or substituted cycloalkyl group, or two R$^1$ or R$^2$ groups on adjacent carbon atoms, together with the carbon atoms to which they are attached, form a cycloalkyl or substituted cycloalkyl group;

n is 2 or 3;

R$^3$ is hydrogen;

R$^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof;

or a salt, hydrate or solvate thereof.

11. The composition of claim 1, wherein the opioid prodrug is a compound of formula KC-(Va):

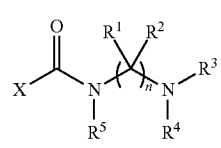

(KC-(Va))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R¹ is independently selected from hydrogen, alkyl, substituted alkyl, aryl, substituted aryl, acyl, and aminoacyl;
each R² is independently selected from hydrogen, alkyl, substituted alkyl, aryl, substituted aryl, acyl, and aminoacyl;
or R¹ and R² together with the carbon to which they are attached form a cycloalkyl, substituted cycloalkyl, aryl, or substituted aryl group, or two R¹ or R² groups on adjacent carbon atoms, together with the carbon atoms to which they are attached, form a cycloalkyl, substituted cycloalkyl, aryl, or substituted aryl group;
n is an integer from 2 to 4;
R³ is hydrogen;
R⁴ is a trypsin-cleavable moiety;
or a salt, hydrate or solvate thereof.

12. The composition of claim 1, wherein the opioid prodrug is a compound of formula KC-(Vb):

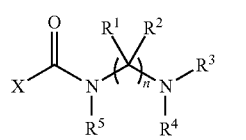

(KC-(Vb))

wherein:
X represents a residue of a ketone-containing opioid, wherein the hydrogen atom of the corresponding enolic group of the ketone is replaced by a covalent bond to —C(O)—NR⁵—(C(R¹)(R²))$_n$—NR³R⁴;
R⁵ is selected from alkyl, substituted alkyl, arylalkyl, substituted arylalkyl, aryl and substituted aryl;
each R¹ is independently selected from hydrogen, alkyl, substituted alkyl, aryl, substituted aryl, acyl, and aminoacyl;
each R² is independently selected from hydrogen, alkyl, substituted alkyl, aryl, substituted aryl, acyl, and aminoacyl;
or R¹ and R² together with the carbon to which they are attached form a cycloalkyl, substituted cycloalkyl, aryl, or substituted aryl group, or two R¹ or R² groups on adjacent carbon atoms, together with the carbon atoms to which they are attached, form a cycloalkyl, substituted cycloalkyl, aryl, or substituted aryl group;
n is an integer from 2 to 4;
R³ is hydrogen;
R⁴ is a GI enzyme-cleavable moiety;
or a salt, hydrate or solvate thereof.

13. The composition of claim 1, wherein the opioid prodrug is a compound of formula KC-(VI):

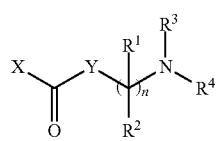

KC-(VI)

wherein:
X represents a residue of a ketone-containing opioid, wherein the hydrogen atom of the corresponding enolic group of the ketone is replaced by a covalent bond to —C(O)—Y—(C(R¹)(R²))$_n$—NR³R⁴;

Y is —NR⁵—, —O— or —S—;
n is an integer from 1 to 4;
each R¹, R², R³ and R⁵ is independently hydrogen, alkyl, substituted alkyl, aryl or substituted aryl, or R¹ and R² together with the carbon to which they are attached form a cycloalkyl or substituted cycloalkyl group;
R⁴ is

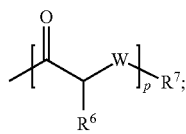

each R⁶ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, R⁶ and R⁷ together with the atoms to which they are bonded form a cycloheteroalkyl or substituted cycloheteroalkyl ring;
R⁷ is hydrogen, alkyl, substituted alkyl, acyl, substituted acyl, alkoxycarbonyl, substituted alkoxycarbonyl, aryl, substituted aryl, arylalkyl or substituted arylalkyl;
p is an integer from 1 to 10;
each W is independently —NR⁸—, —O— or —S—; and
each R⁸ is independently hydrogen, alkyl, substituted alkyl, aryl or substituted aryl, or optionally, each R⁶ and R⁸ independently together with the atoms to which they are bonded form a cycloheteroalkyl or substituted cycloheteroalkyl ring.

14. The composition of claim 1, wherein the opioid prodrug is a compound of formula KC-(VII):

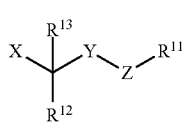

(KC-(VII))

or salts, solvates or hydrates thereof wherein:
X represents a residue of a ketone-containing opioid, wherein the hydrogen atom of the corresponding enolic group of the ketone is replaced by a covalent bond —(CR¹²R¹³)—Y—Z—R¹¹;
R¹² and R¹³ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;
Y is aryl, heteroaryl or arylaryl optionally substituted with one or more —F, —Cl, —Br, —I, —R¹⁴, —O⁻, —OR¹⁴, —SR¹⁴, —S⁻, —NR¹⁴R¹⁵, —CF₃, —CN, —OCN, —SCN, —NO, —NO₂, —N₃, —S(O)₂O⁻, —S(O)₂OH, —S(O)₂R¹⁴, —OS(O₂)O⁻, —OS(O)₂R¹⁴, —P(O)(O⁻)₂, —P(O)(OR¹⁴)(O⁻), —OP(O)(OR¹⁴)(OR¹⁵), —C(O)R¹⁴, —C(S)R¹⁴, —C(O)OR¹⁴, —C(O)NR¹⁴R¹⁵, —C(O)O⁻, —C(S)OR¹⁴, —NR¹⁶C(O)NR¹⁴R¹⁵, —NR¹⁶C(S)NR¹⁴R¹⁵, —NR¹⁷C(NR¹⁶)NR¹⁵R¹⁴ or —C(NR¹⁶)NR¹⁵R¹⁴;
R¹⁴, R¹⁵, R¹⁶ and R¹⁷ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^{14}$ and $R^{15}$ together with the nitrogen atom to which they are bonded form a cycloheteroalkyl or substituted cycloheteroalkyl ring;

Z is $N(R^{18})$—, —O— or —S—;

$R^{18}$ is hydrogen, alkyl, substituted alkyl, aryl, substituted aryl, arylalkyl, substituted arylalkyl, heteroaryl, substituted heteroaryl, heteroarylalkyl or substituted heteroarylalkyl or

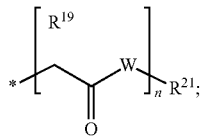

each W is independently —$NR^{20}$—, —O— or —S—;

each $R^{19}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{19}$ and $R^{20}$ together with the atoms to which they are bonded form a cycloheteroalkyl or substituted cycloheteroalkyl ring;

each $R^{20}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{20}$ and $R^{21}$ together with the atoms to which they are bonded form a cycloheteroalkyl or substituted cycloheteroalkyl ring;

$R^{21}$ is hydrogen, alkyl, substituted alkyl, aryl, substituted aryl, arylalkyl or substituted arylalkyl;

n is an integer from 0 to 5;

$R^{11}$ is

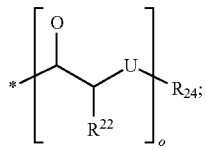

each U is independently —$NR^{23}$—, —O— or —S—;

each $R^{22}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{22}$ and $R^{23}$ together with the atoms to which they are bonded form a cycloheteroalkyl or substituted cycloheteroalkyl ring;

each $R^{23}$ is independently hydrogen, alkyl, substituted alkyl, aryl, substituted aryl, or optionally, $R^{23}$ and $R^{24}$ together with the atoms to which they are bonded form a cycloheteroalkyl or substituted cycloheteroalkyl ring;

$R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100;

provided that Z is oriented para or ortho to X—$(CR^{12}R^{13})$— and that both $R^{18}$ and $R^{11}$ are not hydrogen.

15. The composition of claim 1, wherein the opioid prodrug is a compound of formula KC-(VIII):

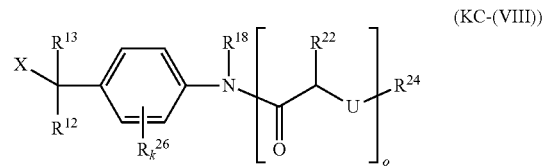

or salts, solvates or hydrates thereof wherein:

X represents a residue of a ketone-containing opioid, wherein the hydrogen atom of the corresponding enolic group of the ketone is replaced by a covalent bond to —$(CR^{12}R^{13})$—Y—Z—$R^{11}$;

$R^{12}$ and $R^{13}$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

$R_k^{26}$ are each independently selected from the group consisting of one or more of —F, —Cl, —Br, —I, —$R^{14}$, —$O^-$, —$OR^{14}$, —$SR^{14}$, —$S^-$, —$NR^{14}R^{15}$, —$CF_3$, —CN, —OCN, —SCN, —NO, —$NO_2$, —$N_3$, —$S(O)_2O^-$, —$S(O)_2OH$, —$S(O)_2R^{14}$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{15}R^{14}$ and —$C(NR^{16})NR^{15}R^{14}$, and k is 0, 1, 2, 3, or 4;

$R^{14}$, $R^{15}$, $R^{16}$ and $R^{17}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^4$ and $R^5$ together with the nitrogen atom to which they are bonded form a cycloheteroalkyl or substituted cycloheteroalkyl ring;

$R^{18}$ is hydrogen or methyl;

$R^{22}$ is a side chain of an amino acid or a derivative of a side chain of an amino acid;

each U is independently —$NR^{23}$—, —O— or —S—;

each $R^{23}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{23}$ and $R^{24}$ together with the atoms to which they are bonded form a cycloheteroalkyl or substituted cycloheteroalkyl ring; and $R^{24}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 100.

16. The composition of claim 1, wherein the opioid prodrug is a compound of formula KC-(IX):

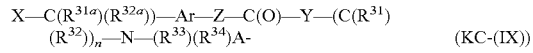

or a salt, hydrate or solvate thereof wherein:

X represents a residue of a ketone-containing opioid, wherein the hydrogen atom of the corresponding enolic group of the ketone is replaced by a covalent bond to —$(C(R^{31a})(R^{32a})$—Ar—Z—C(O)—Y—$(C(R^{31})(R^{32}))_n$—N—$(R^{33})(R^{34})$;

R$^{31}$a and R$^{32}$a are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Ar is aryl, heteroaryl or arylaryl optionally substituted with one or more —F, —Cl, —Br, —I, —R$^{34a}$, —O$^-$, —OR$^{34a}$, —SR$^{34a}$, —S—, —NR$^{34a}$R$^{35a}$, —CF$_3$, —CN, —OCN, —SCN, —NO, —NO$_2$, —N$_3$, —S(O)$_2$O', —S(O)$_2$OH, —S(O)$_2$R$^{34a}$, —OS(O$_2$)O'', —OS(O)$_2$R$^{34a}$, —P(0)(0'')$_2$, —P(O)(OR$^{34a}$)(O''), —OP(O)(OR$^{34a}$)(OR$^{35a}$), —C(0)R$^{34a}$, —C(S)R$^{34a}$, —C(O)OR$^{34a}$, —C(O)NR$^{34a}$R$^{35a}$, —C(O)O; —C(S)OR$^{34a}$, —NR$^{36a}$C(O)NR$^{34a}$R$^{35a}$, —NR$^{36a}$C(S)NR$^{34a}$R$^{35a}$, —NR$^{37a}$C(NR$^{36a}$)NR$^{35a}$R$^{34a}$ or —C(NR$^{36a}$)NR$^{35a}$R$^{34a}$, or tethered to a polymer;

R$^{34a}$, R$^{35a}$, R$^{36a}$ and R$^{37a}$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally R$^{34}$ and R$^{35}$ together with the nitrogen atom to which they are bonded form a cycloheteroalkyl or substituted cycloheteroalkyl ring;

Z is O, S or NH;

Y is —NR$^{35}$—, —O— or —S—;

n is an integer from 1 to 10;

each R$^{31}$, R$^{32}$, R$^{33}$ and R$^{35}$ is independently hydrogen, alkyl, substituted alkyl, aryl or substituted aryl, or R$^{31}$ and R$^{32}$ together with the carbon to which they are attached form a cycloalkyl or substituted cycloalkyl group, or two R$^{31}$ or R$^{32}$ groups on adjacent carbon atoms, together with the carbon atoms to which they are attached, form a cycloalkyl or substituted cycloalkyl group;

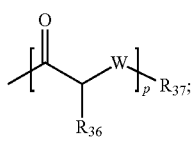

each R$^{36}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, R$^{36}$ and R$^{37}$ together with the atoms to which they are bonded form a cycloheteroalkyl or substituted cycloheteroalkyl ring;

R$^{37}$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 5;

each W is independently —NR$^{38}$—, —O— or —S—;

each R$^{38}$ is independently hydrogen, alkyl, substituted alkyl, aryl or substituted aryl, or optionally, each R$^{36}$ and R$^{38}$ independently together with the atoms to which they are bonded form a cycloheteroalkyl or substituted cycloheteroalkyl ring; and A' represents an anion.

17. A method to treat a patient comprising administering a pharmaceutical composition or dose unit comprising the composition of claim 1 to a patient in need thereof.

18. The composition of claim 5, wherein R$^3$ is hydrogen.
19. The composition of claim 6, wherein R$^3$ is hydrogen.
20. The composition of claim 8, wherein R$^3$ is hydrogen.
21. The composition of claim 9, wherein R$^3$ is hydrogen.
22. The composition of claim 11, wherein X is hydrocodone or oxycodone.
23. The composition of claim 11, wherein R$^5$ is alkyl or substituted alkyl.
24. The composition of claim 23, wherein R$^5$ is ethyl or methyl.
25. The composition of claim 23, wherein R$^5$ is methyl.
26. The composition of claim 11, wherein each R$^1$ and R$^2$ is independently selected from hydrogen, alkyl, substituted alkyl and aminoacyl.
27. The composition of claim 26, wherein R$^1$ and R$^2$ are hydrogen.
28. The composition of claim 26, wherein R$^1$ and R$^2$ which are on the same carbon are alkyl.
29. The composition of claim 26, wherein R$^1$ and R$^2$ which are on the same carbon are methyl.
30. The composition of claim 26, wherein the alkyl is methyl.
31. The composition of claim 26, wherein the aminoacyl is —C(O)NR$^{10a}$R$^{10b}$, wherein each R$^{10a}$ and R$^{10b}$ is independently selected from hydrogen, alkyl, substituted alkyl, and acyl.
32. The composition of claim 31, wherein R$^{10a}$ and R$^{10b}$ are methyl.
33. The composition of claim 11, wherein each R$^4$ is

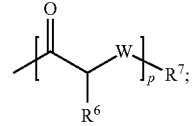

p is 1 or 2;
each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
each W is —NR$^8$—;
each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring; and
R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl.

34. The composition of claim 33, wherein p is 1 and wherein R$^6$ is a side chain of an amino acid residue selected from lysine, arginine, homolysine, homoarginine, ornithine, arginine mimics, arginine homologues, arginine truncates, arginine with varying oxidation, lysine mimics, lysine homologues, lysine truncates, and lysine with varying oxidation states.

35. The composition of claim 33, wherein p is 1 and wherein R$^6$ is a side chain of an amino acid residue selected from L-lysine and L-arginine.

36. The composition of claim 33, wherein p is 2, and wherein a first R$^6$ is a side chain of an amino acid residue selected from lysine, arginine, homolysine, homoarginine, ornithine, arginine mimics, arginine homologues, arginine truncates, arginine with varying oxidation, lysine mimics, lysine homologues, lysine truncates, and lysine with varying oxidation states and a second $R^6$ is a side chain of an amino acid residue selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative thereof.

37. The composition of claim 33, wherein each $R^6$ is independently a side chain of an amino acid residue selected from glycine, L-lysine or L-arginine.

38. The composition of claim 33, wherein a first $R^6$ is a side chain of an amino acid residue selected from L-lysine or L-arginine and a second $R^6$ is a side chain of glycine.

39. The composition of claim 33, wherein each $R^8$ is hydrogen.

40. The composition of claim 33, wherein $R^7$ is selected from hydrogen and acyl.

41. The composition of claim 40, wherein $R^7$ is selected from hydrogen, acetyl, benzoyl, malonyl, piperonyl and succinyl.

42. The composition of claim 41, wherein $R^7$ is acetyl or malonyl.

43. The composition of claim 11, wherein the opioid prodrug is a compound selected from the group consisting of:

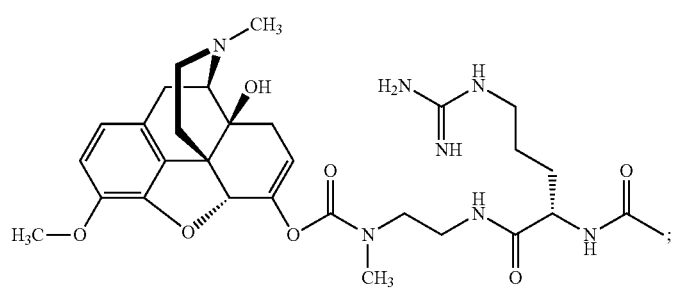
(KC-2)

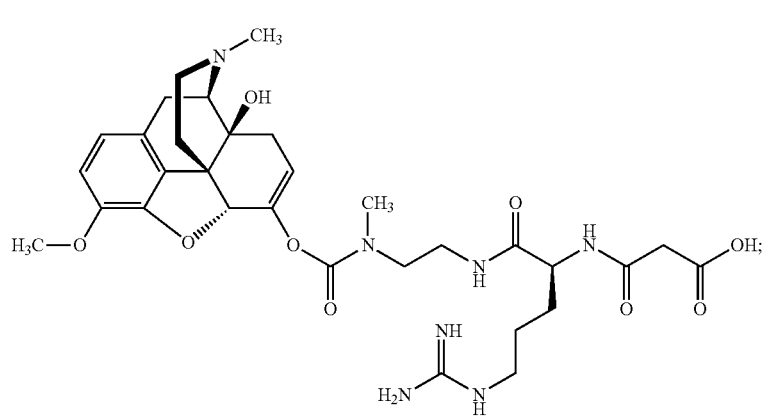
(KC-3)

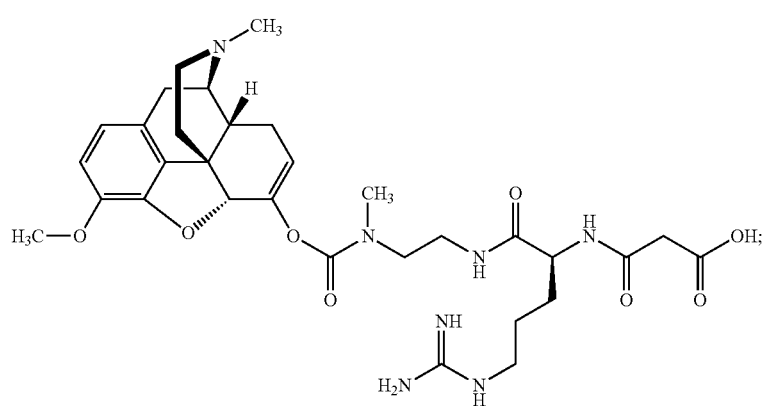
(KC-4)

-continued

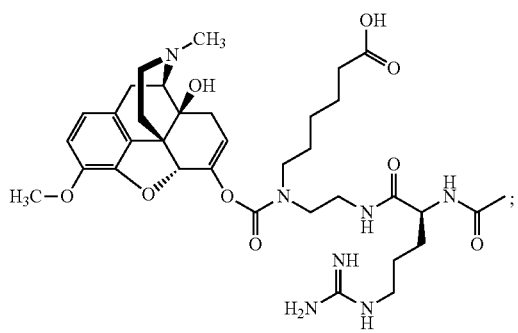
(KC-5)

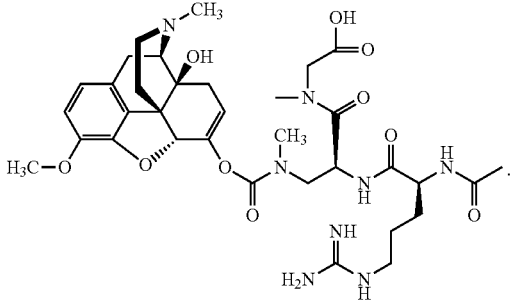
(KC-6)

44. The composition of claim 11, wherein:
X is hydrocodone;
$R^5$ is methyl;
n is 2;
each $R^1$ is independently selected from hydrogen and —C(O)NR$^{10a}$R$^{10b}$), wherein $R^{10a}$ and $R^{10b}$ are methyl;
each $R^2$ is hydrogen;
$R^3$ is hydrogen;
$R^4$ is

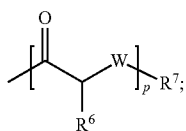

wherein p is 2;
each $R^6$ is independently hydrogen or —CH$_2$CH$_2$CH$_2$NH(C=NH)NH$_2$;
each W is —NR$^8$—;
each $R^8$ is hydrogen; and
$R^7$ is malonyl or acetyl;
or a salt, hydrate or solvate thereof.

45. The composition of claim 11, wherein:
X is hydrocodone;
$R^5$ is methyl;
n is 2;
each $R^1$ is independently selected from hydrogen and methyl;
each $R^2$ is independently selected from hydrogen and methyl;
$R^3$ is hydrogen;
$R^4$ is

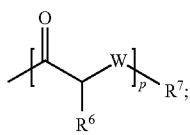

wherein p is 2;
each $R^6$ is independently hydrogen or —CH$_2$CH$_2$CH$_2$NH(C=NH)NH$_2$;
each W is —NR$^8$—;
each $R^8$ is hydrogen; and
$R^7$ is acetyl;
or a salt, hydrate or solvate thereof.

46. The composition of claim 11, wherein:
X is oxycodone;
$R^5$ is methyl;
n is 2;
each $R^1$ is independently selected from hydrogen and —C(O)NR$^{10a}$R$^{10b}$, wherein $R^{10a}$ and $R^{10b}$ are —CH$_2$C(O)OH;
each $R^2$ is hydrogen;
$R^3$ is hydrogen;
$R^4$ is

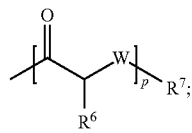

wherein p is 2;
each $R^6$ is independently hydrogen or —CH$_2$CH$_2$CH$_2$NH(C=NH)NH$_2$;
each W is —NR$^8$—;
each $R^8$ is hydrogen; and
$R^7$ is acetyl;
or a salt, hydrate or solvate thereof.

47. The composition of claim 11, wherein:
X is oxycodone;
$R^5$ is methyl;
n is 3;
each $R^1$ is independently selected from hydrogen and dimethyl;
each $R^2$ is independently selected from hydrogen and dimethyl;
$R^3$ is hydrogen;
$R^4$ is

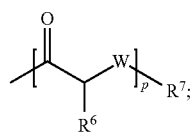

wherein p is 2;
each $R^6$ is independently hydrogen or —CH$_2$CH$_2$CH$_2$NH(C=NH)NH$_2$;
each W is —NR$^8$—;
each $R^8$ is hydrogen; and
$R^7$ is malonyl;
or a salt, hydrate or solvate thereof.

48. The composition of claim 11, wherein:
X is oxycodone;
$R^5$ is methyl;
n is 2;
each $R^1$ is independently selected from hydrogen and —C(O)NR$^{10a}$R$^{10b}$, wherein R$^{10a}$ and R$^{10b}$ are methyl;
each $R^2$ is hydrogen;
$R^3$ is hydrogen;
$R^4$ is

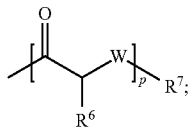

wherein p is 2;
each $R^6$ is independently hydrogen or —CH$_2$CH$_2$CH$_2$NH(C=NH)NH$_2$;
each W is —NR$^8$—;
each $R^8$ is hydrogen; and
$R^7$ is malonyl or acetyl;
or a salt, hydrate or solvate thereof.

49. The composition of claim 39, wherein:
X is oxycodone;
$R^5$ is methyl;
n is 2;
each $R^1$ is independently selected from hydrogen and methyl;
each $R^2$ is independently selected from hydrogen and methyl;
$R^3$ is hydrogen;
$R^4$ is

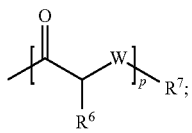

wherein p is 2;
each $R^6$ is independently hydrogen or —CH$_2$CH$_2$CH$_2$NH(C=NH)NH$_2$;
each W is —NR$^8$—;
each $R^8$ is hydrogen; and
$R^7$ is acetyl;
or a salt, hydrate or solvate thereof.

50. The composition of claim 11, wherein:
X is hydrocodone;
$R^5$ is methyl;
n is 2;
each $R^1$ is independently selected from hydrogen and —C(O)NR$^{10a}$R$^{10b}$, wherein R$^{10a}$ and R$^{10b}$ are —CH$_2$C(O)OH;
each $R^2$ is hydrogen;
$R^3$ is hydrogen;
$R^4$ is

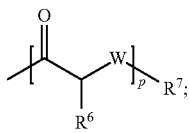

wherein p is 2;
each $R^6$ is independently hydrogen or —CH$_2$CH$_2$CH$_2$NH(C=NH)NH$_2$;
each W is —NR$^8$—;
each $R^8$ is hydrogen; and
$R^7$ is acetyl;
or a salt, hydrate or solvate thereof.

51. The composition of claim 11, wherein:
X is hydrocodone;
$R^5$ is methyl;
n is 3;
each $R^1$ is independently selected from hydrogen and dimethyl;
each $R^2$ is independently selected from hydrogen and dimethyl;
$R^3$ is hydrogen;
$R^4$ is

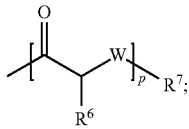

wherein p is 2;
each $R^6$ is independently hydrogen or —CH$_2$CH$_2$CH$_2$NH(C=NH)NH$_2$;
each W is —NR$^8$—;
each $R^8$ is hydrogen; and
$R^7$ is malonyl;
or a salt, hydrate or solvate thereof.

* * * * *